United States Patent
Shinozuka et al.

(10) Patent No.: US 9,493,448 B2
(45) Date of Patent: *Nov. 15, 2016

(54) CYCLOALKANE DERIVATIVES

(71) Applicant: Daiichi Sankyo Company, Limited, Tokyo (JP)

(72) Inventors: Tsuyoshi Shinozuka, Tokyo (JP); Hiroyuki Kobayashi, Tokyo (JP); Sayaka Suzuki, Tokyo (JP); Kyosuke Tanaka, Tokyo (JP); Hiroko Kimoto, Tokyo (JP); Yuki Domon, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 104 days.

This patent is subject to a terminal disclaimer.

(21) Appl. No.: 14/502,708

(22) Filed: Sep. 30, 2014

(65) Prior Publication Data

US 2015/0018551 A1 Jan. 15, 2015

Related U.S. Application Data

(63) Continuation of application No. 13/756,173, filed on Jan. 31, 2013, now Pat. No. 8,889,741.

(30) Foreign Application Priority Data

Feb. 9, 2012 (JP) ................. 2012-025754
Nov. 27, 2012 (JP) ................. 2012-259122

(51) Int. Cl.
*C07D 403/12* (2006.01)
*C07D 401/12* (2006.01)
*C07D 285/08* (2006.01)
*C07D 417/12* (2006.01)

(52) U.S. Cl.
CPC ......... *C07D 417/12* (2013.01); *C07D 285/08* (2013.01); *C07D 401/12* (2013.01); *C07D 403/12* (2013.01)

(58) Field of Classification Search
CPC C07D 285/08; C07D 401/12; C07D 403/12; C07D 417/12
See application file for complete search history.

(56) References Cited

FOREIGN PATENT DOCUMENTS

| | | |
|---|---|---|
| JP | 2010-533652 A | 10/2010 |
| WO | WO-2006/038594 A1 | 4/2006 |
| WO | WO-2009/012242 A2 | 1/2009 |
| WO | WO-2010/079443 A1 | 7/2010 |
| WO | WO-2012/004714 A2 | 1/2012 |
| WO | WO-2013/064983 A1 | 5/2013 |

OTHER PUBLICATIONS

European Search Report issued in Application No. 13746373.3, dated Jul. 13, 2015.
Cox, J.J., et al., "An SCN9A channelopathy causes congenital inability to experience pain," Nature, (2006), 444: pp. 894-898.
English translation of International Search Report issued in PCT Application No. PCT/JP2013/052985 on Apr. 23, 2013, 4 pages.
Frampton, J.E., et al., "Pregabalin in the Treatment of Painful Diabetic Peripheral Neuropathy," Drugs, (2004), 64(24): pp. 2813-2820.
Nassar, M.A., et al., "Nociceptor-specific gene deletion reveals a major role for Na 1.7 (PN1) in acute and inflammatory pain," Proc. Natl. Acad. Sci., (2004, 101(340: pp. 12706-12711.
Notice of Allowance on U.S. Appl. No. 13/756,173, mailed Jul. 2, 2014.
Office Action dated Apr. 20, 2015 issued in Chinese Application No. 201380017715.1.

*Primary Examiner* — Kendra D Carter
(74) *Attorney, Agent, or Firm* — Foley & Lardner LLP

(57) ABSTRACT

Disclosed herein are therapeutic agents and/or preventive agents for pain or therapeutic agents and/or preventive agents for a sodium channel associated disease. The present invention provides compounds represented by the following formula (I) or pharmacologically acceptable salts thereof:

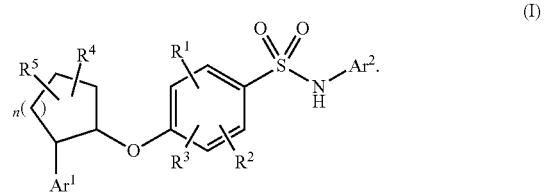

29 Claims, 3 Drawing Sheets

CYCLOALKANE DERIVATIVES

CROSS REFERENCE TO RELATED APPLICATIONS

This application is a continuation of U.S. application Ser. No. 13/756,173, filed on Jan. 31, 2013, now U.S. Pat. No. 8,889,741, which claims benefit to Japanese Application 2012-025754, filed Feb. 9, 2012, and Japanese Application 2012-259122, filed Nov. 27, 2012, all of which are incorporated herein by their entireties.

BACKGROUND OF THE INVENTION

1. Field of the Invention

The present invention relates to a novel cycloalkane derivative, a pharmacologically acceptable salt, or a hydrate thereof, useful as a pharmaceutical, particularly, with an analgesic action. The present invention further relates to a method for treating and/or preventing pain by administering the novel cycloalkane derivative of the present invention. The present invention also relates to the compound, a pharmacologically acceptable salt, or a hydrate thereof, for treating and/or preventing the crisis of a sodium channel associated disease. In addition, the present invention relates to a method for treating and/or preventing a sodium channel associated disease by administering the novel cycloalkane derivative of the present invention.

2. Description of the Related Art

A variety of pains including acute pain such as inflammatory pain and nociceptive pain; intractable chronic pain such as neurogenic pain, myogenic pain and fibromyalgia; and phantom limb pain probably derived from a psychogenic factor are known as pathologic pains. Since pain greatly degrades the quality of life of a patient in many cases, social loss caused by pain is incalculable.

Currently, nonsteroidal analgesics, nonnarcotic analgesics, narcotic analgesics, antiepileptic drugs and antidepressants are used as therapeutic agents for pain. Although a method for treating most cases of inflammatory pain and nociceptive pain has been established, there are very limited effective therapeutic agents for chronic pains such as neurogenic pain for which a nonsteroidal antiinflammatory drug is ineffective and which is resistant to narcotic analgesics.

Pregabalin and the like are currently used as therapeutic agents for neurogenic pain, but it is reported that pregabalin shows an effective therapeutic ratio based on self-evaluation of patients of painful diabetic neuropathy of approximately 50% (Non Patent Literature 1), and hence, it cannot be said that patient satisfaction with treatment is always attained.

Voltage-gated sodium channels (Navs) are ion channels each including an α subunit having four domains and auxiliary β subunits, at least nine subtypes thereof have been reported so far, and these subtypes respectively have different expression distributions and physiological actions so as to regulate biological functions.

The sodium channels are an essence of neural activity, and drugs such as a local anesthetic of lidocaine, an antiarrhythmic of mexiletine and an antiepileptic of carbamazepine are known as inhibitors of the sodium channels. Such drugs have, however, low selectivity for the Nav subtypes. Since sodium channels of different subtypes are expressed in muscles, cardiac muscle cells and the central nervous system as shown in Table 1, there arises a problem of an adverse drug action caused when such a drug is systemically administered.

TABLE 1

| Subtype | Main expression site |
|---|---|
| Nav1.1 | Central nervous system |
| Nav1.2 | Central nervous system |
| Nav1.3 | Central nervous system |
| Nav1.4 | Skeletal muscle |
| Nav1.5 | Cardiac muscle cells |
| Nav1.6 | Sensory/motor nervous system |
| Nav1.7 | Sensory nervous system |
| Nav1.8 | Sensory nervous system |
| Nav1.9 | Sensory nervous system |

On the other hand, it is known that Nav 1.7 defect causes pain insensitivity in a human (Non Patent Literature 2), and since similar tendency is observed in KO mice (Non Patent Literature 3), it is regarded that a Nav 1.7 selective inhibitor is a promising target of therapeutic agents for various pains.

Patent Literature 1 relates to a Nav 1.7 modulator and specifically describes, for example, a compound represented by formula (A) below (in Example 811). The feature of the compound described in this patent literature is that two aromatic rings are connected through an oxygen atom, and further, N-substituted sulfonamide is connected to one of the aromatic rings (phenyl group). The compound of the present invention differs therefrom in that cycloalkane is connected to an aromatic ring through an oxygen atom. Patent Literature 1 neither describes nor suggests the structure of the compound of the present invention.

[Formula 1]

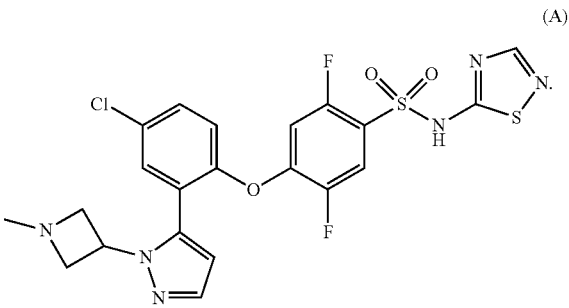

(A)

Specifically, the compound disclosed in Patent Literature 1 is described in the claim as falling within a structure represented by formula (B) below. The moiety B in this structure is defined as "phenyl or Het$^2$, wherein Het$^2$ is defined as a 5- or 6-membered aromatic heterocyclic group containing (a) one to four nitrogen atoms, (b) one oxygen atom or one sulfur atom, or (c) one oxygen atom or one sulfur atom and one or two nitrogen atoms". Thus, the moiety B is an aromatic substituent. The patent literature neither discloses that this moiety is a saturated substituent nor discloses that cycloalkane is formed.

[Formula 2]

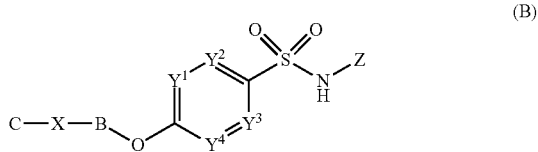

(B)

Patent Literature 2 relates to an N-type calcium channel inhibitor and specifically describes, for example, a compound represented by formula (C) below (in Example 5(11)). The compound described in this patent literature has a structure in which an aromatic ring and a saturated heterocyclic ring are connected through a polymethylene (oxy) chain. An N-substituted sulfonamide is bonded to aromatic ring (phenyl group), and two substituents are further introduced in the nitrogen atom of this sulfonamide. Specifically, the feature of this compound is that the nitrogen atom of the sulfonamide is di-substituted. The compound of the present invention differs therefrom in that: a saturated ring is not a heterocyclic ring; cycloalkane and an aromatic ring are connected through an oxygen atom and not through a polymethylene chain; and a sulfonamide moiety is mono-substituted at its nitrogen atom. Patent Literature 2 neither describes nor suggests the compound of the present invention at all.

[Formula 3]

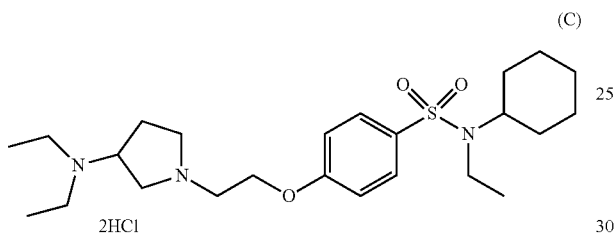

(C)

2HCl

Neither does the compound of the present invention fall within a structure represented by formula (D) below described in claims of the Patent Literature 2, nor the structure of the compound of the present invention is suggested from the description related to this structure.

[Formula 4]

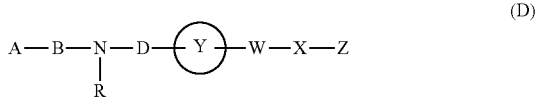

(D)

PRIOR ART LITERATURE

Patent Literature

[Patent Literature 1] WO2010/079443
[Patent Literature 2] WO2006/038594

Non Patent Literature

[Non Patent Literature 1] Drugs 64 (24): 2813-2820, 2004
[Non Patent Literature 2] Cox, J. J. et al., Nature, 2006, 444 (7121), 894-898
[Non Patent Literature 3] Nassar, M. A. et al., Proc. Natl. Acad. Sci., 2004, 101(34), 12706-12711

SUMMARY OF THE INVENTION

The Problem to be Solved by the Invention

An object of the present invention is to provide a sodium channel inhibitor that has high selectivity with high pain inhibitory activities and is further directed to reduction in adverse drug action caused by systemic administration, in response to, for example, a low level of satisfaction at conventional therapeutic agents for neurogenic pain and the low activities and selectivity of conventional sodium channel inhibitory activity.

The Means to Solve the Problem

The present inventors have earnestly conducted studies and consequently completed the present invention by finding that a compound represented by formula (I) below having a structure in which a phenyl group to which an N-aromatic substituent-substituted sulfonamide group is connected, and a cyclic alkyl group having an aromatic group as a substituent is connected through an oxygen atom to the para position of the sulfonamide group, a salt, or a hydrate thereof, exhibits excellent pain control and sodium channel inhibitory activities with high selectivity.

Specifically, the present invention relates to:
(1) A compound represented by formula (I) or a pharmacologically acceptable salt, or hydrate thereof:

[Formula 5]

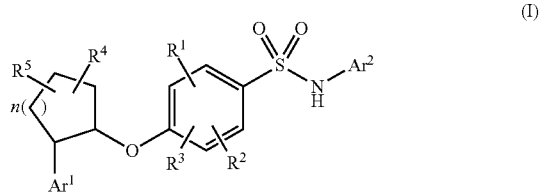

(I)

wherein $Ar^1$ and $Ar^2$ each independently represents a heteroaryl group or an aryl group, $R^1$, $R^2$ and $R^3$ each independently represents a hydrogen atom, a halogen atom, a C1-C6 alkyl group, a halogenated C1-C6 alkyl group, a hydroxy C1-C6 alkyl group, a C1-C6 alkoxy C1-C6 alkyl group, a C3-C7 cycloalkyl group or a cyano group, $R^4$ and $R^5$ each independently represents a hydrogen atom, a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group or a C1-C6 alkoxy group, and n represents an integer of 1 to 3, and wherein the heteroaryl group or the aryl group optionally has one or two substituents independently selected from a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group, a carboxy group, a cyano group, an amino group, a C1-C3 alkylamino group and a di-C1-C3 alkylamino group, and when the heteroaryl group or the aryl group has two substituents, the two substituents may be the same or different from each other.

The present invention further relates to the following:
(2) The compound or a pharmacologically acceptable salt thereof according to (1), wherein in formula (I), $Ar^1$ and $Ar^2$ each independently represents a heteroaryl group, $R^1$, $R^2$ and $R^3$ each independently represents a hydrogen atom, a halogen atom, a C1-C6 alkyl group, a halogenated C1-C6 alkyl group or a C3-C7 cycloalkyl group, $R^4$ and $R^5$ each independently represents a hydrogen atom, a halogen atom, a C1-C6 alkyl group or a halogenated C1-C6 alkyl group, and the substituent on the heteroaryl group is one or two substituents selected from the group consisting of a halogen atom, a C1-C6 alkyl group, a halogenated C1-C6 alkyl group, a hydroxyl group, a hydroxy C1-C6 alkyl group, a C3-C7 cycloalkyl group, an amino group, a C1-C3 alkylamino group and a di-C1-C3 alkylamino group.

(3) The compound or a pharmacologically acceptable salt thereof according to (1) or (2), wherein the heteroaryl group is a 5- or 6-membered nitrogen-containing aromatic heterocyclic group.

(4) The compound or a pharmacologically acceptable salt thereof according to any of (1) to (3), wherein $Ar^1$ is a pyridyl group, a pyridazinyl group, a pyrimidinyl group, a pyrazolyl group or an imidazolyl group optionally having a substituent.

(5) The compound or a pharmacologically acceptable salt thereof according to any of (1) to (4), wherein $Ar^1$ is a pyridyl group, a pyridazinyl group, a pyrimidinyl group, a pyrazolyl group or an imidazolyl group optionally having one or two substituents selected from the group consisting of a chlorine atom, a fluorine atom, a methyl group, an ethyl group, a trifluoromethyl group, an amino group, a methylamino group and a dimethylamino group.

(6) The compound or a pharmacologically acceptable salt thereof according to any of (1) to (5), wherein $Ar^2$ is a thiadiazolyl group, a thiazolyl group, a pyrimidinyl group, an isoxazolyl group, an oxazolyl group or an isothiazolyl group optionally having a substituent.

(7) The compound or a pharmacologically acceptable salt thereof according to any of (1) to (6), wherein $Ar^2$ is a thiadiazolyl group, a thiazolyl group, a pyrimidinyl group, an isoxazolyl group, an oxazolyl group or an isothiazolyl group optionally having a chlorine atom, a fluorine atom or a methyl group as a substituent.

(8) The compound or a pharmacologically acceptable salt thereof according to any of (1) to (7), wherein $R^1$, $R^2$ and $R^3$ each independently represents a hydrogen atom, a chlorine atom, a fluorine atom, a methyl group, an ethyl group, a trifluoromethyl group or a cyano group.

(9) The compound or a pharmacologically acceptable salt thereof according to any of (1) to (8), wherein $R^4$ and $R^5$ each independently represents a hydrogen atom, a fluoro group or a methyl group.

(10) The compound, pharmaceutically acceptable salt, or hydrate thereof according to (1), wherein the compound represented by formula (I) is 2,5-difluoro-4-{[(1S*,2R*)-2-(1-methyl-1H-pyrazol-5-yl)cyclopentyl]oxy}-N-(pyrimidin-4-yl)benzenesulfonamide;
2,5-difluoro-4-{[(1S*,2R*)-2-(1-methyl-1H-pyrazol-5-yl)cyclopentyl]oxy}-N-(1,3-thiazol-2-yl)benzenesulfonamide;
3-chloro-4-{[(1S*,2R*)-2-(1-methyl-1H-pyrazol-5-yl)cyclopentyl]oxy}-N-(pyrimidin-4-yl)benzenesulfonamide;
2,5-difluoro-4-{[(1S*,2R*)-2-(1-methyl-1H-pyrazol-5-yl)cyclohexyl]oxy}-N-(pyrimidin-4-yl)benzenesulfonamide;
2-fluoro-4-{[(1S*,2R*)-2-(1-methyl-1H-pyrazol-5-yl)cyclopentyl]oxy}-N-(pyrimidin-4-yl)benzenesulfonamide;
2,5-difluoro-4-{[(1S,2R)-2-(1-methyl-1H-pyrazol-5-yl)cyclopentyl]oxy}-N-(pyrimidin-4-yl)benzenesulfonamide;
2,5-difluoro-4-{[(1S*,2R*)-2-(1H-pyrazol-4-yl)cyclohexyl]oxy}-N-(pyrimidin-4-yl)benzenesulfonamide;
4-{[(1S*,2R*)-2-(1-ethyl-1H-pyrazol-5-yl)cyclopentyl]oxy}-2,3-difluoro-N-(pyrimidin-4-yl)benzenesulfonamide;
2,3-difluoro-4-{[(1S*,2R*)-2-(1-methyl-1H-pyrazol-5-yl)cyclohexyl]oxy}-N-(pyrimidin-4-yl)benzenesulfonamide;
4-{[(1S*,2R*)-5,5-difluoro-2-(1-methyl-1H-pyrazol-5-yl)cyclohexyl]oxy}-2,5-difluoro-N-(pyrimidin-4-yl)benzenesulfonamide;
5-chloro-2-fluoro-4-{[(1S*,2R*)-2-(1-methyl-1H-pyrazol-5-yl)cyclohexyl]oxy}-N-(pyrimidin-4-yl)benzenesulfonamide;
2-fluoro-4-{[(1S*,2R*)-2-(1-methyl-1H-pyrazol-5-yl)cycloheptyl]oxy}-N-(pyrimidin-4-yl)benzenesulfonamide;
2-fluoro-3-methyl-4-{[(1S*,2R*)-2-(1-methyl-1H-pyrazol-5-yl)cyclohexyl]oxy}-N-(pyrimidin-4-yl)benzenesulfonamide;
4-{[(1S*,2R*)-2-(3-amino-1H-pyrazol-4-yl)cyclohexyl]oxy}-2-fluoro-5-methyl-N-(pyrimidin-4-yl)benzenesulfonamide;
4-{[((1S*,2R*)-2-(3-amino-1H-pyrazol-4-yl)cyclohexyl]oxy}-5-chloro-2-fluoro-N-(pyrimidin-4-yl)benzenesulfonamide;
4-{[(1S*,2R*)-2-(3-amino-1H-pyrazol-4-yl)cyclohexyl]oxy}-2-fluoro-3-methyl-N-(pyrimidin-4-yl)benzenesulfonamide;
2,6-difluoro-4-{[(1S*,2R*)-2-(1H-pyrazol-4-yl)cyclohexyl]oxy}-N-(pyrimidin-4-yl)benzenesulfonamide;
4-{[(1S,2R)-5,5-difluoro-2-(1-methyl-1H-pyrazol-5-yl)cyclohexyl]oxy}-2,5-difluoro-N-(pyrimidin-4-yl)benzenesulfonamide;
4-{[(1S,2R)-2-(1-ethyl-1H-pyrazol-5-yl)cyclopentyl]oxy}-2,3-difluoro-N-(pyrimidin-4-yl)benzenesulfonamide;
5-chloro-2-fluoro-4-{[(1S,2R)-2-(1-methyl-1H-pyrazol-5-yl)cyclohexyl]oxy}-N-(pyrimidin-4-yl)benzenesulfonamide;
2-fluoro-4-{[(1S,2R)-2-(1-methyl-1H-pyrazol-5-yl)cyclopentyl]oxy}-N-(pyrimidin-4-yl)benzenesulfonamide;
4-{[(1S*,2R*)-5,5-difluoro-2-(1H-pyrazol-4-yl)cyclohexyl]oxy}-2-fluoro-5-methyl-N-(pyrimidin-4-yl)benzenesulfonamide;
4-{[(1S*,2R*)-4,4-difluoro-2-(1-methyl-1H-pyrazol-5-yl)cyclopentyl]oxy}-2-fluoro-5-methyl-N-(pyrimidin-4-yl)benzenesulfonamide;
4-{[(1S*,2R*)-5,5-difluoro-2-(1-methyl-1H-pyrazol-5-yl)cyclohexyl]oxy}-2-fluoro-5-methyl-N-(pyrimidin-4-yl)benzenesulfonamide;
2-fluoro-5-methyl-4-{[(1S*,2R*)-2-(1H-pyrazol-5-yl)cyclopentyl]oxy}-N-(pyrimidin-4-yl)benzenesulfonamide;
5-chloro-2-fluoro-4-{[(1S*,2R*)-2-(1H-pyrazol-5-yl)cyclopentyl]oxy}-N-(pyrimidin-4-yl)benzenesulfonamide;
4-{[(1S,2R)-5,5-difluoro-2-(1H-pyrazol-4-yl)cyclohexyl]oxy}-2-fluoro-5-methyl-N-(pyrimidin-4-yl)benzenesulfonamide;
2-fluoro-5-methyl-4-{[(1S,2R)-2-(1H-pyrazol-5-yl)cyclopentyl]oxy}-N-(pyrimidin-4-yl)benzenesulfonamide;
5-chloro-2-fluoro-4-{[(1S,2R)-2-(1H-pyrazol-5-yl)cyclopentyl]oxy}-N-(pyrimidin-4-yl)benzenesulfonamide;
5-chloro-4-{[(1S*,2R*)-5,5-difluoro-2-(1H-pyrazol-4-yl)cyclohexyl]oxy}-2-fluoro-N-(pyrimidin-4-yl)benzenesulfonamide; or
2,6-difluoro-4-{[(1S,2R)-2-(1H-pyrazol-4-yl)cyclohexyl]oxy}-N-(pyrimidin-4-yl)benzenesulfonamide.

(11) The compound, pharmacologically acceptable salt, or hydrate thereof according to (1), wherein the compound represented by formula (I) is 2-fluoro-4-{[(1S*,2R*)-2-(1-methyl-1H-pyrazol-5-yl)cyclopentyl]oxy}-N-(pyrimidin-4-yl)benzenesulfonamide;
2,5-difluoro-4-{[(1S*,2R*)-2-(1H-pyrazol-4-yl)cyclohexyl]oxy}-N-(pyrimidin-4-yl)benzenesulfonamide;

4-{[(1S*,2R*)-2-(1-ethyl-1H-pyrazol-5-yl)cyclopentyl]
oxy}-2,3-difluoro-N-(pyrimidin-4-yl)benzenesulfonamide;
4-{[(1S*,2R*)-5,5-difluoro-2-(1-methyl-1H-pyrazol-5-yl)
cyclohexyl]oxy}-2,5-difluoro-N-(pyrimidin-4-yl)benzenesulfonamide;
5-chloro-2-fluoro-4-{[(1S*,2R*)-2-(1-methyl-1H-pyrazol-5-yl)cyclohexyl]oxy}-N-(pyrimidin-4-yl)benzenesulfonamide;
2,6-difluoro-4-{[(1S*,2R*)-2-(1H-pyrazol-4-yl)cyclohexyl]
oxy}-N-(pyrimidin-4-yl)benzenesulfonamide;
4-{[(1S,2R)-5,5-difluoro-2-(1-methyl-1H-pyrazol-5-yl)cyclohexyl]oxy}-2,5-difluoro-N-(pyrimidin-4-yl)benzenesulfonamide;
4-{[(1S,2R)-2-(1-ethyl-1H-pyrazol-5-yl)cyclopentyl]oxy}-2,3-difluoro-N-(pyrimidin-4-yl)benzenesulfonamide;
5-chloro-2-fluoro-4-{[(1S,2R)-2-(1-methyl-1H-pyrazol-5-yl)cyclohexyl]oxy}-N-(pyrimidin-4-yl)benzenesulfonamide;
2-fluoro-4-{[(1S,2R)-2-(1-methyl-1H-pyrazol-5-yl)cyclopentyl]oxy}-N-(pyrimidin-4-yl)benzenesulfonamide;
4-{[(1S*,2R*)-5,5-difluoro-2-(1H-pyrazol-4-yl)cyclohexyl]
oxy}-2-fluoro-5-methyl-N-(pyrimidin-4-yl)benzenesulfonamide;
2-fluoro-5-methyl-4-{[(1S*,2R*)-2-(1H-pyrazol-5-yl)cyclopentyl]oxy}-N-(pyrimidin-4-yl)benzenesulfonamide;
5-chloro-2-fluoro-4-{[(1S*,2R*)-2-(1H-pyrazol-5-yl)cyclopentyl]oxy}-N-(pyrimidin-4-yl)benzenesulfonamide;
4-{[(1S,2R)-5,5-difluoro-2-(1H-pyrazol-4-yl)cyclohexyl]
oxy}-2-fluoro-5-methyl-N-(pyrimidin-4-yl)benzenesulfonamide;
2-fluoro-5-methyl-4-{[(1S,2R)-2-(1H-pyrazol-5-yl)cyclopentyl]oxy}-N-(pyrimidin-4-yl)benzenesulfonamide; or
2,6-difluoro-4-{[(1S,2R)-2-(1H-pyrazol-4-yl)cyclohexyl]
oxy}-N-(pyrimidin-4-yl)benzenesulfonamide.

(12) The compound or pharmacologically acceptable salt thereof according to (1), wherein the compound represented by formula (I) is
2-fluoro-4-{[(1S*,2R*)-2-(1-methyl-1H-pyrazol-5-yl)cyclopentyl]oxy}-N-(pyrimidin-4-yl)benzenesulfonamide;
4-{[(1S*,2R*)-2-(1-ethyl-1H-pyrazol-5-yl)cyclopentyl]
oxy}-2,3-difluoro-N-(pyrimidin-4-yl)benzenesulfonamide;
5-chloro-2-fluoro-4-{[(1S*,2R*)-2-(1-methyl-1H-pyrazol-5-yl)cyclohexyl]oxy}-N-(pyrimidin-4-yl)benzenesulfonamide;
2,6-difluoro-4-{[(1S*,2R*)-2-(1H-pyrazol-4-yl)cyclohexyl]
oxy}-N-(pyrimidin-4-yl)benzenesulfonamide;
4-{[(1S,2R)-2-(1-ethyl-1H-pyrazol-5-yl)cyclopentyl]oxy}-2,3-difluoro-N-(pyrimidin-4-yl)benzenesulfonamide;
5-chloro-2-fluoro-4-{[(1S,2R)-2-(1-methyl-1H-pyrazol-5-yl)cyclohexyl]oxy}-N-(pyrimidin-4-yl)benzenesulfonamide;
2-fluoro-4-{[(1S,2R)-2-(1-methyl-1H-pyrazol-5-yl)cyclopentyl]oxy}-N-(pyrimidin-4-yl)benzenesulfonamide;
4-{[(1S*,2R*)-5,5-difluoro-2-(1H-pyrazol-4-yl)cyclohexyl]
oxy}-2-fluoro-5-methyl-N-(pyrimidin-4-yl)benzenesulfonamide;
4-{[(1S,2R)-5,5-difluoro-2-(1H-pyrazol-4-yl)cyclohexyl]
oxy}-2-fluoro-5-methyl-N-(pyrimidin-4-yl)benzenesulfonamide; or
2,6-difluoro-4-{[(1S,2R)-2-(1H-pyrazol-4-yl)cyclohexyl]
oxy}-N-(pyrimidin-4-yl)benzenesulfonamide.

(13) A pharmaceutical composition comprising a compound, a pharmacologically acceptable salt, or a hydrate thereof according to any of (1) to (12), and a pharmaceutically acceptable carrier.

(14) The pharmaceutical composition according to (13), for treating and/or preventing pain.

(15) The pharmaceutical composition according to (13), for treating and/or preventing a disease or symptom selected from the group consisting of acute pain; chronic pain; pain caused by injury of soft tissues or peripheral tissues; postherpetic neuralgia; central pain; neuropathic pain; migraine; pain associated with osteoarthritis or rheumatoid arthritis; contusion; pain associated with sprain or trauma; spondylalgia; pain caused by injury of the spinal cord or brain stem; low back pain; sciatic neuralgia; toothache; myofascial pain syndrome; perineal section pain; gout pain; cardiac pain; muscle pain; eye pain; inflammatory pain; orofacial pain; abdominal pain; dysmenorrhea; labor pain or pain associated with endometriosis; somatic pain; pain associated with nerve or radicular injury; amputation; tic douloureux; pain associated with neuroma or vasculitis; pain caused by diabetic neuropathy or diabetic peripheral neuropathic pain; pain caused by chemotherapy-induced neuropathy; atypical prosopalgia; neuropathic low back pain; trigeminal neuralgia; occipital neuralgia; myelomere or intercostal neuralgia; HIV-associated neuralgia; AIDS-associated neuralgia; hyperalgesia; pain of thermal burn; idiopathic pain; pain caused by chemotherapy; occipital neuralgia; psychogenic pain; pain associated with gallstone; neuropathic or non-neuropathic pain associated with cancer; phantom limb pain; functional abdominal pain; headache; acute or chronic tension headache; sinus headache; cluster headache; temporomandibular joint pain; maxillary sinus pain; pain caused by ankylosing spondylarthritis; postoperative pain; scar pain; chronic non-neuropathic pain; fibromyalgia; amyotrophic lateral sclerosis; epilepsy (particularly, partial epilepsy, adult epilepsy partial seizure and partial seizure of an epileptic patient); and generalized anxiety disorder and restless legs syndrome.

(16) The pharmaceutical composition according to (13), for treating and/or preventing pain caused by diabetic neuropathy.

(17) The pharmaceutical composition according to (13), for treating and/or preventing a sodium channel associated disease.

(18) Use of a compound or a pharmacologically acceptable salt thereof according to any of (1) to (12), for producing a pharmaceutical composition.

(19) The use according to (18), wherein the pharmaceutical composition is a pharmaceutical composition for treating and/or preventing pain.

(20) The use according to (18), wherein the pharmaceutical composition is a pharmaceutical composition for treating and/or preventing pain caused by diabetic neuropathy.

(21) The use according to (18), wherein the pharmaceutical composition is a pharmaceutical composition for treating and/or preventing a sodium channel associated disease.

(22) A formulation intended for administration to a mammal for treating and/or preventing pain, comprising a pharmacologically effective dose of a compound or a pharmacologically acceptable salt thereof according to any of (1) to (12).

(23) The formulation according to (22), wherein the pain is pain caused by diabetic neuropathy.

(24) The formulation according to (23), wherein the mammal is a human.

(25) A sodium channel inhibitor comprising a pharmacologically effective dose of a compound or a pharmacologically acceptable salt thereof according to any of (1) to (12).

(26) The sodium channel inhibitor according to (25), wherein the sodium channel inhibitor is intended for administration to a mammal.

(27) The sodium channel inhibitor according to (26), wherein the mammal is a human.

(28) A method for treating and/or preventing pain, comprising administering a compound or a pharmacologically acceptable salt thereof according to any of (1) to (12).

(29) A method for treating and/or preventing a disease or symptom selected from the following group, comprising administering a compound or a pharmacologically acceptable salt thereof according to any of (1) to (12): acute pain; chronic pain; pain caused by injury of soft tissues or peripheral tissues; postherpetic neuralgia; central nervous pain; neuropathic pain; migraine; pain associated with osteoarthritis or rheumatoid arthritis; contusion; pain associated with sprain or trauma; spondylalgia; pain caused by injury of the spinal cord or brain stem; low back pain; sciatic neuralgia; toothache; myofascial pain syndrome; perineal section pain; gout pain; cardiac pain; muscle pain; eye pain; inflammatory pain; orofacial pain; abdominal pain; dysmenorrhea; labor pain or pain associated with endometriosis; somatic pain; pain associated with nerve or radicular injury; amputation; tic douloureux; pain associated with neuroma or vasculitis; pain caused by diabetic neuropathy or diabetic peripheral neuropathic pain; pain caused by chemotherapy-induced neuropathy; atypical prosopalgia; neuropathic low back pain; trigeminal neuralgia; occipital neuralgia; myelomere or intercostal neuralgia; HIV-associated neuralgia; AIDS-associated neuralgia; idiopathic pain; pain of thermal burn; pang; pain caused by chemotherapy; occipital neuralgia; psychogenic pain; pain associated with gallstone; neuropathic or non-neuropathic pain associated with cancer; phantom limb pain; functional abdominal pain; headache; acute or chronic tension headache; sinus headache; cluster headache; temporomandibular joint pain; maxillary sinus pain; pain caused by ankylosing spondylarthritis; postoperative pain; scar pain; chronic non-neuropathic patient pain; fibromyalgia; amyotrophic lateral sclerosis; epilepsy (particularly, partial epilepsy, adult epilepsy partial seizure and partial seizure of an epileptic patient); and generalized anxiety disorder and restless legs syndrome.

(30) A method for treating and/or preventing pain caused by diabetic neuropathy, comprising administering a compound or a pharmacologically acceptable salt thereof according to any of (1) to (12).

(31) A method for treating and/or preventing a sodium channel associated disease, comprising administering a compound or a pharmacologically acceptable salt thereof according to any of (1) to (12).

Advantageous Effects of Invention

The present compound represented by formula (I), a pharmacologically acceptable salt thereof, or a hydrate thereof has excellent voltage-gated sodium channel 1.7 (Nav 1.7) inhibiting activities and has excellent subtype selectivity, and hence has an excellent pain relief effect and shows excellent sodium channel inhibiting activities in warm-blooded animals (preferably mammals including humans).

DETAILED DESCRIPTION OF THE PREFERRED EMBODIMENTS

Figure 1:
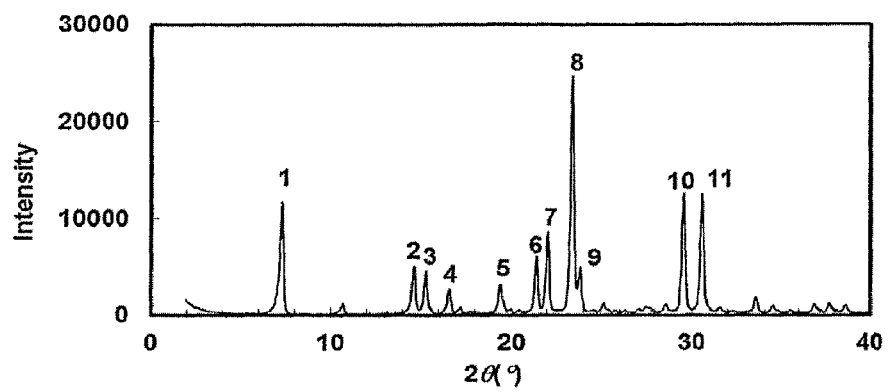
Figure 1 is a diagram showing the powder x-ray diffraction of 4-{[(1R,2S)-2-(1-ethyl-1H-pyrazol-5-yl)cyclopentyl]oxy}-2,3-difluoro-N-(pyrimidin-4-yl)benzenesulfonamide in a free form.

The present invention will now be described in detail.

In the present specification, a "halogen atom" refers to a fluorine atom, a chlorine atom, a bromine atom or an iodine atom.

In the present specification, a "C1-C6 alkyl group" refers to a linear or branched alkyl group having 1 to 6 carbon atoms, and includes a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group and a 2-ethylbutyl group.

In the present specification, a "C1-C3 alkyl group" refers to a linear or branched alkyl group having 1 to 3 carbon atoms, and includes, for example, a methyl group, an ethyl group, a propyl group and an isopropyl group.

In the present specification, a "halogenated C1-C6 alkyl group" refers to a group obtained by substituting a "C1-C6 alkyl group" defined above with a "halogen atom" defined above. The number of halogen atoms as substituents is not particularly limited but the substitution may be from mono-substitution to per-substitution. The substitution position is not particularly limited but the terminal carbon atom of the alkyl group is more preferably mono-substituted. The halogenated C1-C6 alkyl group includes, for example, a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group, a 2-fluoroethyl group, a 2-iodoethyl group, a 3-chloropropyl group, a 4-fluorobutyl group and a 6-iodohexyl group.

In the present specification, a "hydroxy C1-C6 alkyl group" refers to a group obtained by substituting a "C1-C6 alkyl group" defined above with a hydroxy group. The substitution position of the hydroxy group is not particularly limited but the terminal carbon atom of the alkyl group is more preferably substituted. The hydroxy C1-C6 alkyl group includes, for example, a hydroxymethyl group, a 2-hydroxyethyl group, a 3-hydroxypropyl group, a 4-hydroxybutyl group, a 5-hydroxypentyl group, a 6-hydroxyhexyl group, a 1-hydroxyethyl group, a 1-hydroxypropyl group and a 2-hydroxypropyl group.

In the present specification, a "C1-C6 alkoxy group" refers to a group formed by bonding an oxygen atom to the terminal of a "C1-C6 alkyl group" defined above. The C1-C6 alkoxy group includes, for example, a methoxy group, an ethoxy group, a propoxy group, an isopropoxy group, a butoxy group, an isobutoxy group, a sec-butoxy group, a tert-butoxy group, a pentoxy group, an isopentoxy group, a 2-methylbutoxy group, a neopentoxy group, a hexyloxy group, a 4-methylpentoxy group, a 3-methylpentoxy group and a 2-methylpentoxy group.

In the present specification, a "C1-C6 alkoxy C1-C6 alkyl group" refers to a group obtained by substituting a "C1-C6 alkyl group" defined above with a "C1-C6 alkoxy group" defined above. The substitution position of the alkoxy group is not particularly limited but the terminal carbon atom of the alkyl group is preferably substituted. The C1-C6 alkoxy C1-C6 alkyl group includes, for example, a methoxymethyl group, an ethoxymethyl group, a propoxymethyl group, a butoxymethyl group, a 3-methoxypropyl group, a 3-ethoxypropyl group, a 4-methoxybutyl group, a 5-methoxypentyl group and a 6-methoxyhexyl group.

In the present specification, a "C3-C7 cycloalkyl group" refers to a saturated cyclic hydrocarbon group having 3 to 7 carbon atoms, and includes a cyclopropyl group, a cyclobutyl group, a cyclopentyl group, a cyclohexyl group and a cycloheptyl group.

In the present specification, a "C1-C3 alkylamino group" refers to an amino group which one "C1-C3 alkyl group" defined above is bonded to its nitrogen atom. The C1-C3 alkylamino group includes, for example, a methylamino group, an ethylamino group, a propylamino group and an isopropylamino group.

In the present specification, a "di-C1-C3 alkylamino group" refers to an amino group which two "C1-C3 alkyl groups" defined above are bonded to its nitrogen atom. The two alkyl groups may be the same or different from each other. The di-C1-C3 alkylamino group includes, for example, a dimethylamino group, an ethylmethylamino group, a diethylamino group, a methylpropylamino group, an ethylpropylamino group, a dipropylamino group, an isopropylmethylamino group, an ethylisopropylamino group and a diisopropylamino group.

In the present specification, an "aryl group" refers to an aromatic hydrocarbon substituent and includes, for example, a phenyl group and a naphthyl group, and the aryl group may be bonded in any position.

In the present specification, a "heteroaryl group" refers to a 5- or 6-membered aromatic heterocyclic substituent having 1 to 4 heteroatoms independently selected from the group consisting of a nitrogen atom, an oxygen atom and a sulfur atom. The heteroaryl group includes, for example, a pyridyl group, a pyrimidinyl group, a pyridazinyl group, a pyrazinyl group, a triazolyl group, a pyrazolyl group, an imidazolyl group, a tetrazolyl group, an isoxazolyl group, an oxazolyl group, an isothiazolyl group, a thiazolyl group, a thiadiazolyl group, an oxadiazolyl group, a thiophenyl group and a furanyl group. Such an aromatic heterocyclic group may be bonded in any position (it is noted that the above-described names of the groups are mentioned merely as generic designation of substituents but do not specify bonding position).

The compound of the present invention has a structure represented by formula (I). Specifically, an N-monoaromatic substituent-substituted sulfonamide group is bonded to a phenyl group (the aromatic group on the nitrogen atom of this sulfonamide group is referred to as Ar²); a cycloalkyl group is connected through an oxygen atom to the para position with respect to the position at which the sulfonamide group is bonded; and an aromatic group (referred to as Ar¹) is bonded to the carbon atom adjacent to the carbon atom where the cycloalkyl group is bonded to the oxygen atom.

[Formula 6]

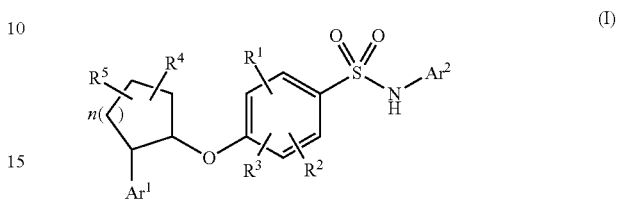

(I)

In the compound of formula (I), two aromatic groups represented by Ar¹ and Ar² may each independently represent an aryl group (aromatic hydrocarbon group) or a heteroaryl group (aromatic heterocyclic group). Each of these aromatic groups may further have a substituent. Also, the phenyl group to which a sulfonamide is connected may have from one to three substituents. The cycloalkyl group connected through the oxygen atom to the phenyl group to which sulfonamide is connected can be any 5- to 7-membered ring in size. This ring may have 1 or 2 substituents, and when the ring has two such groups, the two groups may be the same or different from each other.

The aromatic group Ar¹ may be an aryl group but more preferably is a heteroaryl group. The heteroaryl group can be any monocyclic 5- or 6-membered ring containing 1 to 4 heteroatoms. The heteroatom(s) are preferably nitrogen atom(s).

The 5-membered heteroaryl group can be selected from those exemplified above but is preferably a group containing only nitrogen atom(s) as heteroatom(s). Preferable examples thereof can include a pyrazolyl group and an imidazolyl group. A pyrazolyl group is more preferred.

The connecting position of such a 5-membered heteroaryl group to the cyclic alkyl group is not particularly limited. In the case of a pyrazolyl group or an imidazolyl group, examples can include pyrazol-1-yl, pyrazol-3-yl, pyrazol-4-yl, imidazol-1-yl and imidazol-4-yl. Among them, pyrazol-3-yl, pyrazol-4-yl, imidazol-4-yl or the like is preferred.

The 6-membered heteroaryl group preferably contains only nitrogen atom(s) as heteroatom(s), as in the 5-membered ring. A pyridyl group or a pyridazinyl group is preferred. The binding site is not limited but is preferably pyridin-4-yl, pyridin-3-yl or pyridazin-4-yl.

Ar¹ may have a substituent and may have 1 or 2 substituents independently selected from the group consisting of a halogen atom, a C1-C6 alkyl group, a halogenated C1-C6 alkyl group, a hydroxyl group, a hydroxy C1-C6 alkyl group, a C3-C7 cycloalkyl group, an amino group, a C1-C3 alkylamino group and a di-C1-C3 alkylamino group. Among them, a halogen atom, a C1-C6 alkyl group, a halogenated C1-C6 alkyl group, an amino group, a C1-C3 alkylamino group or a di-C1-C3 alkylamino group is more preferred. Examples of such substituents can include a chlorine atom, a fluorine atom, a methyl group, an ethyl group, a trifluoromethyl group, an amino group, a methylamino group and a dimethylamino group. The substituent of Ar¹ is preferably an amino group or an alkyl group. The alkyl group is preferably a methyl group or an ethyl group. The alkyl group may substitute on a nitrogen atom or a carbon atom.

Examples of Ar¹ can include a phenyl group, a 1H-pyrazol-4-yl group, a 1-methyl-1H-pyrazol-5-yl group, a 1-ethyl-1H-pyrazol-5-yl group, a 3-amino-1H-pyrazol-4-yl group, a 1H-imidazol-1-yl group, a 1-methyl-1H-imidazol-5-yl group, a pyridin-3-yl group, a 2-aminopyridin-3-yl group, a 2-methylpyridin-3-yl group and a 2-pyridazin-4-yl group. Among them, a phenyl group, a 1-methyl-1H-pyrazol-5-yl group, a 1-ethyl-1H-pyrazol-5-yl group, a 1H-pyrazol-4-yl group or a 3-amino-1H-pyrazol-4-yl group is preferred.

Likewise, the aromatic group Ar² is more preferably a heteroaryl group. The heteroaryl group can be any 5- or 6-membered ring containing two or more heteroatoms. Examples of the 5-membered heteroaryl group can include an imidazolyl group, a triazolyl group, an isoxazolyl group, an oxazolyl group, an isothiazolyl group, a thiazolyl group, a thiadiazolyl group and an oxadiazolyl group. Examples of the 6-membered heteroaryl group can include a pyridyl group, a pyrimidinyl group, a pyridazinyl group and a pyrazinyl group. Among them, a thiadiazolyl group, a thiazolyl group or a pyrimidinyl group is more preferred.

Ar² may have a substituent and may have 1 or 2 substituents independently selected from the group consisting of a halogen atom, a C1-C6 alkyl group, a halogenated C1-C6 alkyl group, a hydroxyl group, a hydroxy C1-C6 alkyl group, a C3-C7 cycloalkyl group, an amino group, a C1-C3 alkylamino group and a di-C1-C3 alkylamino group. Among them, a halogen atom or a C1-C6 alkyl group is preferred. Such a substituent is a chlorine atom, a fluorine atom or a methyl group.

Examples of Ar² can include a 1,2,4-thiadiazol-5-yl group, a 1,3-thiazol-4-yl group, a pyrimidin-4-yl group, a 6-fluoropyrimidin-4-yl group and a 2-fluoropyrimidin-4-yl group. Among them, a pyrimidin-4-yl group is more preferred.

The phenyl group constituting the benzenesulfonamide may have from 1 to 3 substituents. Examples of such substituents can include a halogen atom, a C1-C6 alkyl group, a halogenated C1-C6 alkyl group, a hydroxy C1-C6 alkyl group, a C1-C6 alkoxy C1-C6 alkyl group, a C3-C7 cycloalkyl group and a cyano group. Among them, a halogen atom, a C1-C6 alkyl group or a halogenated C1-C6 alkyl group is preferred. One to three groups independently selected from a chlorine atom, a fluorine atom, a methyl group, an ethyl group, a trifluoromethyl group and a cyano group are more preferred. When the phenyl group has two or more such groups, the two or more groups may be the same or different from each other.

Examples of the optionally substituted phenyl group constituting the benzenesulfonamide can include a 3-methylphenyl group, a 3-chlorophenyl group, a 3-fluorophenyl group, a 2,3-difluorophenyl group, a 2,5-difluorophenyl group, a 2,6-difluorophenyl group, a 2-chloro-5-fluorophenyl group, a 5-chloro-2-fluorophenyl group, a 3-trifluoromethylphenyl group, a 2-fluoro-3-methylphenyl group, a 2-fluoro-5-methylphenyl group, a 5-ethyl-2-fluorophenyl group, a 3-cyanophenyl group and a 5-cyano-2-fluorophenyl group. Among them, a 2-fluorophenyl group, a 2,5-difluorophenyl group, a 5-chloro-2-fluorophenyl group or a 2-fluoro-3-methylphenyl group is preferred (here, the position number is indicated with the position bonded to the sulfonamide group as 1).

The cycloalkyl moiety can be any 5- to 7-membered cyclic alkyl but is preferably 5- or 6-membered cyclic alkyl.

This cycloalkyl group may have 1 or 2 substituents independently selected from the group consisting of a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group and a C1-C6 alkoxy group. Among them, a halogen atom, a C1-C6 alkyl group or a halogenated C1-C6 alkyl group is preferred. A fluorine atom or a methyl group is more preferred.

In the compound of the present invention, the aromatic group Ar¹ on the cycloalkyl group and the phenyloxy moiety having the sulfonamide group can be substituted on adjacent carbon atoms to form the following four isomers having diastereomeric relationship, all of which are included in the present invention. Among them, the more preferred conformation is that of (1b).

[Formula 7]

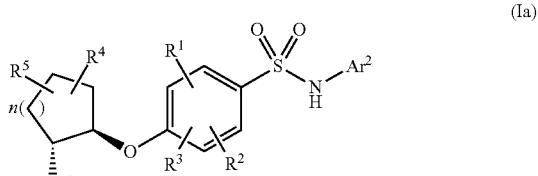

(Ia)

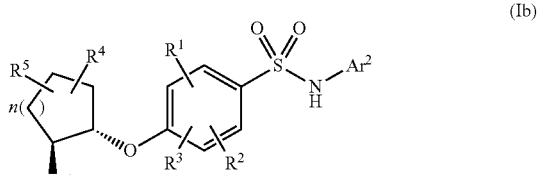

(Ib)

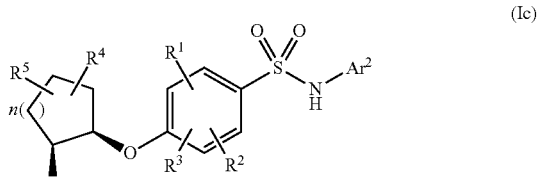

(Ic)

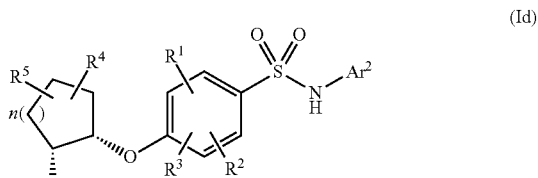

(Id)

The present compound represented by formula (I) may be in the form of a pharmacologically acceptable salt if desired. A pharmacologically acceptable salt means a salt that is not greatly toxic but may be used as a pharmaceutical. The present compound represented by formula (I) may be changed into the form of a salt by causing a reaction between the compound and an acid if it has a basic group.

Examples of salts based on a basic substituent and a basic heteroaryl group include halogenated hydroacid salts such as hydrofluoride, hydrochloride, hydrobromide and hydroiodide; inorganic acid salts such as hydrochloride, nitrate, perchlorate, sulfate and phosphate; lower alkane sulfonates such as methanesulfonate, trifluoromethanesulfonate and ethanesulfonate; aryl sulfonates such as benzenesulfonate and p-toluenesulfonate; organic acid salts such as acetate, malate, fumarate, succinate, citrate, ascorbate, tartrate, oxalate and maleate; and amino acid salts such as glycine salt, lysine salt, arginine salt, ornithine salt, glutamate and aspartate. Among these, preferably, inorganic acid salts or aryl sulfonate is used, and more preferably, hydrochloride, benzenesulfonate or p-toluenesulfonate is used.

Examples of salts based on an acidic substituent N include alkali metal salts such as sodium salt, potassium salt and lithium salt; alkali earth metal salts such as calcium salt and magnesium salt; metal salts such as aluminum salt and iron salt; inorganic salts such as ammonium salt; amine salts of organic salts such as t-octyl amine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, tris(hydroxymethyl)aminomethane salt; and amino acid salts such as glycine salt, lysine salt, arginine salt, ornithine salt, glutamate and aspartate.

When the compound represented by formula (I) is allowed to stand in the air or recrystallized, it may absorb moisture to have absorbed water, so as to be changed into a hydrate, and such a hydrate is also included in the salt of the present invention.

The compound represented by formula (I) or a salt thereof sometimes absorbs a solvent of a given type so as to be changed into a solvate, and such a solvate is also included in the salt of the present invention.

The compound represented by formula (I) has asymmetric carbon atoms in its molecule and thus includes optical isomers. These isomers and mixtures of these isomers are all represented by a single formula, i.e., formula (I). Accordingly, single optical isomers of the compound represented by formula (I) and mixtures of these optical isomers at any ratio are all included in the scope of the present invention.

The optical isomers as described above can be obtained by synthesizing the compound according to the present invention by using optically active starting compounds or using the approach of asymmetric synthesis or asymmetric induction. Alternatively, the optical isomers can be obtained by isolation from the synthesized compound according to the present invention by using a general optical resolution method or, for example, a separation method using an optically active carrier.

The present compounds may also contain, at a non-natural ratio, atomic isotope(s) of one or more of the atoms constituting such a compound. Examples of the atomic isotope(s) include deuterium ($^2H$), tritium ($^3H$), iodine-125 ($^{125}I$) and carbon-14 ($^{14}C$). Moreover, the compounds may be radiolabeled with a radioisotope such as tritium ($^3H$), iodine-125 ($^{125}I$) or carbon-14 ($^{14}C$). Such a radiolabeled compound is useful as therapeutic or preventive agents, research reagents, for example, assay reagents, and diagnostic agents, for example, in vivo image diagnostic agents. All isotopic variants of the present compounds are included in the scope of the present invention no matter whether or not they are radioactive.

The present compound represented by formula (I) and a pharmacologically acceptable salt thereof have excellent voltage-gated sodium channel 1.7 (Nav 1.7) inhibiting activities and have excellent subtype selectivity, and hence have an excellent pain relief effect as well as showing excellent sodium channel inhibiting activities in warm-blooded animals (preferably mammals including humans).

Accordingly, the present compound and a pharmacologically acceptable salt thereof have excellent treatment efficacy and/or preventive efficacy for the following diseases or symptoms: Pain caused by diabetic neuropathy; acute pain; chronic pain; pain caused by injury of soft tissues or peripheral tissues; postherpetic nerve pain; central pain; neuropathic pain; megrim; pain associated with osteoarthritis or rheumatoid arthritis; contusion; pain associated with sprain or injury; spondylalgia; pain caused by damage of the spinal cord or brain stem; low back pain; sciatic neuralgia; toothache; myofascial pain syndrome; perineal section pain; gout pain; cardiac pain; muscle pain; eye pain; inflammatory pain; orofacial pain; abdominal pain; dysmenorrhea; labor pain or pain associated with endometriosis; somatic pain; pain associated with nerve or radicular injury; amputation; tic douloureux; pain associated with neuroma or vasculitis; pain caused by diabetic neuropathy or diabetic peripheral neuropathic pain; pain caused by chemotherapy-induced neuropathy; atypical prosopalgia; neuropathic low back pain; trigeminal neuralgia; occipital neuralgia; myelomere or intercostal neuralgia; HIV-associated neuralgia; AIDS-associated neuralgia; hyperalgesia; pain of thermal burn; idiopathic pain; pain caused by chemotherapy; occipital neuralgia; psychogenic pain; pain associated with gallstone; neuropathic or non-neuropathic pain associated with cancer; phantom limb pain; functional abdominal pain; headache; acute or chronic tension headache; sinus headache; cluster headache; temporomandibular joint pain; maxillary sinus pain; pain caused by ankylosing spondylitis; postoperative pain; scar pain; chronic non-neuropathic pain, fibromyalgia and the like.

The present compound can be expected to further show excellent treatment efficacy and/or preventive efficacy for dysuria, multiple sclerosis, interstitial cystitis, cystalgia syndrome, irritable colon syndrome, dysuric multiple sclerosis, irregular pulse, myotonia, numbness, brain infarction and the like.

The present compound or a pharmacologically acceptable salt thereof can be administered in various forms. Examples of the route of administration include oral administration using tablets, capsules, granules, emulsions, pills, powders, syrups (solutions) and the like, and parenteral administration using injections (intravenous, intramuscular, subcutaneous or intraperitoneal administration), drip infusions, suppositories (rectal administration) and the like. These various formulations can be prepared as drug products according to usually employed methods by appropriately selecting and using aids generally used in the field of pharmaceutical formulation, such as excipients, binders, disintegrants, lubricants, flavoring agents, dissolving aids, suspending agents and coating agents, to be added to an active ingredient.

When used as a tablet, examples of a usable carrier include excipients such as lactose, saccharose, sodium chloride, glucose, urea, starch, calcium carbonate, kaolin, crystalline cellulose and silicic acid; binders such as water, ethanol, propanol, simple syrup, a glucose solution, a starch solution, a gelatin solution, carboxymethylcellulose, shellac, methylcellulose, potassium phosphate and polyvinylpyrrolidone; disintegrants such as dry starch, sodium alginate, powdered agar, powdered laminaran, sodium hydrogencarbonate, calcium carbonate, polyoxyethylene sorbitan fatty acid ester, sodium lauryl sulfate, stearic monoglyceride, starch and lactose; disintegration inhibitors such as saccharose, stearin, cocoa butter and hydrogenated oil; absorption enhancers such as quaternary ammonium salt and sodium lauryl sulfate; humectants such as glycerine and starch; adsorbents such as starch, lactose, kaolin, bentonite and colloidal silicic acid; and lubricants such as purified talc, stearate, powdered boric acid and polyethylene glycol. Furthermore, tablets having a general coating, for example, sugar-coated tablets, gelatin-coated tablets, enteric-coated tablets, film-coated tablets, double-layer tablets and multi-layered tablets can be prepared as required.

When used as a pill, examples of a usable carrier include excipients such as glucose, lactose, cocoa butter, starch, hydrogenated vegetable oil, kaolin and talc; binders such as powdered gum arabic, powdered tragacanth, gelatin and ethanol; and disintegrants such as laminaran and agar.

When used as a suppository, a wide range of carriers conventionally known in this field can be used, and examples include polyethylene glycol, cocoa butter, higher alcohols, higher alcohol esters, gelatin and semisynthetic glycerides.

When used as an injection, the formulations can be prepared as a solution, an emulsion or a suspension. These solutions, emulsions and suspensions are preferably sterilized and isotonic with blood. A solvent used for producing these solutions, emulsions and suspensions is not particularly limited so long as it can be used as a diluent for medical use, and examples of the solvent include water, ethanol, propylene glycol, ethoxylated isostearyl alcohol, polyoxylated isostearyl alcohol and polyoxy ethylene sorbitan fatty acid esters. In this case, a sufficient amount of sodium chloride, glucose or glycerine may be included in the formulation to prepare an isotonic solution, and general dissolving aids, buffers, soothing agents and the like may also be included.

Furthermore, coloring agents, preservatives, perfumes, flavoring agents, sweeteners and the like can be added to the above-mentioned formulations if necessary. Moreover, other pharmaceuticals can also be added.

The amount of active ingredient compound contained in the formulations is not particularly limited but is widely and appropriately selected, and is generally 0.5 to 70% by weight and preferably 1 to 30% by weight of the whole composition.

The dose varies depending on the symptoms, age and the like of a patient (a warm-blooded animal, in particular, a human). In the case of oral administration, a daily dosage for an adult is from a lower limit of 0.1 mg (preferably 1 mg and more preferably 10 mg) to an upper limit of 2000 mg (preferably 100 mg), which is administered dividedly as 1 to 6 doses depending upon the symptoms.

The present compound represented by formula (I) can be produced in according with methods A to C described below. The compound represented by formula (V) can be produced in according with methods D to H.

Solvents used in reactions of respective steps of the methods A to K below are not particularly limited as long as they do not inhibit the reactions but dissolve to some extent compounds involved in the reactions. The solvents are selected from, for example, the group consisting of the following solvents. Alternatively, the solvents may be mixtures thereof. The group of usable solvents consists of hydrocarbons such as pentane, hexane, octane, petroleum ether, ligroin and cyclohexane; amides such as formamide, N,N-dimethylformamide, N,N-dimethylacetamide, N-methyl-2-pyrrolidone, N-methyl-2-pyrrolidinone and hexamethylphosphoric triamide; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, 2-butanol, 2-methyl-1-propanol, t-butanol, isoamyl alcohol, diethylene glycol, glycerin, octanol, cyclohexanol and methyl cellosolve; sulfoxides such as dimethyl sulfoxide; sulfones such as sulfolane; nitriles such as acetonitrile, propionitrile, butyronitrile and isobutyronitrile; esters such as ethyl formate, ethyl acetate, propyl acetate, butyl acetate and diethyl carbonate; ketones such as acetone, methyl ethyl ketone, 4-methyl-2-pentanone, methyl isobutyl ketone, isophorone and cyclohexanone; nitro compounds such as nitro ethane and nitro benzene; halogenated hydrocarbons such as dichloromethane, 1,2-dichloroethane, chlorobenzene, dichlorobenzene, chloroform and carbon tetrachloride; aromatic hydrocarbons such as benzene, toluene and xylene; carboxylic acids such as acetic acid, formic acid, propionic acid, butyric acid and trifluoroacetic acid; and water.

Examples of bases used in the reactions described below include alkali metal carbonates such as sodium carbonate, potassium carbonate, lithium carbonate and cesium carbonate; alkali metal hydrogencarbonates such as sodium hydrogencarbonate, potassium hydrogencarbonate and lithium hydrogencarbonate; alkali metal hydrides such as lithium hydride, sodium hydride and potassium hydride; alkali metal hydroxides such as sodium hydroxide, potassium hydroxide, barium hydroxide and lithium hydroxide; inorganic bases of alkali metal fluorides such as sodium fluoride and potassium fluoride; alkali metal alkoxides such as sodium methoxide, sodium ethoxide, sodium-t-butoxide, potassium methoxide, potassium ethoxide, potassium-t-butoxide and lithium methoxide; alkali metal trialkyl siloxides such as sodium trimethylsiloxide, potassium trimethylsiloxide and lithium trimethylsiloxide; mercaptan alkali metals such as methyl mercaptan sodium and ethyl mercaptan sodium; organic bases such as N-methyl morpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]nona-5-ene (DBN), 1,4-diazabicyclo[2.2.2]octane (DABCO) and 1,8-diazabicyclo[5.4.0]undeca-7-ene (DBU); and organometallic bases such as butyl lithium, lithium diisopropylamide and lithium bis(trimethylsilyl)amide.

Examples of acids used in the reactions described below include: inorganic acids such as hydrochloric acid, sulfuric acid, nitric acid, perchloric acid, hypochlorous acid, phosphoric acid, boric acid, hydrofluoric acid, tetrafluoroboric acid and fluorosulfonic acid; organic acids such as formic acid, acetic acid, oxalic acid, citric acid, gluconic acid, lactic acid, tartaric acid, benzoic acid, methanesulfonic acid, benzenesulfonic acid, p-toluenesulfonic acid and trifluoromethanesulfonic acid; and Lewis acids such as boron trifluoride, a boron trifluoride-diethyl ether complex, a boron trifluoride-dimethyl sulfide complex, a boron trifluoride-pyridine complex, a boron trifluoride-tetrahydrofuran complex, boron trichloride, boron triiodide, trimethylaluminum, triethylaluminum and titanium tetrachloride.

Examples of palladium catalysts used in the reactions described below include divalent or zero-valent palladium catalysts such as tetrakis(triphenylphosphine) palladium (0), palladium-activated carbon, palladium hydroxide-activated carbon, palladium (II) acetate, palladium (II) trifluoroacetate, palladium black, palladium (II) bromide, palladium (II) chloride, palladium (II) iodide, palladium (II) cyanide, palladium (II) nitrate, palladium (II) oxide, palladium (II) sulfate, dichlorobis(acetonitrile) palladium (II), dichlorobis(benzonitrile) palladium (II), dichloro(1,5-cyclooctadiene) palladium (II), acetylacetone palladium (II), palladium (II) sulfide, [1,1'-bis(diphenylphosphino)ferrocene]palladium (II) dichloride, [1,2-bis(diphenylphosphino)ethane]palladium (II), dichloride tris(dibenzylidene-acetone)dipalladium (0), tetrakis(acetonitrile) palladium (II) tetrafluoroborate and an aryl chloride-palladium dimer.

Examples of copper catalysts used in the reactions described below include zero-valent, monovalent or divalent copper catalysts and complexes thereof, such as copper, copper (I) chloride, copper (I) bromide, copper (I) iodide, copper (I) trifluoromethanesulfonate, a copper (I) bromide-dimethyl sulfide complex, copper (II) bromide, copper (II) acetate, copper (II) sulfate and copper (II) acetate.

Examples of a ligand of the copper catalyst used in the reactions described below include diamine ligands, such as N,N'-dimethylethylenediamine, trans-N,N'-dimethylcyclohexane-1,2-diamine, 2-(diphenylphosphino)-2'-(N,N-dimethylamino)biphenyl, 1,10-phenanthroline and N,N'-dimethyl-1,2-cyclohexanediamine.

Examples of dehydrogenation or halogen metal exchange reagents used in the reactions described below include: alkyl alkali metals such as methyl lithium, ethyl lithium, isopropyl lithium, n-butyl lithium, sec-butyl lithium and tert-butyl lithium; alkyl magnesium halides such as methyl magnesium chloride, methyl magnesium bromide, ethyl magnesium chloride, ethyl magnesium bromide, isopropyl magnesium chloride and isopropyl magnesium bromide; and organic metal bases such as lithium diisopropylamide, lithium tetramethylpiperidine and lithium bis(trimethylsilyl) amide.

Examples of hydroboration reagents used in the reactions described below include: borane complexes such as a borane-tetrahydrofuran complex, a borane-dimethyl sulfide complex, a borane-dimethylamine complex and a borane-morpholine complex; and dialkyl borane such as isopinocampheylborane, disiamylborane and 9-borabicyclo[3.3.1]nonane.

Examples of oxidation reagents used in the reactions described below include hydrogen peroxide water and sodium perborate tetrahydrate.

Examples of an epoxidation reagent used in the reaction of step F1 described below include: peracids such as 3-chloroperbenzoic acid, perbenzoic acid and peracetic acid; peroxides such as t-butyl hydroperoxide (TBHP) and hydrogen peroxide; and potassium peroxymonosulfate.

Examples of reducing agents used in the reactions described below include: alkali metal borohydrides such as sodium borohydride, lithium borohydride, sodium cyanoborohydride and sodium triacetoxyborohydride; borane complexes such as a borane-tetrahydrofuran complex and a borane-dimethyl sulfide complex; aluminum hydride compounds such as diisobutyl aluminum hydride, lithium aluminum hydride and lithium triethoxyaluminium hydride; and alkali metals such as sodium tellurium hydride, diisobutyl aluminum hydride and sodium bis(methoxyethoxy) aluminum hydride.

In the reaction conducted in each step of the methods A to I, the reaction temperature is varied depending upon the solvent, starting material, reagent and the like, and the reaction time is varied depending upon the solvent, starting material, reagent, reaction temperature and the like.

In the reaction conducted in each step of the methods A to I, after completing the reaction, an objective compound is collected from a reaction mixture according to a method generally employed in this technical field. For example, the reaction mixture is appropriately neutralized, and if there is an insoluble material, it is removed by filtration. Thereafter, water and a water-nonmiscible organic solvent such as ethyl acetate are added to the resultant, so as to separate an organic layer containing the objective compound. The organic layer is washed with water or the like, dried over anhydrous magnesium sulfate, anhydrous sodium sulfate, anhydrous sodium hydrogencarbonate or the like, and filtered, and the solvent is evaporated, so as to yield the objective compound.

The thus obtained objective compound may be, if necessary, separated and purified by a method generally employed in this technical field, for example, by appropriate combination of methods usually employed for separation/purification of an organic compound, such as recrystallization and reprecipitation, followed by elution with an appropriate eluent by using chromatography. If the objective compound is insoluble in a solvent, it may be purified by washing a solid crude product with that solvent. Alternatively, the objective compound of each step may be used as it is in a next reaction without purification.

Next, reactions conducted in respective steps of the methods A to K will be described.

The method A is a method for producing the compound represented by formula (I).

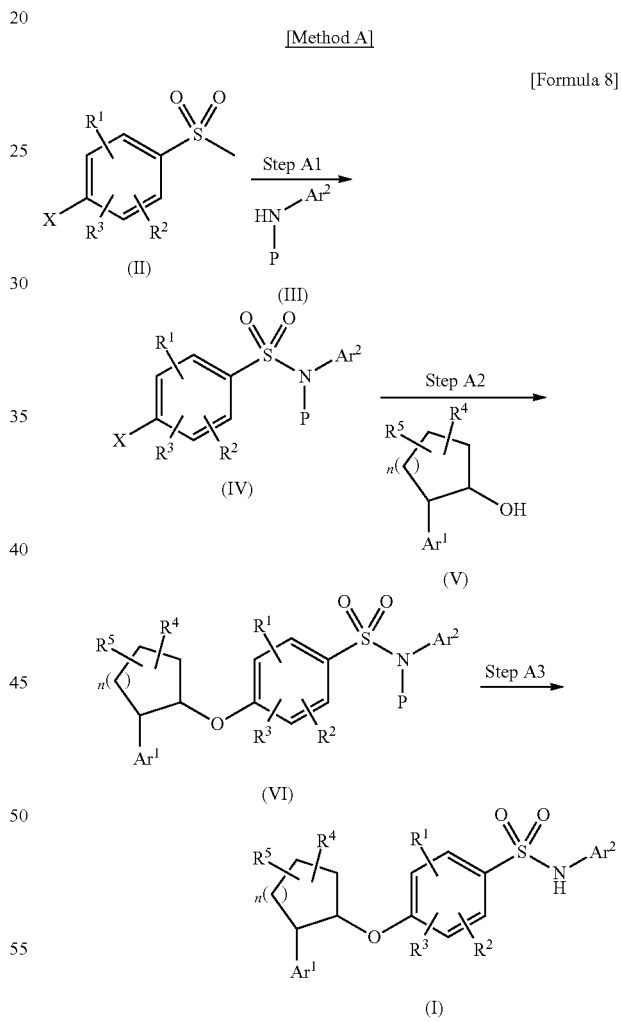

In the present specification, $Ar^1$, $Ar^2$, $R^1$, $R^2$, $R^3$, $R^4$, $R^5$ and n represent the same as defined above, P, $P^1$, $P^2$, $P^3$ and $P^4$ each represents a protecting group, X represents a halogen atom, Y represents a substituent that can work as a nucleophile or an electrophile in a cross-coupling reaction caused by a transition-metal catalyst, such as a halogen atom, a substituent including a boron atom, or a substituent including a tin atom.

P, P¹ or P² is not particularly limited as long as it is a protecting group generally used for an amino group. Examples thereof include a formyl group, a phenylcarbonyl group, a methoxycarbonyl group, an ethoxycarbonyl group, a t-butoxycarbonyl group, a phenyloxycarbonyl group, a 9-fluorenylmethyloxycarbonyl group, an adamantyloxycarbonyl group, a benzyloxycarbonyl group, a benzylcarbonyl group, a benzyl group, a 2,4-dimethoxybenzyl group, a benzhydryl group, a trityl group and a phthaloyl group.

P³ or P⁴ is not particularly limited as long as it is acetal generally used as a protecting group for a carbonyl group. The protecting group is, for example, a methyl group or an ethyl group. P³ or P⁴ may have a cyclic structure forming a 1,3-dioxane or 1,3-dioxolane ring.

Y is not particularly limited as long as it is used as a substituent that can work as a nucleophile or an electrophile in a cross-coupling reaction caused by a transition-metal catalyst. Examples thereof include an iodo group, a bromo group, a chloro group, a boronyl group and a tributylstannyl group.

Step A1

This step is the step of producing a compound represented by formula (IV).

This step is conducted by causing a reaction, in a solvent and in the presence of a base, between a compound represented by formula (II) and a compound represented by formula (III).

The compound represented by formula (II) and the compound represented by formula (III) used in this step are known compounds or may be easily produced from known compounds used as starting materials by known methods or methods similar to the known methods.

The solvent used in this step is preferably any one of ethers, nitriles or halogenated hydrocarbons, and more preferably, tetrahydrofuran, acetonitrile or dichloromethane.

The base used in this step is preferably any one of alkali metal carbonates or organic bases, and more preferably, potassium carbonate, pyridine, 4-(N,N-dimethylamino)pyridine, 1,4-diazabicyclo[2.2.2]octane (DABCO), LiHMDS or 1,8-diazabicyclo[5.4.0]undec-7-ene (DBU).

The reaction temperature to be employed in this step is generally 0° C. to 100° C. and preferably 0° C. to room temperature.

The reaction time of this reaction is from 0.5 hours to 48 hours, and the reaction is generally completed in approximately 1 hour to approximately 24 hours.

Step A2

This step is the step of producing a compound represented by formula (VI).

This step is conducted by causing a reaction, in a solvent and in the presence of a base, between the compound represented by formula (IV) and a compound represented by formula (V).

The solvent used in this step is preferably any one of ethers or amides, and more preferably, tetrahydrofuran or N,N-dimethylformamide.

The base used in this step is preferably any one of alkali metal alkoxides, alkali metal hydrides or alkali metal hydroxides, and more preferably, sodium t-butoxide, potassium t-butoxide, sodium methoxide, potassium methoxide, sodium hydride, potassium hydride, sodium hydroxide or potassium hydroxide.

The reaction temperature to be employed in this step is generally 0° C. to 200° C. and preferably 0° C. to room temperature.

The reaction time of this reaction is from 0.5 hours to 48 hours, and the reaction is generally completed in approximately 1 hour to approximately 24 hours.

Step A3

This step is the step of producing the compound represented by formula (I).

This step is conducted by causing a reaction, in a solvent and, if desired, in the presence of a scavenger, between an acid and the compound represented by formula (VI).

The solvent used in this step is preferably any one of ethers or halogenated hydrocarbons, and more preferably, tetrahydrofuran, 1,4-dioxane or dichloromethane.

The scavenger used in this step is preferably trialkylsilane or aryl ether, and more preferably, triethylsilane or anisole.

The acid used in this step is preferably an organic acid or an inorganic acid, and more preferably, trichloroacetic acid, trifluoroacetic acid, acetic acid, sulfuric acid or hydrochloric acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

Also, this step is conducted by deprotecting the compound represented by formula (VI) in a solvent and in the presence of a palladium catalyst under the hydrogen atmosphere.

The solvent used in this case is preferably any one of ethers or alcohols, and more preferably, tetrahydrofuran, methanol or ethanol.

The catalyst is preferably a zero-valent palladium catalyst, and more preferably, palladium-activated carbon or palladium hydroxide-activated carbon.

The reaction temperature is generally −20° C. to 120° C. and preferably 0° C. to 80° C.

The reaction time of this reaction is from 1 hour to 48 hours, and the reaction is generally completed in approximately 2 hours to approximately 24 hours.

A compound represented by formula (Ia) or (Ib) is an optical isomer of the compound represented by formula (I) and is produced by combining the method A with method B described below.

The method B is a method for producing optical isomers (VIa) and (VIb) of the compound (VI) by optical resolution after step A2 in the method A. The compound represented by formula (Ia) or (Ib) is produced through step A3 from the optical isomer (VIa) or (VIb).

[Method B]

[Formula 9]

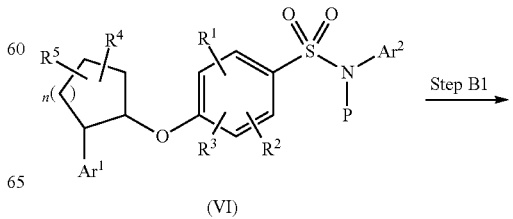

(VI)  Step B1 →

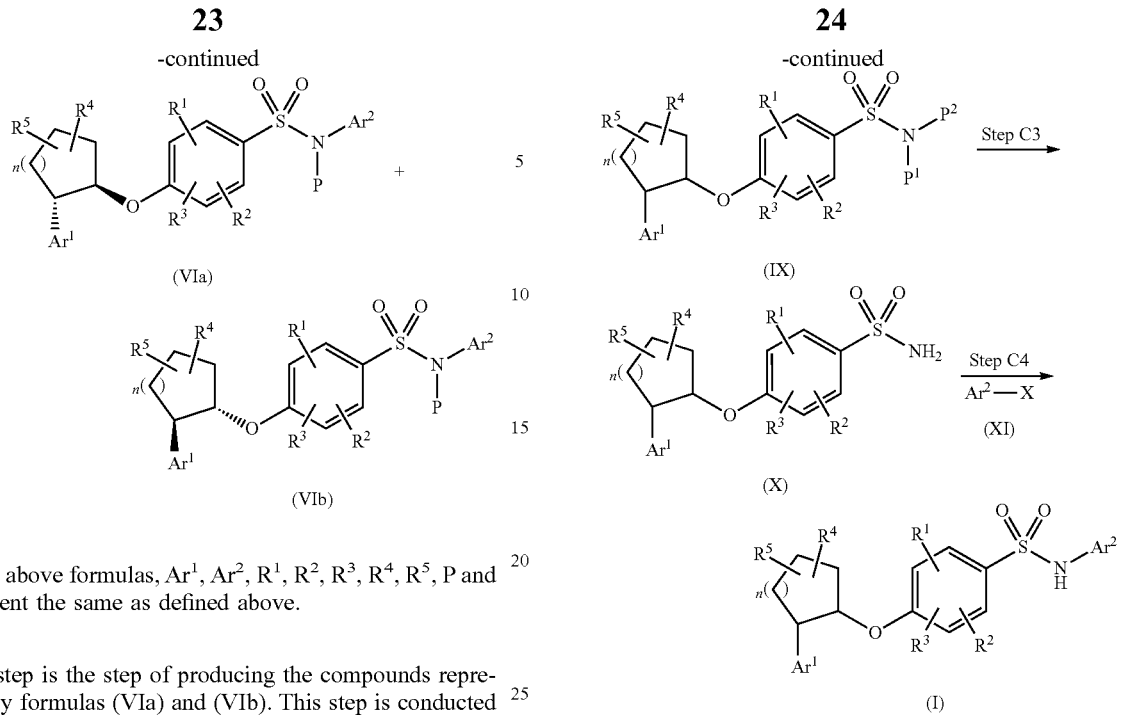

(VIa)

(VIb)

In the above formulas, $Ar^1$, $Ar^2$, $R^1$, $R^2$, $R^3$, $R^4$, $R^5$, P and n represent the same as defined above.

Step B1

This step is the step of producing the compounds represented by formulas (VIa) and (VIb). This step is conducted by an optical resolution of the compound represented by formula (VI) into the compounds represented by (VIa) and (VIb) by using a chiral column.

The solvent used in this step is preferably any one of hydrocarbons, alcohols or mixed solvents thereof, and more preferably, a mixed solvent of hexane and isopropanol or a mixed solvent of hexane and ethanol.

The column used in the optical resolution is not particularly limited as long as it is a chiral column capable of optical resolution. CHIRALPAK (registered trademark) AD-H or CHIRALPAK (registered trademark) IC manufactured by Daicel Corp. is preferred.

The temperature to be employed in this step is generally 0° C. to 40° C. and preferably 0° C. to room temperature. The method C is another method for producing the compound represented by formula (I).

[Method C]

[Formula 10]

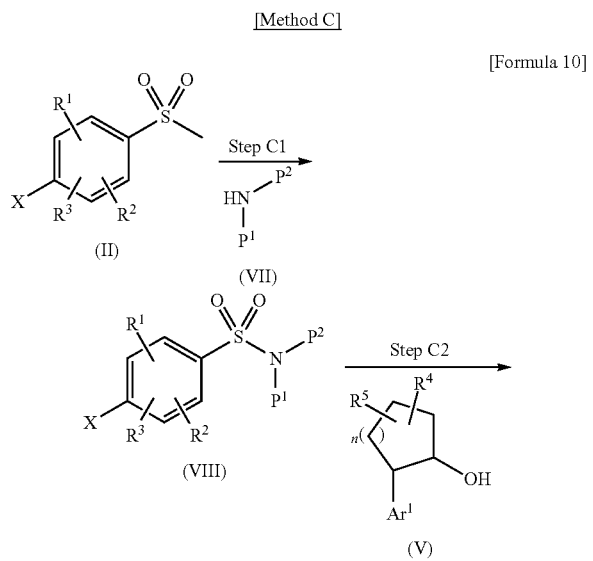

In the above formulas, $Ar^1$, $Ar^2$, $R^1$, $R^2$, $R^3$, $R^4$, $R^5$, $P^1$, $P^2$, X and n represent the same as defined above.

Step C1

This step is the step of producing a compound represented by formula (VIII).

This step is conducted by causing a reaction, in a solvent and in the presence of a base, between a compound represented by formula (II) and a compound represented by formula (VII).

The compound represented by formula (II) and the compound represented by formula (VII) used in this step are known compounds or may be easily produced from known compounds used as starting materials by known methods or methods similar to the known methods.

The solvent used in this step is preferably any one of ethers, nitriles or halogenated hydrocarbons, and more preferably, tetrahydrofuran, acetonitrile or dichloromethane.

The base used in this step is preferably any one of alkali metal carbonates or organic bases, and more preferably, potassium carbonate, pyridine, 4-(N,N-dimethylamino)pyridine, 1,4-diazabicyclo[2.2.2]octane (DABCO), LiHMDS or 1,8-diazabicyclo[5.4.0]undec-7-ene (DBU).

The reaction temperature to be employed in this step is generally 0° C. to 100° C. and preferably 0° C. to room temperature.

The reaction time of this reaction is from 0.5 hours to 48 hours, and the reaction is generally completed in approximately 1 hour to approximately 24 hours.

Step C2

This step is the step of producing a compound represented by formula (IX).

This step is conducted by causing a reaction, in a solvent and in the presence of a base, between the compound represented by formula (V) and the compound represented by formula (VIII).

The solvent used in this step is preferably any one of ethers or amides, and more preferably, tetrahydrofuran or N,N-dimethylformamide.

The base used in this step is preferably any one of alkali metal alkoxides, alkali metal hydrides or alkali metal hydroxides, and more preferably, sodium t-butoxide, potassium t-butoxide, sodium methoxide, potassium methoxide, sodium hydride, potassium hydride, sodium hydroxide or potassium hydroxide.

The reaction temperature to be employed in this step is generally 0° C. to 200° C. and preferably 0° C. to room temperature.

The reaction time of this reaction is from 0.5 hours to 48 hours, and the reaction is generally completed in approximately 1 hour to approximately 24 hours.

Step C3

This step is the step of producing a compound represented by formula (X).

This step is conducted by causing a reaction, in a solvent and, if desired, in the presence of a scavenger, between an acid and the compound represented by formula (IX).

The solvent used in this step is preferably any one of ethers or halogenated hydrocarbons, and more preferably, tetrahydrofuran, 1,4-dioxane or dichloromethane.

The scavenger used in this step is preferably trialkylsilane or aryl ether, and more preferably, triethylsilane or anisole.

The acid used in this step is preferably an organic acid or an inorganic acid, and more preferably, trichloroacetic acid, trifluoroacetic acid, acetic acid, sulfuric acid or hydrochloric acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

Alternatively, this step is also conducted by deprotecting the compound represented by formula (IX) in a solvent and in the presence of a palladium catalyst under the hydrogen atmosphere.

The solvent used in this case is preferably any one of ethers or alcohols, and more preferably, tetrahydrofuran, methanol or ethanol.

The catalyst used is preferably a zero-valent palladium catalyst, and more preferably, palladium-activated carbon or palladium hydroxide-activated carbon.

The reaction temperature is generally −20° C. to 120° C. and preferably 0° C. to 80° C.

The reaction time is generally 1 hour to 48 hours and preferably 2 hours to 24 hours.

Step C4

This step is the step of producing the compound represented by formula (I).

This step is conducted by causing a reaction, in a solvent and in the presence of a base, between the compound represented by formula (X) and a compound represented by formula (XI). This step may be conducted in the presence of a copper catalyst and a ligand thereof.

The compound represented by formula (XI) used in this step is a known compound or may be easily produced from known compounds used as starting materials by known methods or methods similar to the known methods.

The solvent used in this step is preferably any one of ethers, amides or halogenated hydrocarbons, and more preferably, tetrahydrofuran, N,N-dimethylformamide or dichloromethane.

The base used in this step is preferably any one of organic bases or alkali metal carbonates, and more preferably, triethylamine, cesium carbonate or potassium carbonate.

The copper catalyst used in this step is preferably copper (I) chloride, copper (I) bromide, copper (I) iodide or copper (I) trifluoromethanesulfonate.

The ligand used in this step is preferably N,N'-dimethylethylenediamine, trans-N,N'-dimethylcyclohexane-1,2-diamine or N,N'-dimethyl-1,2-cyclohexanediamine.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

The compound represented by formula (V) can be produced in according with methods D to H.

The method D is a method for producing the compound represented by formula (V).

[Method D]

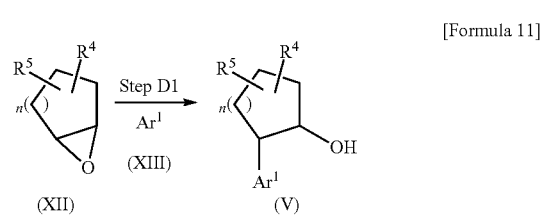

[Formula 11]

In the above formulas, $Ar^1$, $R^4$, $R^5$ and n represent the same as defined above.

Step D1

This step is the step of producing the compound represented by formula (V).

This step is conducted by converting a compound represented by formula (XIII) to a metal salt by deprotonation or halogen metal exchange in a solvent and then reacting the metal salt with a compound represented by formula (XII).

The compound represented by formula (XII) and the compound represented by formula (XIII) used in this step are known compounds or may be easily produced from known compounds used as starting materials by known methods or methods similar to the known methods.

The solvent used in this step is preferably any one of ethers, hydrocarbons or halogenated hydrocarbons, and more preferably, tetrahydrofuran, toluene or dichloromethane.

The deprotonation or halogen metal exchange reagent used in this step is preferably alkyl magnesium halide or alkyl alkali metal, and more preferably, n-butyl lithium, sec-butyl lithium or isopropyl magnesium chloride.

The reaction temperature to be employed in this step is generally −100° C. to 100° C. and preferably −80° C. to room temperature.

The reaction time of this reaction is from 0.5 hours to 48 hours, and the reaction is generally completed in approximately 1 hour to approximately 24 hours.

The method E is another method for producing the compound represented by formula (V).

[Method E]

[Formula 12]

(XIV) →[Step E1, Ar¹—Y (XV)] (XVI) →[Step E2] (V)

In the above formulas, Ar¹, R⁴, R⁵, Y and n represent the same as defined above.

Step E1

This step is the step of producing a compound represented by formula (XVI).

This step is conducted by causing a reaction, in a solvent and in the presence of a catalyst, between a compound represented by formula (XIV) and a compound represented by formula (XV).

The compounds represented by formulas (XIV) and (XV) used in this step are known compounds or may be easily produced from known compounds used as starting materials by known methods or methods similar to the known methods.

The solvent used in this step is preferably any one of ethers; amides, water or mixed solvents thereof, and more preferably, a mixed solvent of 1,4-dioxane or water, tetrahydrofuran or N,N-dimethylformamide.

The catalyst used in this step is preferably a zero-valent palladium catalyst or a divalent palladium catalyst, and more preferably, tetrakis(triphenylphosphine)palladium (0), [1,1'-bis(diphenylphosphino)ferrocene]palladium (II) dichloride or [1,2-bis(diphenylphosphino)ethane]palladium (II) dichloride.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

Step E2

This step is the step of producing the compound represented by formula (V).

This step is conducted by hydroborating the compound represented by formula (XVI) in a solvent, followed by oxidation.

The solvent used in this step is preferably any one of ethers, and more preferably, 1,4-dioxane or tetrahydrofuran.

The hydroboration agent used in this step is preferably a borane-tetrahydrofuran complex or a borane-dimethyl sulfide complex.

The oxidizing agent used in this step is preferably hydrogen peroxide or sodium perborate tetrahydrate.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

The method F is another method for producing the compound represented by formula (V).

[Method F]

[Formula 13]

(XVI) →[Step F1] (XVII) →[Step F2] (V)

In the above formulas, Ar¹, R⁴, R⁵ and n represent the same as defined above.

Step F1

This step is the step of producing a compound represented by formula (XVII).

This step is conducted by epoxidizing the compound represented by formula (XVI) in a solvent.

The solvent used in this step is preferably any one of ketones or halogenated hydrocarbons, and more preferably, chloroform or dichloromethane.

The epoxidation reagent used in this step is preferably 3-chloroperbenzoic acid or potassium peroxymonosulfate.

The reaction temperature to be employed in this step is generally −20° C. to 120° C. and preferably 0° C. to 80° C.

The reaction time of this step is from 1 hour to 48 hours, and the reaction is generally completed in approximately 2 hours to approximately 24 hours.

Step F2

This step is the step of producing the compound represented by formula (V).

This step is conducted by reducing the compound represented by formula (XVII) in a solvent.

The solvent used in this step is preferably any one of ethers or alcohols, and more preferably, tetrahydrofuran, methanol or ethanol.

The reducing agent used in this step is preferably any one of alkali metal borohydrides or aluminum hydride compounds, and more preferably, sodium borohydride or lithium aluminum hydride.

The reaction temperature to be employed in this step is generally −20° C. to 120° C. and preferably 0° C. to 80° C.

The reaction time of this reaction is from 1 hour to 48 hours, and the reaction is generally completed in approximately 2 hours to approximately 24 hours.

This step is also conducted by reducing the compound represented by formula (XVII) in a solvent and in the presence of a catalyst under a hydrogen atmosphere or under a nitrogen atmosphere in the presence of a catalyst.

The solvent used in this step is preferably any one of ethers or alcohols, and more preferably, tetrahydrofuran, methanol or ethanol.

The catalyst used in this step is preferably a palladium catalyst or a nickel catalyst, and more preferably, palladium-activated carbon, palladium hydroxide-activated carbon or Raney nickel.

The reaction temperature to be employed in this step is generally 0° C. to 200° C. and preferably room temperature to 120° C.

The reaction time of this reaction is from 1 hour to 48 hours, and the reaction is generally completed in approximately 2 hours to approximately 24 hours.

The method G is another method for producing the compound represented by formula (V).

[Method G]

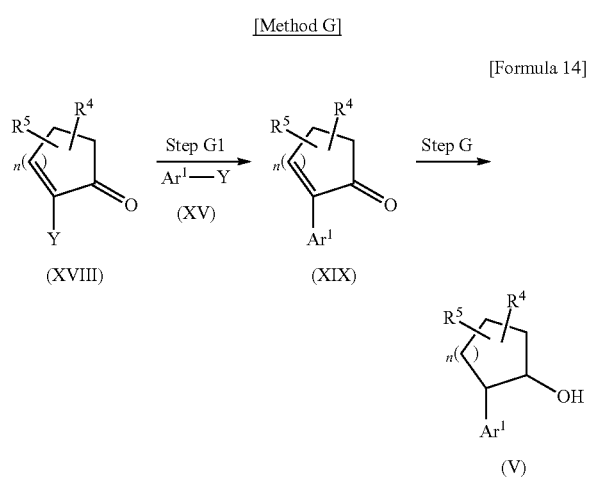

[Formula 14]

In the above formulas, $Ar^1$, $R^4$, $R^5$, $P^1$, $P^2$, Y and n represent the same as defined above.

Step G1

This step is the step of producing a compound represented by formula (XIX).

This step is conducted by causing a reaction, in a solvent and in the presence of a catalyst, between a compound represented by formula (XVIII) and a compound represented by formula (XV).

The compounds represented by formulas (XVIII) and (XV) used in this step are known compounds or may be easily produced from known compounds used as starting materials by known methods or methods similar to the known methods.

The solvent used in this step is preferably any one of ethers, amides, water or mixed solvents thereof, and more preferably, a mixed solvent of 1,4-dioxane and water, tetrahydrofuran or N,N-dimethylformamide.

The catalyst used in this step is preferably a zero-valent palladium catalyst or a divalent palladium catalyst, and more preferably, tetrakis(triphenylphosphine)palladium (0), [1,1′-bis(diphenylphosphino)ferrocene]palladium (II) dichloride or [1,2-bis(diphenylphosphino)ethane]palladium (II) dichloride.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

Step G2

This step is the step of producing the compound represented by formula (V).

This step is conducted by reducing the compound represented by formula (XIX) in a solvent.

The solvent used in this step is preferably any one of ethers or alcohols, and more preferably, tetrahydrofuran, ethanol or methanol.

The reducing agent used in this step is preferably any one of alkali metal borohydrides or aluminum hydride compounds, and more preferably, sodium borohydride or lithium aluminum hydride.

The reaction temperature to be employed in this step is generally −20° C. to 120° C. and preferably 0° C. to 80° C.

The reaction time of this reaction is from 1 hour to 48 hours, and the reaction is generally completed in approximately 2 hours to approximately 24 hours.

This step is also conducted by reducing the compound represented by formula (XIX) in a solvent and in the presence of a catalyst under a hydrogen atmosphere or under a nitrogen atmosphere in the presence of a catalyst.

The solvent used in this step is preferably any one of ethers or alcohols, and more preferably, tetrahydrofuran, methanol or ethanol.

The catalyst used in this step is preferably a palladium catalyst or a nickel catalyst, and more preferably, palladium-activated carbon, palladium hydroxide-activated carbon or Raney nickel.

The reaction temperature to be employed in this step is generally 0° C. to 200° C. and preferably room temperature to 120° C.

The reaction time of this reaction is from 1 hour to 48 hours, and the reaction is generally completed in approximately 2 hours to approximately 24 hours.

A compound represented by formula (Va) or (Vb) is an optical isomer of the compound represented by formula (V) and is produced by combining the methods D to G with method H described below.

The method H is a method for producing the optical isomers (Va) and (Vb) of the compound (V) by optical resolution. The compound represented by formula (Ia) or (Ib) is produced through steps A2 and A3 from the optical isomer (Va) or (Vb).

[Method H]

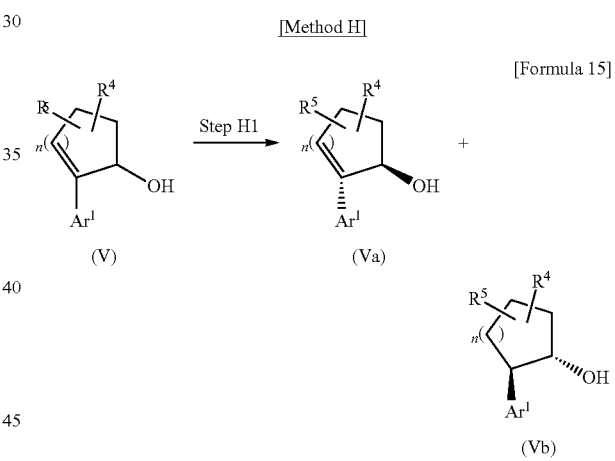

[Formula 15]

In the above formulas, $Ar^1$, $R^4$, $R^5$ and n represent the same as defined above.

Step H1

This step is the step of producing the compounds represented by formulas (Va) and (Vb). This step is conducted by optically resolving the compound represented by formula (V) into the compounds represented by formulas (Va) and (Vb) by using a chiral column.

The solvent used in this step is preferably any one of hydrocarbons, alcohols or mixed solvents thereof, and more preferably, a mixed solvent of hexane and isopropanol or a mixed solvent of hexane and ethanol.

The column used in the optical resolution can be any of those exemplified above.

The temperature to be employed in this step is generally 0° C. to 40° C. and preferably 0° C. to room temperature.

The method I is another method for producing the compound represented by formula (XVI).

[Formula 16]

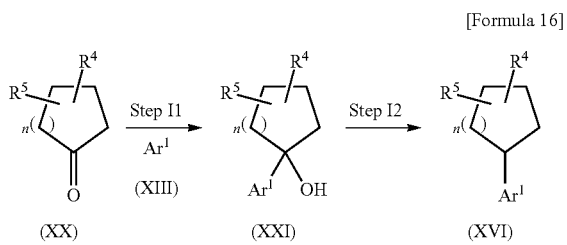

In the above formulas, $Ar^1$, $R^4$, $R^5$ and n represent the same as defined above.

Step I1

This step is the step of producing a compound represented by formula (XXI).

This step is conducted by converting a compound represented by formula (XIII) to a metal salt by deprotonation or halogen metal exchange in a solvent and then reacting the metal salt with a compound represented by formula (XX).

The compounds represented by formulas (XIII) and (XX) used in this step are known compounds or may be easily produced from known compounds used as starting materials by known methods or methods similar to the known methods.

The solvent used in this step is preferably any one of ethers, hydrocarbons or halogenated hydrocarbons, and more preferably, tetrahydrofuran, toluene or dichloromethane.

The deprotonation or halogen metal exchange reagent used in this step is preferably alkyl magnesium halide or alkyl alkali metal, and more preferably, n-butyl lithium, sec-butyl lithium or isopropyl magnesium chloride.

The reaction temperature to be employed in this step is generally −100° C. to 100° C. and preferably −80° C. to room temperature.

The reaction time of this reaction is from 0.5 hours to 48 hours, and the reaction is generally completed in approximately 1 hour to approximately 24 hours.

Step I2

This step is the step of producing the compound represented by formula (XVI).

This step is conducted by causing a reaction, in a solvent, between an acid and the compound represented by formula (XXI).

The solvent used in this step is preferably any one of alcohols, aromatic hydrocarbons or halogenated hydrocarbons, and more preferably, ethanol, toluene or dichloromethane.

The acid used in this step is preferably an organic acid or an inorganic acid, and more preferably, hydrochloric acid, sulfuric acid, acetic acid or p-toluenesulfonic acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

[Method J]

[Formula 17]

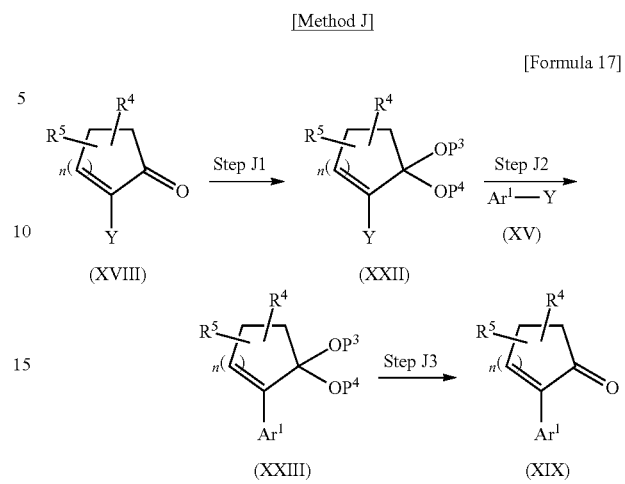

In the above formulas, $Ar^1$, $R^4$, $R^5$, $P^3$, $P^4$, Y and n represent the same as defined above.

Step J1

This step is the step of producing a compound represented by formula (XXII).

This step is conducted by causing a reaction, in a solvent and in the presence of a dehydrating agent or under dehydration conditions, between an acid and the compound represented by formula (XVIII).

The solvent used in this step is preferably any one of aromatic hydrocarbons, and more preferably, toluene or benzene.

The acid used in this step is preferably an organic acid or an inorganic acid, and more preferably, hydrochloric acid, sulfuric acid or p-toluenesulfonic acid.

The dehydrating agent used in this step is preferably orthoester, and more preferably, hydrochloric acid or trimethoxymethane, trimethoxyethane or triethoxyethane.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

Step J2

This step is the step of producing a compound represented by formula (XXIII).

This step is conducted by causing a reaction, in a solvent and in the presence of a catalyst, between the compound represented by formula (XXII) and a compound represented by formula (XV).

The compound represented by formula (XV) used in this step is a known compound or may be easily produced from known compounds used as starting materials by known methods or methods similar to the known methods.

The solvent used in this step is preferably any one of ethers, amides, water or mixed solvents thereof, and more preferably, a mixed solvent of 1,4-dioxane and water, tetrahydrofuran or N,N-dimethylformamide.

The catalyst used in this step is preferably a zero-valent palladium catalyst or a divalent palladium catalyst, and more preferably, tetrakis(triphenylphosphine)palladium (0), [1,1'-bis(diphenylphosphino) ferrocene]palladium (II) dichloride or [1,2-bis(diphenylphosphino)ethane]palladium (II) dichloride.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

Step J3

This step is the step of producing the compound represented by formula (XIX).

This step is conducted by causing a reaction, in an aqueous solvent, between an acid and the compound represented by formula (XXIII).

The solvent used in this step is preferably any one of alcohols or ethers, and more preferably, ethanol, 1,4-dioxane or tetrahydrofuran.

The acid used in this step is preferably an organic acid or an inorganic acid, and more preferably, hydrochloric acid or sulfuric acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

The method K is another method for producing an optically active compound represented by formula (XVIIb) of the compound represented by formula (XVII). Also, an enantiomer thereof may be produced by appropriately selecting a reagent in step K1.

[Method K]

[Formula 18]

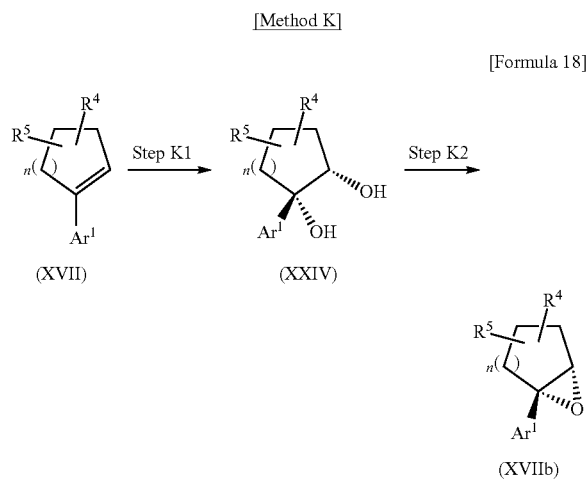

(XVII)    (XXIV)

(XVIIb)

In the above formulas, Ar$^1$, R$^4$, R$^5$ and n represent the same as defined above.

Step K1

This step is the step of producing a compound represented by formula (XXIV).

This step is conducted by converting the compound represented by formula (XVI) to optically active diol in a solvent.

The solvent used in this step is preferably any one of alcohols, water or mixed solvents thereof, and more preferably, a mixed solvent of t-butanol and water.

The reagent for asymmetric conversion to diol used in this step is preferably AD-mixα or AD-mixβ (Sigma-Aldrich Corp.).

The reaction temperature to be employed in this step is generally –20° C. to 120° C. and preferably 0° C. to 80° C.

The reaction time of this step is on the order of 1 hour to 48 hours, and the reaction is generally completed in approximately 2 hours to approximately 24 hours.

Step K2

This step is the step of producing the compound represented by formula (XVIIb).

This step is conducted by subjecting the compound represented by formula (XXIV) to (I) a reaction with orthoester in the presence of an acid, (II) a reaction with acid halide in the presence of a base, or (III) a treatment with a base, in a solvent.

The solvent used in (I) is preferably any one of halogenated hydrocarbons, and more preferably, dichloromethane.

The acid used in (I) is preferably an inorganic acid or an organic acid, and more preferably, hydrochloric acid, sulfuric acid or p-toluenesulfonic acid.

The orthoester used in (I) is preferably trimethoxymethane, trimethoxyethane or triethoxyethane.

The reaction temperature to be employed in (I) is generally –20° C. to 120° C. and preferably 0° C. to 80° C.

The reaction time of (I) is from 1 hour to 96 hours, and the reaction is generally completed in approximately 2 hours to approximately 48 hours.

The solvent used in (II) is preferably any one of nitriles, and more preferably, acetonitrile.

The base used in (II) is preferably any one of alkali metal salts, and more preferably, potassium bromide, sodium bromide or lithium bromide.

The acid halide used in (II) is preferably acetic acid halide, formic acid halide or propionic acid halide, and more preferably, propionyl bromide or acetyl bromide.

The reaction temperature to be employed in (II) is generally –20° C. to 120° C. and preferably 0° C. to room temperature.

The reaction time of (II) is from 1 hour to 48 hours, and the reaction is generally completed in approximately 2 hours to approximately 24 hours.

The solvent used in (III) is preferably any one of alcohols, and more preferably, ethanol or methanol.

The base used in (III) is preferably any one of alkali metal carbonates, and more preferably, potassium carbonate, lithium carbonate or sodium carbonate.

The reaction temperature to be employed in (III) is generally –20° C. to 120° C. and preferably 0° C. to room temperature.

The reaction time of (III) is from 1 hour to 48 hours, and the reaction is generally completed in approximately 2 hours to approximately 24 hours.

EXAMPLES

The present invention will now be described in more detail with reference to examples and test examples, but the scope of the present invention is not limited to these examples.

In the examples described below, elution in column chromatography was performed under observation by TLC (Thin Layer Chromatography). In the TLC observation, silica gel 60F254 manufactured by Merck & Co. was adopted as a TLC plate; a solvent used as an eluting solvent in column chromatography was adopted as a developing solvent; and a UV detector was adopted as a detection method. Silica gel SK-85 (230-400 mesh) also manufactured by Merck & Co. or Chromatorex NH (200-350 mesh) manufactured by Fuji Silysia Chemical Ltd. was used as silica gel for columns. In addition to general column chromatography, an automatic chromatography apparatus (Purif- α2 or Purif-espoir2) manufactured by Shoko Scientific Co., Ltd. was appropriately used. A solvent described in each example was used as an eluting solvent at a specified ratio (or at a ratio changed appropriately if necessary). Abbreviations used in the examples mean the following:

mg: milligram, g: gram, mL: milliliter, MHz: megahertz.

In the examples described below, nuclear magnetic resonance (hereinafter, referred to as $^1$H-NMR) spectra were indicated in δ values (ppm) in terms of chemical shift values with tetramethylsilane used as standard. Splitting patterns were represented by s for singlet, d for doublet, t for triplet, q for quartet, m for multiplet, and br for broad.

Powder x-ray diffraction data was determined with the following equipment under the following measurement conditions:

Equipment manufacturer: Rigaku Corp.
Model: RINT TTR-III
Source: Cu—Kα rays
Wavelength (angstrom): 1.54
Detector: scintillation counter
Optical system: parallel beam method
Tube voltage (kV): 50
Tube current (mA): 300
Scanning range 2θ (deg): 2 to 40
Sampling step (deg): 0.02
Scanning rate (deg/min): 2
Sample holder: non-reflecting sample holder Example 1

2,5-Difluoro-4-{[(1S*,2R*)-2-phenylcyclohexyl]oxy}-N-(1,2,4-thiadiazol-5-yl)benzenesulfonamide

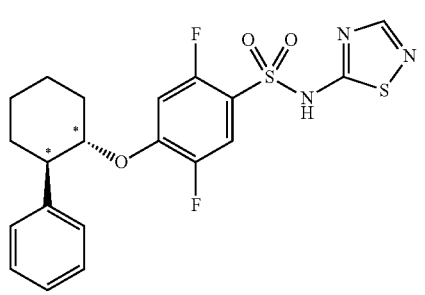

[Formula 19]

(1a) N-(2,4-dimethoxybenzyl)-2,5-difluoro-4-{[(1S*,2R*)-2-phenylcyclohexyl]oxy}-N-(1,2,4-thiadiazol-5-yl)benzenesulfonamide To a solution of N-(2,4-dimethoxybenzyl)-2,4,5-trifluoro-N-(1,2,4-thiadiazol-5-yl)benzenesulfonamide (WO 2010/079443; 600 mg, 1.35 mmol) and (1S*,2R*)-2-phenylcyclohexanol (240 mg, 1.36 mmol) in DMSO (6.0 mL), sodium hydride (63%; 100 mg, 2.63 mmol) was added with cooling on ice, and the reaction solution was stirred at room temperature for 1 hour. Water (100 mL) was added to the reaction solution, followed by extraction with ethyl acetate (50 mL). The thus obtained organic layer was washed twice with water (200 mL) and dried over anhydrous sodium sulfate. After vacuum concentration, the residue was purified with silica gel chromatography (hexane/ethyl acetate=4:1) to yield the title compound (270 mg, 33%) as a colorless oil.

$^1$H-NMR (400 MHz, CDCl$_3$) δ ppm: 1.40-1.68 (4H, m), 1.86-2.05 (3H, m), 2.17-2.21 (1H, m), 2.82-2.89 (1H, m), 3.65 (3H, s), 3.71 (3H, s), 4.25 (1H, dt, d=3.9, 10.6 Hz), 5.21 (2H, s), 6.18 (1H, d, J=2.4 Hz), 6.30-6.34 (2H, m), 7.13-7.24 (6H, m), 7.34 (1H, dd, J=6.7, 10.2 Hz), 8.17 (1H, s).

(1b) 2,5-Difluoro-4-{[(1S*,2R*)-2-phenylcyclohexyl]oxy}-N-(1,2,4-thiadiazol-5-yl)benzenesulfonamide To a solution of the N-(2,4-dimethoxybenzyl)-2,5-difluoro-4-{[(1S*,2R*)-2-phenylcyclohexyl]oxy}-N-(1,2,4-thiadiazol-5-yl)benzenesulfonamide (270 mg, 0.449 mmol) prepared in Example 1a and triethylsilane (0.30 mL) in dichloromethane (3.0 mL), trifluoroacetic acid (3.0 mL) was added at room temperature, and the reaction solution was stirred for 1 hour. The reaction solution was concentrated, and the residue was purified with silica gel chromatography (dichloromethane/methanol=95:5) to yield the title compound (186 mg, 92%) as a colorless solid.

$^1$H-NMR (400 MHz, CDCl$_3$) δ ppm: 1.39-1.70 (4H, m), 1.82-2.02 (3H, m), 2.20-2.23 (1H, m), 2.83-2.89 (1H, m), 4.27 (1H, dt, d=4.33, 10.6 Hz), 6.47 (1H, dd, J=5.1, 11.4 Hz), 7.10-7.21 (5H, m), 7.49 (1H, dd, J=4.7, 9.8 Hz), 8.05 (1H, s).

MS (FAB) m/z: 452 [M+H]+.

Example 2

2,5-Difluoro-4-{[(1S,2R)-2-phenylcyclohexyl]oxy}-N-(1,2,4-thiadiazol-5-yl)benzenesulfonamide

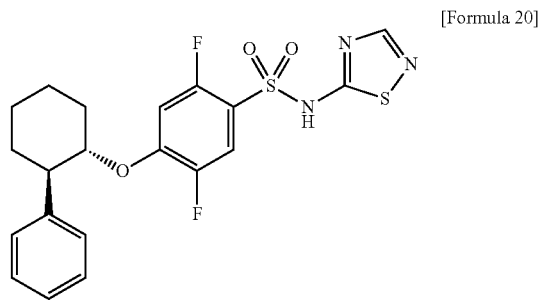 [SMILES: O=S(=O)(Nc1ncns1)c1cc(F)c(O[C@H]2CCCC[C@@H]2c2ccccc2)cc1F]

[Formula 20]

(2a) N-(2,4-dimethoxybenzyl)-2,5-difluoro-4-{[(1S,2R)-2-phenylcyclohexyl]oxy}-N-(1,2,4-thiadiazol-5-yl)benzenesulfonamide The reaction and aftertreatment were conducted in the same manner as in Example 1a by using N-(2,4-dimethoxybenzyl)-2,4,5-trifluoro-N-(1,2,4-thiadiazol-5-yl)benzenesulfonamide (WO 2010/079443; 126 mg, 0.283 mmol), (1S,2R)-2-phenylcyclohexanol (50.0 mg, 0.284 mmol), sodium hydride (63%; 21.6 mg, 0.567 mol) and DMSO (2.0 mL), to yield the title compound (55.7 mg, 33%) as a colorless oil.

$^1$H-NMR (400 MHz, CDCl$_3$) δ ppm: 1.40-1.68 (4H, m), 1.86-2.05 (3H, m), 2.17-2.21 (1H, m), 2.82-2.89 (1H, m), 3.65 (3H, s), 3.71 (3H, s), 4.25 (1H, dt, d=3.9, 10.6 Hz), 5.21 (2H, s), 6.18 (1H, d, J=2.4 Hz), 6.30-6.34 (2H, m), 7.13-7.24 (6H, m), 7.34 (1H, dd, J=6.7, 10.2 Hz), 8.17 (1H, s).

(2b) 2,5-Difluoro-4-{[(1S,2R)-2-phenylcyclohexyl]oxy}-N-(1,2,4-thiadiazol-5-yl)benzenesulfonamide The reaction and aftertreatment were conducted in the same manner as in Example 1b by using the N-(2,4-dimethoxybenzyl)-2,5-difluoro-4-{[(1S,2R)-2-phenylcyclohexyl]oxy}-N-(1,2,4-thiadiazol-5-yl)benzenesulfonamide (55.7 mg, 0.0926 mmol) prepared in Example 2a, triethylsilane (0.10 mL), trifluoroacetic acid (1.0 mL) and dichloromethane (1.0 mL), to yield the title compound (31.0 mg, 74%) as a colorless solid.

$^1$H-NMR (400 MHz, CDCl$_3$) δ ppm: 1.39-1.70 (4H, m), 1.82-2.02 (3H, m), 2.20-2.23 (1H, m), 2.83-2.89 (1H, m), 4.27 (1H, dt, d=4.33, 10.6 Hz), 6.47 (1H, dd, J=5.1, 11.4 Hz), 7.10-7.21 (5H, m), 7.49 (1H, dd, J=4.7, 9.8 Hz), 8.05 (1H, s).

MS (ESI) m/z: 452 [M+H]+;
$[α]_D^{25}$=−53.24 (c 0.216, DMSO).

Example 3

2,5-Difluoro-4-{[(1R*,2R*)-2-phenylcyclohexyl]oxy}-N-(1,2,4-thiadiazol-5-yl)benzenesulfonamide

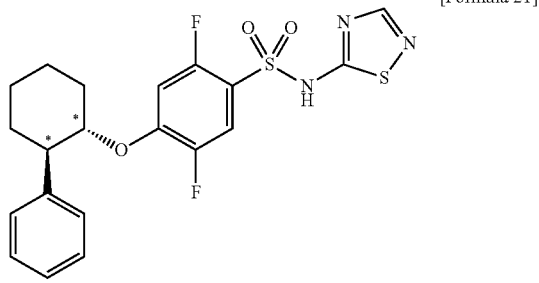

[Formula 21]

(3a) N-(2,4-Dimethoxybenzyl)-2,5-difluoro-4-{[(1R*,2R*)-2-phenylcyclohexyl]oxy}-N-(1,2,4-thiadiazol-5-yl)benzenesulfonamide The reaction and aftertreatment were conducted in the same manner as in Example 1a by using the N-(2,4-dimethoxybenzyl)-2,4,5-trifluoro-N-(1,2,4-thiadiazol-5-yl)benzenesulfonamide (WO 2010/079443; 177 mg, 0.397 mmol), (1R*,2R*)-2-phenylcyclohexanol (70.0 mg, 0.397 mmol), sodium hydride (63%; 30.3 mg, 0.794 mol) and DMSO (5.0 mL), to yield the title compound (53.0 mg, 22%) as a colorless oil.

$^1$H-NMR (400 MHz, CDCl$_3$) δ ppm: 1.47-1.70 (4H, m), 1.78-1.81 (1H, m), 1.95-1.99 (1H, m), 2.07-2.10 (1H, m), 2.28 (1H, dq, J=3.5, 12.9 Hz), 2.87 (1H, dt, J=3.5, 11.7 Hz), 3.65 (3H, s), 3.72 (3H, s), 4.55 (1H, s), 5.20 (1H, d, J=16.0 Hz), 5.25 (1H, d, J=16.0 Hz), 6.17 (1H, d, J=2.7 Hz), 6.24 (1H, dd, J=2.7, 11.7 Hz), 6.33 (1H, dd, J=2.4, 8.6 Hz), 7.13-7.28 (6H, m), 7.43 (1H, dd, J=6.3, 10.2 Hz), 8.16 (1H, s).

(3b) 2,5-Difluoro-4-{[(1R*,2R*)-2-phenylcyclohexyl]oxy}-N-(1,2,4-thiadiazol-5-yl)benzenesulfonamide The reaction and aftertreatment were conducted in the same manner as in Example 1b by using the N-(2,4-dimethoxybenzyl)-2,5-difluoro-4-{[(1R*,2R*)-2-phenylcyclohexyl]oxy}-N-(1,2,4-thiadiazol-5-yl)benzenesulfonamide (53.0 mg, 0.088 mmol) prepared in Example 3a, triethylsilane (0.10 mL), trifluoroacetic acid (1.0 mL) and dichloromethane (1.0 mL), to yield the title compound (44.6 mg, 99%) as a colorless solid.

$^1$H-NMR (400 MHz, CDCl$_3$) δ ppm: 1.50-1.80 (5H, m), 1.95-1.98 (1H, m), 2.10-2.13 (1H, m), 2.29 (1H, dq, J=3.5, 12.5 Hz), 2.86 (1H, d, J=12.1 Hz), 4.56 (1H, s), 6.39 (1H, dd, J=6.3, 11.3 Hz), 7.13-7.28 (5H, m), 7.58 (1H, dd, J=6.7, 9.8 Hz), 8.04 (1H, s).

MS (ESI) m/z: 452 [M+H]+

Example 4

2,5-Difluoro-4-{[(1S*,2R*)-2-(1-methyl-1H-pyrazol-5-yl)cyclohexyl]oxy}-N-(1,2,4-thiadiazol-5-yl)benzenesulfonamide

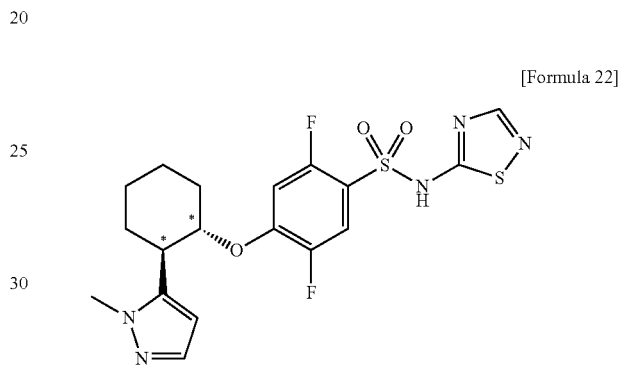

[Formula 22]

(4a) (1S*,2R*)-2-(1-Methyl-1H-pyrazol-5-yl)cyclohexanol

To a solution of 1-methylpyrazole (9.34 g, 114 mmol) and N,N,N',N'-tetramethylethylenediamine (17.1 mL, 114 mmol) in THF (300 mL), butyl lithium (1.63 M solution in hexane; 81.7 mL, 133 mmol) was added at −78° C. The reaction solution was stirred at −78° C. for 30 minutes. Then, cyclohexene oxide (13.9 mL, 137 mmol) was added thereto, and the mixture was stirred at room temperature for 15 hours. To the reaction solution, water (1 L) was added, followed by extraction with ethyl acetate (500 mL). The thus obtained organic layer was dried over anhydrous sodium sulfate. After vacuum concentration, the residue was purified with silica gel chromatography (ethyl acetate) to yield the title compound (11.2 g, 55%) as a colorless solid.

$^1$H-NMR (400 MHz, CDCl$_3$) δ ppm: 1.30-1.48 (4H, m), 1.76-1.91 (4H, m), 2.09-2.15 (1H, m), 2.57-2.63 (1H, m), 3.59-3.65 (1H, m), 3.86 (3H, s), 6.08 (1H, d, J=2.0 Hz), 7.44 (1H, d, J=2.0 Hz).

(4b) N-(2,4-Dimethoxybenzyl)-2,5-difluoro-4-{[(1S*,2R*)-2-(1-methyl-1H-pyrazol-5-yl)cyclohexyl]oxy}-N-(1,2,4-thiadiazol-5-yl)benzenesulfonamide The reaction and aftertreatment were conducted in the same manner as in Example 1a by using the N-(2,4-dimethoxybenzyl)-2,4,5-trifluoro-N-(1,2,4-thiadiazol-5-yl)benzenesulfonamide (WO 2010/079443; 600 mg, 1.35 mmol), (1S*,2R*)-2-(1-methyl-1H-pyrazol-5-yl)cyclohexanol (240 mg, 1.33 mmol) prepared in Example 4a, sodium hydride (63%; 100 mg, 2.63 mmol) and DMSO (6.0 mL), to yield the title compound (340 mg, 42%) as a colorless solid.

$^1$H-NMR (400 MHz, CDCl$_3$) δ ppm: 1.39-1.70 (4H, m), 1.87-1.90 (1H, m), 1.94-1.98 (1H, m), 2.05-2.09 (1H, m), 2.17-2.21 (1H, m), 2.97-3.03 (1H, m), 3.65 (3H, s), 3.74 (3H, s), 3.90 (3H, s), 4.08 (1H, dt, J=3.9, 10.2 Hz), 5.21 (1H, d, J=15.7 Hz), 5.28 (1H, d, J=15.7 Hz), 6.04 (1H, d, J=2.0 Hz), 6.19 (1H, d, J=2.0 Hz), 6.34 (1H, dd, J=2.4, 8.6 Hz), 6.34-6.39 (1H, m), 7.15 (1H, d, J=8.2 Hz), 7.36 (1H, d, J=1.6 Hz), 7.41 (1H, dd, J=6.7, 10.2 Hz), 8.18 (1H, s).

(4c) 2,5-Difluoro-4-{[(1S*,2R*)-2-(1-methyl-1H-pyrazol-5-yl)cyclohexyl]oxy}-N-(1,2,4-thiadiazol-5-yl)benzenesulfonamide The reaction and aftertreatment were conducted in the same manner as in Example 1b by using the N-(2,4-dimethoxybenzyl)-2,5-difluoro-4-{[(1S*,2R*)-2-(1-methyl-1H-pyrazol-5-yl)cyclohexyl]oxy}-N-(1,2,4-thiadiazol-5-yl)benzenesulfonamide (340 mg, 0.561 mmol) prepared in Example 4b, triethylsilane (0.4 mL), trifluoroacetic acid (4.0 mL) and dichloromethane (4.0 mL), to yield the title compound (259 mg, 43%) as a colorless solid.

$^1$H-NMR (400 MHz, DMSO-d$_6$) δ ppm: 1.37-1.60 (4H, m), 1.71-1.81 (2H, m), 1.90-1.94 (1H, m), 2.16-2.19 (1H, m), 3.07-3.13 (1H, m), 3.79 (3H, s), 4.57 (1H, dt, J=4.3, 9.8 Hz), 6.09 (1H, d, J=2.0 Hz), 7.22 (1H, d, J=2.0 Hz), 7.34 (1H, dd, J=6.7, 11.7 Hz), 7.54 (1H, dd, J=6.7, 10.6 Hz), 8.53 (1H, s).

MS (FAB) m/z: 456 [M+H]+.

Example 5

2,5-Difluoro-4-{[(1S*,2R*)-2-(1-methyl-1H-pyrazol-5-yl)cyclohexyl]oxy}-N-(1,3-thiazol-4-yl)benzenesulfonamide Na salt

[Formula 23]

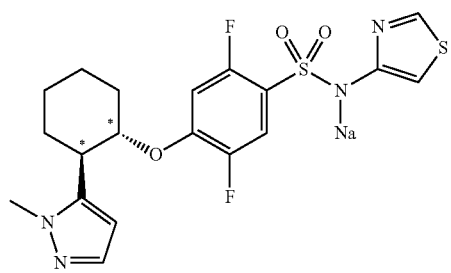

(5a) Tert-butyl [(2,5-difluoro-4-{[(1S*,2R*)-2-(1-methyl-1H-pyrazol-5-yl)cyclohexyl]oxy}phenyl)sulfonyl](1,3-thiazol-4-yl)carbamate The reaction and aftertreatment were conducted in the same manner as in Example 1a by using tert-butyl(1,3-thiazol-4-yl)[(2,4,5-trifluorophenyl)sulfonyl]carbamate (WO 2010/079443; 219 mg, 0.555 mmol), the (1S*,2R*)-2-(1-methyl-1H-pyrazol-5-yl)cyclohexanol (100 mg, 0.555 mmol) prepared in Example 4a, sodium hydride (63%; 42.3 mg, 1.11 mol) and DMF (3.0 mL), to yield the title compound (177 mg, 57%) as a colorless oil.

$^1$H-NMR (400 MHz, CDCl$_3$) δ ppm: 1.35 (9H, s), 1.44-1.70 (4H, m), 1.88-1.91 (1H, m), 1.96-1.99 (1H, m), 2.06-2.10 (1H, m), 2.26-2.30 (1H, m), 3.00-3.06 (1H, m), 3.92 (3H, s), 4.18 (1H, dt, J=3.9, 10.2 Hz), 6.04 (1H, d, J=2.0 Hz), 6.57 (1H, dd, J=6.3, 11.0 Hz), 7.36 (1H, d, J=2.0 Hz), 7.49 (1H, d, J=2.4 Hz), 7.76 (1H, dd, J=6.3, 10.2 Hz), 8.78 (1H, d, J=2.4 Hz).

(5b) 2,5-Difluoro-4-{[(1S*,2R*)-2-(1-methyl-1H-pyrazol-5-yl)cyclohexyl]oxy}-N-(1,3-thiazol-4-yl)benzenesulfonamide The reaction and aftertreatment were conducted in the same manner as in Example 1b by using the tert-butyl [(2,5-difluoro-4-{[(1S*,2R*)-2-(1-methyl-1H-pyrazol-5-yl)cyclohexyl]oxy}phenyl)sulfonyl](1,3-thiazol-4-yl)carbamate (177 mg, 0.319 mmol) prepared in Example 5a, trifluoroacetic acid (1.0 mL) and dichloromethane (1.0 mL), to yield the title compound (260 mg, 87%) as a colorless solid.

$^1$H-NMR (400 MHz, CDCl$_3$) δ ppm: 1.40-1.69 (4H, m), 1.85-1.88 (1H, m), 1.92-1.95 (1H, m), 2.03-2.07 (1H, m), 2.21-2.25 (1H, m), 2.95-3.01 (1H, m), 3.89 (3H, s), 4.09 (1H, dt, J=3.9, 10.6 Hz), 6.01 (1H, d, J=2.0 Hz), 6.48 (1H, dd, J=6.3, 11.0 Hz), 6.89 (1H, d, J=2.4 Hz), 7.33 (1H, d, J=1.6 Hz), 7.51 (1H, dd, J=7.0, 10.2 Hz), 8.72 (1H, d, J=2.4 Hz).

(5c) 2,5-Difluoro-4-{[(1S*,2R*)-2-(1-methyl-1H-pyrazol-5-yl)cyclohexyl]oxy}-N-(1,3-thiazol-4-yl)benzenesulfonamide Na salt To a solution of the 2,5-difluoro-4-{[(1S*,2R*)-2-(1-methyl-1H-pyrazol-5-yl)cyclohexyl]oxy}-N-(1,3-thiazol-4-yl)benzenesulfonamide (51.0 mg, 0.112 mmol) prepared in Example 5b in methanol (5.0 mL), a 1 M sodium hydroxide solution (0.112 mL, 0.112 mol) was added. The reaction solution was concentrated to yield the title compound (47.0 mg, 88%) as a colorless solid.

$^1$H-NMR (400 MHz, CD$_3$OD) δ ppm: 1.24-2.01 (7H, m), 2.24-2.26 (1H, m), 3.04-3.09 (1H, m), 3.86 (3H, s), 4.28-4.32 (1H, m), 6.14 (1H, s), 6.27 (1H, s), 6.74-6.78 (1H, m), 7.27 (1H, s), 7.43-7.46 (1H, m), 8.53 (1H, s).

MS (ESI) m/z: 455 [M+H]+

Example 6

2,5-Difluoro-4-{[(1S*,2R*)-2-phenylcyclopentyl]oxy}-N-(1,2,4-thiadiazol-5-yl)benzenesulfonamide

[Formula 24]

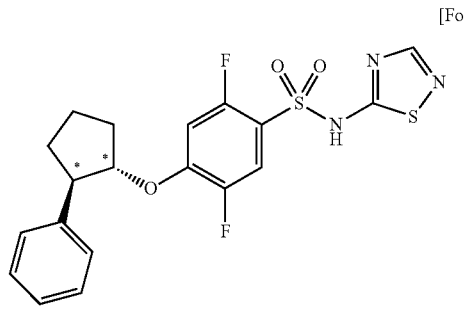

(6a) N-(2,4-Dimethoxybenzyl)-2,5-difluoro-4-{[(1S*,2R*)-2-phenylcyclopentyl]oxy}-N-(1,2,4-thiadiazol-5-yl)benzenesulfonamide The reaction and aftertreatment were conducted in the same manner as in Example 1a by using the N-(2,4-dimethoxybenzyl)-2,4,5-trifluoro-N-(1,2,4-thiadiazol-5-yl)benzenesulfonamide (WO 2010/079443; 500 mg, 1.12 mmol), (1S*,2R*)-2-phenylcyclopentanol (200 mg, 1.23 mmol), sodium hydride (63%; 100 mg, 2.63 mol) and DMSO (5.0 mL), to yield the title compound (220 mg, 33%) as a colorless oil.

$^1$H-NMR (400 MHz, CDCl$_3$) δ ppm: 1.76-1.85 (1H, m), 1.92-1.98 (3H, m), 2.14-2.21 (1H, m), 2.27-2.35 (1H, m), 3.30-3.35 (1H, m), 3.70 (6H, s), 4.59-4.63 (1H, m), 5.27 (2H, s), 6.22 (1H, d, J=2.4 Hz), 6.32 (1H, dd, J=2.4, 8.2 Hz), 6.36-6.39 (1H, m), 7.15 (1H, d, J=8.6 Hz), 7.21-7.24 (3H, m), 7.31-7.35 (2H, m), 7.48 (1H, dd, J=6.7, 10.2 Hz), 8.17 (1H, s).

(6b) 2,5-Difluoro-4-{[(1S*,2R*)-2-phenylcyclopentyl]oxy}-N-(1,2,4-thiadiazol-5-yl)benzenesulfonamide The reaction and aftertreatment were conducted in the same manner as in Example 1b by using the N-(2,4-dimethoxybenzyl)-2,5-difluoro-4-{[(1S*,2R*)-2-phenylcyclopentyl]oxy}-N-(1,2,4-thiadiazol-5-yl)benzenesulfonamide (220 mg, 374 mmol) prepared in Example 6a, triethylsilane (0.3 mL), trifluoroacetic acid (3.0 mL) and dichloromethane (3.0 mL), to yield the title compound (155 mg, 95%) as a colorless solid.

$^1$H-NMR (400 MHz, CDCl$_3$) δ ppm: 1.75-1.83 (1H, m), 1.91-1.99 (3H, m), 2.13-2.22 (1H, m), 2.26-2.34 (1H, m), 3.31-3.37 (1H, m), 4.63-4.66 (1H, m), 6.53 (1H, dd, J=6.3, 11.3 Hz), 7.21-7.23 (3H, m), 7.28-7.32 (2H, m), 7.63 (1H, dd, J=7.0, 10.2 Hz), 8.07 (1H, s).

MS (ESI) m/z: 438 [M+H]+.

Example 7

2,5-Difluoro-4-{[(1S*,2R*)-2-phenylcycloheptyl]oxy}-N-(1,2,4-thiadiazol-5-yl)benzenesulfonamide

[Formula 25]

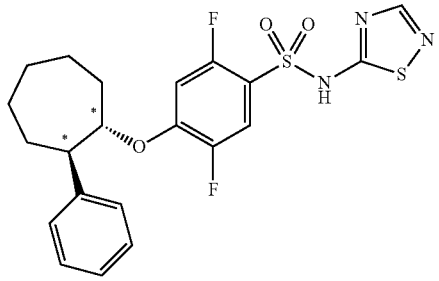

(7a) N-(2,4-Dimethoxybenzyl)-2,5-difluoro-4-{[(1S*,2R*)-2-phenylcycloheptyl]oxy}-N-(1,2,4-thiadiazol-5-yl)benzenesulfonamide The reaction and aftertreatment were conducted in the same manner as in Example 1a by using the N-(2,4-dimethoxybenzyl)-2,4,5-trifluoro-N-(1,2,4-thiadiazol-5-yl)benzenesulfonamide (WO 2010/079443; 350 mg, 0.786 mmol), (1S*,2R*)-2-phenylcycloheptanol (150 mg, 0.788 mmol), sodium hydride (63%; 60 mg, 1.58 mol) and DMSO (4.0 mL), to yield the title compound (140 mg, 29%) as a colorless oil.

$^1$H-NMR (400 MHz, CDCl$_3$) δ ppm: 1.49-1.68 (4H, m), 1.80-2.00 (6H, m), 3.04 (1H, dt, J=2.4, 9.4 Hz), 3.62 (3H, s), 3.73 (3H, s), 4.37-4.41 (1H, m), 5.20 (1H, d, J=15.7 Hz), 5.25 (1H, d, J=15.7 Hz), 6.16 (1H, d, J=2.4 Hz), 6.22 (1H, dd, J=6.3, 11.4 Hz), 6.33 (1H, dd, J=2.4, 8.2 Hz), 7.13-7.25 (6H, m), 7.34 (1H, dd, J=6.7, 10.2 Hz), 8.16 (1H, s).

(7b) 2,5-Difluoro-4-{[(1S*,2R*)-2-phenylcycloheptyl]oxy}-N-(1,2,4-thiadiazol-5-yl)benzenesulfonamide The reaction and aftertreatment were conducted in the same manner as in Example 1a by using the N-(2,4-dimethoxybenzyl)-2,5-difluoro-4-{[(1S*,2R*)-2-phenylcycloheptyl]oxy}-N-(1,2,4-thiadiazol-5-yl)benzenesulfonamide (140 mg, 0.227 mmol) prepared in Example 7a, triethylsilane (0.3 mL), trifluoroacetic acid (3.0 mL) and dichloromethane (3.0 mL), to yield the title compound (84.4 mg, 80%) as a colorless solid.

$^1$H-NMR (400 MHz, CDCl$_3$) δ ppm: 1.53-1.64 (4H, m), 1.81-2.01 (6H, m), 3.05 (1H, dt, J=1.6, 9.8 Hz), 4.38-4.43 (1H, m), 6.35 (1H, dd, J=6.3, 11.7 Hz), 7.10-7.24 (5H, m), 7.52 (1H, dd, J=6.7, 9.8 Hz), 8.04 (1H, s).

MS (ESI) m/z: 466 [M+H]+.

Example 8

2,5-Difluoro-4-{[(1S*,2R*)-2-(1-methyl-1H-pyrazol-5-yl)cyclopentyl]oxy}-N-(1,2,4-thiadiazol-5-yl)benzenesulfonamide

[Formula 26]

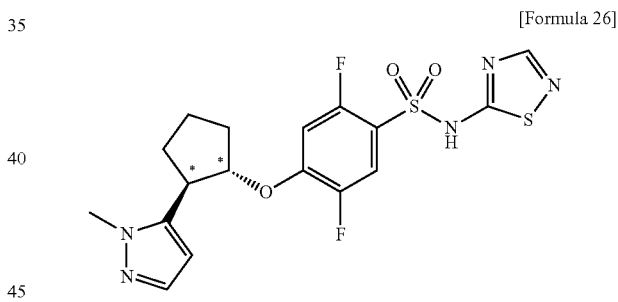

(8a) (1S*,2R*)-2-(1-Methyl-1H-pyrazol-5-yl)cyclopentanol

To a solution of 1-methylpyrazole (13.4 g, 163 mmol) in THF (1 L), n-butyl lithium (1.63 M solution in hexane; 100 mL, 163 mmol) was added dropwise at −78° C. for 40 minutes. To the reaction solution, cyclopentene oxide (15.1 g, 179 mmol) was added at −78° C., and the reaction solution was stirred at room temperature for 20 hours. To the reaction solution, a saturated aqueous solution of sodium hydrogencarbonate (100 mL) was added, followed by extraction with ethyl acetate (500 mL). The thus obtained organic layer was dried over anhydrous sodium sulfate. After vacuum concentration, the residue was purified with silica gel chromatography (dichloromethane/methanol=97:3) to yield the title compound (5.77 g, 21%) as a colorless oil.

$^1$H-NMR (500 MHz, CDCl$_3$) δ ppm: 1.63-1.91 (4H, m), 2.05-2.12 (1H, m), 2.17-2.24 (1H, m), 3.03 (1H, q, J=8.3 Hz), 3.86 (3H, s), 4.24 (1H, q, J=6.4 Hz), 6.03 (1H, s), 7.39 (1H, s).

(8b) N-(2,4-dimethoxybenzyl)-2,5-difluoro-4-{[(1S*,2R*)-2-(1-methyl-1H-pyrazol-5-yl)cyclopentyl]oxy}-N-(1,2,4-thiadiazol-5-yl)benzenesulfonamide The reaction and aftertreatment were conducted in the same manner as in Example 1a by using N-(2,4-dimethoxybenzyl)-2,4,5-trifluoro-N-(1,2,4-thiadiazol-5-yl)benzenesulfonamide (WO 2010/079443; 500 mg, 1.12 mmol), the (1S*,2R*)-2-(1-methyl-1H-pyrazol-5-yl)cyclopentanol (200 mg, 1.20 mmol) prepared in Example 8a, sodium hydride (63%; 100 mg, 2.63 mol) and DMSO (5.0 mL), to yield the title compound (340 mg, 51%) as a colorless oil.

$^1$H-NMR (400 MHz, CDCl$_3$) δ ppm: 1.76-1.99 (4H, m), 2.17-2.24 (1H, m), 2.27-2.35 (1H, m), 3.44-3.50 (1H, m), 3.71 (6H, s), 3.87 (3H, s), 4.57-4.61 (1H, m), 5.29 (2H, s), 6.06 (1H, d, J=2.0 Hz), 6.24 (1H, d, J=2.4 Hz), 6.34 (1H, dd, J=2.4, 8.2 Hz), 6.45 (1H, dd, J=6.3, 11.0 Hz), 7.16 (1H, d, J=8.3 Hz), 8.41 (1H, d, J=2.0 Hz), 7.53 (1H, dd, J=6.7, 10.2 Hz), 8.18 (1H, s).

(8c) 2,5-Difluoro-4-{[(1S*,2R*)-2-(1-methyl-1H-pyrazol-5-yl)cyclopentyl]oxy}-N-(1,2,4-thiadiazol-5-yl)benzenesulfonamide The reaction and aftertreatment were conducted in the same manner as in Example 1b by using the N-(2,4-dimethoxybenzyl)-2,5-difluoro-4-{[(1S*,2R*)-2-(1-methyl-1H-pyrazol-5-yl)cyclopentyl]oxy}-N-(1,2,4-thiadiazol-5-yl)benzenesulfonamide (340 mg, 0.574 mmol) prepared in Example 8b, triethylsilane (0.4 mL), trifluoroacetic acid (4.0 mL) and dichloromethane (4.0 mL), to yield the title compound (211 mg, 83%) as a colorless solid.

$^1$H-NMR (400 MHz, CDCl$_3$) δ ppm: 1.76-2.00 (4H, m), 2.18-2.35 (2H, m), 3.34-3.50 (1H, m), 3.87 (3H, s), 4.60-4.64 (1H, m), 6.07 (1H, d, J=1.6 Hz), 6.59 (1H, dd, J=6.3, 11.0 Hz), 7.43 (1H, d, J=2.0 Hz), 7.66 (1H, dd, J=6.7, 9.8 Hz), 8.07 (1H, s).

MS (ESI) m/z: 442 [M+H]+.

Example 9

2,5-Difluoro-4-{[(1S*,2R*)-2-(1-methyl-1H-pyrazol-5-yl)cycloheptyl]oxy}-N-(1,2,4-thiadiazol-5-yl)benzenesulfonamide

[Formula 27]

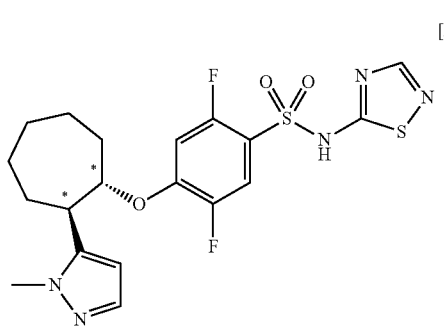

(9a) (1S*,2R*)-2-(1-Methyl-1H-pyrazol-5-yl)cycloheptanol

The reaction and aftertreatment were conducted in the same manner as in Example 4a by using 1-methylpyrazole (3.66 g, 44.6 mmol), N,N,N',N'-tetramethylethylenediamine (6.68 mL, 44.6 mmol), n-butyl lithium (1.63 M solution in hexane; 32 mL, 52.2 mmol), 1,2-epoxycycloheptane (5.0 g, 44.6 mmol) and THF (60 mL), to yield the title compound (1.13 g, 13%) as a colorless oil.

$^1$H-NMR (500 MHz, CDCl$_3$) δ ppm: 1.56-1.89 (9H, m), 1.98-2.05 (1H, m), 2.76-2.82 (1H, m), 3.80-3.86 (1H, m), 3.84 (3H, s), 6.06 (1H, d, J=2.0 Hz), 7.41 (1H, d, J=2.4 Hz).

(9b) N-(2,4-Dimethoxybenzyl)-2,5-difluoro-4-{[(1S*,2R*)-2-(1-methyl-1H-pyrazol-5-yl)cycloheptyl]oxy}-N-(1,2,4-thiadiazol-5-yl)benzenesulfonamide The reaction and aftertreatment were conducted in the same manner as in Example 1a by using the N-(2,4-dimethoxybenzyl)-2,4,5-trifluoro-N-(1,2,4-thiadiazol-5-yl)benzenesulfonamide (WO 2010/079443; 450 mg, 1.01 mmol), the (1S*,2R*)-2-(1-methyl-1H-pyrazol-5-yl)cycloheptanol (200 mg, 1.03 mmol) prepared in Example 9a, sodium hydride (63%; 100 mg, 2.63 mol) and DMSO (5.0 mL), to yield the title compound (146 mg, 23%) as a colorless oil.

$^1$H-NMR (400 MHz, CDCl$_3$) δ ppm: 1.58-1.97 (10H, m), 3.22 (1H, dt, J=2.7, 9.4 Hz), 3.65 (3H, s), 3.74 (3H, s), 3.89 (3H, s), 4.30-4.35 (1H, m), 5.23 (1H, d, J=16.0 Hz), 5.29 (1H, d, J=16.0 Hz), 6.01 (1H, d, J=2.0 Hz), 6.19 (1H, d, J=2.4 Hz), 6.31-6.35 (2H, m), 7.16 (1H, d, J=8.6 Hz), 7.35 (1H, d, J=1.6 Hz), 7.41 (1H, dd, J=6.7, 10.2 Hz), 8.18 (1H, s).

(9c) 2,5-Difluoro-4-{[(1S*,2R*)-2-(1-methyl-1H-pyrazol-5-yl)cycloheptyl]oxy}-N-(1,2,4-thiadiazol-5-yl)benzenesulfonamide The reaction and aftertreatment were conducted in the same manner as in Example 1b by using the N-(2,4-dimethoxybenzyl)-2,5-difluoro-4-{[(1S*,2R*)-2-(1-methyl-1H-pyrazol-5-yl)cycloheptyl]oxy}-N-(1,2,4-thiadiazol-5-yl)benzenesulfonamide (146 mg, 0.236 mmol) prepared in Example 9b, triethylsilane (0.3 mL), trifluoroacetic acid (3.0 mL) and dichloromethane (3.0 mL), to yield the title compound (86.0 mg, 78%) as a colorless solid.

$^1$H-NMR (400 MHz, DMSO-d$_6$) δ ppm: 1.54-1.91 (10H, m), 3.26-3.29 (1H, m), 3.77 (3H, s), 4.78-4.82 (1H, m), 6.12 (1H, s), 7.20 (1H, s), 7.28 (1H, dd, J=6.3, 11.7 Hz), 7.54 (1H, dd, J=6.7, 10.2 Hz), 8.52 (1H, s).

MS (ESI) m/z: 470 [M+H]+.

Example 10

5-Chloro-2-fluoro-4-{[(1S*,2R*)-2-(1-methyl-1H-pyrazol-5-yl)cyclohexyl]oxy}-N-(1,3-thiazol-4-yl)benzenesulfonamide Na salt

[Formula 28]

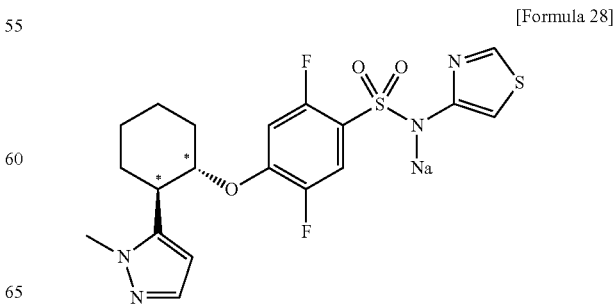

(10a) Tert-butyl[(5-chloro-2-fluoro-4-{[(1S*,2R*)-2-(1-methyl-1H-pyrazol-5-yl)cyclohexyl]oxy}phenyl)sulfonyl](1,3-thiazol-4-yl) carbamic acid The reaction and aftertreatment were conducted in the same manner as in Example 1a by using the tert-butyl[(5-chloro-2,4-difluorophenyl)sulfonyl](1,3-thiazol-4-yl) carbamic acid (WO 2010/079443; 479 mg, 1.17 mmol), the (1S*,2R*)-2-(1-methyl-1H-pyrazol-5-yl)cyclohexanol (200 mg, 1.11 mmol) prepared in Example 4a, sodium hydride (63%; 84.5 mg, 2.22 mol) and DMF (10 mL), to yield the title compound (367 mg, 58%) as a colorless oil.

$^1$H-NMR (400 MHz, CDCl$_3$) δ ppm: 1.34 (9H, s), 1.40-1.67 (4H, m), 1.86-1.89 (1H, m), 1.94-1.96 (1H, m), 2.05-2.08 (1H, m), 2.21-2.25 (1H, m), 3.02-3.09 (1H, m), 3.93 (3H, s), 4.21 (1H, dt, J=3.9, 10.2 Hz), 6.03 (1H, d, J=2.0 Hz), 6.55 (1H, d, J=11.7 Hz), 7.34 (1H, d, J=1.6 Hz), 7.48 (1H, d, J=2.0 Hz), 8.00 (1H, d, J=7.4 Hz), 8.77 (1H, d, J=2.4 Hz).

(10b) 5-Chloro-2-fluoro-4-{[(1S*,2R*)-2-(1-methyl-1H-pyrazol-5-yl)cyclohexyl]oxy}-N-(1,3-thiazol-4-yl)benzenesulfonamide The reaction and aftertreatment were conducted in the same manner as in Example 1b by using the tert-butyl[(5-chloro-2-fluoro-4-{[(1S*,2R*)-2-(1-methyl-1H-pyrazol-5-yl)cyclohexyl]oxy}phenyl)sulfonyl](1,3-thiazol-4-yl) carbamic acid (367 mg, 0.643 mmol) prepared in Example 10a, trifluoroacetic acid (1.0 mL) and dichloromethane (1.0 mL), to yield the title compound (304 mg, 99%) as a colorless solid.

$^1$H-NMR (400 MHz, CDCl$_3$) δ ppm: 1.38-1.69 (4H, m), 1.85-1.89 (1H, m), 1.92-1.95 (1H, m), 2.05-2.07 (1H, m), 2.18-2.21 (1H, m), 3.00-3.06 (1H, m), 3.92 (3H, s), 4.10-4.16 (1H, m), 6.02 (1H, d, J=2.0 Hz), 6.48 (1H, d, J=11.7 Hz), 6.89 (1H, d, J=2.4 Hz), 7.34 (1H, d, J=2.0 Hz), 7.80 (1H, d, J=2.4 Hz), 8.74 (1H, d, J=2.4 Hz), 11.36 (1H, brs).

(10c) 5-Chloro-2-fluoro-4-{[(1S*,2R*)-2-(1-methyl-1H-pyrazol-5-yl)cyclohexyl]oxy}-N-(1,3-thiazol-4-yl)benzenesulfonamide Na salt The reaction and aftertreatment were conducted in the same manner as in Example 5c by using the 5-Chloro-2-fluoro-4-{[(1S*,2R*)-2-(1-methyl-1H-pyrazol-5-yl)cyclohexyl]oxy}-N-(1,3-thiazol-4-yl)benzenesulfonamide (303 mg, 0.643 mmol) prepared in Example 10b, a 1 M sodium hydroxide solution (0.643 mL, 0.643 mol), to yield the title compound (300 mg, 95%) as a colorless solid.

$^1$H-NMR (400 MHz, CD$_3$OD) δ ppm: 1.44-1.60 (3H, m), 1.66-1.77 (1H, m), 1.85-1.90 (2H, m), 1.97-2.01 (1H, m), 2.21-2.24 (1H, m), 3.07-3.14 (1H, m), 3.89 (3H, s), 4.36-4.42 (1H, m), 6.15 (1H, d, J=2.0 Hz), 6.28-6.30 (1H, m), 6.80 (1H, d, J=11.7 Hz), 7.28 (1H, s), 7.71 (1H, d, J=7.4 Hz), 8.54 (1H, d, J=2.4 Hz).

MS (ESI) m/z: 471 [M+H]+

Example 11

5-Chloro-2-fluoro-4-{[(1S*,2R*)-2-(1-methyl-1H-pyrazol-5-yl)cyclopentyl]oxy}-N-(1,3-thiazol-4-yl)benzenesulfonamide Na salt

[Formula 29]

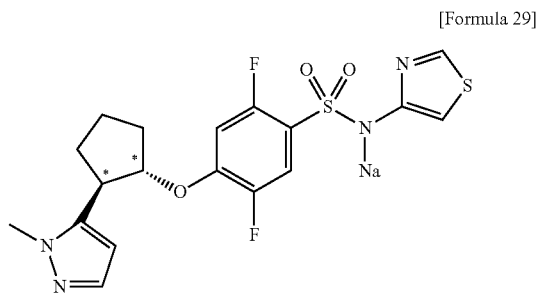

Tert-butyl[(5-chloro-2-fluoro-4-{[(1S*,2R*)-2-(1-methyl-1H-pyrazol-5-yl)cyclopentyl]oxy}phenyl)sulfonyl](1,3-thiazol-4-yl)carbamate The reaction and aftertreatment were conducted in the same manner as in Example 1a by using tert-butyl [(5-chloro-2,4-difluorophenyl)sulfonyl](1,3-thiazol-4-yl)carbamate (WO 2010/079443; 600 mg, 1.46 mmol), the (1S*,2R*)-2-(1-methyl-1H-pyrazol-5-yl)cyclopentanol (270 mg, 1.62 mmol) prepared in Example 8a, sodium hydride (63%; 110 mg, 2.89 mmol) and DMF (6.0 mL), to yield the title compound (520 mg, 64%) as a colorless oil.

$^1$H-NMR (500 MHz, CDCl$_3$) δ ppm: 1.38 (9H, s), 1.80-2.01 (4H, m), 2.24-2.36 (2H, m), 3.50-3.55 (1H, m), 3.91 (3H, s), 4.67-4.70 (1H, m), 6.08 (1H, d, J=2.0 Hz), 6.60 (1H, d, J=11.2 Hz), 7.42 (1H, d, J=1.5 Hz), 7.51 (1H, d, J=2.4 Hz), 8.11 (1H, d, J=7.3 Hz), 8.79 (1H, d, J=2.4 Hz).

(11b) 5-Chloro-2-fluoro-4-{[(1S*,2R*)-2-(1-methyl-1H-pyrazol-5-yl)cyclopentyl]oxy}-N-(1,3-thiazol-4-yl)benzenesulfonamide The reaction and aftertreatment were conducted in the same manner as in Example 1b by using the tert-butyl [(5-chloro-2-fluoro-4-{[(1S*,2R*)-2-(1-methyl-1H-pyrazol-5-yl)cyclopentyl]oxy}phenyl)sulfonyl](1,3-thiazol-4-yl)carbamate (520 mg, 0.934 mmol) prepared in Example 11a, trifluoroacetic acid (5.0 mL) and dichloromethane (5.0 mL), to yield the title compound (427 mg, 99%) as a colorless solid.

$^1$H-NMR (500 MHz, CDCl$_3$) δ ppm: 1.78-1.95 (4H, m), 2.18-2.33 (2H, m), 3.46-3.50 (1H, m), 3.87 (3H, s), 4.58-4.61 (1H, m), 6.04 (1H, d, J=2.0 Hz), 6.51 (1H, d, J=11.2 Hz), 6.92 (1H, s), 7.39 (1H, s), 7.87 (1H, d, J=7.3 Hz), 7.84 (1H, d, J=2.4 Hz), 11.2 (1H, brs).

(11c) 5-Chloro-2-fluoro-4-{[(1S*,2R*)-2-(1-methyl-1H-pyrazol-5-yl)cyclopentyl]oxy}-N-(1,3-thiazol-4-yl)benzenesulfonamide Na salt The reaction and aftertreatment were conducted in the same manner as in Example 5c by using the 5-chloro-2-fluoro-4-{[(1S*,2R*)-2-(1-methyl-1H-pyrazol-5-yl)cyclopentyl]oxy}-N-(1,3-thiazol-4-yl)benzenesulfonamide (427 g, 0.934 mmol) prepared in Example 11b and a 2 M aqueous sodium hydroxide solution (0.467 mL, 0.934 mol), to yield the title compound (412 mg, 92%) as a colorless solid.

$^1$H-NMR (500 MHz, DMSO-$d_6$) δ ppm: 1.59-1.71 (2H, m), 1.78-1.84 (2H, m), 2.18-2.25 (2H, m), 3.42-3.46 (1H, m), 3.77 (3H, s), 4.84-4.87 (1H, m), 5.96-5.98 (1H, m), 6.16 (1H, d, J=2.0 Hz), 6.97 (1H, d, J=11.2 Hz), 7.29 (1H, d, J=2.0 Hz), 7.66 (1H, d, J=7.3 Hz), 7.55 (1H, d, J=2.0 Hz).

MS (ESI) m/z: 457 [M+H]+.

Example 12

5-Chloro-4-{[(1S*,2R*)-2-(1-ethyl-1H-pyrazol-5-yl)cyclohexyl]oxy}-2-fluoro-N-(1,3-thiazol-4-yl)benzenesulfonamide

[Formula 30]

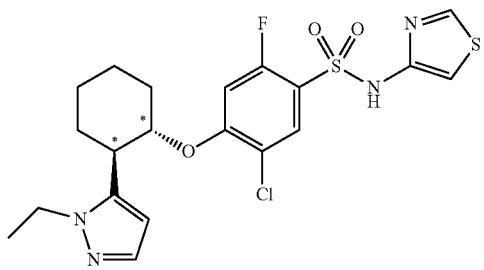

(12a) (1S*,2R*)-2-(1-Ethyl-1H-pyrazol-5-yl)cyclohexanol

The reaction and aftertreatment were conducted in the same manner as in Example 4a by using 1-ethylpyrazole (2.50 g, 26.0 mmol), butyl lithium (1.63 M solution in hexane; 18.1 mL, 29.5 mmol), cyclohexene oxide (2.97 g, 30.3 mmol) and THF (60 mL), to yield the title compound (2.86 g, 57%) as a colorless oil.

$^1$H-NMR (400 MHz, CDCl$_3$) δ ppm: 1.30-1.47 (4H, m), 1.43 (3H, t, J=7.4 Hz), 1.66 (1H, brs), 1.76-1.79 (1H, m), 1.87-1.90 (2H, m), 2.10-2.13 (1H, m), 2.56-2.62 (1H, m), 3.61-3.66 (1H, m), 4.10-4.26 (2H, m), 6.07 (1H, d, =J2.0 Hz), 7.47 (1H, d, J=1.6 Hz).

(12b) Tert-butyl[(5-chloro-2-fluoro-4-{[(1S*,2R*)-2-(1-ethyl-1H-pyrazol-5-yl)cyclopentyl]oxy}phenyl)sulfonyl](1,3-thiazol-4-yl)carbamic acid The reaction and aftertreatment were conducted in the same manner as in Example 1a by using the tert-butyl[(5-chloro-2,4-difluorophenyl)sulfonyl](1,3-thiazol-4-yl)carbamic acid (WO 2010/079443; 222 mg, 0.540 mmol), (1S*,2R*)-2-(1-ethyl-1H-pyrazol-5-yl)cyclohexanol (100 mg, 0.515 mmol) prepared in Example 12a, sodium hydride (63%; 39.2 mg, 1.03 mmol) and DMF (5.0 mL), to yield the title compound (125 mg, 41%) as a colorless oil.

$^1$H-NMR (400 MHz, CDCl$_3$) δ ppm: 1.35 (9H, s), 1.44 (3H, t, J=7.4 Hz), 1.44-1.70 (4H, m), 1.87-1.90 (1H, m), 1.96-1.98 (1H, m), 2.05-2.09 (1H, m), 2.24-2.27 (1H, m), 3.04-3.10 (1H, m), 4.12-4.34 (3H, m), 6.04 (1H, s), 6.59 (1H, d, J=11.7 Hz), 7.38 (1H, s), 7.50 (1H, s), 8.01 (1H, d, J=8.6 Hz), 8.79 (1H, s).

(12c) 5-Chloro-2-fluoro-4-{[(1S*,2R*)-2-(1-ethyl-1H-pyrazol-5-yl)cyclopentyl]oxy}-N-(1,3-thiazol-4-yl)benzenesulfonamide The reaction and aftertreatment were conducted in the same manner as in Example 1b by using the tert-butyl[(5-chloro-2-fluoro-4-{[(1S*,2R*)-2-(1-ethyl-1H-pyrazol-5-yl)cyclopentyl]oxy}phenyl)sulfonyl](1,3-thiazol-4-yl)carbamic acid (125 mg, 0.213 mmol) prepared in Example 12b, trifluoroacetic acid (1.0 mL) and dichloromethane (1.0 mL), to yield the title compound (70.0 mg, 68%) as a colorless solid.

$^1$H-NMR (400 MHz, CDCl$_3$) δ ppm: 1.41 (3H, t, J=7.0 Hz), 1.46-1.67 (4H, m), 1.84-1.87 (1H, m), 1.91-1.94 (1H, m), 2.03-2.06 (1H, m), 2.19-2.22 (1H, m), 3.00-3.06 (1H, m), 4.10-4.21 (2H, m), 4.28-4.37 (1H, m), 6.00 (1H, d, J=2.0 Hz), 6.49 (1H, d, J=11.7 Hz), 6.88 (1H, d, J=2.0 Hz), 7.37 (1H, d, J=2.0 Hz), 7.80 (1H, d, J=7.4 Hz), 8.75 (1H, d, J=2.0 Hz), 11.40 (1H, brs).

MS (ESI) m/z: 485 [M+H]+.

Example 13

5-chloro-2-fluoro-4-{[(1S*,2S*)-2-(1H-imidazol-1-yl)cyclohexyl]oxy}-N-(1,3-thiazol-4-yl)benzenesulfonamide

[Formula 31]

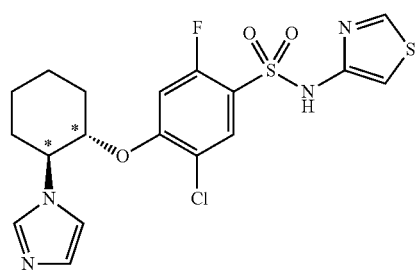

(13a) Tert-butyl[(5-chloro-2-fluoro-4-{[(1S*,2R*)-2-(1H-imidazol-1-yl)cyclohexyl]oxy}phenyl)sulfonyl](1,3-thiazol-4-yl)carbamic acid The reaction and aftertreatment were conducted in the same manner as in Example 1a by using the tert-butyl[(5-chloro-2,4-difluorophenyl)sulfonyl](1,3-thiazol-4-yl) carbamic acid (WO 2010/079443; 390 mg, 0.949 mmol), (1S*,2R*)-2-(1H-imidazol-1-yl)cyclohexanol (Heterocycles, 31(3), 537-48, 1990; 160 mg, 0.963 mmol), sodium hydride (63%; 75.0 mg, 1.97 mmol) and DMF (4.0 mL), to yield the title compound (340 mg, 64%) as a colorless oil.

$^1$H-NMR (400 MHz, CDCl$_3$) δ ppm: 1.36 (9H, s), 1.50-1.65 (3H, m), 1.87-2.00 (3H, m), 2.30-2.35 (2H, m), 4.21-4.28 (2H, m), 6.46 (1H, d, J=11.0 Hz), 7.01 (2H, d, J=1.2 Hz), 7.49 (1H, d, J=2.0 Hz), 7.63 (1H, s), 8.03 (1H, d, J=7.4 Hz), 8.78 (1H, d, J=2.4 Hz).

(13b) 5-Chloro-2-fluoro-4-{[(1S*,2S*)-2-(1H-imidazol-1-yl)cyclohexyl]oxy}-N-(1,3-thiazol-4-yl)benzenesulfonamide The reaction and aftertreatment were conducted in the same manner as in Example 1b by using the tert-butyl[(5-chloro-2-fluoro-4-{[(1S*,2R*)-2-(1H-imidazol-1-yl)cyclohexyl]oxy}phenyl)sulfonyl](1,3-thiazol-4-yl) carbamic acid (340 mg, 0.610 mmol) prepared in Example 13a, trifluoroacetic acid (5.0 mL) and dichloromethane (5.0 mL), to yield the title compound (292 mg, 67%) as a colorless solid.

¹H-NMR (400 MHz, CDCl₃) δ ppm: 1.48-1.60 (4H, m), 1.90-1.95 (1H, m), 2.03-2.05 (1H, m), 2.25-2.37 (2H, m), 4.30-4.37 (1H, m), 4.65-4.72 (1H, m), 6.70 (1H, d, J=11.0 Hz), 6.93 (1H, d, J=2.4 Hz), 7.25-7.28 (2H, m), 7.84 (1H, d, J=7.4 Hz), 8.71 (1H, d, J=2.4 Hz), 9.25 (1H, brs).

MS (ESI) m/z: 457 [M+H]+.

Example 14

2,5-Difluoro-4-{[(1S*,2R*)-2-(1-methyl-1H-pyrazol-5-yl)cyclopentyl]oxy}-N-(pyrimidin-4-yl)benzenesulfonamide

[Formula 32]

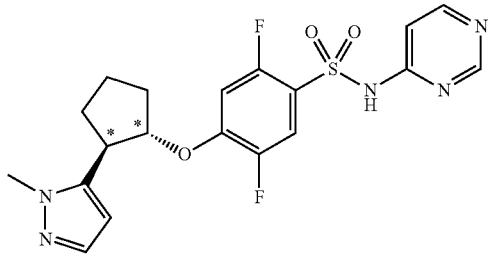

(14a) N-(2,4-dimethoxybenzyl)pyrimidin-4-amine

A solution of 4-aminopyrimidine (20.0 g, 210 mmol), 2,4-dimethoxybenzaldehyde (69.9 g, 421 mmol) and piperidine (2.08 mL, 21.0 mmol) in toluene (1 L) was stirred for 7 hours under reflux, and the solvent was subjected to azeotropic distillation with water. After allowing to cool, the reaction solution was diluted with ethanol (500 mL). Sodium borohydride (7.96 g, 210 mmol) was added thereto with cooling on ice, and the mixture was stirred at room temperature for 16 hours. To the reaction solution, water (500 mL) was added, and an organic layer was extracted. The thus obtained organic layer was dried over anhydrous sodium sulfate. After vacuum concentration, the residue was purified with silica gel chromatography (ethyl acetate/methanol=95:5) to yield the title compound (27.0 g, 52%) as a colorless solid.

¹H-NMR (500 MHz, CDCl₃) δ ppm: 3.80 (3H, s), 3.84 (3H, s), 4.44 (2H, brs), 5.33 (1H, brs), 6.34 (1H, d, J=5.9 Hz), 6.44 (1H, dd, J=2.4, 8.3 Hz), 6.48 (1H, d, J=2.0 Hz), 7.18 (1H, d, J=8.3 Hz), 8.15 (1H, d, J=5.4 Hz), 8.55 (1H, s).

(14b) N-(2,4-dimethoxybenzyl)-2,4,5-trifluoro-N-(pyrimidin-4-yl)benzenesulfonamide To a solution of the N-(2,4-dimethoxybenzyl)pyrimidin-4-amine (0.76 g, 3.10 mmol) prepared in Example 14a and 1,4-diazabicyclo[2.2.2]octane (0.70 g, 6.20 mmol) in acetonitrile (20 mL), 2,4,5-trifluorobenzenesulfonyl chloride (1.43 g, 6.20 mmol) was added with cooling on ice, and the reaction solution was stirred at room temperature for 1 hour. The reaction solution was filtered, the filtrate was vacuum concentrated, and the residue was purified with silica gel chromatography (hexane/ethyl acetate=67:33) to yield the title compound (0.72 g, 53%) as a colorless solid.

¹H-NMR (500 MHz, CDCl₃) δ ppm: 3.78 (3H, s), 3.80 (3H, s), 5.23 (2H, s), 6.42-6.43 (2H, m), 6.99-7.04 (1H, m), 7.13 (1H, d, J=5.9 Hz), 7.22 (1H, d, J=9.3 Hz), 7.91-7.96 (1H, m), 8.48 (1H, d, J=6.4 Hz), 8.78 (1H, s).

(14c) N-(2,4-dimethoxybenzyl)-2,5-difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (0.76 g, 1.73 mmol) prepared in Example 14b, the (1S*,2R*)-2-(1-methyl-1H-pyrazol-5-yl)cyclopentanol (0.29 g, 1.73 mmol) prepared in Example 8a, sodium hydride (63%; 100 mg, 2.59 mmol) and DMF (10 mL), to yield the title compound (0.89 g, 88%) as a colorless oil.

¹H-NMR (500 MHz, CDCl₃) δ ppm: 1.78-1.97 (4H, m), 2.20-2.33 (2H, m), 3.45-3.49 (1H, m), 3.77 (3H, s), 3.79 (3H, s), 3.86 (3H, s), 4.60-4.64 (1H, m), 5.23 (2H, s), 6.05 (1H, d, J=2.0 Hz), 6.40-6.42 (2H, m), 6.52 (1H, dd, J=5.9, 10.7 Hz), 7.18-7.20 (2H, m), 7.40 (1H, d, J=2.0 Hz), 7.76 (1H, dd, J=6.4, 10.3 Hz), 8.45 (1H, d, J=5.9 Hz), 8.78 (1H, s).

(14d) 2,5-Difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[((1S*,2R*)-2-(1-methyl-1H-pyrazol-5-yl)cyclopentyl]oxy}-N-(pyrimidin-4-yl)benzenesulfonamide (0.54 g, 1.24 mmol) prepared in Example 14c, triethylsilane (1.98 mL, 12.4 mmol), trifluoroacetic acid (0.96 mL, 12.4 mmol) and dichloromethane (20 mL), to yield the title compound (0.54 g, 99%) as a colorless solid.

¹H-NMR (500 MHz, DMSO-d₆) δ ppm: 1.66-1.83 (4H, m), 2.19-2.27 (2H, m), 3.47-3.51 (1H, m), 3.76 (3H, s), 4.92-4.95 (1H, m), 6.17 (1H, s), 6.97 (1H, brs), 7.20-7.24 (1H, m), 7.30 (1H, s), 7.68-7.71 (1H, m), 8.25 (1H, brs), 8.57 (1H, s).

MS (ESI) m/z: 436 [M+H]+.

Example 15

2,5-Difluoro-4-{[(1S*,2R*)-2-(1-methyl-1H-pyrazol-5-yl)cyclopentyl]oxy}-N-(1,3-thiazol-2-yl)benzenesulfonamide

[Formula 33]

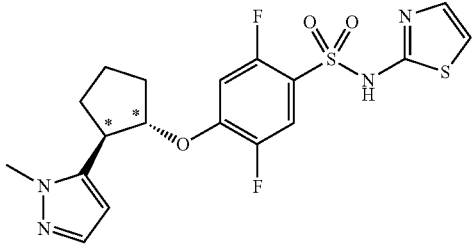

(15a) N-(2,4-dimethoxybenzyl)-2,4,5-trifluoro-N-(1,3-thiazol-2-yl)benzenesulfonamide To a solution of N-(2,4-dimethoxybenzyl)-N-(1,3-thiazol)-2-amine (WO 2010/035166; 1.00 g, 4.00 mmol) in THF (12 mL), LiHMDS (1.0 M in THF, 4.8 mL, 4.8 mmol) was added at −78° C. The reaction solution was stirred at −78° C. for 5 minutes. Then, 2,4,5-trifluorobenzenesulfonyl chloride (1.05 g, 4.42 mmol) was added thereto, and the mixture was stirred at room temperature for 2 hours. Water (100 mL) was added to the reaction solution, followed by extraction with ethyl acetate (50 mL). The thus obtained organic layer was washed twice with water (200 mL) and dried over anhydrous sodium sulfate. After vacuum concentration, the residue was purified with silica gel chromatography (hexane/ethyl acetate=4:1) to yield the title compound (960 mg, 54%) as a colorless oil.

$^1$H-NMR (400 MHz, CDCl$_3$) δ ppm: 3.73 (3H, s), 3.77 (3H, s), 5.19 (2H, s), 6.36-6.39 (2H, m), 7.01-7.07 (2H, m), 7.19 (1H, d, J=8.2 Hz), 7.42 (1H, d, J=3.5 Hz), 7.70-7.76 (1H, m).

(15b) N-(2,4-Dimethoxybenzyl)-2,5-difluoro-4-{[(1S*,2R*)-2-(1-methyl-1H-pyrazol-5-yl)cyclopentyl]oxy}-N-(1,3-thiazol-2-yl)benzenesulfonamide The reaction and aftertreatment were conducted in the same manner as in Example 1a by using the N-(2,4-dimethoxybenzyl)-2,4,5-trifluoro-N-(1,3-thiazol-2-yl)benzenesulfonamide (184 mg, 0.414 mmol) prepared in Example 15a, (1S*,2R*)-2-(1-methyl-1H-pyrazol-5-yl)cyclopentanol (68.7 mg, 0.414 mmol) prepared in Example 8a, sodium hydride (63%; 31.6 mg, 0.830 mol) and DMF (2.0 mL), to yield the title compound (180 mg, 73%) as a colorless oil.

$^1$H-NMR (500 MHz, CDCl$_3$) δ ppm: 1.76-1.83 (1H, m), 1.88-1.98 (3H, m), 2.19-2.25 (1H, m), 2.27-2.33 (1H, m), 3.44-3.49 (1H, m), 3.73 (3H, s), 3.75 (3H, s), 3.86 (3H, s), 4.61-4.64 (1H, m), 5.18 (2H, s), 6.05 (1H, d, J=2.0 Hz), 6.36-6.38 (2H, m), 6.56 (1H, dd, J=6.4, 11.2 Hz), 6.98 (1H, d, J=3.4 Hz), 7.19 (1H, d, J=8.3 Hz), 7.38-7.41 (2H, m), 7.58 (1H, dd, J=6.4, 10.3 Hz).

(15c) 2,5-Difluoro-4-{[((1S*,2R*)-2-(1-methyl-1H-pyrazol-5-yl)cyclopentyl]oxy}-N-(1,3-thiazol-2-yl)benzenesulfonamide The reaction and aftertreatment were conducted in the same manner as in Example 1b by using the 2,4-dimethoxybenzyl)-2,5-difluoro-4-{[(1S*,2R*)-2-(1-methyl-1H-pyrazol-5-yl)cyclopentyl]oxy}-N-(1,3-thiazol-2-yl)benzenesulfonamide (180 mg, 0.305 mmol) prepared in Example 15b, triethylsilane (0.1 mL), trifluoroacetic acid (1.0 mL) and dichloromethane (1.0 mL), to yield the title compound (110 mg, 82%) as a colorless solid.

$^1$H-NMR (500 MHz, CDCl$_3$) δ ppm: 1.77-1.96 (4H, m), 2.19-2.23 (1H, m), 2.27-2.32 (1H, m), 3.44-3.48 (1H, m), 3.86 (3H, s), 4.59-4.62 (1H, m), 6.05 (1H, s), 6.54-6.57 (2H, m), 7.17 (1H, d, J=4.4 Hz), 7.40 (1H, s), 7.71 (1H, dd, J=6.4, 9.8 Hz).

MS (ESI) m/z: 441 [M+H]+.

Example 16

3-Fluoro-4-{[(1S*,2R*)-2-(1-methyl-1H-pyrazol-5-yl)cyclopentyl]oxy}-N-(1,3-thiazol-2-yl)benzenesulfonamide

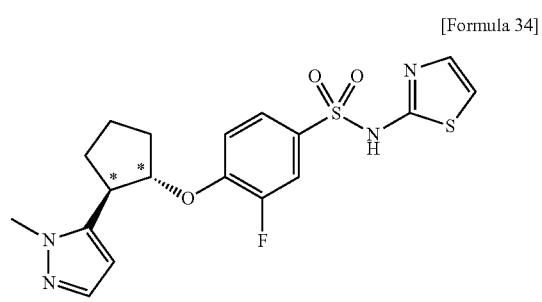 [SMILES: Cn1nccc1[C@H]1CCC[C@@H]1Oc1ccc(S(=O)(=O)Nc2nccs2)cc1F]

[Formula 34]

(16a) N-(2,4-dimethoxybenzyl)-3,4-difluorobenzenesulfonamide

To a solution of 2,4-dimethoxybenzylamine (3.35 mL, 22.3 mmol) and pyridine (9.02 mL, 111.5 mmol) in dichloromethane (75 mL), 3,4-difluorobenzenesulfonyl chloride (3.04 mL, 22.3 mmol) was added with cooling on ice, and the reaction solution was stirred at room temperature for 16 hours. To the reaction solution, 2 M hydrochloric acid (100 mL) was added, and an organic layer was extracted. The thus obtained organic layer was dried over anhydrous sodium sulfate and vacuum concentrated to yield the title compound (7.66 g, 99%) as a colorless solid.

$^1$H-NMR (400 MHz, CDCl$_3$) δ ppm: 3.72 (3H, s), 3.77 (3H, s), 4.14 (2H, d, J=6.3 Hz), 5.13 (1H, t, J=5.9 Hz), 6.29 (1H, d, J=2.4 Hz), 6.33 (1H, dd, J=2.4, 8.2 Hz), 6.94 (1H, d, J=8.2 Hz), 7.13-7.19 (1H, m), 7.47-7.53 (2H, m).

(16b) N-(2,4-dimethoxybenzyl)-3-fluoro-4-{[(1S*,2R*)-2-(1-methyl-1H-pyrazol-5-yl)cyclopentyl]oxy}benzenesulfonamide The reaction and aftertreatment were conducted in the same manner as in Example 1a by using the N-(2,4-dimethoxybenzyl)-3,4-difluorobenzenesulfonamide (1.00 g, 2.91 mmol) prepared in Example 16a, the (1S*,2R*)-2-(1-methyl-1H-pyrazol-5-yl)cyclopentanol (0.73 g, 4.37 mmol) prepared in Example 8a, sodium hydride (63%; 0.55 g, 14.6 mmol) and DMF (15 mL), to yield the title compound (920 mg, 65%) as a colorless solid.

$^1$H-NMR (400 MHz, CDCl$_3$) δ ppm: 1.78-1.99 (4H, m), 2.16-2.34 (2H, m), 3.43-3.49 (1H, m), 3.69 (3H, s), 3.72 (3H, s), 3.87 (3H, s), 4.08 (2H, d, J=6.3 Hz), 4.64-4.68 (1H, m), 5.24 (1H, t, J=6.3 Hz), 6.07 (1H, d, J=2.0 Hz), 6.26 (1H, d, J=2.0 Hz), 6.30 (1H, dd, J=2.0, 8.2 Hz), 6.73 (1H, t, J=8.6 Hz), 6.95 (1H, d, J=8.2 Hz), 7.40-7.43 (3H, m).

MS (ESI) m/z: 490 [M+H]+.

(16c) 3-Fluoro-4-{[(1S*,2R*)-2-(1-methyl-1H-pyrazol-5-yl)cyclopentyl]oxy}benzenesulfonamide The reaction and aftertreatment were conducted in the same manner as in Example 1b by using the N-(2,4-dimethoxybenzyl)-3-fluoro-4-{[(1S*,2R*)-2-(1-methyl-1H-pyrazol-5-yl)cyclopentyl]oxy}benzenesulfonamide (0.92 g, 1.88 mmol) prepared in Example 16b, triethylsilane (1.5 mL), trifluoroacetic acid (15 mL) and dichloromethane (15 mL), to yield the title compound (0.60 g, 94%) as a colorless solid.

$^1$H-NMR (400 MHz, CDCl$_3$) δ ppm: 1.77-1.97 (4H, m), 2.18-2.36 (2H, m), 3.44-3.50 (1H, m), 3.86 (3H, s), 4.70-4.74 (1H, m), 6.07 (1H, d, J=1.6 Hz), 6.86 (1H, t, J=8.2 Hz), 7.41 (1H, d, J=2.0 Hz), 7.60-7.64 (2H, m).

(16d) 3-Fluoro-4-{[(1S*,2R*)-2-(1-methyl-1H-pyrazol-5-yl)cyclopentyl]oxy}-N-(1,3-thiazol-2-yl)benzenesulfonamide A solution of the 3-fluoro-4-{[(1S*,2R*)-2-(1-methyl-1H-pyrazol-5-yl)cyclopentyl]oxy}benzenesulfonamide (0.07 g, 0.21 mmol) prepared in Example 16c, 2-bromothiazole (0.07 g, 0.41 mmol), copper iodide (0.01 g, 0.04 mmol), trans-N,N'-dimethylcyclohexane-1,2-diamine (0.01 g, 0.09 mmol) and cesium carbonate (0.20 g, 0.62 mmol) in DMF (2.0 mL) was stirred at 120° C. for 20 hours under the nitrogen atmosphere. After allowing to cool, the reaction solution was vacuum concentrated, and the residue was purified with HPLC to yield the title compound (75 mg, 86%) as a colorless solid.

$^1$H-NMR (400 MHz, CDCl$_3$) δ ppm: 1.78-1.98 (4H, m), 2.20-2.36 (2H, m), 3.42-3.49 (1H, m), 3.90 (3H, s), 4.66-4.69 (1H, m), 6.11 (1H, s), 6.54 (1H, d, J=6.7 Hz), 6.83 (1H, t, J=8.2 Hz), 7.14 (1H, d, J=4.7 Hz), 7.48 (1H, s), 7.58-7.63 (2H, m).

MS (ESI) m/z: 423 [M+H]+.

Example 17

3-Fluoro-N-(6-fluoropyrimidin-4-yl)-4-{[(1S*,2R*)-2-(1-methyl-1H-pyrazol-5-yl)cyclopentyl]oxy}benzenesulfonamide

[Formula 35]

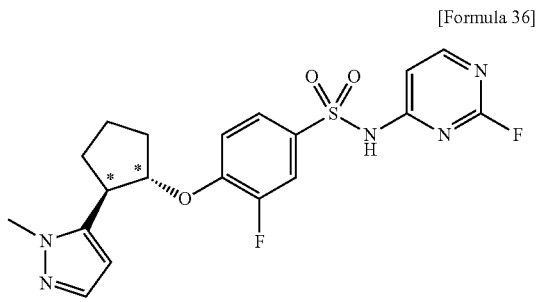 [SMILES: Cn1nccc1[C@H]1CCC[C@@H]1Oc1ccc(S(=O)(=O)Nc2ccnc(F)n2)cc1F]

The reaction and aftertreatment were conducted in the same manner as in Example 16d by using the 3-fluoro-4-{[(1S*,2R*)-2-(1-methyl-1H-pyrazol-5-yl)cyclopentyl]oxy}benzenesulfonamide (0.07 g, 0.21 mmol) prepared in Example 16c, 4,6-difluoropyrimidine (0.07 g, 0.62 mmol), potassium carbonate (0.11 g, 0.83 mmol) and DMF (2.0 mL), to yield the title compound (56 mg, 63%) as a colorless solid.

$^1$H-NMR (400 MHz, CDCl$_3$) δ ppm: 1.76-1.98 (4H, m), 2.23-2.36 (2H, m), 3.44-3.49 (1H, m), 3.85 (3H, s), 4.69-4.72 (1H, m), 6.06 (1H, d, J=1.6 Hz), 6.85 (1H, s), 6.88 (1H, t, J=8.2 Hz), 7.41 (1H, d, J=2.0 Hz), 7.61-7.67 (2H, m), 8.63 (1H, s).

MS (ESI) m/z: 436 [M+H]+.

Example 18

3-Fluoro-N-(2-fluoropyrimidin-4-yl)-4-{[(1S*,2R*)-2-(1-methyl-1H-pyrazol-5-yl)cyclopentyl]oxy}benzenesulfonamide

[Formula 36]

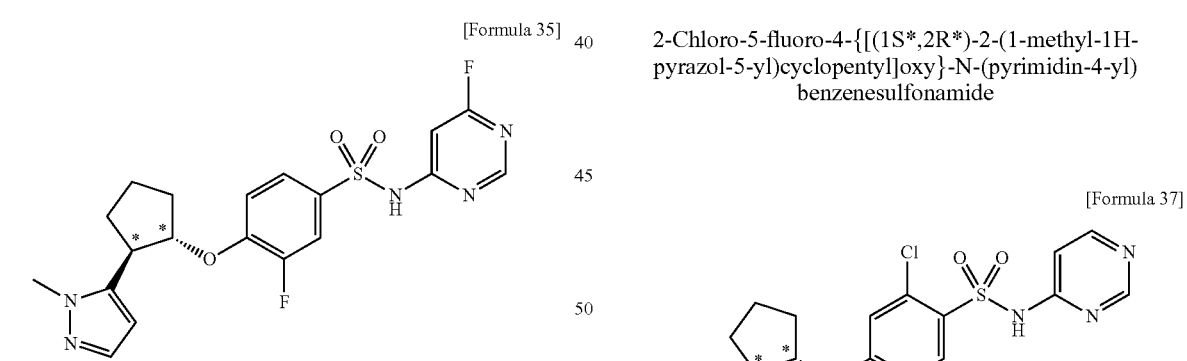

The reaction and aftertreatment were conducted in the same manner as in Example 16d by using 3-fluoro-4-{[((1S*,2R*)-2-(1-methyl-1H-pyrazol-5-yl)cyclopentyl]oxy}benzenesulfonamide (0.10 g, 0.29 mmol) prepared in Example 16c, 2,4-difluoropyrimidine (0.10 g, 0.88 mmol), potassium carbonate (0.16 g, 1.18 mmol) and DMF (3.0 mL), to yield the title compound (56 mg, 63%) as a colorless solid.

$^1$H-NMR (400 MHz, CDCl$_3$) δ ppm: 1.77-1.96 (4H, m), 2.21-2.32 (2H, m), 3.42-3.47 (1H, m), 3.84 (3H, s), 4.68-4.71 (1H, m), 6.06 (1H, d, J=1.6 Hz), 6.84 (1H, t, J=8.6 Hz), 7.05 (1H, t, J=3.5 Hz), 7.41 (1H, d, J=2.0 Hz), 7.64-7.68 (2H, m), 8.34 (1H, d, J=7.0 Hz).

MS (ESI) m/z: 436 [M+H]+.

Example 19

2-Chloro-5-fluoro-4-{[(1S*,2R*)-2-(1-methyl-1H-pyrazol-5-yl)cyclopentyl]oxy}-N-(pyrimidin-4-yl)benzenesulfonamide

[Formula 37]

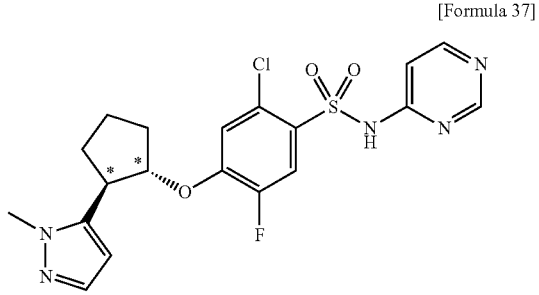 [SMILES: Cn1nccc1[C@H]1CCC[C@@H]1Oc1cc(Cl)c(S(=O)(=O)Nc2ccncn2)cc1F]

(19a) 2-Chloro-N-(2,4-dimethoxybenzyl)-4,5-difluoro-N-(pyrimidin-4-yl)benzenesulfonamide The reaction and aftertreatment were conducted in the same manner as in Example 14b by using the N-(2,4-dimethoxybenzyl)pyrimidin-4-amine (150 mg, 0.611 mmol) prepared in Example 14a, 2-Chloro-4,5-difluorobenzenesulfonyl chloride (302 mg, 1.22 mmol), 1,4-diazabicyclo[2.2.2]

octane (137 mg, 1.22 mmol) and acetonitrile (5.0 mL), to yield the title compound (58.8 mg, 21%) as a colorless oil.

$^1$H-NMR (500 MHz, CDCl$_3$) δ ppm: 3.78 (3H, s), 3.85 (3H, s), 5.29 (2H, s), 6.43-6.46 (2H, m), 6.95 (1H, d, J=7.3 Hz), 7.26-7.31 (2H, m), 8.23 (1H, t, J=8.3 Hz), 8.43 (1H, d, J=5.9 Hz), 8.69 (1H, s).

(19b) 2-Chloro-N-(2,4-dimethoxybenzyl)-5-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the 2-chloro-N-(2,4-dimethoxybenzyl)-4,5-difluoro-N-(pyrimidin-4-yl)benzenesulfonamide (58.8 mg, 0.129 mmol) prepared in Example 19a, the (1S*,2R*)-2-(1-methyl-1H-pyrazol-5-yl)cyclopentanol (25.7 mg, 0.155 mmol) prepared in Example 8a, sodium hydride (63%; 5.9 mg, 0.155 mmol) and DMF (2.0 mL), to yield the title compound (50.6 mg, 64%) as a colorless oil.

$^1$H-NMR (500 MHz, CDCl$_3$) δ ppm: 1.64-1.99 (4H, m), 2.17-2.34 (2H, m), 3.44-3.49 (1H, m), 3.77 (3H, s), 3.83 (3H, s), 3.85 (3H, s), 4.64-4.67 (1H, m), 5.27 (1H, d, J=17.1 Hz), 5.32 (1H, d, J=17.1 Hz), 6.05 (1H, s), 6.41-6.45 (2H, m), 6.79 (1H, d, J=6.8 Hz), 7.01 (1H, d, J=5.9 Hz), 7.25 (1H, d, J=8.3 Hz), 8.05 (1H, d, J=10.3 Hz), 8.39 (1H, d, J=6.4 Hz), 8.70 (1H, s).

(19c) 2-Chloro-5-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the 2-chloro-N-(2,4-dimethoxybenzyl)-5-fluoro-4-{[(1S*,2R*)-2-(1-methyl-1H-pyrazol-5-yl)cyclopentyl]oxy}-N-(pyrimidin-4-yl)benzenesulfonamide (50.6 mg, 0.0840 mmol) prepared in Example 19b, triethylsilane (0.05 mL), trifluoroacetic acid (1.0 mL) and dichloromethane (1.0 mL), to yield the title compound (15.0 mg, 39%) as a colorless solid.

$^1$H-NMR (500 MHz, CDCl$_3$) δ ppm: 1.78-1.99 (4H, m), 2.23-2.32 (2H, m), 3.42-3.48 (1H, m), 3.85 (3H, s), 4.64-4.67 (1H, m), 6.06 (1H, d, J=2.0 Hz), 6.85 (1H, d, J=7.3 Hz), 7.05 (1H, d, J=7.3 Hz), 7.39 (1H, s), 7.98 (1H, d, J=10.7 Hz), 8.34 (1H, J=5.9 Hz), 8.65 (1H, s).

MS (ESI) m/z: 452 [M+H]+.

Example 20

5-Chloro-2-fluoro-4-{[(1S*,2R*)-2-(1-methyl-1H-pyrazol-5-yl)cyclopentyl]oxy}-N-(pyrimidin-4-yl)benzenesulfonamide

[Formula 38]

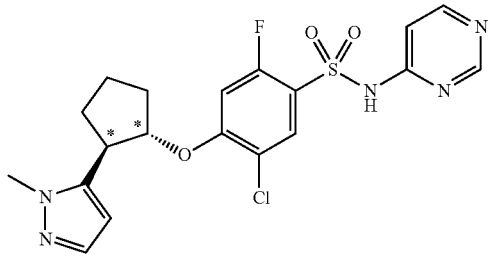

(20a) 5-Chloro-N-(2,4-dimethoxybenzyl)-2,4-difluoro-N-(pyrimidin-4-yl)benzenesulfonamide The reaction and aftertreatment were conducted in the same manner as in Example 14b by using the N-(2,4-dimethoxybenzyl)pyrimidine-4-amine (150 mg, 0.611 mmol) prepared in Example 14, 5-chloro-2,4-difluorobenzenesulfonyl chloride (302 mg, 1.22 mmol), 1,4-diazabicyclo[2.2.2]octane (137 mg, 1.22 mmol) and acetonitrile (5.0 mL), to yield the title compound (71.7 mg, 26%) as a colorless oil.

$^1$H-NMR (500 MHz, CDCl$_3$) δ ppm: 3.78 (3H, s), 3.79 (3H, s), 5.23 (2H, s), 6.41-6.43 (2H, m), 6.98 (1H, d, J=9.3 Hz), 7.16 (1H, d, J=7.3 Hz), 7.22 (1H, d, J=8.8 Hz), 8.13 (1H, t, J=7.3 Hz), 8.49 (1H, d, J=5.9 Hz), 8.79 (1H, s).

(20b) 5-Chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (71.7 mg, 0.157 mmol) prepared in Example 20a, the (1S*,2R*)-2-(1-methyl-1H-pyrazol-5-yl)cyclopentanol (31.1 mg, 0.187 mmol) prepared in Example 8a, sodium hydride (63%; 7.1 mg, 0.186 mmol) and DMF (2.0 mL), to yield the title compound (79.1 mg, 84%) as a colorless oil.

$^1$H-NMR (500 MHz, CDCl$_3$) δ ppm: 1.73-1.98 (4H, m), 2.17-2.35 (0.2H, m), 3.48-3.52 (1H, m), 3.76 (3H, s), 3.78 (3H, s), 3.88 (3H, s), 4.60-4.63 (1H, m), 5.22 (1H, d, J=17.1 Hz), 5.26 (1H, d, J=17.1 Hz), 6.06 (1H, d, J=1.5 Hz), 6.39-6.41 (2H, m), 6.48 (1H, d, J=11.7 Hz), 7.18-7.21 (2H, m), 7.40 (1H, s), 8.02 (1H, d, J=7.3 Hz), 8.46 (1H, d, J=5.9 Hz), 8.79 (1H, s).

(20c) 5-Chloro-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide (79.1 mg, 0.131 mmol) prepared in Example 20b, triethylsilane (0.05 mL), trifluoroacetic acid (1.0 mL) and dichloromethane (1.0 mL), to yield the title compound (30.0 mg, 51%) as a colorless solid.

$^1$H-NMR (500 MHz, CDCl$_3$) δ ppm: 1.79-1.96 (4H, m), 2.20-2.33 (2H, m), 3.48-3.52 (1H, m), 3.89 (3H, s), 4.60-4.63 (1H, m), 6.05 (1H, s), 6.54 (1H, d, J=11.7 Hz), 7.26-7.27 (1H, m), 7.39 (1H, s), 8.02 (1H, d, J=7.3 Hz), 8.39 (1H, J=4.9 Hz), 8.81 (1H, s).

MS (ESI) m/z: 452 [M+H]+.

Example 21

4-{[(1S*,2R*)-2-(1-Methyl-1H-pyrazol-5-yl)cyclopentyl]oxy}-N-(pyrimidin-4-yl)-3-(trifluoromethyl)benzenesulfonamide

[Formula 39]

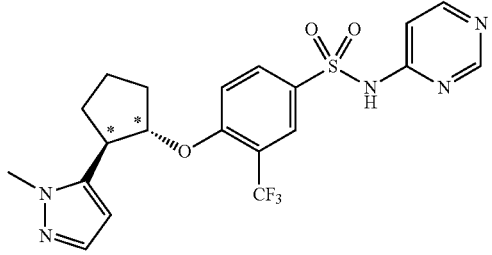

(21a) N-(2,4-dimethoxybenzyl)-4-fluoro-N-(pyrimidin-4-yl)-3-(trifluoromethyl)benzenesulfonamide The reaction and aftertreatment were conducted in the same manner as in Example 14b by using the N-(2,4-dimethoxybenzyl)pyrimidin-4-amine (150 mg, 0.611 mmol) prepared in Example 14a, 4-fluoro-3-(trifluoromethyl)benzenesulfonyl chloride (321 mg, 1.22 mmol), 1,4-diazabicyclo[2.2.2]octane (137 mg, 1.22 mmol) and acetonitrile (5.0 mL), to yield the title compound (94.7 mg, 33%) as a colorless oil.

$^1$H-NMR (500 MHz, CDCl$_3$) δ ppm: 3.65 (3H, s), 3.78 (3H, s), 5.16 (2, s), 6.36 (1H, s), 6.40 (1H, d, J=8.3 Hz), 7.12-7.14 (2H, m), 7.27-7.30 (1H, m), 8.14-8.16 (2H, m), 8.53 (1H, d, J=5.9 Hz), 8.55 (1H, s).

(21b) N-(2,4-dimethoxybenzyl)-4-{[(1S*,2R*)-2-(1-methyl-1H-pyrazol-5-yl)cyclopentyl]oxy}-N-(pyrimidin-4-yl)-3-(trifluoromethyl)benzenesulfonamide The reaction and aftertreatment were conducted in the same manner as in Example 1a by using the N-(2,4-dimethoxybenzyl)-4-fluoro-N-(pyrimidin-4-yl)-3-(trifluoromethyl)benzenesulfonamide (94.7 mg, 0.201 mmol) prepared in Example 21a, the (1S*,2R*)-2-(1-methyl-1H-pyrazol-5-yl)cyclopentanol (40.1 mg, 0.241 mmol) prepared in Example 8a, sodium hydride (63%; 9.2 mg, 0.241 mmol) and DMF (2.0 mL), to yield the title compound (123 mg, 99%) as a colorless oil.

$^1$H-NMR (500 MHz, CDCl$_3$) δ ppm: 1.62-1.94 (4H, m), 2.10-2.35 (2H, m), 3.44-3.47 (1H, m), 3.70 (3H, s), 3.76 (3H, s), 3.80 (3H, s), 4.80-4.82 (1H, m), 5.17 (2H, s), 6.07 (1H, d, J=2.0 Hz), 6.37-6.39 (2H, m), 6.84 (1H, d, J=8.8 Hz), 7.10 (1H, d, J=9.3 Hz), 7.16 (1H, d, J=6.8 Hz), 7.38 (1H, d, J=2.0 Hz), 7.99 (1H, dd, J=2.4, 8.8 Hz), 8.08 (1H, d, J=2.0 Hz), 8.47 (1H, d, J=5.9 Hz), 8.82 (1H, s).

(21c) 4-{[(1S*,2R*)-2-(1-Methyl-1H-pyrazol-5-yl)cyclopentyl]oxy}-N-(pyrimidin-4-yl)-3-(trifluoromethyl)benzenesulfonamide The reaction and aftertreatment were conducted in the same manner as in Example 1b by using the N-(2,4-dimethoxybenzyl)-4-{[(1S*,2R*)-2-(1-methyl-1H-pyrazol-5-yl)cyclopentyl]oxy}-N-(pyrimidin-4-yl)-3-(trifluoromethyl)benzenesulfonamide (123 mg, 0.199 mmol) prepared in Example 21b, triethylsilane (0.10 mL), trifluoroacetic acid (1.0 mL) and dichloromethane (1.0 mL), to yield the title compound (50.0 mg, 54%) as a colorless solid.

$^1$H-NMR (500 MHz, CDCl$_3$) δ ppm: 1.76-1.97 (4H, m), 2.15-2.36 (2H, m), 3.43-3.47 (1H, m), 3.80 (3H, s), 4.80-4.82 (1H, m), 6.07 (1H, s), 6.90 (1H, d, J=8.8 Hz), 7.20 (1H, d, J=5.9 Hz), 7.42 (1H, s), 8.04 (1H, dd, J=2.4, 8.8 Hz), 8.16 (1H, J=2.0 Hz), 8.44 (1H, d, J=5.4 Hz), 8.82 (1H, s).

MS (ESI) m/z: 468 [M+H]+.

Example 22

2,5-Difluoro-4-{[(1S*,2R*)-2-(1H-pyrazol-5-yl)cyclohexyl]oxy}-N-(pyrimidin-4-yl)benzenesulfonamide

[Formula 40]

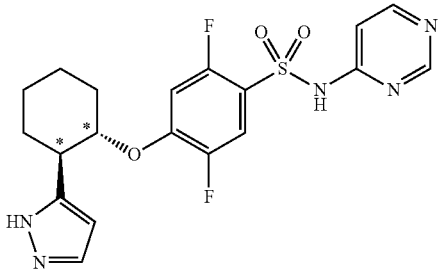

(22a) (1S*,2R*)-2-[1-(Tetrahydro-2H-pyran-2-yl)-1H-pyrazol-5-yl]cyclohexanol The reaction and aftertreatment were conducted in the same manner as in Example 8a by using 1-(tetrahydro-2H-pyran-2-yl)-1H-pyrazole (5.50 g, 36.1 mmol), n-butyl lithium (1.63 M solution in hexane; 24 mL, 39.1 mmol), cyclohexene oxide (3.80 g, 38.7 mmol) and THF (100 mL), to yield the title compound (270 mg, 3.0%) in the form of a diastereomeric mixture as a colorless oil.

(22b) N-(2,4-dimethoxybenzyl)-2,5-difluoro-N-(pyrimidin-4-yl)-4-({(1S*,2R*)-2-[1-(tetrahydro-2H-pyran-2-yl)-1H-pyrazol-5-yl]cyclohexyl}oxy)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (360 mg, 0.819 mmol) prepared in Example 14b, the (1S*,2R*)-2-[1-(tetrahydro-2H-pyran-2-yl)-1H-pyrazol-5-yl]cyclohexanol (202 mg, 0.807 mmol) prepared in Example 22a, sodium hydride (63%; 50 mg, 1.32 mmol) and DMF (4.0 mL), to yield the title compound (366 mg, 68%) in the form of a diastereomeric mixture as a colorless oil.

(22c) 2,5-Difluoro-4-{[(1S*,2R*)-2-(1H-pyrazol-5-yl)cyclohexyl]oxy}-N-(pyrimidin-4-yl)benzenesulfonamide To a solution of the N-(2,4-dimethoxybenzyl)-2,5-difluoro-N-(pyrimidin-4-yl)-4-({(1S*,2R*)-2-[1-(tetrahydro-2H-pyran-2-yl)-1H-pyrazol-5-yl]cyclohexyl}oxy)benzenesulfonamide (366 mg, 0.547 mmol) prepared in Example 22b and triethylsilane (0.40 mL) in dichloromethane (4.0 mL), trifluoroacetic acid (4.0 mL) was added at room temperature, and the reaction solution was stirred for 1 hour. To the reaction solution, methanol (4.0 mL) was added, and the mixture was further stirred at room temperature for 1 hour. The reaction solution was concentrated, and the residue was purified with silica gel chromatography (dichloromethane/methanol=95:5) to yield the title compound (182 mg, 61%) as a colorless solid.

$^1$H-NMR (500 MHz, DMSO-d$_6$) δ ppm: 1.32-1.77 (6H, m), 1.90-1.92 (1H, m), 2.10-2.23 (1H, m), 2.91-2.96 (1H, m), 4.64-4.68 (1H, m), 6.06 (1H, d, J=2.0 Hz), 6.96 (1H, brs), 7.22-7.26 (1H, m), 7.38 (1H, s), 7.57-7.60 (1H, m), 8.25 (1H, brs), 8.58 (1H, s).

MS (ESI) m/z: 436 [M+H]+.

Example 23

3-Chloro-4-({[(1S*,2R*)-2-(1-methyl-1H-pyrazol-5-yl)cyclopentyl]oxy}-N-(pyrimidin-4-yl)benzenesulfonamide

[Formula 41]

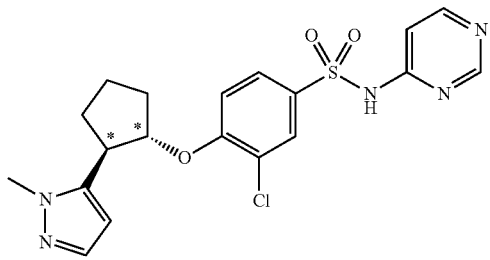

(23a) 3-Chloro-N-(2,4-dimethoxybenzyl)-4-fluoro-N-(pyrimidin-4-yl)benzenesulfonamide The reaction and aftertreatment were conducted in the same manner as in Example 14b by using the N-(2,4-dimethoxybenzyl)pyrimidin-4-amine (150 mg, 0.611 mmol) prepared in Example 14a, 3-chloro-4-fluorobenzenesulfonyl chloride (280 mg, 1.22 mmol), 1,4-diazabicyclo[2.2.2]octane (137 mg, 1.22 mmol) and acetonitrile (5.0 mL), to yield the title compound (127 mg, 47%) as a colorless amorphous solid.

$^1$H-NMR (500 MHz, CDCl$_3$) δ ppm: 3.68 (3H, s), 3.78 (3H, s), 5.18 (2H, s), 6.39 (1H, s), 6.41 (1H, d, J=10.3 Hz), 7.13-7.27 (3H, m), 7.80-7.83 (1H, m), 7.87 (1H, d, J=8.8 Hz), 8.51 (1H, d, J=5.9 Hz), 8.86 (1H, s).

(23b) 3-Chloro-N-(2,4-dimethoxybenzyl)-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the 3-chloro-N-(2,4-dimethoxybenzyl)-4-fluoro-N-(pyrimidin-4-yl)benzenesulfonamide (127 mg, 0.290 mmol) prepared in Example 23a, the (1S*,2R*)-2-(1-methyl-1H-pyrazol-5-yl)cyclopentanol (50.6 mg, 0.304 mmol) prepared in Example 8a, sodium hydride (63%; 16.6 mg, 0.435 mmol) and DMF (2.0 mL), to yield the title compound (123 mg, 73%) as a colorless oil.

$^1$H-NMR (500 MHz, CDCl$_3$) δ ppm: 1.78-1.99 (4H, m), 2.20-2.34 (2H, m), 3.47-3.51 (1H, m), 3.72 (3H, s), 3.76 (3H, s), 3.88 (3H, s), 4.68-4.71 (1H, m), 5.19 (2H, s), 6.07 (1H, d, J=2.0 Hz), 6.38-6.40 (2H, m), 6.76 (1H, d, J=9.3 Hz), 7.13 (1H, d, J=8.3 Hz), 7.23 (1H, dd, J=2.0, 5.9 Hz), 7.41 (1H, d, J=2.0 Hz), 7.70 (1H, dd, J=2.0, 8.8 Hz), 7.80 (1H, d, J=2.4 Hz), 8.47 (1H, d, J=5.9 Hz), 8.83 (1H, s).

(23c) 3-Chloro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the 3-chloro-N-(2,4-dimethoxybenzyl)-4-{[(1S*,2R*)-2-(1-methyl-1H-pyrazol-5-yl)cyclopentyl]oxy}-N-(pyrimidin-4-yl)benzenesulfonamide (123 mg, 0.211 mmol) prepared in Example 23b, triethylsilane (0.10 mL), trifluoroacetic acid (1.0 mL) and dichloromethane (1.0 mL), to yield the title compound (85.0 mg, 54%) as a colorless solid.

$^1$H-NMR (500 MHz, CDCl$_3$) δ ppm: 1.79-1.97 (4H, m), 2.20-2.32 (2H, m), 3.46-3.50 (1H, m), 3.86 (3H, s), 4.70-4.72 (1H, m), 6.07 (1H, s), 6.80 (1H, d, J=8.8 Hz), 7.17 (1H, d, J=5.4 Hz), 7.40 (1H, s), 7.79 (1H, dd, J=2.4, 8.8 Hz), 7.97 (1H, J=2.4 Hz), 8.41 (1H, brs), 8.77 (1H, s).

MS (ESI) m/z: 434 [M+H]+.

Example 24

2,5-Difluoro-N-(2-fluoropyrimidin-4-yl)-4-{[(1S*,2R*)-2-(1-methyl-1H-pyrazol-5-yl)cyclopentyl]oxy}benzenesulfonamide

[Formula 42]

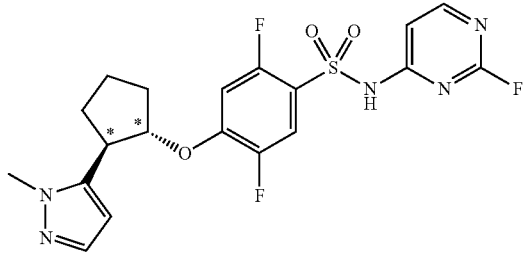

(24a) N-(2,4-dimethoxybenzyl)-2-fluoropyrimidin-4-amine

A solution of 2,4-difluoropyrimidine (600 mg, 5.17 mmol) and 2,4-dimethoxybenzylamine (860 mg, 5.17 mmol) in THF (17 mL) was stirred at room temperature for 1 hour. The reaction solution was vacuum concentrated, and the residue was then purified with silica gel chromatography (hexane/ethyl acetate=1:2) to yield the title compound (594 mg, 43%) as a colorless solid.

$^1$H-NMR (400 MHz, DMSO-d$_6$) δ ppm: 3.74 (3H, s), 3.80 (3H, s), 4.36 (2H, d, J=5.5 Hz), 6.47-6.50 (2H, m), 6.58 (1H, d, J=2.4 Hz), 7.13 (1H, d, J=8.6 Hz), 7.89-7.91 (1H, m), 8.19 (1H, brs).

(24b) N-(2,4-dimethoxybenzyl)-2,4,5-trifluoro-N-(2-fluoropyrimidin-4-yl)benzenesulfonamide The reaction and aftertreatment were conducted in the same manner as in Example 15a by using the N-(2,4-dimethoxybenzyl)-2-fluoropyrimidin-4-amine (0.20 g, 0.76 mmol) prepared in Example 24a, LiHMDS (1.0 M in THF, 0.91 mL, 0.91 mmol), 2,4,5-trifluorobenzenesulfonyl chloride (0.19 g, 0.84 mmol) and THF (3.0 mL), to yield the title compound (0.22 g, 63%) as a colorless solid.

$^1$H-NMR (500 MHz, CDCl$_3$) δ ppm: 3.79 (3H, s), 3.81 (3H, s), 5.23 (2H, s), 6.43-6.45 (2H, m), 7.01-7.06 (2H, m), 7.23 (1H, d, J=7.8 Hz), 7.97 (1H, q, J=8.3 Hz), 7.34 (1H, dd, J=2.0, 5.9 Hz).

(24c) N-(2,4-dimethoxybenzyl)-2,5-difluoro-N-(2-fluoropyrimidin-4-yl)-4-{[(1S*,2R*)-2-(1-methyl-1H-pyrazol-5-yl)cyclopentyl]oxy}benzenesulfonamide The reaction and aftertreatment were conducted in the same manner as in Example 1a by using the N-(2,4-dimethoxybenzyl)-2,4,5-trifluoro-N-(2-fluoropyrimidin-4-yl)benzenesulfonamide (0.10 g, 0.23 mmol) prepared in Example 24b, the (1S*,2R*)-2-(1-methyl-1H-pyrazol-5-yl)cyclopentanol (0.04 g, 0.23 mmol) prepared in Example 8a, sodium hydride (63%; 0.01 g, 0.28 mmol) and DMF (1.0 mL), to yield the title compound (648 mg, 46%) as a colorless amorphous solid.

$^1$H-NMR (400 MHz, CDCl$_3$) δ ppm: 1.76-1.98 (4H, m), 2.21-2.36 (2H, m), 3.45-3.50 (1H, m), 3.77 (3H, s), 3.80 (3H, s), 3.86 (3H, s), 4.61-4.65 (1H, m), 5.22 (2H, s), 6.06 (1H, d, J=2.0 Hz), 6.42-6.44 (2H, m), 6.54 (1H, dd, J=6.3, 11.0 Hz), 7.09 (1H, dd, J=3.5, 5.9 Hz), 7.21 (1H, d, J=9.0 Hz), 7.41 (1H, d, J=2.0 Hz), 7.78 (1H, dd, J=6.7, 10.2 Hz), 8.31 (1H, dd, J=2.0, 5.5 Hz).

(24d) 2,5-Difluoro-N-(2-fluoropyrimidin-4-yl)-4-{[(1S*,2R*)-2-(1-methyl-1H-pyrazol-5-yl)cyclopentyl]oxy}benzenesulfonamide The reaction and aftertreatment were conducted in the same manner as in Example 1b by using the N-(2,4-dimethoxybenzyl)-2,5-difluoro-N-(2-fluoropyrimidin-4-yl)-4-{[(1S*,2R*)-2-(1-methyl-1H-pyrazol-5-yl)cyclopentyl]oxy}benzenesulfonamide (648 mg, 0.13 mmol) prepared in Example 24c, triethylsilane (0.11 mL), trifluoroacetic acid (0.13 g) and dichloromethane (1.3 mL), to yield the title compound (0.06 g, 78%) as a colorless solid.

$^1$H-NMR (400 MHz, CD$_3$OD) δ ppm: 1.75-1.98 (4H, m), 2.26-2.35 (2H, m), 3.50-3.55 (1H, m), 3.80 (3H, s), 4.83-4.88 (1H, m), 6.19 (1H, d, J=2.0 Hz), 6.87 (1H, dd, J=3.9, 5.9 Hz), 6.94 (1H, dd, J=6.7, 11.3 Hz), 7.35 (1H, d, J=2.0 Hz), 7.78 (1H, dd, J=6.7, 10.6 Hz), 8.24 (1H, dd, J=2.4, 5.9 Hz).

MS (ESI) m/z: 454 [M+H]+.

Example 25

2,5-Difluoro-4-{[(1S*,2R*)-2-(1-methyl-1H-pyrazol-5-yl)cyclohexyl]oxy}-N-(pyrimidin-4-yl)benzenesulfonamide

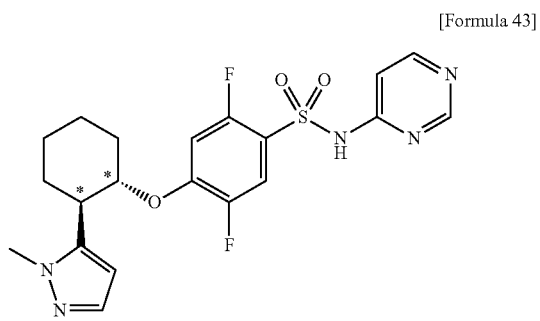 [SMILES: Cn1nccc1[C@H]1CCCC[C@@H]1Oc1cc(F)c(S(=O)(=O)Nc2ccncn2)cc1F]

[Formula 43]

(25a) N-(2,4-dimethoxybenzyl)-2,5-difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (244 mg, 0.555 mmol) prepared in Example 14b, the (1S*,2R*)-2-(1-methyl-1H-pyrazol-5-yl)cyclohexanol (100 mg, 0.555 mmol) prepared in Example 4a, sodium hydride (63%; 31.7 mg, 0.793 mmol) and DMF (3 mL), to yield the title compound (268 mg, 80%) as a colorless oil.

$^1$H-NMR (500 MHz, CDCl$_3$) δ ppm: 1.39-1.68 (4H, m), 1.86-1.96 (2H, m), 2.04-2.07 (1H, m), 2.22-2.25 (1H, m), 2.98-3.03 (1H, m), 3.76 (3H, s), 3.77 (3H, s), 3.91 (3H, s), 4.08-4.14 (1H, m), 5.19 (1H, d, J=17.1 Hz), 5.23 (1H, d, J=16.6 Hz), 6.02 (1H, d, J=2.0 Hz), 6.39-6.40 (2H, m), 6.47 (1H, dd, J=6.4, 11.2 Hz), 7.17-7.19 (2H, m), 7.33 (1H, d, J=1.5 Hz), 7.67 (1H, dd, J=6.4, 9.8 Hz), 8.45 (1H, d, J=5.9 Hz), 8.78 (1H, s).

(25b) 2,5-Difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*)-2-(1-methyl-1H-pyrazol-5-yl)cyclohexyl]oxy}-N-(pyrimidin-4-yl)benzenesulfonamide (268 mg, 0.447 mmol) prepared in Example 25a, triethylsilane (0.20 mL), trifluoroacetic acid (2.0 mL) and dichloromethane (2.0 mL), to yield the title compound (130 mg, 65%) as a colorless solid.

$^1$H-NMR (500 MHz, CDCl$_3$) δ ppm: 1.38-1.68 (4H, n), 1.86-1.89 (1H, m), 1.93-1.95 (1H, m), 2.05-2.07 (1H, m), 2.22-2.25 (1H, m), 2.97-3.02 (1H, m), 3.90 (3H, s), 4.07-4.12 (1H, m), 6.02 (1H, d, J=2.0 Hz), 6.50 (1H, dd, J=6.4, 11.2 Hz), 7.24 (1H, d, J=6.4 Hz), 7.33 (1H, d, J=2.0 Hz), 7.66 (1H, dd, J=6.8, 10.3 Hz), 8.38 (1H, d, J=6.4 Hz), 8.80 (1H, s).

MS (ESI) m/z: 450 [M+H]+.

Example 26

3-Cyano-4-{[(1S*,2R*)-2-(1-methyl-1H-pyrazol-5-yl)cyclopentyl]oxy}-N-(pyrimidin-4-yl)benzenesulfonamide

[Formula 44]

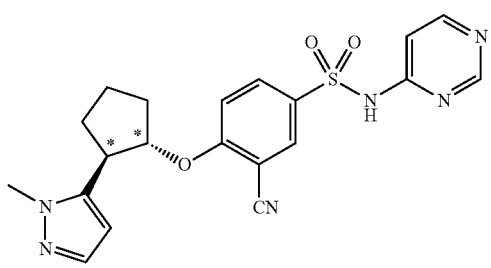

(26a) 3-Cyano-N-(2,4-dimethoxybenzyl)-4-fluoro-N-(pyrimidin-4-yl)benzenesulfonamide The reaction and aftertreatment were conducted in the same manner as in Example 14b by using the N-(2,4-dimethoxybenzyl)pyrimidine-4-amine (600 mg, 2.44 mmol) prepared in Example 14a, 3-cyano-4-fluorobenzenesulfonyl chloride (1.07 g, 4.87 mmol), 1,4-diazabicyclo[2.2.2]octane (549 mg, 4.89 mmol) and acetonitrile (12 mL), to yield the title compound (200 mg, 19%) as a colorless amorphous solid.

$^1$H-NMR (500 MHz, CDCl$_3$) δ ppm: 3.60 (3H, s), 3.80 (3H, s), 5.15 (2H, s), 6.36 (1H; d, J=2.4 Hz), 6.45 (1H, dd, J=2.4, 8.3 Hz), 7.11 (1H, dd, J=1.0, 5.9 Hz), 7.16 (1H, d, J=8.3 Hz), 7.30 (1H, t, J=8.8 Hz), 8.01 (1H, dd, J=2.0, 5.4 Hz), 8.20-8.23 (1H, m), 8.55 (1H, d, J=5.9 Hz), 8.87 (1H, s).

(26b) 3-Cyano-N-(2,4-dimethoxybenzyl)-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using 3-cyano-N-(2,4-dimethoxybenzyl)-4-fluoro-N-(pyrimidin-4-yl)benzenesulfonamide (200 mg, 0.47 mmol) prepared in Example 26a, the (1S*,2R*)-2-(1-methyl-1H-pyrazol-5-yl)cyclopentanol (81.5 mg, 0.49 mmol) prepared in Example 8a, sodium hydride (63%; 26.7 mg, 0.70 mmol) and DMF (2.0 mL), to yield the title compound (91.0 mg, 34%) as a colorless solid.

$^1$H-NMR (500 MHz, CDCl$_3$) δ ppm: 1.79-2.01 (4H, m), 2.24-2.36 (2H, m), 3.50-3.54 (1H, m), 3.67 (3H, s), 3.78 (3H, s), 3.89 (3H, s), 4.75-4.78 (1H, m), 5.15 (2H, s), 6.07 (1H, d, J=2.0 Hz), 6.38-6.42 (2H, m), 6.82 (1H, d, J=9.3 Hz), 7.11-7.13 (2H, m), 7.42 (1H, d, J=1.5 Hz), 7.97 (1H, d, J=2.4 Hz), 8.03 (1H, dd, J=2.4, 8.8 Hz), 8.50 (1H, d, J=5.9 Hz), 8.84 (1H, s).

(26c) 3-Cyano-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using 3-cyano-N-(2,4-dimethoxybenzyl)-4-{[(1S*,2R*)-2-(1-methyl-1H-pyrazol-5-yl)cyclopentyl]oxy}-N-(pyrimidin-4-yl)benzenesulfonamide (91.0 mg, 0.16 mmol) prepared in Example 26b, triethylsilane (0.10 mL), trifluoroacetic acid (1.0 mL) and dichloromethane (1.0 mL), to yield the title compound (53.3 mg, 79%) as a colorless solid.

$^1$H-NMR (500 MHz, CDCl$_3$) δ ppm: 1.80-1.99 (4H, m), 2.25-2.36 (2H, m), 3.50-3.54 (1H, m), 3.89 (3H, s), 4.76-4.79 (1H, m), 6.08 (1H, s), 6.89 (1H, d, J=9.3 Hz), 7.14 (1H, d, J=5.4 Hz), 7.42 (1H, s), 8.09 (1H, dd, J=2.4, 8.8 Hz), 8.17 (1H, d, J=2.4 Hz), 8.39 (1H, s), 8.75 (1H, s).

MS (ESI) m/z: 425 [M+H]+.

Example 27

2,6-Difluoro-4-{[(1S*,2R*)-2-(1-methyl-1H-pyrazol-5-yl)cyclopentyl]oxy}-N-(pyrimidin-4-yl)benzenesulfonamide

[Formula 45]

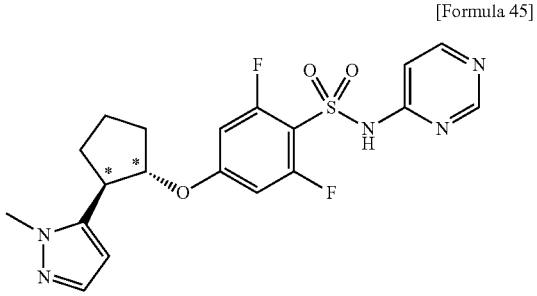 [SMILES: Cn1nccc1[C@H]1CCC[C@@H]1Oc1cc(F)c(S(=O)(=O)Nc2ccncn2)c(F)c1]

(27a) N-(2,4-dimethoxybenzyl)-2,4,6-trifluoro-N-(pyrimidin-4-yl)benzenesulfonamide The reaction and aftertreatment were conducted in the same manner as in Example 14b by using the N-(2,4-dimethoxybenzyl)pyrimidin-4-amine (600 mg, 2.44 mmol) prepared in Example 14a, 2,4,6-trifluorobenzenesulfonyl chloride (1.50 g, 6.51 mmol), 1,4-diazabicyclo([2.2.2]octane (549 mg, 4.89 mmol) and acetonitrile (12 mL), to yield the title compound (192 mg, 18%) as a colorless amorphous solid.

$^1$H-NMR (500 MHz, CDCl$_3$) δ ppm: 3.78 (3H, s), 3.73 (3H, s), 5.26 (2H, s), 6.42-6.46 (2H, m), 6.78 (2H, t, J=8.3 Hz), 7.07 (1H, dd, J=1.5, 5.9 Hz), 7.24 (1H, d, J=8.8 Hz), 8.46 (1H, d, J=6.4 Hz), 8.78 (1H, s).

(27b) N-(2,4-Dimethoxybenzyl)-2,6-difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (192 mg, 0.44 mmol) prepared in Example 27a, the (1S*,2R*)-2-(1-methyl-1H-pyrazol-5-yl)cyclopentanol (76.3 mg, 0.46 mmol) prepared in Example 8a, sodium hydride (63%; 25.0 mg, 0.66 mmol) and DMF (2.0 mL), to yield the title compound (192 mg, 75%) as a colorless oil.

$^1$H-NMR (500 MHz, CDCl$_3$) δ ppm: 1.72-1.95 (4H, m), 2.17-2.32 (2H, m), 3.35-3.39 (1H, m), 3.77 (3H, s), 3.82 (6H, a), 4.62-4.65 (1H, m), 5.27 (2H, s), 6.04 (1H, d, J=2.0

Hz), 6.39-6.44 (4H, m), 7.16 (1H, d, J=7.3 Hz), 7.22 (1H, d, J=7.3 Hz), 7.41 (1H, d, J=2.0 Hz), 8.44 (1H, d, J=5.9 Hz), 8.78 (1H, s).

(27c) 2,6-Difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,6-difluoro-4-{[(1S*,2R*)-2-(1-methyl-1H-pyrazol-5-yl)cyclopentyl]oxy}-N-(pyrimidin-4-yl)benzenesulfonamide (192 mg, 0.33 mmol) prepared in Example 27b, triethylsilane (0.20 mL), trifluoroacetic acid (2.0 mL) and dichloromethane (2.0 mL), to yield the title compound (106 mg, 74%) as a colorless solid.

$^1$H-NMR (500 MHz, CDCl$_3$) δ ppm: 1.72-1.95 (4H, m), 2.17-2.31 (2H, m), 3.35-3.39 (1H, m), 3.82 (3H, s), 4.61-4.64 (1H, m), 6.04 (1H, d, J=2.0 Hz), 6.41 (2H, d, J=10.7 Hz), 7.40-7.42 (2H, m), 8.42 (1H, d, J=5.9 Hz), 8.87 (1H, s).
MS (ESI) m/z: 436 [M+H]+.

Example 28

4-{[(1S*,2R*)-2-(1-Ethyl-1H-pyrazol-5-yl)cyclohexyl]oxy}-2,5-difluoro-N-(pyrimidin-4-yl)benzenesulfonamide

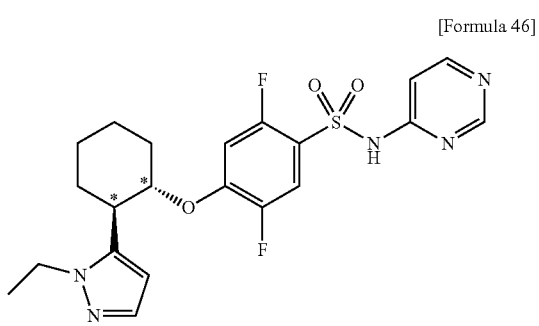 [SMILES: CCn1nccc1[C@H]1CCCC[C@@H]1Oc1cc(F)c(S(=O)(=O)Nc2ccncn2)cc1F]

[Formula 46]

(28a) N-(2,4-Dimethoxybenzyl)-4-{[(1S*,2R*)-2-(1-ethyl-1H-pyrazol-5-yl)cyclohexyl]oxy}-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (270 mg, 0.615 mmol) prepared in Example 14b, the (1S*,2R*)-2-(1-ethyl-1H-pyrazol-5-yl)cyclohexanol (120 mg, 0.618 mmol) prepared in Example 12a, sodium hydride (63%; 50 mg, 1.31 mmol) and DMF (3 mL), to yield the title compound (220 mg, 58%) as a colorless oil.

$^1$H-NMR (500 MHz, CDCl$_3$) δ ppm: 1.39-1.66 (4H, m), 1.43 (3H, t, J=7.3 Hz), 1.85-1.88 (1H, m), 1.94-1.96 (1H, m), 2.03-2.06 (1H, m), 2.22-2.25 (1H, m), 2.97-3.03 (1H, m), 3.76 (3H, s), 3.77 (3H, s), 4.12-4.32 (3H, m), 5.19 (1H, d, J=16.6 Hz), 5.23 (1H, d, J=17.1 Hz), 6.00 (1H, d, J=2.0 Hz), 6.38-6.40 (2H, m), 6.47 (1H, dd, J=6.4, 11.2 Hz), 7.17-7.19 (2H, m), 7.36 (1H, d, J=1.5 Hz), 7.66 (1H, dd, J=6.8, 10.3 Hz), 8.45 (1H, d, J=5.9 Hz), 8.78 (1H, s).

(28b) 4-{[(1S*,2R*)-2-(1-Ethyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(l-ethyl-1H-pyrazol-5-yl)cyclohexyl]oxy}-2,5-difluoro-N-(pyrimidin-4-yl)benzenesulfonamide (220 mg, 0.359 mmol) prepared in Example 28a, triethylsilane (0.30 mL), trifluoroacetic acid (3.0 mL) and dichloromethane (3.0 mL), to yield the title compound (160 mg, 96%) as a colorless solid.

$^1$H-NMR (500 MHz, CD$_3$OD) δ ppm: 1.37 (3H, t, J=7.3 Hz), 1.43-1.73 (4H, m), 1.81-1.83 (1H, m), 1.89-1.91 (1H, m), 1.96-1.99 (1H, m), 2.23-2.25 (1H, m), 3.06-3.11 (1H, m), 4.11-4.18 (1H, m), 4.26-4.33 (1H, m), 4.46-4.50 (1H, m), 6.14 (1H, d, J=2.0 Hz), 6.97 (1H, dd, J=6.8, 11.7 Hz), 7.01 (1H, d, J=7.3 Hz), 7.27 (1H, d, J=2.0 Hz), 7.64 (1H, dd, J=6.4, 10.3 Hz), 8.26 (1H, d, J=6.4 Hz), 8.54 (1H, s).
MS (ESI) m/z: 464 [M+H]+.

Example 29

2-Fluoro-4-{[(1S*,2R*)-2-(1-methyl-1H-pyrazol-5-yl)cyclopentyl]oxy}-N-(pyrimidin-4-yl)benzenesulfonamide

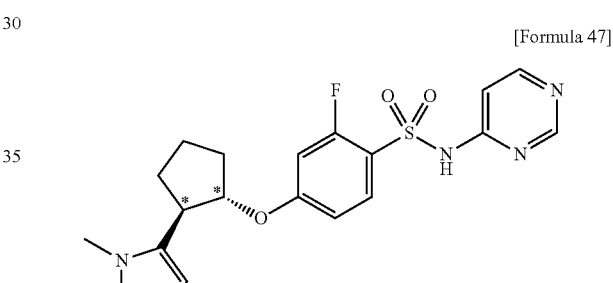

[Formula 47]

(29a) N-(2,4-Dimethoxybenzyl)-2,4-difluoro-N-(pyrimidin-4-yl)benzenesulfonamide

The reaction and aftertreatment were conducted in the same manner as in Example 14b by using the N-(2,4-dimethoxybenzyl)pyrimidine-4-amine (0.40 g, 1.63 mmol) prepared in Example 14a, 2,4-difluorobenzenesulfonyl chloride (0.69 g, 3.26 mmol), 1,4-diazabicyclo[2.2.2]octane (0.37 g, 3.26 mmol) and acetonitrile (11 mL), to yield the title compound (403.8 mg, 59%) as a colorless solid.

$^1$H-NMR (400 MHz, CDCl$_3$) δ ppm: 3.77 (3H, s), 3.80 (3H, s), 5.26 (2H, s), 6.41-6.44 (2H, m), 6.87-6.92 (1H, m), 7.01-7.06 (1H, m), 7.16 (1H, dd, J=1.6, 5.9 Hz), 7.22 (1H, d, J=8.2 Hz), 8.12 (1H, dt, J=5.9, 8.6 Hz), 8.45 (1H, d, J=5.9 Hz), 8.75 (1H, d, J=1.2 Hz).

(29b) N-(2,4-Dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (0.40 g, 0.95 mmol) prepared in Example 29a, the (1S*,2R*)-2-(1-methyl-1H-pyrazol-5-yl)cyclopentanol (0.16 g, 0.95 mmol) prepared in Example 8a, sodium hydride (63%; 0.040 g, 1.14 mmol) and DMF (5.0 mL), to yield the title compound (268.5 mg, 50%) as a colorless oil.

$^1$H-NMR (400 MHz, CDCl$_3$) δ ppm: 1.59-1.99 (4H, m), 2.17-2.33 (2H, m), 3.35-3.40 (1H, m), 3.76 (3H, s), 3.80 (3H, s), 3.82 (3H, s), 4.65-4.69 (1H, m), 5.26 (2H, s), 6.05 (1H, d, J=2.0 Hz), 6.39-6.43 (2H, m), 6.53 (1H, dd, J=2.4, 12.1 Hz), 6.67 (1H, dd, J=2.4, 9.0 Hz), 7.17-7.23 (2H, m), 7.37-7.41 (1H, m), 7.94 (1H, t, J=8.6 Hz), 8.41 (1H, d, J=5.5 Hz), 8.75 (1H, d, J=0.8 Hz).

(29C) 2-Fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide (0.27 g, 0.47 mmol) prepared in Example 29b, triethylsilane (0.38 mL, 2.36 mmol), trifluoroacetic acid (0.47 g, 0.44 mmol) and dichloromethane (5.0 mL), to yield the title compound (0.21 g, 22%) as a colorless solid.

$^1$H-NMR (400 MHz, CD$_3$OD) δ ppm: 1.76-1.95 (4H, m), 2.26-2.33 (2H, m), 3.45-3.49 (1H, m), 3.80, (3H, s), 4.86-4.91 (1H, m), 6.24 (1H, d, J=2.4 Hz), 6.77-6.86 (2H, m), 7.15 (1H, d, J=7.4 Hz), 7.43 (1H, d, J=2.0 Hz), 7.95 (1H, t, J=8.6 Hz), 8.40 (1H, d, J=5.9 Hz), 8.68 (1H, s).

MS (ESI) m/z: 418 [M+H]+.

Example 30

2,3-Difluoro-4-{[(1S*,2R*)-2-(1-methyl-1H-pyrazol-5-yl)cyclopentyl]oxy}-N-(pyrimidin-4-yl)benzenesulfonamide

[Formula 48]

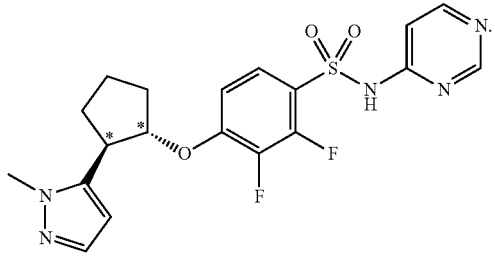

(30a) N-(2,4-Dimethoxybenzyl)-2,3,4-trifluoro-N-(pyrimidin-4-yl)benzenesulfonamide The reaction and aftertreatment were conducted in the same manner as in Example 14b by using the N-(2,4-dimethoxybenzyl)pyrimidine-4-amine (400 mg, 1.63 mmol) prepared in Example 14a, 2,3,4-trifluorobenzenesulfonyl chloride (752 mg, 3.26 mmol), 1,4-diazabicyclo[2.2.2]octane (366 mg, 3.26 mmol) and acetonitrile (8.0 mL), to yield the title compound (221 mg, 31%) as a colorless amorphous solid.

$^1$H-NMR (500 MHz, CDCl$_3$) δ ppm: 3.78 (3H, s), 3.80 (3H, s), 5.24 (2H, s), 6.42-6.44 (2H, m), 7.11-7.16 (2H, m), 7.22 (1H, d, J=7.8 Hz), 7.84-7.89 (1H, m), 8.48 (1H, d, J=5.9 Hz), 8.76 (1H, s).

(30b) N-(2,4-Dimethoxybenzyl)-2,3-difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (190 mg, 0.43 mmol) prepared in Example 30a, the (1S*,2R*)-2-(1-methyl-1H-pyrazol-5-yl)cyclopentanol (75.5 mg, 0.45 mmol) prepared in Example 8a, sodium hydride (63%; 24.7 mg, 0.65 mmol) and DMF (2.0 mL), to yield the title compound (190 mg, 75%) as a colorless oil.

$^1$H-NMR (500 MHz, CDCl$_3$) δ ppm: 1.77-1.97 (4H, m), 2.22-2.34 (2H, m), 3.44-3.48 (1H, m), 3.76 (3H, s), 3.79 (3H, s), 3.85 (3H, s), 4.72-4.75 (1H, m), 5.24 (1H, d, J=17.1 Hz), 5.28 (1H, d, J=16.6 Hz), 6.07 (1H, d, J=2.0 Hz), 6.39-6.42 (2H, m), 6.64 (1H, t, J=8.8 Hz), 7.19-7.21 (2H, m), 7.41 (1H, d, J=2.0 Hz), 7.71 (1H, t, J=8.8 Hz), 8.45 (1H, d, J=5.9 Hz), 8.76 (1H, s).

(30c) 2,3-Difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,3-difluoro-4-{[(1S*,2R*)-2-(1-methyl-1H-pyrazol-5-yl)cyclopentyl]oxy}-N-(pyrimidin-4-yl)benzenesulfonamide (190 mg, 0.32 mmol) prepared in Example 30b, triethylsilane (0.10 mL), trifluoroacetic acid (1.0 mL) and dichloromethane (1.0 mL), to yield the title compound (58.5 mg, 41%) as a colorless solid.

$^1$H-NMR (500 MHz, CDCl$_3$) δ ppm: 1.77-1.96 (4H, m), 2.20-2.34 (2H, m), 3.44-3.48 (1H, m), 3.84 (3H, s), 4.71-4.74 (1H, m), 6.06 (1H, d, J=1.5 Hz), 6.66 (1H, t, J=7.8 Hz), 7.24-7.25 (1H, m), 7.41 (1H, s), 7.70 (1H, t, J=9.3 Hz), 8.37 (1H, d, J=6.4 Hz), 8.81 (1H, s).

MS (ESI) m/z: 436 [M+H]+.

Example 31

2,5-Difluoro-4-{[(1S,2R)-2-(1-methyl-1H-pyrazol-5-yl)cyclopentyl]oxy}-N-pyrimidin-4-yl)benzenesulfonamide

[Formula 49]

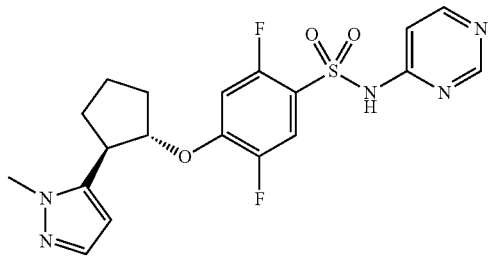

(31a) N-(2,4-dimethoxybenzyl)-2,5-difluoro-4-{[(1S,2R)-2-(1-methyl-1H-pyrazol-5-yl)cyclopentyl]oxy}-N-(pyrimidin-4-yl)benzenesulfonamide The N-(2,4-dimethoxybenzyl)-2,5-difluoro-4-{[(1S*,2R*)-2-(1-methyl-1H-pyrazol-5-yl)cyclopentyl]oxy}-N-(pyrimidin-4-yl)benzenesulfonamide prepared in Example 14c was optically resolved with CHIRALPAK AD (Daicel Corp.; hexane/isopropanol=4:1) to yield the title compound as a colorless oil.

(31b) 2,5-Difluoro-4-{[(1S,2R)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[((1S,2R)-2-(1-methyl-1H-pyrazol-5-yl)cyclopentyl]oxy}-N-(pyrimidin-4-yl)benzenesulfonamide (411 mg, 0.70 mmol) prepared in Example 31a, triethylsilane (0.20 mL), trifluoroacetic acid (2.0 mL) and dichloromethane (2.0 mL), to yield the title compound (241 mg, 79%) as a colorless solid.

$[\alpha]_D^{25}$=58.9 (c 1.02, DMSO).

Example 32

2,5-Difluoro-4-{[(1S*,2R*)-2-(1H-imidazol-1-yl)cyclohexyl]oxy}-N-(pyrimidin-4-yl)benzenesulfonamide

[Formula 50]

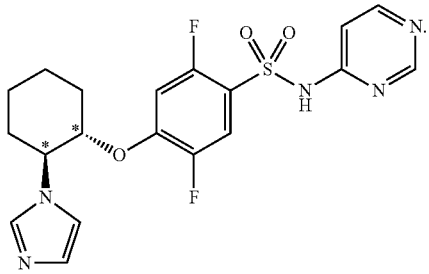

(32a) N-(2,4-dimethoxybenzyl)-2,5-difluoro-4-{[(1S*,2S*)-2-(1H-imidazol-1-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (260 mg, 0.592 mmol) prepared in Example 14b, (1S*,2S*)-2-(1H-imidazol-1-yl)cyclohexanol (Tetrahedron, 2007, 63, 469-473; 100 mg, 0.602 mmol), sodium hydride (63%; 50 mg, 1.31 mmol) and DMF (3.0 mL), to yield the title compound (315 mg, 91%) as a colorless oil.

$^1$H-NMR (500 MHz, CDCl$_3$) δ ppm: 1.43-1.63 (3H, m), 1.82-1.97 (3H, m), 2.26-2.31 (2H, m), 3.77 (3H, s), 3.78 (3H, s), 4.14-4.17 (2H, m), 5.19 (1H, d, J=16.6 Hz), 5.23 (1H, d, J=17.1 Hz), 6.35 (1H, dd, J=5.9, 10.7 Hz), 6.39-6.41 (2H, m), 6.96 (2H, s), 7.16-7.19 (2H, m), 7.58 (1H, s), 7.68 (1H, dd, J=6.4, 9.8 Hz), 8.46 (1H, d, J=5.9 Hz), 8.78 (1H, s).

(32b) 2,5-Difluoro-4-{[(1S*,2R*)-2-(1H-imidazol-1-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2S*)-2-(1H-imidazol-1-yl)cyclohexyl]oxy}-N-(pyrimidin-4-yl)benzenesulfonamide (315 mg, 0.538 mmol) prepared in Example 32a, triethylsilane (0.40 mL), trifluoroacetic acid (4.0 mL) and dichloromethane (4.0 mL), to yield the title compound (220 mg, 94%) as a colorless solid.

$^1$H-NMR (500 MHz, CD$_3$OD) δ ppm: 1.55-1.62 (3H, m), 1.91-1.96 (2H, m), 2.05-2.13 (1H, m), 2.26-2.28 (1H, m), 2.36-2.38 (1H, m), 4.60-4.71 (2H, m), 6.99 (1H, d, J=6.4 Hz), 7.06 (1H, dd, J=6.4, 11.2 Hz), 7.48 (1H, s), 7.69 (1H, dd, J=6.4, 10.3 Hz), 7.76 (1H, s), 8.23 (1H, d, J=6.4 Hz), 8.52 (1H, s), 9.03 (1H, s).

MS (ESI) m/z: 436 [M+H]+.

Example 33

2,5-Difluoro-4-{[(1S*,2R*)-2-(1H-pyrazol-4-yl)cyclohexyl]oxy}-N-(pyrimidin-4-yl)benzenesulfonamide

[Formula 51]

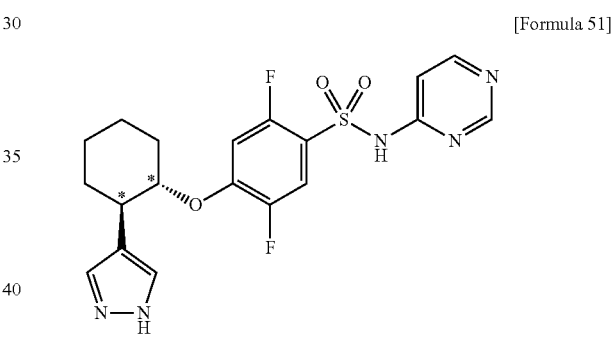

(33a) 4-Cyclohex-1-en-1-yl-1-(tetrahydro-2H-pyran-2-yl)-1H-pyrazole

A solution of 4-iodo-1-(tetrahydro-2H-pyran-2-yl)-1H-pyrazole (J. Org. Chem. 2007, 72, 3589-3591; 2.00 g, 7.19 mmol), 2-cyclohex-1-en-1-yl-4,4,5,5-tetramethyl-1,3,2-dioxaborolane (1.50 g, 7.21 mmol), [1,1'-bis(diphenylphosphino)ferrocene]dichloropalladium (II) (300 mg, 0.41 mmol) and potassium carbonate (3.00 g, 21.7 mmol) in DMF (13 mL) was stirred at 90° C. for 3 hours under microwave irradiation. After allowing to cool, water (50 mL) was added to the reaction solution, followed by extraction with ethyl acetate (50 mL). The thus obtained organic layer was washed twice with water (100 mL) and dried over anhydrous sodium sulfate. After vacuum concentration, the residue was purified with column chromatography (hexane/ethyl acetate=9:1) to yield the title compound (637 mg, 38%) as a colorless oil.

$^1$H-NMR (500 MHz, CDCl$_3$) δ ppm: 1.58-1.76 (8H, m), 2.03-2.05 (2H, m), 2.08-2.16 (2H, m), 2.25-2.28 (2H, m), 3.69 (1H, dt, J=2.4, 11.2 Hz), 4.04-4.07 (1H, m), 5.34 (1H, dd, J=2.4, 9.8 Hz), 6.00-6.02 (1H, m), 6.96 (1H, brs), 7.52 (1H, s), 7.61 (1H, s).

(33b) (1S*,2R*)-2-[1-(Tetrahydro-2H-pyran-2-yl)-1H-pyrazol-4-yl]cyclohexanol To a solution of the 4-cyclohex-1-en-1-yl-1-(tetrahydro-2H-pyran-2-yl)-1H-pyrazole (775 mg, 3.34 mmol) prepared in Example 33a in THF (4 mL), a borane-THF complex (0.95 M; 3.4 mL, 3.23 mmol) was added with cooling on ice, and the reaction solution was stirred for 30 minutes with cooling on ice. To the reaction solution, a borane-THF complex (0.95 M; 3.4 mL, 3.23 mmol) was added again, and the mixture was stirred at room temperature for 90 minutes. To the reaction solution, water (5 mL) and subsequently sodium perborate tetrahydrate (1.00 g, 6.50 mmol) were added, and the mixture was stirred for 5 hours. To the reaction solution, sodium thiosulfate (2.0 g) was added, followed by extraction with ethyl acetate (50 mL). The thus obtained organic layer was dried over anhydrous sodium sulfate. After vacuum concentration, the residue was purified with column chromatography (dichloromethane/methanol=97:3) to yield the title compound (590 mg, 71%) as a colorless oil.

$^1$H-NMR (400 MHz, CDCl$_3$) δ ppm: 1.24-1.94 (10H, m), 2.05-2.14 (4H, m), 2.37-2.43 (1H, m), 3.38-3.44 (1H, m), 3.67-3.73 (1H, m), 4.07 (1H, dd, J=3.9, 11.7 Hz), 5.34 (1H, dd, J=2.7, 9.8 Hz), 7.49 (1H, s), 7.50 (1H, s).

(33c) N-(2,4-dimethoxybenzyl)-2,5-difluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (340 mg, 0.774 mmol) prepared in Example 14b, the (1S*,2R*)-2-[1-(tetrahydro-2H-pyran-2-yl)-1H-pyrazol-4-yl]cyclohexanol (198 mg, 0.791 mmol) prepared in Example 33b, sodium hydride (63%; 50 mg, 1.31 mmol) and DMF (4.0 mL), to yield the title compound (302 mg, 58%) as a colorless oil.

$^1$H-NMR (500 MHz, CDCl$_3$) δ ppm: 1.40-1.67 (8H, m), 1.82-2.17 (6H, m), 2.85-2.90 (1H, m), 3.63-3.67 (1H, m), 3.76 (3H, s), 3.78 (3H, s), 3.97-4.01 (2H, m), 5.22 (2H, s), 5.25-5.29 (1H, m), 6.39-6.41 (2H, m), 6.46-6.50 (1H, m), 7.17-7.20 (2H, m), 7.43-7.46 (2H, m), 7.69 (1H, dd, J=6.4, 9.8 Hz), 8.45 (1H, d, J=5.9 Hz), 8.78 (1H, s).

(33d) 2,5-Difluoro-4-{[(1S*,2R*)-2-(1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-2,5-difluoro-(N-pyrimidin-4-yl)-4-({(1S*,2R*)-2-[1-(tetrahydro-2H-pyran-2-yl)-1H-pyrazol-4-yl]cyclohexyl}oxy)benzenesulfonamide (302 mg, 0.451 mmol) prepared in Example 33c, triethylsilane (0.40 mL), trifluoroacetic acid (4.0 mL), dichloromethane (4.0 mL) and methanol (4.0 mL), to yield the title compound (246 mg, 55%) as a colorless solid.

$^1$H-NMR (500 MHz, CD$_3$OD) δ ppm: 1.37-1.57 (3H, m), 1.65-1.72 (1H, m), 1.78-1.81 (1H, m), 1.85-1.87 (1H, m), 2.03-2.05 (1H, m), 2.15-2.19 (1H, m), 2.82-2.88 (1H, m), 4.26-4.31 (1H, m), 6.94 (1H, dd, J=6.8, 12.2 Hz), 7.02 (1H, d, J=5.4 Hz), 7.45 (2H, s), 7.66 (1H, dd, J=6.8, 10.3 Hz), 8.26 (1H, d, J=6.4 Hz), 8.54 (1H, s).
MS (ESI) m/z: 436 [M+H]+.

Example 34

4-{[(1S*,2R*)-2-(3-Amino-1H-pyrazol-4-yl)cyclohexyl]oxy}-2,5-difluoro-N-(pyrimidin-4-yl)benzenesulfonamide

[Formula 52]

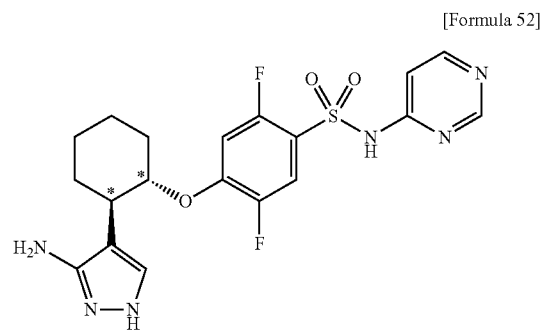 [SMILES: Nc1n[nH]cc1[C@H]1CCCC[C@@H]1Oc1cc(F)c(S(=O)(=O)Nc2ccncn2)cc1F]

(34a) 4-Cyclohex-1-en-1-yl-3-nitro-1-(tetrahydro-2H-pyran-2-yl)-1H-pyrazole

The reaction and aftertreatment were conducted in the same manner as in Example 33a by using 4-bromo-3-nitro-1-(tetrahydro-2H-pyran-2-yl)-1H-pyrazole (WO 2010/079443; 1.20 g, 4.35 mmol), 2-cyclohex-1-en-1-yl-4,4,5,5-tetramethyl-1,3,2-dioxaborolane (1.20 g, 5.77 mmol), [1,1'-bis(diphenylphosphino)ferrocene]dichloropalladium (II) (250 mg, 0.342 mmol), potassium carbonate (2.00 g, 14.5 mmol) and DMF (13 mL), to yield the title compound (950 mg, 79%) as a yellow oil.

$^1$H-NMR (500 MHz, CDCl$_3$) δ ppm: 1.64-1.76 (8H, m), 1.99-2.06 (2H, m), 2.14-2.18 (2H, m), 2.21-2.24 (2H, m), 3.69-3.74 (1H, m), 4.05-4.08 (1H, m), 5.40 (1H, dd, J=2.9, 9.3 Hz), 5.84-5.86 (1H, m), 7.52 (1H, s).

(34b) (1S*,2R*)-2-[3-Nitro-1-(tetrahydro-2H-pyran-2-yl)-1H-pyrazol-4-yl]cyclohexanol The reaction and aftertreatment were conducted in the same manner as in Example 33b by using the 4-cyclohex-1-en-1-yl-3-nitro-1-(tetrahydro-2H-pyran-2-yl)-1H-pyrazole (950 mg, 3.43 mmol) prepared in Example 34a, a borane-THF complex (0.95 M; 8.0 mL, 7.60 mmol), sodium perborate tetrahydrate (1.10 g, 7.15 mmol), THF (5.0 mL) and water (7.0 mL), to yield the title compound (320 mg, 32%) as a colorless oil.

$^1$H-NMR (500 MHz, CDCl$_3$) δ ppm: 1.31-1.86 (8H, m), 2.01-2.17 (6H, m), 3.11-3.16 (1H, m), 3.50-3.55 (1H, m), 3.68-3.73 (1H, m), 4.04-4.09 (1H, m), 5.38-5.42 (1H, m), 7.62 (1H, s).

(34c) N-(2,4-dimethoxybenzyl)-2,5-difluoro-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (240 mg, 0.546 mmol) prepared in Example 14b, the (1S*,2R*)-2-[3-nitro-1-(tetrahydro-2H-pyran-2-yl)-1H-pyrazol-4-yl]cyclohexanol (160 mg, 0.542 mmol) prepared in Example 34b, sodium hydride (63%; 50 mg, 1.31 mmol) and DMF (3.0 mL), to yield the title compound (310 mg, 80%) as a colorless oil.

$^1$H-NMR (500 MHz, CDCl$_3$) δ ppm: 1.45-1.69 (8H, m), 1.81-2.23 (6H, m), 3.54-3.59 (1H, m), 3.61-3.70 (1H, m), 3.77 (3H, s), 3.79 (3H, s), 3.95-4.01 (1H, m), 4.28-4.33 (1H, m), 5.22 (2H, s), 5.30-5.36 (1H, m), 6.40-6.41 (2H, m), 6.56-6.51 (1H, m), 7.18-7.20 (2H, m), 7.49 (1H, d, J=12.2 Hz), 7.64-7.69 (1H, m), 7.46 (1H, d, J=5.9 Hz), 8.78 (1H, s).

(34d) 4-{[(1S*,2R*)-2-(3-Amino-1H-pyrazol-4-yl)cyclohexyl]oxy}-2,5-difluoro-N-(pyrimidin-4-yl)benzenesulfonamide A solution of the N-(2,4-dimethoxybenzyl)-2,5-difluoro-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide (310 mg, 0.434 mmol) prepared in Example 34c, an iron powder (300 mg, 5.37 mol) and a saturated aqueous solution of ammonium chloride (5.0 mL) in ethanol (10 mL) was heated under reflux with stirring for 1 hour. After allowing to cool, the reaction solution was filtered through celite, and the filtrate was subjected to extraction with dichloromethane (100 mL). The organic layer was dried over anhydrous sodium sulfate and vacuum concentrated to yield crude amine. To a solution of the crude amine and triethylsilane (0.30 mL) in dichloromethane (3.0 mL), trifluoroacetic acid (3.0 mL) was added at room temperature, and the reaction solution was stirred for 1 hour. To the reaction solution, methanol (3.0 mL) was added, and the mixture was further stirred at room temperature for 1 hour. The reaction solution was concentrated, and the residue was purified with silica gel chromatography (dichloromethane/methanol=90:10) to yield the title compound (41.1 mg, 21%) as a colorless solid.

$^1$H-NMR (500 MHz, CD$_3$OD) δ ppm: 1.41-1.56 (3H, m), 1.64-1.73 (1H, m), 1.81-1.84 (1H, m), 1.87-1.89 (1H, m), 1.96-1.99 (1H, m), 2.21-2.23 (1H, m), 2.80-2.85 (1H, m), 4.34-4.39 (1H, m), 7.00-7.03 (2H, m), 7.58 (1, brs), 7.69 (1H, dd, J=6.4, 10.3 Hz), 8.26 (1H, d, J=5.9 Hz), 8.53 (1H, s).

MS (ESI) m/z: 451 [M+H]+.

Example 35

4-{[(1S*,2R*)-2-(2-Aminopyridin-4-yl)cyclohexyl]oxy}-2,5-difluoro-N-(pyrimidin-4-yl)benzenesulfonamide

[Formula 53]

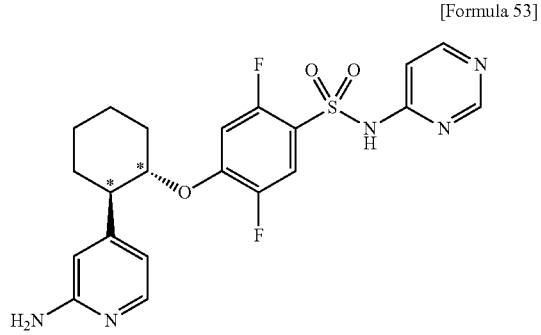 [SMILES: Nc1cc([C@H]2CCCC[C@@H]2Oc2cc(F)c(S(=O)(=O)Nc3ccncn3)cc2F)ccn1]

(35a) 4-Cyclohex-1-en-1-ylpyridin-2-amine

The reaction and aftertreatment were conducted in the same manner as in Example 33a by using 2-amino-4-chloropyridine (927 mg, 7.21 mmol), 2-cyclohex-1-en-1-yl-4,4,5,5-tetramethyl-1,3,2-dioxaborolane (1.50 g, 7.21 mmol), tetrakis(triphenylphosphine)palladium (0) (416 mg, 0.360 mmol), potassium carbonate (3.98 g, 14.5 mmol) and DMF (13 mL), to yield the title compound (180 mg, 14%) as a colorless solid.

$^1$H-NMR (500 MHz, CDCl$_3$) δ ppm: 1.63-1.68 (2H, m), 1.74-1.79 (2H, m), 2.17-2.22 (2H, m), 2.31-2.34 (2H, m), 4.39 (2H, brs), 6.27-6.29 (1H, m), 6.46 (1H, s), 6.68 (1H, dd, J=1.5, 5.4 Hz), 7.98 (1H, d, J=5.9 Hz).

(35b) (1S*,2R*)-2-(2-Aminopyridin-4-yl)cyclohexanol

The reaction and aftertreatment were conducted in the same manner as in Example 33b by using the 4-cyclohex-1-en-1-ylpyridin-2-amine (180 mg, 1.03 mmol) prepared in Example 35a, a borane-THF complex (0.95 M; 5.17 mL, 4.91 mmol), sodium perborate tetrahydrate (159 mg, 1.03 mmol), THF (5.0 mL) and water (5.0 mL), to yield the title compound (27.0 mg, 14%) as a brown solid.

$^1$H-NMR (500 MHz, CDCl$_3$) δ ppm: 1.25-1.84 (4H, m), 1.95-2.21 (4H, m), 2.30-2.36 (1H, m), 3.62-3.69 (1H, m), 4.62 (2H, brs), 6.40 (1H, s), 6.56 (1H, d, J=4.4 Hz), 7.92 (1H, brs).

(35c) 4-{[(1S*,2R*)-2-(2-Aminopyridin-4-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (64.8 mg, 0.147 mmol) prepared in Example 14b, the (1S*,2R*)-2-(2-aminopyridin-4-yl)cyclohexanol (27.0 mg, 0.140 mmol) prepared in Example 35b, sodium hydride (63%; 8.0 mg, 0.210 mmol) and DMF (2.0 mL), to yield the title compound (42.7 mg, 50%) as a colorless oil.

$^1$H-NMR (500 MHz, CDCl$_3$) δ ppm: 1.37-1.69 (4H, m), 1.82-1.85 (1H, m), 1.92-1.98 (2H, m), 2.23 (1H, d, J=12.3 Hz), 2.73-2.79 (1H, m), 3.76 (3H, s), 3.77 (3H, s), 4.25 (1H, dt, J=4.4, 10.7 Hz), 4.36 (2H, brs), 5.21 (2H, s), 6.36-6.40 (3H, m), 6.52-6.54 (2H, m), 7.17-7.20 (2H, m), 7.64 (1H, dd, J=6.4, 9.8 Hz), 7.93 (1H, d, J=4.9 Hz), 8.45 (1H, d, J=5.9 Hz), 8.78 (1H, s).

(35d) 4-{[(1S*,2R*)-2-(2-Aminopyridin-4-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2R*)-2-(2-aminopyridin-4-yl)cyclohexyl]oxy}-N-(2,4-dimethoxybenzyl)-2,5-difluoro-N-(pyrimidin-4-yl)benzenesulfonamide (42.7 mg, 0.0698 mmol) prepared in Example 35c, triethylsilane (0.10 mL), trifluoroacetic acid (1.0 mL) and dichloromethane (1.0 mL), to yield the title compound (18.6 mg, 58%) as a colorless solid.

$^1$H-NMR (500 MHz, CD$_3$OD) δ ppm: 1.42-1.70 (4H, m), 1.82-1.94 (3H, m), 2.27-2.29 (1H, m), 2.90-2.96 (1H, m), 4.64 (1H, dt, J=4.4, 10.3 Hz), 6.84-6.86 (2H, m), 6.96 (1H, d, J=6.4 Hz), 7.09 (1H, dd, J=6.8, 11.2 Hz), 7.64 (1H, dd, J=6.4, 10.3 Hz), 7.72 (1H, d, J=6.4 Hz), 8.18 (1H, d, J=6.4 Hz), 8.49 (1H, s).

MS (ESI) m/z: 462 [M+H]+.

Example 36

4-{[(1S*,2R*)-2-(2-Aminopyridin-4-yl)cyclopentyl]oxy}-2,5-difluoro-N-(pyrimidin-4-yl)benzenesulfonamide

[Formula 54]

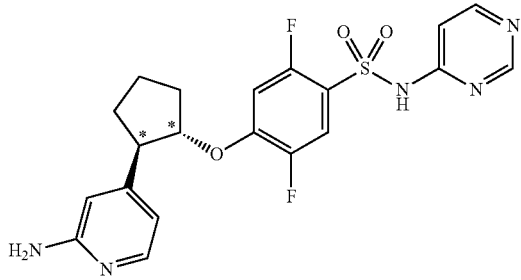

(36a) 4-Cyclopent-1-en-1-ylpyridine-2-amine

The reaction and aftertreatment were conducted in the same manner as in Example 33a by using the 2-amino-4-chloropyridine (1.07 g, 8.32 mmol), 2-cyclopent-1-en-1-yl-4,4,5,5-tetramethyl-1,3,2-dioxaborolane (1.61 g, 8.29 mmol), [1,1'-bis(diphenylphosphino)ferrocene]dichloropalladium(II) (303 mg, 0.414 mmol), potassium carbonate (4.59 g, 33.2 mmol) and DMF (15 mL), to yield the title compound (552 mg, 41%) as a colorless solid.

$^1$H-NMR (500 MHz, CDCl$_3$) δ ppm: 2.00-2.04 (2H, m), 2.51-2.55 (2H, m), 2.62-2.66 (2H, m), 4.39 (2H, brs), 6.34 (1H, t, J=2.0 Hz), 6.46 (1H, s), 6.74 (1H, d, J=5.4 Hz), 7.99 (1H, d, J=5.4 Hz).

(36b) (1S*,2R*)-2-(2-Aminopyridin-4-yl)cyclopentanol

The reaction and aftertreatment were conducted in the same manner as in Example 33b by using the 4-cyclopent-1-en-1-ylpyridine-2-amine (552 mg, 3.44 mmol) prepared in Example 36a, a borane-THF complex (0.95 M; 18.1 mL, 17.2 mmol), sodium perborate tetrahydrate (531 mg, 3.44 mmol), THF (18 mL) and water (18 mL), to yield the title compound (110 mg, 18%) as a colorless oil.

$^1$H-NMR (500 MHz, CDCl$_3$) δ ppm: 1.50-1.59 (2H, m), 1.75-1.82 (2H, m), 2.00-2.05 (2H, m), 2.83-2.90 (1H, m), 3.66-3.68 (1H, m), 4.47 (2H, brs), 6.37 (1H, s), 6.54 (1H, d, J=6.4 Hz), 7.90 (1H, d, J=5.4 Hz).

(36c) 4-{[(1S*,2R*)-2-(2-Aminopyridin-4-yl)cyclopentyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (285 mg, 0.649 mmol) prepared in Example 14b, the (1S*,2R*)-2-(2-aminopyridin-4-yl)cyclopentanol (110 mg, 0.617 mmol) prepared in Example 36b, sodium hydride (63%; 35.3 mg, 0.927 mmol) and DMF (3.0 mL), to yield the title compound (185 mg, 50%) as a colorless oil.

$^1$H-NMR (500 MHz, CDCl$_3$) δ ppm: 1.70-1.79 (2H, m), 1.91-1.97 (2H, m), 2.11-2.19 (1H, m), 2.24-2.30 (1H, m), 3.23 (1H, dt, J=4.9, 8.8 Hz), 3.76 (3H, s), 3.79 (3H, s), 4.45 (2H, brs), 4.61-4.64 (1H, m), 5.23 (2H, s), 6.35 (1H, s), 6.40-6.41 (2H, m), 6.49-6.52 (2H, m), 7.18-7.20 (2H, m), 7.74 (1H, dd, J=6.4, 9.8 Hz), 8.00 (1H, d, J=5.4 Hz), 8.45 (1H, d, J=5.9 Hz), 8.78 (1H, s).

(36d) 4-{[(1S*,2R*)-2-(2-Aminopyridin-4-yl)cyclopentyl]oxy}-2,5-difluoro-N-(pyrimidin-4-yl)benzenesulfonamide The reaction and aftertreatment were conducted in the same manner, as in Example 1b by using the 4-{[(1S*,2R*)-2-(2-aminopyridin-4-yl)cyclopentyl]oxy}-N-(2,4-dimethoxybenzyl)-2,5-difluoro-N-(pyrimidin-4-yl)benzenesulfonamide (185 mg, 0.310 mmol) prepared in Example 36c, triethylsilane (0.20 mL), trifluoroacetic acid (2.0 mL) and dichloromethane (2.0 mL), to yield the title compound (122 mg, 88%) as a colorless solid.

$^1$H-NMR (500 MHz, CD$_3$OD) δ ppm: 1.77-1.97 (4H, m), 2.25-2.37 (2H, m), 3.35-3.40 (1H, m), 4.89-4.92 (1H, m), 6.84-6.86 (2H, m), 6.96-7.00 (2H, m), 7.74 (1H, dd, J=6.8, 10.3 Hz), 7.77 (1H, d, J=6.4 Hz), 8.23 (1H, d, J=6.4 Hz), 8.52 (1H, s).

MS (ESI) m/z: 448 [M+H]+.

Example 37

4-{[(1S*,2R*)-2-(1-Ethyl-1H-pyrazol-5-yl)cyclopentyl]oxy}-2,5-difluoro-N-(pyrimidin-4-yl)benzenesulfonamide

[Formula 55]

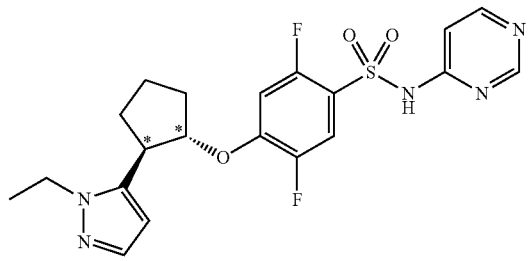

(37a) (1S*,2R*)-2-(1-Ethyl-1H-pyrazol-5-yl)cyclopentanol

The reaction and aftertreatment were conducted in the same manner as in Example 4a by using 1-ethylpyrazole (97%, 2.53 g, 25.5 mmol), N,N,N',N'-tetramethylethylenediamine (3.83 mL, 25.5 mmol), butyl lithium (1.63 M solution in hexane; 18.3 mL, 29.8 mmol), cyclopentene oxide (2.66 g, 31.6 mmol) and THF (60 mL), to yield the title compound (750 mg, 16%) as a colorless oil.

$^1$H-NMR (500 MHz, CDCl$_3$) δ ppm: 1.42 (3H, t, J=7.3 Hz), 1.63-1.91 (4H, m), 2.04-2.23 (2H, m), 3.02 (1H, q, J=8.3 Hz), 4.01-4.23 (3H, m), 6.01 (1H, d, J=1.5 Hz), 7.41 (1H, s).

(37b) N-(2,4-Dimethoxybenzyl)-4-{[(1S*,2R*)-2-(1-ethyl-1H-pyrazol-5-yl)cyclopentyl]oxy}-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (200 mg, 0.455 mmol) prepared in Example 14b, (1S*,2R*)-2-(1-ethyl-1H-pyrazol-5-yl)cyclopentanol (78.0 mg, 0.432 mmol) prepared in Example 37a, sodium hydride (63%; 24.7 mg, 0.648 mmol) and DMF (2.0 mL), to yield the title compound (210 mg, 81%) as a colorless oil.

$^1$H-NMR (500 MHz, CDCl$_3$) δ ppm: 1.38 (3H, t, J=7.3 Hz), 1.75-1.97 (4H, m), 2.19-2.34 (2H, m), 3.47 (1H, dt, J=4.9, 8.3 Hz), 3.76 (3H, s), 3.79 (3H, s), 4.11-4.23 (2H, m), 4.63-4.66 (1H, m), 5.23 (2H, s), 6.04 (1H, d, J=2.0 Hz), 6.39-6.42 (2H, m), 6.52 (1H, dd, J=6.4, 10.7 Hz), 7.17-7.20 (2H, m), 7.43 (1H, d, J=2.0 Hz), 7.76 (1H, dd, J=6.4, 9.8 Hz), 8.45 (1H, d, J=5.9 Hz), 8.77 (1H, s).

(37c) 4-{[(1S*,2R*)-2-(1-Ethyl-1H-pyrazol-5-yl)cyclopentyl]oxy}-2,5-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclopentyl]oxy}-2,5-difluoro-N-(pyrimidin-4-yl)benzenesulfonamide (210 mg, 0.350 mmol) prepared in Example 37b, triethylsilane (0.20 mL), trifluoroacetic acid (2.0 mL) and dichloromethane (2.0 mL), to yield the title compound (113 mg, 72%) as a colorless solid.

$^1$H-NMR (500 MHz, CDCl$_3$) δ ppm: 1.38 (3H, t, J=7.3 Hz), 1.75-1.83 (1H, m), 1.88-1.98 (3H, m), 2.19-2.34 (2H, m), 3.44-3.48 (1H, m), 4.10-4.24 (2H, m), 4.63-4.66 (1H, m), 6.04 (1H, s), 6.58 (1H, dd, J=6.4, 10.7 Hz), 7.25-7.27 (1H, m), 7.43 (1H, m), 7.74 (1H, dd, J=6.8, 10.3 Hz), 8.39 (1H, d, J=5.9 Hz), 8.82 (1H, s).

MS (ESI) m/z: 450 [M+H]+.

Example 38

4-{[(1S*,2R*)-2-(1-Ethyl-1H-pyrazol-5-yl)cyclopentyl]oxy}-2,3-difluoro-N-(pyrimidin-4-yl)benzenesulfonamide

[Formula 56]

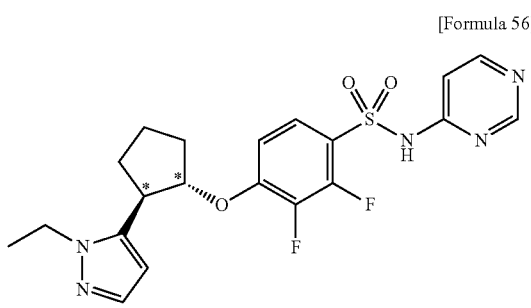

(38a) N-(2,4-Dimethoxybenzyl)-4-{[(1S*,2R*)-2-(1-ethyl-1H-pyrazol-5-yl)cyclopentyl]oxy}-2,3-difluoro-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (76.8 mg, 0.175 mmol) prepared in Example 30a, the (1S*,2R*)-2-(1-ethyl-1H-pyrazol-5-yl)cyclopentanol (30.0 mg, 0.166 mmol) prepared in Example 37a, sodium hydride (63%; 9.5 mg, 0.249 mmol) and DMF (1.0 mL), to yield the title compound (80.0 mg, 80%) as a colorless oil.

$^1$H-NMR (500 MHz, CDCl$_3$) δ ppm: 1.39 (3H, t, J=7.3 Hz), 1.74-1.83 (2H, m), 1.92-1.98 (2H, m), 2.22-2.35 (2H, m), 3.46 (1H, dt, J=4.9, 8.8 Hz), 3.76 (3H, s), 3.79 (3H, s), 4.12-4.21 (2H, m), 4.74-4.76 (1H, m), 5.23 (1H, d, J=16.6 Hz), 5.28 (1H, d, J=16.6. Hz), 6.05 (1H, d, J=1.5 Hz), 6.39-6.42 (2H, m), 6.64 (1H, t, J=8.3 Hz), 7.19-7.20 (2H, m), 7.45 (1H, d, J=1.5 Hz), 7.70 (1H, dt, J=1.5, 7.3 Hz), 8.44 (1H, d, J=5.9 Hz), 8.76 (1H, s).

(38b) 4-{[(1S*,2R*)-2-(1-Ethyl-1H-pyrazol-5-yl)cyclopentyl]oxy}-2,3-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclopentyl]oxy}-2,3-difluoro-N-(pyrimidin-4-yl)benzenesulfonamide (80.0 mg, 0.133 mmol) prepared in Example 38a, triethylsilane (0.10 mL), trifluoroacetic acid (1.0 mL) and dichloromethane (1.0 mL), to yield the title compound (30.0 mg, 50%) as a colorless solid.

$^1$H-NMR (500 MHz, CDCl$_3$) δ ppm: 1.38 (3H, t, J=7.3 Hz), 1.75-1.83 (1H, m), 1.93-1.96 (3H, m), 2.22-2.34 (2H, m), 3.46 (1H, dt, J=4.6, 8.3 Hz), 4.10-4.22 (2H, m), 4.73-4.76 (1H, m), 6.05 (1H, d, J=1.5 Hz), 6.65 (1H, t, J=8.8 Hz), 7.20 (1H, d, J=6.4 Hz), 7.44 (1H, d, J=1.5 Hz), 7.68-7.72 (1H, m), 8.35 (1H, d, J=6.4 Hz), 8.73 (1H, s).

MS (ESI) m/z: 450 [M+H]+.

Example 39

2,5-Difluoro-4-{[(1S*,2R*)-2-(pyridin-3-yl)cyclohexyl]oxy}-N-(pyrimidin-4-yl)benzenesulfonamide

[Formula 57]

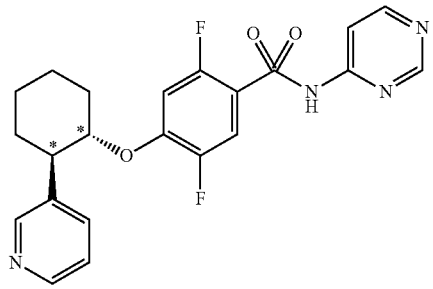

(39a) 3-Cyclohex-1-en-1-ylpyridine

A solution of 3-bromopyridine (0.38 g, 2.40 mmol), 2-cyclohex-1-en-1-yl-4,4,5,5-tetramethyl-1,3,2-dioxaborolane (0.50 g, 2.40 mmol), tetrakis(triphenylphosphine)palladium (0) (0.14 g, 0.12 mmol) and cesium carbonate (1.72 g, 5.29 mmol) in 1,4-dioxane (8.0 mL) and water (4.0 mL) was stirred at 90° C. for 4 hours. After allowing to cool, the reaction solution was subjected to extraction with ethyl acetate (50 mL), and the organic layer was dried over anhydrous sodium sulfate. After vacuum concentration, the residue was purified with column chromatography (hexane/ethyl acetate=2:1) to yield the title compound (347.3 mg, 99%) as a colorless oil.

$^1$H-NMR (400 MHz, CDCl$_3$) δ ppm: 1.65-1.83 (4H, m), 2.20-2.25 (2H, m), 2.37-2.42 (2H, m), 6.16-6.18 (1H, m), 7.22 (1H, dd, J=4.7, 7.8 Hz), 7.64 (1H, dt, J=2.0, 9.8 Hz), 8.45 (1H, dd, J=1.2, 6.3 Hz), 8.64 (1H, d, J=2.4 Hz).

(39b) (1S*,2R*)-2-(Pyridin-3-yl)cyclohexanol

The reaction and aftertreatment were conducted in the same manner as in Example 33b by using the 3-cyclohex-1-en-1-ylpyridine (0.34 g, 2.14 mmol) prepared in Example 39a, a borane-THF complex (0.95 M; 5.62 mL, 5.34 mmol), sodium perborate tetrahydrate (0.85 g, 5.55 mmol), THF (2.1 mL) and water (3.2 mL), to yield the title compound (0.12 g, 32%) as a colorless amorphous solid.

$^1$H-NMR (500 MHz, CDCl$_3$) δ ppm: 1.32-1.56 (4H, m), 1.75-1.88 (3H, m), 2.12-2.16 (1H, m), 2.43-2.49 (1H, m), 3.64-3.71 (1H, m), 7.22 (1H, dd, J=4.7, 7.8 Hz), 7.56 (1H, dt, J=2.0, 5.9 Hz), 8.37 (1H, dd, J=1.6, 4.7 Hz), 8.44 (1H, d, J=2.4 Hz).

(39c) N-(2,4-dimethoxybenzyl)-2,5-difluoro-4-{[(1S*,2R*)-2-(pyridin-3-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (0.12 g, 0.27 mmol) prepared in Example 14b, the (1S*,2R*)-2-pyridin-3-ylcyclohexanol (0.05 g, 0.27 mmol) prepared in Example 39b, sodium hydride (63%; 0.02 g, 0.41 mmol) and DMF (1.4 mL), to yield the title compound (112.8 mg, 69%) as a colorless amorphous solid.

$^1$H-NMR (400 MHz, CDCl$_3$) δ ppm: 1.42-1.74 (4H, m), 1.86-1.87 (1H, m), 1.96-2.01 (2H, m), 2.25-2.28 (1H, m), 2.89-2.95 (1H, m), 3.76 (3H, s), 3.78 (3H, s), 4.26 (1H, dt, J=4.3, 10.6 Hz), 5.18 (1H, d, J=17.6 Hz), 5.22 (1H, d, J=17.6 Hz), 6.38-6.40 (2H, m), 6.49 (1H, dd, J=6.3, 11.3 Hz), 7.15-7.18 (3H, m), 7.53 (1H, dt, J=2.0, 9.4 Hz), 7.62 (1H, dd, J=6.7, 9.8 Hz), 8.41 (1H, dd, J=1.2, 4.7 Hz), 8.44 (1H, d, J=5.9 Hz), 8.53 (1H, d, J=2.4 Hz), 8.77 (1H, s).

(39d) 2,5-Difluoro-4-{[(1S*,2R*)-2-(pyridin-3-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*)-2-pyridin-3-ylcyclohexyl]oxy}-N-(pyrimidin-4-yl)benzenesulfonamide (0.11 g, 0.19 mmol) prepared in Example 39c, triethylsilane (0.15 mL), trifluoroacetic acid (0.19 g) and dichloromethane (1.9 mL), to yield the title compound (77 mg, 92%) as a colorless solid.

$^1$H-NMR (400 MHz, CD$_3$OD) δ ppm: 1.47-1.65 (3H, m), 1.77-1.94 (3H, m), 2.00-2.04 (1H, m), 2.29-2.33 (1H, m), 3.10-3.16 (1H, m), 4.64 (1H, dt, J=3.9, 10.2 Hz), 6.99 (1H, dd, J=0.8, 6.3 Hz), 7.05 (1H, dd, J=6.7, 11.7 Hz), 7.62 (1H, dd, J=6.7, 10.6 Hz), 7.73 (1H, dd, J=5.5, 8.2 Hz), 8.24 (1H, dd, J=0.8, 6.7 Hz), 8.33 (1H, dt, J=1.6, 8.2 Hz), 6.53-8.54 (2H, m), 8.77 (1H, d, J=1.6 Hz).

MS (ESI) m/z: 447 [M+H]+.

Example 40

2,3-Difluoro-4-{[(1S*,2R*)-2-(1-methyl-1H-pyrazol-5-yl)cyclohexyl]oxy}-N-(pyrimidin-4-yl)benzenesulfonamide

[Formula 58]

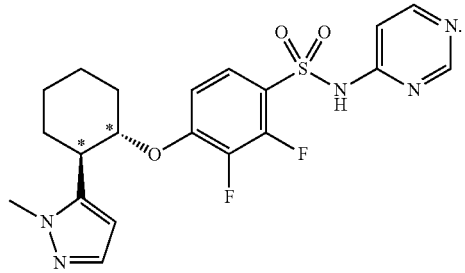

(40a) N-(2,4-dimethoxybenzyl)-2,3-difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (0.40 g, 0.91 mmol) prepared in Example 30a, the (1S*,2R*)-2-(1-methyl-1H-pyrazol-5-yl)cyclohexanol (0.16 g, 0.91 mmol) prepared in Example 4a, sodium hydride (63%; 0.050 g, 1.37 mmol) and DMF (4.6 mL), to yield the title compound (373 mg, 68%) as a colorless amorphous solid.

$^1$H-NMR (400 MHz, CDCl$_3$) δ ppm: 1.34-1.71 (4H, m), 1.86-1.97 (2H, m), 2.04-2.08 (1H, m), 2.25-2.28 (1H, m), 2.98-3.04 (1H, m), 3.76 (3H, s), 3.78 (3H, s), 3.90 (3H, s), 4.19-4.25 (1H, m), 5.20 (1H, d, J=16.8 Hz), 5.25 (1H, d, J=17.2 Hz), 6.04 (1H, d, J=2.0 Hz), 6.38-6.41 (2H, m), 6.59 (1H, t, J=8.6 Hz), 7.17-7.20 (2H, m), 7.34 (1H, d, J=1.6 Hz), 7.62-7.66 (1H, m), 8.44 (1H, d, J=5.9 Hz), 8.76 (1H, s).

(40b) 2,3-Difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,3-difluoro-4-{[(1S*,2R*)-2-(1-methyl-1H-pyrazol-5-yl)cyclohexyl]oxy}-N-(pyrimidin-4-yl)benzenesulfonamide (0.050 g, 0.09 mmol) prepared in Example 40a, triethylsilane (0.07 mL), trifluoroacetic acid (0.09 mL) and dichloromethane (0.9 mL), to yield the title compound (0.040 g, 86%) as a colorless solid.

$^1$H-NMR (400 MHz, CD$_3$OD) δ ppm: 1.45-1.61 (3H, m), 1.67-1.78 (1H, m), 1.83-1.86 (1H, m), 1.91-1.93 (1H, m), 1.99-2.03 (1H, m), 2.27-2.30 (1H, m), 3.09-3.15 (1H, m), 3.86 (3H, s), 4.44-4.50 (1H, m), 6.14 (1H, d, J=2.0 Hz), 6.91-6.96 (1H, m), 7.02 (1H, d, J=6.3 Hz), 7.25 (1H, d, J=2.0 Hz), 7.62-7.67 (1H, m), 8.25 (1H, d, J=6.3 Hz), 8.52 (1H, s).

MS (ESI) m/z: 450 [M+H]+.

Example 41

4-{[(1S*,2R*)-2-(1-Ethyl-1H-pyrazol-5-yl)cyclohexyl]oxy}-2,3-difluoro-N-(pyrimidin-4-yl)benzenesulfonamide

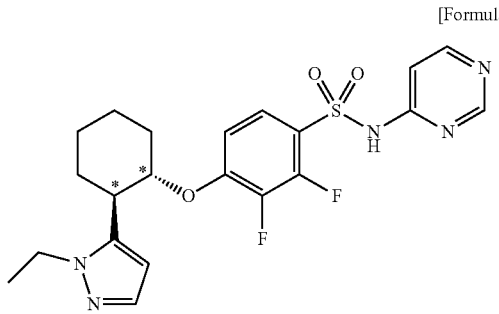

[Formula 59]

(41a) N-(2,4-Dimethoxybenzyl)-4-{[(1S*,2R*)-2-(1-ethyl-1H-pyrazol-5-yl)cyclohexyl]oxy}-2,3-difluoro-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (0.050 g, 0.11 mmol) prepared in Example 30a, the (1S*,2R*)-2-(1-ethyl-1H-pyrazol-5-yl)cyclohexanol (0.020 g, 0.11 mmol) prepared in Example 12a, sodium hydride (63%; 0.010 g, 0.17 mmol) and DMF (0.6 mL), to yield the title compound (55.4 mg, 81%) as a colorless amorphous solid.

$^1$H-NMR (400 MHz, CDCl$_3$) δ ppm: 1.35-1.68 (4H, m), 1.42 (3H, t, J=7.4 Hz), 1.86-1.89 (1H, m), 1.94-1.96 (1H, m), 2.03-2.07 (1H, m), 2.25-2.28 (1H, m), 2.98-3.04 (1H, m), 3.76 (3H, s), 3.78 (3H, s), 4.09-4.31 (3H, m), 5.19 (1H, d, J=16.8 Hz), 5.25 (1H, d, J=16.8 Hz), 6.02 (1H, d, J=2.0 Hz), 6.39-6.41 (2H, m), 6.58-6.62 (1H, m), 7.17-7.20 (2H, m), 7.37 (1H, d, J=2.0 Hz), 7.62-7.66 (1H, m), 8.44 (1H, d, J=5.9 Hz), 8.76 (1H, d, J=1.2 Hz).

(41b) 4-{[(1S*,2R*)-2-(1-Ethyl-1H-pyrazol-5-yl)cyclohexyl]oxy}-2,3-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclohexyl]oxy}-2,3-difluoro-N-(pyrimidin-4-yl)benzenesulfonamide (0.060 g, 0.09 mmol) prepared in Example 41a, triethylsilane (0.07 mL), trifluoroacetic acid (0.09 mL) and dichloromethane (0.9 mL), to yield the title compound (34.9 mg, 82%) as a colorless solid.

$^1$H-NMR (400 MHz, CD$_3$OD) δ ppm: 1.36 (3H, t, J=7.4 Hz), 1.45-1.75 (4H, m), 1.82-1.85 (1H, m), 1.90-1.93 (1H, m), 1.97-2.02 (1H, m), 2.25-2.32 (1H, m), 3.07-3.14 (1H, m), 4.11-4.19 (1H, m), 4.25-4.34 (1H, m), 4.49-4.55 (1H, m), 6.14 (1H, d, J=2.0 Hz), 6.94-6.98 (1H, m), 7.02 (1H, d, J=6.3 Hz), 7.29 (1H, d, J=2.0 Hz), 7.63-7.68 (1H, m), 8.26 (1H, d, J=6.3 Hz), 8.53 (1H, s).

MS (ESI) m/z: 462 [M−H]−.

Example 42

2,5-Difluoro-4-{[(1S*,2R*)-2-(1-methyl-1H-pyrazol-5-yl)cycloheptyl]oxy}-N-(pyrimidin-4-yl)benzenesulfonamide

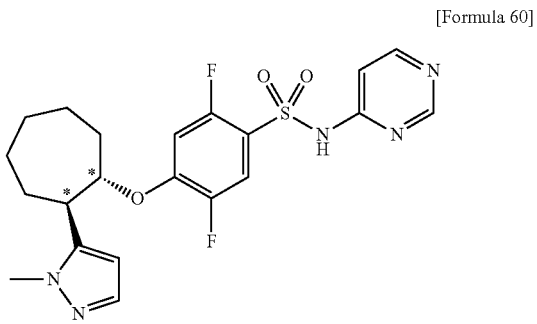 [SMILES: Cn1nccc1[C@H]1CCCCC[C@@H]1Oc1cc(F)c(S(=O)(=O)Nc2ccncn2)cc1F]

[Formula 60]

(42a) N-(2,4-Dimethoxybenzyl)-2,5-difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (100 mg, 0.228 mmol) prepared in Example 14b, the (1S*,2R*)-2-(1-methyl-1H-pyrazol-5-yl)cycloheptanol (30 mg, 0.154 mmol) prepared in Example 9a, sodium hydride (63%; 40 mg, 1.05 mmol) and DMF (2 mL), to yield the title compound (50 mg, 53%) as a colorless oil.

$^1$H-NMR (500 MHz, CDCl$_3$) δ ppm: 1.57-1.99 (10H, m), 3.23 (1H, dt, J=3.4, 9.8 Hz), 3.76 (3H, s), 3.78 (3H, s), 3.89 (3H, s), 4.34-4.38 (1H, m), 5.19 (1H, d, J=16.6 Hz), 5.23 (1H, d, J=17.1 Hz), 6.00 (1H, d, J=2.0 Hz), 6.39-6.42 (3H, m), 7.17-7.19 (2H, m), 7.33 (1H, d, J=2.0 Hz), 7.67 (1H, dd, J=6.4, 9.8 Hz), 8.45 (1H, d, J=5.9 Hz), 8.78 (1H, s).

(42b) 2,5-Difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*)-2-(1-methyl-1H-pyrazol-5-yl)cycloheptyl]oxy}-N-(pyrimidin-4-yl)benzenesulfonamide (50 mg, 0.0815 mmol) prepared in Example 42a, triethylsilane (0.10 mL), trifluoroacetic acid (1.0 mL) and dichloromethane (1.0 mL), to yield the title compound (32 mg, 85%) as a colorless solid.

$^1$H-NMR (500 MHz, CDCl$_3$) δ ppm: 1.61-1.98 (10H, m), 3.22 (1H, dt, J=2.9, 9.3 Hz), 3.89 (3H, s), 4.32-4.36 (1H, m), 6.00 (1H, d, J=2.0 Hz), 6.45 (1H, dd, J=6.4, 11.2 Hz), 7.21 (1H, brs), 7.32 (1H, d, J=2.0 Hz), 7.66 (1H, dd, J=6.8, 9.8 Hz), 8.40 (1H, d, J=6.4 Hz), 8.78 (1H, s).

MS (ESI) m/z: 464 [M+H]+.

Example 43

2-Fluoro-5-methyl-4-{[(1S*,2R*)-2-(1-methyl-1H-pyrazol-5-yl)cyclopentyl]oxy}-N-(pyrimidin-4-yl)benzenesulfonamide

[Formula 61]

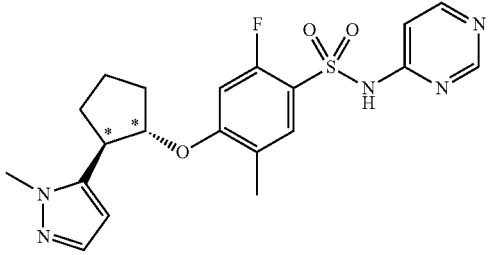

(43a) N-(2,4-dimethoxybenzyl)-2,4-difluoro-5-methyl-N-(pyrimidin-4-yl)benzenesulfonamide The reaction and aftertreatment were conducted in the same manner as in Example 14b by using the N-(2,4-dimethoxybenzyl)pyrimidin-4-amine (1.0 g, 4.08 mmol) prepared in Example 14a, 2,4-difluoro-5-methylbenzenesulfonyl chloride (WO 2010/079443; 1.85 g, 8.15 mmol), 1,4-diazabicyclo[2.2.2]octane (0.91 g, 8.15 mmol) and THF (20 mL), to yield the title compound (1.41 g, 79%) as a colorless amorphous solid.

$^1$H-NMR (500 MHz, CDCl$_3$) δ ppm: 2.31 (3H, s), 3.77 (3H, s), 3.79 (3H, s), 5.25 (2H, s), 6.40-6.42 (2H, m), 6.83 (1H, t, J=9.3 Hz), 7.20-7.23 (2H, m), 7.89 (1H, t, J=7.8 Hz), 8.45 (1H, d, J=5.9 Hz), 8.77 (1H, s).

(43b) N-(2,4-Dimethoxybenzyl)-2-fluoro-5-methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (0.30 g, 0.69 mmol) prepared in Example 43a, the (1S*,2R*)-2-(1-methyl-1H-pyrazol-5-yl)cyclopentanol (0.12 g, 0.72 mmol) prepared in Example 8a, sodium hydride (63%; 0.040 g, 1.05 mmol) and DMF (10 mL), to yield the title compound (0.20 g, 50%) as a colorless oil.

$^1$H-NMR (500 MHz, CDCl$_3$) δ ppm: 1.74-1.95 (4H, m), 2.16-2.34 (2H, m), 2.20 (3H, s), 3.41 (1H, dt, J=4.9, 8.3 Hz), 3.76 (3H, s), 3.80 (3H, s), 3.84 (3H, s), 4.62-4.65 (1H, m), 5.26 (2H, s), 6.04 (1H, d, J=2.0 Hz), 6.37-6.42 (3H, m), 7.20 (1H, d, J=8.3 Hz), 7.26-7.28 (1H, m), 7.40 (1H, d, J=1.5 Hz), 7.76 (1H, d, J=7.8 Hz), 8.42 (1H, d, J=5.9 Hz), 8.76 (1H, s).

(43c) 2-Fluoro-5-methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2-fluoro-5-methyl-4-{[(1S*,2R*)-2-(1-methyl-1H-pyrazol-5-yl)cyclopentyl]oxy}-N-(pyrimidin-4-yl)benzenesulfonamide (0.20 g, 0434 mmol) prepared in Example 43b, triethylsilane (0.10 mL), trifluoroacetic acid (0.50 mL) and dichloromethane (4.0 mL), to yield the title compound (0.16 g, 98%) as a colorless amorphous solid.

$^1$H-NMR (500 MHz, CDCl$_3$) δ ppm: 1.73-1.93 (4H, m), 2.18-2.34 (2H, m), 2.21 (3H, s), 3.41 (1H, dt, J=4.4, 7.8 Hz), 3.84 (3H, s), 4.62-4.65 (1H, m), 6.04 (1H, d, J=1.5 Hz), 6.44 (1H, d, J=11.7 Hz), 7.24-7.25 (1H, m), 7.39 (1H, d, J=2.0 Hz), 7.75 (1H, d, J=7.8 Hz), 8.41 (1H, d, J=5.9 Hz), 8.86 (1H, brs).

MS (ESI) m/z: 432 [M+H]+.

Example 44

2-Fluoro-4-{[(1S*,2R*)-2-(1-methyl-1H-pyrazol-5-yl)cyclohexyl]oxy}-N-(pyrimidin-4-yl)benzenesulfonamide

[Formula 62]

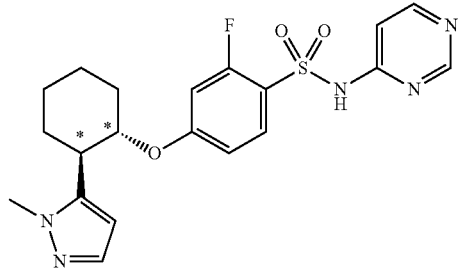

(44a) N-(2,4-Dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (0.40 g, 0.95 mmol) prepared in Example 29a, the (1S*,2R*)-2-(1-methyl-1H-pyrazol-5-yl)cyclohexanol (0.17 g, 0.95 mmol) prepared in Example 4a, sodium hydride (63%; 0.040 g, 1.14 mmol) and DMF (4.8 mL), to yield the title compound (489 mg, 89%) as a colorless amorphous solid.

$^1$H-NMR (500 MHz, CDCl$_3$) δ ppm: 1.25-1.63 (4H, m), 1.86-1.88 (1H, m), 1.93-1.95 (1H, m), 2.03-2.06 (1H, m), 2.24-2.26 (1H, m), 2.91-2.96 (1H, m), 3.77 (3H, s), 3.79 (3H, s), 3.88 (3H, s), 4.13-4.18 (1H, m), 5.23 (2H, s), 5.99 (1H, d, J=2.0 Hz), 6.39-6.44 (3H, m), 6.58 (1H, dd, J=2.0, 8.8 Hz), 7.20 (2H, dd, J=8.3, 11.2 Hz), 7.34 (1H, d, J=2.0 Hz), 7.86 (1H, t, J=8.3 Hz), 8.42 (1H, d, J=5.9 Hz), 8.75 (1H, s).

(44b) 2-Fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide (0.49 g, 0.84 mmol) prepared in Example 44a, triethylsilane (0.67 mL), trifluoroacetic acid (0.84 mL) and dichloromethane (8.4 mL), to yield the title compound (318 mg, 88%) as a colorless solid.

$^1$H-NMR (400 MHz, CD$_3$OD) δ ppm: 1.25-1.74 (4H, m), 1.81-1.90 (2H, m), 1.97-2.02 (1H, m), 2.21-2.24 (1H, m), 3.02-3.08 (1H, m), 3.84 (3H, s), 4.42 (1H, dt, J=3.9, 10.2 Hz), 6.12 (1H, d, J=2.4 Hz), 6.69 (1H, dd, J=2.4, 12.5 Hz), 6.74 (1H, dd, J=2.7, 9.0 Hz), 7.03 (1H, dd, J=1.2, 6.3 Hz), 7.24 (1H, d, J=1.6 Hz), 7.84 (1H, t, J=8.6 Hz), 8.30 (1H, d, J=6.3 Hz), 8.85 (1H, d, J=2.0 Hz).

MS (ESI) m/z: 432 [M+H]+.

Example 45

4-{[(1S*,2R*)-2-(1-Ethyl-1H-pyrazol-5-yl)cyclohexyl]oxy}-2-fluoro-N-(pyrimidin-4-yl)benzenesulfonamide

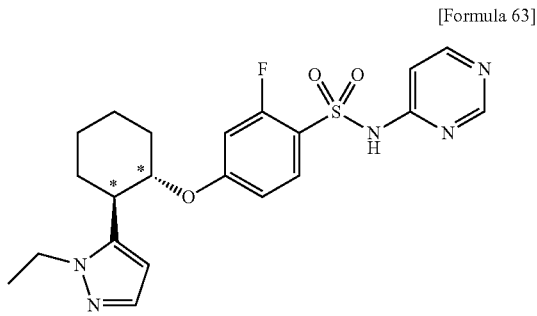 [SMILES: CCn1nccc1[C@H]1CCCC[C@@H]1Oc1ccc(S(=O)(=O)Nc2ccncn2)c(F)c1]

[Formula 63]

(45a) N-(2,4-Dimethoxybenzyl)-4-{[(1S*,2R*)-2-(1-ethyl-1H-pyrazol-5-yl)cyclohexyl]oxy}-2-fluoro-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (0.40 g, 0.95 mmol) prepared in Example 29a, the (1S*,2R*)-2-(1-ethyl-1H-pyrazol-5-yl)cyclohexanol (0.18 g, 0.95 mmol) prepared in Example 12a, sodium hydride (63%; 0.040 g, 1.14 mmol) and DMF (4.8 mL), to yield the title compound (506.4 mg, 90%) as a colorless oil.

$^1$H-NMR (500 MHz, CDCl$_3$) δ ppm: 1.36-1.50 (3H, m), 1.44 (3H, t, J=6.8 Hz), 1.57-1.62 (1H, m), 1.85-1.88 (1H, m), 1.93-1.94 (1H, m), 2.02-2.05 (1H, m), 2.22-2.28 (1H, m), 2.91-2.96 (1H, m), 3.76 (3H, s), 3.79 (3H, s), 4.10-4.28 (3H, m), 5.23 (2H, s), 5.98 (1H, d, J=2.0 Hz), 6.39-6.44 (3H, m), 6.58 (1H, dd, J=2.4, 8.8 Hz), 7.21 (2H, dd, J=8.3, 13.2 Hz), 7.36 (1H, d, J=2.0 Hz), 7.86 (1H, t, J=8.3 Hz), 8.42 (1H, d, J=5.9 Hz), 8.75 (1H, s).

(45b) 4-{[(1S*,2R*)-2-(1-Ethyl-1H-pyrazol-5-yl)cyclohexyl]oxy}-2-fluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclohexyl]oxy}-2-fluoro-N-(pyrimidin-4-yl)benzenesulfonamide (0.51 g, 0.85 mmol) prepared in Example 45a, triethylsilane (0.68 mL), trifluoroacetic acid (0.85 mL) and dichloromethane (8.5 mL), to yield the title compound (333.4 mg, 88%) as a colorless solid.

$^1$H-NMR (400 MHz, CD$_3$OD) δ ppm: 1.29-1.73 (4H, m), 1.37 (3H, t, J=7.4 Hz), 1.81-1.90 (2H, m), 1.97-2.01 (1H, m), 2.22-2.26 (1H, m), 3.00-3.07 (1H, m), 4.07-4.18 (1H, m), 4.23-4.31 (1H, m), 4.46 (1H, dt, J=3.9, 10.2 Hz), 6.12 (1H, d, J=2.0 Hz), 6.67 (1H, dd, J=2.4, 12.5 Hz), 6.73 (1H, dd, J=2.4, 9.0 Hz), 7.04 (1H, dd, J=1.2, 6.3 Hz), 7.28 (1H, d, J=2.4 Hz), 7.84 (1H, t, J=8.6 Hz), 8.30 (1H, d, J=6.3 Hz), 8.55 (1H, s).

MS (ESI) m/z: 446 [M+H]+.

Example 46

2,6-Difluoro-4-{[(1S*,2R*)-2-(1-methyl-1H-pyrazol-5-yl)cyclohexyl]oxy}-N-(pyrimidin-4-yl)benzenesulfonamide

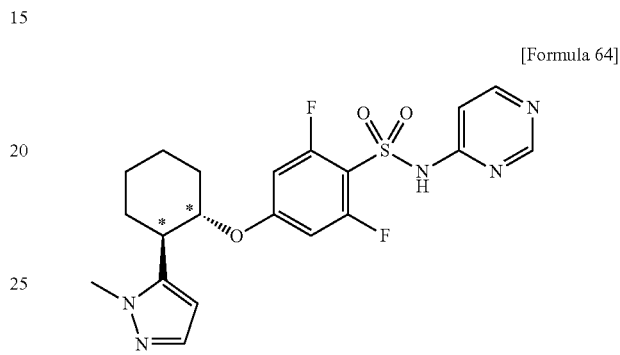

[Formula 64]

(46a) N-(2,4-Dimethoxybenzyl)-2,6-difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (0.19 g, 0.43 mmol) prepared in Example 27a, the (1S*,2R*)-2-(1-methyl-1H-pyrazol-5-yl)cyclohexanol (0.080 g, 0.45 mmol) prepared in Example 4a, sodium hydride (63%; 0.030 g, 0.79 mmol) and DMF (5 mL), to yield the title compound (0.12 g, 48%) as a colorless amorphous solid.

$^1$H-NMR (500 MHz, CDCl$_3$) δ ppm: 1.38-1.67 (4H, m), 1.86-1.88 (1H, m), 1.94-1.95 (1H, m), 2.03-2.06 (1H, m), 2.22-2.24 (1H, m), 2.90-2.95 (1H, m), 3.77 (3H, s), 3.81 (3H, s), 3.86 (3H, s), 4.10-4.15 (1H, m), 5.24 (2H, s), 5.99 (1H, d, J=2.0 Hz), 6.29 (2H, d, J=10.7 Hz), 6.40-6.44 (2H, m), 7.14 (1H, dd, J=1.0, 5.9 Hz), 7.21 (1H, d, J=8.3 Hz), 7.34 (1H, d, J=2.0 Hz), 8.44 (1H, d, J=5.9 Hz), 8.78 (1H, s).

(46b) 2,6-Difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,6-difluoro-4-{[(1S*,2R*)-2-(1-methyl-1H-pyrazol-5-yl)cyclohexyl]oxy}-N-(pyrimidin-4-yl)benzenesulfonamide (0.12 g, 0.21 mmol) prepared in Example 46a, triethylsilane (0.10 mL), trifluoroacetic acid (0.50 mL) and dichloromethane (2.0 mL), to yield the title compound (0.030 g, 30%) as a colorless solid.

$^1$H-NMR (400 MHz, CDCl$_3$) δ ppm: 1.38-1.65 (4H, m), 1.85-1.88 (1H, m), 1.93-1.95 (1H, m), 2.03-2.08 (1H, m), 2.22-2.24 (1H, m), 2.89-2.96 (1H, m), 3.86 (3H, s), 4.09-4.15 (1H, m), 6.00 (1H, d, J=2.0 Hz), 6.32 (2H, d, J=10.6

Hz), 7.34 (1H, d, J=2.0 Hz), 7.41 (1H, d, J=6.7 Hz), 8.41 (1H, d, J=6.3 Hz), 8.80 (1H, s).
MS (ESI) m/z: 450 [M+H]+.

Example 47

4-{[(1S*,2R*)-5,5-Difluoro-2-(1-methyl-1H-pyrazol-5-yl)cyclohexyl]oxy}-2,5-difluoro-N-(pyrimidin-4-yl)benzenesulfonamide

[Formula 65]

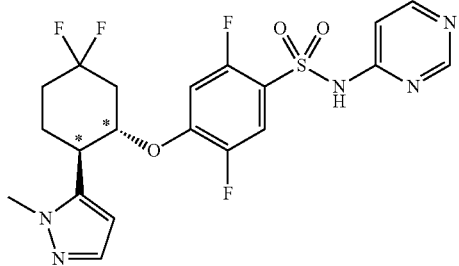

(47a) 5-(4,4-Difluorocyclohex-1-en-1-yl)-1-methyl-1H-pyrazole

The reaction and aftertreatment were conducted in the same manner as in Example 39a by using 5-iodo-1-methyl-1H-pyrazole (1.90 g, 9.14 mmol), 2-(4,4-difluorocyclohex-1-en-1-yl)-4,4,5,5-tetramethyl-1,3,2-dioxaborolane (1.00 g, 4.10 mmol), tetrakis(triphenylphosphine)palladium (0) (240 mg, 0.208 mmol), cesium carbonate (2.70 g, 8.29 mmol), 1,4-dioxane (10 mL) and water (5 mL), to yield the title compound (767 mg, 94%) as a colorless oil.
$^1$H-NMR (500 MHz, CDCl$_3$) δ ppm: 2.13-2.22 (2H, m), 2.56-2.60 (2H, m), 2.73 (2H, t, J=14.2 Hz), 3.86 (3H, s), 5.73 (1H, brs), 6.14 (1H, d, J=2.0 Hz), 7.42 (1H, d, J=2.0 Hz).

(47b) (1S*,2R*)-5,5-Difluoro-2-(1-methyl-1H-pyrazol-5-yl)cyclohexanol

The reaction and aftertreatment were conducted in the same manner as in Example 33b by using the 5-(4,4-difluorocyclohex-1-en-1-yl)-1-methyl-1H-pyrazole (767 mg, 3.87 mmol) prepared in Example 47a, a borane-THF complex (0.95 M; 12.2 mL, 11.6 mmol), sodium perborate tetrahydrate (1.20 g, 7.80 mmol), THF (4.0 mL) and water (8.0 mL), to yield the title compound (148 mg, 18%) as a colorless oil.
$^1$H-NMR (500 MHz, CDCl$_3$) δ ppm: 1.68-1.95 (4H, m), 2.16-2.21 (1H, m), 2.51-2.57 (1H, m), 2.61-2.66 (1H, m), 3.76-3.83 (1H, m), 3.80 (3H, s), 3.89 (1H, brs), 6.02 (1H, d, J=2.0 Hz), 7.26 (1H, d, J=1.5 Hz).

(47c) 4-{[(1S*,2R*)-5,5-Difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (160 mg, 0.364 mmol) prepared in Example 14b, the (1S*,2R*)-5,5-difluoro-2-(1-methyl-1H-pyrazol-5-yl)cyclohexanol (76 mg, 0.351 mmol) prepared in Example 47b, sodium hydride (63%; 40 mg, 1.05 mmol) and DMF (2.0 mL), to yield the title compound (212 mg, 92%) as a colorless solid.
$^1$H-NMR (500 MHz, CDCl$_3$) δ ppm: 1.92-2.12 (4H, m), 2.29-2.33 (1H, m), 2.71-2.77 (1H, m), 3.07-3.12 (1H, m), 3.77 (3H, s), 3.78 (3H, s), 3.92 (3H, s), 4.32 (1H, dt, J=4.9, 10.7 Hz), 5.19 (1H, d, J=17.1 Hz), 5.23 (1H, d, J=17.1 Hz), 6.07 (1H, d, J=2.0 Hz), 6.39-6.44 (3H, m), 7.15-7.19 (2H, m), 7.36 (1H, d, J=2.0 Hz), 7.71 (1H, dd, J=6.4, 9.8 Hz), 8.46 (1H, d, J=5.9 Hz), 8.78 (1H, s).

(47d) 4-{[(1S*,2R*)-5,5-Difluoro-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2R*)-5,5-difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (212 mg, 0.334 mmol) prepared in Example 47c, triethylsilane (0.30 mL), trifluoroacetic acid (3.0 mL) and dichloromethane (3.0 mL), to yield the title compound (153 mg, 95%) as a colorless solid.
$^1$H-NMR (500 MHz, DMSO-d$_6$) δ ppm: 1.36-1.77 (1H, m), 1.96-2.28 (4H, m), 2.64-2.71 (1H, m), 3.35-3.40 (1H, m), 3.79 (3H, s), 4.71 (1H, dt, J=4.4, 10.7 Hz), 6.19 (1H, d, J=1.5 Hz), 6.94 (1H, brs), 7.12-7.16 (1H, m), 7.18 (1H, d, J=2.0 Hz), 7.61-7.64 (1H, m), 8.24 (1H, brs), 8.56 (1H, s).
MS (ESI) m/z: 486 [M+H]+.

Example 48

5-Chloro-2-fluoro-4-{[(1S*,2R*)-2-(1-methyl-1H-pyrazol-5-yl)cyclohexyl]oxy}-N-(pyrimidin-4-yl)benzenesulfonamide

[Formula 66]

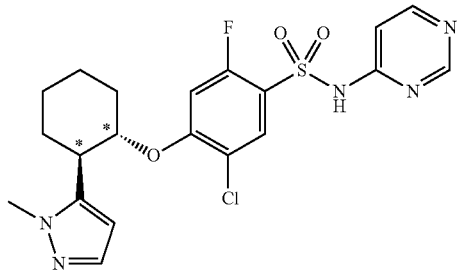

(48a) 5-Chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (0.234 g, 0.513 mmol) prepared in Example 20a, the (1S*,2R*)-2-(1-methyl-1H-pyrazol-5-yl)cyclohexanol (0.116 g, 0.644 mmol) prepared in Example 4a, sodium hydride (63%; 0.023 g, 0.600 mmol) and DMF (2 mL), to yield the title compound (0.273 g, 86%) as a colorless solid.

¹H-NMR (400 MHz, CDCl₃) δ ppm: 1.40-1.68 (4H, m), 1.85-1.97 (2H, m), 2.04-2.10 (1H, m), 2.18-2.23 (1H, m), 3.02-3.09 (1H, m), 3.76 (3H, s), 3.76 (3H, s), 3.93 (3H, s), 4.09-4.17 (1H, m), 5.21 (2H, s), 6.03 (1H, d, J=2.0 Hz), 6.38-6.45 (3H, m), 7.17-7.22 (2H, m), 7.35 (1H, d, J=2.0 Hz), 7.92 (1H, d, J=7.4 Hz), 8.46 (1H, d, J=5.9 Hz), 8.79 (1H, d, J=1.2 Hz).

(48b) 5-Chloro-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide (0.27 g, 0.438 mmol) prepared in Example 48a, triethylsilane (0.168 mL, 1.05 mmol), trifluoroacetic acid (3.4 mL) and dichloromethane (3.4 mL), to yield the title compound (0.148 g, 72%) as a colorless solid.

¹H-NMR (400 MHz, CDCl₃) δ ppm: 1.36-1.70 (4H, m), 1.85-1.96 (2H, m), 2.03-2.11 (1H, m), 2.18-2.23 (1H, m), 3.01-3.09 (1H, m), 3.93 (3H, s), 4.09-4.17 (1H, m), 6.03 (1H, d, J=2.0 Hz), 6.47 (1H, d, J=11.7 Hz), 7.23-7.27 (1H, m), 7.34 (1H, d, J=2.0 Hz), 7.94 (1H, d, J=7.8 Hz), 8.39 (1H, d, J=6.3 Hz), 8.81 (1H, s).

MS (ESI) m/z: 466 [M+H]+.

Example 49

2,5-Difluoro-4-{[(1S*,2R*)-2-(1-methyl-1H-imidazol-5-yl)cyclohexyl]oxy}-N-(pyrimidin-4-yl)benzenesulfonamide

[Formula 67]

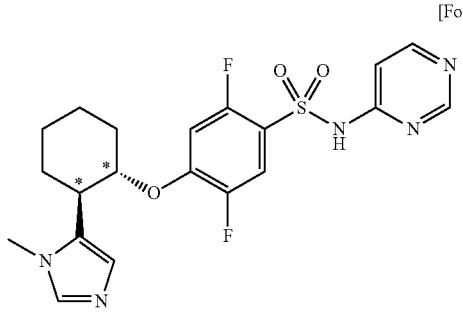

(49a) 2-(1-Methyl-1H-imidazol-5-yl)cyclohex-2-en-1-one

The reaction and aftertreatment were conducted in the same manner as in Example 39a by using (6-oxocyclohex-1-en-1-yl)boric acid (J. Org. Chem. 2011, 76, 3946-3959; 790 mg, 5.65 mmol), 5-bromo-1-methyl-1H-imidazole (910 mg, 5.65 mmol), tetrakis(triphenylphosphine)palladium (0) (326 mg, 0.282 mmol), cesium carbonate (4.00 g, 12.3 mmol), 1,4-dioxane (10 mL) and water (5 mL), to yield the title compound (80 mg, 8%) as a brown oil.

¹H-NMR (500 MHz, CDCl₃) δ ppm: 2.10-2.17 (2H, m), 2.54-2.60 (4H, m), 3.46 (3H, s), 6.92 (1H, d, J=1.0 Hz), 7.10 (1H, t, J=4.4 Hz), 7.44 (1H, s).

(49b) 2-(1-Methyl-1H-imidazol-5-yl)cyclohexanol

To a solution of the 2-(1-methyl-1H-imidazol-5-yl)cyclohex-2-en-1-one (80 mg, 0.454 mmol) prepared in Example 49a in methanol (2.0 mL), sodium borohydride (50 mg, 1.32 mmol) was added at room temperature, and the reaction solution was stirred at room temperature for 30 minutes. To the reaction solution, a saturated aqueous solution of ammonium chloride (20 mL) was added, followed by extraction with dichloromethane (50 mL). The thus obtained organic layer was dried over anhydrous sodium sulfate and vacuum concentrated to yield the title compound (50 mg, 61%) in the form of a trans/cis (2:1) mixture as a colorless oil.

(49c) N-(2,4-Dimethoxybenzyl)-2,5-difluoro-4-{[(1S*,2R*)-2-(1-methyl-1H-imidazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (120 mg, 0.273 mmol) prepared in Example 14b, 2-(1-methyl-1H-imidazol-5-yl)cyclohexanol (50 mg, 0.277 mmol) prepared in Example 49b, sodium hydride (63%; 40 mg, 1.05 mmol) and DMF (2.0 mL), to yield the title compound (46 mg, 28%) as a colorless oil.

¹H-NMR (500 MHz, CDCl₃) δ ppm: 1.38-1.53 (3H, m), 1.68-1.77 (1H, m), 1.88-1.95 (2H, m), 2.06-2.24 (2H, m), 2.85-2.90 (1H, m), 3.66 (3H, s), 3.77 (3H, s), 3.78 (3H, s), 4.03-4.08 (1H, m), 5.19 (1H, d, J=16.6 Hz), 5.24 (1H, d, J=16.6 Hz), 6.39-6.41 (2H, m), 6.47 (1H, dd, J=6.4, 11.2 Hz), 6.85 (1H, s), 7.16-7.20 (2H, m), 7.29 (1H, s), 7.68 (1H, dd, J=6.4, 9.8 Hz), 8.45 (1H, d, J=5.9 Hz), 8.78 (1H, s).

(49d) 2,5-Difluoro-4-{[(1S*,2R*)-2-(1-methyl-1H-imidazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*)-2-(1-methyl-1H-imidazol-5-yl)cyclohexyl]oxy}-N-(pyrimidin-4-yl)benzenesulfonamide (46 mg, 0.0767 mmol) prepared in Example 49c, triethylsilane (0.10 mL), trifluoroacetic acid (1.0 mL), dichloromethane (1.0 mL), to yield the title compound (33 mg, 96%) as a colorless solid.

¹H-NMR (400 MHz, DMSO-d₆) δ ppm: 1.34-1.83 (6H, m), 1.95-1.99 (1H, m), 2.19-2.22 (1H, m), 3.11-3.16 (1H, m), 3.84 (3H, s), 4.49 (1H, dt, J=3.5, 10.2 Hz), 6.94 (1H, d, J=6.3 Hz), 7.32 (1H, dd, J=3.1, 11.7 Hz), 7.45 (1H, s), 7.65 (1H, dd, J=6.7, 10.6 Hz), 8.23 (1H, d, J=6.6 Hz), 8.56 (1H, s), 8.71 (1H, brs).

MS (ESI) m/z: 448 [M–H]–.

Example 50

4-{[(1S*,2R*)-2-(1-Ethyl-1H-pyrazol-5-yl)cyclopentyl]oxy}-2,6-difluoro-N-(pyrimidin-4-yl)benzenesulfonamide

[Formula 68]

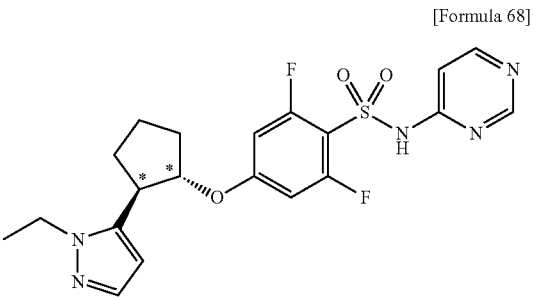 [SMILES: CCn1nccc1[C@H]1CCC[C@@H]1Oc1cc(F)c(S(=O)(=O)Nc2ccncn2)c(F)c1]

(50a) N-(2,4-Dimethoxybenzyl)-4-{[(1S*,2R*)-2-(1-ethyl-1H-pyrazol-5-yl)cyclopentyl]oxy}-2,6-difluoro-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (311 mg, 0.703 mmol) prepared in Example 27a, the (1S*,2R*)-2-(1-ethyl-1H-pyrazol-5-yl)cyclopentanol (127 mg, 0.703 mmol) prepared in Example 37a, sodium hydride (63%; 35.1 mg, 0.921 mmol) and DMF (5.0 mL), to yield the title compound (231 mg, 55%) as a colorless oil.

$^1$H-NMR (500 MHz, CDCl$_3$) δ ppm: 1.38 (3H, t, J=7.3 Hz), 1.73-1.95 (4H, m), 2.18-2.31 (2H, m), 3.36 (1H, dt, J=4.9, 8.3 Hz), 3.77 (3H, s), 3.82 (3H, s), 4.09-4.15 (2H, m), 4.62-4.65 (1H, m), 5.26 (2H, s), 6.03 (1H, d, J=2.0 Hz), 6.37-6.44 (4H, m), 7.16 (1H, dd, J=1.0, 5.9 Hz), 7.22 (1H, d, J=8.3 Hz), 7.44 (1H, d, J=2.0 Hz), 8.44 (1H, d, J=5.9 Hz), 8.78 (1H, s).

(50b) 4-{[(1S*,2R*)-2-(1-Ethyl-1H-pyrazol-5-yl)cyclopentyl]oxy}-2,6-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclopentyl]oxy}-2,6-difluoro-N-(pyrimidin-4-yl)benzenesulfonamide (231 mg, 0.385 mmol) prepared in Example 50a, triethylsilane (0.20 mL), trifluoroacetic acid (2.0 mL) and dichloromethane (2.0 mL), to yield the title compound (151 mg, 87%) as a colorless amorphous solid.

$^1$H-NMR (500 MHz, CDCl$_3$) δ ppm: 1.38 (3H, t, J=7.3 Hz), 1.71-1.77 (1H, m), 1.84-1.95 (3H, m), 2.17-2.32 (2H, m), 3.37 (1H, dt, J=4.9, 8.3 Hz), 4.09-4.18 (2H, m), 4.61-4.64 (1H, m), 6.02 (1H, d, J=2.0 Hz), 6.41 (2H, d, J=10.7 Hz), 7.40 (1H, d, J=5.9 Hz), 7.43 (1H, d, J=2.0 Hz), 8.42 (1H, d, J=6.4 Hz), 8.86 (1H, s).

MS (ESI) m/z: 450 [M+H]+.

Example 51

2,3-Difluoro-4-{[(1S*,2R*)-2-(1-methyl-1H-pyrazol-5-yl)cycloheptyl]oxy}-N-(pyrimidin-4-yl)benzenesulfonamide

[Formula 69]

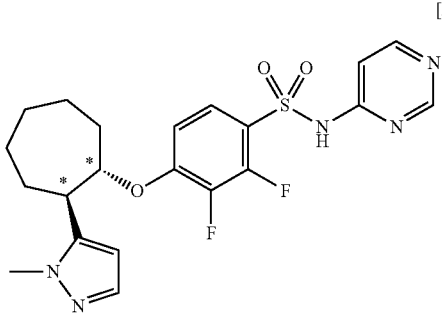

(51a) N-(2,4-Dimethoxybenzyl)-2,3-difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (201 mg, 0.457 mmol) prepared in Example 30a, the (1S*,2R*)-2-(1-methyl-1H-pyrazol-5-yl)cycloheptanol (84.5 mg, 0.585 mmol) prepared in Example 9a, sodium hydride (63%; 24.9 mg, 0.654 mmol) and DMF (3.0 mL), to yield the title compound (190 mg, 72%) as a colorless oil.

$^1$H-NMR (500 MHz, CDCl$_3$) δ ppm: 1.60-2.00 (10H, m), 3.23 (1H, dt, J=2.9, 9.3 Hz), 3.77 (3H, s), 3.78 (3H, s), 3.89 (3H, s), 4.45-4.49 (1H, m), 5.20 (1H, d, J=17.1 Hz), 5.25 (1H, d, J=16.6 Hz), 6.02 (1H, d, J=2.0 Hz), 6.40-6.41 (2H, m), 6.53 (1H, t, J=8.3 Hz), 7.19 (2H, d, J=8.3 Hz), 7.33 (1H, d, J=1.5 Hz), 7.66 (1H, t, J=9.3 Hz), 8.44 (1H, d, J=5.9 Hz), 8.76 (1H, s).

(51b) 2,3-Difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1b by using the N-(2,4-dimethoxybenzyl)-2,3-difluoro-4-{[(1S*,2R*)-2-(1-methyl-1H-pyrazol-5-yl)cycloheptyl]oxy}-N-(pyrimidin-4-yl)benzenesulfonamide (190 mg, 0.310 mmol) prepared in Example 51a, triethylsilane (0.20 mL), trifluoroacetic acid (2.0 mL) and dichloromethane (2.0 mL), to yield the title compound (102 mg, 71%) as a colorless solid.

$^1$H-NMR (500 MHz, CDCl$_3$) δ ppm: 1.59-2.00 (10H, m), 3.23 (1H, dt, J=2.9, 9.3 Hz), 3.88 (3H, s), 4.44-4.48 (1H, m), 6.03 (1H, s), 6.55 (1H, t, J=7.3 Hz), 7.27 (1H, d, J=6.4 Hz), 7.34 (1H, brs), 7.65 (1H, t, J=7.3 Hz), 8.35 (1H, d, J=6.4 Hz), 8.83 (1H, s).

MS (ESI) m/z: 464 [M+H]+.

Example 52

3-Methyl-4-{[(1S*,2R*)-2-(1-methyl-1H-pyrazol-5-yl)cyclopentyl]oxy}-N-(pyrimidin-4-yl)benzenesulfonamide

[Formula 70]

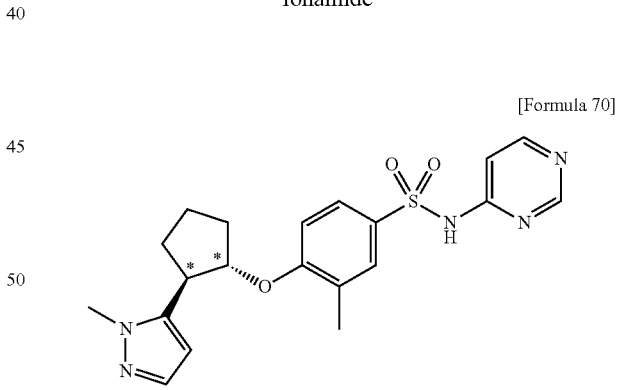

(52a) N-(2,4-dimethoxybenzyl)-4-fluoro-3-methyl-N-(pyrimidin-4-yl)benzenesulfonamide The reaction and aftertreatment were conducted in the same manner as in Example 14b by using the N-(2,4-dimethoxybenzyl)pyrimidin-4-amine (590 mg, 2.40 mmol) prepared in Example 14a, 4-fluoro-3-methylbenzenesulfonyl chloride (WO 2010/079443; 1000 mg, 4.79 mmol), 1,4-diazabicyclo[2.2.2]octane (537 mg, 4.79 mmol) and THF (20 mL), to yield the title compound (598 mg, 50%) as a colorless oil.

¹H-NMR (500 MHz, CDCl₃) δ ppm: 2.28 (3H, s), 3.73 (3H, s), 3.78 (3H, s), 5.22 (2H, s), 6.39-6.41 (2H, m), 7.08 (1H, t, J=8.8 Hz), 7.14 (1H, d, J=7.8 Hz), 7.26-7.29 (1H, m), 7.64 (1H, dd, J=2.0, 6.8 Hz), 7.70-7.73 (1H, m), 8.48 (1H, d, J=5.9 Hz), 8.83 (1H, s).

(52b) N-(2,4-Dimethoxybenzyl)-3-methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-4-fluoro-3-methyl-N-(pyrimidin-4-yl)benzenesulfonamide (500 mg, 1.20 mmol) prepared in Example 52a, the (1S*,2R*)-2-(1-methyl-1H-pyrazol-5-yl)cyclopentanol (209 mg, 1.26 mmol) prepared in Example 8a, sodium hydride (60%; 71.9 mg, 1.80 mmol) and DMF (15 mL), to yield the title compound (356 mg, 53%) as a colorless solid.

¹H-NMR (500 MHz, CDCl₃) δ ppm: 1.62-1.96 (4H, m), 2.18-2.32 (2H, m), 2.18 (3H, s), 3.40 (1H, dt, J=4.9, 8.3 Hz), 3.75 (3H, s), 3.76 (3H, s), 3.82 (3H, s), 4.71-4.74 (1H, m), 5.23 (1H, s), 6.05 (1H, d, J=2.0 Hz), 6.39 (1H, dd, J=2.4, 10.7 Hz), 6.42 (1H, d, J=2.0 Hz), 6.66 (1H, d, J=8.8 Hz), 7.13 (1H, d, J=8.8 Hz), 7.33 (1H, dd, J=1.0, 5.9 Hz), 7.37-7.39 (1H, m), 7.53 (1H, dd, J=1.0, 2.4 Hz), 7.65 (1H, dd, J=2.4, 8.8 Hz), 8.42 (1H, d, J=6.4 Hz), 8.78 (1H, s).

(52c) 3-Methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-3-methyl-4-{[(1S*,2R*)-2-(1-methyl-1H-pyrazol-5-yl)cyclopentyl]oxy}-N-(pyrimidin-4-yl)benzenesulfonamide (356 mg, 0.632 mmol) prepared in Example 52b, triethylsilane (0.20 mL), trifluoroacetic acid (1.0 mL) and dichloromethane (4.0 mL), to yield the title compound (202 mg, 68%) as a colorless solid.

¹H-NMR (500 MHz, CDCl₃) δ ppm: 1.75-1.93 (4H, m), 2.17-2.32 (2H, m), 2.22 (3H, s), 3.40 (1H, dt, J=4.0, 7.8 Hz), 3.81 (3H, s), 4.71-4.74 (1H, m), 6.05 (1H, d, J=2.0 Hz), 6.69 (1H, d, J=8.8 Hz), 7.23 (1H, d, J=4.4 Hz), 7.40 (1H, d, J=2.0 Hz), 7.69-7.73 (2H, m), 8.46 (1H, d, J=5.9 Hz), 8.81 (1H, s).
MS (ESI) m/z: 413 [M+H]+.

Example 53

2,5-Difluoro-4-{[(1S*,2R*)-2-(pyridazin-4-yl)cyclohexyl]oxy}-N-(pyrimidin-4-yl)benzenesulfonamide

[Formula 71]

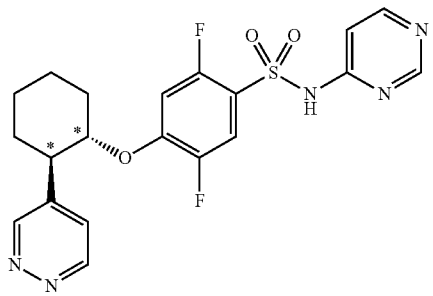

(53a) 4-Cyclohex-1-en-1-ylpyridazine

The reaction and aftertreatment were conducted in the same manner as in Example 39a by using 4-bromopyridazine hydrobromide (0.50 g, 2.09 mmol), 2-cyclohex-1-en-1-yl-4,4,5,5-tetramethyl-1,3,2-dioxaborolane (0.43 g, 2.09 mmol), tetrakis(triphenylphosphine)palladium (0) (0.12 g, 0.10 mmol), cesium carbonate (1.50 g, 4.59 mmol), 1,4-dioxane (7.0 mL) and water (3.5 mL), to yield the title compound (301 mg, 99%) as a colorless solid.

¹H-NMR (400 MHz, CDCl₃) δ ppm: 1.67-1.85 (4H, m), 2.27-2.30 (2H, m), 2.36-2.40 (2H, m), 6.54-6.56 (1H, m), 7.35 (1H, dd, J=2.4, 5.5 Hz), 9.07 (1H, dd, J=1.2, 5.5 Hz), 9.25 (1H, dd, J=1.2, 2.7 Hz).

(53b) (1S*,2R*)-2-Pyridazin-4-ylcyclohexanol

To a solution of the 4-(cyclohex-1-en-1-yl)pyridazine (0.15 g, 0.94 mmol) prepared in Example 53a in dichloromethane (9.4 mL), 3-chloroperbenzoic acid (0.76 g, 3.09 mmol) was added with cooling on ice, and the reaction solution was stirred at room temperature for 4 hours. A highly polar compound was removed with a silica gel pad (dichloromethane) to yield crude epoxide. A solution of the crude epoxide and Raney nickel in ethanol (3.0 mL) was stirred at 70° C. for 3 hours under a hydrogen atmosphere. The reaction solution was filtered, and the residue was then purified with silica gel chromatography to yield the title compound (35 mg, 31%) as a colorless amorphous solid.

¹H-NMR (500 MHz, CDCl₃) δ ppm: 1.31-1.55 (4H, m), 1.80-1.90 (3H, m), 2.15-2.17 (1H, m), 2.46-2.52 (1H, m), 3.71 (1H, dt, J=4.4, 10.3 Hz), 7.35 (1H, dd, J=2.4, 5.4 Hz), 8.96 (1H, d, J=5.4 Hz), 9.01 (1H, s).

(53c) N-(2,4-Dimethoxybenzyl)-2,5-difluoro-4-{[(1S*,2R*)-2-(pyridazin-4-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (0.04 g, 0.08 mmol) prepared in Example 14b, the (1S*,2R*)-2-pyridazin-4-ylcyclohexanol (0.01 g, 0.08 mmol) prepared in Example 53b, sodium hydride (63%; 5 mg, 0.12 mmol) and DMF (0.40 mL), to yield the title compound (44 mg, 93%) as a colorless amorphous solid.

¹H-NMR (500 MHz, CDCl₃) δ ppm: 1.46-1.70 (4H, m), 1.90-1.92 (1H, m), 1.96-2.05 (2H, m), 2.28-2.31 (1H, m), 2.91-2.97 (1H, m), 3.76 (3H, s), 3.77 (3H, s), 4.28 (1H, dt, J=4.4, 10.3 Hz), 5.18 (1H, d, J=17.1 Hz), 5.22 (1H, d, J=17.1 Hz), 6.38-6.42 (2H, m), 6.57 (1H, dd, J=6.4, 11.2 Hz), 7.17-7.18 (2H, m), 7.35 (1H, dd, J=2.0, 5.4 Hz), 7.66 (1H, dd, J=6.8, 10.3 Hz), 8.45 (1H, d, J=5.9 Hz), 8.77 (1H, s), 9.08 (1H, d, J=5.4 Hz), 9.15 (1H, s).

(53d) 2,5-Difluoro-4-{[(1S*,2R*)-2-(pyridazin-4-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*)-2-(pyridazin-4-yl)cyclohexyl]oxy}-N-(pyrimidin-4-yl)benzenesulfonamide (0.04 g, 0.07 mmol) prepared in Example 53c, triethylsilane (0.06 mL), trifluoroacetic acid (0.07 mL) and dichloromethane (0.74 mL), to yield the title compound (30 mg, 94%) as a colorless solid.

¹H-NMR (500 MHz, DMSO-d₆) δ ppm: 1.36-1.63 (4H, m), 1.74-1.88 (3H, m), 2.20-2.23 (1H, m), 2.94-2.98 (1H, m), 4.86 (1H, dt, J=3.9, 10.7 Hz), 6.84-7.03 (1H, m), 7.33 (1H, brs), 7.56 (1H, brs), 7.61 (1H, dd, J=2.4, 5.4 Hz), 8.23 (1H, brs), 8.55 (1H, s), 9.06 (1H, d, J=5.4 Hz), 9.21 (1H, s).

MS (ESI) m/z: 448 [M+H]+.

Example 54

3-Methyl-4-{[(1S*,2R*)-2-(1-methyl-1H-pyrazol-5-yl)cyclohexyl]oxy}-N-(pyrimidin-4-yl)benzenesulfonamide

[Formula 72]

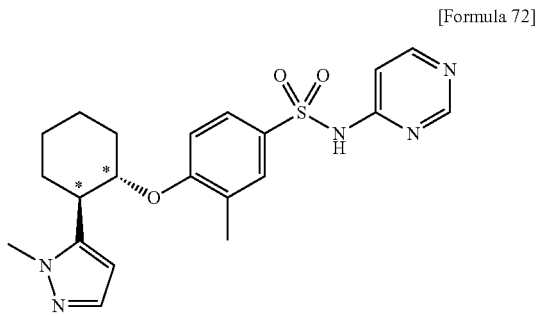 [SMILES: Cc1cc(S(=O)(=O)Nc2ccncn2)ccc1O[C@H]1CCCC[C@@H]1c1ccnn1C]

(54a) N-(2,4-Dimethoxybenzyl)-3-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-4-fluoro-3-methyl-N-(pyrimidin-4-yl)benzenesulfonamide (0.25 g, 0.60 mmol) prepared in Example 52a, the (1S*,2R*)-2-(1-methyl-1H-pyrazol-5-yl)cyclohexanol (0.11 g, 0.63 mmol) prepared in Example 4a, sodium hydride (63%; 0.040 g, 0.90 mmol) and DMF (10 mL), to yield the title compound (79 mg, 23%) as a colorless amorphous solid.

(54b) 3-Methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-3-methyl-4-{[(1S*,2R*)-2-(1-methyl-1H-pyrazol-5-yl)cyclohexyl]oxy}-N-(pyrimidin-4-yl)benzenesulfonamide (79 mg, 0.14 mmol) prepared in Example 54a, triethylsilane (0.1 mL), trifluoroacetic acid (1.0 mL) and dichloromethane (4.0 mL), to yield the title compound (49 mg, 84%) as a colorless solid.

¹H-NMR (500 MHz, CDCl₃) δ ppm: 1.38-1.65 (4H, m), 1.85-1.93 (2H, m), 2.05 (3H, s), 2.05-2.07 (1H, m), 2.24-2.29 (1H, m), 3.00 (1H, dt, J=3.4, 9.8 Hz), 3.88 (3H, s), 4.21-4.26 (1H, m), 5.98 (1H, d, J=2.0 Hz), 6.71 (1H, d, J=8.8 Hz), 7.21 (1H, brs), 7.33 (1H, s), 7.62 (1H, brs), 7.67 (1H, d, J=8.3 Hz), 8.47 (1H, d, J=5.9 Hz), 8.84 (1H, s).

MS (ESI) m/z: 427 [M+H]+.

Example 55

3-Cyano-4-{[(1S*,2R*)-2-(1-methyl-1H-pyrazol-5-yl)cycloheptyl]oxy}-N-(pyrimidin-4-yl)benzenesulfonamide

[Formula 73]

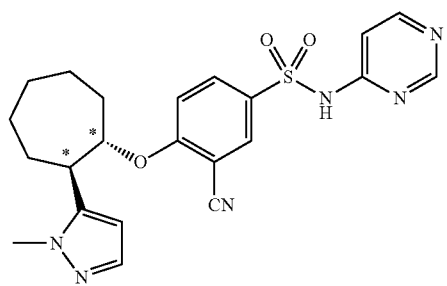

(55a) 3-Cyano-N-(2,4-dimethoxybenzyl)-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1a by using the 3-cyano-N-(2,4-dimethoxybenzyl)-4-fluoro-N-(pyrimidin-4-yl)benzenesulfonamide (198 mg, 0.46 mmol) prepared in Example 26a, the (1S*,2R*)-2-(1-methyl-1H-pyrazol-5-yl)cycloheptanol (94.1 mg, 0.48 mmol) prepared in Example 9a, sodium hydride (60%; 27.7 mg, 0.69 mmol) and DMF (10 mL), to yield the title compound (195 mg, 70%) as a colorless solid.

¹H-NMR (400 MHz, CDCl₃) δ ppm: 1.58-1.72 (3H, m), 1.75-1.95 (5H, m), 1.97-2.02 (1H, m), 1.99 (1H, d, J=4.7 Hz), 3.30 (1H, dt, J=2.4, 9.0 Hz), 3.62 (3H, s), 3.79 (3H, s), 3.94 (3H, s), 4.58 (1H, dd, J=5.5, 9.4 Hz), 5.11 (1H, d, J=16.8 Hz), 5.16 (1H, d, J=16.8 Hz), 6.02 (1H, d, J=2.0 Hz), 6.41 (1H, dd, J=2.4, 8.2 Hz), 6.35 (1H, d, J=2.4 Hz), 6.74 (1H, d, J=9.4 Hz), 7.12 (1H, d, J=6.3 Hz), 7.11 (1H, d, J=4.3 Hz), 7.32 (1H, s), 7.87 (1H, d, J=2.4 Hz), 8.00 (1H, dd, J=2.4, 9.0 Hz), 8.50 (1H, d, J=5.9 Hz), 8.85 (1H, s).

(55b) 3-Cyano-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1b by using 3-cyano-N-(2,4-dimethoxybenzyl)-4-{[(1S*,2R*)-2-(1-methyl-1H-pyrazol-5-yl)cycloheptyl]oxy}-N-(pyrimidin-4-yl)benzenesulfonamide (195 mg, 0.32 mmol) prepared in Example 55a, triethylsilane (0.10 mL), trifluoroacetic acid (1.0 mL) and dichloromethane (4.0 mL), to yield the title compound (102 mg, 70%) as a colorless solid.

¹H-NMR (500 MHz, CDCl₃) δ ppm: 1.55-1.74 (3H, m), 1.76-1.95 (5H, m), 1.96-2.14 (2H, m), 3.30 (1H, dt, J=2.7, 9.2 Hz), 3.94 (3H, s), 4.58 (1H, dd, J=6.4, 13.2 Hz), 6.02 (1H, d, J=2.0 Hz), 6.81 (1H, d, J=9.3 Hz), 7.16 (1H, d, J=5.9 Hz), 7.32 (1H, d, J=2.0 Hz), 7.98 (1H, dd, J=2.4, 8.8 Hz), 8.07 (1H, s), 8.41 (1H, d, J=6.4 Hz), 8.78 (1H, brs).

MS (ESI) m/z: 452 [M+H]+.

Example 56

3-Cyano-4-{[(1S*,2R*)-2-(1-methyl-1H-pyrazol-5-yl)cyclohexyl]oxy}-N-(pyrimidin-4-yl)benzenesulfonamide

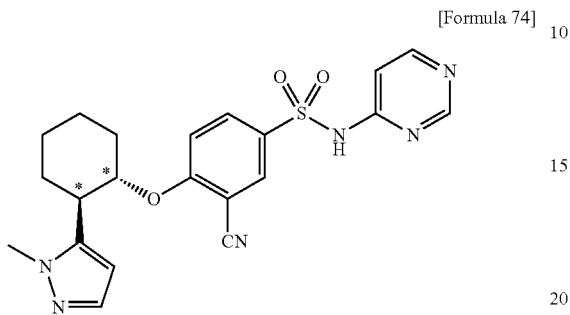

[Formula 74]

(56a) 3-Cyano-N-(2,4-dimethoxybenzyl)-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the 3-cyano-N-(2,4-dimethoxybenzyl)-4-fluoro-N-(pyrimidin-4-yl)benzenesulfonamide (0.20 g, 0.466 mmol) prepared in Example 26a, the (1S*,2R*)-2-(1-methyl-1H-pyrazol-5-yl)cyclohexanol (0.084 g, 0.466 mmol) prepared in Example 4a, sodium hydride (63%; 0.027 g, 0.699 mmol) and DMF (3.0 mL), to yield the title compound (0.090 g, 34%) as a colorless amorphous solid.

$^1$H-NMR (400 MHz, CDCl$_3$) δ ppm: 1.36-1.68 (4H, m), 1.87-1.90 (1H, m), 1.97-1.99 (1H, m), 2.05-2.10 (1H, m), 2.20-2.24 (1H, m), 3.04-3.11 (1H, m), 3.63 (3H, s), 3.79 (3H, s), 3.95 (3H, s), 4.34 (1H, dt, J=3.9, 10.2 Hz), 5.10 (1H, d, J=16.8 Hz), 5.15 (1H, d, J=16.0 Hz), 6.04 (1H, d, J=1.6 Hz), 6.36 (1H, d, J=2.4 Hz), 6.41 (1H, dd, J=2.4, 8.2 Hz), 6.79 (1H, d, J=9.0 Hz), 7.09-7.13 (2H, m), 7.34 (1H, d, J=1.6 Hz), 7.85 (1H, d, J=2.4 Hz), 7.98 (1H, dd, J=2.4, 9.0 Hz), 8.50 (1H, d, J=5.9 Hz), 8.84 (1H, d, J=0.8 Hz).

(56b) 3-Cyano-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using 3-cyano-N-(2,4-dimethoxybenzyl)-4-{[(1S*,2R*)-2-(1-methyl-1H-pyrazol-5-yl)cyclohexyl]oxy}-N-(pyrimidin-4-yl)benzenesulfonamide (0.090 g, 0.15 mmol) prepared in Example 56a, triethylsilane (0.10 mL), trifluoroacetic acid (1.0 mL) and dichloromethane (1.0 mL), to yield the title compound (43 mg, 64%) as a colorless solid.

$^1$H-NMR (500 MHz, DMSO-d$_6$) δ ppm: 1.38-1.63 (4H, m), 1.72-1.74 (1H, m), 1.80-1.82 (1H, m), 1.90-1.93 (1H, m), 2.16-2.18 (1H, m), 3.11-3.16 (1H, m), 3.84 (3H, s), 4.67 (1H, t, J=3.9, 9.8 Hz), 6.07 (1H, d, J=2.0 Hz), 6.93 (1H, brs), 7.17 (1H, d, J=1.5 Hz), 7.38 (1H, d, J=9.3 Hz), 8.00 (1H, dd, J=2.0, 9.3 Hz), 8.10 (1H, s), 8.25 (1H, brs), 8.60 (1H, s).

MS (ESI) m/z: 439 [M+H]+.

Example 57

3-Methyl-4-{[(1S*,2R*)-2-(1-methyl-1H-pyrazol-5-yl)cycloheptyl]oxy}-N-(pyrimidin-4-yl)benzenesulfonamide

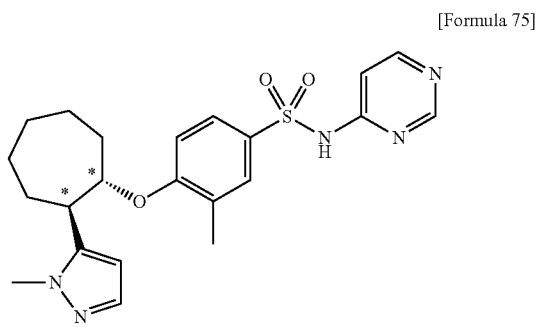 [SMILES: Cc1cc(S(=O)(=O)Nc2ccncn2)ccc1O[C@H]1CCCCC[C@@H]1c1ccnn1C]

[Formula 75]

(57a) N-(2,4-Dimethoxybenzyl)-3-methyl-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1a by using the N-(2,4-dimethoxybenzyl)-4-fluoro-3-methyl-N-(pyrimidin-4-yl)benzenesulfonamide (258 mg, 0.62 mmol) prepared in Example 52a, the (1S*,2R*)-2-(1-methyl-1H-pyrazol-5-yl)cycloheptanol (120 mg, 0.62 mmol) prepared in Example 9a, sodium hydride (63%; 35.3 mg, 2.33 mmol) and DMF (10 mL), to yield the title compound (182 mg, 50%) as a colorless oil.

$^1$H-NMR (400 MHz, CDCl$_3$) δ ppm: 1.61-1.99 (10H, m), 2.01 (3H, s), 3.21 (1H, dt, J=3.5, 9.0 Hz), 3.73 (3H, s), 3.77 (3H, s), 3.86 (3H, s), 4.47-4.51 (1H, m), 5.22 (2H, s), 5.98 (1H, d, J=2.0 Hz), 6.37-6.40 (2H, m), 6.61 (1H, d, J=9.0 Hz), 7.13 (1H, d, J=8.2 Hz), 7.32-7.34 (2H, m), 7.45 (1H, s), 7.63 (1H, dd, J=2.0, 9.0 Hz), 8.44 (1H, d, J=5.9 Hz), 8.80 (1H, s).

(57b) 3-Methyl-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1b by using the N-(2,4-dimethoxybenzyl)-3-methyl-4-{[(1S*,2R*)-2-(1-methyl-1H-pyrazol-5-yl)cycloheptyl]oxy}-N-(pyrimidin-4-yl)benzenesulfonamide (182 mg, 0.31 mmol) prepared in Example 57a, triethylsilane (0.15 mL), trifluoroacetic acid (1.0 mL) and dichloromethane (1.0 mL), to yield the title compound (100 mg, 74%) as a colorless solid.

$^1$H-NMR, (500 MHz, CDCl$_3$) δ ppm: 1.58-2.04 (10H, m), 2.04 (3H, s), 3.19-3.23 (1H, m), 3.87 (3H, s), 4.47-4.51 (1H, m), 5.98 (1H, s), 6.64 (1H, d, J=8.8 Hz), 7.26-7.33 (2H, m), 7.61 (1H, s), 7.68 (1H, dd, J=2.4, 8.8 Hz), 8.49 (1H, brs), 8.97 (1H, brs).

MS (ESI) m/z: 442 [M+H]+.

Example 58

2-Fluoro-4-{[(1S*,2R*)-2-(1-methyl-1H-pyrazol-5-yl)cycloheptyl]oxy}-N-(pyrimidin-4-yl)benzenesulfonamide

[Formula 76]

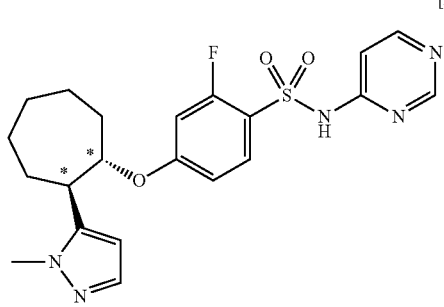

(58a) N-(2,4-Dimethoxybenzyl)-2-fluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (0.30 g, 0.71 mmol) prepared in Example 29a, the (1S*,2R*)-2-(1-methyl-1H-pyrazol-5-yl)cycloheptanol (0.14 g, 0.71 mmol) prepared in Example 9a, sodium hydride (63%; 0.040 g, 1.07 mmol) and DMF (3.6 mL), to yield the title compound (260.2 mg, 61%) as a colorless amorphous solid.

$^1$H-NMR (500 MHz, CDCl$_3$) δ ppm: 1.25-1.38 (4H, m), 1.60-1.98 (6H, m), 3.16 (1H, dt, J=2.9, 8.8 Hz), 3.76 (3H, s), 3.79 (3H, s), 3.86 (3H, s), 4.39-4.43 (1H, m), 5.24 (2H, s), 5.98 (1H, d, J=2.0 Hz), 6.39-6.41 (3H, m), 6.55 (1H, dd, J=2.0, 8.8 Hz), 7.19 (1H, d, J=8.3 Hz), 7.23 (1H, dd, J=1.0, 5.9 Hz), 7.33 (1H, d, J=1.5 Hz), 7.88 (1H, t, J=8.3 Hz), 8.42 (1H, d, J=5.9 Hz), 8.76 (1H, s).

(58b) 2-Fluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1b by using the N-(2,4-dimethoxybenzyl)-2-fluoro-4-{[(1S*,2R*)-2-(1-methyl-1H-pyrazol-5-yl)cycloheptyl]oxy}-N-(pyrimidin-4-yl)benzenesulfonamide (0.26 g, 0.44 mmol) prepared in Example 58a, triethylsilane (0.35 mL), trifluoroacetic acid (0.44 mL) and dichloromethane (4.4 mL), to yield the title compound (0.15 g, 77%) as a colorless solid.

$^1$H-NMR (500 MHz, DMSO-d$_6$) δ ppm: 1.51-1.92 (10H, m), 3.20-3.23 (1H, m), 3.77 (3H, s), 4.69-4.73 (1H, m), 6.08 (1H, d, J=2.0 Hz), 6.77 (1H, d, J=9.3 Hz), 6.87 (1H, d, J=11.7 Hz), 6.99 (1H, brs), 7.17 (1H, d, J=1.5 Hz), 7.76 (1H, t, J=5.9 Hz), 8.31 (1H, brs), 8.56 (1H, s).

MS (ESI) m/z: 446 [M+H]+.

Example 59

4-{[(1S*,2R*)-2-(1-Ethyl-1H-pyrazol-5-yl)cyclohexyl]oxy}-2,6-difluoro-N-(pyrimidin-4-yl)benzenesulfonamide

[Formula 77]

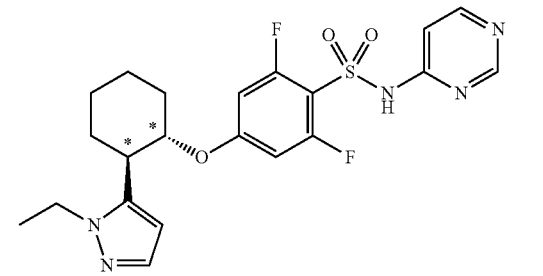

(59a) N-(2,4-Dimethoxybenzyl)-4-{[(1S*,2R*)-2-(1-ethyl-1H-pyrazol-5-yl)cyclohexyl]oxy}-2,6-difluoro-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (0.20 g, 0.45 mmol) prepared in Example 27a, the (1S*,2R*)-2-(1-ethyl-1H-pyrazol-5-yl)cyclohexanol (0.088 g, 0.45 mmol) prepared in Example 12a, sodium hydride (63%; 0.027 g, 0.67 mmol) and DMF (3.0 mL), to yield the title compound (0.085 g, 55%) as a colorless oil.

$^1$H-NMR (500 MHz, CDCl$_3$) δ ppm: 1.39-1.64 (4H, m), 1.44 (3H, t, J=7.3 Hz), 1.86-1.88 (1H, m), 1.94-1.95 (1H, m), 2.02-2.05 (1H, m), 2.23-2.26 (1H, m), 2.90-2.95 (1H, m), 3.77 (3H, s), 3.81 (3H, s), 4.01-4.25 (3H, m), 5.24 (2H, s), 5.98 (1H, d, J=2.0 Hz), 6.29 (2H, d, J=10.7 Hz), 6.41 (1H, dd, J=2.4, 10.7 Hz), 6.43-6.44 (1H, m), 7.16 (1H, d, J=7.3 Hz), 7.21 (1H, d, J=8.3 Hz), 8.38 (1H, d, J=2.0 Hz), 8.44 (1H, d, J=5.9 Hz), 8.78 (1H, s).

(59b) 4-{[(1S*,2R*)-2-(1-Ethyl-1H-pyrazol-5-yl)cyclohexyl]oxy}-2,6-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclohexyl]oxy}-2,6-difluoro-N-(pyrimidin-4-yl)benzenesulfonamide (0.080 g, 0.13 mmol) prepared in Example 59a, triethylsilane (0.10 mL), trifluoroacetic acid (1.0 mL) and dichloromethane (1.0 mL), to yield the title compound (25 mg, 42%) as a colorless solid.

$^1$H-NMR (400 MHz, DMSO-d$_6$) δ ppm: 1.24-1.56 (4H, m), 1.29 (3H, t, J=7.0 Hz), 1.69-1.79 (2H, m), 1.86-1.89 (1H, m), 2.10-2.13 (1H, m), 2.97-3.04 (1H, m), 4.03-4.16 (2H, m), 4.57 (1H, dt, J=3.5, 9.8 Hz), 6.06 (1H, s), 6.73 (2H, d, J=11.7 Hz), 6.92 (1H, brs), 7.22 (1H, s), 8.29 (1H, brs), 8.58 (1H, s).

MS (ESI) m/z: 464 [M+H]+.

Example 60

5-Chloro-2-fluoro-4-{[(1S*,2R*)-2-(1-methyl-1H-pyrazol-5-yl)cycloheptyl]oxy}-N-(pyrimidin-4-yl)benzenesulfonamide

[Formula 78]

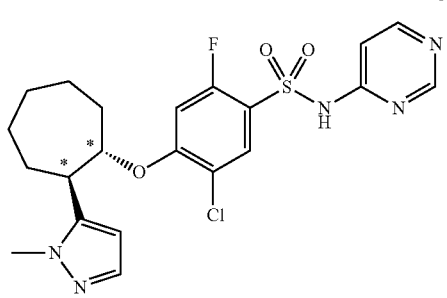

(60a) 5-Chloro-N-(2,4-dimethoxybenzyl)-2-fluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (300 mg, 0.66 mmol) prepared in Example 20a, the (1S*,2R*)-2-(1-methyl-1H-pyrazol-5-yl)cycloheptanol (134 mg, 0.69 mmol) prepared in Example 9a, sodium hydride (60%; 39.5 mg, 0.99 mmol) and DMF (10 mL), to yield the title compound (202 mg, 49%) as a colorless solid.

$^1$H-NMR (500 MHz, CDCl$_3$) δ ppm: 1.55-1.71 (1H, m), 1.61 (3H, dd, J=4.4, 8.8 Hz), 1.77-1.86 (2H, m), 1.87-1.98 (4H, m), 3.27 (1H, t, J=9.3 Hz), 3.76 (6H, s), 3.91 (3H, s), 4.40 (1H, dd, J=6.1, 12.9 Hz), 5.19 (1H, d, J=16.6 Hz), 5.23 (1H, d, J=16.6 Hz), 6.01 (1H, s), 6.37-6.42 (3H, m), 7.19 (1H, d, J=8.8 Hz), 7.22 (1H, d, J=5.9 Hz), 7.34 (1H, s), 7.94 (1H, d, J=7.3 Hz), 8.46 (1H, d, J=5.9 Hz), 8.80 (1H, s).

(60b) 5-Chloro-2-fluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S*,2R*)-2-(1-methyl-1H-pyrazol-5-yl)cycloheptyl]oxy}-N-(pyrimidin-4-yl)benzenesulfonamide (202 mg, 0.32 mmol) prepared in Example 60a, triethylsilane (0.10 mL), trifluoroacetic acid (0.5 mL) and dichloromethane (2.0 mL), to yield the title compound (135 mg, 88%) as a colorless solid.

$^1$H-NMR (500 MHz, CDCl$_3$) δ ppm: 1.56-2.00 (10H, m), 3.26 (1H, dt, J=2.9, 9.0 Hz), 3.90 (3H, s), 4.34-4.45 (1H, m), 6.00 (1H, d, J=2.0 Hz), 6.43 (1H, d, J=11.7 Hz), 7.18 (1H, brs), 7.33 (1H, d, J=2.0 Hz), 7.94 (1H, d, J=7.3 Hz), 8.40 (1H, d, J=6.4 Hz), 8.74 (1H, brs).

MS (ESI) m/z: 479 [M+H]+.

Example 61

5-Ethyl-2-fluoro-4-{[(1S*,2R*)-2-(1-methyl-1H-pyrazol-5-yl)cyclopentyl]oxy}-N-(pyrimidin-4-yl)benzenesulfonamide

[Formula 79]

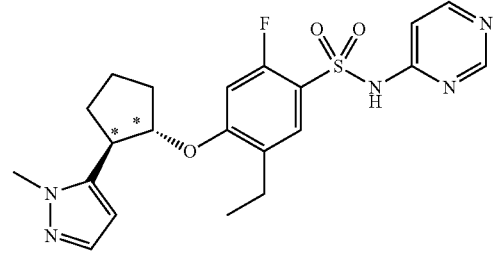

(61a) 5-Bromo-N-(2,4-dimethoxybenzyl)-2,4-difluoro-N-(pyrimidin-4-yl)benzenesulfonamide The reaction and aftertreatment were conducted in the same manner as in Example 14b by using the N-(2,4-dimethoxybenzyl)pyrimidin-4-amine (0.50 g, 2.06 mmol) prepared in Example 14a, 5-bromo-2,4-difluorobenzenesulfonyl chloride (0.90 g, 3.08 mmol), 1,4-diazabicyclo[2.2.2]octane (0.46 g, 4.11 mmol) and THF (10 mL), to yield the title compound (0.60 g, 58%) as a colorless amorphous solid.

$^1$H-NMR (500 MHz, CDCl$_3$) δ ppm: 3.78 (3H, s), 3.79 (3H, s), 5.23 (2H, s), 6.41-6.43 (2H, m), 6.95 (1H, dd, J=7.8, 9.3 Hz), 7.16 (1H, dd, J=1.5, 5.9 Hz), 7.22 (1H, d, J=8.3 Hz), 8.27 (1H, t, J=7.3 Hz), 8.49 (1H, d, J=5.9 Hz), 8.80 (1H, s).

(61b) 5-Bromo-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the 5-bromo-N-(2,4-dimethoxybenzyl)-2,4-difluoro-N-(pyrimidin-4-yl)benzenesulfonamide (1.0 g, 2.00 mmol) prepared in Example 61a, the (1S*,2R*)-2-(1-methyl-1H-pyrazol-5-yl)cyclopentanol (0.35 g, 2.10 mmol) prepared in Example 8a, sodium hydride (63%; 0.12 g, 3.00 mmol) and DMF (10 mL), to yield the title compound (771 mg, 60%) as a colorless amorphous solid.

$^1$H-NMR (400 MHz, CDCl$_3$) δ ppm: 1.77-1.98 (4H, m), 2.18-2.38 (2H, m), 3.51 (1H, dt, J=5.1, 8.6 Hz), 3.77 (3H, s), 3.79 (3H, s), 3.89 (3H, s), 4.60-4.64 (1H, m), 5.23 (2H, s), 6.06 (1H, d, J=2.0 Hz), 6.39-6.41 (2H, m), 6.46 (1H, d, J=11.3 Hz), 7.19-7.21 (2H, m), 7.41 (1H, d, J=1.6 Hz), 8.19 (1H, d, J=7.4 Hz), 8.46 (1H, d, J=5.9 Hz), 8.79 (1H, s).

(61c) N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)-5-vinylbenzenesulfonamide The reaction and aftertreatment were conducted in the same manner as in Example 39a by using the 5-bromo-N-(2,4-dimethoxybenzyl)-2-fluoro-4-{[(1S*,2R*)-2-(1-methyl-1H-pyrazol-5-yl)cyclopentyl]oxy}-N-(pyrimidin-4- yl)benzenesulfonamide (0.20 g, 0.31 mmol) prepared in Example 61b, 4,4,5,5-tetramethyl-2-vinyl-1,3,2-dioxaborolane (0.11 mL, 0.62 mmol), a [1,1'-bis(diphenylphosphino)ferrocene]dichloropalladium (II)-dichloromethane mixture (0.04 g, 0.03 mmol), sodium carbonate (0.07 g, 0.62 mmol), DMF (8.0 mL) and water (2.0 mL), to yield the title compound (113 mg, 63%) as a colorless amorphous solid.

$^1$H-NMR (500 MHz, CDCl$_3$) δ ppm: 1.74-1.82 (1H, m), 1.91-1.96 (3H, m), 2.16-2.36 (2H, m), 3.42 (1H, dt, J=4.4, 8.3 Hz), 3.76 (3H, s), 3.79 (3H, s), 3.82 (3H, s), 4.65-4.68 (1H, m), 5.25 (2H, s), 5.38 (1H, d, J=11.2 Hz), 5.80 (1H, d, J=17.6 Hz), 6.04 (1H, d, J=1.5 Hz), 6.39-6.43 (3H, m), 6.88 (1H, d, J=11.2, 18.1 Hz), 7.20 (1H, d, J=8.3 Hz), 7.25-7.26 (1H, m), 7.40 (1H, d, J=2.0 Hz), 8.08 (1H, d, J=8.3 Hz), 8.44 (1H, d, J=6.4 Hz), 8.77 (1H, s).

(61d) 5-Ethyl-2-fluoro-4-{[(1S*,2R*)-2-(1-methyl-1H-pyrazol-5-yl)cyclopentyl]oxy}-N-(pyrimidin-4-yl)benzenesulfonamide To a solution of the N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)-5-vinylbenzenesulfonamide (29 mg, 0.05 mmol) prepared in Example 61c and triethylsilane (0.10 mL) in dichloromethane (4.0 mL), trifluoroacetic acid (0.5 mL) was added at room temperature, and the mixture was stirred for 1 hour. The reaction mixture was concentrated to yield a mixture of the title compound and a vinyl-derivative.

To a solution of this mixture in methanol (0.5 mL) and ethyl acetate (0.5 mL), palladium carbon (10%; 5 mg) was added, and the mixture was stirred at room temperature for 3 hours under a hydrogen atmosphere. The reaction solution was filtered through celite, and the residue was purified with silica gel chromatography to yield the title compound (8.5 mg, 38%) as a colorless solid.

$^1$H-NMR (500 MHz, CDCl$_3$) δ ppm: 1.19 (3H, t, J=7.8 Hz), 1.72-1.81 (1H, m), 1.86-1.95 (3H, m), 2.15-2.34 (2H, m), 2.58-2.66 (2H, m), 3.38-3.42 (1H, m), 3.83 (3H, s), 4.64-4.67 (1H, m), 6.03 (1H, d, J=1.5 Hz), 6.45 (1H, d, J=12.2 Hz), 7.22 (1H, brs), 7.39 (1H, d, J=1.5 Hz), 7.75 (1H, d, J=8.3 Hz), 8.40 (1H, d, J=6.4 Hz), 8.84 (1H, brs).

MS (ESI) m/z: 446 [M+H]+.

Example 62

5-Cyano-2-fluoro-4-{[(1S*,2R*)-2-(1-methyl-1H-pyrazol-5-yl)cyclopentyl]oxy}-N-(pyrimidin-4-yl)benzenesulfonamide

[Formula 80]

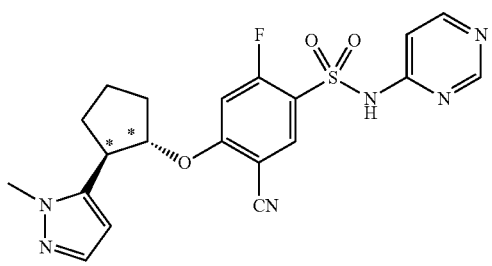

(62a) Methyl 5-{[(2,4-dimethoxybenzyl)(pyrimidin-4-yl)amino]sulfonyl}-2,4-difluorobenzoate The reaction and aftertreatment were conducted in the same manner as in Example 14b by using the N-(2,4-dimethoxybenzyl)pyrimidin-4-amine (378 mg, 1.54 mmol) prepared in Example 14a, methyl 5-(chlorosulfonyl)-2,4-difluorobenzoate (500 mg, 1.85 mmol), 1,4-diazabicyclo[2.2.2]octane (208 mg, 1.85 mmol) and THF (15.0 mL), to yield the title compound (332 mg, 45%) as a pale yellow oil.

$^1$H-NMR (500 MHz, CDCl$_3$) δ ppm: 3.77 (3H, s), 3.79 (3H, s), 3.98 (3H, s), 5.30 (2H, s), 6.40-6.44 (2H, m), 6.96 (1H, t, J=9.4 Hz), 7.17 (1H, d, J=6.8 Hz), 7.22 (1H, d, J=8.8 Hz), 8.48 (1H, d, J=5.9 Hz), 8.70 (1H, t, J=7.8 Hz), 8.78 (1H, s).

(62b) Methyl 5-{[(2,4-dimethoxybenzyl) (pyrimidin-4-yl)amino]sulfonyl}-4-fluoro-2-{[(1S*,2R*)-2-(1-methyl-1H-pyrazol-5-yl)cyclopentyl]oxy}benzoate The reaction and aftertreatment were conducted in the same manner as in Example 1a by using the methyl 5-{[(2,4-dimethoxybenzyl)(pyrimidin-4-yl)amino]sulfonyl}-2,4-difluorobenzoate (332 mg, 0.692 mmol) prepared in Example 62a, the (1S*,2R*)-2-(1-methyl-1H-pyrazol-5-yl)cyclopentanol (115 mg, 0.692 mmol) prepared in Example 8a, sodium hydride (63%; 32.1 mg, 0.830 mmol) and DMF (2.0 mL), to yield the title compound (83.3 mg, 19%) as a colorless oil.

$^1$H-NMR (500 MHz, CDCl$_3$) δ ppm: 1.63-1.99 (4H, m), 2.15-2.39 (2H, m), 3.48-3.54 (1H, m), 3.76 (3H, s), 3.79 (3H, s), 3.87 (3H, s), 3.91 (3H, s), 4.63-4.68 (1H, m), 5.23 (2H, s), 6.05 (1H, s), 6.37-6.43 (2H, m), 6.50 (1H, d, J=12.2 Hz), 7.17-7.22 (2H, m), 7.40 (1H, s), 8.44 (1H, d, J=5.9 Hz), 8.55 (1H, d, J=8.3 Hz), 8.77 (1H, s).

(62c) 5-{[(2,4-Dimethoxybenzyl) (pyrimidin-4-yl)amino]sulfonyl}-4-fluoro-2-{[(1S*,2R*)-2-(1-methyl-1H-pyrazol-5-yl)cyclopentyl]oxy}benzamide To a solution of the methyl 5-{[(2,4-dimethoxybenzyl)(pyrimidin-4-yl)amino]sulfonyl}-4-fluoro-2-{[(1S*,2R*)-2-(1-methyl-1H-pyrazol-5-yl)cyclopentyl]oxy}benzoate (83.3 mg, 0.133 mmol) prepared in Example 62b in THF (2.0 mL), a 5 M aqueous sodium hydroxide solution (2.0 mL) was added, and the reaction solution was stirred at room temperature for 15 hours. To the reaction solution, 1 M hydrochloric acid (10 mL) was added with cooling on ice, followed by extraction with ethyl acetate. The thus obtained organic layer was washed with saturated saline. The organic layer was dried over anhydrous sodium sulfate and vacuum concentrated, and THF (2.0 mL) was added to the obtained residue. To the reaction solution, 4-methylmorpholine (20.0 µL, 0.183 mmol) and isobutyl chloroformate (23.0 µL, 0.183 mmol) were added in that order with cooling on ice, and the mixture was stirred for 1 hour with cooling on ice. Then, 28% ammonia water (2.0 mL) was added thereto, and the mixture was stirred at room temperature for 12 hours. To the reaction solution, saturated saline was added, followed by extraction with ethyl acetate. The thus obtained organic layer was washed with saturated saline. The organic layer was dried over anhydrous sodium sulfate and vacuum concentrated, and the obtained residue was purified with silica gel chromatography (dichloromethane/methanol=85:15) to yield the title compound (64.2 mg, 86%) as a colorless amorphous solid.

¹H-NMR (500 MHz, CDCl₃) δ ppm: 1.62-2.08 (4H, m), 2.16-2.42 (2H, m), 3.37-3.44 (1H, m), 3.77 (3H, s), 3.79 (3H, s), 3.80 (3H, s), 4.87-4.91 (1H, m), 5.30 (2H, s), 6.06 (1H, s), 6.38-6.43 (2H, m), 6.54 (1H, d, J=11.7 Hz), 7.17-7.23 (3H, m), 7.29 (1H, d, J=6.8 Hz), 7.43 (1H, s), 8.44 (1H, d, J=5.9 Hz), 8.78 (1H, s), 8.87 (1H, d, J=8.8 Hz).

(62d) 5-Cyano-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide To a solution of the 5-{[(2,4-dimethoxybenzyl)(pyrimidin-4-yl)amino]sulfonyl}-4-fluoro-2-{[(1S*,2R*)-2-(1-methyl-1H-pyrazol-5-yl)cyclopentyl]oxy}benzamide (64.3 mg, 0.107 mmol) prepared in Example 62c in dichloromethane (2.0 mL), triethylamine (41.0 µL, 0.300 mmol) and trifluoroacetic acid (21.0 µL, 0.150 mmol) were added with cooling on ice, and the reaction solution was stirred at room temperature for 2 hours. To the reaction solution, triethylamine (41.0 µL, 0.300 mmol) and trifluoroacetic acid (21.0 µL, 0.150 mmol) were added, and the mixture was stirred at room temperature for 1 hour. The reaction solution was purified with silica gel chromatography (ethyl acetate) to yield the title compound (32.3 mg, 53%) as a colorless oil.

¹H-NMR (500 MHz, CDCl₃) δ ppm; 1.76-2.04 (4H, m), 2.21-2.41 (2H, m), 3.50-3.58 (1H, m), 3.77 (6H, s), 3.90 (3H, s), 4.64-4.72 (1H, m), 5.21 (2H, s), 6.06 (1H, s), 6.38-6.44 (2H, m), 6.52 (1H, d, J=11.2 Hz), 7.12 (1H, d, J=5.9 Hz), 7.19 (1H, d, J=8.8 Hz), 7.41 (1H, s), 8.26 (1H, d, J=7.8 Hz), 8.48 (1H, d, J=5.9 Hz), 8.79 (1H, s).

(62e) 5-Cyano-2-fluoro-4-{[(1S*,2R*)-2-(1-methyl-1H-pyrazol-5-yl)cyclopentyl]oxy}-(N-pyrimidin-4-yl)benzenesulfonamide The reaction and aftertreatment were conducted in the same manner as in Example 1b by using the 5-cyano-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide (32.3 mg, 0.0545 mmol) prepared in Example 62d, triethylsilane (0.20 mL), trifluoroacetic acid (2.0 mL) and dichloromethane (2.0 mL), to yield the title compound (21.5 mg, 89%) as a colorless solid.

¹H-NMR (500 MHz, DMSO-d₆) δ ppm: 1.65-1.77 (2H, m), 1.79-1.89 (2H, m), 2.19-2.34 (2H, m), 3.48-3.57 (1H, m), 3.80 (3H, s), 4.96-5.07 (1H, m), 6.17 (1H, s), 6.90-7.05 (1H, m), 7.25-7.36 (2H, m), 8.07-7.31 (2H, m), 8.56 (1H, s).
MS (ESI) m/z: 443 [M+H]+.

Example 63

2,6-Difluoro-4-{[(1S*,2R*)-2-(1-methyl-1H-pyrazol-5-yl)cycloheptyl]oxy}-N-(pyrimidin-4-yl)benzenesulfonamide

[Formula 81]

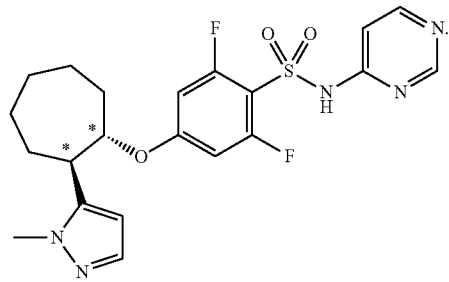

(63a) N-(2,4-Dimethoxybenzyl)-2,6-difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (0.20 g, 0.455 mmol) prepared in Example 27a, the (1S*,2R*)-2-(1-methyl-1H-pyrazol-5-yl)cycloheptanol (0.08 g, 0.409 mmol) prepared in Example 9a, sodium hydride (63%; 0.027 g, 0.682 mmol) and DMF (5 mL), to yield the title compound (0.14 g, 52%) as a colorless amorphous solid.

¹H-NMR (500 MHz, CDCl₃) δ ppm: 1.60-1.98 (10H, m), 3.15 (1H, dt, J=2.9, 9.3 Hz), 3.77 (3H, s), 3.81 (3H, s), 3.85 (3H, s), 4.36-4.40 (1H, m), 5.25 (2H, s), 5.98 (1H, d, J=2.0 Hz), 6.27 (2H, d, J=10.7 Hz), 6.41 (1H, dd, J=2.4, 8.3 Hz), 6.44 (1H, d, J=2.0 Hz), 7.16 (1H, dd, J=1.5, 5.9 Hz), 7.21 (1H, d, J=8.3 Hz), 7.33 (1H, d, J=2.0 Hz), 8.44 (1H, d, J=5.9 Hz), 8.78 (1H, s).

(63b) 2,6-Difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1b by using the N-(2,4-dimethoxybenzyl)-2,6-difluoro-4-{[(1S*,2R*)-2-(1-methyl-1H-pyrazol-5-yl)cycloheptyl]oxy}-N-(pyrimidin-4-yl)benzenesulfonamide (0.14 g, 0.23 mmol) prepared in Example 63a, triethylsilane (0.15 mL), trifluoroacetic acid (2.0 mL) and dichloromethane (2.0 mL), to yield the title compound (60 mg, 40%) as a colorless solid.

¹H-NMR (500 MHz, DMSO-d₆) δ ppm: 1.52-1.92 (10H, m), 3.18-3.21 (1H, m), 3.76 (3H, s), 4.73-4.77 (1H, m), 6.10 (1H, d, J=2.0 Hz), 6.72 (2H, d, J=11.2 Hz), 6.94 (1H, brs), 7.19 (1H, d, J=1.5 Hz), 8.29 (1H, brs), 8.58 (1H, s).
MS (ESI) m/z: 464 [M+H]+.

Example 64

2-Fluoro-5-methyl-4-{[(1S*,2R*)-2-(1-methyl-1H-pyrazol-5-yl)cyclohexyl]oxy}-N-(pyrimidin-4-yl)benzenesulfonamide

[Formula 82]

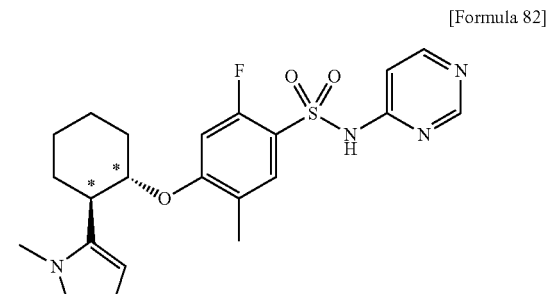

(64a) N-(2,4-Dimethoxybenzyl)-2-fluoro-5-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (0.30 g, 0.69 mmol) prepared in Example 43a, the (1S*,2R*)-2-(1-methyl-1H-pyrazol-5-yl)cyclohexanol (0.21 g, 1.15 mmol) prepared in Example 4a, sodium hydride (63%; 0.070 g, 1.65 mmol) and DMF (10 mL), to yield the title compound (0.17 g, 42%) as a colorless oil.

$^1$H-NMR (500 MHz, CDCl$_3$) δ ppm: 1.40-1.64 (4H, m), 1.86-1.88 (1H, m), 1.92-1.93 (1H, m), 2.02-2.06 (1H, m), 2.02 (3H, s), 2.23-2.26 (1H, m), 2.97-3.02 (1H, m), 3.76 (3H, s), 3.78 (3H, s), 3.89 (3H, s), 4.01-4.14 (1H, m), 5.24 (2H, s), 5.98 (1H, d, J=2.0 Hz), 6.36-6.40 (3H, m), 7.19 (1H, d, J=8.8 Hz), 7.28 (1H, dd, J=1.5, 5.9 Hz), 7.35 (1H, d, J=2.0 Hz), 7.66 (1H, d, J=7.8 Hz), 8.43 (1H, d, J=5.9 Hz), 8.77 (1H, d, J=1.0 Hz).

(64b) 2-Fluoro-5-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2-fluoro-5-methyl-4-{[(1S*,2R*)-2-(1-methyl-1H-pyrazol-5-yl)cyclohexyl]oxy}-N-(pyrimidin-4-yl)benzenesulfonamide (0.17 g, 0.29 mmol) prepared in Example 64a, triethylsilane (0.10 mL), trifluoroacetic acid (1.0 mL) and dichloromethane (4.0 mL), to yield the title compound (129 mg, 99%) as a colorless solid.

$^1$H-NMR (500 MHz, CDCl$_3$) δ ppm: 1.40-1.60 (4H, m), 1.85-1.87 (1H, m), 1.91-1.92 (1H, m), 2.04-2.06 (1H, m), 2.05 (3H, s), 2.23-2.25 (1H, m), 2.96-3.02 (1H, m), 3.88 (3H, s), 4.10-4.14 (1H, m), 5.98 (1H, d, J=2.0 Hz), 6.42 (1H, d, J=12.2 Hz), 7.23 (1H, d, J=5.4 Hz), 7.34 (1H, d, J=1.5 Hz), 7.67 (1H, d, J=8.3 Hz), 8.40 (1H, d, J=6.4 Hz), 8.86 (1H, brs).

MS (ESI) m/z: 446 [M+H]+.

Example 65

2-Fluoro-3-methyl-4-{[(1S*,2R*)-2-(1-methyl-1H-pyrazol-5-yl)cyclopentyl]oxy}-N-(pyrimidin-4-yl)benzenesulfonamide

[Formula 83]

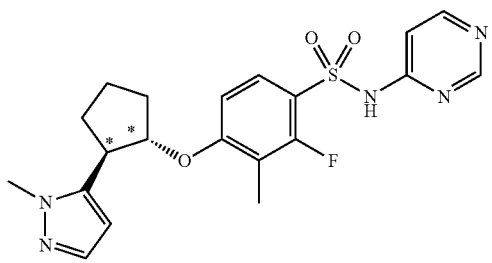

(65a) 2,4-Difluoro-3-methylbenzenesulfonyl chloride

To 1,3-difluoro-2-methylbenzene (5.00 g, 39.0 mmol), chlorosulfuric acid (10.5 mL, 158 mmol) was added with cooling on ice, and the mixture was stirred at room temperature for 5 hours. To the reaction solution, water (100 mL) was added with cooling on ice, followed by extraction with dichloromethane (100 mL). The thus obtained organic layer was dried over anhydrous sodium sulfate. After vacuum concentration, the residue was purified with silica gel chromatography to yield the title compound (8.65 g, 98%) as a colorless amorphous solid.

$^1$H-NMR (500 MHz, CDCl$_3$) δ ppm: 2.32 (3H, s), 7.05 (1H, dt, d=1.5, 8.8 Hz), 7.82-7.87 (1H, m).

(65b) N-(2,4-dimethoxybenzyl)-2,4-difluoro-3-methyl-N-(pyrimidin-4-yl)benzenesulfonamide The reaction and aftertreatment were conducted in the same manner as in Example 14b by using the N-(2,4-dimethoxybenzyl)pyrimidin-4-amine (1.00 g, 4.08 mmol) prepared in Example 14a, the 2,4-difluoro-3-methylbenzenesulfonyl chloride (1.85 g, 8.15 mmol) prepared in Example 65a, 1,4-diazabicyclo[2.2.2]octane (0.91 g, 8.15 mmol) and THF (20 mL), to yield the title compound (1.75 g, 99%) as a colorless amorphous solid.

$^1$H-NMR (500 MHz, CDCl$_3$) δ ppm: 2.05 (3H, s), 3.78 (3H, s), 3.81 (3H, s), 5.28 (2H, s), 6.41-6.44 (2H, m), 6.99 (1H, dt, J=1.5, 9.3 Hz), 7.20 (1H, dd, J=1.5, 5.9 Hz), 7.22 (1H, d, J=8.3 Hz), 7.92-7.96 (1H, m), 8.44 (1H, d, J=5.9 Hz), 8.75 (1H, d, J=1.0 Hz).

(65c) N-(2,4-Dimethoxybenzyl)-2-fluoro-3-methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-3-methyl-N-(pyrimidin-4-yl)benzenesulfonamide (0.30 g, 0.69 mmol) prepared in Example 65b, the (1S*,2R*)-2-(1-methyl-1H-pyrazol-5-yl)cyclopentanol (0.12 g, 0.72 mmol) prepared in Example 8a, sodium hydride (63%; 0.040 g, 1.05 mmol) and DMF (10 mL), to yield the title compound (181 mg, 45%) as a colorless amorphous solid.

(65d) 2-Fluoro-3-methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2-fluoro-3-methyl-4-{[(1S*,2R*)-2-(1-methyl-1H-pyrazol-5-yl)cyclopentyl]oxy}-N-(pyrimidin-4-yl)benzenesulfonamide (0.18 g, 0.31 mmol) prepared in Example 65c, triethylsilane (0.10 mL), trifluoroacetic acid (0.50 mL) and dichloromethane (2.0 mL), to yield the title compound (134 mg, 99%) as a colorless solid.

$^1$H-NMR (500 MHz, CDCl$_3$) δ ppm: 1.74-1.95 (4H, m), 2.18 (3H, s), 2.21-2.33 (2H, m), 3.40 (1H, dt, J=4.4, 8.3 Hz), 3.82 (3H, s), 4.74-4.77 (1H, m), 6.06 (1H, d, J=2.0 Hz), 6.54 (1H, d, J=8.8 Hz), 7.24-7.25 (1H, m), 7.42 (1H, d, J=2.0 Hz), 7.79 (1H, t, J=8.8 Hz), 8.40 (1H, d, J=6.0 Hz), 8.88 (1H, brs).

MS (ESI) m/z: 432 [M+H]+.

Example 66

2-Fluoro-3-methyl-4-{[(1S*,2R*)-2-(1-methyl-1H-pyrazol-5-yl)cyclohexyl]oxy}-N-(pyrimidin-4-yl)benzenesulfonamide

[Formula 84]

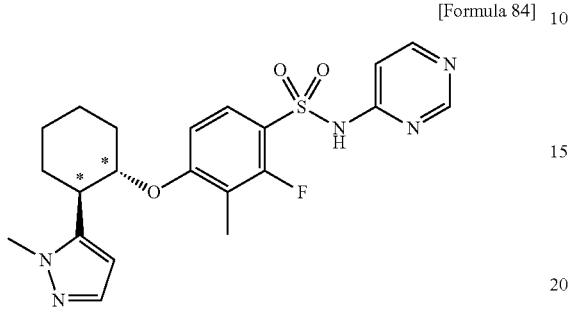

(66a) N-(2,4-Dimethoxybenzyl)-2-fluoro-3-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-3-methyl-N-(pyrimidin-4-yl)benzenesulfonamide (0.30 g, 0.70 mmol) prepared in Example 65b, the (1S*,2R*)-2-(1-methyl-1H-pyrazol-5-yl)cyclohexanol (0.10 g, 0.70 mmol) prepared in Example 4a, sodium hydride (63%; 0.070 g, 1.65 mmol) and DMF (10 mL), to yield the title compound (175.6 mg, 40%) as a colorless solid.

$^1$H-NMR (500 MHz, CDCl$_3$) δ ppm: 1.43-1.64 (4H, m), 1.86-1.94 (2H, m), 1.89 (3H, s), 2.03-2.07 (1H, m), 2.27-2.29 (1H, m), 2.97-3.02 (1H, m), 3.76 (3H, s), 3.79 (3H, s), 3.87 (3H, s), 4.27 (1H, dt, J=3.9, 9.8 Hz), 5.26 (2H, s), 5.98 (1H, d, J=2.0 Hz), 6.39-6.42 (2H, m), 6.55 (1H, d, J=9.3 Hz), 7.19 (1H, d, J=8.3 Hz), 7.25 (1H, dd, J=1.5, 6.4 Hz), 7.35 (1H, d, J=2.0 Hz), 7.77 (1H, t, J=8.3 Hz), 8.41 (1H, d, J=6.4 Hz), 8.75 (1H, s).

(66b) 2-Fluoro-3-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2-fluoro-3-methyl-4-{[(1S*,2R*)-2-(1-methyl-1H-pyrazol-5-yl)cyclohexyl]oxy}-N-(pyrimidin-4-yl)benzenesulfonamide (175.6 mg, 0.29 mmol) prepared in Example 66a, triethylsilane (0.10 mL), trifluoroacetic acid (0.5 mL) and dichloromethane (2.0 mL), to yield the title compound (122 mg, 93%) as a colorless solid.

$^1$H-NMR (500 MHz, CDCl$_3$) δ ppm: 1.40-1.65 (4H, m), 1.86-1.93 (2H, m), 2.05-2.10 (1H, m), 2.18 (3H, s), 2.26-2.28 (1H, m), 2.97-3.02 (1H, m), 3.86 (3H, s), 4.26 (1H, dt, J=4.4, 10.3 Hz), 5.99 (1H, d, J=2.0 Hz), 6.54 (1H, d, J=9.3 Hz), 7.20 (1H, brs), 7.34 (1H, d, J=1.5 Hz), 7.74 (1H, t, J=8.3 Hz), 8.39 (1H, d, J=6.4 Hz), 8.86 (1H, brs).

MS (ESI) m/z: 446 [M+H]+.

Example 67

4-{[(1S*,2R*)-4,4-Dimethyl-2-(1-methyl-1H-pyrazol-5-yl)cyclohexyl]oxy}-2,5-difluoro-N-(pyrimidin-4-yl)benzenesulfonamide

[Formula 85]

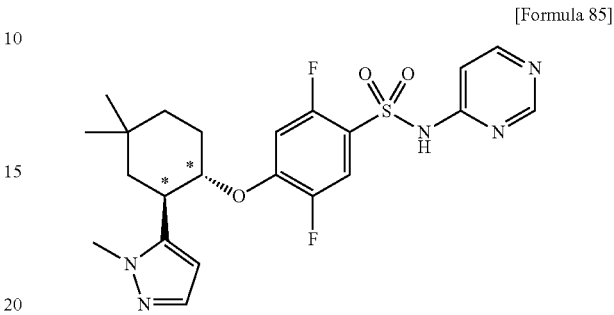

(67a) 6-Iodo-8,8-dimethyl-1,4-dioxaspiro[4.5]dec-6-ene

A solution of 2-iodo-4,4-dimethylcyclohex-2-en-1-one (Synlett, 2005, 1263-1266; 5.46 g, 21.8 mmol), ethylene glycol (3.00 g, 48.3 mmol), p-toluenesulfonic acid hydrate (100 mg) in benzene (100 mL) was stirred for 7 hours under reflux, and the solvent was subjected to azeotropic distillation with water. After allowing to cool, a saturated aqueous solution of sodium hydrogencarbonate (100 mL) was added to the reaction solution, and an organic layer was extracted. The thus obtained organic layer was dried over anhydrous sodium sulfate. After vacuum concentration, the residue was purified with silica gel chromatography (hexane/ethyl acetate=95:5) to yield the title compound (5.78 g, 90%) as a colorless oil.

$^1$H-NMR (500 MHz, CDCl$_3$) δ ppm: 1.03 (6H, s), 1.65-1.68 (2H, m), 1.95-1.98 (2H, m), 3.96-3.99 (2H, m), 4.19-4.22 (2H, m), 6.39 (1H, s).

(67b) 5-(8,8-Dimethyl-1,4-dioxaspiro[4.5]dec-6-en-6-yl)-1-methyl-1H-pyrazole The reaction and aftertreatment were conducted in the same manner as in Example 33a by using the 6-iodo-8,8-dimethyl-1,4-dioxaspiro[4.5]dec-6-ene (1.5 g, 5.10 mmol) prepared in Example 67a, 1-methyl-5-(4,4,5,5-tetramethyl-1,3,2-dioxaboran-2-yl)-1H-pyrazole (1.00 g, 4.81 mmol), tetrakis(triphenylphosphine)palladium (0) (240 mg, 0.208 mmol), cesium carbonate (3.40 g, 10.4 mmol), dioxane (7.0 mL) and water (3.0 mL), to yield the title compound (580 mg, 49%) as a brown oil.

$^1$H-NMR (500 MHz, CDCl$_3$) δ ppm: 1.11 (6H, s), 1.71-1.74 (2H, m), 1.91-1.93 (2H, m), 3.51-3.54 (2H, m), 3.78 (3H, s), 3.79-3.82 (2H, m), 5.65 (1H, s), 6.16 (1H, d, J=2.0 Hz), 7.40 (1H, d, J=2.0 Hz).

(67c) 4,4-Dimethyl-2-(1-methyl-1H-pyrazol-5-yl)cyclohex-2-en-1-one

A solution of the 5-(8,8-dimethyl-1,4-dioxaspiro[4.5]dec-6-en-6-yl)-1-methyl-1H-pyrazole (580 mg, 2.34 mmol) prepared in Example 67b and 2 M hydrochloric acid (2.0 mL)

in THF (5.0 mL) was stirred for 1 hour under reflux. After allowing to cool, a 1 M aqueous sodium hydroxide solution (5.0 mL) was added to the reaction solution, followed by extraction with ethyl acetate (50 mL). The thus obtained organic layer was dried over anhydrous sodium sulfate. After vacuum concentration, the residue was purified with silica gel chromatography (hexane/ethyl acetate=1:1) to yield the title compound (432 mg, 91%) as a colorless oil.

$^1$H-NMR (400 MHz, CDCl$_3$) δ ppm: 1.27 (6H, s), 1.99 (2H, t, J=6.7 Hz), 2.63 (2H, t, J=7.0 Hz), 3.68 (3H, s), 6.13 (1H, d, J=2.0 Hz), 6.78 (1H, s), 7.44 (1H, d, J=2.0 Hz).

(67d) 4,4-Dimethyl-2-(1-methyl-1H-pyrazol-5-yl)cyclohexanol

To a solution of the 4,4-dimethyl-2-(1-methyl-1H-pyrazol-5-yl)cyclohex-2-en-1-one (432 mg, 2.12 mmol) prepared in Example 67c in methanol (6.0 mL), sodium borohydride (200 mg, 5.29 mmol) was added with cooling on ice, and the reaction solution was stirred at room temperature for 1 hour. To the reaction solution, a saturated aqueous solution of ammonium chloride (20 mL) was added, followed by extraction with dichloromethane (50 mL). The thus obtained organic layer was dried over anhydrous sodium sulfate and vacuum concentrated to yield a mixture of the title compound and an allyl alcohol derivative.

A solution of this mixture and palladium hydroxide carbon (10%; 300 mg) in ethanol (6.0 mL) was stirred at room temperature for 3 hours under a hydrogen atmosphere. The reaction solution was filtered through celite, and the residue was purified with silica gel chromatography (dichloromethane/methanol=97:3) to yield the title compound (347 mg, 79%) in the form of a trans/cis (3:1) mixture.

(67e) N-(2,4-dimethoxybenzyl)-4-{[(1S*,2R*)-4,4-dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (337 mg, 0.767 mmol) prepared in Example 14b, the 4,4-dimethyl-2-(1-methyl-1H-pyrazol-5-yl)cyclohexanol (160 mg, 0.768 mmol) prepared in Example 67d, sodium hydride (63%; 80 mg, 2.10 mmol) and DMF (4.0 mL), to yield the title compound (293 mg, 61%) as a colorless oil.

$^1$H-NMR (500 MHz, CDCl$_3$) δ ppm: 1.04 (3H, s), 1.12 (3H, s), 1.41-1.47 (1H, m), 1.57-1.62 (2H, m), 1.68-1.81 (2H, m), 2.04-2.08 (1H, m), 3.21-3.26 (1H, m), 3.76 (3H, s), 3.78 (3H, s), 3.91 (3H, s), 4.08 (1H, dt, J=4.4, 11.2 Hz), 5.19 (1H, d, J=17.1 Hz), 5.23 (1H, d, J=17.1 Hz), 6.01 (1H, d, J=2.0 Hz), 6.39-6.41 (2H, m), 6.45 (1H, dd, J=6.4, 11.2 Hz), 7.17-7.18 (2H, m), 7.33 (1H, d, J=2.0 Hz), 7.67 (1H, dd, J=6.8, 10.3 Hz), 8.45 (1H, d, J=5.9 Hz), 8.78 (1H, d, J=1.0 Hz).

(67f) 4-{[(1S*,2R*)-4,4-Dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-4,4-dimethyl-2-(1-methyl-1H-pyrazol-5-yl)cyclohexyl]oxy}-2,5-difluoro-N-(pyrimidin-4-yl)benzenesulfonamide (293 mg, 0.467 mmol) prepared in Example 67e, triethylsilane (0.40 mL), trifluoroacetic acid (4.0 mL) and dichloromethane (4.0 mL), to yield the title compound (198 mg, 89%) as a colorless solid.

$^1$H-NMR (500 MHz, DMSO-d$_6$) δ ppm: 0.97 (3H, s), 1.08 (3H, s), 1.44-1.69 (5H, m), 1.98-2.02 (1H, m), 3.26 (1H, dt, J=4.4, 10.3 Hz), 3.79 (3H, s), 4.52 (1H, dt, J=4.4, 10.3 Hz), 6.05 (1H, d, J=2.0 Hz), 6.94 (1H, brs), 7.18 (1H, d, J=2.0 Hz), 7.26 (1H, brs), 7.61 (1H, brs), 8.24 (1H, brs), 8.56 (1H, s).

MS (ESI) m/z: 478 [M+H]+.

Example 68

4-{[(1S*,2R*)-2-(3-Amino-1H-pyrazol-4-yl)cyclohexyl]oxy}-2-fluoro-5-methyl-N-(pyrimidin-4-yl)benzenesulfonamide

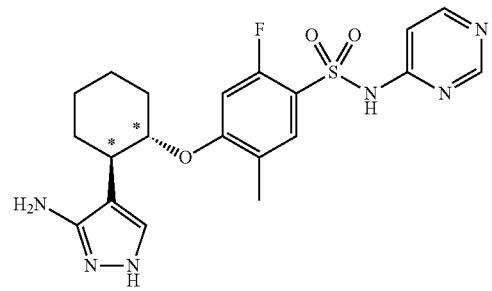

[Formula 86]

(68a) N-(2,4-dimethoxybenzyl)-2-fluoro-5-methyl-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (243 mg, 0.559 mmol) prepared in Example 43a, the (1S*,2R*)-2-[3-nitro-1-(tetrahydro-2H-pyran-2-yl)-1H-pyrazol-4-yl]cyclohexanol (165 mg, 0.559 mmol) prepared in Example 34b, sodium hydride (63%; 64.4 mg, 0.671 mmol) and DMF (8.0 mL), to yield the title compound (291 mg, 73%) as a pale yellow solid.

$^1$H-NMR (500 MHz, CDCl$_3$) δ ppm: 1.45-1.68 (8H, m), 1.79-2.26 (6H, m), 2.05 (3H, s), 3.62-3.69 (2H, m), 3.76 (3H, a), 3.79 (3H, s), 3.89-4.01 (1H, m), 4.10-4.18 (1H, m), 5.25 (2H, s), 5.3.0-5.34 (1H, m), 6.38-6.47 (3H, m), 7.19 (1H, d, J=8.3 Hz), 7.29 (1H, dt, J=1.5, 6.4 Hz), 7.43 (1H, d, J=22.9 Hz), 7.65 (1H, dd, J=3.4, 8.3 Hz), 8.44 (1H, d, J=5.9 Hz), 8.77 (1H, s).

(68b) 2-Fluoro-5-methyl-4-{(1S*,2R*)-2-(3-nitro-1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-2-fluoro-5-methyl-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide (291 mg, 0.409 mmol) prepared in Example 68a, triethylsilane (0.10 mL), trifluoroacetic acid (1.0 mL), dichloromethane (2.0 mL) and methanol (1.0 mL), to yield the title compound (172 mg, 88%) as a pale yellow solid.

¹H-NMR (500 MHz, CDCl₃) δ ppm: 1.43-1.52 (3H, m), 1.70-1.72 (1H, m), 1.84-1.97 (2H, m), 1.97 (3H, s), 2.09-2.21 (2H, m), 3.64-3.69 (1H, m), 4.15-4.17 (1H, m), 6.37 (1H, d, J=12.2 Hz), 7.49 (1H, brs), 7.59 (1H, d, J=8.3 Hz), 7.74 (1H, s), 8.49 (1H, d, J=6.4 Hz), 8.98 (1H, s).

(68c) 4-{[(1S*,2R*)-2-(3-Amino-1H-pyrazol-4-yl)cyclohexyl]oxy}-2-fluoro-5-methyl-N-(pyrimidin-4-yl)benzenesulfonamide A solution of the 2-fluoro-5-methyl-4-{(1S*,2R*)-2-(3-nitro-1H-pyrazol-4-yl)cyclohexyl]oxy}-N-(pyrimidin-4-yl)benzenesulfonamide (40 mg, 0.0840 mmol) prepared in Example 68b and palladium carbon (10%; 30 mg) in methanol (1.0 mL) and ethyl acetate (1.0 mL) was stirred at 60° C. for 5 hours under a hydrogen atmosphere. The reaction solution was filtered through celite, and the residue was purified with silica gel chromatography (dichloromethane/methanol) to yield the title compound (10.8 mg, 29%) as a colorless solid.

¹H-NMR (500 MHz, CDCl₃) δ ppm: 1.25-1.61 (4H, m), 1.79-1.91 (2H, m), 2.05-2.17 (2H, m), 2.16 (3H, s), 2.67-2.72 (1H, m), 4.00 (1H, dt, J=3.9, 9.8 Hz), 6.40 (1H, d, J=12.2 Hz), 7.16 (1H, s), 7.29 (1H, brs), 7.66 (1H, d, J=8.8 Hz), 8.41 (1H, d, J=6.4 Hz), 8.77 (1H, brs).

MS (ESI) m/z: 447 [M+H]+.

Example 69

4-{[(1S*,2R*)-2-(2-Aminopyridin-3-yl)cyclohexyl]oxy}-2,5-difluoro-N-(pyrimidin-4-yl)benzenesulfonamide

[Formula 87]

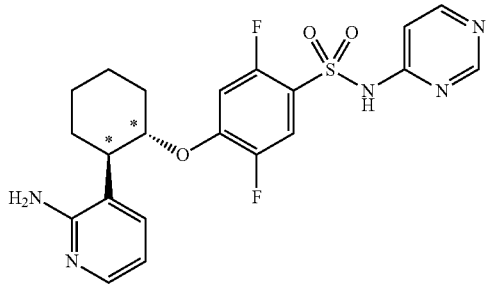

(69a) 3-Cyclohex-1-en-1-ylpyridin-2-amine

The reaction and aftertreatment were conducted in the same manner as in Example 39a by using 3-bromopyridin-2-amine (0.42 g, 2.40 mmol), 2-cyclohex-1-en-1-yl-4,4,5,5-tetramethyl-1,3,2-dioxaborolane (0.50 g, 2.40 mmol), tetrakis(triphenylphosphine)palladium (0) (0.14 g, 0.12 mmol), cesium carbonate (1.72 g, 5.29 mmol), 1,4-dioxane (8.0 mL) and water (4.0 mL), to yield the title compound (403.3 mg, 96%) as a colorless oil.

¹H-NMR (500 MHz, CDCl₃) δ ppm: 1.67-1.71 (2H, m), 1.74-1.79 (2H, m), 2.15-2.19 (2H, m), 2.20-2.24 (2H, m), 4.55 (2H, brs), 5.82-5.84 (1H, m), 6.64 (1H, dd, J=4.9, 6.8 Hz), 7.21 (1H, dd, J=2.0, 7.3 Hz), 7.95 (1H, dd, J=1.0, 6.4 Hz).

(69b) (1S*,2R*)-2-(2-Aminopyridin-3-yl)cyclohexanol

The reaction and aftertreatment were conducted in the same manner as in Example 33b by using the 3-cyclohex-1-en-1-ylpyridin-2-amine (0.40 g, 2.31 mmol) prepared in Example 69a, a borane-THF complex (0.95 M; 7.30 mL, 6.94 mmol), sodium perborate tetrahydrate (0.93 g, 6.01 mmol), THF (2.3 mL) and water (3.5 mL), to yield the title compound (45.4 mg, 10%) as a colorless amorphous solid.

¹H-NMR (500 MHz, CDCl₃) δ ppm: 1.27-1.51 (4H, m), 1.77-1.86 (3H, m), 2.08-2.10 (1H, m), 2.47 (1H, t, J=10.3 Hz), 3.55-3.59 (1H, m), 6.62-6.65 (1H, m), 7.37 (1H, d, J=7.3 Hz), 7.73 (1H, d, J=3.9 Hz).

(69c) 4-{[(1S*,2R*)-2-(2-Aminopyridin-3-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (0.11 g, 0.25 mmol) prepared in Example 14b, the (1S*,2R*)-2-(2-aminopyridin-3-yl)cyclohexanol (0.05 g, 0.25 mmol) prepared in Example 69b, sodium hydride (63%; 0.01 g, 0.38 mmol) and DMF (1.3 mL), to yield the title compound (34 mg, 22%) as a colorless amorphous solid.

¹H-NMR (500 MHz, CDCl₃) δ ppm: 1.41-1.76 (4H, m), 1.88-1.97 (3H, m), 2.27-2.29 (1H, m), 2.91-2.96 (1H, m), 3.76 (6H, s), 4.19 (1H, dt, J=4.4, 10.7 Hz), 4.72 (2H, brs), 5.19 (2H, s), 6.38-6.41 (2H, m), 6.51 (1H, dd, J=6.4, 11.2 Hz), 6.66 (1H, dd, J=4.9, 7.8 Hz), 7.17-7.19 (2H, m), 7.37 (1H, dd, J=1.5, 7.3 Hz), 7.66 (1H, dd, J=6.8, 10.3 Hz), 7.92 (1H, dd, J=2.0, 4.9 Hz), 8.45 (1H, d, J=5.9 Hz), 8.77 (1H, d, J=1.5 Hz).

(69d) 4-{[(1S*,2R*)-2-(2-Aminopyridin-3-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2R*)-2-(2-aminopyridin-3-yl)cyclohexyl]oxy}-N-(2,4-dimethoxybenzyl)-2,5-difluoro-N-(pyrimidin-4-yl)benzenesulfonamide (0.06 g, 0.09 mmol) prepared in Example 69c, triethylsilane (0.07 mL), trifluoroacetic acid (0.09 mL) and dichloromethane (0.90 mL), to yield the title compound (34.2 mg, 82%) as a colorless solid.

¹H-NMR (500 MHz, CD₃OD) δ ppm: 1.47-1.69 (4H, m), 1.82-1.92 (3H, m), 2.27-2.30 (1H, m), 3.04-3.09 (1H, m), 4.58 (1H, dt, J=4.4, 9.8 Hz), 6.66 (1H, dd, J=6.8, 7.8 Hz), 6.88 (1H, dd, J=1.0, 6.4 Hz), 6.99 (1H, dd, J=6.4, 11.2 Hz), 7.60 (1H, dd, J=6.8, 10.7 Hz), 7.69-7.73 (2H, m), 8.14 (1H, d, J=6.4 Hz), 8.44 (1H, s).

MS (ESI) m/z: 462 [M+H]+.

Example 70

2,5-Difluoro-4-{[(1S*,2R*)-2-(2-methylpyridin-3-yl)cyclohexyl]oxy}-N-(pyrimidin-4-yl)benzenesulfonamide

[Formula 88]

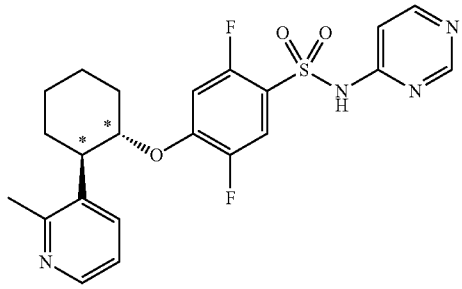

(70a) 3-(Cyclohex-1-en-1-yl)-2-methylpyridine

The reaction and aftertreatment were conducted in the same manner as in Example 39a by using 3-bromo-2-methylpyridine (0.41 g, 2.40 mmol), 2-(cyclohex-1-en-1-yl)-4,4,5,5-tetramethyl-1,3,2-dioxaborolane (0.50 g, 2.40 mmol), tetrakis(triphenylphosphine) palladium (0) (0.14 g, 0.12 mmol), cesium carbonate (1.72 g, 5.29 mmol), 1,4-dioxane (8.0 mL) and water (4.0 mL), to yield the title compound (353.2 mg, 85%) as a colorless oil.

$^1$H-NMR (500 MHz, CDCl$_3$) δ ppm: 1.67-1.78 (4H, m), 2.17-2.19 (4H, m), 2.51 (3H, s), 5.59-5.61 (1H, m), 7.06 (1H, dd, J=4.9, 7.8 Hz), 7.34 (1H, dd, J=2.0, 7.8 Hz), 8.37 (1H, dd, J=2.0, 4.9 Hz).

(70b) (1S*,2R*)-2-(2-Methylpyridin-3-yl)cyclohexanol

The reaction and aftertreatment were conducted in the same manner as in Example 33b by using the 3-(cyclohex-1-en-1-yl)-2-methylpyridine (0.35 g, 2.03 mmol) prepared in Example 70a, a borane-THF complex (0.95 M; 6.40 mL, 6.08 mmol), sodium perborate tetrahydrate (0.81 g, 5.27 mmol), THF (2.0 mL) and water (3.0 mL), to yield the title compound (106.3 mg, 27%) as a colorless amorphous solid.

$^1$H-NMR (500 MHz, CDCl$_3$) δ ppm: 1.24-1.47 (4H, m), 1.76-1.87 (3H, m), 2.13-2.15 (1H, m), 2.56 (3H, s), 2.71-2.76 (1H, m), 3.72-3.77 (1H, m), 7.10 (1H, dd, J=4.9, 7.8 Hz), 7.55 (1H, dd, J=1.5, 7.8 Hz), 8.24 (1H, dd, J=1.5, 4.9 Hz).

(70c) N-(2,4-Dimethoxybenzyl)-2,5-difluoro-4-{[(1S*,2R*)-2-(2-methylpyridin-3-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (0.25 g, 0.57 mmol) prepared in Example 14b, the (1S*,2R*)-2-(2-methylpyridin-3-yl)cyclohexanol (0.11 g, 0.57 mmol) prepared in Example 70b, sodium hydride (63%; 0.03 g, 0.85 mmol) and DMF (2.8 mL), to yield the title compound (45.7 mg, 13%) as a colorless amorphous solid.

$^1$H-NMR (500 MHz, CDCl$_3$) δ ppm: 1.43-1.60 (4H, m), 1.88-1.98 (3H, m), 2.27-2.30 (1H, m), 2.67 (3H, s), 3.15-3.20 (1H, m), 3.76 (3H, s), 3.77 (3H, s), 4.29 (1H, dt, J=4.4, 10.3 Hz), 5.20 (2H, s), 6.38-6.43 (2H, m), 6.50 (1H, dd, J=5.9, 10.7 Hz), 7.03 (1H, dd, J=4.9, 7.8 Hz), 7.16-7.22 (2H, m), 7.44 (1H, dd, J=2.0, 8.3 Hz), 7.61 (1H, dd, J=6.8, 10.3 Hz), 8.29 (1H, dd, J=1.5, 3.4 Hz), 8.44 (1H, d, J=5.4 Hz), 8.77 (1H, s).

(70d) 2,5-Difluoro-4-{[(1S*,2R*)-2-(2-methylpyridin-3-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*)-2-(2-methylpyridin-3-yl)cyclohexyl]oxy}-N-(pyrimidin-4-yl)benzenesulfonamide (0.05 g, 0.08 mmol) prepared in Example 70c, triethylsilane (0.06 mL), trifluoroacetic acid (0.08 mL) and dichloromethane (0.75 mL), to yield the title compound (34 mg, 98%) as a colorless solid.

$^1$H-NMR (500 MHz, CD$_3$OD) δ ppm: 1.45-1.75 (4H, m), 1.84-1.94 (3H, m), 2.29-2.31 (1H, m), 2.65 (3H, s), 3.18-3.24 (1H, m), 4.61 (1H, dt, J=3.9, 9.8 Hz), 6.95 (1H, dd, J=1.0, 6.4 Hz), 6.99 (1H, dd, J=6.8, 11.7 Hz), 7.16 (1H, dd, J=4.9, 7.8 Hz), 7.57 (1H, dd, J=6.8, 10.7 Hz), 7.82 (1H, dd, J=2.0, 7.8 Hz), 8.14 (1H, dd, J=1.5, 4.9 Hz), 8.21 (1H, d, J=6.4 Hz), 8.49 (1H, s).

MS (ESI) m/z: 461 [M+H]+.

Example 71

4-{[(1S*,2R*)-2-(3-Amino-1H-pyrazol-4-yl)cyclohexyl]oxy}-5-chloro-2-fluoro-N-(pyrimidin-4-yl)benzenesulfonamide

[Formula 89]

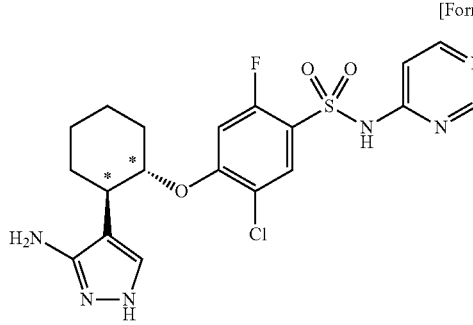

(71a) 5-Chloro-N-(2,4-dimethoxybenzyl)-2-fluoro-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (196 mg, 0.430 mmol) prepared in Example 20a, the (1S*,2R*)-2-[3-nitro-1-(tetrahydro-2H-pyran-2-yl)-1H-pyrazol-4-yl]cyclohexanol (127 mg, 0.430 mmol) prepared in Example 34b, sodium hydride (63%; 49.5 mg, 0.516 mmol) and DMF (6.0 mL), to yield the title compound (264 mg, 84%) as a pale yellow amorphous solid.

$^1$H-NMR (500 MHz, CDCl$_3$) δ ppm: 1.45-1.69 (8H, m), 1.81-2.24 (6H, m), 3.61-3.70 (2H, m), 3.77 (3H, s), 3.78 (3H, s), 3.92-4.00 (1H, m), 4.27-4.32 (1H, m), 5.22 (2H, s), 5.32-5.36 (1H, m), 6.38-6.41 (2H, m), 6.56 (1H, t, J=12.2 Hz), 7.18 (1H, d, J=9.3 Hz), 7.20-7.23 (1H, m), 7.47 (1H, d, J=29.8 Hz), 7.91 (1H, dd, J=5.4, 7.3 Hz), 7.47 (1H, d, J=5.9 Hz), 8.79 (1H, s).

(71b) 5-Chloro-2-fluoro-4-{(1S*,2R*)-2-(3-nitro-1H-pyrazol-4-yl)cyclohexyl]oxy}-N-(pyrimidin-4-yl)benzenesulfonamide The reaction and aftertreatment were conducted in the same manner as in Example 22c by using the 5-chloro-N-(2,4-dimethoxybenzyl)-2-fluoro-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide (264 mg, 0.362 mmol) prepared in Example 71a, triethylsilane (0.10 mL), trifluoroacetic acid (0.5 mL), dichloromethane (2.0 mL) and methanol (1.0 mL), to yield the title compound (162 mg, 90%) as a white solid.

$^1$H-NMR (500 MHz, DMSO-d$_6$) δ ppm: 1.31-1.57 (0.4H, m), 1.71-1.80 (2H, m), 1.96-1.99 (1H, m), 2.17-2.19 (1H, m, 3.48-3.53 (1H, m), 4.56-4.61 (1H, m), 7.24-7.31 (2H, m), 7.73-7.76 (2H, m), 7.90-7.91 (1H, m), 8.56 (1H, s).

(71c) 4-{[(1S*,2R*)-2-(3-Amino-1H-pyrazol-4-yl)cyclohexyl]oxy}-5-chloro-2-fluoro-N-(pyrimidin-4-yl)benzenesulfonamide A solution of the 5-chloro-2-fluoro-4-{(1S*,2R*)-2-(3-nitro-1H-pyrazol-4-yl)cyclohexyl]oxy}-N-(pyrimidin-4-yl)benzenesulfonamide (0.05 g, 0.101 mmol) prepared in Example 71b, an iron powder (56 mg, 1.01 mol) and a saturated aqueous solution of ammonium chloride (2.0 mL) in ethanol (2.0 mL) was stirred for 15 hours under heated reflux. After allowing to cool, the reaction solution was filtered through celite, and the filtrate was subjected to extraction with ethyl acetate (100 mL). The organic layer was dried over anhydrous sodium sulfate and vacuum concentrated, and the residue was purified with silica gel chromatography (dichloromethane/methanol) to yield the title compound (29.9 mg, 64%) as a colorless solid.

$^1$H-NMR (500 MHz, CD$_3$OD) δ ppm: 1.38-1.54 (3H, m), 1.66-1.75 (1H, m), 1.80-1.88 (2H, m), 1.97-2.01 (2H, m), 2.72-2.77 (1H, m), 4.38 (1H, dt, J=3.9, 5.9 Hz), 6.95-6.99 (3H, m), 7.92 (1H, d, J=7.8 Hz), 8.24 (1H, d, J=5.9 Hz), 8.52 (1H, s).

MS (ESI) m/z: 467 [M+H]+.

Example 72

4-{[(1S*,2R*)-5,5-Dimethyl-2-(1-methyl-1H-pyrazol-5-yl)cyclohexyl]oxy}-2,5-difluoro-N-(pyrimidin-4-yl)benzenesulfonamide

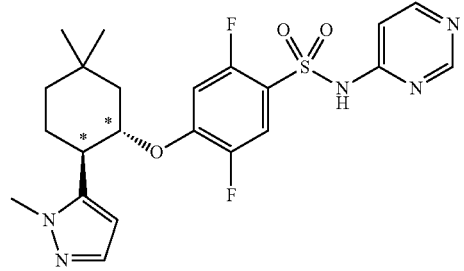

[Formula 90]

(72a) 6-Iodo-9,9-dimethyl-1,4-dioxaspiro[4.5]dec-6-ene

The reaction and aftertreatment were conducted in the same manner as in Example 67a by using 2-iodo-5,5-dimethylcyclohex-2-en-1-one (J. Org. Chem., 1994, 59, 5393-5396; 6.10 g, 24.4 mmol), ethylene glycol (3.00 g, 48.3 mmol), p-toluenesulfonic acid hydrate (230 mg, 1.22 mmol) and benzene (70 mL), to yield the title compound (3.33 g, 46%) as a brown oil.

$^1$H-NMR (500 MHz, CDCl$_3$) δ ppm: 1.01 (6H, s), 1.84 (2H, s), 1.96 (2H, d, J=3.9 Hz), 3.95-3.98 (2H, m), 4.18-4.21 (2H, m), 6.59 (1H, t, J=4.4 Hz).

(72b) 5-(9,9-Dimethyl-1,4-dioxaspiro[4.5]dec-6-en-6-yl)-1-methyl-1H-pyrazole The reaction and aftertreatment were conducted in the same manner as in Example 39a by using the 6-iodo-9,9-dimethyl-1,4-dioxaspiro[4.5]dec-6-ene (1.4 g, 4.76 mmol) prepared in Example 72a, 1-methyl-5-(4,4,5,5-tetramethyl-1,3,2-dioxaboran-2-yl)-1H-pyrazole (1.00 g, 4.81 mmol), tetrakis(triphenylphosphine)palladium (0) (240 mg, 0.208 mmol), cesium carbonate (3.40 g, 10.4 mmol), 1,4-dioxane (10 mL) and water (5.0 mL), to yield the title compound (758 mg, 64%) as a colorless oil.

$^1$H-NMR (500 MHz, CDCl$_3$) δ ppm: 1.09 (6H, s), 1.80 (2H, s), 2.07 (2H, d, J=3.9 Hz), 3.44-3.47 (2H, m), 3.77-3.79 (2H, m), 3.80 (3H, s), 5.88 (1H, t, J=3.9 Hz), 6.17 (1H, d, J=1.5 Hz), 7.41 (1H, d, J=2.0 Hz).

(72c) 5,5-Dimethyl-2-(1-methyl-1H-pyrazol-5-yl)cyclohex-2-en-1-one

The reaction and aftertreatment were conducted in the same manner as in Example 67c by using the 5-(9,9-dimethyl-1,4-dioxaspiro[4.5]dec-6-en-6-yl)-1-methyl-1H-pyrazole (758 mg, 3.05 mmol) prepared in Example 72b, 2 M hydrochloric acid (2.0 mL) and THF (5.0 mL), to yield the title compound (581 mg, 93%) as a colorless oil.

$^1$H-NMR (500 MHz, CDCl$_3$) δ ppm: 1.14 (6H, s), 1.58 (2H, s), 2.46 (2H, d, J=2.9 Hz), 3.70 (3H, s), 6.14 (1H, d, J=1.5 Hz), 6.98 (1H, t, J=3.9 Hz), 7.44 (1H, d, J=1.5 Hz).

(72d) (1S*,2R*)-5,5-Dimethyl-2-(1-methyl-1H-pyrazol-5-yl)cyclohexanol

To a solution of the 5,5-dimethyl-2-(1-methyl-1H-pyrazol-5-yl)cyclohex-2-en-1-one (581 mg, 2.84 mmol) prepared in Example 72c in methanol (6.0 mL), sodium borohydride (200 mg, 5.29 mmol) was added with cooling on ice, and the reaction solution was stirred at room temperature for 30 minutes. To the reaction solution, a saturated aqueous solution of ammonium chloride (50 mL) was added, followed by extraction with ethyl acetate (100 mL). The thus obtained organic layer was dried over anhydrous sodium sulfate. After vacuum concentration, the residue was purified with silica gel chromatography (dichloromethane/methanol=98:2) to yield the title compound (40 mg, 6.8%) as a colorless oil.

$^1$H-NMR (500 MHz, CDCl$_3$) δ ppm: 1.01 (3H, s), 1.02 (3H, s), 1.29-1.34 (2H, m), 1.44-1.48 (1H, m), 1.55-1.64 (1H, m), 1.72-1.83 (2H, m), 2.47-2.52 (1H, m), 3.81 (1H, dt, J=4.4, 11.2 Hz), 3.84 (3H, s), 6.08 (1H, d, J=1.5 Hz), 7.42 (1H, d, J=1.5 Hz).

(72e) N-(2,4-dimethoxybenzyl)-4-{[(1S*,2R*)-5,5-dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (85 mg, 0.193 mmol) prepared in Example 14b, the (1S*,2R*)-5,5-dimethyl-2-(1-methyl-1H-pyrazol-5-yl)cyclohexanol (40 mg, 0.192 mmol) prepared in Example 72d, sodium hydride (63%; 30 mg, 0.788 mmol) and DMF (2.0 mL), to yield the title compound (100 mg, 83%) as a colorless oil.

$^1$H-NMR (500 MHz, CDCl$_3$) δ ppm: 1.06 (3H, s), 1.10 (3H, s), 1.39-1.48 (2H, m), 1.55-1.62 (1H, m), 1.81-1.96 (3H, m), 2.91-2.96 (1H, m), 3.77 (3H, s), 3.78 (3H, s), 3.90 (3H, s), 4.30 (1H, dt, J=3.9, 11.2 Hz), 5.19 (1H, d, J=16.6 Hz), 5.24 (1H, d, J=17.1 Hz), 6.05 (1H, d, J=2.0 Hz), 6.38-6.42 (3H, m), 7.18-7.20 (2H, m), 7.36 (1H, d, J=1.5 Hz), 7.67 (1H, dd, J=6.4, 9.8 Hz), 8.46 (1H, d, J=5.9 Hz), 8.79 (1H, d, J=1.0 Hz).

(72f) 4-{[(1S*,2R*)-5,5-Dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-5,5-dimethyl-2-(1-methyl-1H-pyrazol-5-yl)cyclohexyl]oxy}-2,5-difluoro-N-(pyrimidin-4-yl)benzenesulfonamide (100 mg, 0.159 mmol) prepared in Example 72e, triethylsilane (0.20 mL), trifluoroacetic acid (2.0 mL) and dichloromethane (2.0 mL), to yield the title compound (70 mg, 92%) as a colorless solid.

$^1$H-NMR (500 MHz, DMSO-d$_6$) δ ppm: 0.98 (3H, s), 1.09 (3H, s), 1.36-1.43 (3H, m), 1.68-1.90 (3H, m), 3.01 (1H, dt, J=4.4, 11.7 Hz), 3.77 (3H, s), 4.68 (1H, dt, J=3.9, 10.7 Hz), 6.21 (1H, d, J=2.0 Hz), 6.98 (1H, brs), 7.08 (1H, dd, J=6.4, 11.2 Hz), 7.19 (1H, d, J=2.0 Hz), 7.60-7.63 (1H, m), 8.24 (1H, brs), 8.57 (1H, s).

MS (ESI) m/z: 478 [M+H]+.

Example 73

4-{[(1S*,2R*)-2-(3-Amino-1H-pyrazol-4-yl)cyclohexyl]oxy}-2-fluoro-3-methyl-N-(pyrimidin-4-yl)benzenesulfonamide

[Formula 91]

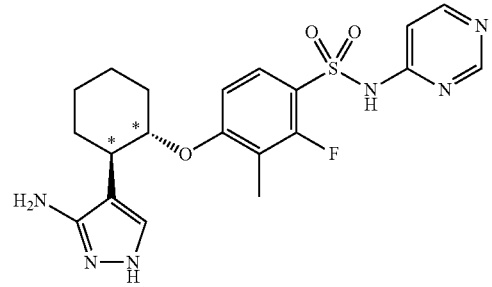

(73a) N-(2,4-Dimethoxybenzyl)-2-fluoro-3-methyl-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide The reaction and aftertreatment were conducted in the same manner as in Example 1a by using the N-(2,4-dimethoxybenzyl)-2,4-difluoro-3-methyl-N-(pyrimidin-4-yl)benzenesulfonamide (155 mg, 0.356 mmol) prepared in Example 65b, the (1S*,2R*)-2-[3-nitro-1-(tetrahydro-2H-pyran-2-yl)-1H-pyrazol-4-yl]cyclohexanol (105 mg, 0.356 mmol) prepared in Example 34b, sodium hydride (63%; 41.0 mg, 0.427 mmol) and DMF (6.0 mL), to yield the title compound (209 mg, 83%) as a colorless solid.

$^1$H-NMR (500 MHz, CDCl$_3$) δ ppm: 1.48-1.65 (8H, m), 1.82-2.28 (6H, m), 2.05 (3H, s), 3.58-3.68 (2H, m), 3.77 (3H, s), 3.80 (3H, s), 3.87-4.00 (1H, m), 4.29-4.35 (1H, m), 5.27 (2H, s), 5.30-5.33 (1H, m), 6.39-6.43 (2H, m), 6.65 (1H, dd, J=8.8, 15.1 Hz), 7.19 (1H, d, J=8.8 Hz), 7.22-7.24 (1H, m), 7.43 (1H, d, J=24.4 Hz), 7.81 (1H, dd, J=8.8, 17.6 Hz), 7.41 (1H, d, J=5.9 Hz), 8.74 (1H, s).

(73b) 2-Fluoro-3-methyl-4-{(1S*,2R*)-2-(3-nitro-1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-2-fluoro-3-methyl-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide (209 mg, 0.294 mmol) prepared in Example 73a, triethylsilane (0.10 mL), trifluoroacetic acid (0.5 mL), dichloromethane (2.0 mL) and methanol (1.0 mL), to yield the title compound (139 mg, 99%) as a white solid.

$^1$H-NMR (500 MHz, CD$_3$OD) δ ppm: 1.46-1.71 (4H, m), 1.82-1.93 (2H, m), 1.83 (3H, s), 2.06-2.09 (1H, m), 2.26-2.29 (1H, m), 3.57-3.63 (1H, m), 4.55 (1H, dt, J=4.4, 10.7 Hz), 6.85 (1H, d, J=8.8 Hz), 7.08 (1H, d, J=6.4 Hz), 7.69 (1H, s), 7.77 (1H, t, J=8.8 Hz), 8.35 (1H, d, J=6.4 Hz), 8.62 (1H, s).

(73c) 4-{[(1S*,2R*)-2-(3-Amino-1H-pyrazol-4-yl)cyclohexyl]oxy}-2-fluoro-3-methyl-N-(pyrimidin-4-yl)benzenesulfonamide The reaction and aftertreatment were conducted in the same manner as in Example 68c by using the 2-fluoro-3- methyl-4-{(1S*,2R*)-2-(3-nitro-1H-pyrazol-4-yl)cyclohexyl]oxy}-N-(pyrimidin-4-yl)benzenesulfonamide (139 mg, 0.292 mmol) prepared in Example 73b, palladium carbon (10%; 18 mg), methanol (1.0 mL) and ethyl acetate (1.0 mL), to yield the title compound (34 mg, 26%) as a white solid.

¹H-NMR (500 MHz, CD₃OD) δ ppm: 1.42-1.66 (3H, m), 1.78-1.82 (1H, m), 1.85-1.89 (1H, m), 1.98-2.02 (2H, m), 2.15 (3H, s), 2.19-2.23 (1H, m), 2.73-2.78 (1H, m), 4.40 (1H, dt, J=3.9, 9.8 Hz), 6.83 (1H, d, J=8.8 Hz), 7.04 (1H, d, J=6.4 Hz), 7.17 (1H, s), 7.74 (1H, t, J=8.3 Hz), 8.30 (1H, d, J=6.4 Hz), 8.55 (1H, s).

MS (ESI) m/z: 447 [M+H]+.

Example 74

2,5-Difluoro-4-{[(1S*,2R*)-2-phenylcyclohexyl]oxy}-N-(1,2,4-thiadiazol-5-yl)benzenesulfonamide Na salt

[Formula 92]

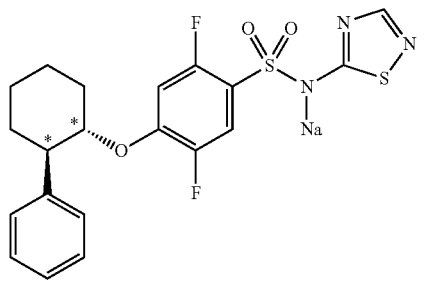

The reaction and aftertreatment were conducted in the same manner as in Example 5c by using the 2,5-difluoro-4-{[(1S*,2R*)-2-phenylcyclohexyl]oxy}-N-(1,2,4-thiadiazol-5-yl)benzenesulfonamide (114 mg, 0.252 mmol) prepared in Example 1b, a 1 M sodium hydroxide solution (0.252 mL, 0.252 mol) and methanol (3.0 mL), to yield the title compound (119 mg, 99%) as a colorless solid.

¹H-NMR (400 MHz, DMSO-d₆) δ ppm: 1.31-1.61 (4H, m), 1.70-1.83 (3H, m), 2.14-2.17 (1H, m), 2.76-2.83 (1H, m), 4.74 (1H, dt, J=3.9, 10.1 Hz), 7.07-7.34 (7H, m), 7.87 (1H, s).

Example 75

2,5-Difluoro-4-{[(1R,2S)-2-phenylcyclohexyl]oxy}-N-(1,2,4-thiadiazol-5-yl)benzenesulfonamide

[Formula 93]

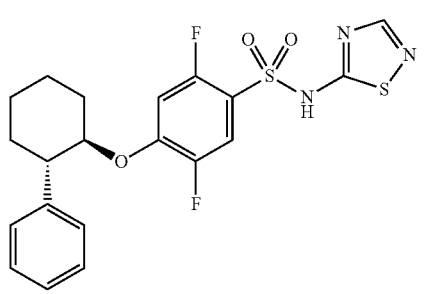

(75a) N-(2,4-dimethoxybenzyl)-2,5-difluoro-4-{[(1R,2S)-2-phenylcyclohexyl]oxy}-N-(1,2,4-thiadiazol-5-yl)benzenesulfonamide The reaction and aftertreatment were conducted in the same manner as in Example 1a by using N-(2,4-dimethoxybenzyl)-2,4,5-trifluoro-N-(1,2,4-thiadiazol-5-yl)benzenesulfonamide (WO 2010/079443; 126 mg, 0.283 mmol), (1R,2S)-2-phenylcyclohexanol (50.0 mg, 0.284 mmol), sodium hydride (63%; 21.6 mg, 0.567 mol) and DMSO (2.0 mL), to yield the title compound (53.6 mg, 31%) as a colorless oil.

(75b) 2,5-Difluoro-4-{[(1R,2S)-2-phenylcyclohexyl]oxy}-N-(1,2,4-thiadiazol-5-yl)benzenesulfonamide The reaction and aftertreatment were conducted in the same manner as in Example 1b by using the N-(2,4-dimethoxybenzyl)-2,5-difluoro-4-{[(1R,2S)-2-phenylcyclohexyl]oxy}-N-(1,2,4-thiadiazol-5-yl)benzenesulfonamide (53.6 mg, 0.0891 mmol) prepared in Example 75a, triethylsilane (0.10 mL), trifluoroacetic acid (1.0 mL) and dichloromethane (1.0 mL), to yield the title compound (40.2 mg, 99%) as a colorless solid.

[α]_D^{25}=56.9 (c 0.232, DMSO).

Example 76

2,5-Difluoro-4-{[(1S,2R)-2-phenylcyclohexyl]oxy}-N-(1,2,4-thiadiazol-5-yl)benzenesulfonamide Na salt

[Formula 94]

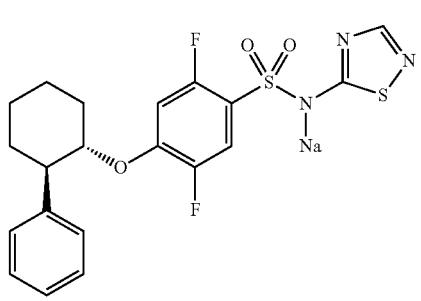

The reaction and aftertreatment were conducted in the same manner as in Example 5c by using the 2,5-difluoro-4-{[(1S,2R)-2-phenylcyclohexyl]oxy}-N-(1,2,4-thiadiazol-5-yl)benzenesulfonamide (386 mg, 0.855 mmol) prepared in Example 2b, and a 1 M sodium hydroxide solution (0.855 mL, 0.855 mol), to yield the title compound (386 mg, 99%) as a colorless solid.

[α]_D^{25}=−44.1 (c 1.06, DMSO).

Example 77

2,5-Difluoro-4-{[(1S*,2R*)-2-(1-methyl-1H-pyrazol-5-yl)cyclopentyl]oxy}-N-(pyrimidin-4-yl)benzenesulfonamide Na salt

[Formula 95]

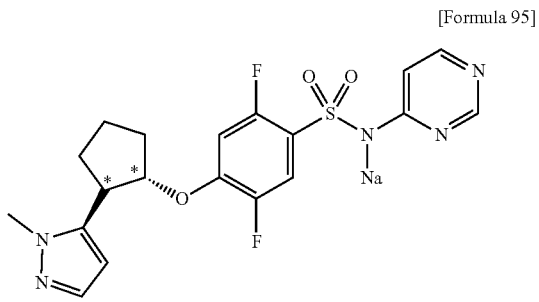

The reaction and aftertreatment were conducted in the same manner as in Example 5c by using the 2,5-difluoro-4-{[(1S*,2R*)-2-(1-methyl-1H-pyrazol-5-yl)cyclopentyl]oxy}-N-(pyrimidin-4-yl)benzenesulfonamide (15.3 mg, 0.035 mmol) prepared in Example 14d, and a 1 M sodium hydroxide solution (0.035 mL, 0.035 mol), to yield the title compound (11.0 mg, 68%) as a colorless solid.

$^1$H-NMR (500 MHz, CD$_3$OD) δ ppm: 1.75-1.99 (4H, m), 2.24-2.32 (2H, m), 3.48-3.52 (1H, m), 3.81 (3H, s), 4.78-4.82 (1H, m), 6.19 (1H, d, J=2.0 Hz), 6.71 (1H, d, J=7.3 Hz), 6.81 (1H, dd, J=6.4, 10.7 Hz), 7.35 (1H, d, J=2.0 Hz), 7.65 (1H, dd, J=6.4, 10.7 Hz), 8.00 (1H, d, J=6.4 Hz), 8.31 (1H, s).

Example 78

2,5-Difluoro-4-{[(1R,2S)-2-(1-methyl-1H-pyrazol-5-yl)cyclopentyl]oxy}-N-(pyrimidin-4-yl)benzenesulfonamide

[Formula 96]

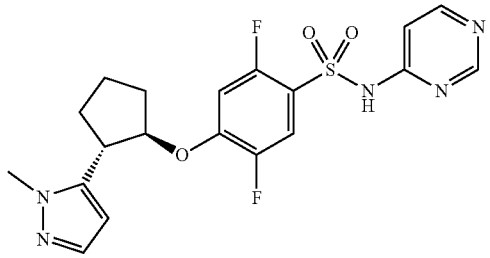

(78a) N-(2,4-Dimethoxybenzyl)-2,5-difluoro-4-{[(1R,2S)-2-(1-methyl-1H-pyrazol-5-yl)cyclopentyl]oxy}-N-(pyrimidin-4-yl)benzenesulfonamide The N-(2,4-dimethoxybenzyl)-2,5-difluoro-4-{[(1S*,2R*)-2-(1-methyl-1H-pyrazol-5-yl)cyclopentyl]oxy}-N-(pyrimidin-4-yl)benzenesulfonamide prepared in Example 14c was optically resolved with CHIRALPAK AD (Daicel Corp.; hexane/isopropanol=4:1), to yield the title compound as a colorless oil.

(78b) 2,5-Difluoro-4-{[(1R,2S)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1R,2S)-2-(1-methyl-1H-pyrazol-5-yl)cyclopentyl]oxy}-N-(pyrimidin-4-yl)benzenesulfonamide (436 mg, 0.74 mmol) prepared in Example 78a, triethylsilane (0.20 mL), trifluoroacetic acid (2.0 mL) and dichloromethane (2.0 mL), to yield the title compound (239 mg, 74%) as a colorless solid.

$[α]_D^{25}$=−72.7 (c 1.04, DMSO).

Example 79

3-Chloro-2-fluoro-4-{[(1S*,2R*)-2-(1-methyl-1H-pyrazol-5-yl)cyclohexyl]oxy}-N-(pyrimidin-4-yl)benzenesulfonamide

[Formula 97]

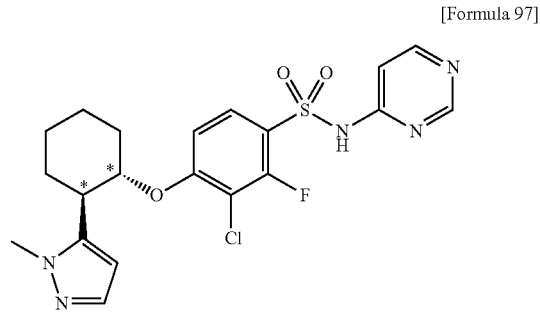 [SMILES: Cn1nccc1[C@H]1CCCC[C@@H]1Oc1ccc(S(=O)(=O)Nc2ccncn2)c(F)c1Cl]

(79a) 3-Chloro-N-(2,4-dimethoxybenzyl)-2,4-difluoro-N-(pyrimidin-4-yl)benzenesulfonamide The reaction and aftertreatment were conducted in the same manner as in Example 14b by using the N-(2,4-dimethoxybenzyl)pyrimidin-4-amine (1.00 g, 4.07 mmol) prepared in Example 14a, 3-chloro-2,4-difluorobenzenesulfonyl chloride (1.51 g, 6.11 mmol), 1,4-diazabicyclo[2.2.2]octane (0.69 g, 6.11 mmol) and THF (20 mL), to yield the title compound (0.983 g, 53%) as a colorless amorphous solid.

$^1$H-NMR (500 MHz, CDCl$_3$) δ ppm: 3.78 (3H, s), 3.81 (3H, s), 5.25 (2H, s), 6.41-6.43 (2H, m), 7.11-7.15 (2H, m), 7.22 (1H, d, J=8.8 Hz), 8.01-8.05 (1H, m), 8.47 (1H, d, J=5.9 Hz), 8.75 (1H, d, J=1.0 Hz).

(79b) 3-Chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the 3-chloro-N-(2,4-dimethoxybenzyl)-2,4-difluoro-N-(pyrimidin-4-yl)benzenesulfonamide (0.30 g, 0.69 mmol) prepared in Example 79a, the (1S*,2R*)-2-(1-methyl-1H-pyrazol-5-yl)cyclohexanol (0.12 g, 0.66 mmol) prepared in Example 4a, sodium hydride (63%; 0.050 g, 1.31 mmol) and DMF (2.0 mL), to yield the title compound (314 mg, 77%) as a colorless amorphous solid.

$^1$H-NMR (500 MHz, CDCl$_3$) δ ppm: 1.41-1.63 (4H, m), 1.88-1.97 (2H, m), 2.07-2.09 (1H, m), 2.23-2.26 (1H, m), 3.03-3.08 (1H, m), 3.77 (3H, s), 3.78 (3H, s), 3.92 (3H, s), 4.29 (1H, dt, J=3.9, 10.3 Hz), 5.21 (1H, d, J=17.1 Hz), 5.26 (1H, d, J=17.1 Hz), 6.05 (1H, d, J=2.0 Hz), 6.39-6.41 (2H, m), 6.60 (1H, d, J=9.3 Hz), 7.16 (1H, dd, J=1.5, 5.9 Hz), 7.19 (1H, d, J=9.3 Hz), 7.36 (1H, d, J=2.0 Hz), 7.81 (1H, dd, J=7.8, 8.8 Hz), 8.44 (1H, d, J=5.9 Hz), 8.76 (1H, s).

(79c) 3-Chloro-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 3-chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide (314 mg, 0.51 mmol) prepared in Example 79b, triethylsilane (0.50 mL), trifluoroacetic acid (5.0 mL) and dichloromethane (5.0 mL), to yield the title compound (183 mg, 77%) as a colorless solid.
$^1$H-NMR (500 MHz, CDCl$_3$) δ ppm: 1.38-1.70 (4H, m), 1.87-1.95 (2H, m), 2.06-2.10 (1H, m), 2.22-2.25 (1H, m), 3.03-3.08 (1H, m), 3.92 (3H, s), 4.28 (1H, dt, J=4.4, 10.7 Hz), 6.04 (1H, d, J=2.0 Hz), 6.61 (1H, dd, J=1.0, 9.3 Hz), 7.20-7.21 (1H, m), 7.36 (1H, d, J=2.0 Hz), 7.78 (1H, t, J=7.8 Hz), 8.35 (1H, d, J=6.4 Hz), 8.81 (1H, s).
MS (ESI) m/z: 466 [M+H]+.

Example 80

3-Chloro-2-fluoro-4-{[(1S*,2R*)-2-(1-methyl-1H-pyrazol-5-yl)cyclopentyl]oxy}-N-(pyrimidin-4-yl)benzenesulfonamide

[Formula 98]

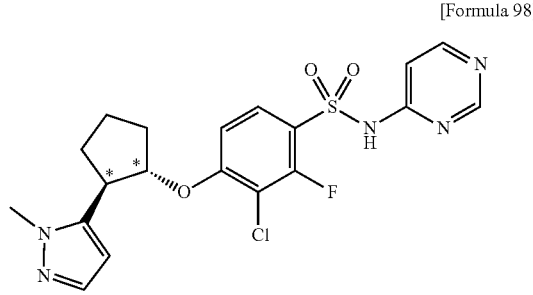

(80a) 3-Chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the 3-chloro-N-(2,4-dimethoxybenzyl)-2,4-difluoro-N-(pyrimidin-4-yl)benzenesulfonamide (463 mg, 1.02 mmol) prepared in Example 79a, the (1S*,2R*)-2-(1-methyl-1H-pyrazol-5-yl)cyclopentanol (169 mg, 1.02 mmol) prepared in Example 8a, sodium hydride (63%; 50 mg, 1.31 mmol) and DMF (3.0 mL), to yield the title compound (347 mg, 57%) as a colorless amorphous solid.
$^1$H-NMR (500 MHz, CDCl$_3$) δ ppm: 1.80-1.98 (4H, m), 2.22-2.35 (2H, m), 3.50 (1H, dt, J=4.9, 8.8 Hz), 3.76 (0.3H, s), 3.80 (3H, s), 3.87 (3H, s), 4.73-4.76 (1H, m), 5.24 (1H, d, J=17.1 Hz), 5.29 (1H, d, J=17.1 Hz), 0.6.08 (1H, d, J=2.0 Hz), 6.40-6.42 (2H, m), 6.63 (1H, dd, J=1.0, 8.8 Hz), 7.18 (1H, dd, J=1.5, 5.9 Hz), 7.20 (1H, d, J=7.8 Hz), 7.42 (1H, d, J=1.5 Hz), 7.88 (1H, dd, J=7.8, 8.8 Hz), 8.44 (1H, d, J=6.4 Hz), 8.76 (1H, d, J=1.0 Hz).

(80b) 3-Chloro-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the 3-chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide (344 mg, 0.31 mmol) prepared in Example 80a, triethylsilane (0.50 mL), trifluoroacetic acid (5.0 mL) and dichloromethane (5.0 mL), to yield the title compound (227 mg, 88%) as a colorless solid.
$^1$H-NMR (500 MHz, CDCl$_3$) δ ppm: 1.78-1.98 (4H, m), 2.22-2.35 (2H, m), 3.49 (1H, dt, J=4.9, 8.3 Hz), 3.86 (3H, s), 4.72-4.75 (1H, m), 6.07 (1H, d, J=2.0 Hz), 6.64 (1H, d, J=7.8 Hz), 7.24-7.25 (1H, m), 7.42 (1H, d, J=2.0 Hz), 7.86 (1H, dd, J=7.8, 8.8 Hz), 8.37 (1H, d, J=6.4 Hz), 8.84 (1H, brs).
MS (ESI) m/z: 452 [M+H]+.

Example 81

2-Fluoro-5-methyl-4-{[(1S*,2R*)-2-(1H-pyrazol-4-yl)cyclohexyl]oxy}-N-(pyrimidin-4-yl)benzenesulfonamide

[Formula 99]

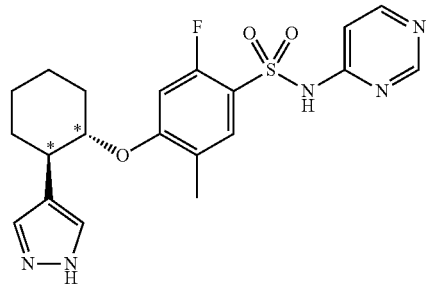

(81a) N-(2,4-dimethoxybenzyl)-2-fluoro-5-methyl-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (200 mg, 0.459 mmol) prepared in Example 43a, the (1S*,2R*)-2-[1-(tetrahydro-2H-pyran-2-yl)-1H-pyrazol-4-yl]cyclohexanol (114 mg, 0.459 mmol) prepared in Example 33b, sodium hydride (63%; 27 mg, 0.680 mmol) and DMF (7.0 mL), to yield the title compound (170 mg, 56%) as a colorless oil.
$^1$H-NMR (500 MHz, CDCl$_3$) δ ppm: 1.41-1.69 (8H, m), 1.80-2.18 (6H, m), 2.15 (3H, s), 2.85-2.90 (1H, m), 3.62-3.67 (1H, m), 3.76 (3H, s), 3.79 (3H, s), 3.98-4.02 (2H, m), 5.25 (1H, d, J=8.3 Hz), 5.26-5.28 (1H, m), 6.37-6.42 (3H, m), 7.19 (1H, d, J=8.3 Hz), 7.30 (1H, dt, J=1.5, 5.9 Hz), 7.38 (1H, d, J=6.4 Hz), 7.41 (1H, s), 7.68 (1H, d, J=8.3 Hz), 8.43 (1H, d, J=5.9 Hz), 8.77 (1H, s).

(81b) 2-Fluoro-5-methyl-4-{[(1S*,2R*)-2-(1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-2-fluoro-5-methyl-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide (150 mg, 0.22 mmol) prepared in Example 81a, triethylsilane (0.15 mL), trifluoroacetic acid (1.5 mL), dichloromethane (1.5 mL) and methanol (1.5 mL), to yield the title compound (70 mg, 72%) as a colorless solid.

$^1$H-NMR (500 MHz, DMSO-$d_6$) δ ppm: 1.30-1.37 (2H, m), 1.45-1.75 (4H, m), 1.92-1.94 (1H, m), 2.06 (3H, s), 2.06-2.10 (1H, m), 2.75-2.80 (1H, m), 4.35 (1H, dt, J=3.9, 9.8 Hz), 6.97 (1H, d, J=12.7 Hz), 6.99 (1H, brs), 7.41 (2H, s), 7.62 (1H, d, J=8.3 Hz), 8.31 (1H, brs), 8.58 (1H, s).

MS (ESI) m/z: 432 [M+H]+.

Example 82

4-{[(1S*,2R*)-2-(3-Aminopyridazin-4-yl)cyclohexyl]oxy}-2,5-difluoro-N-(pyrimidin-4-yl)benzenesulfonamide

[Formula 100]

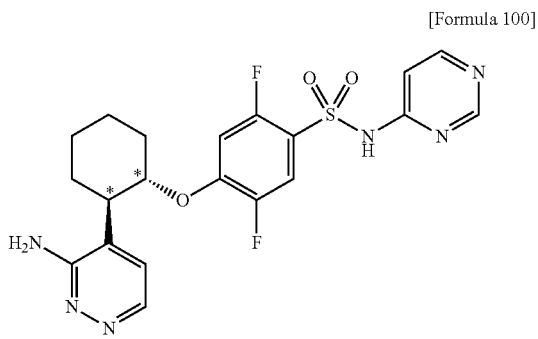 [SMILES: Nc1nnccc1[C@H]1CCCC[C@@H]1Oc1cc(F)c(S(=O)(=O)Nc2ccncn2)cc1F]

(82a) 6-(4,4,5,5-Tetramethyl-1,3,2-dioxaborolan-2-yl)-1,4-dioxaspiro[4.5]dec-6-ene To a solution of 6-iodo-1,4-dioxaspiro[4.5]dec-6-ene (Synlett, 2008, 1086-1090; 2.70 g, 10.2 mmol) in THF (30 mL), butyl lithium (1.65 M solution in hexane; 6.7 mL, 11.1 mmol) was added at −78° C. The reaction solution was stirred at −78° C. for 1 hour. Then, 4,4,5,5-tetramethyl-2-(propan-2-yloxy)-1,3,2-dioxaborolane (4.0 mL, 19.8 mmol) was added thereto, and the mixture was stirred at −78° C. for 2 hours. To the reaction solution, water (50 mL) was added, followed by extraction with ethyl acetate (50 mL). The thus obtained organic layer was dried over anhydrous sodium sulfate. After vacuum concentration, the residue was purified with silica gel chromatography (hexane/ethyl acetate=9:1) to yield the title compound (1.52 g, 56%) as a colorless oil.

$^1$H-NMR (500 MHz, CDCl$_3$) δ ppm: 1.26 (12H, s), 1.72-1.80 (4H, m), 2.07-2.10 (2H, m), 3.93-3.95 (2H, m), 4.16-4.18 (2H, m), 6.71 (1H, t, J=3.4 Hz).

(82b) 6-Chloro-4-(1,4-dioxaspiro[4.5]dec-6-en-6-yl)pyridazin-3-amine

The reaction and aftertreatment were conducted in the same manner as in Example 39a by using the 6-(4,4,5,5-tetramethyl-1,3,2-dioxaborolan-2-yl)-1,4-dioxaspiro[4.5]dec-6-ene (0.64 g, 2.40 mmol) prepared in Example 82a, 4-bromo-6-chloropyridazin-3-amine (0.50 g, 2.40 mmol), tetrakis(triphenylphosphine)palladium (0) (0.14 g, 0.12 mmol), cesium carbonate (1.72 g, 5.29 mmol), dioxane (8.0 mL) and water (4.0 mL), to yield the title compound (275.7 mg, 43%) as a colorless oil.

$^1$H-NMR (500 MHz, CDCl$_3$) δ ppm: 1.85-1.89 (4H, m), 2.20-2.23 (2H, m), 3.70-3.73 (2H, m), 3.89-3.92 (2H, m), 5.72 (2H, brs), 6.03 (1H, t, J=3.9 Hz), 7.05 (1H, s).

(82c) 4-(1,4-Dioxaspiro[4.5]dec-6-en-6-yl)pyridazin-3-amine

A solution of the 6-chloro-4-(1,4-dioxaspiro[4.5]dec-6-en-6-yl)pyridazin-3-amine (0.10 g, 0.37 mmol) prepared in Example 82b, ammonium formate (0.14 g, 2.24 mmol) and palladium carbon (10%; 0.10 g) in ethanol (3.7 mL) was stirred at 80° C. for 4 hours. After allowing to cool, the reaction solution was filtered through celite and concentrated to yield the title compound in a crude form.

(82d) 2-(3-Aminopyridazin-4-yl)cyclohex-2-en-1-one

The reaction and aftertreatment were conducted in the same manner as in Example 67c by using the crude 4-(1,4-dioxaspiro[4.5]dec-6-en-6-yl)pyridazin-3-amine prepared in Example 82c, 2 M hydrochloric acid (0.37 mL) and THF (0.92 mL), to yield the title compound (69 mg, 99%, 2 steps) as a colorless oil.

$^1$H-NMR (500 MHz, CDCl$_3$) δ ppm: 2.13-2.18 (2H, m), 2.58-2.64 (4H, m), 4.97 (2H, brs), 6.99 (1H, d, J=4.9 Hz), 7.19 (1H, t, J=4.4 Hz), 8.61 (1H, d, J=4.4 Hz).

(82e) (1S*,2R*)-2-(3-Aminopyridazin-4-yl)cyclohexanol

The reaction and aftertreatment were conducted in the same manner as in Example 72d by using the 2-(3-aminopyridazin-4-yl)cyclohex-2-en-1-one (40 mg, 0.20 mmol) prepared in Example 82d, sodium borohydride (20 mg, 0.59 mmol) and methanol (2.0 mL), to yield the title compound (39 mg, 99%) as a colorless oil.

$^1$H-NMR (400 MHz, CDCl$_3$) δ ppm: 1.23-1.95 (7H, m), 2.10-2.14 (1H, m), 2.52-2.57 (1H, m), 3.58-3.63 (1H, m), 5.43 (2H, brs), 7.07 (1H, d, J=4.9 Hz), 8.33 (1H, d, J=4.9 Hz).

(82f) 4-{[(1S,2R*)-2-(3-Aminopyridazin-4-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (90 mg, 0.20 mmol) prepared in Example 14b, the (1S*,2R*)-2-(3-aminopyridazin-4-yl)cyclohexanol (40 mg, 0.20 mmol) prepared in Example 82e, sodium hydride (63%; 10 mg, 0.31 mmol) and DMF (1.0 mL), to yield the title compound (45.6 mg, 36%) as a colorless amorphous solid.

$^1$H-NMR (500 MHz, CDCl$_3$) δ ppm: 1.39-1.59 (3H, m), 1.68-1.76 (1H, m), 1.91-1.98 (3H, m), 2.30-2.33 (1H, m), 2.91-2.97 (1H, m), 3.76 (3H, s), 3.76 (3H, s), 4.16-4.23 (1H, m), 5.03 (2H, brs), 5.18 (1H, d, J=17.1 Hz), 5.22 (1H, d, J=16.6 Hz), 6.38-6.43 (2H, m), 6.57 (1H, dd, J=6.4, 11.2

Hz), 7.10 (1H, d, J=4.9 Hz), 7.15-7.20 (2H, m), 7.71 (1H, dd, J=6.4, 10.3 Hz), 8.45 (1H, d, J=5.9 Hz), 8.59 (1H, d, J=4.9 Hz), 8.77 (1H, s).

(82g) 4-{[(1S*,2R*)-2-(3-Aminopyridazin-4-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2R*)-2-(3-aminopyridazin-4-yl)cyclohexyl]oxy}-N-(2,4-dimethoxybenzyl)-2,5-difluoro-N-(pyrimidin-4-yl)benzenesulfonamide (45 mg, 0.073 mmol) prepared in Example 82f, triethylsilane (0.06 mL), trifluoroacetic acid (0.08 mL) and dichloromethane (0.76 mL), to yield the title compound (25 mg, 74%) as a colorless solid.

$^1$H-NMR (500 MHz, CD$_3$OD) δ ppm: 1.48-1.60 (4H, m), 1.82-1.98 (3H, m), 2.29-2.31 (1H, m), 3.06-3.11 (1H, m), 4.66-4.71 (1H, m), 6.96 (1H, dd, J=1.0, 6.4 Hz), 7.10 (1H, dd, J=6.4, 11.2 Hz), 7.36 (1H, d, J=4.9 Hz), 7.65 (1H, dd, J=6.8, 10.3 Hz), 8.21 (1H, d, J=6.4 Hz), 8.28 (1H, d, J=4.9 Hz), 8.49 (1H, s).

MS (ESI) m/z: 463 [M+H]+.

Example 83

2,3-Difluoro-4-{[(1S*,2R*)-2-(1H-pyrazol-4-yl)cyclohexyl]oxy}-N-(pyrimidin-4-yl)benzenesulfonamide

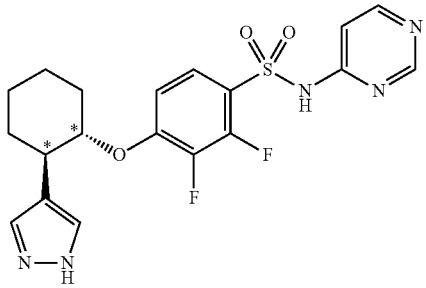

[Formula 101]

(83a) N-(2,4-Dimethoxybenzyl)-2,3-difluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (200 mg, 0.45 mmol) prepared in Example 30a, the (1S*,2R*)-2-[1-(tetrahydro-2H-pyran-2-yl)-1H-pyrazol-4-yl]cyclohexanol (110 mg, 0.45 mmol) prepared in Example 33b, sodium hydride (63%; 27 mg, 0.680 mmol) and DMF (5.0 mL), to yield the title compound (80 mg, 26%) as a colorless oil.

$^1$H-NMR (500 MHz, CDCl$_3$) δ ppm: 1.36-1.66 (8H, m), 1.81-2.24 (6H, m), 2.85-2.90 (1H, m), 3.62-3.67 (1H, m), 3.76 (3H, s), 3.79 (3H, s), 3.98-4.01 (1H, m), 4.06-4.11 (1H, m), 5.24 (2H, s), 5.24-5.28 (1H, m), 6.39-6.41 (1H, m), 6.60-6.64 (1H, m), 7.17-7.21 (2H, m), 7.43-7.46 (2H, m), 7.63 (1H, t, J=8.8 Hz), 8.44 (1H, d, J=6.4 Hz), 8.77 (1H, s).

(83b) 2,3-Difluoro-4-{[(1S*,2R*)-2-(1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-2,3-difluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide (70 mg, 0.10 mmol) prepared in Example 83a, triethylsilane (0.10 mL), trifluoroacetic acid (1.0 mL), dichloromethane (1.0 mL) and methanol (1.0 mL), to yield the title compound (15 mg, 33%) as a colorless solid.

$^1$H-NMR (500 MHz, DMSO-d$_6$) δ ppm: 1.33-1.79 (6H, m), 1.94-1.96 (1H, m), 2.11-2.13 (1H, m), 2.77-2.82 (1H, m), 4.42 (1H, dt, J=3.9, 10.3 Hz), 6.96 (1H, d, J=6.9 Hz), 7.10 (1H, t, J=8.3 Hz), 7.42 (2H, s), 7.56 (1H, t, J=8.8 Hz), 8.24 (1H, d, J=5.9 Hz), 8.55 (1H, s), 12.8 (1H, brs).

MS (ESI) m/z: 436 [M+H]+.

Example 84

4-{[(1S*,2R*)-5,5-Difluoro-2-(1-methyl-1H-pyrazol-5-yl)cyclohexyl]oxy}-2-fluoro-3-methyl-N-(pyrimidin-4-yl)benzenesulfonamide

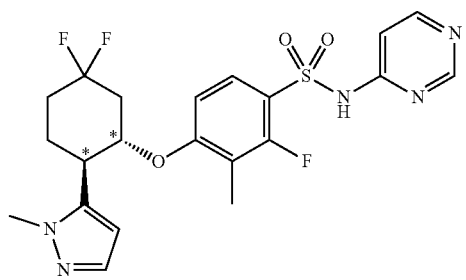

[Formula 102]

(84a) 4-{[(1S*,2R*)-5,5-Difluoro-2-(1-methyl-1H-pyrazol-5-yl)cyclohexyl]oxy}-N-(2,4-dimethoxybenzyl)-2-fluoro-3-methyl-N-(pyrimidin-4-yl)benzenesulfonamide The reaction and aftertreatment were conducted in the same manner as in Example 1a by using the N-(2,4-dimethoxybenzyl)-2,4-difluoro-3-methyl-N-(pyrimidin-4-yl)benzenesulfonamide (60 mg, 0.14 mmol) prepared in Example 65b, the (1S*,2R*)-5,5-difluoro-2-(1-methyl-1H-pyrazol-5-yl)cyclohexanol (30 mg, 0.14 mmol) prepared in Example 47b, sodium hydride (63%; 20 mg, 0.21 mmol) and DMF (5.0 mL), to yield the title compound (51 mg, 59%) as a colorless solid.

$^1$H-NMR (500 MHz, CDCl$_3$) δ ppm: 1.90-2.17 (4H, m), 1.90 (3H, s), 2.30-2.31 (1H, m), 2.73-2.80 (1H, m), 3.07-3.12 (1H, m), 3.77 (3H, s), 3.79 (3H, s), 3.88 (3H, s), 4.51 (1H, dt, J=4.4, 10.7 Hz), 5.26 (2H, s), 6.04 (1H, d, J=2.0 Hz), 6.39-6.42 (2H, m), 6.54 (1H, d, J=8.8 Hz), 7.20 (1H, d, J=7.8 Hz), 7.25 (1H, dd, J=1.5, 5.9 Hz), 7.38 (1H, d, J=2.0 Hz), 7.80 (1H, t, J=8.3 Hz), 8.42 (1H, d, J=5.9 Hz), 8.76 (1H, d, J=1.0 Hz).

(84b) 4-{[(1S*,2R*)-5,5-Difluoro-2-(1-methyl-1H-pyrazol-5-yl)cyclohexyl]oxy}-2-fluoro-3-methyl-N-(pyrimidin-4-yl)benzenesulfonamide The reaction and aftertreatment were conducted in the same manner as in Example 1b by using the 4-{[(1S*,2R*)-5,5-difluoro-2-(1-methyl-1H-pyrazol-5-yl)cyclohexyl]oxy}-N-(2,4-dimethoxybenzyl)-2-fluoro-3-methyl-N-(pyrimidin-4-yl)benzenesulfonamide (51 mg, 0.081 mmol) prepared in Example 84a, triethylsilane (0.10 mL), trifluoroacetic acid (0.5 mL) and dichloromethane (2.0 mL), to yield the title compound (31 mg, 79%) as a colorless solid.

$^1$H-NMR (500 MHz, CDCl$_3$) δ ppm: 1.90-2.12 (4H, m), 1.93 (3H, s), 2.31-2.35 (1H, m), 2.73-2.78 (1H, m), 3.07-3.12 (1H, m), 3.89 (3H, s), 4.50 (1H, dt, J=3.9, 10.7 Hz), 6.05 (1H, d, J=2.0 Hz), 6.55 (1H, d, J=8.8 Hz), 7.20 (1H, brs), 7.40 (1H, d, J=2.0 Hz), 7.76 (1H, t, J=8.8 Hz), 8.42 (1H, brs), 8.78 (1H, brs).

MS (ESI) m/z: 482 [M+H]+.

Example 85

4-{[(1S*,2R*)-2-(3-Amino-1H-pyrazol-4-yl)cyclopentyl]oxy}-2-fluoro-5-methyl-N-(pyrimidin-4-yl)benzenesulfonamide

[Formula 103]

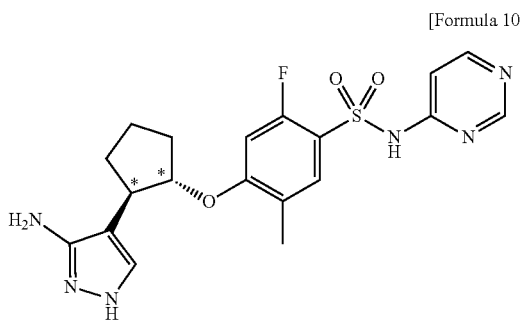

(85a) 4-(Cyclopent-1-en-1-yl)-3-nitro-1-(tetrahydro-2H-pyran-2-yl)-1H-pyrazole The reaction and aftertreatment were conducted in the same manner as in Example 33a by using 4-bromo-3-nitro-1-(tetrahydro-2H-pyran-2-yl)-1H-pyrazole (WO 2010/079443; 1.20 g, 4.35 mmol), 2-cyclopent-1-en-1-yl-4,4,5,5-tetramethyl-1,3,2-dioxaborolane (1.20 g, 6.18 mmol), [1,1'-bis(diphenylphosphino)ferrocene]dichloropalladium (II) (250 mg, 0.342 mmol), potassium carbonate (2.00 g, 14.5 mmol) and DMF (13 mL), to yield the title compound (1.02 g, 89%) as a yellow oil.

$^1$H-NMR (500 MHz, CDCl$_3$) δ ppm: 1.63-1.73 (3H, m), 1.96-2.05 (4H, m), 2.13-2.18 (1H, m), 2.51-2.55 (2H, m), 2.60-2.65 (2H, m), 3.69-3.74 (1H, m), 4.05-4.08 (1H, m), 5.41 (1H, dd, J=2.9, 8.8 Hz), 6.31-6.33 (1H, m), 7.60 (1H, s).

(85b) (1S*,2R*)-2-[3-Nitro-1-(tetrahydro-2H-pyran-2-yl)-1H-pyrazol-4-yl]cyclopentanol The reaction and aftertreatment were conducted in the same manner as in Example 33b by using the 4-(cyclopent-1-en-1-yl)-3-nitro-1-(tetrahydro-2H-pyran-2-yl)-1H-pyrazole (1.02 g, 3.87 mmol) prepared in Example 85a, a borane-THF complex (0.95 M solution in THF; 10 mL, 9.50 mmol), sodium perborate tetrahydrate (1.20 g, 7.80 mmol), THF (4.0 mL) and water (4.0 mL), to yield a mixture of the title compound and a by-product.

(85c) N-(2,4-dimethoxybenzyl)-2-fluoro-5-methyl-4-({(1S*,2R*)-2-[3-nitro-1-(tetrahydro-2H-pyran-2-yl)-1H-pyrazol-4-yl]cyclopentyl}oxy)-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (0.19 g, 0.43 mmol) prepared in Example 43a, the (1S*,2R*)-2-[3-nitro-1-(tetrahydro-2H-pyran-2-yl)-1H-pyrazol-4-yl]cyclopentanol (0.12 g, 0.43 mmol) prepared in Example 85b, sodium hydride (63%; 61 mg, 0.64 mmol) and DMF (8.0 mL), to yield the title compound (129 mg, 43%) as a colorless solid.

$^1$H-NMR (500 MHz, CDCl$_3$) δ ppm: 1.66-2.05 (10H, m), 2.16 (3H, s), 2.16-2.23 (1H, m), 2.34-2.35 (1H, m), 3.68-3.71 (1H, m), 3.76 (3H, s), 3.79 (3H, s), 3.85-3.86 (1H, m), 4.04-4.06 (1H, m), 4.66-4.67 (1H, m), 5.26 (2H, s), 5.38-5.40 (1H, m), 6.39-6.47 (3H, m), 7.20 (1H, d, J=7.8 Hz), 7.30 (1H, d, J=5.9 Hz), 7.55 (1H, s), 7.72 (1H, d, J=7.8 Hz), 8.43 (1H, d, J=5.9 Hz), 8.77 (1H, s).

(85d) 2-Fluoro-5-methyl-4-{(1S*,2R*)-2-(3-nitro-1H-pyrazol-4-yl)cyclopentyl]oxy}-N-(pyrimidin-4-yl)benzenesulfonamide The reaction and aftertreatment were conducted in the same manner as in Example 22c by using the N-(2,4-dimethoxybenzyl)-2-fluoro-5-methyl-4-({(1S*,2R*)-2-[3-nitro-1-(tetrahydro-2H-pyran-2-yl)-1H-pyrazol-4-yl]cyclopentyl}oxy)-N-(pyrimidin-4-yl)benzenesulfonamide (101 mg, 0.185 mmol) prepared in Example 85c, triethylsilane (0.10 mL), trifluoroacetic acid (0.5 mL), dichloromethane (2.0 mL) and methanol (1.0 mL), to yield the title compound (65 mg, 76%) as a colorless solid.

$^1$H-NMR (500 MHz, CD$_3$OD) δ ppm: 1.70-1.99 (4H, m), 2.18 (3H, s), 2.23-2.35 (3H, m), 3.83-3.86 (1H, m), 6.75 (18, d, J=12.2 Hz), 7.10 (1H, d, J=6.4 Hz), 7.76 (1H, d, J=8.3 Hz), 7.80 (1H, s), 8.35 (1H, d, J=6.4 Hz), 8.62 (1H, s).

(85e) 4-{[(1S*,2R*)-2-(3-Amino-1H-pyrazol-4-yl)cyclopentyl]oxy}-2-fluoro-5-methyl-N-(pyrimidin-4-yl)benzenesulfonamide The reaction and aftertreatment were conducted in the same manner as in Example 71c by using the 2-fluoro-5-methyl-4-{(1S*,2R*)-2-(3-nitro-1H-pyrazol-4-yl)cyclopentyl]oxy}-N-(pyrimidin-4-yl)benzenesulfonamide (65 mg, 0.141 mmol) prepared in Example 85d, an iron powder (78.5 mg, 1.41 mol), a saturated aqueous solution of ammonium chloride (1.0 mL) and ethanol (2.0 mL), to yield the title compound (30.6 mg, 50%) as a colorless solid.

$^1$H-NMR (500 MHz, CD$_3$OD) δ ppm: 1.44-1.88 (5H, m), 1.98 (3H, s), 2.20-2.22 (1H, m), 2.74-2.78 (1H, m), 4.38-4.42 (1H, m), 6.83 (1H, d, J=8.8 Hz), 7.06 (1H, d, J=7.3 Hz), 7.19 (1H, d, J=2.9 Hz), 7.75 (1H, t, J=8.8 Hz), 8.31 (1H, d, J=6.4 Hz), 8.56 (1H, s).

MS (ESI) m/z: 432 [M+H]+.

Example 86

5-Chloro-2-fluoro-4-{[(1S*,2R*)-2-(1-methyl-1H-pyrazol-5-yl)cyclohexyl]oxy}-N-(1,3,4-thiadiazol-2-yl)benzenesulfonamide

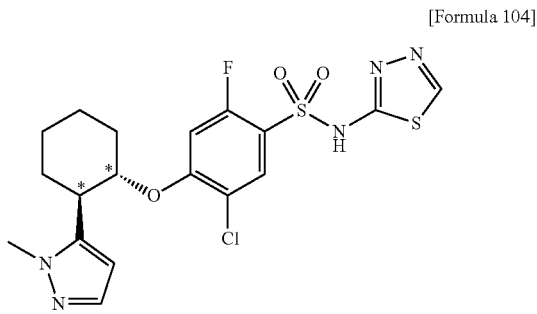 [SMILES: Cn1nccc1[C@H]1CCCC[C@@H]1Oc1cc(F)c(S(=O)(=O)Nc2nncs2)cc1Cl]

[Formula 104]

(86a) 5-Chloro-N-(2,4-dimethoxybenzyl)-2,4-difluoro-N-(1,3,4-thiadiazol-2-yl)benzenesulfonamide To a solution of N-(2,4-dimethoxybenzyl)-1,3,4-thiadiazol-2-amine (WO 2010/079443; 5.00 g, 19.9 mmol) in THF (60 mL), lithium bis(trimethylsilyl)amide (1.0 M solution in THF; 24.0 mL, 24.0 mmol) was added at −78° C. The reaction solution was stirred at room temperature for 10 minutes, and a solution of 5-chloro-2,4-difluorobenzenesulfonyl chloride (5.41 g, 21.9 mmol) in THF (15 mL) was then added thereto at −78° C. The reaction solution was stirred at room temperature for 2 hours, and water (100 mL) was then added to the reaction solution, followed by extraction with ethyl acetate (100 mL). The thus obtained organic layer was washed with saturated saline (100 mL) and dried over anhydrous sodium sulfate. After vacuum concentration, the residue was purified with silica gel chromatography (hexane/ethyl acetate=9:1) to yield the title compound (5.31 g, 58%) as a colorless solid.

$^1$H-NMR (500 MHz, CDCl$_3$) δ ppm: 3.70 (3H, s), 3.76 (3H, s), 5.33 (2H, s), 6.26 (1H, d, J=2.4 Hz), 6.35 (1H, dd, J=2.4, 8.3 Hz), 6.96 (1H, t, J=8.3 Hz), 7.25-7.26 (1H, m), 7.81 (1H, t, J=8.3 Hz), 8.84 (1H, s).

(86b) 5-Chloro-N-(2,4-dimethoxybenzyl)-2-fluoro-4-{[(1S*,2R*)-2-(1-methyl-1H-pyrazol-5-yl)cyclohexyl]oxy}-N-(1,3,4-thiadiazol-2-yl)benzenesulfonamide The reaction and aftertreatment were conducted in the same manner as in Example 1a by using the 5-chloro-N-(2,4-dimethoxybenzyl)-2,4-difluoro-N-(1,3,4-thiadiazol-2-yl)benzenesulfonamide (0.80 g, 1.73 mmol) prepared in Example 86a, the (1S*,2R*)-2-(1-methyl-1H-pyrazol-5-yl)cyclohexanol (0.311 g, 1.73 mmol) prepared in Example 4a, sodium hydride (63%; 0.078 g, 2.05 mmol) and DMF (6.0 mL), to yield the title compound (0.466 g, 43%) as a colorless solid.

$^1$H-NMR (400 MHz, CDCl$_3$) δ ppm: 1.40-1.67 (4H, m), 1.87-1.98 (2H, m), 2.05-2.08 (1H, m), 2.17-2.20 (1H, m), 3.02-3.07 (1H, m), 3.67 (3H, s), 3.73 (3H, s), 3.93 (3H, s), 4.10-4.15 (1H, m), 5.25 (1H, d, J=15.1 Hz), 5.31 (1H, d, J=15.1 Hz), 6.04 (1H, d, J=2.0 Hz), 6.24 (1H, d, J=2.4 Hz), 6.33 (1H, dd, J=2.4, 5.9 Hz), 6.41 (1H, d, J=11.7 Hz), 7.23 (1H, d, J=8.8 Hz), 7.36 (1H, d, J=2.0 Hz), 7.68 (1H, d, J=7.3 Hz), 8.79 (1H, s).

(86c) 5-Chloro-2-fluoro-4-{[(1S*,2R*)-2-(1-methyl-1H-pyrazol-5-yl)cyclohexyl]oxy}-N-(1,3,4-thiadiazol-2-yl)benzenesulfonamide The reaction and aftertreatment were conducted in the same manner as in Example 1b by using the 5-chloro-N-(2,4-dimethoxybenzyl)-2-fluoro-4-{[(1S*,2R*)-2-(1-methyl-1H-pyrazol-5-yl)cyclohexyl]oxy}-N-(1,3,4-thiadiazol-2-yl)benzenesulfonamide (0.466 g, 0.749 mmol) prepared in Example 86b, triethylsilane (0.50 mL), trifluoroacetic acid (5.0 mL) and dichloromethane (5.0 mL), to yield the title compound (0.191 g, 54%) as a colorless solid.

$^1$H-NMR (400 MHz, CD$_3$OD) δ ppm: 1.43-1.64 (3H, m), 1.68-1.76 (1H, m), 1.82-1.85 (1H, m), 1.90-1.92 (1H, m), 1.99-2.02 (1H, m), 2.22-2.24 (1H, m), 3.11-3.16 (1H, m), 3.88 (3H, s), 4.49 (1H, dt, J=3.9, 10.3 Hz), 6.16 (1H, d, J=2.0 Hz), 6.95 (1H, d, J=11.7 Hz), 7.28 (1H, d, J=2.0 Hz), 7.75 (1H, d, J=7.3 Hz), 8.54 (1H, s).

MS (ESI) m/z: 472 [M+H]+.

Example 87

5-Chloro-2-fluoro-4-{[(1S*,2R*)-2-(1-methyl-1H-pyrazol-5-yl)cyclopentyl]oxy}-N-(1,3,4-thiadiazol-2-yl)benzenesulfonamide

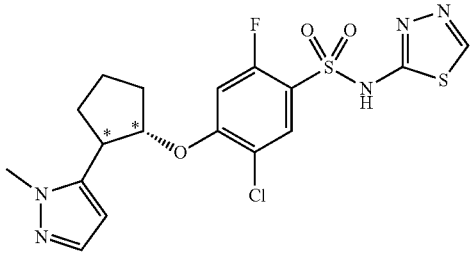

[Formula 105]

(87a) 5-Chloro-N-(2,4-dimethoxybenzyl)-2-fluoro-4-{[(1S*,2R*)-2-(1-methyl-1H-pyrazol-5-yl)cyclopentyl]oxy}-N-(1,3,4-thiadiazol-2-yl)benzenesulfonamide The reaction and aftertreatment were conducted in the same manner as in Example 1a by using the 5-chloro-N-(2,4-dimethoxybenzyl)-2,4-difluoro-N-(1,3,4-thiadiazol-2-yl)benzenesulfonamide (0.870 g, 1.88 mmol) prepared in Example 86a, the (1S*,2R*)-2-(1-methyl-1H-pyrazol-5-yl)cyclopentanol (0.313 mg, 1.88 mmol) prepared in Example 8a, sodium hydride (63%; 0.085 g, 2.23 mmol) and DMF (8.0 mL), to yield the title compound (0.377 g, 33%) as a colorless solid.

$^1$H-NMR (400 MHz, CDCl$_3$) δ ppm: 1.80-1.98 (4H, m), 2.17-2.34 (2H, m), 3.51 (1H, dt, J=4.9, 8.3 Hz), 3.72 (3H, s), 3.72 (3H, s), 3.89 (3H, s), 4.59-4.62 (1H, m), 5.30 (2H, s), 6.06 (1H, d, J=2.0 Hz), 6.27 (1H, d, J=2.4 Hz), 6.34 (1H, dd, J=2.4, 8.8 Hz), 6.47 (1H, d, J=11.7 Hz), 7.25 (1H, d, J=8.3 Hz), 7.41 (1H, d, J=2.0 Hz), 7.78 (1H, d, J=6.8 Hz), 8.80 (1H, s).

(87b) 5-Chloro-2-fluoro-4-{[(1S*,2R*)-2-(1-methyl-1H-pyrazol-5-yl)cyclopentyl]oxy}-N-(1,3,4-thiadiazol-2-yl)benzenesulfonamide The reaction and aftertreatment were conducted in the same manner as in Example 1b by using the 5-chloro-N-(2,4-dimethoxybenzyl)-2-fluoro-4-{[(1S*,2R*)-2-(1-methyl-1H-pyrazol-5-yl)cyclopentyl]oxy}-N-(1,3,4-thiadiazol-2-yl)benzenesulfonamide (0.377 g, 0.620 mmol) prepared in Example 87a, triethylsilane (0.50 mL), trifluoroacetic acid (5.0 mL) and dichloromethane (5.0 mL), to yield the title compound (0.212 g, 75%) as a colorless solid.

$^1$H-NMR (400 MHz, CD$_3$OD) δ ppm: 1.79-1.98 (4H, m), 2.29-2.36 (2H, m), 3.54 (1H, dt, J=5.9, 7.8 Hz), 3.84 (3H, s), 4.85-4.90 (1H, m), 6.21 (1H, d, J=2.0 Hz), 6.94 (1H, d, J=11.7 Hz), 7.37 (1H, d, J=2.0 Hz), 7.85 (1H, d, J=7.3 Hz), 8.55 (1H, s).

MS (ESI) m/z: 458 [M+H]+.

Example 88

4-{[(1S*,2R*)-4,4-Difluoro-2-(1-methyl-1H-pyrazol-5-yl)cyclohexyl]oxy}-2,5-difluoro-N-(pyrimidin-4-yl)benzenesulfonamide

[Formula 106]

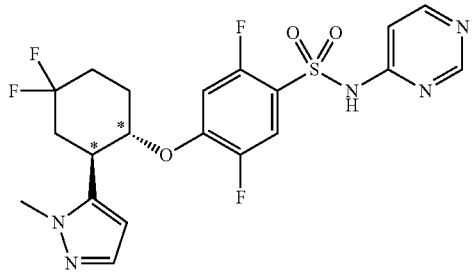

(88a) [(4,4-Difluorocyclohex-1-en-1-yl)oxy](trimethyl)silane

To a solution of N,N-diisopropylamine (3.30 g, 32.6 mmol) in THF (50 mL), n-butyl lithium (1.65 M solution in hexane (18.0 mL, 29.7 mmol) was added dropwise with cooling on ice. The reaction solution was stirred at 0° C. for 30 minutes. Then, 4,4-difluorocyclohexanone (3.60 g, 26.8 mmol) was added thereto at −78° C., and the reaction solution was stirred at −78° C. for 1 hour. To the reaction solution, chlorotrimethylsilane (4.4 mL, 34.8 mmol) and triethylamine (8.0 mL, 57.4 mmol) were added, and the mixture was stirred at −78° C. for 2 hours. To the reaction solution, a saturated aqueous solution of sodium hydrogencarbonate (20 mL) was added, followed by extraction with ethyl acetate (20 mL). The thus obtained organic layer was dried over anhydrous sodium sulfate. After vacuum concentration, the residue was purified with silica gel chromatography (hexane/ethyl acetate=98:2) to yield the title compound (2.10 g, 56%) as a colorless oil.

$^1$H-NMR (500 MHz, CDCl$_3$) δ ppm: 0.20 (9H, s), 2.04-2.12 (2H, m), 2.25-2.28 (2H, m), 2.50-2.56 (2H, m), 4.68-4.71 (1H, m).

(88b) 4,4-Difluorocyclohex-2-en-1-one

To a solution of the [(4,4-difluorocyclohex-1-en-1-yl)oxy](trimethyl)silane (3.1 g, 15.0 mmol) prepared in Example 88a in acetonitrile (25 mL), palladium acetate (4.0 g, 17.8 mmol) was added, and the mixture was stirred at room temperature for 45 minutes. The reaction solution was filtered, the filtrate was vacuum concentrated, and the residue was purified with silica gel chromatography (hexane/ethyl acetate=9:1) to yield the title compound (1.0 g, 50%) as a yellow oil.

$^1$H-NMR (400 MHz, CDCl$_3$) δ ppm: 2.47-2.56 (2H, m), 2.68 (2H, t, J=6.7 Hz), 6.19 (1H, d, $^1$H-NMR (400 MHz, CDCl$_3$) δ ppm: 2.47-2.56 (2H, m), 2.68 (2H, t, J=6.7 Hz), 6.19 (1H, d, J=10.6 Hz), 6.76-6.82 (1H, m).

(88c) 4,4-Difluoro-2-iodocyclohex-2-en-1-one

To a solution of the 4,4-difluorocyclohex-2-en-1-one (1.0 g, 7.57 mmol) prepared in Example 88b in a THF-water mixed solvent (1:1; 20 mL), potassium carbonate (1.30 g, 9.41 mmol), iodine (2.9 g, 11.4 mmol) and DMAP (0.56 g, 4.58 mmol) were added, and the reaction solution was stirred at room temperature for 30 minutes. The reaction solution was subjected to extraction with ethyl acetate (20 mL). The thus obtained organic layer was washed with an aqueous sodium thiosulfate solution (20 mL) and dried over anhydrous sodium sulfate. After vacuum concentration, the residue was purified with silica gel chromatography (hexane/ethyl acetate=9:1) to yield the title compound (1.46 g, 75%) as a light brown oil.

$^1$H-NMR (500 MHz, CDCl$_3$) δ ppm: 2.51-2.59 (2H, m), 2.87 (2H, t, J=6.8 Hz), 7.56-7.58 (1H, m).

(88d) 8,8-Difluoro-6-iodo-1,4-dioxaspiro[4.5]dec-6-ene

The reaction and aftertreatment were conducted in the same manner as in Example 67a by using the 4,4-difluoro-2-iodocyclohex-2-en-1-one (1.46 g, 5.66 mmol) prepared in Example 88c, ethylene glycol (750 mg, 12.1 mmol), p-toluenesulfonic acid hydrate (60 mg, 0.31 mmol) and benzene (30 mL), to yield a mixture of the title compound and a by-product.

(88e) 5-(8,8-Difluoro-1,4-dioxaspiro[4.5]dec-6-en-6-yl)-1-methyl-1H-pyrazole The reaction and aftertreatment were conducted in the same manner as in Example 39a by using the 8,8-difluoro-6-iodo-1,4-dioxaspiro[4.5]dec-6-ene (1.34 g, 4.44 mmol) prepared in Example 88d, 1-methyl-5-(4,4,5,5-tetramethyl-1,3,2-dioxaboran-2-yl)-1H-pyrazole (1.40 g, 6.73 mmol), tetrakis(triphenylphosphine)palladium (0) (250 mg, 0.216 mmol), cesium carbonate (3.40 g, 10.4 mmol), dioxane (10 mL) and water (5.0 mL), to yield a mixture of the title compound and a by-product.

(88f) 4,4-Difluoro-2-(1-methyl-1H-pyrazol-5-yl)cyclohex-2-en-1-one

The reaction and aftertreatment were conducted in the same manner as in Example 67c by using the 5-(8,8-difluoro-1,4-dioxaspiro[4.5]dec-6-en-6-yl)-1-methyl-1H- pyrazole (758 mg, 2.96 mmol) prepared in Example 88e, 5 M hydrochloric acid (10 mL) and THF (10 mL), to yield the title compound (170 mg, 14%, 3 steps) as a colorless oil.

$^1$H-NMR (500 MHz, CDCl$_3$) δ ppm: 2.59-2.57 (2H, m), 2.85 (2H, t, J=6.8 Hz), 3.74 (3H, s), 6.29 (1H, d, J=2.0 Hz), 6.84 (1H, t, J=5.9 Hz), 7.48 (1H, d, J=2.0 Hz).

(88g) (1S*,2R*)-4,4-Difluoro-2-(1-methyl-1H-pyrazol-5-yl)cyclohexanol

The reaction and aftertreatment were conducted in the same manner as in Example 67d by using the 4,4-difluoro-2-(1-methyl-1H-pyrazol-5-yl)cyclohex-2-en-1-one (170 mg, 0.80 mmol) prepared in Example 88f, sodium borohydride (60 mg, 1.59 mmol), methanol (3.0 mL), palladium hydroxide carbon (10%; 150 mg) and ethanol (4.0 mL), to yield the title compound (50 mg, 29%) as a colorless solid.

$^1$H-NMR (500 MHz, CDCl$_3$) δ ppm: 1.80-2.00 (3H, m), 2.10-2.13 (1H, m), 2.24-2.31 (2H, m), 2.98-3.03 (1H, m), 3.73 (1H, dt, J=4.4, 10.3 Hz), 3.86 (3H, s), 6.08 (1H, d, J=2.0 Hz), 7.41 (1H, d, J=2.0 Hz).

(88h) 4-{[(1S*,2R*)-4,4-Difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (110 mg, 0.250 mmol) prepared in Example 14b, the (1S*,2R*)-4,4-difluoro-2-(1-methyl-1H-pyrazol-5-yl) cyclohexanol (50 mg, 0.231 mmol) prepared in Example 88 g, sodium hydride (63%; 20 mg, 0.525 mmol) and DMF (2.0 mL), to yield the title compound in a crude form as a colorless solid.

(88i) 4-{[(1S*,2R*)-4,4-Difluoro-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the crude 4-{[(1S*,2R*)-4,4-difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (150 mg, 0.236 mmol) prepared in Example 88h, triethylsilane (0.20 mL), trifluoroacetic acid (2.0 mL) and dichloromethane (2.0 mL), to yield the title compound (98 mg, 80%, 2 steps) as a colorless solid.

$^1$H-NMR (500 MHz, CD$_3$OD) δ ppm: 1.83-1.90 (1H, m), 2.19-2.38 (5H, m), 3.43-3.48 (1H, m), 3.88 (3H, s), 4.62 (1H, dt, J=3.9, 6.4 Hz), 6.22 (1H, d, J=2.0 Hz), 6.97-7.01 (2H, m), 7.27 (1H, d, J=2.0 Hz), 7.69 (1H, dd, J=6.8, 10.7 Hz), 8.25 (1H, d, J=6.4 Hz), 8.54 (1H, s).

MS (ESI) m/z: 486 [M+H]+.

Example 89

4-{[(1S*,2R*)-2-(3-Amino-1H-pyrazol-4-yl)cyclohexyl]oxy}-3-ethyl-N-(pyrimidin-4-yl)benzenesulfonamide

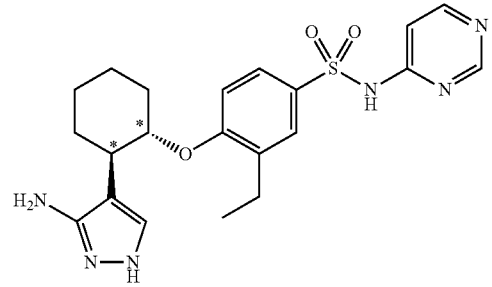

[Formula 107]

(89a) 3-Ethyl-4-fluorobenzenesulfonyl chloride

The reaction and aftertreatment were conducted in the same manner as in Example 65a by using 1-ethyl-2-fluorobenzene (2.30 g, 19.0 mmol) and chlorosulfuric acid (4.9 mL, 74.0 mmol), to yield the title compound in a crude form.

(89b) N-(2,4-dimethoxybenzyl)-3-ethyl-4-fluoro-N-(pyrimidin-4-yl)benzenesulfonamide The reaction and aftertreatment were conducted in the same manner as in Example 14b by using the N-(2,4-dimethoxybenzyl)pyrimidin-4-amine (0.80 g, 3.30 mmol) prepared in Example 14a, the crude 3-ethyl-4-fluorobenzenesulfonyl chloride (1.50 g, 6.50 mmol) prepared in Example 89a, 1,4-diazabicyclo[2.2.2]octane (0.73 g, 6.50 mmol) and THF (20 mL), to yield the title compound (1.35 g, 96%) as a colorless oil.

(89c) N-(2,4-dimethoxybenzyl)-3-ethyl-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide The reaction and aftertreatment were conducted in the same manner as in Example 1a by using the N-(2,4-dimethoxybenzyl)-3-ethyl-4-fluoro-N-(pyrimidin-4-yl)benzenesulfonamide (1.50 g, 3.50 mmol) prepared in Example 89b, the (1S*,2R*)-2-[3-nitro-1-(tetrahydro-2H-pyran-2-yl)-1H-pyrazol-4-yl]cyclohexanol (1.00 g, 3.50 mmol) prepared in Example 34b, sodium hydride (63%; 0.50 g, 5.20 mmol) and DMF (30 mL), to yield the title compound (1.45 g, 59%) in the form of a diastereomeric mixture as a pale yellow solid.

(89d) 3-Ethyl-4-{(1S*,2R*)-2-(3-nitro-1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-3-ethyl-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide (70 mg, 0.0990 mmol) prepared in Example 89c, triethylsilane (0.10 mL), trifluoroacetic acid (0.5 mL), dichloromethane (2.0 mL) and methanol (1.0 mL), to yield the title compound (47 mg, 99%) as a white solid.

$^1$H-NMR (500 MHz, CD$_3$OD) δ ppm: 0.92 (3H, t, J=7.3 Hz), 1.43-1.67 (4H, m), 1.81-1.91 (2H, m), 2.05-2.09 (1H, m), 2.27-2.30 (1H, m), 2.39 (2H, q, J=7.3 Hz), 3.58-3.63 (1H, m), 4.53-4.58 (1H, m), 7.03 (1H, d, J=8.8 Hz), 7.19 (1H, d, J=6.4 Hz), 7.68-7.69 (2H, m), 7.78 (1H, dd, J=2.9, 8.8 Hz), 8.42 (1H, d, J=6.4 Hz), 8.74 (1H, s).

(89e) 4-{[(1S*,2R*)-2-(3-Amino-1H-pyrazol-4-yl)cyclohexyl]oxy}-3-ethyl-N-(pyrimidin-4-yl)benzenesulfonamide The reaction and aftertreatment were conducted in the same manner as in Example 71c by using the 3-ethyl-4-{(1S*,2R*)-2-(3-nitro-1H-pyrazol-4-yl)cyclohexyl]oxy}-N-(pyrimidin-4-yl)benzenesulfonamide (67 mg, 0.142 mmol) prepared in Example 89d, an iron powder (79 mg, 1.42 mol), a saturated aqueous solution of ammonium chloride (1.0 mL) and ethanol (2.0 mL), to yield the title compound (9.1 mg, 15%) as a colorless solid.

$^1$H-NMR (500 MHz, CD$_3$OD) δ ppm: 1.03 (3H, t, J=7.8 Hz), 1.41-1.63 (4H, m), 1.77-1.86 (2H, m), 1.99-2.01 (1H, m), 2.20-2.23 (1H, m), 2.52-2.56 (2H, m), 2.74-2.77 (1H, m), 4.37-4.41 (1H, m), 6.98 (1H, dd, J=2.4, 8.3 Hz), 7.07-7.09 (1H, m), 7.16 (1H, d, J=2.4 Hz), 7.69 (1H, s), 7.73-7.75 (1H, m), 8.32 (1H, dd, J=2.9, 6.4 Hz), 8.60 (1H, s).

MS (ESI) m/z: 443 [M+H]+.

Example 90

4-{[(1S*,2R*)-5,5-Difluoro-2-(1-methyl-1H-pyrazol-5-yl)cyclohexyl]oxy}-2-fluoro-5-methyl-N-(pyrimidin-4-yl)benzenesulfonamide

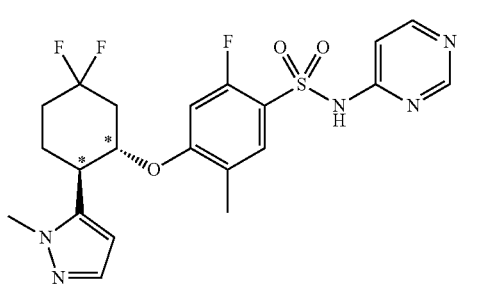

[Formula 108]

(90a) 4-{[(1S*,2R*)-5,5-Difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (180 mg, 0.413 mmol) prepared in Example 43a, the (1S*,2R*)-5,5-difluoro-2-(1-methyl-1H-pyrazol-5-yl)cyclohexanol (89 mg, 0.413 mmol) prepared in Example 47b, sodium hydride (63%; 60 mg, 0.620 mmol) and DMF (5.0 mL), to yield the title compound (172 mg, 66%) as a colorless solid.

$^1$H-NMR (500 MHz, CDCl$_3$) δ ppm: 1.89-2.30 (5H, m), 2.05 (3H, s), 2.67-2.74 (1H, m), 3.07-3.12 (1H, m), 3.76 (3H, s), 3.78 (3H, s), 3.89 (3H, s), 4.36 (1H, dt, J=4.9, 10.7 Hz), 5.23 (2H, s), 6.04 (1H, d, J=2.0 Hz), 6.35-6.41 (3H, m), 7.19 (1H, d, J=8.3 Hz), 7.25 (1H, dd, J=1.0, 6.8 Hz), 7.38 (1H, d, J=1.0 Hz), 7.70 (1H, d, J=7.8 Hz), 8.43 (1H, d, J=5.9 Hz), 8.77 (1H, s).

(90b) 4-{[(1S*,2R*)-5,5-Difluoro-2-(1-methyl-1H-pyrazol-5-yl)cyclohexyl]oxy}-2-fluoro-5-methyl-N-(pyrimidin-4-yl)benzenesulfonamide The reaction and aftertreatment were conducted in the same manner as in Example 1b by using the 4-{[(1S*,2R*)-5,5-difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide (172 mg, 0.272 mmol) prepared in Example 90a, triethylsilane (0.10 mL), trifluoroacetic acid (0.5 mL) and dichloromethane (3.0 mL), to yield the title compound (131 mg, 99%) as a colorless solid.

$^1$H-NMR (500 MHz, CDCl$_3$) δ ppm: 1.91-2.33 (5H, m), 2.05 (3H, s), 2.70-2.74 (1H, m), 3.07-3.12 (1H, m), 3.88 (3H, s), 4.38 (1H, dt, J=4.4, 10.7 Hz), 6.05 (1H, d, J=2.0 Hz), 6.42 (1H, d, J=11.7 Hz), 6.15 (1H, d, J=5.9 Hz), 7.36 (1H, s), 7.71 (1H, d, J=8.3 Hz), 8.36 (1H, d, J=6.4 Hz), 8.70 (1H, s).

MS (ESI) m/z: 482 [M+H]+.

Example 91

4-{[(1S*,2R*)-2-(3-Amino-1H-pyrazol-4-yl)cyclohexyl]oxy}-3-chloro-2-fluoro-N-(pyrimidin-4-yl)benzenesulfonamide

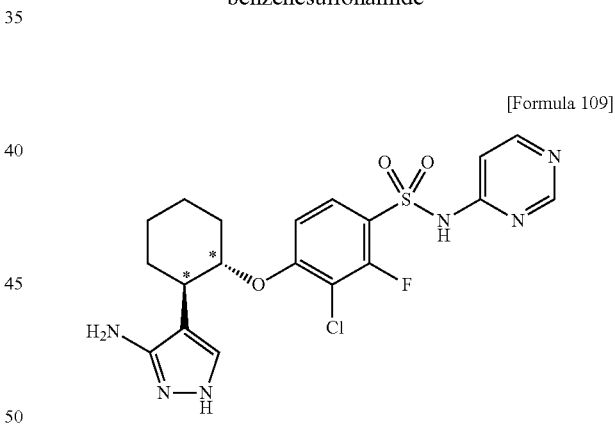

[Formula 109]

(91a) 3-Chloro-N-(2,4-dimethoxybenzyl)-2-fluoro-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide The reaction and aftertreatment were conducted in the same manner as in Example 1a by using the 3-chloro-N-(2,4-dimethoxybenzyl)-2,4-difluoro-N-(pyrimidin-4-yl)benzenesulfonamide (239 mg, 0.525 mmol) prepared in Example 79a, the (1S*,2R*)-2-[3-nitro-1-(tetrahydro-2H-pyran-2-yl)-1H-pyrazol-4-yl]cyclohexanol (155 mg, 0.525 mmol) prepared in Example 34b, sodium hydride (63%; 60.5 mg, 0.630 mmol) and DMF (6.0 mL), to yield the title compound (249 mg, 65%) in the form of a diastereomeric mixture as a colorless amorphous solid.

(91b) 3-Chloro-2-fluoro-4-{(1S*,2R*)-2-(3-nitro-1H-pyrazol-4-yl)cyclohexyl]oxy}-N-(pyrimidin-4-yl)benzenesulfonamide The reaction and aftertreatment were conducted in the same manner as in Example 22c by using the 3-chloro-N-(2,4-dimethoxybenzyl)-2-fluoro-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide (198 mg, 0.341 mmol) prepared in Example 91a, triethylsilane (0.10 mL), trifluoroacetic acid (0.5 mL), dichloromethane (2.0 mL) and methanol (1.0 mL), to yield the title compound (16 mg, 9.4%) as a pale yellow solid.
$^1$H-NMR (500 MHz, CDCl$_3$) δ ppm: 1.46-1.63 (4H, m), 1.79-2.09 (3H, m), 2.31-2.35 (1H, m), 3.72-3.76 (1H, m), 4.23-4.30 (1H, m), 6.69 (1H, d, J=8.8 Hz), 7.48-7.52 (1H, m), 7.73-7.76 (2H, m), 8.43 (1H, d, J=6.9 Hz), 8.92 (1H, s).

(91c) 4-{[(1S*,2R*)-2-(3-Amino-1H-pyrazol-4-yl)cyclohexyl]oxy}-3-chloro-2-fluoro-N-(pyrimidin-4-yl)benzenesulfonamide The reaction and aftertreatment were conducted in the same manner as in Example 71c by using the 3-chloro-2-fluoro-4-{(1S*,2R*)-2-(3-nitro-1H-pyrazol-4-yl)cyclohexyl]oxy}-N-(pyrimidin-4-yl)benzenesulfonamide (16 mg, 0.0322 mmol) prepared in Example 91b, an iron powder (18.0 mg, 0.322 mol), a saturated aqueous solution of ammonium chloride (1.0 mL) and ethanol (2.0 mL), to yield the title compound (9.7 mg, 65%) as a colorless solid.
$^1$H-NMR (500 MHz, CD$_3$OD) δ ppm: 1.42-1.56 (3H, m), 1.68-1.89 (3H, m), 1.98-2.01 (1H, m), 2.15-2.20 (1H, m), 2.75-2.79 (1H, m), 4.44-4.49 (1H, m), 6.97-6.99 (2H, m), 7.30 (1H, brs), 7.82 (1H, t, J=8.3 Hz), 8.23 (1H, brs), 8.52 (1H, brs).
MS (ESI) m/z: 467 [M+H]+.

Example 92

2,5-Difluoro-4-{[(1S*,2R*)-2-(1-methyl-1H-1,2,3-triazol-5-yl)cyclohexyl]oxy}-N-(pyrimidin-4-yl)benzenesulfonamide

[Formula 110]

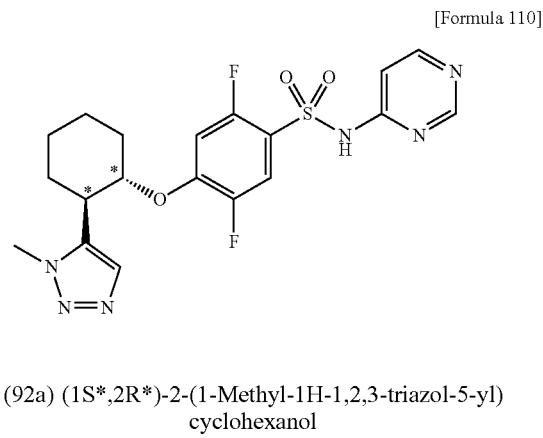

(92a) (1S*,2R*)-2-(1-Methyl-1H-1,2,3-triazol-5-yl)cyclohexanol

The reaction and aftertreatment were conducted in the same manner as in Example 8a by using 1-methyl-1H-1,2,3-triazole (2.00 g, 24.1 mmol), n-butyl lithium (2.69 M solution in hexane; 9.0 mL, 24.2 mmol), cyclohexene oxide (2.40 g, 24.5 mmol) and THF (70 mL), to yield the title compound (197 mg, 4.5%) as a colorless oil.
$^1$H-NMR (500 MHz, CDCl$_3$) δ ppm: 1.25-1.53 (4H, m), 1.78-1.89 (3H, m), 2.11-2.12 (1H, m), 2.55-2.60 (1H, m), 3.55-3.60 (2H, m), 4.01 (3H, s), 7.29 (1H, s).

(92b) N-(2,4-Dimethoxybenzyl)-2,5-difluoro-4-{[(1S*,2R*)-2-(1-methyl-1H-1,2,3-triazol-5-yl)cyclohexyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (240 mg, 0.546 mmol) prepared in Example 14b, the (1S*,2R*)-2-(1-methyl-1H-1,2,3-triazol-5-yl)cyclohexanol (100 mg, 0.552 mmol) prepared in Example 92a, sodium hydride (63%; 50 mg, 1.31 mmol) and DMF (3.0 mL), to yield the title compound (270 mg, 82%) as a colorless oil.
$^1$H-NMR (500 MHz, CDCl$_3$) δ ppm: 1.41-1.54 (3H, m), 1.69-1.77 (1H, m), 1.91-1.99 (2H, m), 2.09-2.12 (1H, m), 2.28-2.30 (1H, m), 3.01-3.06 (1H, m), 3.77 (3H, s), 3.78 (3H, s), 4.06-4.12 (1H, m), 4.12 (3H, s), 5.18 (1H, d, J=17.1 Hz), 5.24 (1H, d, J=17.1 Hz), 6.39-6.41 (2H, m), 6.50 (1H, dd, J=6.4, 10.7 Hz), 7.16 (1H, dd, J=1.5, 5.9 Hz), 7.18 (1H, d, J=8.8 Hz), 7.50 (1H, s), 7.71 (1H, dd, J=6.8, 10.3 Hz), 8.46 (1H, d, J=5.9 Hz), 8.79 (1H, s).

(92c) 2,5-Difluoro-4-{[(1S*,2R*)-2-(1-methyl-1H-1,2,3-triazol-5-yl)cyclohexyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*)-2-(1-methyl-1H-1,2,3-triazol-5-yl)cyclohexyl]oxy}-N-(pyrimidin-4-yl)benzenesulfonamide (270 mg, 0.450 mmol) prepared in Example 92b, triethylsilane (0.30 mL), trifluoroacetic acid (3.0 mL) and dichloromethane (3.0 mL), to yield the title compound (168 mg, 83%) as a colorless solid.
$^1$H-NMR (500 MHz, CD$_3$OD) δ ppm: 1.46-1.64 (3H, m), 1.73-1.92 (3H, m), 2.02-2.05 (1H, m), 2.26-2.28 (1H, m), 3.16-3.21 (1H, m), 4.09 (3H, s), 4.44 (1H, dt, J=3.9, 10.3 Hz), 6.98-7.02 (2H, m), 7.57 (1H, s), 7.68 (1H, dd, J=6.4, 10.3 Hz), 8.25 (1H, d, J=6.4 Hz), 8.53 (1H, s).
MS (ESI) m/z: 451 [M+H]+.

Example 93

4-{[(1S*,2R*)-4,4-Dimethyl-2-(1-methyl-1H-pyrazol-5-yl)cyclopentyl]oxy}-2,5-difluoro-N-(pyrimidin-4-yl)benzenesulfonamide

[Formula 111]

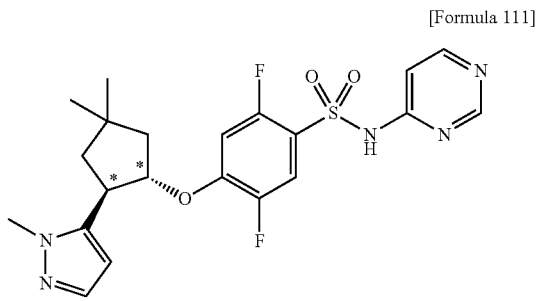 [SMILES: Cn1nccc1[C@H]1CC(C)(C)C[C@@H]1Oc1cc(F)c(S(=O)(=O)Nc2ccncn2)cc1F]

(93a) 6-Iodo-8,8-dimethyl-1,4-dioxaspiro[4.4]non-6-ene

The reaction and aftertreatment were conducted in the same manner as in Example 67a by using 2-iodo-4,4-dimethylcyclopent-2-en-1-one (U.S. Pat. No. 6,222,048; 3.77 g, 16.0 mmol), ethylene glycol (2.0 mL, 32.2 mmol), p-toluenesulfonic acid hydrate (100 mg, 0.526 mmol) and benzene (60 mL), to yield the title compound (3.30 g, 74%) as a colorless oil.

$^1$H-NMR (500 MHz, CDCl$_3$) δ ppm: 1.13 (6H, s), 1.95 (2H, s), 3.95-3.98 (2H, m), 4.18-4.20 (2H, m), 6.23 (1H, s).

(93b) 5-(8,8-Dimethyl-1,4-dioxaspiro[4.4]non-6-en-6-yl)-1-methyl-1H-pyrazole The reaction and aftertreatment were conducted in the same manner as in Example 39a by using the 6-iodo-8,8-dimethyl-1,4-dioxaspiro[4.4]non-6-ene (1.30 g, 4.64 mmol) prepared in Example 93a, 1-methyl-5-(4,4,5,5-tetramethyl-1,3,2-dioxaboran-2-yl)-1H-pyrazole (1.30 g, 6.25 mmol), [1,1'-bis(diphenylphosphino)ferrocene]dichloropalladium (II) (200 mg, 0.245 mmol), cesium carbonate (3.30 g, 10.1 mmol), dioxane (10 mL) and water (5.0 mL), to yield the title compound (1.07 g, 98%) as an orange oil.

$^1$H-NMR (500 MHz, CDCl$_3$) δ ppm: 1.23 (6H, s), 2.03 (2H, s), 3.77-3.79 (2H, m), 3.85-3.90 (2H, m), 3.86 (3H, s), 5.95 (1H, s), 6.27 (1H, d, J=2.0 Hz), 7.43 (1H, d, J=2.0 Hz).

(93c) 4,4-Dimethyl-2-(1-methyl-1H-pyrazol-5-yl)cyclopent-2-en-1-one

The reaction and aftertreatment were conducted in the same manner as in Example 67c by using the 5-(8,8-dimethyl-1,4-dioxaspiro[4.4]non-6-en-6-yl)-1-methyl-1H-pyrazole (1.07 g, 4.56 mmol) prepared in Example 93b, 2 M hydrochloric acid (5.0 mL) and THF (5.0 mL), to yield the title compound (780 mg, 90%) as a light brown solid.

$^1$H-NMR (500 MHz, CDCl$_3$) δ ppm: 1.33 (6H, s), 2.46 (2H, s), 3.90 (3H, s), 6.55 (1H, d, J=2.0 Hz), 7.47 (1H, d, J=2.0 Hz), 7.50 (1H, s).

(93d) 4,4-Dimethyl-2-(1-methyl-1H-pyrazol-5-yl)cyclopentanone

A solution of the 4,4-dimethyl-2-(1-methyl-1H-pyrazol-5-yl)cyclopent-2-en-1-one (780 mg, 4.10 mmol) prepared in Example 93c and palladium carbon (5%; 700 mg) in ethanol (8.0 mL) was stirred for 6 hours under a hydrogen atmosphere. The reaction solution was filtered through celite to yield the title compound (750 mg, 95%) in a crude form as a yellow oil.

$^1$H-NMR (500 MHz, CDCl$_3$) δ ppm: 1.19 (3H, s), 1.28 (3H, s), 2.02 (1H, t, J=12.2 Hz), 2.20-2.32 (3H, m), 3.68 (1H, dd, J=9.3, 12.2 Hz), 6.01 (1H, d, J=2.0 Hz), 7.40 (1H, d, J=2.0 Hz).

(93e) (1S*,2R*)-4,4-Dimethyl-2-(1-methyl-1H-pyrazol-5-yl)cyclopentanol

To a solution of the 4,4-dimethyl-2-(1-methyl-1H-pyrazol-5-yl)cyclopentanone (750 mg, 3.90 mmol) prepared in Example 93d in methanol (8.0 mL), sodium borohydride (150 mg, 3.97 mmol) was added with cooling on ice, and the reaction solution was stirred at room temperature for 1 hour. To the reaction solution, water (50 mL) was added, followed by extraction with ethyl acetate (100 mL). The thus obtained organic layer was dried over anhydrous sodium sulfate. After vacuum concentration, the residue was purified with silica gel chromatography (dichloromethane/methanol=97:3) to yield the title compound (390 mg, 52%) as a colorless oil.

$^1$H-NMR (500 MHz, CDCl$_3$) δ ppm: 1.10 (3H, s), 1.18 (3H, s), 1.54 (1H, dd, J=11.2, 13.2 Hz), 1.59 (1H, dd, J=7.8, 12.7 Hz), 1.93 (1H, dd, J=7.8, 12.7 Hz), 1.99 (1H, dd, J=7.8, 13.2 Hz), 3.11-3.16 (2H, m), 3.78 (3H, s), 4.21-4.27 (1H, m), 6.04 (1H, d, J=2.0 Hz), 7.32 (1H, d, J=2.0 Hz).

(93f) N-(2,4-Dimethoxybenzyl)-4-{[(1S*,2R*)-4,4-dimethyl-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (290 mg, 0.660 mmol) prepared in Example 14b, the (1S*,2R*)-4,4-dimethyl-2-(1-methyl-1H-pyrazol-5-yl)cyclopentanol (130 mg, 0.669 mmol) prepared in Example 93e, sodium hydride (63%; 60 mg, 1.58 mmol) and DMF (3.0 mL), to yield the title compound (309 mg, 76%) as a colorless oil.

$^1$H-NMR (500 MHz, CDCl$_3$) δ ppm: 1.19 (3H, s), 1.24 (3H, s), 1.71-1.77 (2H, m), 2.07 (1H, ddd, J=1.5, 7.8, 13.2 Hz), 2.14 (1H, dd, J=7.8, 13.7 Hz), 3.69-3.75 (1H, m), 3.76 (3H, s), 3.79 (3H, s), 3.88 (3H, s), 4.58-4.62 (1H, m), 5.21 (1H, d, J=17.1 Hz), 5.25 (1H, d, J=17.1 Hz), 6.08 (1H, d, J=2.0 Hz), 6.39-6.42 (2H, m), 6.47 (1H, dd, J=6.4, 10.7 Hz), 7.17-7.20 (2H, m), 7.40 (1H, d, J=2.0 Hz), 7.75 (1H, dd, J=6.8, 10.3 Hz), 8.46 (1H, d, J=5.9 Hz), 8.79 (1H, d, J=1.0 Hz).

(93g) 4-{[(1S*,2R*)-4,4-Dimethyl-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-4,4-dimethyl-2-(1-methyl-1H-pyrazol-5-yl)cyclopentyl]oxy}-2,5-difluoro-N-(pyrimidin-4-yl)benzenesulfonamide (309 mg, 0.504 mmol) prepared in Example 93f, triethylsilane (0.30 mL), trifluoroacetic acid (3.0 mL) and dichloromethane (3.0 mL), to yield the title compound (212 mg, 91%) as a colorless solid.

$^1$H-NMR (500 MHz, CD$_3$OD) δ ppm: 1.18 (3H, s), 1.23 (3H, s), 1.69 (1H, dd, J=4.9, 13.7 Hz), 1.74 (1H, t, J=12.2 Hz), 2.07 (1H, dd, J=8.3, 13.2 Hz), 2.24 (1H, dd, J=7.8, 13.7 Hz), 3.73-3.78 (1H, m), 3.81 (3H, s), 4.83-4.91 (1H, m), 6.23 (1H, d, J=2.0 Hz), 6.88 (1H, dd, J=6.8, 11.7 Hz), 7.03 (1H, d, J=6.4 Hz), 7.36 (1H, d, J=2.0 Hz), 7.75 (1H, dd, J=6.8, 10.3 Hz), 8.27 (1H, d, J=6.4 Hz), 8.56 (1H, s).

MS (ESI) m/z: 464 [M+H]+.

Example 94

2,6-Difluoro-4-{[(1S*,2R*)-2-(1H-pyrazol-4-yl)cyclohexyl]oxy}-N-(pyrimidin-4-yl)benzenesulfonamide

[Formula 112]

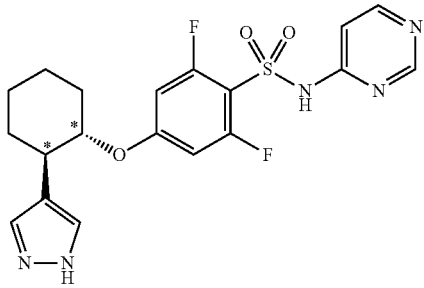

(94a) N-(2,4-dimethoxybenzyl)-2,6-difluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (0.20 g, 0.45 mmol) prepared in Example 27a, the (1S*,2R*)-2-[1-(tetrahydro-2H-pyran-2-yl)-1H-pyrazol-4-yl]cyclohexanol (0.10 g, 0.40 mmol) prepared in Example 33b, sodium hydride (63%; 27 mg, 0.68 mmol), DMF (6.0 mL) and water (0.008 mL), to yield the title compound (100 mg, 33%) as a colorless solid.

$^1$H-NMR (500 MHz, CDCl$_3$) δ ppm: 1.36-1.67 (8H, m), 1.80-2.17 (6H, m), 2.77-2.82 (1H, m), 3.62-3.67 (1H, m), 3.77 (3H, s), 3.82 (3H, s), 3.97-4.02 (2H, m), 5.26 (2H, s), 5.25-5.28 (1H, m), 6.37 (2H, dd, J=2.0, 11.2 Hz), 6.41 (1H, dd, J=2.4, 8.3 Hz), 6.44 (1H, d, J=2.4 Hz), 7.18 (1H, dt, J=1.5, 6.4 Hz), 7.21 (1H, d, J=8.3 Hz), 7.39 (2H, d, J=11.7 Hz), 8.44 (1H, d, J=6.4 Hz), 8.78 (1H, s).

(94b) 2,6-Difluoro-4-{[(1S*,2R*)-2-(1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-2,6-difluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide (100 mg, 0.171 mmol) prepared in Example 94a, triethylsilane (0.10 mL), trifluoroacetic acid (1.0 mL), dichloromethane (1.0 mL) and methanol (1.0 mL), to yield the title compound (40 mg, 54%) as a colorless solid.

$^1$H-NMR (500 MHz, DMSO-d$_6$) δ ppm: 1.24-1.36 (2H, m), 1.44-1.59 (2H, m), 1.68-1.75 (2H, m), 1.92-1.95 (1H, m), 2.07-2.09 (1H, m), 2.68-2.74 (1H, m), 4.36 (1H, dt, J=3.9, 10.3 Hz), 6.78 (2H, d, J=11.7 Hz), 6.95 (1H, brs), 7.42 (2H, s), 8.29 (1H, brs), 8.58 (1H, s).

MS (ESI) m/z: 436 [M+H]+

Example 95

4-{[(1S*,2R*)-2-(1-Ethyl-1H-pyrazol-5-yl)cyclopentyl]oxy}-2,3-difluoro-N-(2-$^2$H) (pyrimidin-4-yl)benzenesulfonamide

[Formula 113]

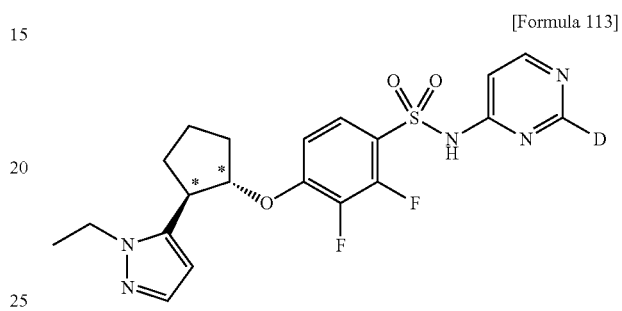

(95a) N-(2,4-dimethoxybenzyl)-2-fluoropyrimidin-4-amine

A solution of 2,4-difluoropyrimidine (1.00 g, 8.62 mmol) and 2,4-dimethoxybenzylamine (1.44 g, 8.62 mmol) in THF (28 mL) was stirred at room temperature for 1 hour. The reaction solution was vacuum concentrated, and the residue was purified with silica gel chromatography to yield the title compound (2.27 g, 62%) as a colorless amorphous solid.

$^1$H-NMR (500 MHz, CDCl$_3$) δ ppm: 3.81 (3H, s), 3.83 (3H, s), 4.55 (2H, brs), 5.74 (1H, brs), 6.28 (1H, brs), 6.44 (1H, dd, J=2.4, 8.3 Hz), 6.48 (1H, d, J=8.3 Hz), 7.23 (1H, brs), 7.92 (1H, brs).

(95b) N-(2,4-dimethoxybenzyl)(2-$^2$H)pyrimidin-4-amine

To a solution of the N-(2,4-dimethoxybenzyl)-2-fluoropyrimidin-4-amine (0.700 g, 2.68 mmol) prepared in Example 95a in THF (9.0 mL), deuterated lithium aluminum hydride (0.220 g, 5.35 mmol) was added, and the reaction solution was stirred at 40° C. for 1 hour. To the reaction solution, water (10 mL) was added, the mixture was filtered through celite, and the filtrate was subjected to extraction with ethyl acetate (20 mL). The thus obtained organic layer was dried over anhydrous sodium sulfate. After vacuum concentration, the residue was purified with silica gel chromatography to yield the title compound (75 mg, 11%) as a colorless solid.

$^1$H-NMR (500 MHz, CDCl$_3$) δ ppm: 3.82 (3H, s), 3.85 (3H, s), 4.45 (2H, brs), 5.56 (1H, brs), 6.36 (1H, d, J=5.9 Hz), 6.46 (1H, dd, J=2.4, 8.3 Hz), 6.50 (1H, d, J=2.4 Hz), 7.20 (1H, d, J=7.8 Hz), 8.15 (1H, d, J=5.4 Hz).

147

(95c) N-(2,4-dimethoxybenzyl)-2,3,4-trifluoro-N-(2-²H) (pyrimidin-4-yl)benzenesulfonamide The reaction and aftertreatment were conducted in the same manner as in Example 14b by using the N-(2,4-dimethoxybenzyl) (2-²H)pyrimidin-4-amine (100 mg, 0.39 mmol) prepared in Example 95b, 2,3,4-trifluorobenzenesulfonyl chloride (180 mg, 0.77 mmol), 1,4-diazabicyclo[2.2.2]octane (50 mg, 0.46 mmol) and THF (0.77 mL), to yield the title compound (68 mg, 40%) as a colorless amorphous solid.

¹H-NMR (500 MHz, CDCl₃) δ ppm: 3.80 (3H, s), 3.82 (3H, s), 5.27 (2H, s), 6.44-6.46 (2H, m), 7.13-7.17 (2H, m), 7.24 (1H, d, J=7.8 Hz), 7.87-7.91 (1H, m), 8.50 (1H, d, J=5.9 Hz).

(95d) N-(2,4-Dimethoxybenzyl)-4-{[(1S*,2R*)-2-(1-ethyl-1H-pyrazol-5-yl)cyclopentyl]oxy}-2,3-difluoro-N-(2-²H)(pyrimidin-4-yl)benzenesulfonamide The reaction and aftertreatment were conducted in the same manner as in Example 1a by using the N-(2,4-dimethoxybenzyl)-2,3,4-trifluoro-N-(2-²H) (pyrimidin-4-yl)benzenesulfonamide (68 mg, 0.15 mmol) prepared in Example 95c, the (1S*,2R*)-2-(1-ethyl-1H-pyrazol-5-yl)cyclopentanol (30 mg, 0.17 mmol) prepared in Example 37a, sodium hydride (63%; 10 mg, 0.25 mmol), DMF (0.77 mL) and water (0.003 mL), to yield the title compound (59.2 mg, 64%) as a colorless amorphous solid.

¹H-NMR (500 MHz, CDCl₃) δ ppm: 1.41 (3H, t, J=7.3 Hz), 1.77-1.84 (2H, m), 1.94-2.00 (2H, m), 2.20-2.37 (2H, m), 3.48 (1H, dt, J=4.9, 8.38 Hz), 3.78 (3H, s), 3.81 (3H, s), 4.12-4.25 (2H, m), 4.75-4.78 (1H, m), 5.25 (1H, d, J=17.1 Hz), 5.30 (1H, d, J=17.1 Hz), 6.07 (1H, d, J=2.0 Hz), 6.41-6.44 (2H, m), 6.66 (1H, t, J=8.8 Hz), 7.20-7.23 (2H, m), 7.46 (1H, d, J=2.0 Hz), 7.73 (1H, dt, J=2.0, 7.3 Hz), 8.46 (1H, d, J=5.9 Hz).

(95e) 4-{[(1S*,2R*)-2-(1-Ethyl-1H-pyrazol-5-yl)cyclopentyl]oxy}-2,3-difluoro-N-(2-²H) (pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclopentyl]oxy}-2,3-difluoro-N-(2-²H) (pyrimidin-4-yl)benzenesulfonamide (59.2 mg, 0.098 mmol) prepared in Example 95d, triethylsilane (0.080 mL), trifluoroacetic acid (0.10 mL) and dichloromethane (1.0 mL), to yield the title compound (34.0 mg, 77%) as a colorless solid.

¹H-NMR (500 MHz, CD₃OD) δ ppm: 1.31 (3H, t, J=6.8 Hz), 1.78-1.97 (4H, m), 2.27-2.37 (2H, m), 3.52 (1H, dt, J=5.9, 8.3 Hz), 4.12-4.21 (2H, m), 4.90-4.93 (1H, m), 6.20 (1H, d, J=2.0 Hz), 6.92 (1H, t, J=7.3 Hz), 7.20 (1H, d, J=6.4 Hz), 7.41 (1H, d; J=2.0 Hz), 7.68-7.72 (1H, m), 8.24 (1H, d, J=6.8 Hz).

MS (ESI) m/z: 451 [M+H]+.

148

Example 96

N-(4-{(1R*,2S*)-2-[5-fluoro-2-methyl-4-((pyrimidin-4-yl)sulfamoyl)phenoxy]cyclohexyl}-1H-pyrazol-3-yl)acetamide

[Formula 114]

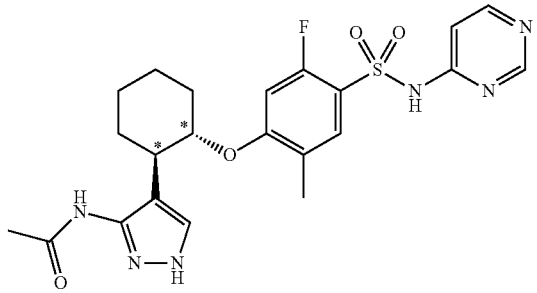

(96a) 4-({(1S*,2R*)-2-[3-Amino-1-(tetrahydro-2H-pyran-2-yl)-1H-pyrazol-4-yl]cyclohexyl}oxy)-N-(2,4-dimethoxybenzyl)-2-fluoro-5-methyl-N-(pyrimidin-4-yl)benzenesulfonamide To a solution of the N-(2,4-dimethoxybenzyl)-2-fluoro-5-methyl-4-({(1S*,2R*)-2-[3-nitro-1-(tetrahydro-2H-pyran-2-yl)-1H-pyrazol-4-yl]cyclohexyl}oxy)-N-(pyrimidin-4-yl)benzenesulfonamide (193 mg, 0.272 mmol) prepared in Example 68a and bis(acetylacetonato)copper (II) (21.3 mg, 0.0815 mmol) in a mixed solvent of THF (4.0 mL) and ethanol (4.0 mL), sodium borohydride (101 mg, 2.66 mmol) was added, and the reaction solution was stirred at room temperature for 20 minutes. To the reaction solution, a saturated aqueous solution of sodium hydrogencarbonate (10 mL) and ethyl acetate (10 mL) were added, the mixture was filtered through celite, and the filtrate was subjected to extraction. The thus obtained organic layer was dried over anhydrous sodium sulfate. After vacuum concentration, the residue was purified with silica gel chromatography to yield the title compound (78 mg, 42%) as a light brown amorphous solid.

¹H-NMR (500 MHz, CDCl₃) δ ppm: 1.38-2.15 (14H, m), 2.15 (3H, s), 2.66-2.71 (1H, m), 3.59-3.62 (1H, m), 3.73 (2H, brs), 3.77 (3H, s), 3.78 (3H, s), 4.00-4.03 (2H, m), 5.04 (1H, dt, J=2.0, 9.82 Hz), 5.25 (2H, s), 6.39-6.44 (3H, m), 7.16 (1H, d, J=2.4 Hz), 7.20 (1H, d, J=7.8 Hz), 7.29 (1H, dt, J=1.5, 5.9 Hz), 7.68 (1H, d, J=7.8 Hz), 8.43 (1H, d, J=6.4 Hz), 8.77 (1H, s).

(96b) N-{4-[(1R*,2S*)-2-{4-[(2,4-dimethoxybenzyl) (pyrimidin-4-yl)sulfamoyl]-5-fluoro-2-methylphenoxy}cyclohexyl]-1-(tetrahydro-2H-pyran-2-yl)-1H-pyrazol-3-yl}acetamide To a solution of the 4-({(1S*,2R*)-2-[3-amino-1-(tetrahydro-2H-pyran-2-yl)-1H-pyrazol-4-yl]cyclohexyl}oxy)-N-(2,4-dimethoxybenzyl)-2-fluoro-5-methyl-N-(pyrimidin-4-yl)benzenesulfonamide (78 mg, 0.115 mmol) prepared in Example 96a in pyridine (0.50 mL), acetic anhydride (0.021 mL, 0.229 mmol) was added, and the reaction solution was stirred at room temperature for 12 hours. To the reaction solution, water (10 mL) and ethyl acetate (10 mL) were added, and the organic layer was washed with water (10 mL)

and then saturated saline (10 mL) and dried over anhydrous sodium sulfate. After vacuum concentration, the residue was purified with silica gel chromatography to yield the title compound (37.2 mg, 45%) as a colorless amorphous solid.

$^1$H-NMR (500 MHz, CDCl$_3$) δ ppm: 1.38-2.16 (14H, m), 2.10 (3H, s), 2.16 (3H, s), 2.73-2.93 (1H, m), 3.62 (2H, brs), 3.77 (3H, s), 3.78 (3H, s), 3.93-4.01 (2H, m), 4.10-4.13 (1H, m), 5.17-5.20 (1H, m), 5.24 (2H, s), 6.35-6.48 (3H, m), 7.18-7.20 (1H, m), 7.30-7.35 (2H, m), 7.67 (1H, d, J=6.8 Hz), 8.43 (1H, d, J=5.8 Hz), 8.77 (1H, s).

(96c) N-(4-{(1R*,2S*)-2-[5-fluoro-2-methyl-4-(pyrimidin-4-ylsulfamoyl)phenoxy]cyclohexyl}-1H-pyrazol-3-yl)acetamide The reaction and aftertreatment were conducted in the same manner as in Example 22c by using the N-{4-[(1R*,2S*)-2-{4-[(2,4-dimethoxybenzyl)(pyrimidin-4-yl)sulfamoyl]-5-fluoro-2-methylphenoxy}cyclohexyl]-1-(tetrahydro-2H-pyran-2-yl)-1H-pyrazol-3-yl}acetamide (78 mg, 0.108 mmol) prepared in Example 96b, triethylsilane (0.10 mL), trifluoroacetic acid (0.50 mL), dichloromethane (2.0 mL) and methanol (1.0 mL), to yield the title compound (33.1 mg, 63%) as a colorless solid.

$^1$H-NMR (500 MHz, CD$_3$OD) δ ppm: 1.38-1.62 (4H, m), 1.76-1.86 (2H, m), 2.04 (3H, s), 2.11-2.24 (2H, m), 2.14 (3H, s), 2.87-2.91 (1H, m), 4.38 (1H, dt, J=3.9, 10.3 Hz), 6.78 (1H, d, J=12.7 Hz), 7.06 (1H, dd, J=1.0, 6.8 Hz), 7.42 (1H, s), 7.67 (1H, d, J=8.3 Hz), 8.32 (1H, d, J=5.9 Hz), 8.57 (1H, s).

MS (ESI) m/z: 489 [M+H]+.

Example 97

4-{[(1S*,2R*,4R*)-4-(Benzyloxy)-2-(1-methyl-1H-pyrazol-5-yl)cyclopentyl]oxy}-2,5-difluoro-N-(pyrimidin-4-yl)benzenesulfonamide

[Formula 115]

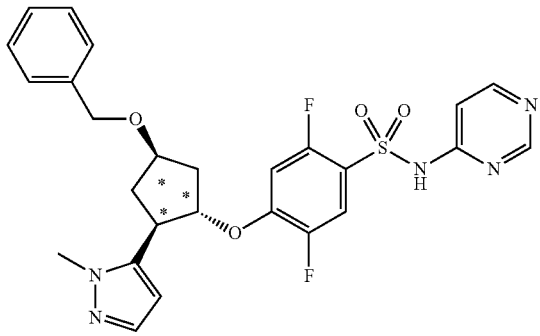

(97a) (1S*,2R*,4R*)-4-(Benzyloxy)-2-(1-methyl-1H-pyrazol-5-yl)cyclopentanol

The reaction and aftertreatment were conducted in the same manner as in Example 4a by using 1-methylpyrazole (2.40 g, 29.2 mmol), n-butyl lithium (2.69 M solution in hexane; 10.9 mL, 29.3 mmol), (1R*,3S*,5S*)-3-benzyloxy-6-oxabicyclo[3.1.0]hexane (Tetrahedron, 2002, 58, 4675-4689; 5.38 g, 28.3 mmol) and THF (90 mL), to yield the title compound (1.71 g, 22%) as a brown oil.

$^1$H-NMR (500 MHz, CDCl$_3$) δ ppm: 1.81-1.87 (1H, m), 1.92-1.98 (1H, m), 2.23-2.28 (1H, m), 2.55-2.60 (1H, m), 2.99-3.04 (1H, m), 3.88 (3H, s), 4.17-4.22 (1H, m), 4.38-4.43 (1H, m), 4.50 (2H, s), 6.14 (1H, d, J=2.0 Hz), 7.26-7.41 (6H, m).

(97b) 4-{[(1S*,2R*,4R*)-4-(Benzyloxy)-2-(1-methyl-1H-pyrazol-5-yl)cyclopentyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (100 mg, 0.228 mmol) prepared in Example 14b, the (1S*,2R*,4R*)-4-(benzyloxy)-2-(1-methyl-1H-pyrazol-5-yl)cyclopentanol (60 mg, 0.220 mmol) prepared in Example 97a, sodium hydride (63%; 40 mg, 1.05 mmol) and DMF (2.0 mL), to yield the title compound (88 mg, 58%) as a colorless oil.

$^1$H-NMR (500 MHz, CDCl$_3$) δ ppm: 1.97-2.03 (1H, m), 2.06-2.14 (1H, m), 2.38-2.43 (1H, m), 2.62-2.68 (1H, m), 3.46-3.51 (1H, m), 3.76 (3H, s), 3.79 (3H, s), 3.86 (3H, s), 4.26-4.31 (1H, m), 4.52 (1H, d, J=11.7 Hz), 4.57 (1H, d, J=11.7 Hz), 4.69-4.73 (1H, m), 5.20 (1H, d, J=17.1 Hz), 5.24 (1H, d, J=17.1 Hz), 6.16 (1H, d, J=2.0 Hz), 6.40-6.42 (2H, m), 6.47 (1H, dd, J=6.4, 11.2 Hz), 7.16 (1H, d, J=6.8 Hz), 7.20 (1H, d, J=7.8 Hz), 7.30-7.42 (6H, m), 7.75 (1H, dd, J=6.4, 10.3 Hz), 8.45 (1H, d, J=5.9 Hz), 8.78 (1H, s).

(97c) 4-{[(1S*,2R*,4R*)-4-(Benzyloxy)-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1b by using the 4-{[(1S*,2R*,4R*)-4-(benzyloxy)-2-(1-methyl-1H-pyrazol-5-yl)cyclopentyl]oxy}-N-(2,4-dimethoxybenzyl)-2,5-difluoro-N-(pyrimidin-4-yl)benzenesulfonamide (88 mg, 0.127 mmol) prepared in Example 97b, triethylsilane (0.20 mL), trifluoroacetic acid (2.0 mL) and dichloromethane (2.0 mL), to yield the title compound (60 mg, 87%) as a colorless solid.

$^1$H-NMR (500 MHz, CD$_3$OD) δ ppm: 1.90-1.96 (1H, m), 2.08-2.15 (1H, m), 2.41-2.46 (1H, m), 2.64-2.70 (1H, m), 3.55-3.60 (1H, m), 3.79 (3H, s), 4.29-4.33 (1H, m), 4.52 (1H, d, J=11.7 Hz), 4.55 (1H, d, J=11.7 Hz), 4.93 (1H, q, J=6.8 Hz), 6.27 (1H, d, J=2.0 Hz), 6.88 (1H, dd, J=6.8, 11.2 Hz), 7.03 (1H, dd, J=1.0, 6.4 Hz), 7.25-7.36 (6H, m), 7.74 (1H, dd, J=6.8, 10.3 Hz), 8.26 (1H, d, J=6.4 Hz), 8.55 (1H, s).

MS (ESI) m/z: 542 [M+H]+.

151

Example 98

4-{[(1S*,2R*,4S*)-4-(Benzyloxy)-2-(1-methyl-1H-pyrazol-5-yl)cyclopentyl]oxy}-2,5-difluoro-N-(pyrimidin-4-yl)benzenesulfonamide

[Formula 116]

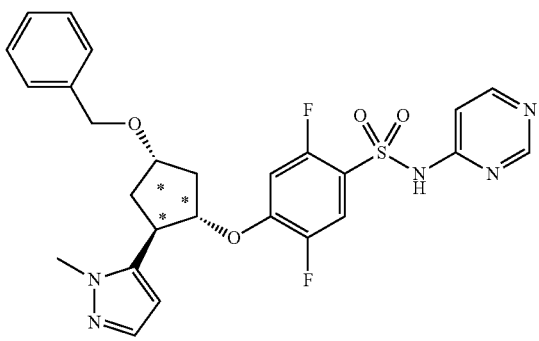

(98a) (1S*,2R*,4S*)-4-(Benzyloxy)-2-(1-methyl-1H-pyrazol-5-yl)cyclopentanol

The reaction and aftertreatment were conducted in the same manner as in Example 4a by using 1-methylpyrazole (3.40 g, 41.4 mmol), n-butyl lithium (2.69 M solution in hexane; 15.4 mL, 41.4 mmol), (1R*,3R*,5S*)-3-benzyloxy-6-oxabicyclo[3.1.0]hexane (Tetrahedron, 2002, 58, 4675-4689; 7.77 g, 40.8 mmol) and THF (120 mL), to yield the title compound (2.58 g, 23%) as a brown oil.

$^1$H-NMR (500 MHz, CDCl$_3$) δ ppm: 1.83-1.89 (1H, m), 2.01-2.05 (1H, m), 2.14-2.19 (1H, m), 2.46-2.50 (1H, m), 2.73 (1H, d, J=8.3 Hz), 3.38-3.42 (1H, m), 3.89 (3H, s), 4.11-4.15 (1H, m), 4.19-4.21 (1H, m), 4.54 (2H, s), 5.94 (1H, d, J=2.0 Hz), 7.29-7.41 (6H, m).

(98b) 4-{[(1S*,2R*,4S*)-4-(Benzyloxy)-2-(1-methyl-1H-pyrazol-5-yl)cyclopentyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (100 mg, 0.228 mmol) prepared in Example 14b, the (1S*,2R*,4S*)-4-benzyloxy-2-(1-methyl-1H-pyrazol-5-yl)cyclopentanol (60 mg, 0.220 mmol) prepared in Example 98a, sodium hydride (63%; 40 mg, 1.05 mmol) and DMF (2.0 mL), to yield the title compound (143 mg, 94%) as a colorless oil.

$^1$H-NMR (500 MHz, CDCl$_3$) δ ppm: 1.92-1.99 (1H, m), 2.03-2.07 (1H, m), 2.41-2.46 (1H, m), 2.57-2.63 (1H, m), 3.76 (3H, s), 3.79 (3H, s), 3.86-3.90 (1H, m), 3.89 (3H, s), 4.18-4.20 (1H, m), 4.52 (2H, s), 4.53-4.57 (1H, m), 5.21 (1H, d, J=17.1 Hz), 5.25 (1H, d, J=17.1 Hz), 6.04 (1H, d, J=1.5 Hz), 6.39-6.42 (2H, m), 6.46 (1H, dd, J=6.4, 10.7 Hz), 7.17-7.20 (2H, m), 7.28-7.38 (5H, m), 7.40 (1H, d, J=2.0 Hz), 7.76 (1H, dd, J=6.4, 9.8 Hz), 8.46 (1H, d, J=5.9 Hz), 8.78 (1H, s).

(98c) 4-{[(1S*,2R*,4S*)-4-(Benzyloxy)-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1b by using the 4-{[(1S*,2R*,4S*)-4-(benzyloxy)-2-(1-methyl-1H-pyrazol-5-yl)cyclopentyl]oxy}-N-(2,4-dimethoxybenzyl)-2,5-difluoro-N-(pyrimidin-4-yl)benzenesulfonamide (143 mg, 0.207 mmol) prepared in Example 98b, triethylsilane (0.20 mL), trifluoroacetic acid (2.0 mL) and dichloromethane (2.0 mL), to yield the title compound (91 mg, 81%) as a colorless solid.

$^1$H-NMR (500 MHz, CD$_3$OD) δ ppm: 1.94-2.03 (2H, m), 2.37-2.41 (1H, m), 2.66-2.72 (1H, m), 3.81 (3H, s), 3.81-3.86 (1H, m), 4.20-4.22 (1H, m), 4.51 (2H, s), 4.79-4.83 (1H, m), 6.20 (1H, d, J=1.5 Hz), 6.90 (1H, dd, J=6.4, 11.2 Hz), 7.03 (1H, d, J=6.4 Hz), 7.23-7.36 (6H, m), 7.76 (1H, dd, J=6.4, 10.3 Hz), 8.26 (1H, d, J=6.4 Hz), 8.55 (1H, s).

MS (ESI) m/z: 542 [M+H]+.

Example 99

4-{[(1S*,2R*)-3,3-Dimethyl-2-(1-methyl-1H-pyrazol-5-yl)cyclopentyl]oxy}-2,5-difluoro-N-(pyrimidin-4-yl)benzenesulfonamide

[Formula 117]

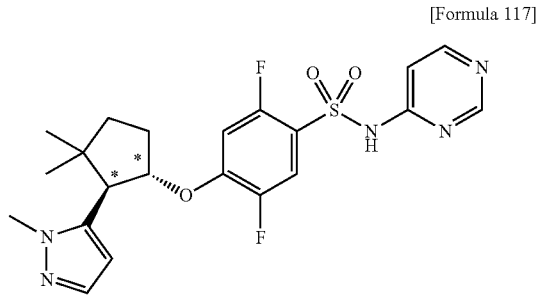 [SMILES: Cn1nccc1[C@@H]1[C@@H](Oc2cc(F)c(S(=O)(=O)Nc3ccncn3)cc2F)CCC1(C)C]

(99a) 2,2-Dimethyl-1-(1-methyl-1H-pyrazol-5-yl)cyclopentanol

The reaction and aftertreatment were conducted in the same manner as in Example 8a by using pyrazole (3.70 g, 45.1 mmol), n-butyl lithium (2.69 M solution in hexane; 17 mL, 45.7 mmol), 2,2-dimethylcyclopentanone (5.00 g, 44.6 mmol) and THF (100 mL), to yield the title compound (630 mg, 7.3%) as a colorless solid.

$^1$H-NMR (500 MHz, CDCl$_3$) δ ppm: 0.77 (3H, s), 1.14 (3H, s), 1.57-1.61 (2H, m), 1.75-1.96 (4H, m), 2.53-2.59 (1H, m), 4.11 (3H, s), 6.07 (1H, d, J=2.0 Hz), 7.36 (1H, d, J=2.0 Hz).

(99b) 5-(5,5-Dimethylcyclopent-1-en-1-yl)-1-methyl-1H-pyrazole

A solution of the 2,2-dimethyl-1-(1-methyl-1H-pyrazol-5-yl)cyclopentanol (630 mg, 3.24 mmol) prepared in Example 99a and p-toluenesulfonic acid hydrate (2.00 g, 10.5 mmol) in toluene (20 mL) was stirred for 8 hours under reflux, and the solvent was subjected to azeotropic distillation with water. After allowing to cool, water (50 mL) was added to the reaction solution, and an organic layer was extracted. The thus obtained organic layer was dried over anhydrous sodium sulfate. After vacuum concentration, the residue was purified with silica gel chromatography (hexane/ethyl acetate=3:1) to yield the title compound (512 mg, 90%) as a brown oil.

$^1$H-NMR (500 MHz, CDCl$_3$) δ ppm: 1.11 (6H, s), 1.86 (2H, t, J=6.8 Hz), 2.47 (2H, dt, J=2.4, 7.3 Hz), 3.81 (3H, s), 5.73 (1H, t, J=2.4 Hz), 6.13 (1H, d, J=2.0 Hz), 7.45 (1H, d, J=2.0 Hz).

(99c) (1S*,2R*)-3,3-Dimethyl-2-(1-methyl-1H-pyrazol-5-yl)cyclopentanol

The reaction and aftertreatment were conducted in the same manner as in Example 33b by using the 5-(5,5-dimethylcyclopent-1-en-1-yl)-1-methyl-1H-pyrazole (500 mg, 2.84 mmol) prepared in Example 99b, a borane-THF complex (0.95 M solution in THF; 12.0 mL, 11.4 mmol), sodium perborate tetrahydrate (2.00 g, 13.0 mmol), THF (2.0 mL) and water (6.0 mL), to yield the title compound (120 mg, 22%) as a colorless oil.

$^1$H-NMR (500 MHz, CDCl$_3$) δ ppm: 0.76 (3H, s), 1.05 (3H, s), 1.60-1.86 (3H, m), 2.18-2.25 (1H, m), 2.78 (1H, d, J=8.8 Hz), 2.81 (1H, brs), 3.78 (3H, s), 4.44 (1H, dt, J=6.4, 8.8 Hz), 6.06 (1H, d, J=2.0 Hz), 7.39 (1H, d, J=2.0 Hz).

(99d) N-(2,4-Dimethoxybenzyl)-4-{[(1S*,2R*)-3,3-dimethyl-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (270 mg, 0.615 mmol) prepared in Example 14b, the (1S*,2R*)-3,3-dimethyl-2-(1-methyl-1H-pyrazol-5-yl)cyclopentanol (120 mg, 0.618 mmol) prepared in Example 99c, sodium hydride (63%; 40 mg, 1.05 mmol) and DMF (3.0 mL), to yield the title compound (263 mg, 70%) as a colorless oil.

$^1$H-NMR (500 MHz, CDCl$_3$) δ ppm: 0.89 (3H, s), 1.13 (3H, s), 1.76-1.94 (3H, m), 2.38-2.45 (1H, m), 3.24 (1H, d, J=6.8 Hz), 3.76 (3H, s), 3.79 (3H, s), 3.87 (3H, s), 4.79-4.83 (1H, m), 5.20 (1H, d, J=17.1 Hz), 5.24 (1H, d, J=17.1 Hz), 6.06 (1H, d, J=2.0 Hz), 6.39-6.41 (2H, m), 6.48 (1H, dd, J=6.4, 11.2 Hz), 7.17-7.20 (2H, m), 7.43 (1H, d, J=2.0 Hz), 7.71 (1H, dd, J=6.4, 9.8 Hz), 8.45 (1H, d, J=5.9 Hz), 8.77 (1H, d, J=1.0 Hz).

(99e) 4-{[(1S*,2R*)-3,3-Dimethyl-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-3,3-dimethyl-2-(1-methyl-1H-pyrazol-5-yl)cyclopentyl]oxy}-2,5-difluoro-N-(pyrimidin-4-yl)benzenesulfonamide (263 mg, 0.429 mmol) prepared in Example 99d, triethylsilane (0.30 mL), trifluoroacetic acid (3.0 mL) and dichloromethane (3.0 mL), to yield the title compound (178 mg, 90%) as a colorless solid.

$^1$H-NMR (500 MHz, CD$_3$OD) δ ppm: 0.88 (3H, s), 1.11 (3H, s), 1.73-1.82 (2H, m), 1.91-1.98 (1H, m), 2.48-2.56 (1H, m), 3.30-3.33 (1H, m), 3.82 (3H, s), 5.10 (1H, dt, J=4.4, 7.8 Hz), 6.24 (1H, d, J=2.0 Hz), 6.94 (1H, dd, J=6.8, 11.7 Hz), 7.02 (1H, d, J=6.4 Hz), 7.39 (1H, d, J=2.0 Hz), 7.70 (1H, dd, J=6.4, 10.3 Hz), 8.27 (1H, d, J=6.4 Hz), 8.54 (1H, s).

MS (FAB) m/z: 464 [M+H]+.

Example 100

4-{[(1S*,2S*,3R*)-3-(Benzyloxy)-2-(1-methyl-1H-pyrazol-5-yl)cyclohexyl]oxy}-2,5-difluoro-N-(pyrimidin-4-yl)benzenesulfonamide

[Formula 118]

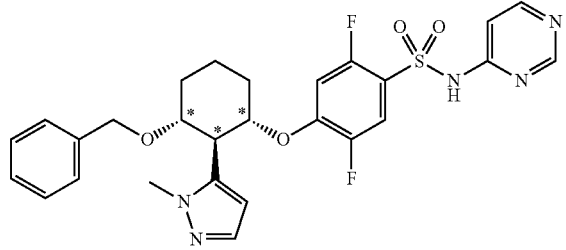

(100a) (1R*,2R*,6S*)-7-Oxabicyclo[4.1.0]heptan-2-ol

To a solution of cyclohex-2-en-1-ol (14.9 g, 152 mmol) in dichloromethane (200 mL), 3-chloroperbenzoic acid (70%; 42.0 g, 170 mmol) was added with cooling on ice, and the reaction solution was stirred for 1 hour with cooling on ice. To the reaction solution, saturated sodium thiosulfate (100 mL) and saturated sodium hydrogencarbonate (100 mL) were added, and an organic layer was extracted. The thus obtained organic layer was dried over anhydrous sodium sulfate. After vacuum concentration, the residue was purified with silica gel chromatography (hexane/ethyl acetate=2:3) to yield the title compound (3.10 g, 18%) as a colorless oil.

$^1$H-NMR (500 MHz, CDCl$_3$) δ ppm: 1.23-1.32 (1H, m), 1.43-1.59 (3H, m), 1.76-1.91 (3H, m), 3.32 (1H, t, J=3.9 Hz), 3.35 (1H, t, J=3.9 Hz), 3.99-4.04 (1H, m).

(100b) (1R*,2R*,6S*)-2-(Benzyloxy)-7-oxabicyclo[4.1.0]heptan-2-ol

To a solution of sodium hydride (63%; 1.20 g, 31.5 mmol) in THF (20 mL), a solution of the (1R*,2R*,6S*)-7-oxabicyclo[4.1.0]heptan-2-ol (3.10 g, 27.2 mmol) prepared in Example 100a in THF (20 mL) was added with cooling on ice, and the mixture was stirred at room temperature for 1 hour. To the reaction solution, benzyl bromide (4.0 mL, 33.4 mmol) was added, and the mixture was stirred at room temperature for 12 hours. To the reaction solution, water (50 mL) was added, followed by extraction with ethyl acetate (50 mL). The thus obtained organic layer was dried over anhydrous sodium sulfate. After vacuum concentration, the residue was purified with silica gel chromatography (hexane/ethyl acetate=4:1) to yield the title compound (2.85 g, 51%) as a light brown oil.

$^1$H-NMR (500 MHz, CDCl$_3$) δ ppm: 1.18-1.25 (1H, m), 1.52-1.67 (3H, m), 1.80-1.84 (2H, m), 3.26-3.27 (1H, m), 3.31-3.32 (1H, m), 3.79-3.81 (1H, m), 4.68 (1H, d, J=12.2 Hz), 4.71 (1H, d, J=12.2 Hz), 7.26-7.41 (5H, m).

(100c) (1S*,2R*,3R*)-3-(Benzyloxy)-2-(1-methyl-1H-pyrazol-5-yl)cyclohexanol

The reaction and aftertreatment were conducted in the same manner as in Example 4a by using 1-methylpyrazole (2.30 g, 28.0 mmol), n-butyl lithium (2.69 M solution in hexane; 10.0 mL, 26.9 mmol), the (1R*,2R*,6S*)-2-(benzyloxy)-7-oxabicyclo[4.1.0]heptan-2-ol (5.60 g, 27.4 mmol) prepared in Example 100b and THF (80 mL), to yield the title compound (1.71 g, 22%) as a brown oil.

¹H-NMR (500 MHz, CDCl₃) δ ppm: 1.32-1.45 (2H, m), 1.81-1.91 (2H, m), 2.08-2.21 (2H, m), 2.75 (1H, t, J=10.3 Hz), 3.25-3.29 (1H, m), 3.73-3.78 (1H, m), 3.85 (3H, s), 4.12 (1H, d, J=11.7 Hz), 4.37 (1H, d, J=11.7 Hz), 6.10 (1H, d, J=2.0 Hz), 6.95 (1H, dd, J=1.5, 7.3 Hz), 7.22-7.26 (4H, m), 7.51 (1H, d, J=2.0 Hz).

Also, a by-product (1R*,2S*,6R*)-2-(benzyloxy)-6-(1-methyl-1H-pyrazol-5-yl)cyclohexanol (3.93 g, 50%) was obtained as a brown oil.

¹H-NMR (500 MHz, CDCl₃) δ ppm: 1.35-1.47 (2H, m), 1.53-1.58 (1H, m), 1.64-1.72 (1H, m), 1.86-1.90 (1H, m), 2.15-2.20 (1H, m), 2.38 (1H, d, J=8.8 Hz), 3.04-3.09 (1H, m), 3.58-3.62 (1H, m), 3.82 (3H, s), 3.89-3.91 (1H, m), 4.53 (1H, d, J=11.7 Hz), 4.73 (1H, d, J=11.7 Hz), 6.07 (1H, d, J=2.0 Hz), 7.30-7.41 (6H, m).

(100d) 4-{[(1S*,2S*,3R*)-3-(Benzyloxy)-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (200 mg, 0.455 mmol) prepared in Example 14b, the (1S*,2R*,3R*)-3-(benzyloxy)-2-(1-methyl-1H-pyrazol-5-yl)cyclohexanol (130 mg, 0.454 mmol) prepared in Example 100c, sodium hydride (63%; 50 mg, 1.31 mmol) and DMF (3.0 mL), to yield the title compound (185 mg, 58%) as a colorless oil.

¹H-NMR (500 MHz, CDCl₃) δ ppm: 1.36-1.57 (3H, m), 1.95-1.98 (1H, m), 2.20-2.29 (2H, m), 3.11 (1H, t, J=10.3 Hz), 3.43-3.48 (1H, m), 3.76 (3H, s), 3.78 (3H, s), 3.89 (3H, s), 4.20 (1H, d, J=11.2 Hz), 4.21-4.26 (1H, m), 4.42 (1H, d, J=11.7 Hz), 5.21 (2H, s), 5.95 (1H, d, J=2.0 Hz), 6.39-6.41 (2H, m), 6.48 (1H, dd, J=6.4, 11.2 Hz), 6.96-6.97 (2H, m), 7.16-7.19 (2H, m), 7.23-7.26 (3H, m), 7.35 (1H, d, J=1.5 Hz), 7.66 (1H, dd, J=6.4, 9.8 Hz), 8.45 (1H, d, J=6.4 Hz), 8.78 (1H, d, J=1.0 Hz).

(100e) 4-{[(1S*,2S*,3R*)-3-(Benzyloxy)-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2S*,3R*)-3-(benzyloxy)-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (185 mg, 0.262 mmol) prepared in Example 100d, triethylsilane (0.30 mL), trifluoroacetic acid (3.0 mL) and dichloromethane (3.0 mL), to yield the title compound (141 mg, 97%) as a colorless solid.

¹H-NMR (500 MHz, CD₃OD) δ ppm: 1.37-1.56 (3H, m), 1.91-1.94 (1H, m), 2.23-2.33 (2H, m), 3.15 (1H, t, J=10.7 Hz), 3.57-3.62 (1H, m), 3.83 (3H, s), 4.18 (1H, d, J=11.2 Hz), 4.49 (1H, d, J=11.7 Hz), 4.58-4.63 (1H, m), 6.15 (1H, d, J=2.0 Hz), 6.94-6.96 (2H, m), 7.01-7.05 (2H, m), 7.19-7.22 (3H, m), 7.61 (1H, d, J=2.0 Hz), 7.64 (1H, dd, J=6.8, 10.3 Hz), 7.27 (1H, d, J=6.4 Hz), 8.55 (1H, s).

MS (ESI) m/z: 556 [M+H]+.

Example 101

2-Fluoro-5-methyl-4-{[(1S*,2R*)-2-(1H-pyrazol-4-yl)cyclopentyl]oxy}-N-(pyrimidin-4-yl)benzenesulfonamide

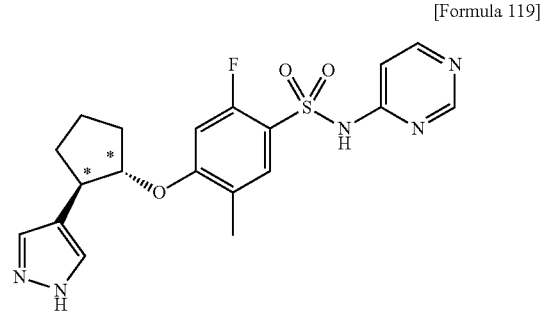 [SMILES: Cc1cc(S(=O)(=O)Nc2ccncn2)c(F)cc1O[C@H]1CCC[C@@H]1c1cn[nH]c1]

[Formula 119]

(101a) 4-(Cyclopent-1-en-1-yl)-1-(tetrahydro-2H-pyran-2-yl)-1H-pyrazole

The reaction and aftertreatment were conducted in the same manner as in Example 39a by using 4-iodo-1-(tetrahydro-2H-pyran-2-yl)-1H-pyrazole (J. Org. Chem., 2007, 72 (9), 3589-3591; 1.51 g, 5.42 mmol), 2-cyclopent-1-en-1-yl-4,4,5,5-tetramethyl-1,3,2-dioxaborolane (1.37 g, 7.05 mmol), [1,1'-bis(diphenylphosphino)ferrocene]dichloropalladium (II) (317 mg, 0.434 mmol), cesium carbonate (6.01 g, 18.4 mmol), dioxane (27 mL) and water (5.0 mL), to yield the title compound (1.00 g, 85%) as a colorless oil.

(101b) (1S*,2R*)-2-[1-(Tetrahydro-2H-pyran-2-yl)-1H-pyrazol-4-yl]cyclopentanol

The reaction and aftertreatment were conducted in the same manner as in Example 33b by using the 4-(cyclopent-1-en-1-yl)-1-(tetrahydro-2H-pyran-2-yl)-1H-pyrazole (1.00 g, 4.60 mmol) prepared in Example 101a, a borane-THF complex (0.95 M solution in THF; 10.6 mL, 10.1 mmol), sodium perborate tetrahydrate (1.49 g, 9.67 mmol), THF (5.0 mL) and water (10 mL), to yield the title compound (421 mg, 38%) as a colorless oil.

¹H-NMR (500 MHz, CDCl₃) δ ppm: 1.57-1.87 (6H, m), 2.03-2.15 (6H, m), 2.81 (1H, q, J=7.3 Hz), 3.66-3.71 (1H, m), 4.01-4.07 (2H, m), 5.32 (1H, dd, J=2.0, 8.3 Hz), 7.44 (1H, s), 7.47 (1H, d, J=2.9 Hz).

(101c) N-(2,4-dimethoxybenzyl)-2-fluoro-5-methyl-N-(pyrimidin-4-yl)-4-({(1S*,2R*)-2-[1-(tetrahydro-2H-pyran-2-yl)-1H-pyrazol-4-yl]cyclopentyl}oxy)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (0.28 g, 0.63 mmol) prepared in Example 43a, the (1S*,2R*)-2-[1-(tetrahydro-2H-pyran-2-yl)-1H-pyrazol-4-yl]cyclopentanol (0.15 g, 0.63 mmol) prepared in Example 101b, sodium hydride (63%; 91 mg, 0.95 mmol) and DMF (6.4 mL), to yield the title compound (403 mg, 97%) as a colorless solid.

¹H-NMR (500 MHz, CDCl₃) δ ppm: 1.57-1.92 (8H, m), 2.03-2.26 (4H, m), 2.20 (3H, s), 3.25-3.30 (1H, m), 3.66-3.71 (1H, m), 3.76 (3H, s), 3.80 (3H, s), 4.04-4.06 (1H, m), 4.46-4.50 (1H, m), 5.27 (2H, s), 5.30-5.34 (1H, m), 6.39-6.45 (3H, m), 7.20 (1H, d, J=8.3 Hz), 7.31 (1H, dd, J=1.5, 6.4 Hz), 7.43 (2H, d, J=2.9 Hz), 7.73 (1H, d, J=8.3 Hz), 8.43 (1H, d, J=6.4 Hz), 8.77 (1H, s).

(101d) 2-Fluoro-5-methyl-4-{[(1S*,2R*)-2-(1H-pyrazol-4-yl)cyclopentyl]oxy}-N-(pyrimidin-4-yl)benzenesulfonamide The reaction and aftertreatment were conducted in the same manner as in Example 22c by using the N-(2,4-dimethoxybenzyl)-2-fluoro-5-methyl-N-(pyrimidin-4-yl)-4-({(1S*,2R*)-2-[1-(tetrahydro-2H-pyran-2-yl)-1H-pyrazol-4-yl]cyclopentyl}oxy)benzenesulfonamide (0.12 g, 0.184 mmol) prepared in Example 101c, triethylsilane (0.10 mL), trifluoroacetic acid (0.50 mL), dichloromethane (1.0 mL) and methanol (1.0 mL), to yield the title compound (45 mg, 59%) as a colorless solid.

¹H-NMR (400 MHz, CD₃OD) δ ppm: 1.70-1.91 (4H, m), 2.19-2.27 (2H, m), 2.20 (3H, s), 3.26-3.30 (1H, m), 4.64-4.68 (1H, m), 6.72 (1H, d, J=12.5 Hz), 7.09 (1H, d, J=6.3 Hz), 7.51 (2H, s), 7.76 (1H, d, J=8.2 Hz), 8.32 (1H, d, J=6.3 Hz), 8.59 (1H, s).

MS (ESI) m/z: 418 [M+H]+

Example 102

4-{[(1S,2R)-5,5-Difluoro-2-(1-methyl-1H-pyrazol-5-yl)cyclohexyl]oxy}-2,5-difluoro-N-(pyrimidin-4-yl)benzenesulfonamide

[Formula 120]

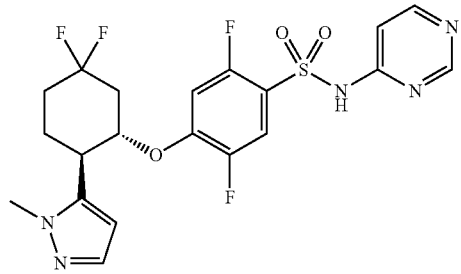

(102a) (1S,2R)-4,4-Difluoro-1-(1-methyl-1H-pyrazol-5-yl)cyclohexane-1,2-diol

To a solution of methanesulfonamide (480 mg, 5.05 mmol) in a mixed solvent of t-butanol (10 mL) and water (10 mL), AD-mixα (Sigma-Aldrich Corp.; 7.10 g) was added, and the reaction solution was stirred at room temperature for 10 minutes. To the reaction solution, a solution of the 5-(4,4-difluorocyclohex-1-en-1-yl)-1-methyl-1H-pyrazole (1.0 g, 5.05 mmol) prepared in Example 47a in t-butanol (5 mL) was added with cooling on ice, and the reaction solution was vigorously stirred at room temperature for 16 hours. To the reaction solution, an aqueous sodium sulfite solution (10 mL) was added, followed by extraction with ethyl acetate (50 mL). The thus obtained organic layer was dried over anhydrous sodium sulfate to yield the title compound in a crude form.

(102b) 5-[(1S,6S)-4,4-Difluoro-7-oxabicyclo[4.1.0]hept-1-yl]-1-methyl-1H-pyrazole A solution of the crude (1S,2R)-4,4-difluoro-1-(1-methyl-1H-pyrazol-5-yl)cyclohexane-1,2-diol prepared in Example 102a, trimethyl orthoacetate (1.60 mL, 12.6 mmol) and p-toluenesulfonic acid (48 mg, 0.25 mmol) in dichloromethane (25 mL) was stirred for 45 hours. The reaction solution was concentrated and diluted with acetonitrile (15 mL). Lithium bromide (220 mg, 2.53 mmol) and acetyl bromide (0.93 mL, 12.6 mmol) were added thereto with cooling on ice, and the reaction solution was stirred for 6 hours with cooling on ice. The reaction solution was concentrated and then diluted with methanol (20 mL). Potassium carbonate (1.75 g, 12.7 mmol) was added thereto, and the reaction solution was stirred at room temperature for 2 hours. To the reaction solution, water (50 mL) was added, followed by extraction with ethyl acetate (100 mL). The thus obtained organic layer was dried over anhydrous sodium sulfate. After vacuum concentration, the residue was purified with silica gel chromatography to yield the title compound (752 mg, 70%, 2 steps) as a colorless solid.

(102c) (1S,2R)-5,5-Difluoro-2-(1-methyl-1H-pyrazol-5-yl)cyclohexanol

A solution of the 5-[(1S,6S)-4,4-difluoro-7-oxabicyclo[4.1.0]hept-1-yl]-1-methyl-1H-pyrazole (50 mg, 0.233 mmol) prepared in Example 102b and Raney nickel (500 mg) in isopropanol (20 mL) was stirred for 3 hours under a hydrogen atmosphere. The reaction solution was filtered, the filtrate was concentrated, and the residue was then purified with silica gel chromatography to yield the title compound (21.2 mg, 42%) as a colorless oil.

(102d) 4-{[(1S,2R)-5,5-Difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (145 mg, 0.33 mmol) prepared in Example 14b, the (1S,2R)-5,5-difluoro-2-(1-methyl-1H-pyrazol-5-yl)cyclohexanol (50 mg, 0.23 mmol) prepared in Example 102c, sodium hydride (63%; 12 mg, 0.33 mmol), DMF (1.6 mL) and water (0.006 mL), to yield the title compound (130 mg, 62%) as a colorless oil.

(102e) 4-{[(1S,2R)-5,5-Difluoro-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the 4-{[(1S,2R)-

5,5-difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (130 mg, 0.20 mmol) prepared in Example 102d, triethylsilane (0.30 mL), trifluoroacetic acid (3.0 mL) and dichloromethane (3.0 mL), to yield the title compound (70 mg, 99%) as a colorless solid.

[α]$_D^{25}$=−7.62 (c 1.03, DMSO).

Example 103

4-{[(1S*,2R*)-5,5-Difluoro-2-(1H-pyrazol-4-yl)cyclohexyl]oxy}-2,5-difluoro-N-(pyrimidin-4-yl)benzenesulfonamide

[Formula 121]

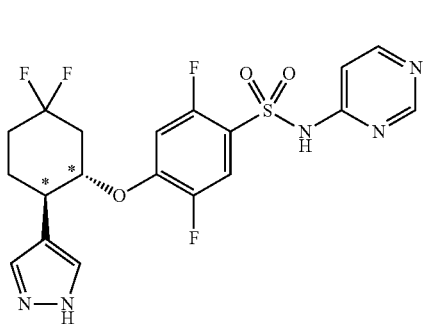

(103a) 4,4-Difluoro-1-[1-(tetrahydro-2H-pyran-2-yl)-1H-pyrazol-4-yl]cyclohexanol The reaction and aftertreatment were conducted in the same manner as in Example 4a by using 4-iodo-1-(tetrahydro-2H-pyran-2-yl)-1H-pyrazole (J. Org. Chem., 2007, 72 (9), 3589-3591; 10.0 g, 35.9 mmol), N,N,N',N'-tetramethylethylenediamine (5.38 mL, 35.9 mmol), t-butyl lithium (1.60 M solution in pentane; 26.2 mL, 43.2 mmol), 4,4-difluorocyclohexanone (4.82 g, 35.9 mmol) and THF (100 mL), to yield the title compound (1.10 g, 11%) as a colorless oil.

$^1$H-NMR (500 MHz, CDCl$_3$) δ ppm: 1.61-1.75 (4H, m), 1.95-2.29 (10H, m), 3.70 (1H, dt, J=2.9, 11.2 Hz), 4.06-4.09 (1H, m), 5.35 (1H, dd, J=3.4, 8.8 Hz), 7.54 (1H, s), 7.59 (1H, s).

(103b) 4-(4,4-Difluorocyclohex-1-en-1-yl)-1-(tetrahydro-2H-pyran-2-yl)-1H-pyrazole The reaction and aftertreatment were conducted in the same manner as in Example 99b by using the 4,4-difluoro-1-[1-(tetrahydro-2H-pyran-2-yl)-1H-pyrazol-4-yl]cyclohexanol (1.10 g, 3.84 mmol) prepared in Example 103a, p-toluenesulfonic acid (0.33 g, 1.92 mmol) and toluene (20 mL), to yield the title compound (0.55 g, 70%) as a colorless oil.

$^1$H-NMR (500 MHz, CDCl$_3$) δ ppm: 1.61-1.72 (2H, m), 2.02-2.18 (6H, m), 2.56-2.57 (2H, m), 2.65 (2H, t, J=14.7 Hz), 3.70 (1H, dt, J=2.4, 11.2 Hz), 4.04-4.07 (1H, m), 5.35 (1H, dd, J=2.9, 9.3 Hz), 5.80-5.83 (1H, m), 7.57 (1H, s), 7.61 (1H, s).

(103c) (1S*,2R*)-5,5-Difluoro-2-[1-(tetrahydro-2H-pyran-2-yl)-1H-pyrazol-4-yl]cyclohexanol The reaction and aftertreatment were conducted in the same manner as in Example 33b by using the 4-(4,4-difluorocyclohex-1-en-1-yl)-1-(tetrahydro-2H-pyran-2-yl)-1H-pyrazole (0.54 g, 2.01 mmol) prepared in Example 103b, a borane-THF complex (0.95 M solution in THF; 4.70 mL, 4.42 mmol), sodium perborate tetrahydrate (0.61 g, 4.02 mmol), THF (20 mL) and water (20 mL), to yield the title compound (0.40 g, 70%) as a colorless oil.

$^1$H-NMR (500 MHz, CDCl$_3$) δ ppm: 1.57-2.20 (11H, m), 2.46-2.58 (2H, m), 3.64-3.73 (2H, m), 4.06-4.09 (1H, m), 5.35 (1H, dd, J=2.9, 9.3 Hz), 7.49 (1H, s), 7.53 (1H, s).

(103d) 4-({(1S*,2R*)-5,5-Difluoro-2-[1-(tetrahydro-2H-pyran-2-yl)-1H-pyrazol-4-yl]cyclohexyl}oxy)-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (184 mg, 0.42 mmol) prepared in Example 14b, the (1S*,2R*)-5,5-difluoro-2-[1-(tetrahydro-2H-pyran-2-yl)-1H-pyrazol-4-yl]cyclohexanol (100 mg, 0.35 mmol) prepared in Example 103c, sodium hydride (63%; 21 mg, 0.52 mmol), DMF (5.0 mL) and water (0.0063 mL), to yield the title compound (180 mg, 75%) as a colorless amorphous solid.

$^1$H-NMR (500 MHz, CDCl$_3$) δ ppm: 1.57-1.67 (3H, m), 1.89-2.08 (6H, m), 2.15-2.17 (1H, m), 2.24-2.28 (1H, m), 2.63-2.68 (1H, m), 2.93-2.98 (1H, m), 3.62-3.68 (1H, m), 3.77 (3H, s), 3.78 (3H, s), 4.00 (1H, d, J=10.7 Hz), 4.16-4.22 (1H, m), 5.21 (2H, s), 5.25-5.30 (1H, m), 6.39-6.41 (2H, m), 6.48 (1H, dd, J=5.9, 10.7 Hz), 7.16-7.19 (2H, m), 7.46-7.48 (2H, m), 7.73 (1H, dd, J=6.4, 9.8 Hz), 8.46 (1H, d, J=5.9 Hz), 8.78 (1H, d, J=2.4 Hz).

(103e) 4-{[(1S*,2R*)-5,5-Difluoro-2-(1H-pyrazol-4-yl)cyclohexyl]oxy}-2,5-difluoro-N-(pyrimidin-4-yl)benzenesulfonamide The reaction and aftertreatment were conducted in the same manner as in Example 22c by using the 4-({(1S*,2R*)-5,5-difluoro-2-[1-(tetrahydro-2H-pyran-2-yl)-1H-pyrazol-4-yl]cyclohexyl}oxy)-N-(2,4-dimethoxybenzyl)-2,5-difluoro-N-(pyrimidin-4-yl)benzenesulfonamide (170 mg, 0.24 mmol) prepared in Example 103d, triethylsilane (0.20 mL), trifluoroacetic acid (2.0 mL), dichloromethane (2.0 mL) and methanol (2.0 mL), to yield the title compound (80 mg, 72%) as a colorless solid.

$^1$H-NMR (500 MHz, DMSO-d$_6$) δ ppm: 1.72-1.81 (1H, m), 1.97-2.20 (4H, m), 2.59-2.63 (1H, m), 2.98-3.02 (1H, m), 4.63 (1H, dt, J=4.4, 10.7 Hz), 6.96 (1H, brs), 7.14-7.18 (1H, m), 7.50 (2H, s), 7.62-7.65 (1H, m), 8.24 (1H, brs), 8.57 (1H, s).

MS (ESI) m/z: 472 [M+H]+.

Example 104

4-{[(1S*,2R*)-5,5-Difluoro-2-(1H-pyrazol-4-yl)cyclohexyl]oxy}-2,6-difluoro-N-(pyrimidin-4-yl)benzenesulfonamide

[Formula 122]

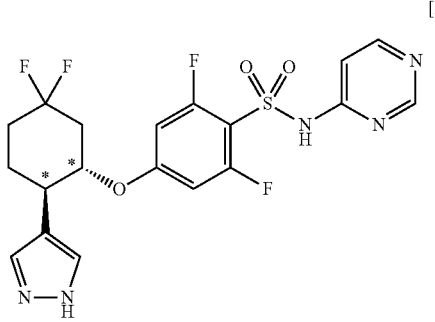

(104a) 4-({(1S*,2R*)-5,5-Difluoro-2-[1-(tetrahydro-2H-pyran-2-yl)-1H-pyrazol-4-yl]cyclohexyl}oxy)-N-(2,4-dimethoxybenzyl)-2,6-difluoro-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (184 mg, 0.42 mmol) prepared in Example 27a, the (1S*,2R*)-5,5-difluoro-2-[1-(tetrahydro-2H-pyran-2-yl)-1H-pyrazol-4-yl]cyclohexanol (100 mg, 0.35 mmol) prepared in Example 103c, sodium hydride (63%; 20 mg, 0.52 mmol), DMF (6.0 mL) and water (0.0060 mL), to yield the title compound (120 mg, 49%) as a colorless amorphous solid.

$^1$H-NMR (500 MHz, CDCl$_3$) δ ppm: 1.59-1.67 (3H, m), 1.86-2.04 (6H, m), 2.14-2.17 (1H, m), 2.22-2.27 (1H, m), 2.64-2.65 (1H, m), 2.86-2.91 (1H, m), 3.63-3.68 (1H, m), 3.77 (3H, s), 3.82 (3H, s), 3.98-4.02 (1H, m), 4.20-4.25 (1H, m), 5.25 (2H, s), 5.25-5.29 (1H, m), 6.36-6.44 (4H, m), 7.14-7.16 (1H, m), 7.21 (1H, d, J=8.3 Hz), 7.41-7.42 (2H, m), 8.44 (1H, d, J=5.9 Hz), 8.78 (1H, s).

(104b) 4-{[(1S*,2R*)-5,5-Difluoro-2-(1H-pyrazol-4-yl)cyclohexyl]oxy}-2,6-difluoro-N-(pyrimidin-4-yl)benzenesulfonamide The reaction and aftertreatment were conducted in the same manner as in Example 22c by using the 4-({(1S*,2R*)-5,5-difluoro-2-[1-(tetrahydro-2H-pyran-2-yl)-1H-pyrazol-4-yl]cyclohexyl}oxy)-N-(2,4-dimethoxybenzyl)-2,6-difluoro-N-(pyrimidin-4-yl)benzenesulfonamide (120 mg, 0.24 mmol) prepared in Example 104a, triethylsilane (0.15 mL), trifluoroacetic acid (1.5 mL), dichloromethane (1.5 mL) and methanol (1.5 mL), to yield the title compound (45 mg, 56%) as a colorless solid.

$^1$H-NMR (500 MHz, DMSO-d$_6$) δ ppm: 1.75-1.80 (1H, m), 1.97-2.13 (4H, m), 2.55-2.57 (1H, m), 2.91-2.96 (1H, m), 4.58 (1H, dt, J=4.4, 10.3 Hz), 6.75 (2H, d, J=11.2 Hz), 6.89-6.99 (1H, m), 7.44 (1H, brs), 7.51 (1H, s), 8.28 (1H, s), 8.58 (1H, s).

MS (ESI) m/z: 472 [M+H]+.

Example 105

4-{[(1S*,2R*)-5,5-Difluoro-2-(1-methyl-1H-pyrazol-5-yl)cyclohexyl]oxy}-2,3-difluoro-N-(pyrimidin-4-yl)benzenesulfonamide

[Formula 123]

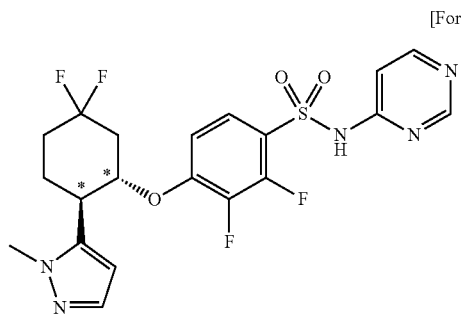

(105a) 4-{[(1S*,2R*)-5,5-Difluoro-2-(1-methyl-1H-pyrazol-5-yl)cyclohexyl]oxy}-N-(2,4-dimethoxybenzyl)-2,3-difluoro-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (145 mg, 0.33 mmol) prepared in Example 30a, the (1S*,2R*)-5,5-difluoro-2-(1-methyl-1H-pyrazol-5-yl)cyclohexanol (50 mg, 0.23 mmol) prepared in Example 47b, sodium hydride (63%; 12.6 mg, 0.33 mmol), DMF (1.6 mL) and water (0.0059 mL), to yield the title compound (113 mg, 62%) as a colorless oil.

$^1$H-NMR (500 MHz, CDCl$_3$) δ ppm: 1.92-2.13 (4H, m), 2.30-2.35 (1H, m), 2.73-2.79 (1H, m), 3.08-3.13 (1H, m), 3.77 (6H, s), 3.91 (3H, s), 4.43 (1H, dt, J=4.9, 11.2 Hz), 5.20 (1H, d, J=16.6 Hz), 5.25 (1H, dd, J=16.6 Hz), 6.08 (1H, d, J=2.4 Hz), 6.40-6.41 (2H, m), 6.55-6.58 (1H, m), 7.17-7.20 (2H, m), 7.37 (1H, d, J=2.0 Hz), 7.64-7.68 (1H, m), 8.45 (1H, d, J=6.4 Hz), 8.77 (1H, s).

(105b) 4-{[(1S*,2R*)-5,5-Difluoro-2-(1-methyl-1H-pyrazol-5-yl)cyclohexyl]oxy}-2,3-difluoro-N-(pyrimidin-4-yl)benzenesulfonamide The reaction and aftertreatment were conducted in the same manner as in Example 1b by using the 4-{[(1S*,2R*)-5,5-difluoro-2-(1-methyl-1H-pyrazol-5-yl)cyclohexyl]oxy}-N-(2,4-dimethoxybenzyl)-2,3-difluoro-N-(pyrimidin-4-yl)benzenesulfonamide (130 mg, 0.20 mmol) prepared in Example 105a, triethylsilane (0.30 mL), trifluoroacetic acid (3.0 mL) and dichloromethane (3.0 mL), to yield the title compound (80 mg, 81%) as a colorless solid.

$^1$H-NMR (500 MHz, CD$_3$OD) δ ppm: 1.93-2.27 (5H, m), 2.72-2.76 (1H, m), 3.35-3.41 (1H, m), 3.89 (3H, s), 4.68 (1H, dt, J=4.9, 10.7 Hz), 6.23 (1H, d, J=2.0 Hz), 6.92 (1H, t, J=7.3 Hz), 7.09 (1H, d, J=6.8 Hz), 7.32 (1H, d, J=2.0 Hz), 7.68-7.72 (1H, m), 7.33 (1H, d, J=6.8 Hz), 8.63 (1H, brs).

MS (ESI) m/z: 486 [M+H]+.

Example 106

2,5-Difluoro-4-{[(1S*,2R*,4R*)-4-fluoro-2-(1-methyl-1H-pyrazol-5-yl)cyclopentyl]oxy}-N-(pyrimidin-4-yl)benzenesulfonamide

[Formula 124]

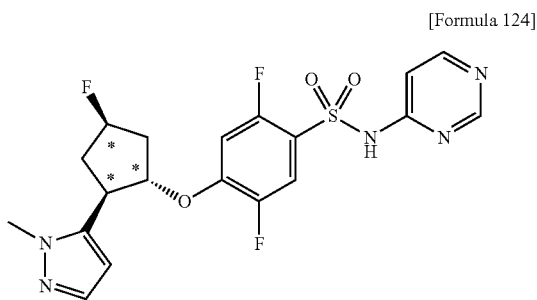 [SMILES: Cn1nccc1[C@H]1C[C@@H](F)C[C@@H]1Oc1cc(F)c(S(=O)(=O)Nc2ccncn2)cc1F]

(106a) 5-[(1R*,2S*,4S*)-4-(Benzyloxy)-2-(methoxymethoxy)cyclopentyl]-1-methyl-1H-pyrazole To a solution of the (1S*,2R*,4S*)-4-benzyloxy-2-(1-methyl-1H-pyrazol-5-yl)cyclopentanol (350 mg, 1.29 mmol) prepared in Example 98a and diisopropylethylamine (1.3 mL, 7.64 mmol) in dichloromethane (5.0 mL), chloromethyl methyl ether (0.48 mL, 6.32 mmol) was added, and the reaction solution was stirred at 40° C. for 5 hours. After allowing to cool, water (10 mL) was added to the reaction solution, and an organic layer was extracted. The thus obtained organic layer was dried over anhydrous sodium sulfate. After vacuum concentration, the residue was purified with silica gel chromatography (hexane/ethyl acetate=1:2) to yield the title compound (250 mg, 62%) as a colorless oil.

$^1$H-NMR (500 MHz, CDCl$_3$) δ ppm: 1.81-1.91 (2H, m), 2.25-2.29 (1H, m), 2.49-2.53 (1H, m), 3.22 (3H, s), 3.42-3.47 (1H, m), 3.87 (3H, s), 4.00-4.05 (1H, m), 4.05-4.10 (1H, m), 4.49-4.55 (3H, m), 4.61 (1H, d, J=6.8 Hz), 6.03 (1H, d, J=2.0 Hz), 7.28-7.36 (5H, m), 7.39 (1H, d, J=1.5 Hz).

(106b) (1S*,3R*,4S*)-3-(Methoxymethoxy)-4-(1-methyl-1H-pyrazol-5-yl)cyclopentanol A solution of the 5-[(1R*,2S*,4S*)-4-(benzyloxy)-2-(methoxymethoxy)cyclopentyl]-1-methyl-1H-pyrazole (250 mg, 0.790 mmol) prepared in Example 106a and palladium carbon (5%; 200 mg) in ethanol (3.0 mL) was stirred for 5 hours under a hydrogen atmosphere. The reaction solution was filtered through celite, the filtrate was concentrated, and the residue was purified with silica gel chromatography (dichloromethane/methanol=96:4) to yield the title compound (150 mg, 84%) as a colorless oil.

$^1$H-NMR (500 MHz, CDCl$_3$) δ ppm: 1.84-1.88 (1H, m), 1.93-1.99 (1H, m), 2.21-2.26 (1H, m), 2.32-2.38 (1H, m), 2.48 (1H, brs), 3.28 (3H, s), 3.53-3.57 (1H, m), 3.89 (3H, s), 4.10-4.13 (1H, m), 4.46 (1H, brs), 4.59 (1H, d, J=6.8 Hz), 4.65 (1H, d, J=6.8 Hz), 5.99 (1H, d, J=2.0 Hz), 7.39 (1H, d, J=2.0 Hz).

(106c) 5-[(1R*,2S*,4S*)-4-Fluoro-2-(methoxymethoxy)cyclopentyl]-1-methyl-1H-pyrazole To a solution of the (1S*,3R*,4S*)-3-(methoxymethoxy)-4-(1-methyl-1H-pyrazol-5-yl)cyclopentanol (150 mg, 0.663 mmol) prepared in Example 106b in dichloromethane (2.0 mL), bis(2-methoxyethyl)amino sulfur trifluoride (0.26 mL, 1.33 mmol) was added with cooling on ice, and the reaction solution was stirred at room temperature for 2 hours. To the reaction solution, an aqueous sodium hydrogencarbonate solution (10 mL) was added, and an organic layer was extracted. The thus obtained organic layer was dried over anhydrous sodium sulfate. After vacuum concentration, the residue was purified with silica gel chromatography (hexane/ethyl acetate=2:3) to yield the title compound (132 mg, 87%) as a colorless oil.

$^1$H-NMR (500 MHz, CDCl$_3$) δ ppm: 1.88-2.08 (2H, m), 2.41-2.50 (1H, m), 2.60-2.71 (1H, m), 3.18-3.23 (1H, m), 3.23 (3H, s), 3.87 (3H, s), 4.26-4.32 (1H, m), 4.55 (1H, d, J=6.8 Hz), 4.60 (1H, d, J=6.8 Hz), 5.17-5.31 (1H, m), 6.17 (1H, d, J=2.0 Hz), 7.41 (1H, d, J=2.0 Hz).

(106d) 5-[(1S*,2R*,4R*)-4-Fluoro-2-(1-methyl-1H-pyrazol-5-yl)cyclopentanol

A solution of the 5-[(1R*,2S*,4S*)-4-fluoro-2-(methoxymethoxy)cyclopentyl]-1-methyl-1H-pyrazole (132 mg, 0.579 mmol) prepared in Example 106c in 2 M hydrochloric acid-methanol (3.0 mL) was stirred at room temperature for 1 hour. To the reaction solution, an aqueous sodium hydrogencarbonate solution (10 mL) was added, and an organic layer was extracted with ethyl acetate (10 mL). The thus obtained organic layer was dried over anhydrous sodium sulfate. After vacuum concentration, the residue was purified with reverse phase chromatography (30% methanol/water) to yield the title compound (90 mg, 85%) as a colorless oil.

$^1$H-NMR (500 MHz, CDCl$_3$) δ ppm: 1.87-2.06 (2H, m), 2.36-2.45 (1H, m), 2.62-2.74 (1H, m), 3.04 (1H, q, J=8.8 Hz), 3.37 (1H, brs), 3.74 (3H, s), 4.42-4.46 (1H, m), 5.14-5.27 (1H, m), 6.12 (1H, d, J=2.0 Hz), 7.32 (1H, d, J=2.0 Hz).

(106e) N-(2,4-Dimethoxybenzyl)-2,5-difluoro-4-{[(1S*,2R*,4R*)-4-fluoro-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (215 mg, 0.489 mmol) prepared in Example 14b, the 5-[(1S*,2R*,4R*)-4-fluoro-2-(1-methyl-1H-pyrazol-5-yl)cyclopentanol (90 mg, 0.489 mmol) prepared in Example 106d, sodium hydride (63%; 50 mg, 1.31 mmol) and DMF (3.0 mL), to yield the title compound (235 mg, 80%) as a colorless oil.

$^1$H-NMR (500 MHz, CDCl$_3$) δ ppm: 2.07-2.26 (2H, m), 2.62-2.84 (2H, m), 3.53-3.58 (1H, m), 3.76 (3H, s), 3.79 (3H, s), 3.85 (3H, s), 4.83 (1H, q, J=6.8 Hz), 5.20 (1H, d, J=17.1 Hz), 5.24 (1H, d, J=17.1 Hz), 5.27-5.40 (1H, m), 6.19 (1H, d, J=2.0 Hz), 6.40-6.42 (2H, m), 6.52 (1H, dd, J=6.4, 10.7 Hz), 7.15 (1H, d, J=1.0, 5.9 Hz), 7.20 (1H, d, J=8.8 Hz), 7.42 (1H, d, J=2.0 Hz), 7.77 (1H, dd, J=6.4, 9.8 Hz), 8.45 (1H, d, J=5.9 Hz), 8.78 (1H, s).

(106f) 2,5-Difluoro-4-{[(1S*,2R*,4R*)-4-fluoro-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*,4R*)-4-fluoro-2-(1-methyl-1H-pyrazol-5-yl)cyclopentyl]oxy}-N-(pyrimidin-4-yl)benzenesulfonamide (235 mg, 0.389 mmol) prepared in Example 106e, triethylsilane (0.30 mL), trifluoroacetic acid (3.0 mL) and dichloromethane (3.0 mL), to yield the title compound (162 mg, 92%) as a colorless solid.

$^1$H-NMR (500 MHz, DMSO-d$_6$) δ ppm: 1.90-2.18 (2H, m), 2.58-2.79 (2H, m), 3.62 (1H, q, J=8.8 Hz), 3.75 (3H, s), 5.13 (1H, q, J=6.9 Hz), 5.27-5.42 (1H, m), 6.24 (1H, d, J=2.4 Hz), 6.96 (1H, brs), 7.21-7.23 (1H, m), 7.31 (1H, d, J=2.0 Hz), 7.68-7.72 (1H, m), 8.24 (1H, brs), 8.58 (1H, s).

MS (ESI) m/z: 454 [M+H]+.

Example 107

4-{[(1S*,2R*)-4,4-Difluoro-2-(1-methyl-1H-pyrazol-5-yl)cyclopentyl]oxy}-2,5-difluoro-N-(pyrimidin-4-yl)benzenesulfonamide

[Formula 125]

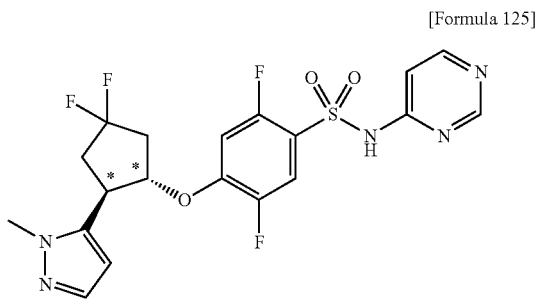 [SMILES: Cn1nccc1[C@H]1CC(F)(F)C[C@@H]1Oc1cc(F)c(S(=O)(=O)Nc2ccncn2)cc1F]

(107a) (1S*,2R*,4S*)-4-(Benzyloxy)-2-(1-methyl-1H-pyrazol-5-yl)cyclopentyl benzoate To a solution of the (1S*,2R*,4S*)-4-(benzyloxy)-2-(1-methyl-1H-pyrazol-5-yl)cyclopentanol (234 mg, 0.859 mmol) prepared in Example 98a and triethylamine (0.40 mL, 2.87 mmol) in dichloromethane (4.0 mL), benzoyl chloride (0.260 mL, 2.24 mmol) was added, and the reaction solution was stirred for 5 hours. To the reaction solution, water (50 mL) was added, and an organic layer was extracted. The thus obtained organic layer was dried over anhydrous sodium sulfate. After vacuum concentration, the residue was purified with column chromatography (hexane/ethyl acetate=3:2) to yield the title compound (297 mg, 92%) as a colorless oil.

$^1$H-NMR (500 MHz, CDCl$_3$) δ ppm: 1.97-2.08 (2H, m), 2.41-2.46 (1H, m), 2.62-2.68 (1H, m), 3.72-3.77 (1H, m), 3.89 (3H, s), 4.22-4.25 (1H, m), 4.51 (1H, d, J=11.7 Hz), 4.56 (1H, d, J=11.7 Hz), 5.33 (1H, dt, J=4.9, 7.3 Hz), 6.06 (1H, d, J=1.5 Hz), 7.28-7.44 (8H, m), 7.54-7.58 (0.1H, m), 8.02 (2H, d, J=8.3 Hz).

(107b) (1S*,2R*,4S*)-4-Hydroxy-2-(1-methyl-1H-pyrazol-5-yl)cyclopentyl benzoate

The reaction and aftertreatment were conducted in the same manner as in Example 106b by using the (1S*,2R*,4S*)-4-(benzyloxy)-2-(1-methyl-1H-pyrazol-5-yl)cyclopentyl benzoate (297 mg, 0.789 mmol) prepared in Example 107a, palladium carbon (5%; 300 mg) and ethanol (3.0 mL), to yield the title compound (205 mg, 91%) as a colorless oil.

$^1$H-NMR (500 MHz, CDCl$_3$) δ ppm: 1.88-1.92 (1H, m), 2.03-2.09 (1H, m), 2.28-2.33 (1H, m), 2.66-2.71 (1H, m), 3.79-3.84 (1H, m), 3.91 (3H, s), 4.58-4.60 (1H, m), 5.31-5.35 (1H, m), 6.06 (1H, d, J=2.0 Hz), 7.39 (1H, d, J=2.0 Hz), 7.43-7.46 (2H, m), 7.56-7.59 (1H, m), 8.01-8.03 (2H, m).

(107c) (1S*,2R*)-2-(1-Methyl-1H-pyrazol-5-yl)-4-oxocyclopentyl benzoate

To a solution of the (1S*,2R*,4S*)-4-hydroxy-2-(1-methyl-1H-pyrazol-5-yl)cyclopentyl benzoate (205 mg, 0.716 mmol) prepared in Example 107b in dichloromethane (3.0 mL), a Dess-Martin reagent (610 mg, 1.44 mmol) was added, and the reaction solution was stirred for 2 hours. To the reaction solution, an aqueous sodium hydrogencarbonate solution (10 mL) was added, and an organic layer was extracted with dichloromethane (10 mL). The thus obtained organic layer was dried over anhydrous sodium sulfate. After vacuum concentration, the residue was purified with silica gel chromatography (hexane/ethyl acetate=2:3) to yield the title compound (140 mg, 69%) as a colorless oil.

$^1$H-NMR (500 MHz, CDCl$_3$) δ ppm: 2.47-2.59 (2H, m), 2.81-2.98 (2H, m), 3.88-3.89 (1H, m), 4.09 (3H, s), 5.57-5.59 (1H, m), 6.03 (1H, d, J=2.0 Hz), 7.43-7.49 (3H, m), 7.60-7.63 (1H, m), 8.02-8.04 (2H, m).

(107d) (1S*,2R*)-4,4-Difluoro-2-(1-methyl-1H-pyrazol-5-yl)cyclopentyl benzoate

The reaction and aftertreatment were conducted in the same manner as in Example 106c by using the (1S*,2R*)-2-(1-methyl-1H-pyrazol-5-yl)-4-oxocyclopentyl benzoate (140 mg, 0.716 mmol) prepared in Example 107c, bis(2-methoxyethyl)amino sulfur trifluoride (0.80 mL, 4.10 mmol) and dichloromethane (3.0 mL), to yield the title compound (90 mg, 60%) as a colorless oil.

$^1$H-NMR (500 MHz, CDCl$_3$) δ ppm: 2.35-2.47 (2H, m), 2.76-2.93 (2H, m), 3.68-3.72 (1H, m), 3.97 (3H, s), 5.38-5.41 (1H, m), 6.19 (1H, d, J=2.0 Hz), 7.43-7.48 (3H, m), 7.58-7.62 (1H, m), 8.01-8.03 (2H, m).

(107e) (1S*,2R*)-4,4-Difluoro-2-(1-methyl-1H-pyrazol-5-yl)cyclopentanol

To a solution of the (1S*,2R*)-4,4-difluoro-2-(1-methyl-1H-pyrazol-5-yl)cyclopentyl benzoate (90 mg, 0.294 mmol) prepared in Example 107d in methanol (3.0 mL), potassium carbonate (60 mg, 0.434 mmol) was added, and the reaction solution was stirred for 30 minutes. To the reaction solution, water (10 mL) was added, and an organic layer was extracted with ethyl acetate (20 mL). The thus obtained organic layer was dried over anhydrous sodium sulfate. After vacuum concentration, the residue was purified with silica gel chromatography (dichloromethane/methanol=96:4) to yield the title compound (48 mg, 81%) as a colorless oil.

$^1$H-NMR (500 MHz, CDCl$_3$) δ ppm: 2.14-2.38 (2H, m), 2.60-2.71 (2H, m), 3.24-3.30 (1H, m), 3.68 (1H, brs), 3.79 (3H, s), 4.26-4.31 (1H, m), 6.08 (1H, d, J=1.5 Hz), 7.33 (1H, d, J=1.5 Hz).

(107f) 4-{[(1S*,2R*)-4,4-Difluoro-2-(1-methyl-1H-pyrazol-5-yl)cyclopentyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (105 mg, 0.239 mmol) prepared in Example 14b, the (1S*,2R*)-4,4-difluoro-2-(1-methyl-1H-pyrazol-5-yl)cyclopentanol (48 mg, 0.237 mmol) prepared in Example 107e, sodium hydride (63%; 30 mg, 0.788 mmol) and DMF (2.0 mL), to yield the title compound (118 mg, 79%) as a colorless oil.

$^1$H-NMR (500 MHz, CDCl$_3$) δ ppm: 2.33-2.45 (2H, m), 2.74-2.92 (2H, m), 3.75-3.80 (1H, m), 3.77 (3H, s), 3.79 (3H, s), 3.90 (3H, s), 4.67 (1H, q, J=6.8 Hz), 5.20 (1H, d, J=16.6 Hz), 5.24 (1H, d, J=16.6 Hz), 6.14 (1H, d, J=2.0 Hz), 6.39-6.47 (3H, m), 7.15 (1H, dd, J=1.5, 5.9 Hz), 7.19 (1H, d, J=8.3 Hz), 7.43 (1H, d, J=2.0 Hz), 7.79 (1H, dd, J=6.8, 10.3 Hz), 8.46 (1H, d, J=5.9 Hz), 8.78 (1H, d, J=1.0 Hz).

(107g) 4-{[(1S*,2R*)-4,4-Difluoro-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclopentyl]oxy}-N-(2,4-dimethoxybenzyl)-2,5-difluoro-N-(pyrimidin-4-yl)benzenesulfonamide (118 mg, 0.190 mmol) prepared in Example 107f, triethylsilane (0.20 mL), trifluoroacetic acid (2.0 mL) and dichloromethane (2.0 mL), to yield the title compound (50 mg, 56%) as a colorless solid.

$^1$H-NMR (500 MHz, DMSO-d$_6$) δ ppm: 2.29-2.43 (2H, m), 2.73-2.80 (1H, m), 2.99-3.01 (1H, m), 3.79-3.84 (1H, m), 3.79 (3H, s), 5.04-5.08 (1H, m), 6.29 (1H, s), 6.98 (1H, brs), 7.20-7.23 (1H, m), 7.33 (1H, s), 7.71 (1H, brs), 8.21 (1H, brs), 8.57 (1H, s).

MS (ESI) m/z: 472 [M+H]+.

Example 108

2-Fluoro-4-{[(1S*,2R*)-2-(1H-pyrazol-4-yl)cyclohexyl]oxy}-N-(pyrimidin-4-yl)benzenesulfonamide

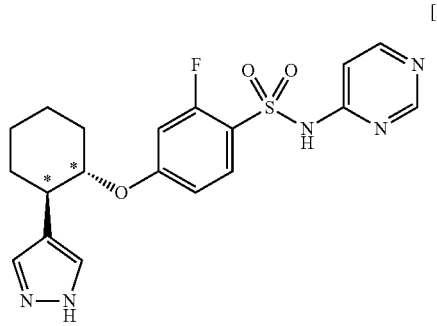

(108a) N-(2,4-dimethoxybenzyl)-2-fluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (0.303 g, 0.719 mmol) prepared in Example 29a, the (1S*,2R*)-2-[1-(tetrahydro-2H-pyran-2-yl)-1H-pyrazol-4-yl]cyclohexanol (0.15 g, 0.599 mmol) prepared in Example 33b, sodium hydride (63%; 35 mg, 0.898 mmol), DMF (5.0 mL) and water (0.010 mL), to yield the title compound (0.14 g, 35%) as a colorless solid.

$^1$H-NMR (500 MHz, CDCl$_3$) δ ppm: 1.37-1.69 (8H, m), 1.80-2.20 (6H, m), 2.79-2.83 (1H, m), 3.62-3.67 (1H, m), 3.77 (3H, s), 3.80 (3H, s), 3.97-4.06 (2H, m), 5.25 (2H, s), 5.25-5.27 (1H, m), 6.39-6.43 (2H, m), 6.50 (1H, dt, J=2.4, 12.2 Hz), 6.64-6.67 (1H, m), 7.20 (1H, d, J=8.3 Hz), 7.24 (1H, dt, J=2.0, 5.9 Hz), 7.38 (1H, d, J=2.0 Hz), 7.42 (1H, s), 7.88 (1H, dt, J=1.0, 8.3 Hz), 8.42 (1H, d, J=5.9 Hz), 8.76 (1H, s).

(108b) 2-Fluoro-4-{[(1S*,2R*)-2-(1H-pyrazol-4-yl)cyclohexyl]oxy}-N-(pyrimidin-4-yl)benzenesulfonamide The reaction and aftertreatment were conducted in the same manner as in Example 22c by using the N-(2,4-dimethoxybenzyl)-2-fluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide (0.12 g, 0.171 mmol) prepared in Example 108a, triethylsilane (0.15 mL), trifluoroacetic acid (1.5 mL), dichloromethane (1.5 mL) and methanol (1.5 mL), to yield the title compound (60 mg, 76%) as a colorless solid.

$^1$H-NMR (500 MHz, DMSO-d$_6$) δ ppm: 1.24-1.38 (2H, m), 1.44-1.60 (2H, m), 1.69-1.76 (2H, m), 1.91-1.96 (1H, m), 2.09-2.12 (1H, m), 2.71-2.76 (1H, m), 4.34 (1H, dt, J=3.9, 10.3 Hz), 6.84 (1H, dd, J=2.0, 8.8 Hz), 6.94 (1H, d, J=12.2 Hz), 6.99 (1H, brs), 7.42 (2H, s), 7.76 (1H, t, J=8.8 Hz), 8.30 (1H, brs), 8.57 (1H, s).

MS (ESI) m/z: 418 [M+H]+.

Example 109

4-{[(1S*,2R*)-5,5-Difluoro-2-(1-methyl-1H-pyrazol-5-yl)cyclohexyl]oxy}-2,6-difluoro-N-(pyrimidin-4-yl)benzenesulfonamide

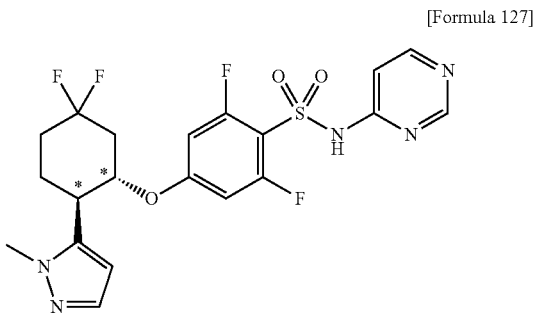 [SMILES: Cn1nccc1[C@H]1CCC(F)(F)C[C@@H]1Oc1cc(F)c(S(=O)(=O)Nc2ccncn2)c(F)c1]

(109a) 4-{[(1S*,2R*)-5,5-Difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (243 mg, 0.55 mmol) prepared in Example 27a, the (1S*,2R*)-5,5-difluoro-2-(1-methyl-1H-pyrazol-5-yl)cyclohexanol (100 mg, 0.46 mmol) prepared in Example 47b, sodium hydride (63%; 27 mg, 0.69 mmol), DMF (4.0 mL) and water (0.008 mL), to yield the title compound (140 mg, 48%) as a colorless amorphous solid.

$^1$H-NMR (500 MHz, CDCl$_3$) δ ppm: 1.90-2.11 (4H, m), 2.29-2.33 (1H, m), 2.69-2.74 (1H, m), 3.00-3.05 (1H, m), 3.77 (3H, s), 3.81 (3H, s), 3.87 (3H, s), 4.36 (1H, dt, J=4.4, 10.7 Hz), 5.24 (2H, s), 6.05 (1H, d, J=2.0 Hz), 6.30 (2H, d, J=10.7 Hz), 6.40-6.44 (2H, m), 7.13 (1H, dd, J=1.5, 5.9 Hz), 7.21 (1H, d, J=8.3 Hz), 7.37 (1H, d, J=2.0 Hz), 8.45 (1H, d, J=5.8 Hz), 8.78 (1H, d, J=1.0 Hz).

(109b) 4-{[(1S*,2R*)-5,5-Difluoro-2-(1-methyl-1H-pyrazol-5-yl)cyclohexyl]oxy}-2,6-difluoro-N-(pyrimidin-4-yl)benzenesulfonamide The reaction and aftertreatment were conducted in the same manner as in Example 1b by using the 4-{[(1S*,2R*)-5,5-difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide (120 mg, 0.188 mmol) prepared in Example 109a, triethylsilane (0.15 mL), trifluoroacetic acid (1.5 mL) and dichloromethane (1.5 mL), to yield the title compound (45 mg, 49%) as a colorless solid.

$^1$H-NMR (500 MHz, DMSO-d$_6$) δ ppm: 1.24-1.29 (1H, m), 1.67-1.76 (1H, m), 1.91-2.22 (3H, m), 2.64-2.66 (1H, m), 3.27-3.33 (1H, m), 3.77 (3H, s), 4.70 (1H, dt, J=4.4, 10.3 Hz), 6.19 (1H, d, J=2.0 Hz), 6.70-6.73 (2H, m), 6.91 (1H, brs), 7.20 (1H, d, J=2.0 Hz), 8.27 (1H, brs), 8.57 (1H, s).

MS (ESI) m/z: 486 [M+H]+.

Example 110

4-{[(1S*,2R*)-5,5-Difluoro-2-(1-methyl-1H-pyrazol-5-yl)cyclohexyl]oxy}-2-fluoro-N-(pyrimidin-4-yl)benzenesulfonamide

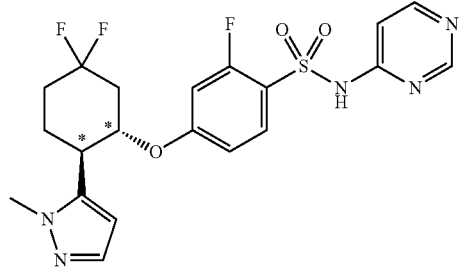

[Formula 128]

(110a) 4-{[(1S*,2R*)-5,5-Difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (0.23 g, 0.55 mmol) prepared in Example 29a, the (1S*,2R*)-5,5-difluoro-2-(1-methyl-1H-pyrazol-5-yl)cyclohexanol (0.10 g, 0.46 mmol) prepared in Example 47b, sodium hydride (63%; 27 mg, 0.69 mmol), DMF (4.0 mL) and water (0.008 mL), to yield the title compound (0.18 g, 64%) as a colorless amorphous solid.

$^1$H-NMR (500 MHz, CDCl$_3$) δ ppm: 1.90-2.11 (4H, m), 2.26-2.32 (1H, m), 2.70-2.75 (1H, m), 3.01-3.06 (1H, m), 3.77 (3H, s), 3.78 (3H, s), 3.89 (3H, s), 4.40 (1H, dt, J=4.4, 10.3 Hz), 5.23 (2H, s), 6.05 (1H, d, J=2.0 Hz), 6.39-6.45 (3H, m), 6.59 (1H, dd, J=2.4, 8.8 Hz), 7.18-7.20 (2H, m), 7.36 (1H, d, J=2.0 Hz), 7.89 (1H, t, J=8.3 Hz), 7.43 (1H, d, J=5.9 Hz), 8.76 (1H, s).

(110b) 4-{[(1S*,2R*)-5,5-Difluoro-2-(1-methyl-1H-pyrazol-5-yl)cyclohexyl]oxy}-2-fluoro-N-(pyrimidin-4-yl)benzenesulfonamide The reaction and aftertreatment were conducted in the same manner as in Example 1b by using the 4-{[(1S*,2R*)-5,5-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide (0.18 g, 0.29 mmol) prepared in Example 110a, triethylsilane (0.20 mL), trifluoroacetic acid (2.0 mL) and dichloromethane (2.0 mL), to yield the title compound (100 mg, 73%) as a colorless solid.

$^1$H-NMR (500 MHz, DMSO-d$_6$) δ ppm: 1.68-1.77 (1H, m), 1.96-2.24 (4H, m), 2.62-2.67 (1H, m), 3.30-3.35 (1H, m), 3.80 (3H, s), 4.64 (1H, dt, J=4.4, 10.3 Hz), 6.17 (1H, d, J=1.5 Hz), 6.79 (1H, dd, J=2.4, 8.8 Hz), 6.85 (1H, dd, J=2.4, 12.2 Hz), 6.96 (1H, brs), 7.20 (1H, d, J=2.0 Hz), 7.76 (1H, t, J=8.3 Hz), 8.29 (1H, brs), 8.57 (1H, s).

MS (ESI) m/z: 468 [M+H]+.

Example 111

2,6-Difluoro-N-(2-fluoropyrimidin-4-yl)-4-{[(1S*,2R*)-2-(1-methyl-1H-pyrazol-5-yl)cyclopentyl]oxy}benzenesulfonamide

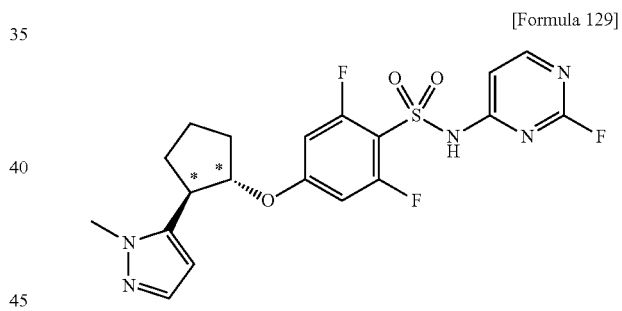

[Formula 129]

(111a) t-Butyl(2,4-dimethoxybenzyl)[(2,4,6-trifluorophenyl)sulfonyl]carbamate

To a solution of 2,4-dimethoxybenzylamine (0.45 mL, 2.99 mmol) and pyridine (1.21 mL, 15.0 mmol) in dichloromethane (15 mL), 2,4,6-trifluorobenzenesulfonyl chloride (0.69 g, 2.99 mmol) was added at 0° C., and the mixture was stirred at room temperature for 1 hour. To the reaction solution, di-tert-butyl dicarbonate (2.94 g, 13.5 mmol) and dimethylaminopyridine (0.15 g, 1.20 mmol) were added, and the mixture was stirred at room temperature for 6 hours. Water (50 mL) was added thereto, and an organic layer was extracted. The thus obtained organic layer was dried over anhydrous sodium sulfate and vacuum concentrated to yield the title compound (0.783 g, 57%) as a colorless amorphous solid.

$^1$H-NMR (400 MHz, CDCl$_3$) δ ppm: 1.31 (9H, s), 3.79 (3H, s), 3.81 (3H, s), 4.98 (2H, s), 6.44 (1H, d, J=2.4 Hz), 6.47 (1H, dd, J=2.4, 8.2 Hz), 6.80 (2H, t, J=8.2 Hz), 7.23 (1H, d, J=8.2 Hz).

(111b) t-Butyl [(2,6-difluoro-4-{[(1S*,2R*)-2-(1-methyl-1H-pyrazol-5-yl)cyclopentyl]oxy}phenyl)sulfonyl](2,4-dimethoxybenzyl)carbamate The reaction and aftertreatment were conducted in the same manner as in Example 1a by using the t-butyl(2,4-dimethoxybenzyl)[(2,4,6-trifluorophenyl)sulfonyl]carbamate (0.78 g, 1.70 mmol) prepared in Example 111a, the (1S*,2R*)-2-(1-methyl-1H-pyrazol-5-yl)cyclopentanol (0.31 g, 1.70 mmol) prepared in Example 8a, sodium hydride (63%; 0.08 g, 2.04 mmol), DMF (8.5 mL) and water (0.05 mL), to yield the title compound (740.3 mg, 70%) as a colorless amorphous solid.

$^1$H-NMR (500 MHz, CDCl$_3$) δ ppm: 1.31 (9H, s), 1.73-1.96 (4H, m), 2.20-2.32 (2H, m), 3.37-3.41 (1H, m), 3.79 (3H, s), 3.81 (3H, s), 3.84 (3H, s), 4.66-4.69 (1H, m), 4.97 (2H, s), 6.06 (1H, d, J=2.0 Hz), 6.42-6.49 (4H, m), 7.24 (1H, d, J=8.8 Hz), 7.41 (1H, d, J=2.0 Hz).

(111c) 2,6-Difluoro-4-{[(1S*,2R*)-2-(1-methyl-1H-pyrazol-5-yl)cyclopentyl]oxy}benzenesulfonamide The reaction and aftertreatment were conducted in the same manner as in Example 1b by using the t-butyl [(2,6-difluoro-4-{[(1S*,2R*)-2-(1-methyl-1H-pyrazol-5-yl)cyclopentyl]oxy}phenyl)sulfonyl](2,4-dimethoxybenzyl)carbamate (0.74 g, 1.22 mmol) prepared in Example 111b, triethylsilane (0.97 mL), trifluoroacetic acid (1.2 mL) and dichloromethane (12 mL), to yield the title compound (232.9 mg, 54%) as a colorless solid.

$^1$H-NMR (500 MHz, CDCl$_3$) δ ppm: 1.72-1.95 (4H, m), 2.19-2.33 (2H, m), 3.35-3.39 (1H, m), 3.82 (3H, s), 4.63-4.66 (1H, m), 5.76 (2H, brs), 6.06 (1H, d, J=2.0 Hz), 6.41 (2H, d, J=10.7 Hz), 7.39 (1H, d, J=1.5 Hz).

(111d) 2,6-Difluoro-N-(2-fluoropyrimidin-4-yl)-4-{[(1S*,2R*)-2-(1-methyl-1H-pyrazol-5-yl)cyclopentyl]oxy}benzenesulfonamide A solution of the 2,6-difluoro-4-{[(1S*,2R*)-2-(1-methyl-1H-pyrazol-5-yl)cyclopentyl]oxy}benzenesulfonamide (0.23 g, 0.65 mmol) prepared in Example 111c, 2,4-difluoropyrimidine (0.23 g, 1.96 mmol) and potassium carbonate (0.36 g, 2.61 mmol) in DMF (6.5 mL) was stirred at 120° C. for 3 hours. After allowing to cool, water (50 mL) was added to the reaction solution, followed by extraction with ethyl acetate (50 mL). The thus obtained organic layer was washed twice with water (50 mL) and dried over anhydrous sodium sulfate. After vacuum concentration, the residue was purified with silica gel chromatography (ethyl acetate/methanol=6:1) to yield the title compound (150 mg, 51%) as a colorless amorphous solid.

$^1$H-NMR (400 MHz, CDCl$_3$) δ ppm: 1.72-1.96 (4H, m), 2.20-2.36 (2H, m), 3.35-3.40 (1H, m), 3.85 (3H, s), 4.63-4.66 (1H, m), 6.05 (1H, d, J=1.6 Hz), 6.44 (2H, d, J=13.3 Hz), 7.19 (1H, dd, J=3.5, 5.9 Hz), 7.46 (1H, d, J=1.6 Hz), 8.40 (1H, dd, J=2.0, 5.5 Hz).

MS (ESI) m/z: 454 [M+H]+.

Example 112

4-{[(1S*,2R*,4R*)-4-(Benzyloxy)-2-(1-methyl-1H-pyrazol-5-yl)cyclohexyl]oxy}-2,5-difluoro-N-(pyrimidin-4-yl)benzenesulfonamide

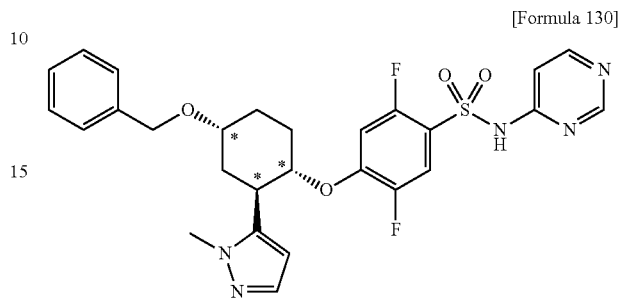

[Formula 130]

(112a) (1S*,2R*,4R*)-4-(Benzyloxy)-2-(1-methyl-1H-pyrazol-5-yl)cyclohexanol

The reaction and aftertreatment were conducted in the same manner as in Example 4a by using 1-methylpyrazole (650 mg, 7.92 mmol), n-butyl lithium (2.69 M solution in hexane; 3.08 mL, 8.28 mmol), (1R*,3R*,6S*)-3-(benzyloxy)-7-oxabicyclo[4.1.0]heptane (Bioorg. Med. Chem. 2004, 12, 1459; 1.54 g, 7.54 mmol) and THF (45 mL), to yield the title compound (790 mg, 37%) as a colorless solid.

$^1$H-NMR (500 MHz, CDCl$_3$) δ ppm: 1.50-1.56 (2H, m), 1.84-1.91 (2H, m), 2.09-2.15 (2H, m), 2.25 (1H, brs), 3.09-3.15 (1H, m), 3.61-3.67 (1H, m), 3.73-3.74 (1H, m), 3.81 (3H, s), 4.50 (1H, d, J=11.7 Hz), 4.58 (1H, d, J=12.2 Hz), 6.05 (1H, d, J=2.0 Hz), 7.26-7.40 (6H, m).

Also, a by-product (1S*,2R*,5S*)-5-(benzyloxy)-2-(1-methyl-1H-pyrazol-5-yl)cyclohexanol (106 mg, 4.9%) was obtained as a colorless solid.

$^1$H-NMR (500 MHz, CDCl$_3$) δ ppm: 1.33-1.58 (3H, m), 1.91-1.95 (1H, m), 2.15-2.19 (1H, m), 2.48-2.52 (1H, m), 2.60-2.65 (1H, m), 3.49-3.54 (1H, m), 3.60-3.65 (1H, m), 3.86 (3H, s), 4.60 (2H, s), 6.02 (1H, d, J=2.0 Hz), 7.29-7.42 (6H, m).

(112b) 4-{[(1S*,2R*,4R*)-4-(Benzyloxy)-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (135 mg, 0.307 mmol) prepared in Example 14b, the (1S*,2R*,4R*)-4-(benzyloxy)-2-(1-methyl-1H-pyrazol-5-yl)cyclohexanol (80 mg, 0.279 mmol) prepared in Example 112a, sodium hydride (63%; 16.0 mg, 0.420 mmol) and DMF (2.0 mL), to yield the title compound (137 mg, 70%) as a colorless oil.

$^1$H-NMR (500 MHz, CDCl$_3$) δ ppm: 1.55-1.61 (1H, m), 1.73-1.79 (1H, m), 1.87-2.04 (2H, m), 2.17-2.21 (1H, m), 2.27-2.30 (1H, m), 3.49-3.54 (1H, m), 3.76 (3H, s), 3.77 (3H, s), 3.82-3.83 (1H, m), 3.90 (3H, s), 4.11-4.15 (1H, m), 4.53 (1H, d, J=12.2 Hz), 4.59 (1H, d, J=12.2 Hz), 5.19 (1H, d, J=16.6 Hz), 5.23 (1H, d, J=17.1 Hz), 6.01 (1H, d, J=2.0 Hz), 6.38-6.40 (2H, m), 6.47 (1H, dd, J=5.9, 10.7 Hz), 7.17-7.19 (2H, m), 7.30-7.37 (6H, m), 7.67 (1H, dd, J=6.4, 9.8 Hz), 8.45 (1H, d, J=5.9 Hz), 8.78 (1H, s).

(112c) 4-{[(1S*,2R*,4R*)-4-(Benzyloxy)-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2R*,4R*)-4-(benzyloxy)-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (137 mg, 0.194 mmol) prepared in Example 112b, triethylsilane (0.10 mL), trifluoroacetic acid (1.0 mL) and dichloromethane (1.0 mL), to yield the title compound (108 mg, 70%) as a colorless solid.
$^1$H-NMR (500 MHz, CDCl$_3$) δ ppm: 1.54-1.60 (1H, m), 1.73-1.79 (1H, m), 2.00-2.05 (2H, m), 2.16-2.20 (1H, m), 2.27-2.29 (1H, m), 3.49-3.54 (1H, m), 3.82-3.83 (1H, m), 3.90 (3H, s), 4.10-4.15 (1H, m), 4.52 (1H, d, J=12.2 Hz), 4.59 (1H, d, J=12.2 Hz), 4.58-4.63 (1H, m), 6.03 (1H, brs), 6.50 (1H, dd, J=6.4, 11.2 Hz), 7.22-7.39 (6H, m), 7.66 (1H, dd, J=6.8, 9.8 Hz), 8.40 (1H, brs), 8.81 (1H, brs).
MS (ESI) m/z: 556 [M+H]+.

Example 113

4-{[(1S*,2R*,5S*)-5-(Benzyloxy)-2-(1-methyl-1H-pyrazol-5-yl)cyclohexyl]oxy}-2,5-difluoro-N-(pyrimidin-4-yl)benzenesulfonamide

[Formula 131]

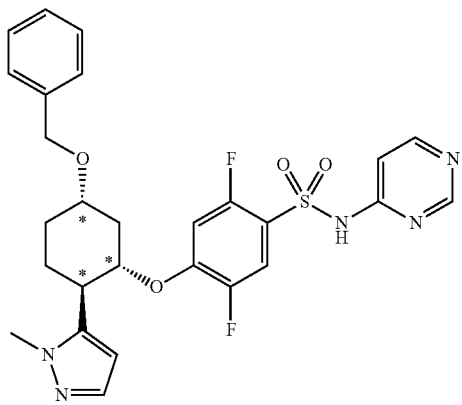

(113a) 4-{[(1S*,2R*,5S*)-5-(Benzyloxy)-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (81.5 mg, 0.185 mmol) prepared in Example 14b, the (1S*,2R*,5S*)-5-(benzyloxy)-2-(1-methyl-1H-pyrazol-5-yl)cyclohexanol (48.3 mg, 0.169 mmol) byproduct of Example 112a, sodium hydride (63%; 9.6 mg, 0.252 mmol) and DMF (1.0 mL), to yield the title compound (94.3 mg, 79%) as a colorless oil.
$^1$H-NMR (500 MHz, CDCl$_3$) δ ppm: 1.45-1.68 (3H, m), 2.04-2.08 (1H, m), 2.27-2.30 (1H, m), 2.57-2.60 (1H, m), 2.98-3.03 (1H, m), 3.52-3.58 (1H, m), 3.76 (3H, s), 3.78 (3H, s), 3.90 (3H, s), 4.07-4.14 (1H, m), 4.57 (1H, d, J=11.7 Hz), 4.62 (1H, d, J=11.7 Hz), 5.21 (2H, s), 5.98 (1H, d, J=2.0 Hz), 6.38-6.41 (3H, m), 7.17-7.20 (2H, m), 7.29-7.37 (6H, m), 7.69 (1H, dd, J=6.4, 9.8 Hz), 8.46 (1H, d, J=5.9 Hz), 8.79 (1H, s).

(113b) 4-{[(1S*,2R*,5S*)-5-(Benzyloxy)-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2R*,5S*)-5-(benzyloxy)-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (94.3 mg, 0.134 mmol) prepared in Example 113a, triethylsilane (0.10 mL), trifluoroacetic acid (1.0 mL) and dichloromethane (1.0 mL), to yield the title compound (56.0 mg, 75%) as a colorless solid.
$^1$H-NMR (500 MHz, CDCl$_3$) δ ppm: 1.45-1.68 (3H; m), 2.05-2.09 (1H, m), 2.28-2.30 (1H, m), 2.57-2.59 (1H, m), 2.98-3.03 (1H, m), 3.54-3.59 (1H, m), 3.88 (3H, s), 4.09-4.14 (1H, m), 4.57 (1H, d, J=11.7 Hz), 4.62 (1H, d, J=11.7 Hz), 5.98 (1H, d, J=2.0 Hz), 6.46 (1H, dd, J=6.4, 10.7 Hz), 7.14 (1H, d, J=6.9 Hz), 7.30-7.37 (6H, m), 7.68 (1H, dd, J=6.8, 10.3 Hz), 8.34 (1H, brs), 8.62 (1H, brs).
MS (ESI) m/z: 556 [M+H]+.

Example 114

2-Fluoro-N-(2-fluoropyrimidin-4-yl)-4-{[(1S*,2R*)-2-(1-methyl-1H-pyrazol-5-yl)cyclopentyl]oxy}benzenesulfonamide

[Formula 132]

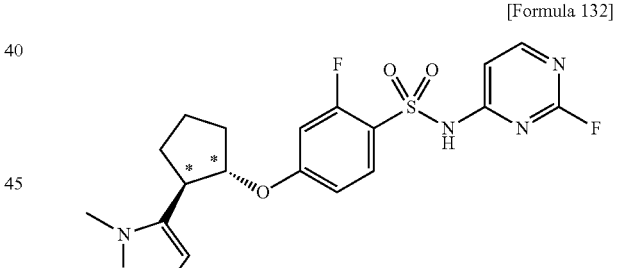

(114a) t-Butyl [(2,4-difluorophenyl)sulfonyl](2,4-dimethoxybenzyl)carbamate

The reaction and aftertreatment were conducted in the same manner as in Example 111a by using 2,4-dimethoxybenzylamine (0.45 mL, 2.99 mmol), pyridine (1.21 mL, 15.0 mmol), dichloromethane (15 mL), 2,4-difluorobenzenesulfonyl chloride (0.41 mL, 2.99 mmol), di-tert-butyl dicarbonate (2.94 g, 13.5 mmol) and dimethylaminopyridine (0.15 g, 1.20 mmol), to yield the title compound (0.40 g, 39%) as a colorless amorphous solid.
$^1$H-NMR (500 MHz, CDCl$_3$) δ ppm: 1.31 (9H, s), 3.82 (3H, s), 3.84 (3H, s), 5.04 (2H, s), 6.47 (1H, d, J=2.4 Hz), 6.52 (1H, dd, J=2.4, 8.8 Hz), 6.96-7.07 (2H, m), 7.27 (1H, d, J=8.3 Hz), 8.03-8.08 (1H, m).

(114b) t-Butyl(2,4-dimethoxybenzyl)[(2-fluoro-4-{[(1S*,2R*)-2-(1-methyl-1H-pyrazol-5-yl)cyclopentyl]oxy}phenyl)sulfonyl]carbamate The reaction and aftertreatment were conducted in the same manner as in Example 1a by using the t-butyl [(2,4-difluorophenyl)sulfonyl](2,4-dimethoxybenzyl)carbamate (0.40 g, 0.90 mmol) prepared in Example 114a, the (1S*,2R*)-2-(1-methyl-1H-pyrazol-5-yl)cyclopentanol (0.15 g, 0.90 mmol) prepared in Example 8a, sodium hydride (63%; 0.04 g, 1.08 mmol), DMF (4.5 mL) and water (0.02 mL), to yield the title compound (277.9 mg, 52%) as a colorless amorphous solid.

$^1$H-NMR (500 MHz, CDCl$_3$) δ ppm: 1.28 (9H, s), 1.75-1.96 (4H, m), 2.21-2.32 (2H, m), 3.37-3.41 (1H, m), 3.80 (3H, s), 3.81 (3H, s), 3.84 (3H, s), 4.69-4.72 (1H, m), 5.00 (2H, s), 6.06 (1H, d, J=2.0 Hz), 6.44 (1H, d, J=2.4 Hz), 6.49 (1H, dd, J=2.4, 8.3 Hz), 6.59 (1H, dd, J=2.4, 12.2 Hz), 6.67 (1H, dd, J=2.4, 8.8 Hz), 7.26 (1H, d, J=8.3 Hz), 7.42 (1H, d, J=2.0 Hz), 7.88 (1H, d, J=8.3 Hz).

(114c) 2-Fluoro-4-{[(1S*,2R*)-2-(1-methyl-1H-pyrazol-5-yl)cyclopentyl]oxy}benzenesulfonamide The reaction and aftertreatment were conducted in the same manner as in Example 1b by using the t-butyl(2,4-dimethoxybenzyl)[(2-fluoro-4-{[(1S*,2R*)-2-(1-methyl-1H-pyrazol-5-yl)cyclopentyl]oxy}phenyl)sulfonyl]carbamate (0.28 g, 0.47 mmol) prepared in Example 114b, triethylsilane (0.38 mL), trifluoroacetic acid (0.47 mL) and dichloromethane (4.7 mL), to yield the title compound (159.4 mg, 99%) as a colorless solid.

$^1$H-NMR (500 MHz, CDCl$_3$) δ ppm: 1.75-1.98 (4H, m), 2.21-2.35 (2H, m), 3.38-3.42 (1H, m), 3.84 (3H, s), 4.69-4.72 (1H, m), 5.29 (2H, brs), 6.08 (1H, d, J=2.0 Hz), 6.63-6.66 (2H, m), 7.41 (1H, d, J=2.0 Hz), 7.77 (1H, t, J=8.8 Hz).

(114d) 2-Fluoro-N-(2-fluoropyrimidin-4-yl)-4-{[(1S*,2R*)-2-(1-methyl-1H-pyrazol-5-yl)cyclopentyl]oxy}benzenesulfonamide The reaction and aftertreatment were conducted in the same manner as in Example 111d by using the 2-fluoro-4-{[(1S*,2R*)-2-(1-methyl-1H-pyrazol-5-yl)cyclopentyl]oxy}benzenesulfonamide (0.16 g, 0.47 mmol) prepared in Example 114c, 2,4-difluoropyrimidine (0.16 g, 1.41 mmol), potassium carbonate (0.26 g, 1.88 mmol) and DMF (4.7 mL), to yield the title compound (143.6 mg, 70%) as a colorless amorphous solid.

$^1$H-NMR (500 MHz, CDCl$_3$) δ ppm: 1.75-1.97 (4H, m), 2.20-2.35 (2H, m), 3.38-3.42 (1H, m), 3.88 (3H, s), 4.69-4.72 (1H, m), 6.08 (1H, d, J=2.0 Hz), 6.61 (1H, d, J=12.2 Hz), 6.71 (1H, d, J=11.2 Hz), 7.10 (1H, dd, J=3.9, 5.9 Hz), 7.49 (1H, d, J=2.0 Hz), 7.94 (1H, t, J=8.3 Hz), 8.37 (1H, dd, J=2.0, 5.9 Hz).

MS (ESI) m/z: 436 [M+H]+.

Example 115

4-{[(1S*,2R*)-2-(1-Ethyl-1H-pyrazol-5-yl)cyclopentyl]oxy}-2-fluoro-N-(pyrimidin-4-yl)benzenesulfonamide

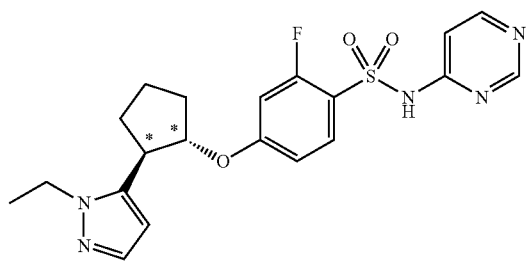

[Formula 133]

(115a) N-(2,4-Dimethoxybenzyl)-4-{[(1S*,2R*)-2-(1-ethyl-1H-pyrazol-5-yl)cyclopentyl]oxy}-2-fluoro-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (0.40 g, 0.95 mmol) prepared in Example 29a, the (1S*,2R*)-2-(1-ethyl-1H-pyrazol-5-yl)cyclopentanol (0.17 g, 0.95 mmol) prepared in Example 37a, sodium hydride (63%; 4 mg, 1.14 mmol), DMF (4.8 mL) and water (0.03 mL), to yield the title compound (453 mg, 82%) as a colorless amorphous solid.

$^1$H-NMR (500 MHz, CDCl$_3$) δ ppm: 1.37 (3H, t, J=7.3 Hz), 1.71-1.93 (4H, m), 2.16-2.30 (2H, m), 3.37 (1H, dt, J=4.4, 7.8 Hz), 3.74 (3H, s), 3.79 (3H, s), 4.10-4.15 (2H, m), 4.67-4.74 (1H, m), 5.27 (2H, s), 6.04 (1H, d, J=2.0 Hz), 6.40 (1H, dd, J=2.0, 10.7 Hz), 6.43 (1H, d, J=2.4 Hz), 6.53 (1H, dd, J=2.4, 12.2 Hz), 6.66 (1H, dd, J=2.4, 11.2 Hz), 7.19-7.23 (2H, m), 7.43 (1H, d, J=2.0 Hz), 7.93 (1H, t, J=8.8 Hz), 8.41 (1H, d, J=5.9 Hz), 8.74 (1H, s).

(115b) 4-{[(1S*,2R*)-2-(1-Ethyl-1H-pyrazol-5-yl)cyclopentyl]oxy}-2-fluoro-N-(pyrimidin-4-yl)benzenesulfonamide The reaction and aftertreatment were conducted in the same manner as in Example 1b by using the N-(2,4-dimethoxybenzyl)-4-{[(1S*,2R*)-2-(1-ethyl-1H-pyrazol-5-yl)cyclopentyl]oxy}-2-fluoro-N-(pyrimidin-4-yl)benzenesulfonamide (0.45 g, 0.78 mmol) prepared in Example 115a, triethylsilane (0.62 mL), trifluoroacetic acid (0.78 mL) and dichloromethane (7.8 mL), to yield the title compound (173 mg, 52%) as a colorless solid.

$^1$H-NMR (500 MHz, CDCl$_3$) δ ppm: 1.38 (3H, t, J=7.3 Hz), 1.72-1.79 (1H, m), 1.86-1.95 (3H, m), 2.19-2.31 (2H, m), 3.37 (1H, dt, J=4.9, 8.3 Hz), 4.09-4.19 (2H, m), 4.66-4.69 (1H, m), 6.03 (1H, d, J=2.0 Hz), 6.56 (1H, dd, J=2.4, 12.2 Hz), 6.66 (1H, dd, J=2.4, 9.3 Hz), 7.23 (1H, brs), 7.43 (1H, d, J=2.0 Hz), 7.90 (1H, t, J=8.3 Hz), 8.39 (1H, d, J=5.9 Hz), 8.85 (1H, s).

MS (ESI) m/z: 432 [M+H]+.

Example 116

4-{[(1S*,2R*)-2-(3-Amino-1H-pyrazol-4-yl)cyclohexyl]oxy}-2,6-difluoro-N-(1,3-thiazol-4-yl)benzenesulfonamide

[Formula 134]

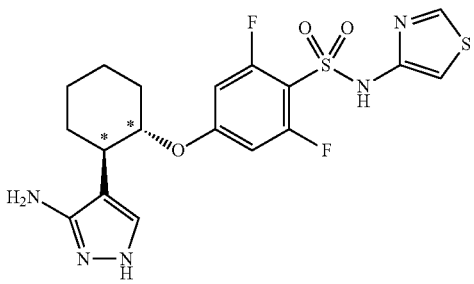

(116a) Tert-butyl 1,3-thiazol-4-yl[(2,4,6-trifluorophenyl)sulfonyl]carbamate The reaction and aftertreatment were conducted in the same manner as in Example 86a by using tert-butyl 1,3-thiazol-4-ylcarbamate (Synthesis, 2010, 3152-3162; 1.00 g, 4.99 mmol), lithium bis(trimethylsilyl)amide (1.0 M solution in THF; 5.99 mL, 5.99 mmol), 2,4,6-trifluorobenzenesulfonyl chloride (1.38 g, 5.99 mmol) and THF (15 mL), to yield the title compound (1.53 g, 78%) as a pale yellow solid.

$^1$H-NMR (500 MHz, CDCl$_3$) δ ppm: 1.39 (9H, s), 6.84 (2H, t, J=8.3 Hz), 7.52 (1H, d, J=2.4 Hz), 8.81 (1H, d, J=2.0 Hz).

(116b) Tert-butyl {[2,6-difluoro-4-({(1S*,2R*)-2-[3-nitro-1-(tetrahydro-2H-pyran-2-yl)-1H-pyrazol-4-yl]cyclohexyl}oxy)phenyl]sulfonyl}1,3-thiazol-4-ylcarbamate The reaction and aftertreatment were conducted in the same manner as in Example 1a by using the tert-butyl 1,3-thiazol-4-yl[(2,4,6-trifluorophenyl)sulfonyl]carbamate (491 mg, 1.24 mmol) prepared in Example 116a, the (1S*,2R*)-2-[3-nitro-1-(tetrahydro-2H-pyran-2-yl)-1H-pyrazol-4-yl]cyclohexanol (350 mg, 1.19 mmol) prepared in Example 34b, sodium hydride (63%; 67.7 mg, 1.78 mmol) and DMF (3.0 mL), to yield the title compound (426 mg, 54%) as a yellow oil.

$^1$H-NMR (500 MHz, CDCl$_3$) δ ppm: 1.37 (9H, s), 1.47-1.68 (6H, m), 1.83-2.27 (8H, m), 3.53-3.58 (1H, m), 3.64-3.69 (1H, m), 3.96-4.01 (1H, m), 4.18-4.23 (1H, m), 5.33-5.37 (1H, m), 6.41 (2H, dd, J=6.4, 10.3 Hz), 7.47 (1H, d, J=5.9 Hz), 7.49 (1H, d, J=2.4 Hz), 8.79 (1H, d, J=2.0 Hz).

(116c) 2,6-Difluoro-4-{[(1S*,2R*)-2-(3-nitro-1H-pyrazol-4-yl)cyclohexyl]oxy}-N-(1,3-thiazol-4-yl)benzenesulfonamide The reaction and aftertreatment were conducted in the same manner as in Example 22c by using the tert-butyl {[2,6-difluoro-4-({(1S*,2R*)-2-[3-nitro-1-(tetrahydro-2H-pyran-2-yl)-1H-pyrazol-4-yl]cyclohexyl}oxy)phenyl]sulfonyl}1,3-thiazol-4-ylcarbamate (426 mg, 0.636 mmol) prepared in Example 116b, trifluoroacetic acid (1.0 mL), dichloromethane (1.0 mL) and methanol (0.1 mL), to yield the title compound (167 mg, 54%) as a colorless solid.

$^1$H-NMR (500 MHz, CDCl$_3$) δ ppm: 1.60-1.68 (4H, m), 1.87-1.96 (2H, m), 2.10-2.26 (2H, m), 3.57-3.62 (1H, m), 4.10-4.14 (1H, m), 6.25 (2H, d, J=10.7 Hz), 6.97 (1H, d, J=2.0 Hz), 7.70 (1H, s), 7.70 (1H, d, J=2.4 Hz), 11.5 (1H, brs).

(116d) 4-{[(1S*,2R*)-2-(3-Amino-1H-pyrazol-4-yl)cyclohexyl]oxy}-2,6-difluoro-N-(1,3-thiazol-4-yl)benzenesulfonamide To a solution of the 2,6-difluoro-4-{[(1S*,2R*)-2-(3-nitro-1H-pyrazol-4-yl)cyclohexyl]oxy}-N-(1,3-thiazol-4-yl)benzenesulfonamide (167 mg, 0.343 mmol) prepared in Example 116c in ethanol (4.0 mL) and water (2.0 mL), ammonium chloride (92.0 mg, 1.72 mmol) and an iron powder (57.6 mg, 1.03 mol) were added, and the reaction solution was stirred for 2 hours under heated reflux. After allowing to cool, the reaction solution was filtered through celite, the filtrate was vacuum concentrated, and the residue was purified with silica gel chromatography (dichloromethane/methanol=93:7) to yield the title compound (145 mg, 92%) as a colorless solid.

$^1$H-NMR (500 MHz, CDCl$_3$) δ ppm: 1.35-1.62 (4H, m), 1.81-2.18 (4H, m), 2.60-2.64 (1H, m), 3.93-3.96 (1H, m), 6.34 (2H, d, J=11.2 Hz), 6.97 (1H, d, J=1.5 Hz), 7.10 (1H, s), 8.64 (1H, s).

MS (ESI) m/z: 456 [M+H]+.

Example 117

4-{[(1S*,2R*)-3,3-Difluoro-2-(1-methyl-1H-pyrazol-5-yl)cyclohexyl]oxy}-2,5-difluoro-N-(pyrimidin-4-yl)benzenesulfonamide

[Formula 135]

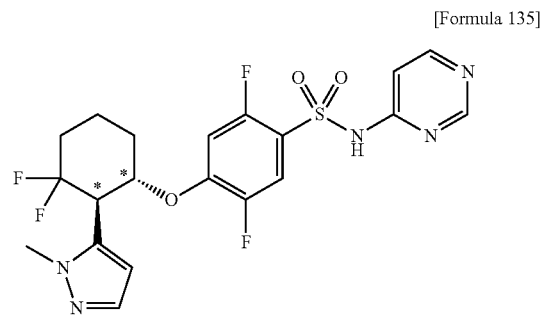 [SMILES: Cn1nccc1[C@@H]1[C@@H](Oc2cc(F)c(S(=O)(=O)Nc3ccncn3)cc2F)CCCC1(F)F]

(117a) (1S*,2S*,3R*)-3-(Benzyloxy)-2-(1-methyl-1H-pyrazol-5-yl)cyclohexyl benzoate The reaction and aftertreatment were conducted in the same manner as in Example 107a by using the (1S*,2R*,3R*)-3-(benzyloxy)-2-(1-methyl-1H-pyrazol-5-yl)cyclohexanol (1.56 g, 5.45 mmol) prepared in Example 100c, triethylamine (2.00 mL, 14.4 mmol), benzoyl chloride (1.50 mL, 12.9 mmol) and dichloromethane (15 mL), to yield the title compound (1.81 g, 85%) as a colorless solid.

$^1$H-NMR (500 MHz, CDCl$_3$) δ ppm: 1.39-1.51 (3H, m), 1.93-1.95 (1H, m), 2.24-2.29 (2H, m), 3.11 (1H, t, J=10.3

Hz), 3.49-3.45 (1H, m), 3.89 (3H, s), 4.13 (1H, d, J=11.2 Hz), 4.39 (1H, d, J=11.2 Hz), 5.16-5.22 (1H, m), 6.09 (1H, d, J=2.0 Hz), 6.97 (2H, dd, J=1.5, 7.3 Hz), 7.23-7.27 (4H, m), 7.34-7.37 (3H, m), 7.48-7.51 (1H, m), 7.79 (1H, dd, J=1.5, 8.3 Hz).

(117b) (1S*,2S*,3R*)-3-Hydroxy-2-(1-methyl-1H-pyrazol-5-yl)cyclohexyl benzoate

The reaction and aftertreatment were conducted in the same manner as in Example 106b by using the (1S*,2S*,3R*)-3-(benzyloxy)-2-(1-methyl-1H-pyrazol-5-yl)cyclohexyl benzoate (1.81 g, 4.64 mmol) prepared in Example 117a, palladium carbon (5%; 1.80 g) and ethanol (20 mL), to yield the title compound (600 mg, 43%) as a colorless oil.
$^1$H-NMR (500 MHz, CDCl$_3$) δ ppm: 1.47-1.63 (2H, m), 1.94-1.98 (1H, m), 2.05-2.06 (1H, m), 2.14-2.17 (1H, m), 2.25-2.27 (1H, m), 3.00 (1H, t, J=10.3 Hz), 3.78-3.82 (1H, m), 3.91 (3H, s), 5.11 (1H, dt, J=3.9, 10.3 Hz), 6.16 (1H, d, J=2.0 Hz), 7.36-7.39 (3H, m), 7.50-7.53 (1H, m), 7.80-7.82 (2H, m).

(117c) (1S*,2R*)-3,3-Difluoro-2-(1-methyl-1H-pyrazol-5-yl)cyclohexyl benzoate

To a solution of the (1S*,2S*,3R*)-3-hydroxy-2-(1-methyl-1H-pyrazol-5-yl)cyclohexyl benzoate (550 mg, 1.83 mmol) prepared in Example 117b in dichloromethane (6.0 mL), a Dess-Martin reagent (2.30 g, 5.42 mmol) was added, and the reaction solution was stirred for 2 hours. To the reaction solution, bis(2-methoxyethyl)amino sulfur trifluoride (3.50 mL, 17.9 mmol) was added, and the reaction solution was stirred for 3 hours. To the reaction solution, an aqueous sodium hydrogencarbonate solution (10 mL) was added, and an organic layer was extracted with dichloromethane (10 mL). The thus obtained organic layer was dried over anhydrous sodium sulfate. After vacuum concentration, the residue was purified with silica gel chromatography (hexane/ethyl acetate=1:1) to yield the title compound (206 mg, 35%) as a colorless solid.
$^1$H-NMR (500 MHz, CDCl$_3$) δ ppm: 1.56-1.99 (4H, m), 2.29-2.40 (2H, m), 3.45 (1H, ddd, J=2.9, 10.7, 24.4 Hz), 3.92 (3H, s), 5.39 (1H, dt, J=4.4, 10.7 Hz), 6.30 (1H, t, J=2.0 Hz), 7.35-7.40 (3H, m), 7.50-7.53 (1H, m), 7.78 (2H, dd, J=1.5, 8.3 Hz).

(117d) (1S*,2R*)-3,3-Difluoro-2-(1-methyl-1H-pyrazol-5-yl)cyclohexanol

The reaction and aftertreatment were conducted in the same manner as in Example 107e by using the (1S*,2R*)-3,3-difluoro-2-(1-methyl-1H-pyrazol-5-yl)cyclohexyl benzoate (206 mg, 0.643 mmol) prepared in Example 117c, potassium carbonate (270 mg, 1.95 mmol) and methanol (4.0 mL), to yield the title compound (600 mg, 43%) as a colorless solid.
$^1$H-NMR (500 MHz, CDCl$_3$) δ ppm: 1.44-1.91 (4H, m), 2.16-2.26 (2H, m), 2.71 (1H, d, J=3.4 Hz), 3.02 (1H, ddd, J=2.4, 10.3, 26.4 Hz), 3.82 (3H, s), 3.92-3.97 (1H, m), 6.29 (1H, t, J=2.4 Hz), 7.44 (1H, d, J=2.0 Hz).

(117e) 4-{[(1S*,2R*)-3,3-Difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (219 mg, 0.498 mmol) prepared in Example 14b, the (1S*,2R*)-3,3-difluoro-2-(1-methyl-1H-pyrazol-5-yl)cyclohexanol (98.0 mg, 0.453 mmol) prepared in Example 117d, sodium hydride (63%; 25.9 mg, 0.680 mmol) and DMF (2.0 mL), to yield the title compound (260 mg, 90%) as a colorless oil.
$^1$H-NMR (500 MHz, CDCl$_3$) δ ppm: 1.60-2.00 (4H, m), 2.33-2.36 (2H, m), 3.44 (1H, ddd, J=52.4, 10.7, 26.4 Hz), 3.76 (3H, s), 3.78 (3H, s), 3.91 (3H, s), 4.46 (1H, dt, J=3.9, 10.3 Hz), 5.19 (1H, d, J=16.6 Hz), 5.23 (1H, d, J=17.1 Hz), 6.24 (1H, t, J=2.4 Hz), 6.39-6.41 (2H, m), 6.53 (1H, dd, J=6.4, 10.7 Hz), 7.16 (1H, d, J=5.9 Hz), 7.19 (1H, d, J=8.8 Hz), 7.36 (1H, d, J=2.0 Hz), 8.48 (1H, dd, J=6.4, 10.3 Hz), 8.46 (1H, d, J=5.9 Hz), 8.78 (1H, s).

(117f) 4-{[(1S*,2R*)-3,3-Difluoro-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1b by using the 4-{[(1S*,2R*)-3,3-difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (260 mg, 0.398 mmol) prepared in Example 117e, triethylsilane (0.20 mL), trifluoroacetic acid (2.0 mL) and dichloromethane (2.0 mL), to yield the title compound (221 mg, 90%) as a colorless solid.
$^1$H-NMR (500 MHz, CDCl$_3$) δ ppm: 1.60-2.01 (4H, m), 2.31-2.37 (2H, m), 3.43 (1H, ddd, J=2.4, 10.7, 26.4 Hz), 3.91 (3H, s), 4.46 (1H, dt, J=3.9, 10.7 Hz), 6.25 (1H, t, J=2.0 Hz), 6.57 (1H, dd, J=5.9, 10.7 Hz), 7.21 (1H, d, J=6.4 Hz), 7.35 (1H, d, J=2.0 Hz), 7.67 (1H, dd, J=6.4, 9.8 Hz), 8.39 (1H, d, J=6.4 Hz), 8.75 (1H, s).
MS (ESI) m/z: 486 [M+H]+.

Example 118

4-{[(1R,2S)-2-(1-Ethyl-1H-pyrazol-5-yl)cyclopentyl]oxy}-2,3-difluoro-N-(pyrimidin-4-yl)benzenesulfonamide

[Formula 136]

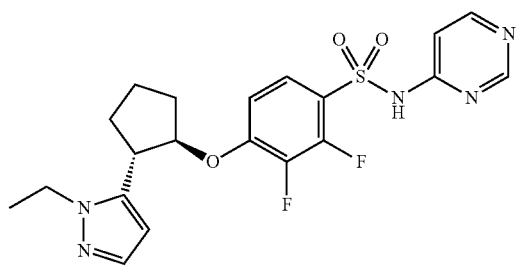

(118a) (1R,2S)-2-(1-Ethyl-1H-pyrazol-5-yl)cyclopentanol

The (1S*,2R*)-2-(1-ethyl-1H-pyrazol-5-yl)cyclopentanol prepared in Example 37a was optically resolved with CHIRALPAK AD-H (Daicel Corp.; hexane/ethanol=8:2) to yield the title compound as a colorless oil.
$[α]_D^{25}$=−54.3 (c 1.03, MeOH).

(118b) N-(2,4-dimethoxybenzyl)-4-{[(1R,2S)-2-(1-ethyl-1H-pyrazol-5-yl)cyclopentyl]oxy}-2,3-difluoro-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (73.0 g, 166 mmol) prepared in Example 30a, the (1S,2R)-2-(1-ethyl-1H-pyrazol-5-yl)cyclopentanol (29.9 g, 166 mol) prepared in Example 118a, sodium hydride (63%; 7.64 g, 200 mmol) and DMF (600 mL), to yield the title compound (77.2 g, 78%) as a colorless oil.

(118c) 4-{[(1R,2S)-2-(1-Ethyl-1H-pyrazol-5-yl)cyclopentyl]oxy}-2,3-difluoro-N-(pyrimidin-4-yl)benzenesulfonamide To a solution of the N-(2,4-dimethoxybenzyl)-4-{[(1S,2R)-2-(1-ethyl-1H-pyrazol-5-yl)cyclopentyl]oxy}-2,3-difluoro-N-(pyrimidin-4-yl)benzenesulfonamide (77.2 g, 129 mmol) prepared in Example 118b and triethylsilane (23 mL) in dichloromethane (230 mL), trifluoroacetic acid (230 mL) was added at room temperature, and the reaction solution was stirred for 1 hour. The reaction solution was concentrated, and the residue was purified with silica gel chromatography (ethyl acetate/methanol=9:1) to yield the title compound as a colorless solid. A suspension of this title compound in ethyl acetate (200 mL) was further irradiated with ultrasonic wave for 20 minutes. The suspension was filtered, and crystals collected by filtration were washed with ethyl acetate and dried at 40° C. for 24 hours to yield the title compound (44.4 g, 77%) as colorless crystals.

MS (ESI) m/z: 450 [M+H]+;

$[\alpha]_D^{25}$=−51.6 (c 1.00, DMSO).

The powder x-ray diffraction pattern of the crystals is shown in Figure 1. Peaks having relative intensity of 11 or larger with the maximum peak intensity as 100 in Figure 1 are shown in Table 2.

TABLE 2

| Peak No. | 2θ | d value | Relative intensity |
|---|---|---|---|
| 1 | 7.30 | 12.10 | 48 |
| 2 | 14.64 | 6.05 | 21 |
| 3 | 15.30 | 5.79 | 18 |
| 4 | 16.60 | 5.34 | 11 |
| 5 | 19.40 | 4.57 | 13 |
| 6 | 21.40 | 4.15 | 25 |
| 7 | 22.06 | 4.03 | 35 |
| 8 | 23.40 | 3.80 | 100 |
| 9 | 23.82 | 3.73 | 21 |
| 10 | 29.54 | 3.02 | 49 |
| 11 | 30.58 | 2.92 | 51 |

Example 119

4-{[(1S,2R)-2-(1-Ethyl-1H-pyrazol-5-yl)cyclopentyl]oxy}-2,3-difluoro-N-(pyrimidin-4-yl)benzenesulfonamide

[Formula 137]

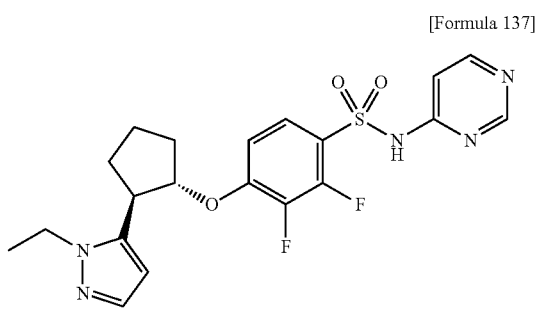 [SMILES: CCn1nccc1[C@H]1CCC[C@@H]1Oc1ccc(S(=O)(=O)Nc2ccncn2)c(F)c1F]

(119a) (1S,2R)-2-(1-Ethyl-1H-pyrazol-5-yl)cyclopentanol

The (1S*,2R*)-2-(1-ethyl-1H-pyrazol-5-yl)cyclopentanol prepared in Example 37a was optically resolved with CHIRALPAK AD-H (Daicel Corp.; hexane/ethanol=8:2) to yield the title compound as a colorless oil.

$[\alpha]_D^{25}$=56.1 (c 1.00, MeOH).

(119b) N-(2,4-Dimethoxybenzyl)-4-{[(1S,2R)-2-(1-ethyl-1H-pyrazol-5-yl)cyclopentyl]oxy}-2,3-difluoro-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (99.1 g, 226 mmol) prepared in Example 30a, the (1S,2R)-2-(1-ethyl-1H-pyrazol-5-yl)cyclopentanol (40.7 g, 226 mol) prepared in Example 119a, sodium hydride (63%; 12.9 g, 339 mmol) and DMF (1.2 L), to yield the title compound (100.3 g, 74%) as a colorless oil.

(119c) 4-{[(1S,2R)-2-(1-Ethyl-1H-pyrazol-5-yl)cyclopentyl]oxy}-2,3-difluoro-N-(pyrimidin-4-yl)benzenesulfonamide To the N-(2,4-dimethoxybenzyl)-4-{[(1S,2R)-2-(1-ethyl-1H-pyrazol-5-yl)cyclopentyl]oxy}-2,3-difluoro-N-(pyrimidin-4-yl)benzenesulfonamide (100.3 g, 167 mmol) prepared in Example 119b and triethylsilane (30 mL) in dichloromethane (300 mL), trifluoroacetic acid (300 mL) was added with cooling on ice, and the reaction solution was stirred at room temperature for 1 hour. The reaction solution was concentrated, and the residue was purified with silica gel chromatography (ethyl acetate/methanol=9:1) to yield the title compound as a colorless solid. A suspension of this title compound in ethyl acetate (200 mL) was further irradiated with ultrasonic wave for 20 minutes. The suspension was filtered, and crystals collected by filtration were washed with ethyl acetate and dried at 40° C. for 24 hours to yield the title compound (32.9 g, 44%) as colorless crystals.

$^1$H-NMR (500 MHz, DMSO-$d_6$) δ ppm: 1.25 (3H, t, J=7.0 Hz), 1.64-1.91 (4H, m), 2.19-2.32 (2H, m), 3.47-3.50 (1H, m), 4.09 (2H, q, J=7.0 Hz), 4.92-4.96 (1H, m), 6.17 (1H, d, J=1.5 Hz), 6.97 (1H, brs), 7.07 (1H, t, J=7.7 Hz), 7.34 (1H, d, J=1.5 Hz), 7.60-7.64 (1H, m), 8.23 (1H, brs), 8.55 (1H, s), 13.2 (1H, brs).

MS (ESI) m/z: 450 [M+H]+;

$[\alpha]_D^{25}$=50.4 (c 1.05, DMSO).

Figure 2:
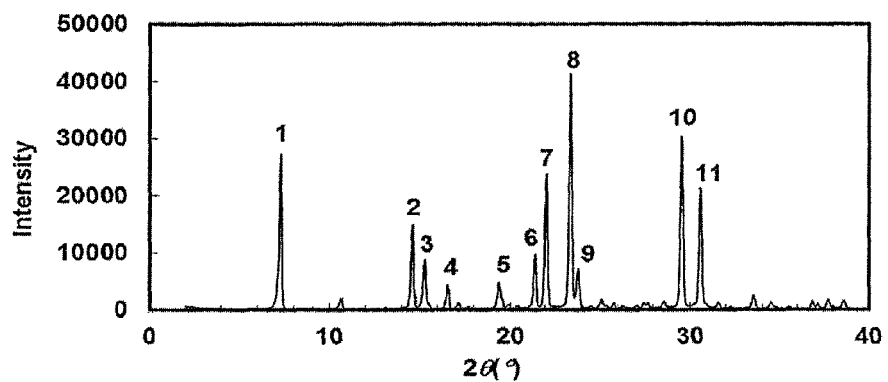
Figure 2 is a diagram showing the powder x-ray diffraction of 4-{[(1S,2R)-2-(1-ethyl-1H-pyrazol-5-yl)cyclopentyl]oxy}-2,3-difluoro-N-(pyrimidin-4-yl)benzenesulfonamide in a free form.

The powder x-ray diffraction pattern of the crystals is shown in Figure 2. Peaks having relative intensity of 11 or larger with the maximum peak intensity as 100 in Figure 2 are shown in Table 3.

TABLE 3

| Peak No. | 2θ | d value | Relative intensity |
|---|---|---|---|
| 1 | 7.30 | 12.10 | 66 |
| 2 | 14.64 | 6.05 | 36 |
| 3 | 15.30 | 5.79 | 22 |
| 4 | 16.56 | 5.35 | 11 |
| 5 | 19.40 | 4.57 | 12 |
| 6 | 21.40 | 4.15 | 24 |
| 7 | 22.04 | 4.03 | 58 |
| 8 | 23.38 | 3.80 | 100 |
| 9 | 23.82 | 3.73 | 18 |
| 10 | 29.54 | 3.02 | 73 |
| 11 | 30.58 | 2.92 | 52 |

Example 120

2,5-Difluoro-4-{[(1S*,2R*,4S*)-4-methoxy-2-(1-methyl-1H-pyrazol-5-yl)cyclopentyl]oxy}-N-(pyrimidin-4-yl)benzenesulfonamide

[Formula 138]

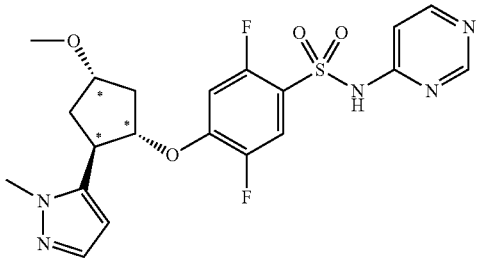

(120a) (1S*,2R*,4S*)-4-{[Tert-butyl(dimethyl)silyl]oxy}-2-(1-methyl-1H-pyrazol-5-yl)cyclopentanol The reaction and aftertreatment were conducted in the same manner as in Example 4a by using 1-methylpyrazole (2.13 g, 25.9 mmol), n-butyl lithium (2.69 M solution in hexane; 10.3 mL, 27.7 mmol), tert-butyl(dimethyl) [(1R*,3S*,5S*)-6-oxabicyclo[3.1.0]hex-3-yloxy]silane (WO 2012/21591; 5.56 g, 25.9 mmol) and THF (150 mL), to yield the title compound (1.42 g, 18%) as a colorless solid.

¹H-NMR (500 MHz, CDCl₃) δ ppm: 0.12 (6H, s), 0.92 (9H, s), 1.85-2.02 (3H, m), 2.29-2.34 (1H, m), 3.46-3.50 (1H, m), 3.92 (3H, s), 4.10-4.13 (1H, m), 4.52-4.54 (1H, m), 5.90 (1H, d, J=2.0 Hz), 7.37 (1H, d, J=1.5 Hz).

(120b) 4-{[(1S*,2R*,4S*)-4-{[Tert-butyl(dimethyl)silyl]oxy}-2-(1-methyl-1H-pyrazol-5-yl)cyclopentyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (1.16 g, 2.64 mmol) prepared in Example 14b, the (1S,2R,4S)-4-{[tert-butyl(dimethyl)silyl]oxy}-2-(1-methyl-1H-pyrazol-5-yl)cyclopentanol (710 mg, 2.39 mmol) prepared in Example 120a, sodium hydride (63%; 137 mg, 3.60 mmol) and DMF (5.0 mL), to yield the title compound (1.37 g, 80%) as a colorless oil.

¹H-NMR (500 MHz, CDCl₃) δ ppm: 0.05 (3H, s), 0.07 (3H, s), 0.89 (9H, s), 1.81-1.85 (1H, m), 1.90-1.98 (1H, m), 2.17-2.22 (1H, m), 2.52-2.58 (1H, m), 3.76 (3H, s), 3.79 (3H, s), 3.88-3.93 (1H, m), 3.90 (3H, s), 4.45-4.47 (1H, m), 4.51-4.55 (1H, m), 5.22 (2H, s), 6.02 (1H, d, J=2.0 Hz), 6.40-6.42 (2H, m), 6.46 (1H, dd, J=6.4, 11.2 Hz), 7.17-7.20 (2H, m), 7.39 (1H, d, J=1.0 Hz), 7.76 (1H, dd, J=6.8, 10.3 Hz), 8.45 (1H, d, J=6.4 Hz), 8.78 (1H, s).

(120c) N-(2,4-dimethoxybenzyl)-2,5-difluoro-4-{[(1S*,2R*,4S*)-4-hydroxy-2-(1-methyl-1H-pyrazol-5-yl)cyclopentyl]oxy}-N-(pyrimidin-4-yl)benzenesulfonamide A solution of the 4-{[(1S*,2R*,4S*)-4-{[tert-butyl(dimethyl)silyl]oxy}-2-(1-methyl-1H-pyrazol-5-yl)cyclopentyl]oxy}-N-(2,4-dimethoxybenzyl)-2,5-difluoro-N-(pyrimidin-4-yl)benzenesulfonamide (1.25 g, 1.75 mmol) prepared in Example 120b and tetrabutyl ammonium fluoride (1.0 M solution in THF; 5.24 mL, 5.25 mmol) in THF (8.0 mL) was stirred at room temperature for 3 hours. To the reaction solution, 1 M hydrochloric acid (10 mL) was added, followed by extraction with ethyl acetate (100 mL). The thus obtained organic layer was dried over anhydrous sodium sulfate. After vacuum concentration, the residue was purified with silica gel chromatography (methylene chloride/methanol) to yield the title compound (1.16 g, 99%) as a yellow oil.

¹H-NMR (500 MHz, CDCl₃) δ ppm: 1.92-2.03 (2H, m), 2.33-2.37 (1H, m), 2.59-2.65 (1H, m), 3.77 (3H, s), 3.80 (3H, s), 3.90 (3H, s), 3.93-3.98 (1H, m), 4.56-4.59 (2H, m), 5.22 (1H, d, J=17.1 Hz), 5.26 (1H, d, J=17.1 Hz), 6.04 (1H, d, 3-2.0 Hz), 6.40-6.42 (2H, m), 6.49 (1H, dd, J=6.4, 10.7 Hz), 7.17-7.20 (2H, m), 7.40 (1H, d, J=2.0 Hz), 7.75 (1H, dd, J=6.4, 9.8 Hz), 8.46 (1H, d, J=5.9 Hz), 8.78 (1H, d, J=1.0 Hz).

(120d) N-(2,4-dimethoxybenzyl)-2,5-difluoro-4-{[(1S*,2R*,4S*)-4-methoxy-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,5-difluoro-4-{[(1S*,2R*,4S*)-4-hydroxy-2-(1-methyl-1H-pyrazol-5-yl)cyclopentyl]oxy}-N-(pyrimidin-4-yl)benzenesulfonamide (114 mg, 0.185 mmol) prepared in Example 120c, dimethyl sulfate (17.9 L, 0.189 mmol), sodium hydride (63%; 10.5 mg, 0.276 mmol) and THF (2.0 mL), to yield the title compound (60.0 mg, 51%) as a colorless oil.

¹H-NMR (500 MHz, CDCl₃) δ ppm: 1.90-1.98 (2H, m), 2.36-2.40 (1H, m), 2.55-2.60 (1H, m), 3.33 (3H, s), 3.76 (3H, s), 3.79 (3H, s), 3.79-3.82 (1H, m), 3.90 (3H, s), 3.97-3.98 (1H, m), 4.51-4.55 (1H, m), 5.21 (1H, d, J=17.8 Hz), 5.25 (1H, d, J=18.1 Hz), 6.05 (1H, s), 6.39-6.42 (2H, m), 6.46 (1H, dd, J=6.4, 11.0 Hz), 7.17-7.20 (2H, m), 7.40 (1H, s), 7.75 (1H, dd, J=6.4, 9.8 Hz), 8.46 (1H, d, J=5.9 Hz), 8.78 (1H, s).

(120e) 2,5-Difluoro-4-{[(1S*,2R*,4S*)-4-methoxy-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*,4S*)-4-methoxy-2-(1-methyl-1H-pyrazol-5-yl)cyclopentyl]oxy}-N-(pyrimidin-4-yl)benzenesulfonamide (60.0 mg, 0.0975 mmol) prepared in Example 120d, triethylsilane (0.10 mL), trifluoroacetic acid (1.0 mL) and dichloromethane (1.0 mL), to yield the title compound (40.0 mg, 88%) as a colorless solid.

$^1$H-NMR (500 MHz, CDCl$_3$) δ ppm: 1.90-1.98 (2H, m), 2.37-2.41 (1H, m), 2.59-2.63 (1H, m), 3.33 (3H, s), 3.77-3.81 (1H, m), 3.89 (3H, s), 3.99-4.00 (1H, m), 4.53-4.58 (1H, m), 6.08 (1H, m), 6.56 (1H, dd, J=6.4, 11.0 Hz), 7.13 (1H, brs), 7.39 (1H, s), 7.75 (1H, dd, J=6.4, 10.0 Hz), 8.32 (1H, s), 8.61 (1H, s).

MS (FAB) m/z: 466 [M+H]+.

Example 121

2,5-Difluoro-4-{[(1S*,2R*,4R*)-4-methoxy-2-(1-methyl-1H-pyrazol-5-yl)cyclopentyl]oxy}-N-(pyrimidin-4-yl)benzenesulfonamide

[Formula 139]

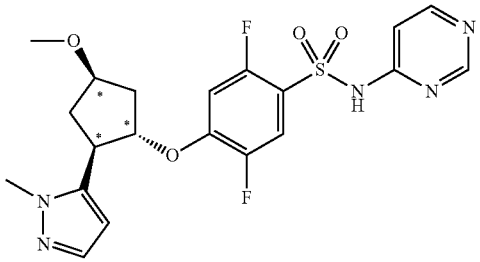

(121a) (1S*,2R*,4R*)-4-{[Tert-butyl(dimethyl)silyl]oxy}-2-(1-methyl-1H-pyrazol-5-yl)cyclopentanol The reaction and aftertreatment were conducted in the same manner as in Example 4a by using 1-methylpyrazole (1.13 g, 13.8 mmol), n-butyl lithium (2.69 M solution in hexane, 5.47 mL, 14.7 mmol), tert-butyl(dimethyl)[(1R*,3S*,5S*)-6-oxabicyclo[3.1.0]hex-3-yloxy]silane (WO 2012/21591; 2.95 g, 13.8 mmol) and THF (90 mL), to yield the title compound (710 mg, 17%) as a colorless solid.

$^1$H-NMR (500 MHz, CDCl$_3$) δ ppm: 0.06 (3H, s), 0.07 (3H, s), 0.89 (9H, s), 1.67-1.73 (1H, m), 1.89-1.93 (1H, m), 2.02-2.07 (1H, m), 2.46-2.52 (1H, m), 2.96-3.01 (2H, m), 3.78 (3H, s), 4.37-4.45 (2H, m), 6.11 (1H, d, J=1.5 Hz), 7.34 (1H, s).

(121b) 4-{[(1S*,2R*,4R*)-4-{[Tert-butyl(dimethyl)silyl]oxy}-2-(1-methyl-1H-pyrazol-5-yl)cyclopentyl]oxy}-N-(2,4-dimethoxybenzyl)-2,5-difluoro-N-(pyrimidin-4-yl)benzenesulfonamide The reaction and aftertreatment were conducted in the same manner as in Example 1a by using the N-(2,4-dimethoxybenzyl)-2,4,5-trifluoro-N-(pyrimidin-4-yl)benzenesulfonamide (1.16 g, 2.64 mmol) prepared in Example 14b, the (1S*,2R*,4R*)-4-{[(tert-butyl(dimethyl)silyl]oxy}-2-(1-methyl-1H-pyrazol-5-yl)cyclopentanol (710 mg, 2.39 mmol) prepared in Example 121a, sodium hydride (63%; 137 mg, 3.60 mmol) and DMF (5.0 mL), to yield the title compound (1.52 g, 89%) as a colorless oil.

$^1$H-NMR (500 MHz, CDCl$_3$) δ ppm: 0.09 (6H, s), 0.91 (9H, s), 1.84-1.90 (1H, m), 2.04-2.10 (1H, m), 2.22-2.27 (1H, m), 2.53-2.58 (1H, m), 3.44-3.49 (1H, m), 3.76 (3H, s), 3.79 (3H, s), 3.85 (3H, s), 4.49-4.54 (1H, m), 4.69-4.73 (1H, m), 5.21 (1H, d, J=17.1 Hz), 5.25 (1H, d, J=17.1 Hz), 6.16 (1H, d, J=2.0 Hz), 6.40-6.42 (2H, m), 6.48 (1H, dd, J=5.9, 10.7 Hz), 7.16 (1H, dd, J=1.5, 5.9 Hz), 7.20 (1H, d, J=8.3 Hz), 7.40 (1H, d, J=2.0 Hz), 7.76 (1H, dd, J=6.8, 10.3 Hz), 8.45 (1H, d, J=5.9 Hz), 8.78 (1H, d, J=1.0 Hz).

(121c) N-(2,4-Dimethoxybenzyl)-2,5-difluoro-4-{[(1S*,2R*,4R*)-4-hydroxy-2-(1-methyl-1H-pyrazol-5-yl)cyclopentyl]oxy}-N-(pyrimidin-4-yl)benzenesulfonamide The reaction and aftertreatment were conducted in the same manner as in Example 120c by using the 4-{[(1S*,2R*,4R*)-4-{[tert-butyl(dimethyl)silyl]oxy}-2-(1-methyl-1H-pyrazol-5-yl)cyclopentyl]oxy}-N-(2,4-dimethoxybenzyl)-2,5-difluoro-N-(pyrimidin-4-yl)benzenesulfonamide (1.39 g, 1.94 mmol) prepared in Example 121b, tetrabutyl ammonium fluoride (1.0 M solution in THF; 5.82 mL, 5.82 mmol) and THF (8.0 mL), to yield the title compound (1.72 g, 99%) as a yellow oil.

$^1$H-NMR (500 MHz, CDCl$_3$) δ ppm: 1.96-2.07 (2H, m), 2.48-2.53 (1H, m), 2.59-2.62 (1H, m), 3.43-3.46 (1H, m), 3.76 (3H, s), 3.80 (3H, s), 3.86 (3H, s), 4.57-4.58 (1H, m), 4.85-4.88 (1H, m), 5.22 (2H, s), 6.22 (1H, d, J=2.0 Hz), 6.38-6.42 (2H, m), 6.77-6.81 (1H, m), 7.13-7.18 (2H, m), 7.35-7.36 (1H, m), 7.69-7.72 (1H, m), 8.43-8.45 (1H, m), 8.77 (1H, s).

(121d) N-(2,4-Dimethoxybenzyl)-2,5-difluoro-4-{[(1S*,2R*,4R*)-4-methoxy-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,5-difluoro-4-{[(1S*,2R*,4R*)-4-hydroxy-2-(1-methyl-1H-pyrazol-5-yl)cyclopentyl]oxy}-N-(pyrimidin-4-yl)benzenesulfonamide (120 mg, 0.199 mmol) prepared in Example 121c, dimethyl sulfate (18.8 L, 0.199 mmol), sodium hydride (63%; 11.1 mg, 0.291 mmol) and THF (2.0 mL), to yield the title compound (65.0 mg, 53%) as a colorless oil.

$^1$H-NMR (400 MHz, CDCl$_3$) δ ppm: 1.87-1.95 (1H, m), 2.05-2.12 (1H, m), 2.31-2.38 (1H, m), 2.60-2.68 (1H, m), 3.35 (3H, s), 3.46-3.53 (1H, m), 3.77 (3H, s), 3.80 (3H, s), 3.86 (3H, s), 4.05-4.14 (1H, m), 4.66-4.71 (1H, m), 5.21 (1H, d, J=16.8 Hz), 5.25 (1H, d, J=16.8 Hz), 6.15 (1H, d, J=2.0 Hz), 6.40-6.42 (2H, m), 6.51 (1H, dd, J=6.3, 11.0 Hz), 7.16 (1H, dd, J=1.2, 7.0 Hz), 7.20 (1H, d, J=8.6 Hz), 7.41 (1H, d, J=2.0 Hz), 7.76 (1H, dd, J=6.3, 9.8 Hz), 8.46 (1H, d, J=5.9 Hz), 8.78 (1H, d, J=1.1 Hz).

(121e) 2,5-Difluoro-4-{[(1S*,2R*,4R*)-4-methoxy-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,5-difluoro-4-{[(1S*,2R*,4R*)-4-methoxy-2-(1-methyl-1H-pyrazol-5-yl)cyclopentyl]oxy}-N-(pyrimidin-4-yl)benzenesulfonamide (65.0 mg, 0.106 mmol) prepared in Example 121d, triethylsilane (0.10 mL), trifluoroacetic acid (1.0 mL) and dichloromethane (1.0 mL), to yield the title compound (40.0 mg, 81%) as a colorless solid.

¹H-NMR (500 MHz, CDCl₃) δ ppm: 1.87-1.93 (1H, m), 2.05-2.11 (1H, m), 2.33-2.38 (1H, m), 2.61-2.67 (1H, m), 3.35 (3H, s), 3.42-3.48 (1H, m), 3.84 (3H, s), 4.05-4.10 (1H, m), 4.68-4.72 (1H, m), 6.15 (1H, s), 6.58 (1H, dd, J=6.4, 11.2 Hz), 7.17 (1H, brs), 7.39 (1H, d, J=2.0 Hz), 7.74 (1H, dd, J=6.8, 10.3 Hz), 8.35 (1H, brs), 8.67 (1H, brs).

MS (FAB) m/z: 466 [M+H]+.

Example 122

5-Chloro-2-fluoro-4-{[(1S,2R)-2-(1-methyl-1H-pyrazol-5-yl)cyclohexyl]oxy}-N-(pyrimidin-4-yl)benzenesulfonamide

[Formula 140]

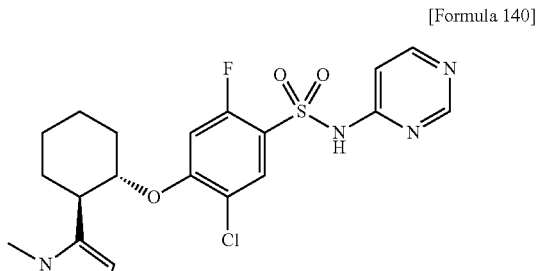

(122a) (1S,2R)-2-(1-Methyl-1H-pyrazol-5-yl)cyclohexanol

The (1S*,2R*)-2-(1-methyl-1H-pyrazol-5-yl)cyclohexanol prepared in Example 4a was optically resolved with CHIRALPAK IB (Daicel Corp.; hexane/ethanol=9:1) to yield the title compound as a colorless oil.

$[\alpha]_D^{25}$=33.3 (c 0.916, MeOH).

(122b) 5-Chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (0.60 g, 1.32 mmol) prepared in Example 20a, the (1S,2R)-2-(1-methyl-1H-pyrazol-5-yl)cyclohexanol (0.19 g, 1.05 mmol) prepared in Example 122a, sodium hydride (63%; 0.050 g, 1.32 mmol), DMF (6.6 mL) and water (0.020 mL), to yield the title compound (0.371 g, 50%) as a colorless solid.

(122c) 5-Chloro-2-fluoro-4-{[(1S,2R)-2-(1-methyl-1H-pyrazol-5-yl)cyclohexyl]oxy}-N-(pyrimidin-4-yl)benzenesulfonamide To a solution of the 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide (0.371 g, 0.602 mmol) prepared in Example 122b and triethylsilane (0.48 mL, 3.01 mmol) in dichloromethane (6.0 mL), trifluoroacetic acid (0.60 mL) was added at room temperature, and the reaction solution was stirred for 1 hour. The reaction solution was concentrated, and the residue was purified with silica gel chromatography (ethyl acetate/methanol=6:1) to yield the title compound (0.28 g, 99%) as a colorless solid.

$[\alpha]_D^{25}$=2.28 (c 1.05, DMSO).

A suspension of the title compound (300 mg, 0.644 mmol) in ethyl acetate (3.0 mL) was stirred for 2 hours under heated reflux. The reaction solution was cooled, and hexane (5.0 mL) was then added to the reaction solution. The suspension was filtered, and crystals collected by filtration were washed with hexane to yield the title compound (290 mg, 97%) as colorless crystals 1.

Figure 3:
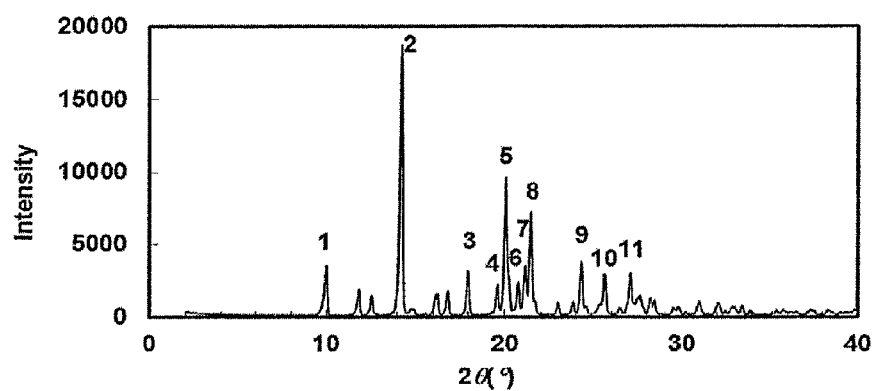
Figure 3 is a diagram showing the powder x-ray diffraction of colorless crystals 1 of 5-chloro-2-fluoro-4-{[(1S,2R)-2-(1-methyl-1H-pyrazol-5-yl)cyclohexyl]oxy}-N-(pyrimidin-4-yl)benzenesulfonamide in a free form.

The powder x-ray diffraction pattern of the colorless crystals 1 is shown in Figure 3. Peaks having relative intensity of 12 of larger with the maximum peak intensity as 100 in Figure 3 are shown in Table 4.

TABLE 4

| Peak No. | 2θ | d value | Relative intensity |
|---|---|---|---|
| 1 | 9.98 | 8.86 | 19 |
| 2 | 14.24 | 6.21 | 100 |
| 3 | 17.98 | 4.93 | 17 |
| 4 | 19.60 | 4.53 | 12 |
| 5 | 20.06 | 4.42 | 52 |
| 6 | 20.76 | 4.28 | 13 |
| 7 | 21.16 | 4.20 | 19 |
| 8 | 21.46 | 4.14 | 39 |
| 9 | 24.34 | 3.65 | 21 |
| 10 | 25.64 | 3.47 | 16 |
| 11 | 27.10 | 3.29 | 17 |

The title compound (300 mg, 0.644 mmol) was further dissolved in a dichloromethane/methanol mixed solution (10:1, 4.0 mL), and this solution was concentrated. To the residue, hexane (5.0 mL) was added, and this suspension was irradiated with ultrasonic wave for 30 minutes. The suspension was filtered, and crystals collected by filtration were washed with hexane to yield the title compound (295 mg, 98%) as colorless crystals 2.

Figure 4:
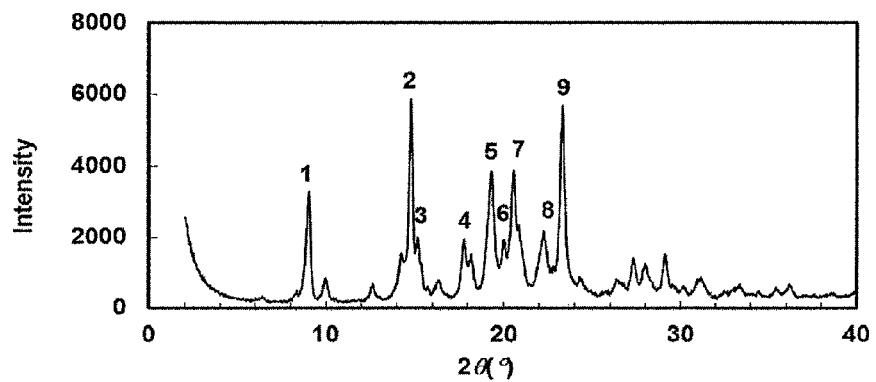
Figure 4 is a diagram showing the powder x-ray diffraction of colorless crystals 2 of 5-chloro-2-fluoro-4-{[(1S,2R)-2-(1-methyl-1H-pyrazol-5-yl)cyclohexyl]oxy}-N-(pyrimidin-4-yl)benzenesulfonamide in a free form.

The powder x-ray diffraction pattern of the colorless crystals 2 is shown in Figure 4. Peaks having relative intensity of 30 or larger with the maximum peak intensity as 100 in Figure 4 are shown in Table 5.

TABLE 5

| Peak No. | 2θ | d value | Relative intensity |
|---|---|---|---|
| 1 | 9.02 | 9.80 | 55 |
| 2 | 14.82 | 5.97 | 100 |
| 3 | 15.22 | 5.82 | 30 |
| 4 | 17.76 | 4.99 | 34 |
| 5 | 19.30 | 4.60 | 66 |
| 6 | 20.00 | 4.44 | 32 |
| 7 | 20.52 | 4.32 | 64 |
| 8 | 22.26 | 3.99 | 36 |
| 9 | 23.32 | 3.81 | 98 |

Example 123

(1S,2R)-2-(1-Methyl-1H-pyrazol-5-yl)cyclohexanol

[Formula 141]

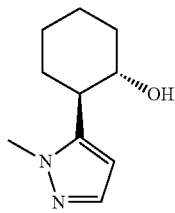

(123a) 1-(1-Methyl-1H-pyrazol-5-yl)cyclohexanol

To a solution of 1-methylpyrazole (6.0 g, 73.1 mmol) and N,N,N',N'-tetramethylethylenediamine (10.96 mL, 73.1 mmol) in THF (125 mL), butyl lithium (2.69 M solution in hexane; 31.8 mL, 85.5 mmol) was added at −78° C. The reaction solution was stirred at −78° C. for 30 minutes. Then, cyclohexanone (9.06 mL, 87.7 mmol) was added thereto, and the mixture was stirred at room temperature for 15 hours. To the reaction solution, water (500 mL) was added, followed by extraction with ethyl acetate (250 mL). The thus obtained organic layer was dried over anhydrous sodium sulfate. After vacuum concentration, the residue was purified with silica gel chromatography (hexane/ethyl acetate=3:21 to yield the title compound (11.32 g, 86%) as a colorless oil.

$^1$H-NMR (500 MHz, CDCl$_3$) δ ppm: 1.60-1.84 (8H, m), 1.99-2.01 (2H, m), 4.05 (3H, s), 6.08 (1H, d, J=2.0 Hz), 7.32 (1H, d, J=1.5 Hz).

(123b) 5-(Cyclohex-1-en-1-yl)-1-methyl-1H-pyrazole

The reaction and aftertreatment were conducted in the same manner as in Example 99b by using the 1-(1-methyl-1H-pyrazol-5-yl)cyclohexanol (11.32 g, 62.8 mmol) prepared in Example 123a, p-toluenesulfonic acid monohydrate (17.9 g, 94.1 mmol) and toluene (100 mL), to yield the title compound (8.89 g, 87%) as a colorless oil.

$^1$H-NMR (500 MHz, CDCl$_3$) δ ppm: 1.66-1.78 (4H, m), 2.19-2.28 (4H, m), 3.85 (3H, s), 5.86-5.88 (1H, m), 6.08 (1H, d, J=1.5 Hz), 7.40 (1H, d, J=2.0 Hz).

(123c) (1S,2S)-1-(1-Methyl-1H-pyrazol-5-yl)cyclohexane-1,2-diol

The reaction and aftertreatment were conducted in the same manner as in Example 102a by using the 5-(cyclohex-1-en-1-yl)-1-methyl-1H-pyrazole (2.66 g, 16.4 mmol) prepared in Example 123b, methanesulfonamide (1.56 g, 16.4 mmol), t-butanol (20 mL), water (20 mL) and AD-mixα (Sigma-Aldrich Corp.; 23.0 g), to yield the title compound (3.22 g, 99%) as a colorless solid.

$^1$H-NMR (400 MHz, CDCl$_3$) δ ppm: 1.29-1.89 (6H, m), 2.09-2.09 (1H, m), 2.16-2.22 (1H, m), 4.05-4.10 (1H, m), 4.07 (3H, s), 4.80 (1H, brs), 6.08 (1H, d, J=2.0 Hz), 7.39 (1H, d, J=2.0 Hz).

(123d) 1-Methyl-5-[(1S,6S)-7-oxabicyclo[4.1.0]hept-1-yl]-1H-pyrazole

The reaction and aftertreatment were conducted in the same manner as in Example 102b by using the (1S,2S)-1-(1-methyl-1H-pyrazol-5-yl)cyclohexane-1,2-diol (423 mg, 2.15 mmol) prepared in Example 123c, trimethyl orthoacetate (0.688 mL, 5.38 mmol), p-toluenesulfonic acid (20.5 mg, 0.11 mmol), dichloromethane (6.0 mL), acetonitrile (6.0 mL), lithium bromide (466 mg, 5.38 mmol), acetyl bromide (0.398 mL, 5.38 mmol), methanol (6.0 mL) and potassium carbonate (743 mg, 5.38 mmol), to yield the title compound (180 mg, 47%).

$^1$H-NMR (400 MHz, CDCl$_3$) δ ppm: 1.29-1.61 (4H, m), 1.96-2.24 (1H, m), 3.27-3.29 (1H, m), 3.92 (3H, s), 4.80 (1H, brs), 6.13 (1H, d, J=1.6 Hz), 7.36 (1H, d, J=1.6 Hz).

(123e) (1S,2R)-2-(1-Methyl-1H-pyrazol-5-yl)cyclohexanol

The reaction and aftertreatment were conducted in the same manner as in Example 102c by using the 1-methyl-5-[(1S,6S)-7-oxabicyclo[4.1.0]hept-1-yl]-1H-pyrazole (0.21 g, 1.17 mmol) prepared in Example 123d, Raney nickel (2.0 g) and isopropanol (5.9 mL), to yield the title compound (0.060 g, 28%).

Example 124

2-Fluoro-4-{[(1S,2R)-2-(1-methyl-1H-pyrazol-5-yl)cyclopentyl]oxy}-N-(pyrimidin-4-yl)benzenesulfonamide

[Formula 142]

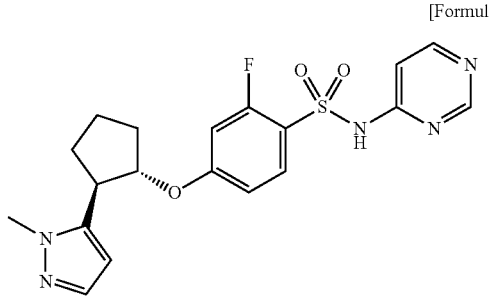

(124a) (1S,2R)-2-(1-Methyl-1H-pyrazol-5-yl)cyclopentanol

The (1S*,2R*)-2-(1-methyl-1H-pyrazol-5-yl)cyclopentanol prepared in Example 8a was optically resolved with CHIRALPAK IC (Daicel Corp.; hexane/ethanol=8:2) to yield the title compound as a colorless oil.

[α]$_D^{25}$=59.0 (c 0.30, MeOH).

(124b) N-(2,4-dimethoxybenzyl)-2-fluoro-4-{[(1S,2R)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (191 mg, 0.45 mmol) prepared in Example 29a, the (1S,2R)-2-(1-methyl-1H-pyrazol-5-yl)cyclopentanol (68 mg, 0.38 mmol) prepared in Example 124a, sodium hydride (63%; 28.7 mg, 0.75 mmol) and DMF (2.0 mL), to yield the title compound (198 mg, 93%) as a colorless oil.

(124c) 2-Fluoro-4-{[(1S,2R)-2-(1-methyl-1H-pyrazol-5-yl)cyclopentyl]oxy}-N-(pyrimidin-4-yl)benzenesulfonamide To a solution of the N-(2,4-dimethoxybenzyl)-2-fluoro-4-{[(1S,2R)-2-(1-methyl-1H-pyrazol-5-yl)cyclopentyl]oxy}-N-(pyrimidin-4-yl)benzenesulfonamide (8.35 g, 14.7 mmol) prepared in Example 124b and triethylsilane (11.75 mL, 73.6 mmol) in dichloromethane (147 mL), trifluoroacetic acid (14.7 mL) was added at room temperature, and the reaction solution was stirred for 1 hour. The reaction solution was concentrated, and the residue was purified with silica gel chromatography (ethyl acetate) to yield the title compound as a colorless solid. A suspension of this title compound in a hexane/dichloromethane mixed solvent was further irradiated with ultrasonic wave for 1 hour. The suspension was filtered, and crystals-collected by filtration were washed with hexane and dried at 40° C. for 24 hours to yield the title compound (5.95 g, 97%) as colorless crystals.

$[\alpha]_D^{25} = 59.7$ (c 1.01, DMSO).

Figure 5:
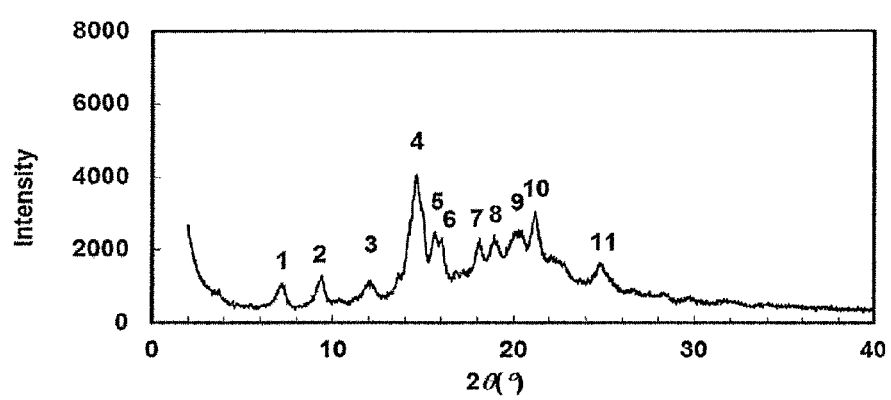
Figure 5 is a diagram showing the powder x-ray diffraction of 2-fluoro-4-{[(1S,2R)-2-(1-methyl-1H-pyrazol-5-yl)cyclopentyl]oxy}-N-(pyrimidin-4-yl)benzenesulfonamide in a free form.

The powder x-ray diffraction pattern of the crystals is shown in Figure 5. Peaks having relative intensity of 24 or larger with the maximum peak intensity as 100 in Figure 5 are shown in Table 6.

TABLE 6

| Peak No. | 2θ | d value | Relative intensity |
|---|---|---|---|
| 1 | 7.18 | 12.30 | 24 |
| 2 | 9.32 | 9.48 | 31 |
| 3 | 11.94 | 7.41 | 25 |
| 4 | 14.60 | 6.06 | 100 |
| 5 | 15.60 | 5.68 | 58 |
| 6 | 15.98 | 5.54 | 57 |
| 7 | 18.08 | 4.90 | 55 |
| 8 | 18.94 | 4.68 | 56 |
| 9 | 20.26 | 4.38 | 62 |
| 10 | 21.18 | 4.19 | 76 |
| 11 | 24.78 | 3.59 | 41 |

Example 125

4-{[(1S*,2R*)-5,5-Difluoro-2-(1-methyl-1H-pyrazol-5-yl)cyclohexyl]oxy}-2-fluoro-5-methyl-N-(1,3,4-thiadiazol-2-yl)benzenesulfonamide

[Formula 143]

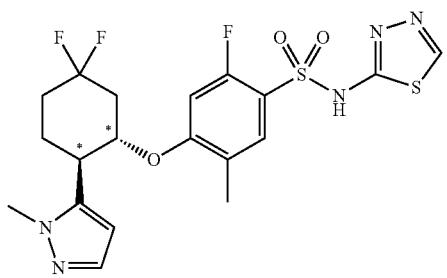

(125a) N-(2,4-dimethoxybenzyl)-2,4-difluoro-5-methyl-N-(1,3,4-thiadiazol-2-yl)benzenesulfonamide The reaction and aftertreatment were conducted in the same manner as in Example 86a by using N-(2,4-dimethoxybenzyl)-1,3,4-thiadiazol-2-amine (WO 2010/079443; 1.00 g, 3.98 mmol), lithium bis(trimethylsilyl)amide (1.0 M solution in THF; 4.78 mL, 4.78 mmol), 2,4-difluoro-5-methylbenzenesulfonyl chloride (WO 2010/079443; 0.989 g, 4.36 mmol) and THF (20 mL), to yield the title compound (1.16 g, 66%) as a colorless amorphous solid.

$^1$H-NMR (500 MHz, CDCl$_3$) δ ppm: 2.23 (3H, s), 3.71 (3H, s), 3.75 (3H, s), 5.30 (2H, s), 6.29 (1H, d, J=2.0 Hz), 6.36 (1H, dd, J=2.4, 8.3 Hz), 6.83 (1H, t, J=9.3 Hz), 7.24 (1H, d, J=8.3 Hz), 7.62 (1H, t, J=7.8 Hz), 8.80 (1H, s).

(125b) 4-{[(1S*,2R*)-5,5-Difluoro-2-(1-methyl-1H-pyrazol-5-yl)cyclohexyl]oxy}-N-(2,4-dimethoxybenzyl)-2-fluoro-5-methyl-N-(1,3,4-thiadiazol-2-yl)benzenesulfonamide The reaction and aftertreatment were conducted in the same manner as in Example 1a by using the N-(2,4-dimethoxybenzyl)-2,4-difluoro-5-methyl-N-(1,3,4-thiadiazol-2-yl)benzenesulfonamide (205 mg, 0.464 mmol) prepared in Example 125a, the (1S*,2R*)-5,5-difluoro-2-(1-methyl-1H-pyrazol-5-yl)cyclohexanol (100 mg, 0.462 mmol) prepared in Example 47b, sodium hydride (63%; 26.1 mg, 0.696 mmol), DMF (2.0 mL) and water (0.013 mL), to yield the title compound (78.8 mg, 27%) as a colorless oil.

$^1$H-NMR (500 MHz, CDCl$_3$) δ ppm: 1.89-2.11 (4H, m), 1.97 (3H, s), 2.29-2.36 (1H, m), 2.68-2.74 (1H, m), 3.07-3.12 (1H, m), 3.68 (3H, s), 3.74 (3H, s), 3.89 (3H, s), 4.36 (1H, dt, J=4.4, 10.7 Hz), 5.24 (1H, d, J=15.6 Hz), 5.29 (1H, d, J=14.6 Hz), 6.05 (1H, d, J=2.0 Hz), 6.27 (1H, d, J=2.4 Hz), 6.33-6.38 (2H, m), 7.22 (1H, d, J=8.3 Hz), 7.39 (1H, d, J=1.5 Hz), 7.47 (1H, d, J=7.3 Hz), 8.77 (1H, s).

(125c) 4-{[(1S*,2R*)-5,5-Difluoro-2-(1-methyl-1H-pyrazol-5-yl)cyclohexyl]oxy}-2-fluoro-5-methyl-N-(1,3,4-thiadiazol-2-yl)benzenesulfonamide The reaction and aftertreatment were conducted in the same manner as in Example 1b by using the 4-{[(1S*,2R*)-5,5-difluoro-2-(1-methyl-1H-pyrazol-5-yl)cyclohexyl]oxy}-N-(2,4-dimethoxybenzyl)-2-fluoro-5-methyl-N-(1,3,4-thiadiazol-2-yl)benzenesulfonamide (78.8 mg, 0.124 mmol) prepared in Example 125b, triethylsilane (0.20 mL), trifluoroacetic acid (2.0 mL) and dichloromethane (2.0 mL), to yield the title compound (48.6 mg, 81%) as a colorless solid.

$^1$H-NMR (500 MHz, CD$_3$OD) δ ppm: 1.87-2.23 (5H, m), 2.02 (3H, s), 2.65-2.70 (1H, m), 3.33-3.37 (1H, m), 3.85 (3H, s), 4.60 (1H, dt, J=4.4, 10.7 Hz), 6.20 (1H, d, J=2.0 Hz), 6.64 (1H, d, J=11.7 Hz), 7.33 (1H, d, J=2.0 Hz), 7.56 (1H, d, J=7.8 Hz), 8.52 (1H, s).

MS (ESI) m/z: 488 [M+H]+.

Example 126

4-{[(1S*,2R*)-4,4-Difluoro-2-(1-methyl-1H-pyrazol-5-yl)cyclohexyl]oxy}-2-fluoro-5-methyl-N-(pyrimidin-4-yl)benzenesulfonamide

[Formula 144]

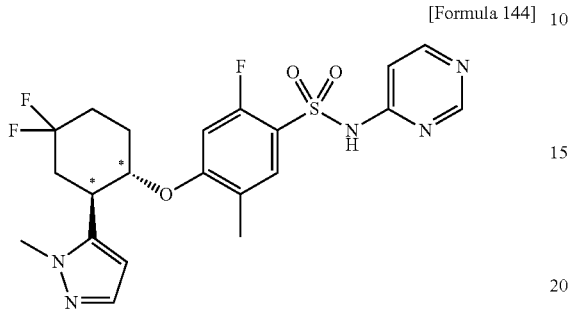

(126a) 4-{[(1S*,2R*)-4,4-Difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (193 mg, 0.44 mmol) prepared in Example 43a, the (1S*,2R*)-4,4-difluoro-2-(1-methyl-1H-pyrazol-5-yl)cyclohexanol (80.0 mg, 0.37 mmol) prepared in Example 88g sodium hydride (63%; 28.2 mg, 0.74 mmol) and DMF (1.0 mL), to yield the title compound (80.0 mg, 34%) as a colorless solid.

$^1$H-NMR (400 MHz, CDCl$_3$) δ ppm: 1.87-2.48 (6H, m), 2.04 (3H, s), 3.38-3.45 (1H, m), 3.76 (3H, s), 3.78 (3H, s), 3.90 (3H, s), 4.23 (1H, dt, J=3.1, 10.6 Hz), 5.23 (2H, s), 6.03 (1H, d, J=2.0 Hz), 6.34 (1H, d, J=11.7 Hz), 6.38-6.41 (2H, m), 7.19 (1H, d, J=8.6 Hz), 7.24-7.26 (1H, m), 7.38 (1H, d, J=2.0 Hz), 7.69 (1H, d, J=8.2 Hz), 8.43 (1H, d, J=6.3 Hz), 8.76 (1H, d, J=0.8 Hz).

(126b) 4-{[(1S*,2R*)-4,4-Difluoro-2-(1-methyl-1H-pyrazol-5-yl)cyclohexyl]oxy}-2-fluoro-5-methyl-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide (80.0 mg, 0.13 mmol) prepared in Example 126a, triethylsilane (0.10 mL), trifluoroacetic acid (1.0 mL) and dichloromethane (1.0 mL), to yield the title compound (61.0 mg, 99%) as a colorless solid.

$^1$H-NMR (400 MHz, CDCl$_3$) δ ppm: 1.83-2.45 (6H, m), 2.06 (3H, s), 3.38-3.45 (1H, m), 3.89 (3H, s), 4.24 (1H, dt, J=3.5, 9.4 Hz), 6.04 (1H, d, J=2.0 Hz), 6.39 (1H, d, J=12.1 Hz), 7.19-7.21 (1H, m), 7.38 (1H, d, J=2.0 Hz), 7.70 (1H, d, J=8.2 Hz), 8.41 (1H, d, J=5.9 Hz), 8.80 (1H, s).

MS (ESI) m/z: 482 [M+H]+.

Example 127

4-{[(1S*,2R*)-5,5-Difluoro-2-(1H-pyrazol-4-yl)cyclohexyl]oxy}-2-fluoro-5-methyl-N-(pyrimidin-4-yl)benzenesulfonamide

[Formula 145]

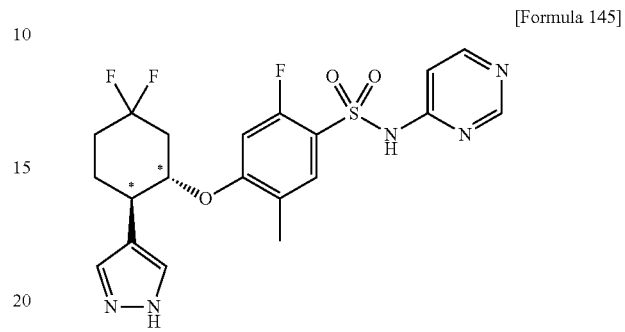

(127a) 4-({(1S*,2R*)-5,5-Difluoro-2-[1-(tetrahydro-2H-pyran-2-yl)-1H-pyrazol-4-yl]cyclohexyl}oxy)-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (0.22 g, 0.50 mmol) prepared in Example 43a, the (1S*,2R*)-5,5-difluoro-2-[1-(tetrahydro-2H-pyran-2-yl)-1H-pyrazol-4-yl]cyclohexanol (0.12 g, 0.42 mmol) prepared in Example 103c, sodium hydride (63%; 25 mg, 0.63 mmol), DMF (6.0 mL) and water (0.0075 mL), to yield the title compound (0.22 g, 76%) as a colorless solid.

$^1$H-NMR (500 MHz, CDCl$_3$) δ ppm: 1.58-1.67 (3H, m), 1.88-2.03 (6H, m), 2.15 (3H, s), 2.15-2.17 (1H, m), 2.23-2.27 (1H, m), 2.63-2.68 (1H, m), 2.93-2.98 (1H, m), 3.62-3.67 (1H, m), 3.76 (3H, s), 3.79 (3H, s), 3.97-4.00 (1H, m), 4.21-4.26 (1H, m), 5.25 (2H, s), 5.25-5.29 (1H, m), 6.38-6.41 (3H, m), 7.19 (1H, d, J=8.3 Hz), 7.26-7.27 (1H, m), 7.41-7.42 (2H, m), 7.71 (1H, d, J=8.3 Hz), 8.43 (1H, d, J=5.9 Hz), 8.77 (1H, s).

(127b) 4-{[(1S*,2R*)-5,5-Difluoro-2-(1H-pyrazol-4-yl)cyclohexyl]oxy}-2-fluoro-5-methyl-N-(pyrimidin-4-yl)benzenesulfonamide The reaction and aftertreatment were conducted in the same manner as in Example 22c by using the 4-({(1S*,2R*)-5,5-difluoro-2-[1-(tetrahydro-2H-pyran-2-yl)-1H-pyrazol-4-yl]cyclohexyl}oxy)-N-(2,4-dimethoxybenzyl)-2-fluoro-5-methyl-N-(pyrimidin-4-yl)benzenesulfonamide (0.20 g, 0.28 mmol) prepared in Example 127a, triethylsilane (0.20 mL), trifluoroacetic acid (2.0 mL), dichloromethane (2.0 mL) and methanol (2.0 mL), to yield the title compound (0.11 g, 85%) as a colorless solid.

$^1$H-NMR (500 MHz, DMSO-d$_6$) δ ppm: 1.74-1.83 (1H, m), 1.99-2.18 (4H, m), 2.07 (3H, s), 2.50-2.55 (1H, m), 2.98-3.03 (1H, m), 4.60 (1H, dt, J=4.4, 9.8 Hz), 6.90 (1H, d, J=12.7 Hz), 7.00 (1H, brs), 7.51 (2H, s), 7.64 (1H, d, J=8.8 Hz), 8.31 (1H, brs), 8.58 (1H, s).

MS (ESI) m/z: 468 [M+H]+.

Example 128

2-Fluoro-4-{[(1R,2S)-2-(1-methyl-1H-pyrazol-5-yl)cyclopentyl]oxy}-N-(pyrimidin-4-yl)benzenesulfonamide

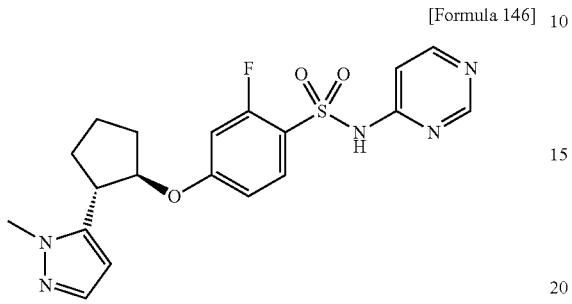

[Formula 146]

(128a) (1R,2S)-2-(1-Methyl-1H-pyrazol-5-yl)cyclopentanol

The (1S*,2R*)-2-(1-methyl-1H-pyrazol-5-yl)cyclopentanol prepared in Example 8a was optically resolved with CHIRALPAK IC (Daicel Corp.; hexane/ethanol=8:2) to yield the title compound as a colorless oil.

$[\alpha]_D^{25}$=−53.3 (c 0.35, MeOH).

(128b) N-(2,4-Dimethoxybenzyl)-2-fluoro-4-{[(1R,2S)-2-(1-methyl-1H-pyrazol-5-yl)cyclopentyl]oxy}-N-(pyrimidin-4-yl)benzenesulfonamide The reaction and aftertreatment were conducted in the same manner as in Example 1a by using the N-(2,4-dimethoxybenzyl)-2-fluoro-N-(pyrimidin-4-yl)benzenesulfonamide (421 mg, 1.00 mmol) prepared in Example 29a, the (1R,2S)-2-(1-methyl-1H-pyrazol-5-yl)cyclopentanol (150 mg, 0.83 mmol) prepared in Example 128a, sodium hydride (63%; 63.4 mg, 1.66 mmol) and DMF (2.0 mL), to yield the title compound (150 mg, 32%) as a colorless oil.

(128c) 2-Fluoro-4-{[(1R,2S)-2-(1-methyl-1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2-fluoro-4-{[(1R,2S)-2-(1-methyl-1H-pyrazol-5-yl)cyclopentyl]oxy}-N-(pyrimidin-4-yl)benzenesulfonamide (150 mg, 0.26 mmol), triethylsilane (0.10 mL), trifluoroacetic acid (1.0 mL) and dichloromethane (1.0 mL), to yield the title compound (98.0 mg, 89%) as a colorless solid.

$[\alpha]_D^{25}$=−53.0 (c 1.02, DMSO).

Example 129

4-{[(1S*,2R*)-4,4-Difluoro-2-(1-methyl-1H-pyrazol-5-yl)cyclohexyl]oxy}-2,6-difluoro-N-(pyrimidin-4-yl)benzenesulfonamide

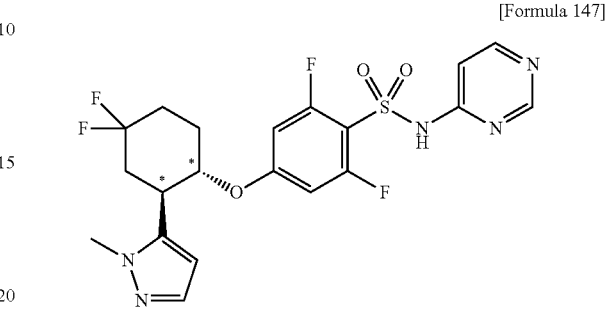

[Formula 147]

(129a) 4-{[(1S*,2R*)-4,4-Difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (150 mg, 0.34 mmol) prepared in Example 27a, the (1S*,2R*)-4,4-difluoro-2-(1-methyl-1H-pyrazol-5-yl)cyclohexanol (61.6 mg, 0.28 mmol) prepared in Example 88 g, sodium hydride (63%; 21.7 mg, 0.57 mmol) and DMF (2.0 mL), to yield the title compound (85.9 mg, 47%) as a colorless oil.

$^1$H-NMR (500 MHz, CDCl$_3$) δ ppm: 1.86-2.47 (6H, m), 3.33-3.38 (1H, m), 3.77 (3H, s), 3.81 (3H, s), 3.87 (3H, s), 4.24 (1H, dt, J=3.9, 10.3 Hz), 5.23 (2H, s), 6.04 (1H, d, J=2.0 Hz), 6.30 (2H, d, J=10.3 Hz), 6.40-6.44 (2H, m), 7.12 (1H, dd, J=1.5, 6.4 Hz), 7.21 (1H, d, J=8.3 Hz), 7.38 (1H, d, J=2.0 Hz), 8.44 (1H, d, J=5.9 Hz), 8.78 (1H, d, J=1.0 Hz).

(129b) 4-{([(1S*,2R*)-4,4-Difluoro-2-(1-methyl-1H-pyrazol-5-yl)cyclohexyl]oxy}-2,6-difluoro-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide (85.9 mg, 0.14 mmol) prepared in Example 129a, triethylsilane (0.10 mL), trifluoroacetic acid (1.0 mL) and dichloromethane (1.0 mL), to yield the title compound (58.0 mg, 88%) as a colorless solid.

$^1$H-NMR (500 MHz, CDCl$_3$) δ ppm: 1.88-2.45 (6H, m), 3.33-3.38 (1H, m), 3.88 (3H, s), 4.25 (1H, dt, J=3.9, 10.3 Hz), 6.06 (1H, d, J=2.0 Hz), 6.33 (2H, d, J=10.7 Hz), 7.38-7.40 (2H, m), 8.41 (1H, d, J=6.4 Hz), 8.85 (1H, s).

MS (ESI) m/z: 486 [M+H]+.

Example 130

4-{[(1S*,2R*)-4,4-Difluoro-2-(1-methyl-1H-pyrazol-5-yl)cyclohexyl]oxy}-2-fluoro-N-(pyrimidin-4-yl)benzenesulfonamide

[Formula 148]

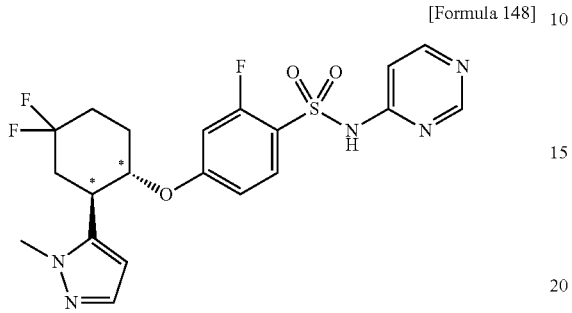

(130a) 4-{[(1S*,2R*)-4,4-Difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (167 mg, 0.40 mmol) prepared in Example 29a, the (1S*,2R*)-4,4-difluoro-2-(1-methyl-1H-pyrazol-5-yl)cyclohexanol (71.5 mg, 0.33 mmol) prepared in Example 88 g, sodium hydride (63%; 25.2 mg, 0.66 mmol) and DMF (2.0 mL), to yield the title compound (79.7 mg, 39%) as a colorless oil.

$^1$H-NMR (500 MHz, CDCl$_3$) δ ppm: 1.85-2.46 (6H, m), 3.34-3.39 (1H, m), 3.76 (3H, s), 3.79 (3H, s), 3.89 (3H, s), 4.28 (1H, dt, J=3.9, 10.3 Hz), 5.23 (2H, s), 6.04 (1H, d, J=2.0 Hz), 6.39-6.45 (3H, m), 6.59 (1H, dd, J=2.4, 11.2 Hz), 7.17-7.20 (2H, m), 7.36 (1H, d, J=1.5 Hz), 7.89 (1H, t, J=8.8 Hz), 8.42 (1H, d, J=5.9 Hz), 8.75 (1H, s).

(130b) 4-{[(1S*,2R*)-4,4-Difluoro-2-(1-methyl-1H-pyrazol-5-yl)cyclohexyl]oxy}-2-fluoro-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide (79.7 mg, 0.13 mmol) prepared in Example 130a, triethylsilane (0.10 mL), trifluoroacetic acid (1.0 mL) and dichloromethane (1.0 mL), to yield the title compound (60 mg, 99%) as a colorless solid.

$^1$H-NMR (500 MHz, CDCl$_3$) δ ppm: 1.85-2.47 (6H, m), 3.33-3.39 (1H, m), 3.89 (3H, s), 4.29 (1H, dt, J=3.9, 10.7 Hz), 6.06 (1H, d, J=2.0 Hz), 6.47 (1H, dd, J=2.4, 11.7 Hz), 6.60 (1H, dd, J=2.4, 6.8 Hz), 7.23 (1H, d, J=5.9 Hz), 7.37 (1H, d, J=2.0 Hz), 7.87 (1H, t, J=8.8 Hz), 8.39 (1H, brs), 8.83 (1H, brs).

MS (ESI) m/z: 468 [M+H]+.

Example 131

5-Chloro-4-{[(1S*,2R*)-4,4-difluoro-2-(1-methyl-1H-pyrazol-5-yl)cyclohexyl]oxy}-2-fluoro-N-(pyrimidin-4-yl)benzenesulfonamide

[Formula 149]

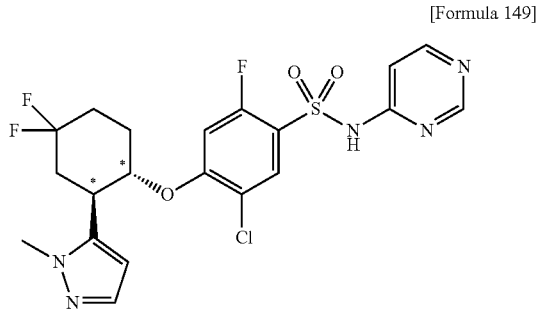 [SMILES: Cn1nccc1[C@H]1CC(F)(F)CC[C@@H]1Oc1cc(F)c(S(=O)(=O)Nc2ccncn2)cc1Cl]

(131a) 5-Chloro-4-{[(1S*,2R*)-4,4-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (167 mg, 0.37 mmol) prepared in Example 20a, the (1S*,2R*)-4,4-difluoro-2-(1-methyl-1H-pyrazol-5-yl)cyclohexanol (65.9 mg, 0.30 mmol) prepared in Example 88 g, sodium hydride (63%; 23.2 mg, 0.61 mmol) and DMF (2.0 mL), to yield the title compound (104 mg, 52%) as a colorless oil.

$^1$H-NMR (500 MHz, CDCl$_3$) δ ppm: 1.94-2.47 (6H, m), 3.44-3.50 (1H, m), 3.76 (6H, s), 3.94 (3H, s), 4.25 (1H, dt, J=4.4, 10.3 Hz), 5.19 (1H, d, J=17.6 Hz), 5.23 (1H, d, J=17.1 Hz), 6.07 (1H, d, J=2.0 Hz), 6.39-6.42 (3H, m), 7.17-7.20 (2H, m), 7.38 (1H, d, J=1.5 Hz), 7.96 (1H, d, J=7.3 Hz), 8.47 (1H, d, J=5.9 Hz), 8.79 (1H, s).

(131b) 5-Chloro-4-{[(1S*,2R*)-4,4-difluoro-2-(1-methyl-1H-pyrazol-5-yl)cyclohexyl]oxy}-2-fluoro-N-(pyrimidin-4-yl)benzenesulfonamide The reaction and aftertreatment were conducted in the same manner as in Example 1b by using the 5-chloro-4-{[(1S*,2R*)-4,4-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide (104 mg, 0.16 mmol) prepared in Example 131a, triethylsilane (0.10 mL), trifluoroacetic acid (1.0 mL) and dichloromethane (1.0 mL), to yield the title compound (72.2 mg, 90%) as a colorless solid.

$^1$H-NMR (500 MHz, CDCl$_3$) δ ppm: 1.94-2.49 (6H, m), 3.44-3.49 (1H, m), 3.94 (3H, s), 4.26 (1H, dt, J=4.4, 10.3 Hz), 6.09 (1H, d, J=2.4 Hz), 6.46 (1H, d, J=11.2 Hz), 7.26-7.27 (1H, m), 7.38 (1H, d, J=1.5 Hz), 7.97 (1H, d, J=7.3 Hz), 8.39 (1H, d, J=6.4 Hz), 8.79 (1H, s).

MS (ESI) m/z: 502 [M+H]+.

Example 132

4-{[(1S*,2R*)-4,4-Difluoro-2-(1-methyl-1H-pyrazol-5-yl)cyclopentyl]oxy}-2,3-difluoro-N-(pyrimidin-4-yl)benzenesulfonamide

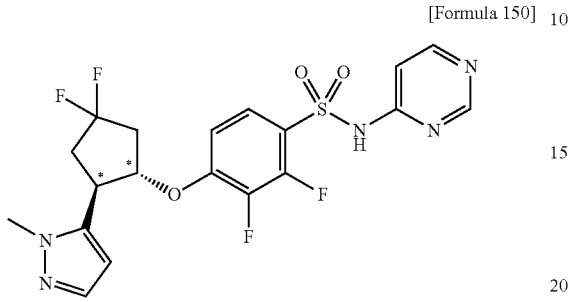

[Formula 150]

(132a) 4-{[(1S*,2R*)-4,4-Difluoro-2-(1-methyl-1H-pyrazol-5-yl)cyclopentyl]oxy}-N-(2,4-dimethoxybenzyl)-2,3-difluoro-N-(pyrimidin-4-yl)benzenesulfonamide The reaction and aftertreatment were conducted in the same manner as in Example 1a by using the N-(2,4-dimethoxybenzyl)-2,3,4-trifluoro-N-(pyrimidin-4-yl)benzenesulfonamide (233 mg, 0.530 mmol) prepared in Example 30a, the (1S*,2R*)-4,4-difluoro-2-(1-methyl-1H-pyrazol-5-yl)cyclopentanol (101 mg, 0.500 mmol) prepared in Example 107e, sodium hydride (63%; 29 mg, 0.750 mmol), DMF (2.0 mL) and water (0.780 mL), to yield the title compound (164 mg, 53%) as a colorless amorphous solid.

$^1$H-NMR (500 MHz, CDCl$_3$) δ ppm: 2.35-2.46 (2H, m), 2.75-2.96 (2H, m), 3.75-3.85 (1H, m), 3.77 (3H, s), 3.79 (3H, s), 3.89 (3H, s), 4.76 (1H, q, J=7.3 Hz), 5.21 (1H, d, J=16.6 Hz), 5.26 (1H, d, J=16.6 Hz), 6.15 (1H, d, J=2.0 Hz), 6.40-6.42 (2H, m), 6.57 (1H, t, J=7.3 Hz), 7.15-7.21 (2H, m), 7.44 (1H, d, J=2.0 Hz), 7.71-7.75 (1H, m), 8.46 (1H, d, J=5.9 Hz), 8.77 (1H, d, J=1.0 Hz).

(132b) 4-{[(1S*,2R*)-4,4-Difluoro-2-(1-methyl-1H-pyrazol-5-yl)cyclopentyl]oxy}-2,3-difluoro-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclopentyl]oxy}-N-(2,4-dimethoxybenzyl)-2,3-difluoro-N-(pyrimidin-4-yl)benzenesulfonamide (161 mg, 0.259 mmol) prepared in Example 132a, triethylsilane (0.30 mL), trifluoroacetic acid (2.0 mL) and dichloromethane (3.0 mL), to yield the title compound (118 mg, 97%) as a colorless solid.

$^1$H-NMR (500 MHz, CDCl$_3$) δ ppm: 2.35-2.47 (2H, m), 2.76-2.98 (2H, m), 3.75-3.80 (1H, m), 3.90 (3H, s), 4.75 (1H, q, J=6.8 Hz), 6.16 (1H, d, J=2.0 Hz), 6.58-6.62 (1H, m), 7.22-7.23 (1H, m), 7.46 (1H, d, J=2.0 Hz), 7.70-7.73 (1H, m), 8.38 (1H, d, J=6.4 Hz), 8.78 (1H, s).

MS (ESI) m/z: 472 [M+H]+.

Example 133

4-{[(1S*,2R*)-4,4-Difluoro-2-(1-methyl-1H-pyrazol-5-yl)cyclopentyl]oxy}-2-fluoro-5-methyl-N-(pyrimidin-4-yl)benzenesulfonamide

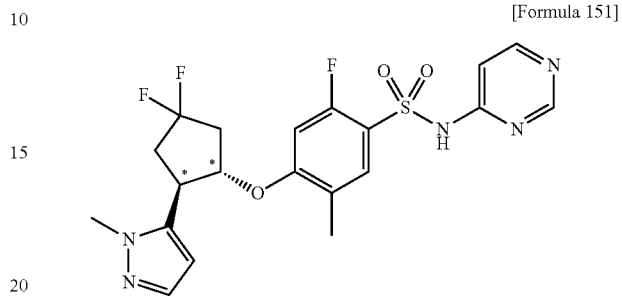

[Formula 151]

(133a) 4-{[(1S*,2R*)-4,4-Difluoro-2-(1-methyl-1H-pyrazol-5-yl)cyclopentyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (231 mg, 0.530 mmol) prepared in Example 43a, the (1S*,2R*)-4,4-Difluoro-2-(1-methyl-1H-pyrazol-5-yl)cyclopentanol (101 mg, 0.500 mmol) prepared in Example 107e, sodium hydride (63%; 29 mg, 0.750 mmol), DMF (2.0 mL) and water (0.780 mL), to yield the title compound (175 mg, 57%) as a colorless amorphous solid.

$^1$H-NMR (500 MHz, CDCl$_3$) δ ppm: 2.21 (3H, s), 2.29-2.43 (2H, m), 2.76-2.89 (2H, m), 3.69-3.81 (1H, m), 3.77 (3H, s), 3.79 (3H, s), 3.87 (3H, s), 4.70 (1H, q, J=6.8 Hz), 5.24 (2H, s), 6.14 (1H, d, J=2.0 Hz), 6.30 (1H, d, J=11.2 Hz), 6.39-6.42 (2H, m), 7.16-7.26 (2H, m), 7.44 (1H, d, J=2.0 Hz), 7.79 (1H, d, J=8.8 Hz), 8.43 (1H, d, J=6.4 Hz), 8.76 (1H, s).

(133b) 4-{[(1S*,2R*)-4,4-Difluoro-2-(1-methyl-1H-pyrazol-5-yl)cyclopentyl]oxy}-2-fluoro-5-methyl-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclopentyl]oxy}-N-(2,4-dimethoxybenzyl)-2-fluoro-5-methyl-N-(pyrimidin-4-yl)benzenesulfonamide (171 mg, 0.277 mmol) prepared in Example 133a, triethylsilane (0.30 mL), trifluoroacetic acid (2.0 mL) and dichloromethane (3.0 mL), to yield the title compound (106 mg, 82%) as a colorless solid.

$^1$H-NMR (500 MHz, CDCl$_3$) δ ppm: 2.22 (3H, s), 2.27-2.43 (2H, m), 2.75-2.89 (2H, m), 3.70-3.75 (1H, m), 3.87 (3H, s), 4.70 (1H, q, J=6.4 Hz), 6.13 (1H, d, J=2.0 Hz), 6.36 (1H, d, J=11.7 Hz), 7.22 (1H, brs), 7.43 (1H, d, J=2.0 Hz), 7.78 (1H, d, J=8.3 Hz), 8.40 (1H, d, J=6.4 Hz), 8.81 (1H, brs).

MS (ESI) m/z: 468 [M+H]+.

Example 134

5-Chloro-4-{[(1S*,2R*)-5,5-difluoro-2-(1-methyl-1H-pyrazol-5-yl)cyclohexyl]oxy}-2-fluoro-N-(1,3,4-thiadiazol-2-yl)benzenesulfonamide

[Formula 152]

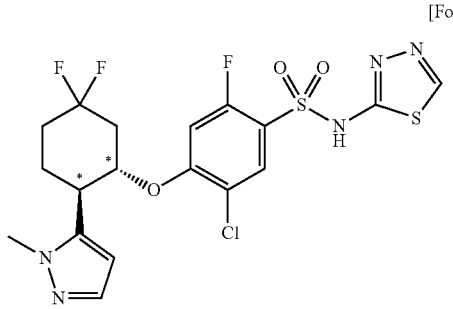

(134a) 5-Chloro-4-{[(1S*,2R*)-5,5-difluoro-2-(1-methyl-1H-pyrazol-5-yl)cyclohexyl]oxy}-N-(2,4-dimethoxybenzyl)-2-fluoro-N-(1,3,4-thiadiazol-2-yl)benzenesulfonamide The reaction and aftertreatment were conducted in the same manner as in Example 1a by using the 5-chloro-N-(2,4-dimethoxybenzyl)-2,4-difluoro-N-(1,3,4-thiadiazol-2-yl)benzenesulfonamide (280 mg, 0.606 mmol) prepared in Example 86a, the (1S*,2R*)-5,5-difluoro-2-(1-methyl-1H-pyrazol-5-yl)cyclohexanol (120 mg, 0.555 mmol) prepared in Example 47b, sodium hydride (63%; 22.1 mg, 0.589 mmol), DMF (2.0 mL) and water (0.011 mL), to yield the title compound (291 mg, 80%) as a colorless oil.

$^1$H-NMR (500 MHz, CDCl$_3$) δ ppm: 1.91-2.14 (4H, m), 2.30-2.35 (1H, m), 2.66-2.71 (1H, m), 3.12-3.17 (1H, m), 3.66 (3H, s), 3.74 (3H, s), 3.93 (3H, s), 4.34 (1H, dt, J=4.9, 10.7 Hz), 5.26 (1H, d, J=15.1 Hz), 5.32 (1H, d, J=15.1 Hz), 6.09 (1H, d, J=2.0 Hz), 6.22 (1H, d, J=2.4 Hz), 6.34 (1H, dd, J=2.4, 8.3 Hz), 6.37 (1H, d, J=11.2 Hz), 7.24 (1H, d, J=8.3 Hz), 7.39 (1H, d, J=2.0 Hz), 7.69 (1H, d, J=7.3 Hz), 8.80 (1H, s).

(134b) 5-Chloro-4-{[(1S*,2R*)-5,5-difluoro-2-(1-methyl-1H-pyrazol-5-yl)cyclohexyl]oxy}-2-fluoro-N-(1,3,4-thiadiazol-2-yl)benzenesulfonamide The reaction and aftertreatment were conducted in the same manner as in Example 1b by using the 5-chloro-4-{[(1S*,2R*)-5,5-difluoro-2-(1-methyl-1H-pyrazol-5-yl)cyclohexyl]oxy}-N-(2,4-dimethoxybenzyl)-2-fluoro-N-(1,3,4-thiadiazol-2-yl)benzenesulfonamide (291 mg, 0.442 mmol) prepared in Example 134a, triethylsilane (0.20 mL), trifluoroacetic acid (2.0 mL) and dichloromethane (2.0 mL), to yield the title compound (183 mg, 81%) as a colorless solid.

$^1$H-NMR (500 MHz, CDCl$_3$) δ ppm: 1.92-2.12 (4H, m), 2.29-2.34 (1H, m), 2.65-2.72 (1H, m), 3.12-3.17 (1H, m), 3.97 (3H, s), 4.35 (1H, dt, J=4.4, 10.7 Hz), 6.11 (1H, d, J=2.4 Hz), 6.46 (1H, d, J=11.2 Hz), 7.45 (1H, d, J=2.0 Hz), 7.92 (1H, d, J=7.3 Hz), 8.23 (1H, s).

MS (ESI) m/z: 508 [M+H]+.

Example 135

4-{[(1S*,2R*)-4,4-Difluoro-2-(1-methyl-1H-pyrazol-5-yl)cyclopentyl]oxy}-2,6-difluoro-N-(pyrimidin-4-yl)benzenesulfonamide

[Formula 153]

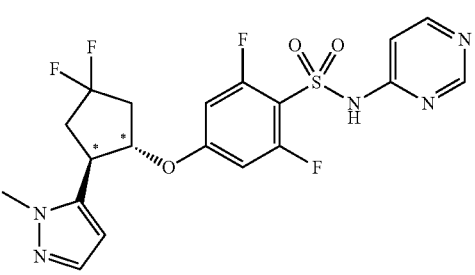

(135a) 4-{[(1S*,2R*)-4,4-Difluoro-2-(1-methyl-1H-pyrazol-5-yl)cyclopentyl]oxy}-N-(2,4-dimethoxybenzyl)-2,6-difluoro-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (233 mg, 0.530 mmol) prepared in the Example 27a, the (1S*,2R*)-4,4-difluoro-2-(1-methyl-1H-pyrazol-5-yl)cyclopentanol (101 mg, 0.500 mmol) prepared in Example 107e, sodium hydride (63%; 29 mg, 0.750 mmol), DMF (2.0 mL) and water (0.780 mL), to yield the title compound (98 mg, 32%) as a colorless solid.

$^1$H-NMR (500 MHz, CDCl$_3$) δ ppm: 2.29-2.40 (2H, m), 2.71-2.91 (2H, m), 3.65-3.70 (1H, m), 3.76 (3H, s), 3.81 (3H, s), 3.83 (3H, s), 4.71 (1H, q, J=6.8 Hz), 5.25 (2H, s), 6.14 (1H, d, J=2.0 Hz), 6.36-6.44 (4H, m), 7.12 (1H, dd, J=1.0, 5.9 Hz), 7.21 (1H, d, J=8.3 Hz), 7.42 (1H, d, J=2.0 Hz), 8.44 (1H, d, J=5.9 Hz), 8.78 (1H, d, J=1.0 Hz).

(135b) 4-{[(1S*,2R*)-4,4-Difluoro-2-(1-methyl-1H-pyrazol-5-yl)cyclopentyl]oxy}-2,6-difluoro-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclopentyl]oxy}-N-(2,4-dimethoxybenzyl)-2,6-difluoro-N-(pyrimidin-4-yl)benzenesulfonamide (98 mg, 0.158 mmol) prepared in Example 135a, triethylsilane (0.30 mL), trifluoroacetic acid (2.0 mL) and dichloromethane (3.0 mL), to yield the title compound (54 mg, 73%) as a colorless solid.

$^1$H-NMR (500 MHz, CDCl$_3$) δ ppm: 2.29-2.41 (2H, m), 2.73-2.89 (2H, m), 3.65-3.70 (1H, m), 3.84 (3H, s), 4.68 (1H, q, J=6.8 Hz), 6.13 (1H, d, J=2.0 Hz), 6.39 (2H, d, J=10.7 Hz), 7.30 (1H, brs), 7.43 (1H, d, J=2.0 Hz), 8.43 (1H, d, J=5.9 Hz), 8.78 (1H, brs).

MS (ESI) m/z: 472 [M+H]+.

Example 136

4-{[(1S*,2R*)-4,4-Difluoro-2-(1-methyl-1H-pyrazol-5-yl)cyclopentyl]oxy}-2-fluoro-N-(pyrimidin-4-yl)benzenesulfonamide

[Formula 154]

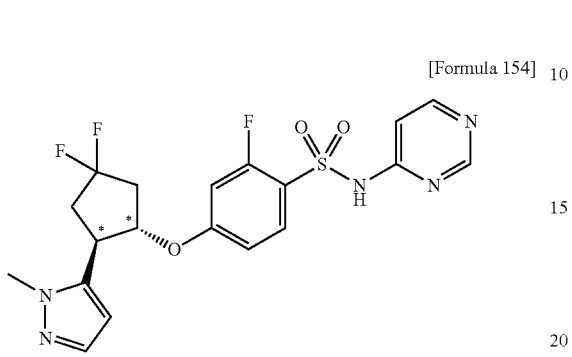

(136a) 4-{[(1S*,2R*)-4,4-Difluoro-2-(1-methyl-1H-pyrazol-5-yl)cyclopentyl]oxy}-N-(2,4-dimethoxybenzyl)-2-fluoro-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (223 mg, 0.530 mmol) prepared in Example 29a, the (1S*,2R*)-4,4-difluoro-2-(1-methyl-1H-pyrazol-5-yl)cyclopentanol (101 mg, 0.500 mmol) prepared in Example 107e, sodium hydride (63%; 29 mg, 0.750 mmol), DMF (2.0 mL) and water (0.780 mL), to yield the title compound (105 mg, 35%) as a colorless amorphous solid.

$^1$H-NMR (500 MHz, CDCl$_3$) δ ppm: 2.31-2.42 (2H, m), 2.74-2.91 (2H, m), 3.66-3.71 (1H, m), 3.77 (3H, s), 3.80 (3H, s), 3.85 (3H, s), 4.73 (1H, q, J=6.4 Hz), 5.24 (2H, s), 6.14 (1H, s), 6.40-6.42 (2H, m), 6.52 (1H, dd, J=2.0, 11.2 Hz), 6.64 (1H, dd, J=2.0, 9.3 Hz), 7.19-7.21 (2H, m), 7.44 (1H, s), 7.97 (1H, t, J=8.8 Hz), 8.43 (1H, d, J=5.9 Hz), 8.76 (1H, s).

(136b) 4-{[(1S*,2R*)-4,4-Difluoro-2-(1-methyl-1H-pyrazol-5-yl)cyclopentyl]oxy}-2-fluoro-N-(pyrimidin-4-yl)benzenesulfonamide The reaction and aftertreatment were conducted in the same manner as in Example 1b by using the 4-{[(1S*,2R*)-4,4-difluoro-2-(1-methyl-1H-pyrazol-5-yl)cyclopentyl]oxy}-N-(2,4-dimethoxybenzyl)-2-fluoro-N-(pyrimidin-4-yl)benzenesulfonamide (105 mg, 0.174 mmol) prepared in Example 136a, triethylsilane (0.30 mL), trifluoroacetic acid (2.0 mL) and dichloromethane (3.0 mL), to yield the title compound (76 mg, 96%) as a colorless solid.

$^1$H-NMR (500 MHz, DMSO-d$_6$) δ ppm: 2.21-2.41 (2H, m), 2.71-2.79 (1H, m), 2.95-3.08 (1H, m), 3.71-3.75 (1H, m), 3.77 (3H, s), 5.04 (1H, q, J=5.9 Hz), 6.29 (1H, d, J=2.0 Hz), 6.88-7.05 (3H, m), 7.33 (1H, d, J=1.5 Hz), 7.82 (1H, brs), 8.36 (1H, brs), 8.56 (1H, brs).

MS (ESI) m/z: 454 [M+H]+.

Example 137

4-{[(1S,2R)-5,5-Difluoro-2-(1-methyl-1H-pyrazol-5-yl)cyclohexyl]oxy}-2-fluoro-5-methyl-N-(pyrimidin-4-yl)benzenesulfonamide

[Formula 155]

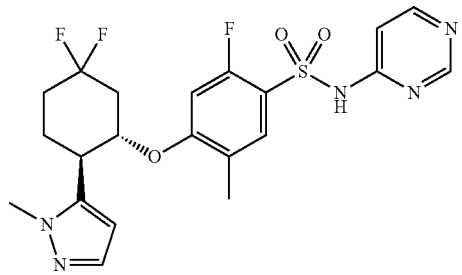

(137a) 4-{[(1S,2R)-5,5-Difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (175 mg, 0.401 mmol) prepared in Example 43a, the (1S,2R)-5,5-difluoro-2-(1-methyl-1H-pyrazol-5-yl)cyclohexanol (72.3 mg, 0.334 mmol) prepared in Example 102c, sodium hydride (63%; 25.5 mg, 0.668 mmol) and DMF (2.0 mL), to yield the title compound (198 mg, 94%) as a colorless oil.

(137b) 4-{[(1S,2R)-5,5-Difluoro-2-(1-methyl-1H-pyrazol-5-yl)cyclohexyl]oxy}-2-fluoro-5-methyl-N-(pyrimidin-4-yl)benzenesulfonamide The reaction and aftertreatment were conducted in the same manner as in Example 1b by using the 4-{[(1S,2R)-5,5-difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide (198 mg, 0.313 mmol) prepared in Example 137a, triethylsilane (0.10 mL), trifluoroacetic acid (1.0 mL) and dichloromethane (1.0 mL), to yield the title compound (80 mg, 53%) as a colorless solid.

[α]$_D^{25}$=−12.4 (c 1.01, DMSO).

Example 138

2-Fluoro-5-methyl-4-{[(1S*,2R*)-2-(1H-pyrazol-5-yl)cyclopentyl]oxy}-N-(pyrimidin-4-yl)benzenesulfonamide

[Formula 156]

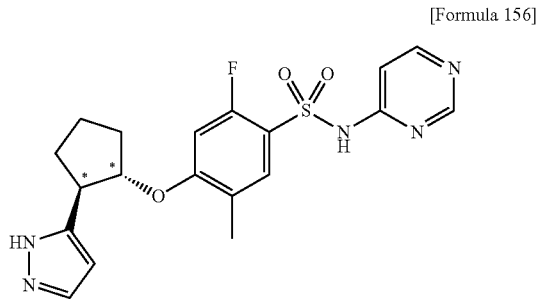 [SMILES: Cc1cc(S(=O)(=O)Nc2ccncn2)c(F)cc1O[C@H]1CCC[C@@H]1c1ccn[nH]1]

(138a) (1S*,2R*)-2-[1-(Tetrahydro-2H-pyran-2-yl)-1H-pyrazol-5-yl]cyclopentanol To a solution of 1-(tetrahydro-2H-pyran-2-yl)-1H-pyrazole (3.04 g, 20.0 mmol) in THF (30 mL), n-butyl lithium (1.63 M solution in hexane; 12.7 mL, 20.7 mmol) was added dropwise at −78° C. for 7 minutes. The reaction solution was stirred for 30 minutes, and boron trifluoride-ethyl ether (3.14 mL, 25.0 mmol) was then added thereto. The reaction solution was further stirred for 10 minutes. Then, cyclopentene oxide (2.08 mL, 24.0 mmol) was added thereto, and the reaction solution was stirred at −78° C. for 3 hours. To the reaction solution, a saturated aqueous solution of sodium hydrogencarbonate (15 mL) was added, followed by extraction four times with ethyl acetate (20 mL). The thus obtained organic layer was dried over anhydrous sodium sulfate. After vacuum concentration, the residue was purified with silica gel chromatography (hexane/ethyl acetate=1:4) to yield the title compound (1.54 g, 33%) in the form of a diastereomeric mixture as a colorless oil.

(138b) N-(2,4-dimethoxybenzyl)-2-fluoro-5-methyl-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (218 mg, 0.50 mmol) prepared in Example 43a, the (1S*,2R*)-2-[1-(tetrahydro-2H-pyran-2-yl)-1H-pyrazol-5-yl]cyclopentanol (154 mg, 0.65 mmol) prepared in Example 138a, sodium hydride (63%; 38 mg, 1.0 mmol), DMF (3.0 mL) and water (1.1 mL), to yield the title compound (165 mg, 51%) in the form of a diastereomeric mixture as a colorless amorphous solid.

(138c) 2-Fluoro-5-methyl-4-{[(1S*,2R*)-2-(1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2-fluoro-5-methyl-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide (155 mg, 0.238 mmol) prepared in Example 138b, triethylsilane (0.30 mL), trifluoroacetic acid (2.0 mL) and dichloromethane (3.0 mL), to yield the title compound (108 mg, 99%) as a colorless solid.

$^1$H-NMR (500 MHz, CD$_3$OD) δ ppm: 1.80-1.94 (4H, m), 2.20 (3H, s), 2.22-2.28 (2H, m), 3.38-3.42 (1H, m), 4.84-4.92 (1H, m), 6.19 (1H, d, J=2.4 Hz), 6.71 (1H, d, J=12.7 Hz), 7.97 (1H, d, J=5.9 Hz), 7.52 (1H, d, J=2.0 Hz), 7.75 (1H, d, J=8.3 Hz), 8.32 (1H, d, J=6.4 Hz), 8.57 (1H, s).

MS (ESI) m/z: 418 [M+H]+.

Example 139

2,6-Difluoro-4-{[(1S*,2R*)-2-(1H-pyrazol-5-yl)cyclopentyl]oxy}-N-(pyrimidin-4-yl)benzenesulfonamide

[Formula 157]

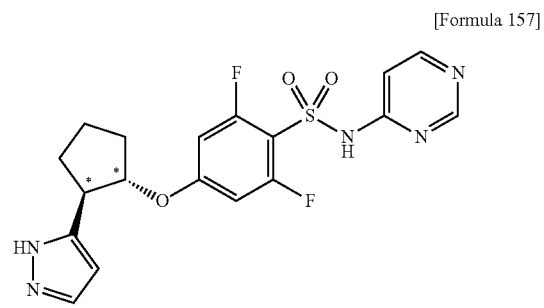 [SMILES: O=S(=O)(Nc1ccncn1)c1c(F)cc(O[C@H]2CCC[C@@H]2c2ccn[nH]2)cc1F]

(139a) N-(2,4-Dimethoxybenzyl)-2,6-difluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (220 mg, 0.50 mmol) prepared in Example 27a, the (1S*,2R*)-2-[1-(tetrahydro-2H-pyran-2-yl)-1H-pyrazol-5-yl]cyclopentanol (154 mg, 0.65 mmol) prepared in Example 138a, sodium hydride (63%; 38 mg, 1.0 mmol), DMF (3.0 mL) and water (1.1 mL), to yield the title compound (122 mg, 37%) in the form of a diastereomeric mixture as a colorless amorphous solid.

(139b) 2,6-Difluoro-4-{[(1S*,2R*)-2-(1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2,6-difluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide (121 mg, 0.185 mmol) prepared in Example 139a, triethylsilane (0.30 mL), trifluoroacetic acid (2.0 mL) and dichloromethane (3.0 mL), to yield the title compound (67 mg, 86%) as a colorless solid.

$^1$H-NMR (500 MHz, CDCl$_3$) δ ppm: 1.83-1.94 (4H, m), 2.17-2.29 (2H, m), 3.42-3.46 (1H, m), 4.82-4.85 (1H, m), 6.20 (1H, d, J=2.4 Hz), 6.47 (2H, d, J=13.2 Hz), 7.45 (1H, d, J=7.3 Hz), 7.57 (1H, d, J=2.0 Hz), 8.41 (1H, d, J=6.4 Hz), 8.87 (1H, d, J=1.0 Hz), 10.06 (2H, brs).

MS (ESI) m/z: 422 [M+H]+.

Example 140

5-Chloro-2-fluoro-4-{[(1S*,2R*)-2-(1H-pyrazol-5-yl)cyclopentyl]oxy}-N-(pyrimidin-4-yl)benzenesulfonamide

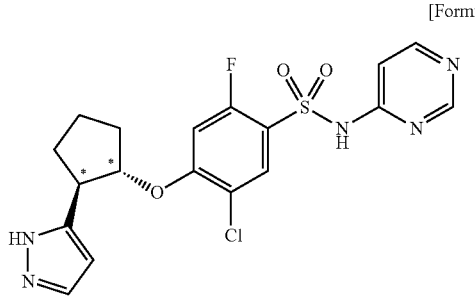

[Formula 158]

(140a) 5-Chloro-N-(2,4-dimethoxybenzyl)-2-fluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (228 mg, 0.50 mmol) prepared in Example 20a, the (1S*,2R*)-2-[1-(tetrahydro-2H-pyran-2-yl)-1H-pyrazol-5-yl]cyclopentanol (154 mg, 0.65 mmol) prepared in Example 138a, sodium hydride (63%; 38 mg, 1.0 mmol), DMF (3.0 mL) and water (1.1 mL), to yield the title compound (128 mg, 38%) in the form of a diastereomeric mixture as a colorless amorphous solid.

(140b) 5-Chloro-2-fluoro-4-{[(1S*,2R*)-2-(1H-pyrazol-5-yl)cyclopentyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide (126 mg, 0.187 mmol) prepared in Example 140a, triethylsilane (0.30 mL), trifluoroacetic acid (2.0 mL) and dichloromethane (3.0 mL), to yield the title compound (63 mg, 77%) as a colorless solid.

$^1$H-NMR (500 MHz, CDCl$_3$) δ ppm: 1.89-2.01 (4H, m), 2.18-2.34 (2H, m), 3.49-3.52 (1H, m), 5.03-5.04 (1H, m), 6.23 (1H, d, J=2.4 Hz), 6.72 (1H, d, J=11.7 Hz), 7.32 (1H, d, J=5.4 Hz), 7.56 (1H, d, J=2.0 Hz), 7.99 (1H, d, J=7.3 Hz), 8.40 (1H, d, J=6.4 Hz), 8.81 (1H, d, J=1.0 Hz).

MS (ESI) m/z: 438 [M+H]+.

Example 141

5-Chloro-4-{[(1S*,2R*)-5,5-difluoro-2-(1-methyl-1H-pyrazol-5-yl)cyclohexyl]oxy}-2-fluoro-N-(pyrimidin-4-yl)benzenesulfonamide

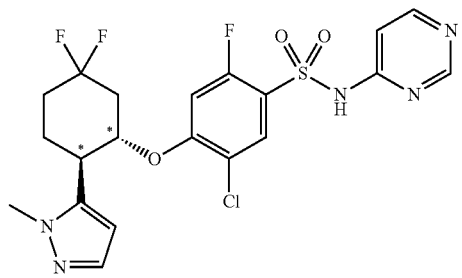

[Formula 159]

(141a) 5-Chloro-4-{[(1S*,2R*)-5,5-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (202 mg, 0.444 mmol) prepared in Example 20a, the (1S*,2R*)-5,5-difluoro-2-(1-methyl-1H-pyrazol-5-yl)cyclohexanol (80.0 mg, 0.370 mmol) prepared in Example 47b, sodium hydride (63%; 21.1 mg, 0.555 mmol) and DMF (2.0 mL), to yield the title compound (212 mg, 88%) as a colorless oil.

$^1$H-NMR (500 MHz, CDCl$_3$) δ ppm: 1.84-2.14 (4H, m), 2.29-2.33 (1H, m), 2.66-2.71 (1H, m), 3.12-3.17 (1H, m), 3.78 (3H, s), 3.78 (3H, s), 3.93 (3H, s), 4.35 (1H, dt, J=5.9, 10.7 Hz), 5.20 (2H, s), 6.08 (1H, d, J=2.4 Hz), 6.39-6.43 (3H, m), 7.17-7.19 (2H, m), 7.37 (1H, d, J=2.0 Hz), 7.96 (1H, d, J=7.3 Hz), 8.47 (1H, d, J=5.9 Hz), 8.79 (1H, s).

(141b) 5-Chloro-4-{[(1S*,2R*)-5,5-difluoro-2-(1-methyl-1H-pyrazol-5-yl)cyclohexyl]oxy}-2-fluoro-N-(pyridin-4-yl)benzenesulfonamide The reaction and aftertreatment were conducted in the same manner as in Example 1b by using the 5-chloro-4-{[(1S*,2R*)-5,5-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide (212 mg, 0.325 mmol) prepared in Example 141a, triethylsilane (0.10 mL), trifluoroacetic acid (1.0 mL) and dichloromethane (1.0 mL), to yield the title compound (135 mg, 83%) as a colorless solid.

$^1$H-NMR (500 MHz, CDCl$_3$) δ ppm: 1.91-2.14 (4H, m), 2.29-2.34 (1H, m), 2.66-2.71 (1H, m), 3.12-3.17 (1H, m), 3.92 (3H, s), 4.37 (1H, dt, J=4.4, 10.7 Hz), 6.09 (1H, d, J=2.0 Hz), 6.48 (1H, d, J=11.2 Hz), 7.19 (1H, d, J=6.4 Hz), 7.36 (1H, d, J=2.0 Hz), 7.97 (1H, d, J=7.3 Hz), 8.37 (1H, d, J=6.4 Hz), 8.70 (1H, s).

MS (ESI) m/z: 502 [M+H]+.

Example 142

5-Chloro-2-fluoro-4-{[(1R,2S)-2-(1-methyl-1H-pyrazol-5-yl)cyclohexyl]oxy}-N-(pyrimidin-4-yl)benzenesulfonamide

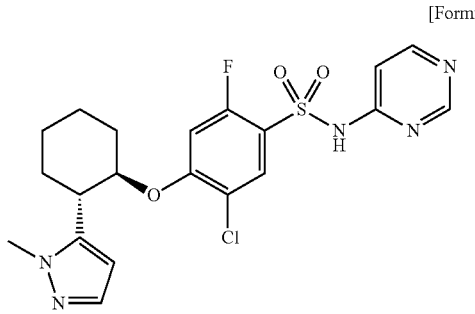

[Formula 160]

(142a) (1R,2S)-2-(1-Methyl-1H-pyrazol-5-yl)cyclohexanol

The (1S*,2R*)-2-(l-methyl-1H-pyrazol-5-yl)cyclohexanol prepared in Example 4a was optically resolved with CHIRALPAK IB (Daicel Corp.; hexane/ethanol=9:1) to yield the title compound as a colorless oil.

$[\alpha]_D^{25}$=−33.1 (c 1.09, MeOH).

(142b) 5-Chloro-N-(2,4-dimethoxybenzyl)-2-fluoro-4-{[(1R,2S)-2-(l-methyl-1H-pyrazol-5-yl)cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (23.1 g, 50.7 mmol) prepared in Example 20a, the (1R,2S)-2-(1-methyl-1H-pyrazol-5-yl)cyclohexanol (9.13 g, 50.7 mmol) prepared in Example 142a, sodium hydride (63%; 2.21 g, 50.6 mmol), DMF (500 mL) and water (0.91 mL), to yield the title compound (23.3 g, 75%) as a colorless solid.

(142c) 5-Chloro-2-fluoro-4-{[(1R,2S)-2-(1-methyl-1H-pyrazol-5-yl)cyclohexyl]oxy}-N-(pyrimidin-4-yl)benzenesulfonamide The reaction and aftertreatment were conducted in the same manner as in Example 122c by using the 5-chloro-N-(2,4-dimethoxybenzyl)-2-fluoro-4-{[(1R,2S)-2-(1-methyl-1H-pyrazol-5-yl)cyclohexyl]oxy}-N-(pyrimidin-4-yl)benzenesulfonamide (23.3 g, 37.8 mmol) prepared in Example 142b, triethylsilane (28.3 mL, 177 mmol), trifluoroacetic acid (50 mL) and dichloromethane (500 mL), to yield the title compound (15.4 g, 88%) as a colorless solid.

$[\alpha]_D^{25}$=−3.21 (c 1.02, DMSO).

Example 143

4-{[(1S,2R)-5,5-Difluoro-2-(1H-pyrazol-4-yl)cyclohexyl]oxy}-2-fluoro-5-methyl-N-(pyrimidin-4-yl)benzenesulfonamide

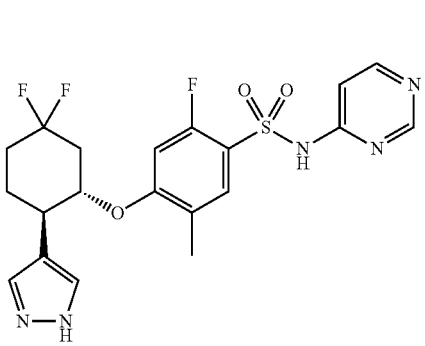

[Formula 161]

(143a) 4,4-Difluoro-1-(1H-pyrazol-4-yl)cyclohexanol

The reaction and aftertreatment were conducted in the same manner as in Example 8a by using 4-iodo-1H-pyrazole (5.82 g, 30.0 mmol), butyl lithium (2.69 M solution in hexane; 22.3 mL, 60.0 mmol), 4,4-difluorocyclohexanone (4.43 g, 33.0 mmol) and THF (120 mL), to yield the title compound (2.32 g, 55%) as a pale yellow solid.

$^1$H-NMR (500 MHz, CDCl$_3$) δ ppm: 1.95-2.05 (6H, m), 2.18-2.35 (2H, m), 2.55 (1H, t, J=7.3 Hz), 7.55 (2H, s).

(143b) 4-(4,4-Difluorocyclohex-1-en-1-yl)-1H-pyrazole

The reaction and aftertreatment were conducted in the same manner as in Example 99b by using the 4,4-difluoro-1-(1H-pyrazol-4-yl)cyclohexanol (0.25 g, 1.24 mmol) prepared in Example 143a, p-toluenesulfonic acid monohydrate (120 mg, 0.62 mmol) and toluene (3.0 mL), to yield the title compound (189 mg, 83%) as a colorless solid.

$^1$H-NMR (500 MHz, CDCl$_3$) δ ppm: 2.11-2.19 (2H, m), 2.57-2.69 (4H, m), 5.82-5.84 (1H, m), 7.61 (2H, s).

(143c) (1S*,2R*)-5,5-Difluoro-2-(1H-pyrazol-4-yl)cyclohexanol

The reaction and aftertreatment were conducted in the same manner as in Example 33b by using the 4-(4,4-difluorocyclohex-1-en-1-yl)-1H-pyrazole (0.30 g, 1.63 mmol) prepared in Example 143b, a borane-THF complex (0.95 M solution in THF; 3.77 mL, 3.59 mmol), sodium perborate tetrahydrate (0.55 g, 3.59 mmol), THF (1.6 mL) and water (2.4 mL), to yield the title compound (0.31 g, 94%) as a colorless solid.

$^1$H-NMR (500 MHz, CDCl$_3$) δ ppm: 1.74-1.99 (4H, m), 2.15-2.22 (1H, m), 2.52-2.59 (2H, m), 3.69 (1H, dt, J=4.4, 10.7 Hz), 7.52 (2H, s).

(143d) (1S*,2R*)-5,5-Difluoro-2-[1-(4-methoxybenzyl)-1H-pyrazol-4-yl]cyclohexanol A solution of the (1S*,2R*)-5,5-difluoro-2-(1H-pyrazol-4-yl)cyclohexanol (0.24 g, 1.17 mmol) prepared in Example 143c, potassium carbonate (0.32 g, 2.34 mmol) and 4-methoxybenzyl chloride (0.16 mL, 1.17 mmol) in acetonitrile (5.9 mL) was stirred at 80° C. for 12 hours. After allowing to cool, water (20 mL) was added to the reaction solution, and an organic layer was extracted with ethyl acetate (20 mL). The thus obtained organic layer was dried over anhydrous sodium sulfate. After vacuum concentration, the residue was purified with silica gel chromatography to yield the title compound (92.9 mg, 25%) as a colorless solid.

$^1$H-NMR (500 MHz, CDCl$_3$) δ ppm: 1.63-1.98 (4H, m), 2.11-2.18 (1H, m), 2.41-2.54 (2H, m), 3.61 (1H, dt, J=4.4, 10.7 Hz), 3.80 (3H, s), 5.15 (2H, s), 6.88 (2H, d, J=8.8 Hz), 7.19 (2H, d, J=8.3 Hz), 7.24 (1H, s), 7.39 (1H, s).

(143e) (1S,2R)-5,5-Difluoro-2-[1-(4-methoxybenzyl)-1H-pyrazol-4-yl]cyclohexanol

The (1S*,2R*)-5,5-difluoro-2-[1-(4-methoxybenzyl)-1H-pyrazol-4-yl]cyclohexanol prepared in Example 143d was optically resolved with CHIRALPAK IA (Daicel Corp.; hexane/isopropanol=8:2) to yield the title compound as a colorless solid.

(143f) 4-({(1S,2R)-5,5-Difluoro-2-[1-(4-methoxybenzyl)-1H-pyrazol-4-yl]cyclohexyl}oxy)-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (0.16 g, 0.37 mmol) prepared in Example 43a, the (1S,2R)-5,5-difluoro-2-[1-(4-methoxybenzyl)-1H-pyrazol-4-yl]cyclohexanol (0.09 g, 0.29 mmol) prepared in Example 143e, sodium hydride (63%; 10 mg, 0.37 mmol), DMF (1.8 mL) and water (0.010 mL), to yield the title compound (177.7 mg, 66%) as a colorless amorphous solid.

$^1$H-NMR (500 MHz, CDCl$_3$) δ ppm: 1.86-2.00 (3H, m), 2.07 (3H, s), 2.12-2.25 (2H, m), 2.64-2.66 (1H, m), 2.90-2.94 (1H, m), 3.78 (3H, s), 3.80 (3H, s), 3.81 (3H, s), 4.22 (1H, dt, J=4.4, 10.3 Hz), 5.13 (2H, s), 5.26 (1H, d, J=16.6 Hz), 5.30 (1H, d, J=17.1 Hz), 6.38-6.43 (3H, m), 6.85 (2H, d, J=6.4 Hz), 7.07 (2H, d, J=8.8 Hz), 7.12 (1H, s), 7.19-7.22 (2H, m), 7.40 (1H, s), 7.72 (1H, d, J=7.8 Hz), 8.44 (1H, d, J=5.9 Hz), 8.78 (1H, d, J=1.0 Hz).

(143 g) 4-{[(1S,2R)-5,5-Difluoro-2-(1H-pyrazol-4-yl)cyclohexyl]oxy}-2-fluoro-5-methyl-N-(pyrimidin-4-yl)benzenesulfonamide A solution of the 4-({(1S*,2R*)-5,5-difluoro-2-[1-(4-methoxybenzyl)-1H-pyrazol-4-yl]cyclohexyl}oxy)-N-(2,4-dimethoxybenzyl)-2-fluoro-5-methyl-N-(pyrimidin-4-yl)benzenesulfonamide (0.15 g, 0.20 mmol) prepared in Example 143f, triethylsilane (0.16 mL) and trifluoroacetic acid (0.20 mL) in dichloromethane (2.0 mL) was stirred at 140° C. for 1 hour under microwave irradiation. The reaction solution was concentrated, and the residue was purified with silica gel chromatography (ethyl acetate) to yield the title compound (90 mg, 94%) as a colorless solid.

Example 144

4-{[(1R,2S)-5,5-Difluoro-2-(1H-pyrazol-4-yl)cyclohexyl]oxy}-2-fluoro-5-methyl-N-(pyrimidin-4-yl)benzenesulfonamide

[Formula 162]

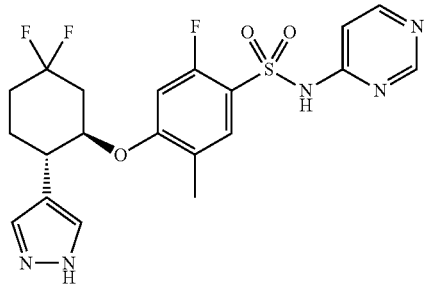

(144a) (1R,2S)-5,5-Difluoro-2-[1-(4-methoxybenzyl)-1H-pyrazol-4-yl]cyclohexanol

The (1S*,2R*)-5,5-difluoro-2-[1-(4-methoxybenzyl)-1H-pyrazol-4-yl]cyclohexanol prepared in Example 143d was optically resolved with CHIRALPAK IA (Daicel Corp.; hexane/isopropanol=8:2) to yield the title compound as a colorless solid.

(144b) 4-({(1R,2S)-5,5-Difluoro-2-[1-(4-methoxybenzyl)-1H-pyrazol-4-yl]cyclohexyl}oxy)-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (0.15 g, 0.34 mmol) prepared in Example 43a, the (1R,2S)-5,5-difluoro-2-[1-(4-methoxybenzyl)-1H-pyrazol-4-yl]cyclohexanol (0.09 g, 0.28 mmol) prepared in Example 144a, sodium hydride (63%; 10 mg, 0.34 mmol), DMF (1.8 mL) and water (0.010 mL), to yield the title compound (158.3 mg, 62%) as a colorless amorphous solid.

(144c) 4-{[(1R,2S)-5,5-Difluoro-2-(1H-pyrazol-4-yl)cyclohexyl]oxy}-2-fluoro-5-methyl-N-(pyrimidin-4-yl)benzenesulfonamide The reaction and aftertreatment were conducted in the same manner as in Example 143g by using the 4-({(1R,2S)-5,5-difluoro-2-[1-(4-methoxybenzyl)-1H-pyrazol-4-yl]cyclohexyl}oxy)-N-(2,4-dimethoxybenzyl)-2-fluoro-5-methyl-N-(pyrimidin-4-yl)benzenesulfonamide (0.15 g, 0.20 mmol) prepared in Example 144b, triethylsilane (0.16 mL), trifluoroacetic acid (0.20 mL) and dichloromethane (2.0 mL), to yield the title compound (60 mg, 63%) as a colorless solid.

$[α]_D^{25}$=−23.1 (c 1.01, DMSO).

Example 145

5-Chloro-2-fluoro-4-{[(1S,2R)-2-(1-methyl-1H-pyrazol-5-yl)cyclohexyl]oxy}-N-(pyrimidin-4-yl)benzenesulfonamide Na salt

[Formula 163]

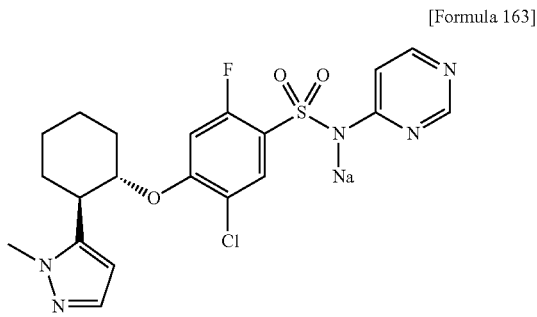

To a solution of the 5-chloro-2-fluoro-4-{[(1S,2R)-2-(1-methyl-1H-pyrazol-5-yl)cyclohexyl]oxy}-N-(pyrimidin-4-yl)benzenesulfonamide (0.12 g, 0.26 mmol) prepared in Example 122c in methanol (5.0 mL), a 2 M sodium hydroxide solution (0.13 mL, 0.262 mol) was added. The reaction solution was concentrated and further freeze dried to yield the title compound (123 mg, 98%) as a colorless amorphous solid.

$^1$H-NMR (500 MHz, CD$_3$OD) δ ppm: 1.42-2.01 (7H, m), 2.22-2.24 (1H, m), 3.09-3.14 (1H, m), 3.90 (3H, s), 4.40-4.41 (1H, m), 6.14 (1H, s), 6.69 (1H, d, J=5.4 Hz), 6.81 (1H, d, J=11.2 Hz), 7.27 (1H, s), 7.82 (1H, d, J=6.8 Hz), 8.00 (1H, d, J=5.4 Hz), 8.30 (1H, s).

Example 146

5-Chloro-4-{[(1S*,2R*)-4,4-difluoro-2-(1-methyl-1H-pyrazol-5-yl)cyclopentyl]oxy}-2-fluoro-N-(pyrimidin-4-yl)benzenesulfonamide

[Formula 164]

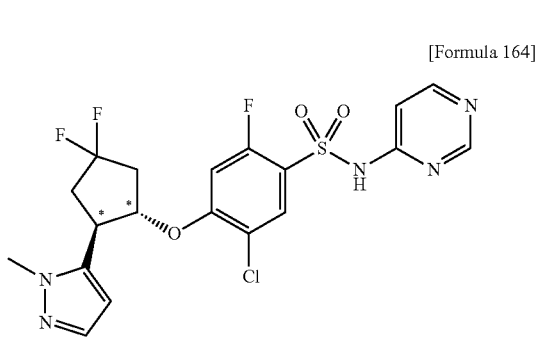 [SMILES: Cn1nccc1[C@H]1CC(F)(F)C[C@@H]1Oc1cc(F)c(S(=O)(=O)Nc2ccncn2)cc1Cl]

(146a) 5-Chloro-4-{[(1S*,2R*)-4,4-difluoro-2-(1-methyl-1H-pyrazol-5-yl)cyclopentyl]oxy}-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (274 mg, 0.600 mmol) prepared in Example 20a, the (1S*,2R*)-4,4-difluoro-2-(1-methyl-1H-pyrazol-5-yl)cyclopentanol (101 mg, 0.500 mmol) prepared in Example 107e, sodium hydride (63%; 29 mg, 0.750 mmol), DMF (2.0 mL) and water (0.016 mL), to yield the title compound (316 mg, 99%) as a colorless amorphous solid.

$^1$H-NMR (500 MHz, CDCl$_3$) δ ppm: 2.29-2.46 (2H, m), 2.72-2.93 (2H, m), 3.75 (3H, s), 3.78 (3H, s), 3.79-3.87 (1H, m), 3.93 (3H, s), 4.71 (1H, q, J=6.8 Hz), 5.20 (1H, d, J=16.6 Hz), 5.24 (1H, d, J=16.6 Hz), 6.15 (1H, d, J=2.0 Hz), 6.37-6.40 (2H, m), 6.47 (1H, d, J=10.7 Hz), 7.17-7.18 (2H, m), 7.42 (1H, d, J=2.0 Hz), 8.03 (1H, d, J=7.3 Hz), 8.46 (1H, d, J=5.9 Hz), 8.78 (1H, d, J=1.0 Hz).

(146b) 5-Chloro-4-{[(1S*,2R*)-4,4-difluoro-2-(1-methyl-1H-pyrazol-5-yl)cyclopentyl]oxy}-2-fluoro-N-(pyrimidin-4-yl)benzenesulfonamide The reaction and aftertreatment were conducted in the same manner as in Example 1b by using the 5-chloro-4-{[(1S*,2R*)-4,4-difluoro-2-(1-methyl-1H-pyrazol-5-yl)cyclopentyl]oxy}-N-(2,4-dimethoxybenzyl)-2-fluoro-N-(pyrimidin-4-yl)benzenesulfonamide (316 mg, 0.495 mmol) prepared in Example 146a, triethylsilane (0.30 mL), trifluoroacetic acid (2.0 mL) and dichloromethane (3.0 mL), to yield the title compound (237 mg, 98%) as a colorless solid.

$^1$H-NMR (500 MHz, CD$_3$OD) δ ppm: 2.28-2.51 (2H, m), 2.72-2.79 (1H, m), 2.95-3.06 (1H, m), 3.81-3.90 (1H, m), 3.87 (3H, s), 5.00 (1H, q, J=6.8 Hz), 6.31 (1H, d, J=2.0 Hz), 6.93 (1H, d, J=11.2 Hz), 7.00 (1H, brs), 7.39 (1H, d, J=2.0 Hz), 8.01 (1H, d, J=7.3 Hz), 8.24 (1H, brs), 8.52 (1H, s).

MS (ESI) m/z: 488 [M+H]+.

Example 147

4-{[(1S*,2R*)-5,5-Difluoro-2-(1H-pyrazol-4-yl)cyclohexyl]oxy}-2-fluoro-N-(pyrimidin-4-yl)benzenesulfonamide

[Formula 165]

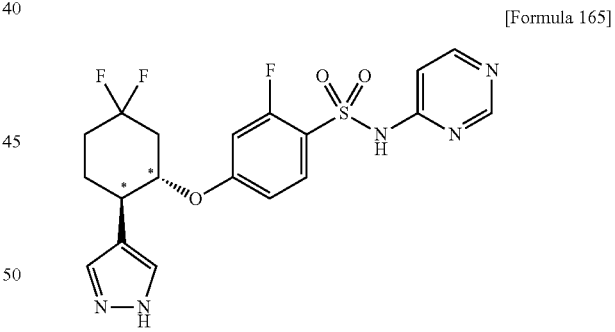

(147a) 4,4-Difluoro-1-[1-(methoxymethyl)-1H-pyrazol-4-yl]cyclohexanol

To a solution of 4-iodo-1-(methoxymethyl)-1H-pyrazole (Organic Letters, 2007, 9, 4947-4950; 1.40 g, 5.88 mmol) in THF (15 mL), isopropyl magnesium chloride (2.0 M solution in THF; 3.8 mL, 7.64 mmol) was added with cooling on ice. The reaction solution was stirred for 30 minutes with cooling on ice. Then, 4,4-difluorocyclohexanone (2.30 g, 17.6 mmol) was added thereto, and the mixture was stirred at room temperature for 1 hour. To the reaction solution, an aqueous ammonium chloride solution (50 mL) was added, followed by extraction with ethyl acetate (50 mL). The thus obtained organic layer was dried over anhydrous sodium sulfate. After vacuum concentration, the residue was purified with silica gel chromatography (hexane/ethyl acetate=7:3) to yield the title compound (0.95 g, 66%) as a colorless oil.

$^1$H-NMR (500 MHz, CDCl$_3$) δ ppm: 1.97-2.07 (6H, m), 2.19-2.32 (2H, m), 3.34 (3H, s), 5.36 (2H, s), 7.54 (1H, s), 7.56 (1H, s).

(147b) 4-(4,4-Difluorocyclohex-1-en-1-yl)-1-(methoxymethyl)-1H-pyrazole

The reaction and aftertreatment were conducted in the same manner as in Example 99b by using the 4,4-difluoro-1-[1-(methoxymethyl)-1H-pyrazol-4-yl]cyclohexanol (0.20 g, 0.81 mmol) prepared in Example 147a, p-toluenesulfonic acid (14 mg, 0.081 mmol) and toluene (5.0 mL), to yield the title compound (0.18 g, 97%) as a colorless oil.

$^1$H-NMR (500 MHz, CDCl$_3$) δ ppm: 2.11-2.20 (2H, m), 2.57-2.70 (4H, m), 3.32 (3H, s), 5.36 (2H, s), 5.84-5.86 (1H, m), 7.52 (1H, s), 7.62 (1H, s).

(147c) (1S*,2R*)-5,5-Difluoro-2-[1-(methoxymethyl)-1H-pyrazol-4-yl]cyclohexanol

The reaction and aftertreatment were conducted in the same manner as in Example 33b by using the 4-(4,4-difluorocyclohex-1-en-1-yl)-1-(methoxymethyl)-1H-pyrazole (0.25 g, 1.09 mmol) prepared in Example 147b, a borane-THF complex (0.95 M; 2.50 mL, 2.41 mmol), sodium perborate tetrahydrate (0.33 g, 2.18 mmol), THF (10 mL) and water (10 mL), to yield the title compound (0.13 g, 48%) as a colorless oil.

$^1$H-NMR (500 MHz, CDCl$_3$) δ ppm: 1.70-1.90 (4H, m), 2.15-2.22 (1H, m), 2.48-2.59 (2H, m), 3.35 (3H, s), 3.66-3.71 (1H, m), 5.36 (2H, s), 7.49 (1H, s), 7.50 (1H, s).

(147d) 4-({(1S*,2R*)-5,5-Difluoro-2-[1-(methoxymethyl)-1H-pyrazol-4-yl]cyclohexyl}oxy)-N-(2,4-dimethoxybenzyl)-2-fluoro-N-(pyrimidin-4-yl)benzenesulfonamide The reaction and aftertreatment were conducted in the same manner as in Example 1a by using the N-(2,4-dimethoxybenzyl)-2,4-difluoro-N-(pyrimidin-4-yl)benzenesulfonamide (205 mg, 0.48 mmol) prepared in Example 29a, the (1S*,2R*)-5,5-difluoro-2-[1-(methoxymethyl)-1H-pyrazol-4-yl]cyclohexanol (0.10 g, 0.40 mmol) prepared in Example 147c, sodium hydride (63%; 24 mg, 0.60 mmol) and DMF (5.0 mL), to yield the title compound (0.18 g, 69%) as a colorless amorphous solid.

$^1$H-NMR (500 MHz, CDCl$_3$) δ ppm: 1.88-2.01 (3H, m), 2.14-2.19 (1H, m), 2.24-2.29 (1H, m), 2.65-2.71 (1H, m), 2.86-2.94 (1H, m), 3.21 (3H, s), 3.77 (3H, s), 3.79 (3H, s), 4.25-4.31 (1H, m), 5.23 (2H, s), 5.28 (2H, s), 6.39-6.41 (2H, m), 6.52 (1H, dd, J=2.4, 11.7 Hz), 6.67 (1H, dd, J=2.4, 8.8 Hz), 7.20 (1H, d, J=8.3 Hz), 7.22 (1H, dd, J=1.5, 7.3 Hz), 7.38 (1H, s), 7.44 (1H, s), 7.91 (1H, t, J=8.8 Hz), 8.43 (1H, d, J=5.9 Hz), 8.76 (1H, d, J=1.0 Hz).

(147e) 4-{[(1S*,2R*)-5,5-Difluoro-2-(1H-pyrazol-4-yl)cyclohexyl]oxy}-2-fluoro-N-(pyrimidin-4-yl)benzenesulfonamide To a solution of the 4-({(1S*,2R*)-5,5-difluoro-2-[1-(methoxymethyl)-1H-pyrazol-4-yl]cyclohexyl}oxy)-N-(2,4-dimethoxybenzyl)-2-fluoro-N-(pyrimidin-4-yl)benzenesulfonamide (0.12 g, 0.19 mmol) prepared in Example 147d and triethylsilane (0.15 mL) in dichloromethane (4.0 mL), trifluoroacetic acid (3.0 mL) was added at room temperature, and the reaction solution was stirred for 2 hours. The reaction solution was concentrated, then ethanol (1.0 mL) and 2 M hydrochloric acid (4.0 mL) were added to the residue, and the mixture was stirred at 100° C. for 3 hours. After allowing to cool, the reaction solution was neutralized with sodium hydrogencarbonate, and the resulting solid was collected by filtration. The solid thus collected by filtration was purified with silica gel chromatography (dichloromethane/methanol=95:5) to yield the title compound (40 mg, 48%) as a colorless solid.

$^1$H-NMR (500 MHz, DMSO-d$_6$) δ ppm: 1.73-1.81 (1H, m), 1.99-2.17 (4H, m), 2.52-2.64 (1H, m), 2.94-2.99 (1H, m), 4.54 (1H, dt, J=4.4, 10.3 Hz), 6.83 (1H, dd, J=2.4, 8.8 Hz), 6.90 (1H, dd, J=2.0, 12.2 Hz), 6.98 (1H, d, J=5.9 Hz), 7.50 (2H, s), 7.78 (1H, t, J=8.8 Hz), 8.29 (1H, brs), 8.56 (1H, s), 12.70 (1H, brs).

MS (ESI) m/z: 454 [M+H]+.

Example 148

2-Fluoro-5-methyl-4-{[(1S,2R)-2-(1H-pyrazol-5-yl)cyclopentyl]oxy}-N-(pyrimidin-4-yl)benzenesulfonamide

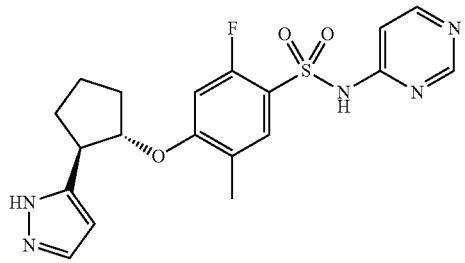

[Formula 166]

(148a) 5-[(1R*,2S*)-2-(Benzyloxy)cyclopentyl]-1-(tetrahydro-2H-pyran-2-yl)-1H-pyrazole To a solution of the (1S*,2R*)-2-[1-(tetrahydro-2H-pyran-2-yl)-1H-pyrazol-5-yl]cyclopentanol (975 mg, 4.13 mmol) prepared in Example 138a in DMF (20 mL), sodium hydride (63%; 236 mg, 6.19 mmol) and benzyl bromide (0.735 mL, 6.19 mmol) were added, and the reaction solution was stirred at room temperature for 7 hours. To the reaction solution, water (50 mL) was added, followed by extraction with ethyl acetate (50 mL). The thus obtained organic layer was washed twice with water (50 mL) and dried over anhydrous sodium sulfate. After vacuum concentration, the residue was purified with silica gel chromatography (hexane/ethyl acetate=7:3) to yield the title compound (1.15 g, 57%) in the form of a diastereomeric mixture as a colorless oil.

(148b) 5-[(1R*,2S*)-2-(Benzyloxy)cyclopentyl]-1H-pyrazole

To a solution of the 5-[(1R*,2S*)-2-(benzyloxy)cyclopentyl]-1-(tetrahydro-2H-pyran-2-yl)-1H-pyrazole (1.15 g, 3.52 mmol) prepared in Example 148a in dichloromethane (10 mL), trifluoroacetic acid (5.0 mL) was added at room temperature, and the reaction solution was stirred for 12 hours. The reaction solution was concentrated, and a saturated aqueous solution of sodium hydrogencarbonate (50 mL) was added to the residue, followed by extraction with ethyl acetate (50 mL). The thus obtained organic layer was washed with saturated saline (50 mL) and dried over anhydrous sodium sulfate. After vacuum concentration, the residue was purified with silica gel chromatography (hexane/ethyl acetate=1:1) to yield the title compound (840 mg, 98%) as a pale yellow oil.

$^1$H-NMR (500 MHz, CDCl$_3$) δ ppm: 1.73-1.92 (4H, m), 2.02-2.10 (1H, m), 2.16-2.23 (1H, m), 3.16-3.21 (1H, m), 3.95 (1H, q, J=6.4 Hz), 4.47 (1H, d, J=11.2 Hz), 4.57 (1H, d, J=11.7 Hz), 6.08 (1H, d, J=2.9 Hz), 7.26-7.34 (5H, m), 7.48 (1H, d, J=2.0 Hz).

(148c) 5-[(1R,2S)-2-(Benzyloxy)cyclopentyl]-1H-pyrazole

The 5-[(1R*,2S*)-2-(benzyloxy)cyclopentyl]-1H-pyrazole prepared in Example 148b was optically resolved with CHIRALPAK AD-H (Daicel Corp.; hexane/isopropanol=9:1) to yield the title compound as a pale yellow oil.

(148d) 3-[(1R,2S)-2-(Benzyloxy)cyclopentyl]-1-(tetrahydro-2H-pyran-2-yl)-1H-pyrazole A solution of the 5-[(1R,2S)-2-(benzyloxy)cyclopentyl]-1H-pyrazole (322 mg, 1.33 mmol) prepared in Example 148c, 3,4-dihydro-2H-pyran (0.728 mL, 7.98 mmol) and p-toluenesulfonic acid hydrate (50 mg, 0.266 mmol) in dichloromethane (5.0 mL) was stirred for 3 hours under reflux. After allowing to cool, the reaction solution was vacuum concentrated, and the residue was purified with silica gel chromatography (hexane/ethyl acetate=7:3) to yield the title compound (402 mg, 93%) in the form of a diastereomeric mixture as a colorless oil.

(148e) (1S,2R)-2-[1-(Tetrahydro-2H-pyran-2-yl)-1H-pyrazol-3-yl]cyclopentanol

The reaction and aftertreatment were conducted in the same manner as in Example 106b by using the 3-[(1R,2S)-2-(benzyloxy)cyclopentyl]-1-(tetrahydro-2H-pyran-2-yl)-1H-pyrazole (403 mg, 1.23 mmol) prepared in Example 148d, palladium carbon (5%; 400 mg) and ethanol (20 mL) to yield the title compound (265 mg, 91%) in the form of a diastereomeric mixture as a colorless oil.

(148f) N-(2,4-dimethoxybenzyl)-2-fluoro-5-methyl-N-(pyrimidin-4-yl)-4-({(1S,2R)-2-[1-(tetrahydro-2H-pyran-2-yl)-1H-pyrazol-3-yl]cyclopentyl}oxy)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (239 mg, 0.55 mmol) prepared in Example 43a, the (1S,2R)-2-[1-(tetrahydro-2H-pyran-2-yl)-1H-pyrazol-3-yl]cyclopentanol (118 mg, 0.50 mmol) prepared in Example 148e, sodium hydride (63%; 29 mg, 0.75 mmol), DMF (3.0 mL) and water (0.016 mL), to yield the title compound (267 mg, 82%) in the form of a diastereomeric mixture as a colorless amorphous solid.

(148 g) 2-Fluoro-5-methyl-4-{[(1S,2R)-2-(1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2-fluoro-5-methyl-N-(pyrimidin-4-yl)-4-({(1S,2R)-2-[1-(tetrahydro-2H-pyran-2-yl)-1H-pyrazol-5-yl]cyclopentyl}oxy)benzenesulfonamide (265 mg, 0.407 mmol) prepared in Example 148f, triethylsilane (0.60 mL), trifluoroacetic acid (4.0 mL) and dichloromethane (6.0 mL), to yield the title compound (168 mg, 99%) as a colorless solid.

$[\alpha]_D^{25}$=60.5 (c 1.02, DMSO).

Example 149

2-Fluoro-5-methyl-4-{[(1R,2S)-2-(1H-pyrazol-5-yl)cyclopentyl]oxy}-N-(pyrimidin-4-yl)benzenesulfonamide

[Formula 167]

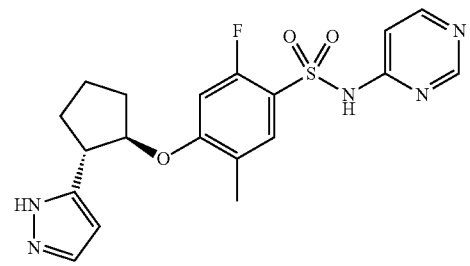

(149a) 5-[(1S,2R)-2-(Benzyloxy)cyclopentyl]-1H-pyrazole

The 5-[(1R*,2S*)-2-(benzyloxy)cyclopentyl]-1H-pyrazole prepared in Example 148b was optically resolved with CHIRALPAK AD-H (Daicel Corp.; hexane/isopropanol=9:1) to yield the title compound as a pale yellow oil.

(149b) 3-[(1S,2R)-2-(Benzyloxy)cyclopentyl]-1-(tetrahydro-2H-pyran-2-yl)-1H-pyrazole The reaction and aftertreatment were conducted in the same manner as in Example 148d by using the 5-[(1S,2R)-2-(benzyloxy)cyclopentyl]-1H-pyrazole (320 mg, 1.32 mmol) prepared in Example 149a, 3,4-dihydro-2H-pyran (0.723 mL, 7.92 mmol), p-toluenesulfonic acid hydrate (50 mg, 0.266 mmol) and dichloromethane (5.0 mL), to yield the title compound (421 mg, 98%) in the form of a diastereomeric mixture as a colorless oil.

(149c) (1R,2S)-2-[1-(Tetrahydro-2H-pyran-2-yl)-1H-pyrazol-3-yl]cyclopentanol

The reaction and aftertreatment were conducted in the same manner as in Example 106b by using the 3-[(1S,2R)-2-(benzyloxy)cyclopentyl]-1-(tetrahydro-2H-pyran-2-yl)-1H-pyrazol (419 mg, 1.28 mmol) prepared in Example 149b, palladium carbon (5%; 400 mg) and ethanol (20 mL), to yield the title compound (269 mg, 89%) in the form of a diastereomeric mixture as a colorless oil.

(149d) N-(2,4-Dimethoxybenzyl)-2-fluoro-5-methyl-N-(pyrimidin-4-yl)-4-({(1R,2S)-2-[1-(tetrahydro-2H-pyran-2-yl)-1H-pyrazol-3-yl]cyclopentyl}oxy)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (239 mg, 0.55 mmol) prepared in Example 43a, the (1R,2S)-2-[1-(tetrahydro-2H-pyran-2-yl)-1H-pyrazol-3-yl]cyclopentanol (118 mg, 0.50 mmol) prepared in Example 149c, sodium hydride (63%; 29 mg, 0.75 mmol), DMF (3.0 mL) and water (0.016 mL), to yield the title compound (227 mg, 70%) in the form of a diastereomeric mixture as a colorless amorphous solid.

(149e) 2-Fluoro-5-methyl-4-{[(1R,2S)-2-(1H-pyrazol-5-yl)cyclopentyl]oxy}-N-(pyrimidin-4-yl)benzenesulfonamide The reaction and aftertreatment were conducted in the same manner as in Example 1b by using the N-(2,4-dimethoxybenzyl)-2-fluoro-5-methyl-N-(pyrimidin-4-yl)-4-({(1R,2S)-2-[1-(tetrahydro-2H-pyran-2-yl)-1H-pyrazol-5-yl]cyclopentyl}oxy)benzenesulfonamide (227 mg, 0.348 mmol) prepared in Example 149d, triethylsilane (0.60 mL), trifluoroacetic acid (4.0 mL) and dichloromethane (6.0 mL), to yield the title compound (143 mg, 98%) as a colorless solid.

$[\alpha]_D^{25}$=−57.8 (c 1.02, DMSO).

Example 150

5-Chloro-2-fluoro-4-{[(1S,2R)-2-(1H-pyrazol-5-yl)cyclopentyl]oxy}-N-(pyrimidin-4-yl)benzenesulfonamide

[Formula 168]

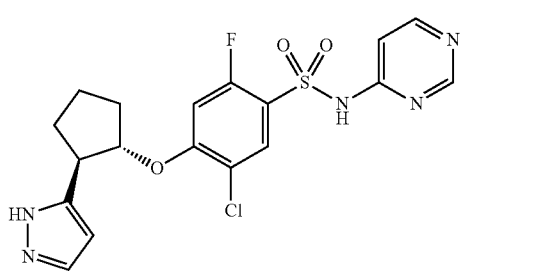

(150a) 5-Chloro-N-(2,4-dimethoxybenzyl)-2-fluoro-N-(pyrimidin-4-yl)-4-({(1S,2R)-2-[1-(tetrahydro-2H-pyran-2-yl)-1H-pyrazol-3-yl]cyclopentyl}oxy)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (251 mg, 0.55 mmol) prepared in Example 20, the (1S,2R)-2-[1-(tetrahydro-2H-pyran-2-yl)-1H-pyrazol-3-yl]cyclopentanol (118 mg, 0.50 mmol) prepared in Example 148e, sodium hydride (63%; 29 mg, 0.75 mmol), DMF (3.0 mL) and water (0.016 mL), to yield the title compound (281 mg, 84%) in the form of a diastereomeric mixture as a colorless amorphous solid.

(150b) 5-Chloro-2-fluoro-4-{[(1S,2R)-2-(1H-pyrazol-5-yl)cyclopentyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-N-(pyrimidin-4-yl)-4-({(1S,2R)-2-[1-(tetrahydro-2H-pyran-2-yl)-1H-pyrazol-3-yl]cyclopentyl}oxy)benzenesulfonamide (281 mg, 0.418 mmol) prepared in Example 150a, triethylsilane (0.60 mL), trifluoroacetic acid (4.0 mL) and dichloromethane (6.0 mL), to yield the title compound (182 mg, 99%) as a colorless solid.

$[\alpha]_D^{25}$=65.0 (c 1.05, DMSO).

Example 151

5-Chloro-2-fluoro-4-{[(1R,2S)-2-(1H-pyrazol-5-yl)cyclopentyl]oxy}-N-(pyrimidin-4-yl)benzenesulfonamide

[Formula 169]

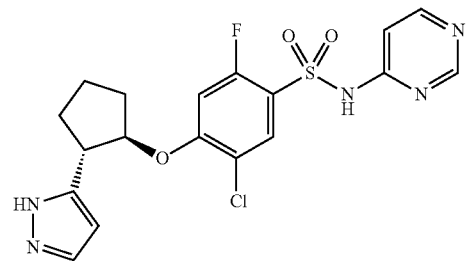

(151a) 5-Chloro-N-(2,4-dimethoxybenzyl)-2-fluoro-N-(pyrimidin-4-yl)-4-({(1R,2S)-2-[1-(tetrahydro-2H-pyran-2-yl)-1H-pyrazol-3-yl]cyclopentyl}oxy)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (251 mg, 0.55 mmol) prepared in Example 20a, the (1R,2S)-2-[1-(tetrahydro-2H-pyran-2-yl)-1H-pyrazol-3-yl]cyclopentanol (118 mg, 0.50 mmol) prepared in Example 149c, sodium hydride (63%; 29 mg, 0.75 mmol), DMF (3.0 mL) and water (0.016 mL), to yield the title compound (287 mg, 85%) in the form of a diastereomeric mixture as a colorless amorphous solid.

(151b) 5-Chloro-2-fluoro-4-{[(1R,2S)-2-(1H-pyrazol-5-yl)cyclopentyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-N-(pyrimidin-4-yl)-4-({(1R,2S)-2-[1-(tetrahydro-2H-pyran-2-yl)-1H-pyrazol-3-yl]cyclopentyl}oxy)benzenesulfonamide (287 mg, 0.427 mmol) prepared in Example 151a, triethylsilane (0.60 mL), trifluoroacetic acid (4.0 mL) and dichloromethane (6.0 mL), to yield the title compound (185 mg, 99%) as a colorless solid.

$[\alpha]_D^{25}$=−52.1 (c 1.04, DMSO).

Example 152

5-Chloro-4-{[(1S*,2R*)-5,5-difluoro-2-(1H-pyrazol-4-yl)cyclohexyl]oxy}-2-fluoro-N-(pyrimidin-4-yl)benzenesulfonamide

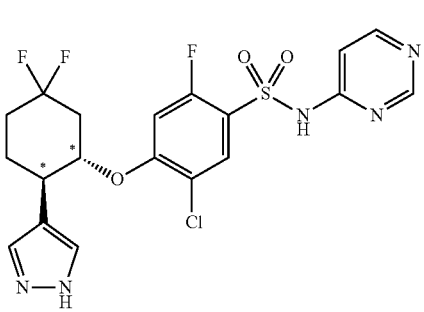

[Formula 170]

(152a) 5-Chloro-4-({(1S*,2R*)-5,5-difluoro-2-[1-(methoxymethyl)-1H-pyrazol-4-yl]cyclohexyl}oxy)-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (0.22 g, 0.48 mmol) prepared in Example 20a, the (1S*,2R*)-5,5-difluoro-2-[1-(methoxymethyl)-1H-pyrazol-4-yl]cyclohexanol (0.10 g, 0.40 mmol) prepared in Example 147c, sodium hydride (63%; 24 mg, 0.60 mmol) and DMF (5.0 mL), to yield the title compound (0.24 g, 87%) as a colorless oil.

$^1$H-NMR (500 MHz, CDCl$_3$) δ ppm: 1.88-2.10 (3H, m), 2.17-2.31 (2H, m), 2.65-2.69 (1H, m), 3.01-3.06 (1H, m), 3.22 (3H, s), 3.7.7 (3H, s), 3.78 (3H, s), 4.21 (1H, dt, J=4.4, 10.3 Hz), 5.21 (2H, s), 5.27 (1H, d, J=10.7 Hz), 5.29 (1H, d, J=10.7 Hz), 6.39-6.41 (2H, m), 6.47 (1H, d, J=11.7 Hz), 7.18-7.20 (2H, m), 7.47 (1H, s), 7.50 (1H, s), 7.99 (1H, d, J=7.3 Hz), 8.46 (1H, d, J=5.9 Hz), 8.79 (1H, d, J=1.0 Hz).

(152b) 5-Chloro-4-{[(1S*,2R*)-5,5-difluoro-2-(1H-pyrazol-4-yl)cyclohexyl]oxy}-2-fluoro-N-(pyrimidin-4-yl)benzenesulfonamide The reaction and aftertreatment were conducted in the same manner as in Example 147e by using the 5-chloro-4-({(1S*,2R*)-5,5-difluoro-2-[1-(methoxymethyl)-1H-pyrazol-4-yl]cyclohexyl}oxy)-N-(2,4-dimethoxybenzyl)-2-fluoro-N-(pyrimidin-4-yl)benzenesulfonamide (0.20 g, 0.29 mmol) prepared in Example 152a, triethylsilane (0.20 mL), dichloromethane (2.0 mL), trifluoroacetic acid (2.0 mL), ethanol (1.0 mL) and 2 M hydrochloric acid (5.0 mL), to yield the title compound (0.060 g, 42%) as a colorless solid.

$^1$H-NMR (500 MHz, DMSO-d$_6$) δ ppm: 1.76-1.84 (1H, m), 2.00-2.19 (4H, m), 2.55-2.59 (1H, m), 3.01-3.05 (1H, m), 4.67 (1H, dt, J=3.9, 9.3 Hz), 6.94 (1H, brs), 7.15 (1H, d, J=12.2 Hz), 7.51 (2H, s), 7.81 (1H, d, J=7.8 Hz), 8.23 (1H, brs), 8.56 (1H, s), 12.88 (1H, brs).

MS (ESI) m/z: 488 [M+H]+.

Example 153

5-Chloro-2-fluoro-4-{[(1S*,2R*)-2-(1-methyl-1H-pyrazol-5-yl)cyclohexyl]oxy}-N-(2-oxo-2,3-dihydropyrimidin-4-yl)benzenesulfonamide

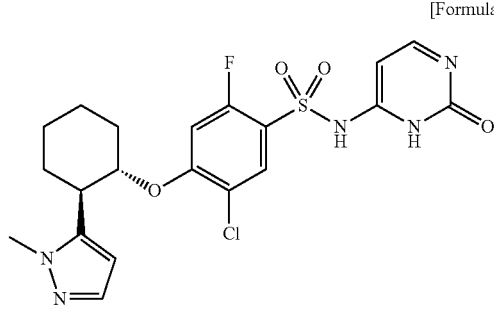

[Formula 171]

(153a) 2-(Benzyloxy)-N-(2,4-dimethoxybenzyl)pyrimidin-4-amine

To a solution of the N-(2,4-dimethoxybenzyl)-2-fluoropyrimidin-4-amine (2.50 g, 9.50 mmol) prepared in Example 95a and benzyl alcohol (1.97 mL, 19.0 mmol) in DMF (48 mL), sodium hydride (0.90 g, 23.7 mmol) was added, and the reaction solution was stirred at room temperature for 6 hours. To the reaction solution, an aqueous ammonium chloride solution (200 mL) was added, followed by extraction with ethyl acetate (100 mL). The thus obtained organic layer was washed twice with water (200 mL) and dried over anhydrous sodium sulfate. After vacuum concentration, the residue was purified with silica gel chromatography (hexane/ethyl acetate=1:2) to yield the title compound (3.29 g, 99%) as a colorless amorphous solid.

$^1$H-NMR (500 MHz, CDCl$_3$) δ ppm: 3.79 (3H, s), 3.82 (3H, s), 4.44 (2H, brs), 5.37 (2H, s), 6.01 (1H, brs), 6.42 (1H, dd, J=2.4, 8.3 Hz), 6.46 (1H, d, J=2.4 Hz), 7.14 (1H, d, J=8.3 Hz), 7.26-7.35 (3H, m), 7.45-7.47 (2H, m), 7.95 (1H, brs).

(153b) N-[2-(benzyloxy)pyrimidin-4-yl]-5-chloro-N-(2,4-dimethoxybenzyl)-2,4-difluorobenzenesulfonamide The reaction and aftertreatment were conducted in the same manner as in Example 86a by using the 2-(benzyloxy)-N-(2,4-dimethoxybenzyl)pyrimidin-4-amine (0.50 g, 1.42 mmol) prepared in Example 153a, 5-chloro-2,4-difluorobenzenesulfonyl chloride (0.36 g, 1.57 mmol), lithium bis(trimethylsilyl)amide (1.0 M solution in THF; 1.71 mL, 1.71 mmol) and THF (5.0 mL), to yield the title compound (487.8 mg, 61%) as a colorless solid.

$^1$H-NMR (500 MHz, CDCl$_3$) δ ppm: 3.81 (3H, s), 3.82 (3H, s), 5.24 (2H, s), 5.29 (2H, s), 6.46-6.48 (2H, m), 6.81 (1H, d, J=5.4 Hz), 7.02 (1H, t, J=8.8 Hz), 7.27 (1H, d, J=9.3 Hz), 7.33-7.41 (5H, m), 8.21 (1H, t, J=7.3 Hz), 8.31 (1H, d, J=5.9 Hz).

(153c) N-[2-(benzyloxy)pyrimidin-4-yl]-5-chloro-N-(2,4-dimethoxybenzyl)-2-fluoro-4-{[(1S,2R)-2-(1-methyl-1H-pyrazol-5-yl)cyclohexyl]oxy}benzenesulfonamide The reaction and aftertreatment were conducted in the same manner as in Example 1a by using the N-[2-(benzyloxy)pyrimidin-4-yl]-5-chloro-N-(2,4-dimethoxybenzyl)-2,4-difluorobenzenesulfonamide (0.49 g, 0.87 mmol) prepared in Example 153b, the (1S,2R)-2-(1-methyl-1H-pyrazol-5-yl)cyclohexanol (0.13 g, 0.69 mmol) prepared in Example 122a, sodium hydride (63%; 0.030 g, 0.87 mmol), DMF (4.3 mL) and water (0.030 mL), to yield the title compound (479.7 mg, 77%) as a colorless amorphous solid.

$^1$H-NMR (500 MHz, CDCl$_3$) δ ppm: 1.36-1.68 (4H, m), 1.85-1.94 (2H, m), 2.04-2.07 (1H, m), 2.18-2.20 (1H, m), 3.02-3.07 (1H, m), 3.76 (3H, s), 3.76 (3H, s), 3.91 (3H, s), 4.12-4.18 (1H, m), 5.16 (2H, s), 5.22 (2H, s), 6.03 (1H, d, J=2.0 Hz), 6.39-6.41 (2H, m), 6.45 (1H, d, J=11.7 Hz), 6.83 (1H, d, J=5.4 Hz), 7.19 (1H, d, J=8.8 Hz), 7.26-7.36 (6H, m), 7.96 (1H, d, J=7.3 Hz), 8.24 (1H, d, J=5.9 Hz).

(153d) 5-Chloro-2-fluoro-4-{[(1S,2R)-2-(1-methyl-1H-pyrazol-5-yl)cyclohexyl]oxy}-N-(2-oxo-2,3-dihydropyrimidin-4-yl)benzenesulfonamide The reaction and aftertreatment were conducted in the same manner as in Example 1b by using the N-[2-(benzyloxy)pyrimidin-4-yl]-5-chloro-N-(2,4-dimethoxybenzyl)-2-fluoro-4-{[(1S,2R)-2-(1-methyl-1H-pyrazol-5-yl)cyclohexyl]oxy}benzenesulfonamide (0.48 g, 0.66 mmol) prepared in Example 153c, triethylsilane (1.6 mL), trifluoroacetic acid (2.0 mL) and dichloromethane (6.6 mL), to yield the title compound (285 mg, 89%) as a colorless solid.

$^1$H-NMR (500 MHz, CDCl$_3$) δ ppm: 1.39-1.68 (4H, m), 1.86-1.95 (2H, m), 2.05-2.08 (1H, m), 2.19-2.23 (1H, m), 3.02-3.07 (1H, m), 3.92 (3H, s), 4.18 (1H, dt, J=3.9, 10.3, Hz), 6.06 (1H, d, J=2.0 Hz), 6.42 (1H, brs), 6.50 (1H, d, J=11.7 Hz), 7.35 (1H, d, J=2.0 Hz), 7.56-7.58 (1H, m), 7.85 (1H, d, J=7.3 Hz), 11.82 (1H, brs).

MS (ESI) m/z: 482 [M+H]+;
$[α]_D^{25}$=−13.9 (c 1.00, DMSO).

Example 154

5-Chloro-2-fluoro-4-({(1S*,2R*)-2-[1-($^{13}$C,$^2$H$_3$)methyl-1H-pyrazol-5-yl]cyclohexyl}oxy)-N-(pyrimidin-4-yl)benzenesulfonamide

[Formula 172]

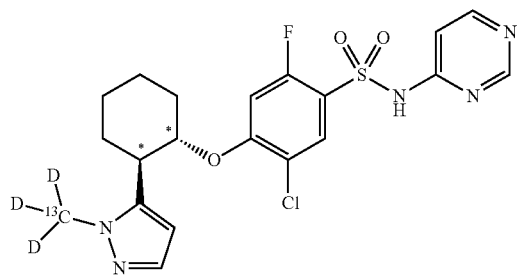

(154a) 1-($^{13}$C,$^2$H$_3$)methyl-1H-pyrazole

To a solution of iodo($^{13}$C,$^2$H$_3$)methane (5.00 g, 34.2 mmol) and 1H-pyrazole (2.16 g, 31.7 mmol) in THF (20 mL), sodium hydride (63%; 1.32 g, 34.5 mmol) was added with cooling on ice, and the mixture was stirred at room temperature for 6 hours. To the reaction solution, methylene chloride (200 mL) was added, the resulting insoluble matter was filtered off, and the filtrate was vacuum concentrated to yield the title compound (1.27 g, 47%) in a crude form as a yellow oil.

$^1$H-NMR (500 MHz, CDCl$_3$) δ ppm: 6.25 (1H, t, J=2.0 Hz), 7.35-7.36 (1H, m), 7.50 (1H, d, J=1.5 Hz).

(154b) (1S*,2R*)-2-[1-($^{13}$C,$^2$H$_3$)methyl-1H-pyrazol-5-yl]cyclohexanol The reaction and aftertreatment were conducted in the same manner as in Example 4a by using the 1-($^{13}$C,$^2$H$_3$)methyl-1H-pyrazole (1.27 g, 14.8 mmol) prepared in Example 154a, N,N,N',N'-tetramethylethylenediamine (2.21 mL, 14.8 mmol), butyl lithium (2.69 M solution in hexane; 6.41 mL, 17.2 mmol), cyclohexene oxide (1.79 mL, 17.7 mmol) and THF (30 mL), to yield the title compound (1.29 g, 48%) as a yellow oil.

$^1$H-NMR (500 MHz, CDCl$_3$) δ ppm: 1.30-1.46 (4H, m), 1.75-1.91 (4H, m), 2.10-2.13 (1H, m), 2.57-2.62 (1H, m), 3.61-3.65 (1H, m), 6.08 (1H, d, J=2.0 Hz), 7.44 (1H, d, J=1.5 Hz).

(154c) 5-Chloro-N-(2,4-dimethoxybenzyl)-2-fluoro-4-({(1S*,2R*)-2-[1-($^{13}$C,$^2$H$_3$)methyl-1H-pyrazol-5-yl]cyclohexyl}oxy)-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (3.19 g, 7.00 mmol) prepared in Example 20a, the (1S*,2R*)-2-[1-($^{13}$C,$^2$H$_3$)methyl-1H-pyrazol-5-yl]cyclohexanol (1.29 g, 7.0 mmol) prepared in Example 154b, sodium hydride (63%; 0.32 g, 8.40 mmol), DMF (20 mL) and water (0.13 mL), to yield the title compound (2.70 g, 62%) as a yellow oil.

$^1$H-NMR (400 MHz, CDCl$_3$) δ ppm: 1.39-1.67 (4H, m), 1.85-1.97 (2H, m), 2.04-2.10 (1H, m), 2.18-2.23 (1H, m), 3.02-3.08 (1H, m), 3.76 (3H, s), 3.77 (3H, s), 4.09-4.17 (1H, m), 5.21 (2H, s), 6.03 (1H, d, J=2.0 Hz), 6.39-6.44 (3H, m), 7.17-7.22 (2H, m), 7.35 (1H, d, J=2.0 Hz), 7.93 (1H, d, J=7.4 Hz), 8.46 (1H, d, J=5.9 Hz), 8.79 (1H, d, J=0.78 Hz).

(154d) 5-Chloro-2-fluoro-4-({(1S*,2R*)-2-[1-($^{13}$C,$^2$H$_3$)methyl-1H-pyrazol-5-yl]cyclohexyl}oxy)-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-({(1S*,2R*)-2-[1-($^{13}$C,$^2$H$_3$)methyl-1H-pyrazol-5-yl]cyclohexyl}oxy)-N-(pyrimidin-4-yl)benzenesulfonamide (2.70 g, 4.35 mmol) prepared in Example 154c, triethylsilane (2.00 mL), trifluoroacetic acid (2.0 mL) and dichloromethane (20 mL), to yield the title compound (0.904 g, 44%) as a colorless solid.

$^1$H-NMR (500 MHz, CDCl$_3$) δ ppm: 1.39-1.69 (4H, m), 1.86-1.96 (2H, m), 2.05-2.08 (1H, m), 2.17-2.22 (1H, m), 3.01-3.06 (1H, m), 4.11-4.16 (1H, m), 6.03 (1H, d, J=2.0 Hz), 6.47 (1H, d, J=11.7 Hz), 7.23 (1H, d, J=6.4 Hz), 7.33 (1H, d, J=2.0 Hz), 7.94 (1H, d, J=7.8 Hz), 8.39 (1H, d, J=6.4 Hz), 8.79 (1H, s).

MS (ESI) m/z: 468 [M−H]−.

Example 155

4-{[(1S*,2R*)-5,5-Difluoro-2-(1H-pyrazol-5-yl)cyclohexyl]oxy}-2-fluoro-5-methyl-N-(pyrimidin-4-yl)benzenesulfonamide

[Formula 173]

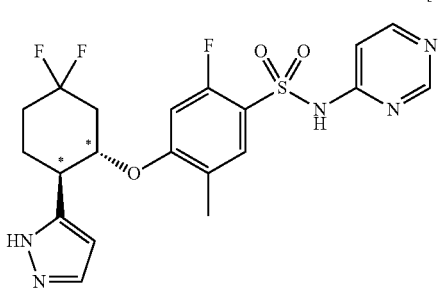

(155a) 1-[(2-Methoxyethoxy)methyl]-1H-pyrazole

To a solution of 1H-pyrazole (13.6 g, 200 mmol) and N,N-diisopropylethylamine (68 mL, 400 mmol) in dichloromethane (150 mL), 2-methoxyethoxymethyl chloride (24.9 mL, 220 mmol) was added with cooling on ice. The reaction solution was stirred at room temperature for 2 hours, and an aqueous sodium hydrogencarbonate solution (500 mL) was then added to the reaction solution, followed by extraction three times with dichloromethane (500 mL). The organic layer was dried over anhydrous sodium sulfate. After vacuum concentration, the residue was purified with silica gel chromatography (hexane/ethyl acetate=1:1) to yield the title compound (29.9 g, 96%) as a colorless oil.

$^1$H-NMR (500 MHz, CDCl$_3$) δ ppm: 3.36 (3H, s), 3.48-3.50 (2H, m), 3.63-3.64 (2H, m), 5.52 (2H, s), 6.35 (1H, t, J=2.0 Hz), 7.56 (1H, d, J=1.0 Hz), 7.60 (1H, d, J=2.4 Hz).

(155b) (1S*,2R*,5R*)-5-(Benzyloxy)-2-{1-[(2-methoxyethoxy)methyl]-1H-pyrazol-5-yl}cyclohexanol To a solution of the 1-[(2-methoxyethoxy)methyl]-1H-pyrazole (3.13 g, 20.1 mmol) prepared in Example 155a in THF (30 mL), butyl lithium (2.69 M solution in hexane; 7.46 mL, 20.1 mmol) and a boron trifluoride-diethyl ether complex (6.30 mL, 50.1 mmol) were added in that order at −78° C. The reaction solution was stirred at −78° C. for 10 minutes. Then, (1S*,3R*,6R*)-3-(benzyloxy)-7-oxabicyclo[4.1.0]heptane (J. Chem. Soc. Perkin Trans. 1 1997, 657; 3.41 g, 16.7 mmol) was added thereto, and the mixture was stirred at −78° C. for 5 hours. To the reaction solution, an aqueous sodium hydrogencarbonate solution (100 mL) was added, followed by extraction three times with ethyl acetate (100 mL). The thus obtained organic layer was dried over anhydrous sodium sulfate. After vacuum concentration, the residue was purified with silica gel chromatography (ethyl acetate) to yield the title compound (3.00 g, 55%) as a mixture (3.00 g, 55%) with (1S*,2R*,4S*)-4-(benzyloxy)-2-{1-[(2-methoxyethoxy)methyl]-1H-pyrazol-5-yl}cyclohexanol.

(155c) (1S*,2R*,5R*)-5-(Benzyloxy)-2-{1-[(2-methoxyethoxy)methyl]-1H-pyrazol-5-yl}cyclohexyl benzoate To a solution of the mixture (2.99 g, 8.30 mmol) of (1S*,2R*,5R*)-5-(benzyloxy)-2-{1-[(2-methoxyethoxy)methyl]-1H-pyrazol-5-yl}cyclohexanol and (1S*,2R*,4S*)-4-(benzyloxy)-2-(1-[(2-methoxyethoxy)methyl]-1H-pyrazol-5-yl)cyclohexanol prepared in Example 155b, triethylamine (4.62 mL, 33.2 mmol), 4-(N,N-dimethylamino)pyridine (203 mg, 1.66 mmol) in dichloroethane (30 mL), and benzoyl chloride (1.93 mL, 16.6 mmol) was added, and the reaction solution was stirred for 5 hours under heated reflux. To the reaction solution, water (100 mL) was added, and an organic layer was extracted and then dried over anhydrous sodium sulfate. After vacuum concentration, the residue was purified with column chromatography (hexane/ethyl acetate=1:9) to yield the title compound (2.72 g, 71%) as a mixture (2.72 g, 71%) with (1R*,2R*,4S*)-4-(benzyloxy)-2-{1-[(2-methoxyethoxy)methyl]-1H-pyrazol-5-yl}cyclohexyl benzoate.

(155d) (1S*,2R*,5R*)-5-Hydroxy-2-{1-[(2-methoxyethoxy)methyl]-1H-pyrazol-5-yl}cyclohexyl benzoate A solution of the mixture (2.72 g, 5.84 mmol) of (1S*,2R*,5R*)-5-(benzyloxy)-2-{1-[(2-methoxyethoxy)methyl]-1H-pyrazol-5-yl}cyclohexyl benzoate and (1R*,2R*,4S*)-4-(benzyloxy)-2-{1-[(2-methoxyethoxy)methyl]-1H-pyrazol-5-yl}cyclohexyl benzoate prepared in Example 155c and palladium carbon (5%; 3.00 g) in ethanol (20 mL) was stirred at 50° C. for 11 hours under a hydrogen atmosphere. The reaction solution was filtered through celite, the filtrate was concentrated, and the residue was purified with silica gel chromatography (ethyl acetate) to yield the title compound (1.06 g, 48%) as a colorless oil.

$^1$H-NMR (500 MHz, CDCl$_3$) δ ppm: 1.69-1.80 (2H, m), 1.90-1.97 (2H, m), 2.06-2.13 (1H, m), 2.34-2.39 (1H, m), 3.26-3.31 (1H, m), 3.37 (3H, s), 3.42-3.51 (2H, m), 3.55-3.65 (2H, m), 4.36 (1H, s), 5.45 (1H, d, J=11.7 Hz), 5.59 (1H, dt, J=4.4, 10.7 Hz), 5.77 (1H, d, J=11.2 Hz), 6.24 (1H, d, J=2.0 Hz), 7.35-7.38 (3H, m), 7.51 (1H, t, J=7.3 Hz), 7.82-7.84 (2H, m).

Also, a by-product (1S*,2R*,4S*)-4-hydroxy-2-{1-[(2-methoxyethoxy)methyl]-1H-pyrazol-5-yl}cyclohexyl benzoate (825 mg, 38%) was obtained as a colorless oil.

$^1$H-NMR (500 MHz, CDCl$_3$) δ ppm: 1.56-1.68 (3H, m), 2.12-2.35 (3H, m), 3.34-3.38 (1H, m), 3.38 (3H, s), 3.42-3.51 (2H, m), 3.53-3.64 (2H, m), 3.86-3.92 (1H, m), 5.16 (1H, dt, J=4.4, 10.3 Hz), 5.42 (1H, d, J=11.2 Hz), 5.76 (1H, d, J=11.2 Hz), 6.20 (1H, d, J=2.0 Hz), 7.35-7.38 (3H, m), 7.51 (1H, t, J=7.3 Hz), 7.81-7.82 (2H, m).

(155e) (1S*,2R*)-2-{1-[(2-Methoxyethoxy)methyl]-1H-pyrazol-5-yl}-5-oxocyclohexyl benzoate The reaction and aftertreatment were conducted in the same manner as in Example 107c by using the (1S*,2R*,5R*)-5-hydroxy-2-{1-[(2-methoxyethoxy)methyl]-1H-pyrazol-5-yl}cyclohexyl benzoate (1.06 g, 2.83 mmol) prepared in Example 155d, a Dess-Martin reagent (1.80 g, 4.25 mmol) and dichloromethane (40 mL), to yield the title compound (945 mg, 90%) as a colorless oil.

$^1$H-NMR (500 MHz, CDCl$_3$) δ ppm: 1.89-1.98 (1H, m), 2.36-2.67 (4H, m), 3.04 (1H, ddd, J=1.5, 4.9, 14.6 Hz), 3.36 (3H, s), 3.43-3.53 (2H, m), 3.57-3.71 (3H, m), 5.48-5.53

(1H, m), 5.52 (1H, d, J=11.2 Hz), 5.82 (1H, d, J=11.2 Hz), 6.24 (1H, d, J=1.5 Hz), 7.38-7.43 (3H, m), 7.54 (1H, t, J=7.3 Hz), 7.85-7.87 (2H, m).

(155f) (1S*,2R*)-5,5-Difluoro-2-{1-[(2-methoxyethoxy)methyl]-1H-pyrazol-5-yl}cyclohexyl benzoate The reaction and aftertreatment were conducted in the same manner as in Example 106c by using the (1S*,2R*)-2-{1-[(2-methoxyethoxy)methyl]-1H-pyrazol-5-yl}-5-oxocyclohexyl benzoate (940 mg, 2.52 mmol) prepared in Example 155e, bis(2-methoxyethyl)amino sulfur trifluoride (2.66 mL, 15.1 mmol) and dichloromethane (10 mL), to yield the title compound (465 mg, 43%) as a colorless oil.

$^1$H-NMR (500 MHz, CDCl$_3$) δ ppm: 1.80-2.29 (5H, m), 2.74-2.81 (1H, m), 3.31-3.34 (1H, m), 3.36 (3H, s), 3.40-3.51 (2H, m), 3.53-3.65 (2H, m), 5.41 (1H, dt, J=4.4, 10.7 Hz), 5.44 (1H, d, J=11.7 Hz), 5.76 (1H, d, J=11.2 Hz), 6.21 (1H, d, J=2.0 Hz), 7.36-7.39 (3H, m), 7.53 (1H, t, J=7.8 Hz), 7.81-7.83 (2H, m).

(155g) (1S*,2R*)-5,5-Difluoro-2-{1-[(2-methoxyethoxy)methyl]-1H-pyrazol-5-yl}cyclohexanol The reaction and aftertreatment were conducted in the same manner as in Example 107e by using the (1S*,2R*)-5,5-difluoro-2-{1-[(2-methoxyethoxy)methyl]-1H-pyrazol-5-yl}cyclohexyl benzoate (463 mg, 1.17 mmol) prepared in Example 155f, potassium carbonate (16 mg, 0.117 mmol) and methanol (10 mL), to yield the title compound (307 mg, 90%) as a colorless oil.

$^1$H-NMR (500 MHz, CDCl$_3$) δ ppm: 1.71-1.99 (4H, m), 2.15-2.21 (1H, m), 2.56-2.63 (1H, m), 2.73-2.79 (1H, m), 2.87-2.92 (1H, m), 3.30 (3H, s), 3.44-3.46 (2H, m), 3.59-3.68 (2H, m), 3.85-3.91 (1H, m), 5.53 (1H, d, J=11.2 Hz), 5.65 (1H, d, J=11.2 Hz), 6.22 (1H, d, J=2.0 Hz), 7.50 (1H, d, J=1.5 Hz).

(155h) 4-{[(1S*,2R*)-5,5-Difluoro-2-{1-[(2-methoxyethoxy)methyl]-1H-pyrazol-5-yl}cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (261 mg, 0.60 mmol) prepared in Example 43a, the (1S*,2R*)-5,5-difluoro-2-{1-[(2-methoxyethoxy)methyl]-1H-pyrazol-5-yl}cyclohexanol (145 mg, 0.50 mmol) prepared in Example 155g, sodium hydride (63%; 29.0 mg, 0.75 mmol), DMF (8.0 mL) and water (0.016 mL), to yield the title compound (280 mg, 79%) as a colorless amorphous solid.

$^1$H-NMR (500 MHz, CDCl$_3$) δ ppm: 1.84-2.04 (3H, m), 1.98 (3H, s), 2.12-2.18 (1H, m), 2.25-2.31 (1H, m), 2.68-2.74 (1H, m), 3.35 (3H, s), 3.39-3.45 (2H, m), 3.47-3.55 (2H, m), 3.65-3.69 (1H, m), 3.76 (3H, s), 3.78 (3H, s), 4.41 (1H, dt, J=3.9, 10.3 Hz), 5.23 (2H, s), 5.44 (1H, d, J=11.2 Hz), 5.83 (1H, d, J=11.7 Hz), 6.10 (1H, d, J=1.5 Hz), 6.38-6.44 (3H, m), 7.19 (1H, d, J=8.8 Hz), 7.25 (1H, dd, J=1.5, 5.9 Hz), 7.41 (1H, d, J=2.0 Hz), 7.68 (1H, d, J=7.3 Hz), 8.43 (1H, d, J=5.9 Hz), 8.76 (1H, s).

(155i) 4-{[(1S*,2R*)-5,5-Difluoro-2-(1H-pyrazol-5-yl)cyclohexyl]oxy}-2-fluoro-5-methyl-N-(pyrimidin-4-yl)benzenesulfonamide To a solution of the 4-{[(1S*,2R*)-5,5-difluoro-2-{1-[(2-methoxyethoxy)methyl]-1H-pyrazol-5-yl}cyclohexyl]oxy}-N-(2,4-dimethoxybenzyl)-2-fluoro-5-methyl-N-(pyrimidin-4-yl)benzenesulfonamide (265 mg, 0.376 mmol) prepared in Example 155h and triethylsilane (0.50 mL) in dichloroethane (5.0 mL), trifluoroacetic acid (5.0 mL) was added at room temperature, and the reaction solution was stirred for 4 hours. The reaction solution was concentrated, then methanol (15 mL) and 6 M hydrochloric acid (5.0 mL) were added to the residue, and the reaction solution was stirred for 5 hours under heated reflux. To the reaction solution, an aqueous sodium hydrogencarbonate solution (50 mL) was added, followed by extraction five times with a dichloromethane/methanol (10:1) mixed solvent (50 mL). The thus obtained organic layer was dried over anhydrous sodium sulfate. After vacuum concentration, the residue was purified with silica gel chromatography (dichloromethane/methanol=10:1) to yield the title compound (125 mg, 71%) as a colorless solid.

$^1$H-NMR (500 MHz, DMSO-d$_6$) δ ppm: 1.78-1.86 (1H, m), 2.00-2.23 (4H, m), 2.00 (3H, s), 2.55-2.63 (1H, m), 3.15-3.20 (1H, m), 3.74-3.78 (1H, m), 6.15 (1H, d, J=2.0 Hz), 6.88 (1H, d, J=12.2 Hz), 7.00 (1H, brs), 7.47 (1H, brs), 7.62 (1H, d, J=8.3 Hz), 8.31 (1H, brs), 8.57 (1H, brs), 12.60 (1H, brs).

MS (ESI) m/z: 468 [M+H]+.

Example 156

5-Chloro-4-{[(1S*,2R*)-5,5-difluoro-2-(1H-pyrazol-5-yl)cyclohexyl]oxy}-2-fluoro-N-(pyrimidin-4-yl)benzenesulfonamide

[Formula 174]

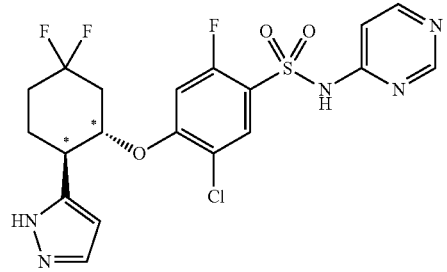

(156a) 5-Chloro-4-{[(1S*,2R*)-5,5-difluoro-2-{1-[(2-methoxyethoxy)methyl]-1H-pyrazol-5-yl}cyclohexyl]oxy}-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (129 mg, 0.283 mmol) prepared in Example 20a, the (1S*,2R*)-5,5-difluoro-2-{1-[(2-methoxyethoxy)methyl]-1H-pyrazol-5-yl}cyclohexanol (68 mg, 0.236 mmol) prepared in Example 155 g, sodium hydride (63%;

13.0 mg, 0.354 mmol), DMF (5.0 mL) and water (0.008 mL), to yield the title compound (105 mg, 61%) as a colorless amorphous solid.

$^1$H-NMR (500 MHz, CDCl$_3$) δ ppm: 1.87-2.16 (4H, m), 2.26-2.32 (1H, m), 2.66-2.70 (1H, m), 3.35 (3H, s), 3.40-3.53 (4H, m), 3.65-3.69 (1H, m), 3.76 (6H, s), 4.39 (1H, dt, J=4.4, 10.7 Hz), 5.20 (2H, s), 5.41 (1H, d, J=11.2 Hz), 6.02 (1H, d, J=11.2 Hz), 6.14 (1H, d, J=2.0 Hz), 6.38-6.40 (2H, m), 6.49 (1H, d, J=11.2 Hz), 7.19 (2H, d, J=8.3 Hz), 7.40 (1H, d, J=2.0 Hz), 7.94 (1H, d, J=7.3 Hz), 8.47 (1H, d, J=5.4 Hz), 8.79 (1H, s).

(156b) 5-Chloro-4-{[(1S*,2R*)-5,5-difluoro-2-(1H-pyrazol-5-yl)cyclohexyl]oxy}-2-fluoro-N-(pyrimidin-4-yl)benzenesulfonamide The reaction and aftertreatment were conducted in the same manner as in Example 155i by using the 5-chloro-4-{[(1S*,2R*)-5,5-difluoro-2-{1-[(2-methoxyethoxy)methyl]-1H-pyrazol-5-yl}cyclohexyl]oxy}-N-(2,4-dimethoxybenzyl)-2-fluoro-N-(pyrimidin-4-yl) benzenesulfonamide (105 mg, 0.145 mmol) prepared in Example 156a, triethylsilane (0.30 mL), trifluoroacetic acid (3.0 mL), dichloromethane (3.0 mL), 6 M hydrochloric acid (5.0 mL) and methanol (15 mL), to yield the title compound (29 mg, 41%) as a colorless solid.

$^1$H-NMR (500 MHz, DMSO-d$_6$) δ ppm: 1.80-1.87 (1H, m), 1.99-2.28 (4H, m), 2.55-2.64 (1H, m), 3.18-3.22 (1H, m), 4.86-4.91 (1H, m), 6.18 (1H, d, J=2.0 Hz), 6.95 (1H, brs), 7.13 (1H, d, J=11.7 Hz), 7.47 (1H, brs), 7.79 (1H, d, J=7.3 Hz), 8.24 (1H, brs), 8.56 (1H, brs), 12.51 (1H, brs).
MS (ESI) m/z: 488 [M+H]+.

Example 157

4-{[(1S*,2R*)-4,4-Difluoro-2-(1H-pyrazol-5-yl)cyclohexyl]oxy}-2-fluoro-5-methyl-N-(pyrimidin-4-yl)benzenesulfonamide

[Formula 175]

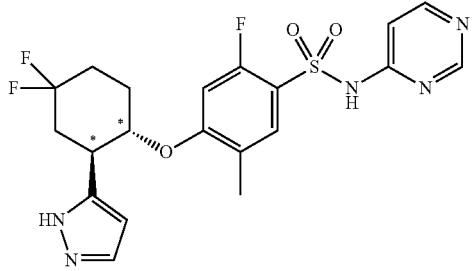

(157a) (1S*,2R*)-2-{1-[(2-Methoxyethoxy)methyl]-1H-pyrazol-5-yl}-4-oxocyclohexyl benzoate The reaction and aftertreatment were conducted in the same manner as in Example 107c by using the by-product (1S*,2R*,4S*)-4-hydroxy-2-{1-[(2-methoxyethoxy)methyl]-1H-pyrazol-5-yl}cyclohexyl benzoate (825 mg, 2.20 mmol) of Example 155d, a Dess-Martin reagent (1.40 g, 3.31 mmol) and dichloromethane (10 mL), to yield the title compound (688 mg, 83%) as a colorless oil.

$^1$H-NMR (500 MHz, CDCl$_3$) δ ppm: 2.09-2.17 (1H, m), 2.25-2.32 (1H, m), 2.54-2.66 (2H, m), 2.71-2.77 (1H, m), 2.94 (1H, dd, J=5.9, 15.1 Hz), 3.33 (3H, s), 3.43-3.50 (2H, m), 3.58-3.69 (2H, m), 3.95 (1H, q, J=6.4 Hz), 5.54 (1H, d, J=11.2 Hz), 5.55-5.58 (1H, m), 5.79 (1H, d, J=11.2 Hz), 6.20 (1H, d, J=1.5 Hz), 7.44-7.47 (3H, m), 7.59 (1H, t, J=7.3 Hz), 7.97-7.99 (2H, m).

(157b) (1S*,2R*)-4,4-Difluoro-2-(1-[(2-methoxyethoxy)methyl]-1H-pyrazol-5-yl)cyclohexyl benzoate The reaction and aftertreatment were conducted in the same manner as in Example 106c by using the (1S*,2R*)-2-{1-[(2-methoxyethoxy)methyl]-1H-pyrazol-5-yl}-4-oxocyclohexyl benzoate (686 mg, 1.84 mmol) prepared in Example 157a, bis(2-methoxyethyl)amino sulfur trifluoride (1.94 mL, 11.1 mmol) and dichloromethane (10 mL), to yield the title compound (547 mg, 75%) as a colorless oil.

$^1$H-NMR (500 MHz, CDCl$_3$) δ ppm: 1.87-2.13 (3H, m), 2.25-2.32 (2H, m), 2.51-2.57 (1H, m), 3.37 (3H, s), 3.47-3.56 (3H, m), 3.60-3.68 (2H, m), 5.26 (1H, dt, J=3.4, 10.7 Hz), 5.44 (1H, d, J=11.2 Hz), 5.75 (1H, d, J=11.2 Hz), 6.21 (1H, d, J=2.0 Hz), 7.36-7.39 (3H, m), 7.53 (1H, t, J=7.3 Hz), 7.82-7.84 (2H, m).

(157c) (1S*,2R*)-4,4-Difluoro-2-{1-[(2-methoxyethoxy)methyl]-1H-pyrazol-5-yl}cyclohexanol The reaction and aftertreatment were conducted in the same manner as in Example 107e by using the (1S*,2R*)-4,4-difluoro-2-{1-[(2-methoxyethoxy)methyl]-1H-pyrazol-5-yl}cyclohexyl benzoate (547 mg, 1.39 mmol) prepared in Example 157b, potassium carbonate (19 mg, 0.139 mmol) and methanol (10 mL), to yield the title compound (404 mg, 99%) as a yellow oil.

$^1$H-NMR (500 MHz, CDCl$_3$) δ ppm: 1.75-1.81 (1H, m), 1.85-2.03 (2H, m), 2.12-2.26 (2H, m), 2.31-2.38 (1H, m), 3.18-3.24 (1H, m), 3.31 (3H, s), 3.43-3.51 (2H, m), 3.60-3.73 (3H, m), 5.53 (1H, d, J=10.7 Hz), 5.61 (1H, d, J=11.2 Hz), 6.22 (1H, s), 7.51 (1H, s).

(157d) 4-{[(1S*,2R*)-4,4-Difluoro-2-{1-[(2-methoxyethoxy)methyl]-1H-pyrazol-5-yl}cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (785 mg, 1.81 mmol) prepared in Example 43a, the (1S*,2R*)-4,4-difluoro-2-{1-[(2-methoxyethoxy)methyl]-1H-pyrazol-5-yl}cyclohexanol (404 mg, 1.39 mmol) prepared in Example 157c, sodium hydride (63%; 79.0 mg, 2.08 mmol), DMF (6.0 mL) and water (0.045 mL), to yield the title compound (358 mg, 36%) as a colorless amorphous solid.

$^1$H-NMR (500 MHz, CDCl$_3$) δ ppm: 1.82-2.14 (3H, m), 2.00 (3H, s), 2.22-2.31 (2H, m), 2.47-2.56 (1H, m), 3.36 (3H, s), 3.44-3.54 (2H, m), 3.64-3.73 (3H, m), 3.75 (3H, s), 3.78 (3H, s), 4.32 (1H, dt, J=3.4, 10.3 Hz), 5.24 (2H, s), 5.44 (1H, d, J=11.2 Hz), 5.81 (1H, d, J=11.2 Hz), 6.13 (1H, d, J=2.0 Hz), 6.38-6.44 (3H, m), 7.18 (1H, d, J=7.8 Hz), 7.27 (1H, d, J=6.4 Hz), 7.42 (1H, d, J=2.0 Hz), 7.68 (1H, d, J=7.8 Hz), 8.43 (1H, d, J=5.9 Hz), 8.76 (1H, s).

(157e) 4-{[(1S*,2R*)-4,4-Difluoro-2-(1H-pyrazol-5-yl)cyclohexyl]oxy}-2-fluoro-5-methyl-N-(pyrimidin-4-yl)benzenesulfonamide The reaction and aftertreatment were conducted in the same manner as in Example 155i by using the 4-{[(1S*,2R*)-4,4-difluoro-2-(1-[(2-methoxyethoxy)methyl]-1H-pyrazol-5-yl)cyclohexyl]oxy}-N-(2,4-dimethoxybenzyl)-2-fluoro-5-methyl-N-(pyrimidin-4-yl)benzenesulfonamide (356 mg, 0.504 mmol) prepared in Example 157d, triethylsilane (0.50 mL), trifluoroacetic acid (5.0 mL), dichloromethane (5.0 mL), 6 M hydrochloric acid (5.0 mL) and methanol (15 mL), to yield the title compound (155 mg, 66%) as a colorless solid.

$^1$H-NMR (500 MHz, DMSO-$d_6$) δ ppm: 1.60-1.67 (1H, m), 1.98 (3H, s), 2.10-2.36 (5H, m), 3.20-3.26 (1H, m), 4.69-4.74 (1H, m), 6.11 (1H, d, J=2.0 Hz), 7.00-7.02 (2H, m), 7.45 (1H, brs), 7.59 (1H, d, J=7.8 Hz), 8.35 (1H, brs), 8.58 (1H, brs), 12.59 (1H, brs).
MS (ESI) m/z: 468 [M+H]+.

Example 158

5-Chloro-2-fluoro-4-{[(1S,2R)-2-(1H-pyrazol-5-yl)cyclohexyl]oxy}-N-(pyrimidin-4-yl)benzenesulfonamide

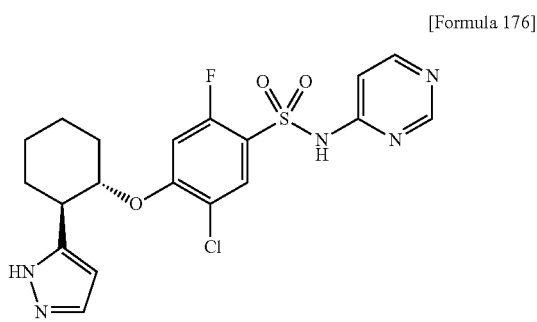 [SMILES: O=S(=O)(Nc1ccncn1)c1cc(Cl)c(O[C@H]2CCCC[C@@H]2c2ccn[nH]2)cc1F]

[Formula 176]

(158a) (1S*,2R*)-2-{1-[(2-Methoxyethoxy)methyl]-1H-pyrazol-5-yl}cyclohexanol The reaction and aftertreatment were conducted in the same manner as in Example 155b by using the 1-[(2-methoxyethoxy)methyl]-1H-pyrazole (2.00 g, 12.8 mmol) prepared in Example 155a, butyl lithium (2.69 M solution in hexane; 4.76 mL, 12.8 mmol), a boron trifluoride-diethyl ether complex (2.68 mL, 21.3 mmol), cyclohexene oxide (1.05 g, 10.7 mmol) and THF (100 mL), to yield the title compound (1.64 g, 60%) as a colorless oil.

$^1$H-NMR (500 MHz, CDCl$_3$) δ ppm: 1.30-1.48 (4H, m), 1.73-2.13 (3H, m), 2.11-2.13 (1H, m), 2.77-2.82 (1H, m), 3.32 (3H, s), 3.45-3.47 (2H, m), 3.57-3.68 (4H, m), 5.52 (1H, d, J=12.2 Hz), 5.64 (1H, d, J=11.2 Hz), 6.18 (1H, d, J=2.0 Hz), 7.48 (1H, d, J=1.0 Hz).

(158b) (1S,2R)-2-{1-[(2-Methoxyethoxy)methyl]-1H-pyrazol-5-yl}cyclohexanol

The (1S*,2R*)-2-{1-[(2-methoxyethoxy)methyl]-1H-pyrazol-5-yl}cyclohexanol prepared in Example 158a was optically resolved with CHIRALFLASH IC (Daicel Corp.; hexane/isopropanol=1:1) to yield the title compound as a colorless oil.

(158c) 5-Chloro-N-(2,4-dimethoxybenzyl)-2-fluoro-4-{[(1S,2R)-2-{1-[(2-methoxyethoxy)methyl]-1H-pyrazol-5-yl}cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (280 mg, 0.614 mmol) prepared in Example 20a, the (1S,2R)-2-{1-[(2-methoxyethoxy)methyl]-1H-pyrazol-5-yl}cyclohexanol (104 mg, 0.409 mmol) prepared in Example 158b, sodium hydride (63%; 18.7 mg, 0.491 mmol) and DMF (2.0 mL), to yield the title compound (242 mg, 86%) as a colorless amorphous solid.

$^1$H-NMR (400 MHz, CDCl$_3$) δ ppm: 1.43-1.69 (4H, m), 1.84-1.95 (2H, m), 2.08-2.21 (2H, m), 3.36 (3H, s), 3.43-3.55 (4H, m), 3.65-3.70 (1H, m), 3.76 (6H, s), 4.17 (1H, dt, J=3.9, 10.2 Hz), 5.21 (2H, s), 5.40 (1H, d, J=11.3 Hz), 6.05 (1H, d, J=11.3 Hz), 6.10 (1H, d, J=2.0 Hz), 6.37-6.40 (2H, m), 6.49 (1H, d, J=11.7 Hz), 7.16-7.19 (1H, m), 7.22 (1H, dd, J=1.6, 6.3 Hz), 7.38 (1H, d, J=1.6 Hz), 7.91 (1H, d, J=7.4 Hz), 8.46 (1H, d, J=5.9 Hz), 8.79 (1H, d, J=0.8 Hz).

(158d) 5-Chloro-2-fluoro-4-{[(1S,2R)-2-(1-[(2-methoxyethoxy)methyl]-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S,2R)-2-{1-[(2-methoxyethoxy)methyl]-1H-pyrazol-5-yl}cyclohexyl]oxy}-N-(pyrimidin-4-yl)benzenesulfonamide (154 mg, 0.223 mmol) prepared in Example 158c, triethylsilane (0.20 mL), trifluoroacetic acid (1.0 mL) and dichloromethane (2.0 mL), to yield the title compound (120 mg, 99%) as a colorless oil.

$^1$H-NMR (500 MHz, CDCl$_3$) δ ppm: 1.43-1.67 (4H, m), 1.85-1.94 (2H, m), 2.08-2.21 (2H, m), 3.36 (3H, s), 3.42-3.45 (4H, m), 3.64-3.69 (1H, m), 4.17 (1H, dt, J=3.9, 10.3 Hz), 5.38 (1H, d, J=11.2 Hz), 6.04 (1H, d, J=11.7 Hz), 6.11 (1H, s), 6.54 (1H, d, J=11.2 Hz), 7.25 (1H, d, J=6.4 Hz), 7.37 (1H, s), 7.93 (1H, dd, J=2.0, 7.3 Hz), 8.37-8.39 (1H, m), 8.80 (1H, s).

(158e) 5-Chloro-2-fluoro-4-{[(1S,2R)-2-(1H-pyrazol-5-yl)cyclohexyl]oxy}-N-(pyrimidin-4-yl)benzenesulfonamide A solution of the 5-chloro-2-fluoro-4-{[(1S,2R)-2-{1-[(2-methoxyethoxy)methyl]-1H-pyrazol-5-yl}cyclohexyl]oxy}-N-(pyrimidin-4-yl)benzenesulfonamide (120 mg, 0.222 mmol) prepared in Example 158d in 6 M HCl (5.0 mL) and methanol (4.0 mL) was stirred for 5 hours under heated reflux. The reaction solution was concentrated, and the residue was purified with silica gel chromatography (dichloromethane/methanol=85:15) to yield the title compound (80.0 mg, 80%) as a pale yellow solid.

$^1$H-NMR (500 MHz, CD$_3$OD) δ ppm: 1.43-1.65 (3H, m), 1.74-1.93 (3H, m), 2.07-2.09 (1H, m), 2.27-2.29 (1H, m), 3.14-3.19 (1H, m), 4.61 (1H, dt, J=3.9, 10.3 Hz), 6.52 (1H, d, J=2.4 Hz), 7.06 (1H, d, J=12.2 Hz), 7.13 (1H, d, J=6.4 Hz), 7.85 (1H, d, J=2.4 Hz), 7.94 (1H, d, J=7.3 Hz), 8.38 (1H, d, J=6.8 Hz), 8.68 (1H, s).
MS (ESI) m/z: 452 [M+H]+;
$[α]_D^{25}$=−2.61 (c 0.998, DMSO).

Example 159

5-Chloro-2-fluoro-4-{[(1R,2S)-2-(1H-pyrazol-5-yl)cyclohexyl]oxy}-N-(pyrimidin-4-yl)benzenesulfonamide

[Formula 177]

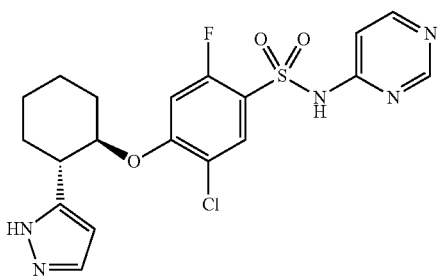

(159a) (1R,2S)-2-{1-[(2-Methoxyethoxy)methyl]-1H-pyrazol-5-yl}cyclohexanol

The (1S*,2R*)-2-{1-[(2-methoxyethoxy)methyl]-1H-pyrazol-5-yl}cyclohexanol prepared in Example 158a was optically resolved with CHIRALFLASH IC (Daicel Corp.; hexane/isopropanol=1:1) to yield the title compound as a colorless oil.

(159b) 5-Chloro-N-(2,4-dimethoxybenzyl)-2-fluoro-4-{[(1R,2S)-2-{1-[(2-methoxyethoxy)methyl]-1H-pyrazol-5-yl}cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (296 mg, 0.649 mmol) prepared in Example 20a, the (1R,2S)-2-{1-[(2-methoxyethoxy)methyl]-1H-pyrazol-5-yl}cyclohexanol (110 mg, 0.432 mmol) prepared in Example 159a, sodium hydride (63%; 19.8 mg, 0.520 mmol) and DMF (2.0 mL), to yield the title compound (188 mg, 63%) as a colorless amorphous solid.

(159c) 5-Chloro-2-fluoro-4-{[(1R,2S)-2-{1-[(2-methoxyethoxy)methyl]-1H-pyrazol-5-yl}cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1R,2S)-2-{1-[(2-methoxyethoxy)methyl]-1H-pyrazol-5-yl}cyclohexyl]oxy}-N-(pyrimidin-4-yl)benzenesulfonamide (188 mg, 0.272 mmol) prepared in Example 159b, triethylsilane (0.20 mL), trifluoroacetic acid (1.0 mL) and dichloromethane (2.0 mL), to yield the title compound (139 mg, 95%) as a colorless oil.

(159d) 5-Chloro-2-fluoro-4-{[(1R,2S)-2-(1H-pyrazol-5-yl)cyclohexyl]oxy}-N-(pyrimidin-4-yl)benzenesulfonamide The reaction and aftertreatment were conducted in the same manner as in Example 158e by using the 5-chloro-2-fluoro-4-{[(1R,2S)-2-{1-[(2-methoxyethoxy)methyl]-1H-pyrazol-5-yl}cyclohexyl]oxy}-N-(pyrimidin-4-yl)benzenesulfonamide (139 mg, 0.257 mmol) prepared in Example 159c, 6 M HCl (5.0 mL) and methanol (4.0 mL), to yield the title compound (101 mg, 73%) as a pale yellow solid.
$[\alpha]_D^{25}=-2.52$ (c 1.05, DMSO).

Example 160

5-Chloro-2-fluoro-4-{[(1S*,2R*,5R*)-5-hydroxy-2-(1-methyl-1H-pyrazol-5-yl)cyclohexyl]oxy}-N-(pyrimidin-4-yl)benzenesulfonamide

[Formula 178]

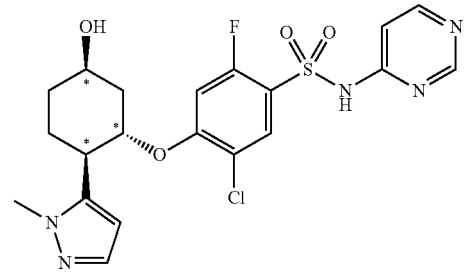

(160a) (1S*,2R*,5R*)-5-{[Tert-butyl(dimethyl)silyl]oxy}-2-(1-methyl-1H-pyrazol-5-yl)cyclohexanol The reaction and aftertreatment were conducted in the same manner as in Example 4a by using the 1-methylpyrazole (500 mg, 6.09 mmol), n-butyl lithium (2.69 M solution in hexane, 2.37 mL, 6.37 mmol), tert-butyl(dimethyl) [(1S*,3R*,6R*)-7-oxabicyclo[4.1.0]hept-3-yloxy]silane (J. Pharm. Pharmacol., 49, 835-842, 1997; 1.32 g, 5.78 mmol) and THF (30 mL), to yield the title compound (932 mg, 52%) as a colorless solid.

$^1$H-NMR (500 MHz, CDCl$_3$) δ ppm: 0.06 (3H, s), 0.08 (3H, s), 0.91 (9H, s), 1.48-1.76 (3H, m), 1.87-2.14 (3H, m), 2.56-2.62 (1H, m), 3.87 (3H, s), 4.03-4.08 (1H, m), 4.24-4.26 (1H, m), 6.11 (1H; d, J=2.0 Hz), 7.44 (1H, d, J=2.0 Hz).

(160b) 4-{[(1S*,2R*,5R*)-5-{[Tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (91.6 mg, 0.201 mmol) prepared in Example 20a, the (1S*,2R*,5R*)-5-{[tert-butyl(dimethyl)silyl]oxy}-2-(1-methyl-1H-pyrazol-5-yl)cyclohexanol (52.0 mg, 0.167 mmol) prepared in Example 160a, sodium hydride (63%; 9.6 mg, 0.252 mmol) and DMF (1.0 mL), to yield the title compound (59.0 mg, 47%) as a colorless oil.

$^1$H-NMR (500 MHz, CDCl$_3$) δ ppm: 0.10 (6H, s), 0.96 (9H, s), 1.61-1.66 (2H, m), 1.82-1.88 (2H, m), 2.14-2.25

(2H, m), 3.04-3.08 (1H, m), 3.76 (3H, s), 3.77 (3H, s), 3.96 (3H, s), 4.30-4.32 (1H, m), 4.62 (1H, dt, J=3.9, 10.7 Hz), 5.18 (1H, d, J=16.6 Hz), 5.25 (1H, d, J=16.6 Hz), 6.05 (1H, d, J=2.0 Hz), 6.39-6.41 (2H, m), 6.50 (1H, d, J=11.7 Hz), 7.18-7.20 (2H, m), 7.36 (1H, d, J=2.0 Hz), 7.93 (1H, d, J=7.3 Hz), 8.46 (1H, d, J=5.9 Hz), 8.79 (1H, d, J=1.0 Hz).

(160c) 5-Chloro-2-fluoro-4-{[(1S*,2R*,5R*)-5-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 4-{[(1S*,2R*,5R*)-5-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (59.0 mg, 0.0791 mmol) prepared in Example 160b, triethylsilane (0.050 mL), trifluoroacetic acid (0.50 mL) and dichloromethane (1.0 mL), to yield the title compound (9.5 mg, 25%) as a colorless solid.

$^1$H-NMR (500 MHz, CD$_3$OD) δ ppm: 1.70-1.92 (4H, m), 2.10-2.19 (1H, m), 2.33-2.35 (1H, m), 3.17-3.22 (1H, m), 3.91 (3H, s), 4.28-4.30 (1H, m), 4.75 (1H, dt, J=3.9, 10.3 Hz), 6.15 (1H, d, J=2.0 Hz), 6.93 (1H, d, J=11.7 Hz), 7.01 (1H, d, J=6.4 Hz), 7.28 (1H, d, J=2.0 Hz), 7.91 (1H, d, J=7.3 Hz), 8.25 (1H, brs), 8.53 (1H, s). MS (ESI) m/z: 482 [M+H]+.

Example 161

5-Chloro-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide

[Formula 179]

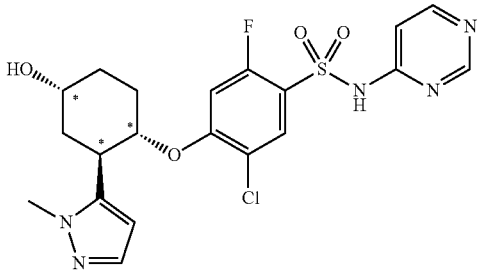

(161a) (1S*,2R*,4R*)-4-{[Tert-butyl(dimethyl)silyl]oxy}-2-(1-methyl-1H-pyrazol-5-yl)cyclohexanol The reaction and aftertreatment were conducted in the same manner as in Example 4a by using 1-methylpyrazole (500 mg, 6.09 mmol), n-butyl lithium (2.69 M solution in hexane, 2.37 mL, 6.37 mmol), tert-butyl(dimethyl)[(1R*,3R*,6S*)-7-oxabicyclo[4.1.0]hept-3-yloxy]silane (J. Pharm. Pharmacol., 49, 835-842, 1997; 1.32 g, 5.78 mmol) and THF (30 mL), to yield the title compound (1.23 g, 69%) as a colorless solid.

$^1$H-NMR (500 MHz, CDCl$_3$) δ ppm: 0.06 (3H, s), 0.07 (3H, s), 0.93 (9H, s), 1.49-1.61 (3H, m), 1.78-1.97 (3H, m), 3.18-3.23 (1H, m), 3.64-3.68 (1H, m), 3.85 (3H, s), 4.05-4.07 (1H, m), 6.07 (1H, d, J=2.0 Hz), 7.44 (1H, d, J=1.5 Hz).

(161b) 4-{[(1S*,2R*,4R*)-4-{[Tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (91.6 mg, 0.201 mmol) prepared in Example 20a, the (1S*,2R*,4R*)-4-{[tert-butyl(dimethyl)silyl]oxy}-2-(1-methyl-1H-pyrazol-5-yl)cyclohexanol (52.0 mg, 0.167 mmol) prepared in Example 161a, sodium hydride (63%; 9.6 mg, 0.252 mmol) and DMF (1.0 mL), to yield the title compound (90.0 mg, 72%) as a colorless oil.

$^1$H-NMR (500 MHz, CDCl$_3$) δ ppm: 0.08 (3H, s), 0.09 (3H, s), 0.94 (9H, s), 1.60-2.09 (6H, m), 3.58-3.63 (1H, m), 3.76 (6H, s), 3.93 (3H, s), 4.13-4.17 (2H, m), 5.21 (2H, s), 5.98 (1H, d, J=2.0 Hz), 6.38-6.41 (2H, m), 6.45 (1H, d, J=11.7 Hz), 7.21 (1H, d, J=9.3 Hz), 7.23 (1H, dd, J=1.0, 5.9 Hz), 7.34 (1H, d, J=1.5 Hz), 7.92 (1H, d, J=7.8 Hz), 8.46 (1H, d, J=5.9 Hz), 8.79 (1H, d, J=1.0 Hz).

(161c) 5-Chloro-N-(2,4-dimethoxybenzyl)-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 120c by using the 4-{[(1S*,2R*,4R*)-4-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (90.0 mg, 0.120 mmol) prepared in Example 161b, tetrabutyl ammonium fluoride (1.0 M solution in THF; 0.241 mL, 0.241 mmol) and THF (5.0 mL), to yield the title compound (65.3 mg, 86%) as a colorless solid.

$^1$H-NMR (500 MHz, CDCl$_3$) δ ppm: 1.83-2.17 (6H, m), 3.59-3.65 (1H, m), 3.76 (6H, s), 3.95 (3H, s), 4.14-4.19 (1H, m), 4.23-4.26 (1H, m), 5.21 (2H, s), 6.02 (1H, d, J=2.0 Hz), 6.38-6.40 (2H, m), 6.43 (1H, d, J=11.7 Hz), 7.18 (1H, d, J=9.3 Hz), 7.22 (1H, dd, J=1.0, 5.9 Hz), 7.35 (1H, d, J=2.0 Hz), 7.93 (1H, d, J=7.8 Hz), 8.46 (1H, d, J=5.9 Hz), 8.79 (1H, s).

(161d) 5-Chloro-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide (65.3 mg, 0.103 mmol) prepared in Example 161c, triethylsilane (0.050 mL), trifluoroacetic acid (0.50 mL) and dichloromethane (1.0 mL), to yield the title compound (32.6 mg, 71%) as a colorless solid.

$^1$H-NMR (500 MHz, CD$_3$OD) δ ppm: 1.77-2.04 (6H, m), 3.56-3.61 (1H, m), 3.90 (3H, s), 4.10-4.13 (1H, m), 4.51-4.56 (1H, m), 6.15 (1H, d, J=2.0 Hz), 6.97 (1H, d, J=12.2 Hz), 7.00 (1H, d, J=6.4 Hz), 7.26 (1H, d, J=2.0 Hz), 7.90 (1H, d, J=7.3 Hz), 8.25 (1H, d, J=6.4 Hz), 8.53 (1H, s).

MS (ESI) m/z: 482[M+H]+.

Example 162

5-Chloro-2-fluoro-4-{[(1S*,2R*,4S*)-4-hydroxy-2-(1-methyl-1H-pyrazol-5-yl)cyclohexyl]oxy}-N-(pyrimidin-4-yl)benzenesulfonamide

[Formula 180]

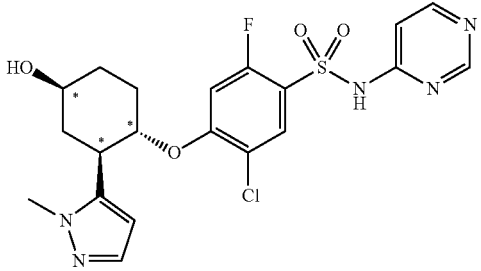

(162a) (1S*,2R*,4R*)-4-{[Tert-butyl(dimethyl)silyl]oxy}-2-(1-methyl-1H-pyrazol-5-yl)cyclohexyl benzoate The reaction and aftertreatment were conducted in the same manner as in Example 107a by using the (1S*,2R*,4R*)-4-{[tert-butyl(dimethyl)silyl]oxy}-2-(1-methyl-1H-pyrazol-5-yl)cyclohexanol (1.07 g, 3.45 mmol) prepared in Example 161a, triethylamine (2.88 mL, 20.7 mmol), benzoyl chloride (2.00 mL, 17.2 mmol) and dichloromethane (10 mL), to yield the title compound (1.30 g, 91%) as a colorless oil.

$^1$H-NMR (500 MHz, CDCl$_3$) δ ppm: 0.09 (3H, s), 0.10 (3H, s), 0.96 (9H, s), 1.67-1.75 (2H, m), 1.83-1.87 (1H, in), 1.95-2.05 (3H, m), 3.52-3.58 (1H, m), 3.87 (3H, s), 4.12-4.14 (1H, m), 5.11-5.16 (1H, m), 6.05 (1H, d, J=2.0 Hz), 7.33 (1H, d, J=2.0 Hz), 7.38 (2H, t, J=7.3 Hz), 7.51 (1H, tt, J=1.5, 7.3 Hz), 7.85-7.87 (2H, m).

(162b) (1S*,2R*,4R*)-4-Hydroxy-2-(1-methyl-1H-pyrazol-5-yl)cyclohexyl benzoate The reaction and aftertreatment were conducted in the same manner as in Example 120c by using the (1S*,2R*,4R*)-4-{[tert-butyl(dimethyl)silyl]oxy}-2-(1-methyl-1H-pyrazol-5-yl)cyclohexyl benzoate (1.30 g, 3.14 mmol) prepared in Example 162a, tetrabutyl ammonium fluoride (1.0 M solution in THF; 9.42 mL, 9.42 mmol) and THF (5.0 mL), to yield the title compound (867 mg, 92%) as a colorless oil.

$^1$H-NMR (500 MHz, CDCl$_3$) δ ppm: 1.78-2.12 (6H, m), 3.53-3.58 (1H, m), 3.89 (3H, s), 4.22-4.25 (1H, m), 5.11-5.16 (1H, m), 6.08 (1H, d, J=1.5 Hz), 7.34 (1H, d, J=2.0 Hz), 7.39 (2H, t, J=7.3 Hz), 7.52 (1H, tt, J=1.5, 7.3 Hz), 7.86-7.88 (2H, m).

(162c) (1S*,2R*)-2-(1-Methyl-1H-pyrazol-5-yl)-4-oxocyclohexyl benzoate

The reaction and aftertreatment were conducted in the same manner as in Example 107c by using the (1S*,2R*,4R*)-4-hydroxy-2-(1-methyl-1H-pyrazol-5-yl)cyclohexyl benzoate (439 mg, 1.46 mmol) prepared in Example 162b, a Dess-Martin reagent (1.24 g, 2.92 mmol) and dichloromethane (10 mL), to yield the title compound (430 mg, 99%) as a colorless oil.

$^1$H-NMR (500 MHz, CDCl$_3$) δ ppm: 2.10-2.16 (1H, m), 2.20-2.27 (1H, m), 2.54-2.59 (1H, m), 2.63-2.67 (1H, m), 2.76-2.82 (1H, m), 2.90-2.94 (1H, m), 3.79 (1H, q, J=5.9 Hz), 4.00 (3H, s), 5.42-5.45 (1H, m), 6.10 (1H, d, J=2.0 Hz), 7.40 (1H, d, J=2.0 Hz), 7.48 (2H, t, J=7.3 Hz), 7.61 (1H, tt, J=1.0, 7.8 Hz), 8.02-8.04 (2H, m).

(162d) (1S*,2R*,4S*)-4-Hydroxy-2-(1-methyl-1H-pyrazol-5-yl)cyclohexyl benzoate To a solution of the (1S*,2R*)-2-(1-methyl-1H-pyrazol-5-yl)-4-oxocyclohexyl benzoate (430 mg, 1.44 mmol) prepared in Example 162c in ethanol (7.0 mL), sodium borohydride (164 mg, 4.34 mmol) was added, and the mixture was stirred at room temperature for 5 hours. To the reaction solution, water (10 mL) was added, followed by extraction with ethyl acetate (50 mL). The thus obtained organic layer was washed twice with water (50 mL) and dried over anhydrous sodium sulfate. After vacuum concentration, the residue was purified with reverse phase chromatography (YMC HPLC COLUMN, YMC-Pack ODS-A; methanol/water=6:4) to yield the title compound (293 mg, 69%) as a colorless solid.

$^1$H-NMR (500 MHz, CDCl$_3$) δ ppm: 1.59-1.70 (3H, m), 2.12-2.29 (3H, m), 3.07-3.13 (1H, m), 3.82-3.86 (1H, m), 3.86 (3H, s), 5.08-5.13 (1H, m), 6.10 (1H, d, J=2.0 Hz), 7.33 (1H, d, J=2.0 Hz), 7.38 (2H, t, J=7.8 Hz), 7.51 (1H, tt, J=1.5, 7.3 Hz), 7.82-7.84 (2H, m).

(162e) (1S*,2R*,4S*)-4-{[Tert-butyl(dimethyl)silyl]oxy}-2-(1-methyl-1H-pyrazol-5-yl)cyclohexyl benzoate To a solution of the (1S*,2R*,4S*)-4-hydroxy-2-(1-methyl-1H-pyrazol-5-yl)cyclohexyl benzoate (293 mg, 0.976 mmol) prepared in Example 162d and 2,6-lutidine (0.136 mL, 1.17 mmol) in dichloromethane (5.0 mL), tert-butyl(dimethyl)silyl trifluoromethanesulfonate (0.269 mL, 1.17 mmol) was added, and the mixture was stirred at room temperature for 1 hour. To the reaction solution, water (10 mL) was added, followed by extraction with dichloromethane (50 mL). The thus obtained organic layer was dried over anhydrous sodium sulfate. After vacuum concentration, the residue was purified with silica gel chromatography (hexane/ethyl acetate=4:1) to yield the title compound (367 mg, 91%) as a colorless solid.

$^1$H-NMR (500 MHz, CDCl$_3$) δ ppm: 0.08 (3H, s), 0.09 (3H, s), 0.90 (9H, s), 1.60-1.76 (3H, m), 2.00-2.05 (1H, m), 2.10-2.15 (1H, m), 2.24-2.28 (1H, m), 3.06-3.11 (1H, m), 3.76-3.83 (1H, m), 3.87 (3H, s), 5.09 (1H, dt, J=4.4, 10.3 Hz), 6.11 (1H, d, J=2.0 Hz), 7.34 (1H, d, J=2.0 Hz), 7.38 (2H, t, J=7.3 Hz), 7.51 (1H, tt, J=2.4, 8.8 Hz), 7.82-7.84 (2H, m).

(162f) (1S*,2R*,4S*)-4-{[Tert-butyl(dimethyl)silyl]oxy}-2-(1-methyl-1H-pyrazol-5-yl)cyclohexanol A solution of the (1S*,2R*,4S*)-4-{[tert-butyl(dimethyl)silyl]oxy}-2-(1-methyl-1H-pyrazol-5-yl)cyclohexyl benzoate (367 mg, 0.885 mmol) prepared in Example 162e and potassium carbonate (245 mg, 1.77 mmol) in methanol (5.0 mL) was stirred at room temperature for 3 hours. To the reaction solution, water (50 mL) was added, followed by extraction with ethyl acetate (50 mL). The thus obtained organic layer was washed twice with water (100 mL) and dried over anhydrous sodium sulfate. After vacuum concentration, the residue was purified with silica gel chromatography (hexane/ethyl acetate=3:2) to yield the title compound (187 mg, 68%) as a colorless oil.

$^1$H-NMR (500 MHz, CDCl$_3$) δ ppm: 0.06 (3H, s), 0.07 (3H, s), 0.88 (9H, s), 1.50-1.61 (3H, m), 1.96-2.06 (3H, m), 2.65-2.71 (1H, m), 3.57-3.62 (1H, m), 3.69-3.76 (1H, m), 3.83 (3H, s), 6.07 (1H, d, J=1.7 Hz), 7.37 (1H, s).

(162g) 4-{[(1S*,2R*,4S*)-4-{[Tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (152 mg, 0.333 mmol) prepared in Example 20a, the (1S*,2R*,4S*)-4-{[tert-butyl(dimethyl)silyl]oxy}-2-(1-methyl-1H-pyrazol-5-yl)cyclohexanol (94.0 mg, 0.303 mmol) prepared in Example 162f, sodium hydride (63%; 17.3 mg, 0.454 mmol) and DMF (2.0 mL), to yield the title compound (81.5 mg, 36%) as a colorless oil.

$^1$H-NMR (500 MHz, CDCl$_3$) δ ppm: 0.08 (3H, s), 0.09 (3H, s), 0.89 (9H, s), 1.50-1.82 (3H, m), 2.01-2.18 (3H, m), 3.15-3.20 (1H, m), 3.76 (6H, s), 3.79-3.84 (1H, m), 3.93 (3H, s), 4.10-4.16 (1H, m), 5.19 (1H, d, J=16.6 Hz), 5.23 (1H, d, J=16.6 Hz), 6.08 (1H, d, J=2.0 Hz), 6.38-6.40 (3H, m), 7.17-7.21 (2H, m), 7.36 (1H, d, J=1.5 Hz), 7.93 (1H, d, J=7.3 Hz), 8.46 (1H, d, J=5.9 Hz), 8.79 (1H, s).

(162h) 5-Chloro-N-(2,4-dimethoxybenzyl)-2-fluoro-4-{[(1S*,2R*,4S*)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 120c by using the 4-{[(1S*,2R*,4S*)-4-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (81.5 mg, 0.109 mmol) prepared in Example 162 g, tetrabutyl ammonium fluoride (1.0 M solution in THF; 0.218 mL, 0.218 mmol) and THF (5.0 mL), to yield the title compound (66.5 mg, 89%) as a colorless oil.

$^1$H-NMR (500 MHz, CDCl$_3$) δ ppm: 1.49-1.79 (3H, m), 2.14-2.28 (3H, m), 3.16-3.21 (1H, m), 3.76 (6H, s), 3.86-3.92 (1H, m), 3.92 (3H, s), 4.11-4.18 (1H, m), 5.20 (2H, s), 6.07 (1H, d, J=2.0 Hz), 6.39-6.42 (3H, m), 7.17-7.21 (2H, m), 7.36 (1H, d, J=2.0 Hz), 7.94 (1H, d, J=7.3 Hz), 8.46 (1H, d, J=5.9 Hz), 8.79 (1H, d, J=1.0 Hz).

(162i) 5-Chloro-2-fluoro-4-{[(1S*,2R*,4S*)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S*,2R*,4S*)-4-hydroxy-2-(1-methyl-1H-pyrazol-5-yl)cyclohexyl]oxy}-N-(pyrimidin-4-yl)benzenesulfonamide (66.5 mg, 0.0975 mmol) prepared in Example 162h, triethylsilane (0.10 mL), trifluoroacetic acid (1.0 mL) and dichloromethane (1.0 mL), to yield the title compound (39.2 mg, 83%) as a colorless solid.

$^1$H-NMR (500 MHz, CD$_3$OD) δ ppm: 1.56-1.77 (3H, m), 2.06-2.22 (3H, m), 3.79-3.85 (1H, m), 3.88 (3H, q), 4.50-4.55 (1H, m), 4.81-4.89 (1H, m), 6.18 (1H, d, J=2.0 Hz), 6.95-7.00 (2H, m), 7.26 (1H, d, J=2.0 Hz), 7.90 (1H, d, J=7.3 Hz), 8.25 (1H, d, J=5.9 Hz), 8.52 (1H, s).

MS (ESI) m/z: 482[M+H]+.

Example 163

5-Chloro-2-fluoro-4-{[(1S*,2R*,5S*)-5-hydroxy-2-(1-methyl-1H-pyrazol-5-yl)cyclohexyl]oxy}-N-(pyrimidin-4-yl)benzenesulfonamide

[Formula 181]

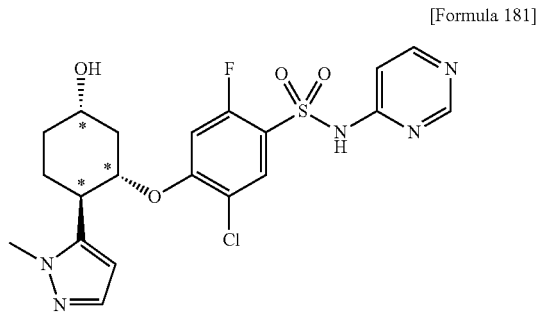 [SMILES: Cn1nccc1[C@H]1CC[C@H](O)C[C@@H]1Oc1cc(F)c(S(=O)(=O)Nc2ccncn2)cc1Cl]

(163a) (1S*,2R*,5R*)-5-{[Tert-butyl(dimethyl)silyl]oxy}-2-(1-methyl-1H-pyrazol-5-yl)cyclohexyl benzoate The reaction and aftertreatment were conducted in the same manner as in Example 107a by using the (1S*,2R*,5R*)-5-{[tert-butyl(dimethyl)silyl]oxy}-2-(1-methyl-1H-pyrazol-5-yl)cyclohexanol (774 mg, 2.49 mmol) prepared in Example 160a, triethylamine (2.08 mL, 14.9 mmol), benzoyl chloride (1.45 mL, 12.6 mmol) and dichloromethane (8.0 mL), to yield the title compound (739 mg, 72%) as a colorless oil.

$^1$H-NMR (500 MHz, CDCl$_3$) δ ppm: 0.09 (3H, s), 0.14 (3H, s), 0.96 (9H, s), 1.58-1.68 (2H, m), 1.79-1.85 (2H, m), 2.07-2.15 (1H, m), 2.29-2.33 (1H, m), 2.97-3.02 (1H, m), 3.88 (3H, s), 4.27-4.30 (1H, m), 5.56 (1H, dt, J=3.9, 10.3 Hz), 6.12 (1H, d, J=2.0 Hz), 7.34 (1H, d, J=2.0 Hz), 7.37 (2H, t, J=7.3 Hz), 7.50 (1H, tt, J=1.5, 7.3 Hz), 7.84-7.86 (2H, m).

(163b) (1S*,2R*,5R*)-5-Hydroxy-2-(1-methyl-1H-pyrazol-5-yl)cyclohexyl benzoate

The reaction and aftertreatment were conducted in the same manner as in Example 120c by using the (1S*,2R*,5R*)-5-{[tert-butyl(dimethyl)silyl]oxy}-2-(1-methyl-1H-pyrazol-5-yl)cyclohexyl benzoate (739 mg, 1.78 mmol) prepared in Example 163a, tetrabutyl ammonium fluoride (1.0 M solution in THF; 5.34 mL, 5.34 mmol) and THF (5.0 mL), to yield the title compound (517 mg, 97%) as a colorless solid.

$^1$H-NMR (500 MHz, CDCl$_3$) δ ppm: 1.67-1.80 (2H, m), 1.87-1.96 (2H, m), 2.08-2.16 (1H, m), 2.35-2.39 (1H, m), 3.04 (1H, dt, J=2.9, 10.3 Hz), 3.90 (3H, s), 4.35 (1H, brs), 5.55 (1H, dt, J=3.9, 10.3 Hz), 6.15 (1H, d, J=2.0 Hz), 7.34-7.39 (3H, m), 7.51 (1H, t, J=7.3 Hz), 7.86 (2H, d, J=8.3 Hz).

(163c) (1S*,2R*)-2-(1-Methyl-1H-pyrazol-5-yl)-5-oxocyclohexyl benzoate

The reaction and aftertreatment were conducted in the same manner as in Example 107c by using the (1S*,2R*,5R*)-5-hydroxy-2-(1-methyl-1H-pyrazol-5-yl)cyclohexyl benzoate (517 mg, 1.72 mmol) prepared in Example 163b, a Dess-Martin reagent (1.46 g, 3.44 mmol) and dichloromethane (10 mL), to yield the title compound (441 mg, 86%) as a colorless solid.

$^1$H-NMR (500 MHz, CDCl$_3$) δ ppm: 1.97-2.06 (1H, m), 2.31-2.37 (1H, m), 2.52-2.59 (1H, m), 2.62-2.69 (2H, m), 3.02-3.06 (1H, m), 3.46 (1H, dt, J=4.4, 9.3 Hz), 3.98 (3H, s), 5.47 (1H, dt, J=5.4, 8.8 Hz), 6.19 (1H, d, J=2.0 Hz), 7.40-7.43 (3H, m), 7.56 (1H, t, J=7.3 Hz), 7.88-7.90 (2H, m).

(163d) (1S*,2R*,5S*)-5-Hydroxy-2-(1-methyl-1H-pyrazol-5-yl)cyclohexyl benzoate The reaction and aftertreatment were conducted in the same manner as in Example 162d by using the (1S*,2R*)-2-(1-methyl-1H-pyrazol-5-yl)-5-oxocyclohexyl benzoate (441 mg, 1.48 mmol) prepared in Example 163c, sodium borohydride (168 mg, 4.44 mmol) and ethanol (7.0 mL), to yield the title compound (290 mg, 65%) as a colorless amorphous solid.

$^1$H-NMR (500 MHz, CDCl$_3$) δ ppm: 1.44-1.65 (3H, m), 2.02-2.06 (1H, m), 2.12-2.14 (1H, m), 2.55-2.59 (1H, m), 2.96 (1H, dt, J=3.9, 11.7 Hz), 3.69-3.73 (1H, m), 3.87 (3H, s), 3.90-3.95 (1H, m), 5.16 (1H, dt, J=4.4, 11.2 Hz), 6.05 (1H, d, J=2.0 Hz), 7.33 (1H, d, J=2.0 Hz), 7.38 (2H, t, J=7.8 Hz), 7.52 (1H, t, J=7.3 Hz), 7.83-7.85 (2H, m).

(163e) (1S*,2R*,5S*)-5-{[Tert-butyl(dimethyl)silyl]oxy}-2-(1-methyl-1H-pyrazol-5-yl)cyclohexyl benzoate The reaction and aftertreatment were conducted in the same manner as in Example 162e by using the (1S*,2R*,5S*)-5-hydroxy-2-(1-methyl-1H-pyrazol-5-yl)cyclohexyl benzoate (290 mg, 0.966 mmol) prepared in Example 163d, 2,6-lutidine (0.136 mL, 1.17 mmol), tert-butyl(dimethyl)silyl trifluoromethanesulfonate (0.269 mL, 1.17 mmol) and dichloromethane (5.0 mL), to yield the title compound (327 mg, 82%) as a colorless oil.

$^1$H-NMR (500 MHz, CDCl$_3$) δ ppm: 0.09 (3H, s), 0.10 (3H, s), 0.89 (9H, s), 1.45-1.67 (3H, m), 1.98-2.04 (0.2H, m), 2.43-2.47 (1H, m), 2.91-2.96 (1H, m), 3.84-3.89 (1H, m), 3.86 (3H, s), 5.16 (1H, dt, J=4.4, 11.2 Hz), 6.05 (1H, d, J=2.0 Hz), 7.33 (1H, d, J=2.0 Hz), 7.37 (2H, t, J=7.3 Hz), 7.51 (1H, tt, J=1.5, 7.3 Hz), 7.84-7.86 (2H, m).

(163f) (1S*,2R*,5S*)-5-{[Tert-butyl(dimethyl)silyl]oxy}-2-(1-methyl-1H-pyrazol-5-yl)cyclohexanol The reaction and aftertreatment were conducted in the same manner as in Example 162f by using the (1S*,2R*,5S*)-5-{[tert-butyl(dimethyl)silyl]oxy}-2-(1-methyl-1H-pyrazol-5-yl)cyclohexyl benzoate (327 mg, 1.09 mmol) prepared in Example 163e, potassium carbonate (301 mg, 2.18 mmol) and methanol (5.0 mL), to yield the title compound (207 mg, 87%) as a colorless oil.

$^1$H-NMR (500 MHz, CDCl$_3$) δ ppm: 0.08 (3H, s), 0.08 (3H, s), 0.89 (9H, s), 1.34-1.45 (2H, m), 1.50-1.57 (1H, m), 1.86-1.94 (2H, m), 2.23-2.26 (1H, m), 2.55-2.59 (1H, m), 3.58-3.63 (1H, m), 3.72-3.78 (1H, m), 3.80 (3H, s), 6.00 (1H, s), 7.33 (1H, s).

(163g) 4-{[(1S*,2R*,5S*)-5-{[Tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (152 mg, 0.333 mmol) prepared in Example 20a, the (1S*,2R*,5S*)-5-{[tert-butyl(dimethyl)silyl]oxy}-2-(1-methyl-1H-pyrazol-5-yl)cyclohexanol (94.0 mg, 0.303 mmol) prepared in Example 163f, sodium hydride (63%; 17.3 mg, 0.454 mmol) and DMF (2.0 mL), to yield the title compound (174 mg, 77%) as a colorless oil.

$^1$H-NMR (500 MHz, CDCl$_3$) δ ppm: 0.07 (3H, s), 0.08 (3H, s), 0.88 (9H, s), 1.47-1.72 (3H, m), 2.01-2.05 (2H, m), 2.32-2.36 (1H, m), 2.98-3.03 (1H, m), 3.76 (6H, s), 3.78-3.82 (1H, m), 3.91 (3H, s), 4.16 (1H, dt, J=3.9, 10.7 Hz), 5.19 (1H, d, J=16.6 Hz), 5.24 (1H, d, J=16.6 Hz), 6.00 (1H, d, J=2.0 Hz), 6.37-6.40 (3H, m), 7.18 (1H, d, J=8.8 Hz), 7.22 (1H, dd, J=1.0, 5.9 Hz), 7.34 (1H, d, J=2.0 Hz), 7.93 (1H, d, J=7.3 Hz), 8.46 (1H, d, J=6.4 Hz), 8.80 (1H, d, J=1.0 Hz).

(163h) 5-Chloro-N-(2,4-dimethoxybenzyl)-2-fluoro-4-{[(1S*,2R*,5S*)-5-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 120c by using the 4-{[(1S*,2R*,5S*)-5-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (174 mg, 0.233 mmol) prepared in Example 163 g, tetrabutyl ammonium fluoride (1.0 M solution in THF; 0.466 mL, 0.466 mmol) and THF (5.0 mL), to yield the title compound (148 mg, 93%) as a colorless oil.

$^1$H-NMR (500 MHz, CDCl$_3$) δ ppm: 1.46-1.69 (3H, m), 2.04-2.08 (1H, m), 2.14-2.17 (1H, m), 2.46-2.49 (1H, m), 3.01-3.06 (1H, m), 3.76 (6H, s), 3.81-3.88 (1H, m), 3.93 (3H, s), 4.18 (1H, dt, J=4.4, 10.7 Hz), 5.20 (1H, d, J=17.1 Hz), 5.23 (1H, d, J=16.6 Hz), 6.01 (1H, d, J=2.0 Hz), 6.39-6.43 (3H, m), 7.17 (1H, d, J=8.8 Hz), 7.22 (1H, d, J=5.9 Hz), 7.35 (1H, d, J=2.0 Hz), 7.93 (1H, d, J=7.3 Hz), 8.46 (1H, d, J=6.4 Hz), 8.79 (1H, s).

(163i) 5-Chloro-2-fluoro-4-{[(1S*,2R*,5S*)-5-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S*,2R*,5S*)-5-hydroxy-2-(1-methyl-1H-pyrazol-5-yl)cyclohexyl]oxy}-N-(pyrimidin-4-yl)benzenesulfonamide (148 mg, 0.217 mmol) prepared in Example 163h, triethylsilane (0.10 mL), trifluoroacetic acid (1.0 mL) and dichloromethane (1.0 mL), to yield the title compound (80.5 mg, 77%) as a colorless solid.

$^1$H-NMR (500 MHz, CD$_3$OD) δ ppm: 1.45-1.75 (3H, m), 1.97-2.08 (2H, m), 2.43-2.46 (1H, m), 3.10-3.15 (1H, m), 3.81-3.86 (1H, in), 3.88 (3H, s), 4.56 (1H, dt, J=3.9, 10.7 Hz), 6.13 (1H, s), 6.96-7.01 (2H, m), 7.25 (1H, s), 7.91 (1H, d, J=7.3 Hz), 8.25 (1H, d, J=6.4 Hz), 8.53 (1H, s).

MS (ESI) m/z: 482 [M+H]+.

Example 164

5-Chloro-2-fluoro-4-{[(1R,2S,4S)-4-hydroxy-2-(1-methyl-1H-pyrazol-5-yl)cyclohexyl]oxy}-N-(pyrimidin-4-yl)benzenesulfonamide

[Formula 182]

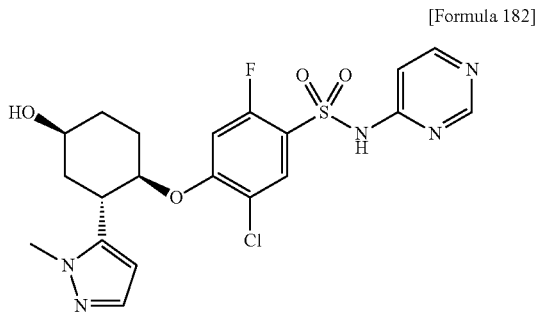 [SMILES: Cn1nccc1[C@@H]1C[C@@H](O)CC[C@H]1Oc1cc(F)c(S(=O)(=O)Nc2ccncn2)cc1Cl]

(164a) (1R,2S,4S)-4-{[Tert-butyl(dimethyl)silyl]oxy}-2-(1-methyl-1H-pyrazol-5-yl)cyclohexanol The (1S*,2R*,4R*)-4-{[tert-butyl(dimethyl)silyl]oxy}-2-(1-methyl-1H-pyrazol-5-yl)cyclohexanol prepared in Example 161a was optically resolved with CHIRALFLASH IC (Daicel Corp.; hexane/isopropanol=6:4) to yield the title compound as a colorless oil.

(164b) 4-{[(1R,2S,4S)-4-{[Tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (243 mg, 0.533 mmol) prepared in Example 20a, the (1R,2S,4S)-4-{[tert-butyl(dimethyl)silyl]oxy}-2-(1-methyl-1H-pyrazol-5-yl)cyclohexanol (138 mg, 0.444 mmol) prepared in Example 164a, sodium hydride (63%; 25.4 mg, 0.667 mmol) and DMF (2.0 mL), to yield the title compound (272 mg, 82%) as a colorless oil.

(164c) 5-Chloro-N-(2,4-dimethoxybenzyl)-2-fluoro-4-{[(1R,2S,4S)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 120c by using the 4-{[(1R,2S,4S)-4-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (272 mg, 0.364 mmol) prepared in Example 164b, tetrabutyl ammonium fluoride (1.0 M solution in THF; 0.729 mL, 0.729 mmol) and THF (5.0 mL), to yield the title compound (189 mg, 82%) as a colorless amorphous solid.

(164d) 5-Chloro-2-fluoro-4-{[(1R,2S,4S)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1R,2S,4S)-4-hydroxy-2-(1-methyl-1H-pyrazol-5-yl)cyclohexyl]oxy}-N-(pyrimidin-4-yl)benzenesulfonamide (189 mg, 0.299 mmol) prepared in Example 164c, triethylsilane (0.050 mL), trifluoroacetic acid (0.50 mL) and dichloromethane (1.0 mL), to yield the title compound (86.0 mg, 60%) as a colorless solid.
$[\alpha]_D^{25}=-10.0$ (c 1.04, DMSO).

Example 165

5-Chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide

[Formula 183]

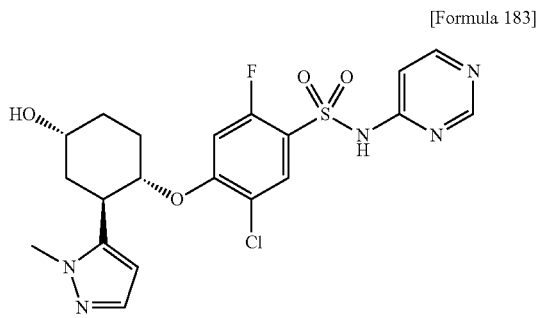 [SMILES: Cn1nccc1[C@H]1C[C@H](O)CC[C@@H]1Oc1cc(F)c(S(=O)(=O)Nc2ccncn2)cc1Cl]

(165a) (1S,2R,4R)-4-{[Tert-butyl(dimethyl)silyl]oxy}-2-(1-methyl-1H-pyrazol-5-yl)cyclohexanol The (1S*,2R*,4R*)-4-{[tert-butyl(dimethyl)silyl]oxy}-2-(1-methyl-1H-pyrazol-5-yl)cyclohexanol prepared in Example 161a was optically resolved with CHIRALFLASH IC (Daicel Corp.; hexane/isopropanol=6:4) to yield the title compound as a colorless oil.

(165b) 4-{[(1S,2R,4R)-4-{[Tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (238 mg, 0.522 mmol) prepared in Example 20a, the (1S,2R,4R)-4-{[tert-butyl(dimethyl)silyl]oxy}-2-(1-methyl-1H-pyrazol-5-yl)cyclohexanol (135 mg, 0.434 mmol) prepared in Example 165a, sodium hydride (63%; 24.8 mg, 0.651 mmol) and DMF (2.0 mL), to yield the title compound (262 mg, 81%) as a colorless oil.

(165c) 5-Chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 120c by using the 4-{[(1S,2R,4R)-4-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (262 mg, 0.351 mmol) prepared in Example 165b, tetrabutyl ammonium fluoride (1.0 M solution in THF; 0.702 mL, 0.702 mmol) and THF (5.0 mL), to yield the title compound (153 mg, 69%) as a colorless amorphous solid.

(165d) 5-Chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide (153 mg, 0.242 mmol) prepared in Example 165c, triethylsilane (0.050 mL), trifluoroacetic acid (0.50 mL) and dichloromethane (1.0 mL), to yield the title compound (92.0 mg, 79%) as a colorless solid.

$[\alpha]_D^{25}$=9.62 (c 0.915, DMSO).

Example 166

(1R,3R,4S)-4-[2-Chloro-5-fluoro-4-(pyrimidin-4-ylsulfamoyl)phenoxy]-3-(1-methyl-1H-pyrazol-5-yl)cyclohexyl acetate

[Formula 184]

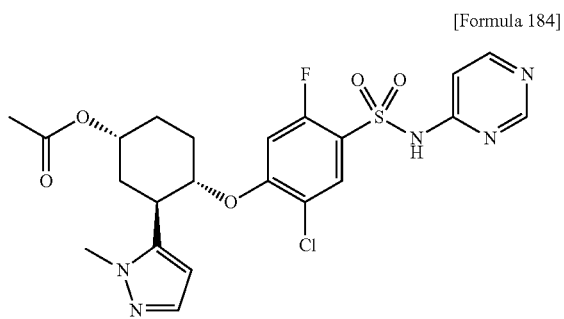 [SMILES: CC(=O)O[C@@H]1CC[C@H](Oc2cc(F)c(S(=O)(=O)Nc3ccncn3)cc2Cl)[C@@H](c2ccnn2C)C1]

A solution of the 5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide (22.0 mg, 0.046 mmol) prepared in Example 165d, acetic anhydride (0.50 mL) and 4-(N,N-dimethylamino)pyridine (0.6 mg, 0.0046 mmol) in pyridine (1.0 mL) was stirred at room temperature for 3 hours. The reaction solution was concentrated, and 1 M HCl (10 mL) was then added to the residue, followed by extraction with dichloromethane (50 mL). The thus obtained organic layer was dried over anhydrous sodium sulfate. After vacuum concentration, the residue was purified with silica gel chromatography (dichloromethane/methanol=10:1) to yield the title compound (22.0 mg, 91%) as a colorless solid.

$^1$H-NMR (500 MHz, CDCl$_3$) δ ppm: 1.68-1.75 (1H, m), 1.88-1.97 (2H, m), 2.05-2.15 (2H, m), 2.15 (3H, s), 2.22-2.27 (1H, m), 3.40-3.45 (1H, m), 3.94 (3H, s), 4.19 (1H, dt, J=3.9, 10.3 Hz), 5.18-5.19 (1H, m), 6.04 (1H, d, J=2.0 Hz), 6.45 (1H, d, J=11.2 Hz), 7.26-7.27 (1H, m), 7.35 (1H, d, J=2.0 Hz), 7.96 (1H, d, J=7.3 Hz), 8.39 (1H, d, J=6.4 Hz), 8.82 (1H, s).

MS (ESI) m/z: 524 [M+H]+.

Example 167

5-Chloro-2-fluoro-4-{[(1S,2S)-2-(1-methyl-1H-pyrazol-5-yl)cyclohexyl]oxy}-N-(pyrimidin-4-yl)benzenesulfonamide

[Formula 185]

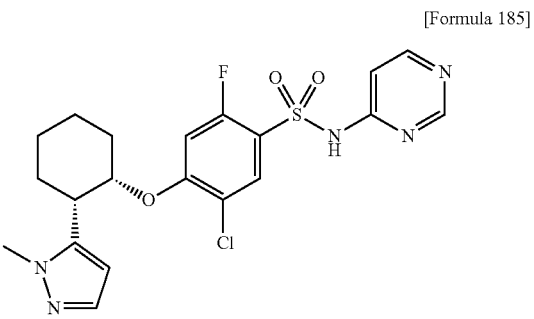 [SMILES: Cn1nccc1[C@@H]1CCCC[C@@H]1Oc1cc(F)c(S(=O)(=O)Nc2ccncn2)cc1Cl]

(167a) (3aS,7aS)-3a-(1-Methyl-1H-pyrazol-5-yl)hexahydro-1,3-benzodioxol-2-one

A solution of the (1S,2S)-1-(1-methyl-1H-pyrazol-5-yl)cyclohexane-1,2-diol (1.21 g, 6.17 mmol) prepared in Example 123c, dimethylaminopyridine (75.3 mg, 0.62 mmol) and carbonyldiimidazole (2.0 g, 12.3 mmol) in toluene (20 mL) was stirred for 3 hours under heated reflux. To the reaction solution, carbonyldiimidazole (1.0 g, 6.17 mmol) was added, and the reaction solution was further stirred for 3 hours under heated reflux. To the reaction solution, carbonyldiimidazole (0.50 g, 3.08 mmol) was further added, and the reaction solution was stirred for 3 hours under heated reflux. After allowing to cool, the reaction solution was vacuum concentrated, and the residue was purified with silica gel chromatography (hexane/ethyl acetate=7:3) to yield the title compound (1.18 g, 86%) as a colorless solid.

$^1$H-NMR (500 MHz, CDCl$_3$) δ ppm: 1.26-1.35 (1H, m), 1.60-1.77 (3H, m), 1.87-1.94 (1H, m), 2.02-2.08 (1H, m), 2.28-2.33 (2H, m), 4.02 (3H, s), 4.90 (1H, t, J=3.4 Hz), 6.19 (1H, d, J=2.0 Hz), 7.45 (1H, d, J=2.0 Hz).

(167b) (1S,2S)-2-(1-Methyl-1H-pyrazol-5-yl)cyclohexanol

A solution of the (3aS,7aS)-3a-(1-methyl-1H-pyrazol-5-yl)hexahydro-1,3-benzodioxol-2-one (500 mg, 2.25 mmol) prepared in Example 167a and palladium carbon (10%; 500 mg) in THF (10 mL) was stirred at 60° C. for 12 hours under a hydrogen atmosphere. The reaction solution was filtered through celite, and the residue was purified with silica gel chromatography (hexane/ethyl acetate=2:1) to yield the title compound (85 mg, 21%) as a colorless oil.

$^1$H-NMR (500 MHz, CDCl$_3$) δ ppm: 1.34-1.44 (2H, m), 1.50-2.00 (6H, m), 2.83-2.87 (1H, m), 3.80 (3H, s), 3.94-3.96 (1H, m), 6.15 (1H, d, J=2.0 Hz), 7.39 (1H, d, J=1.0 Hz).

(167c) 5-Chloro-N-(2,4-dimethoxybenzyl)-2-fluoro-4-{[(1S,2S)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (98.0 mg, 0.215 mmol) prepared in Example 20a, the (1S,2S)-2-(1-methyl-1H-pyrazol-5-yl)cyclohexanol (38.7 mg, 0.215 mmol) prepared in Example 167b, sodium hydride (63%; 12.0 mg, 0.315 mmol) and DMF (1.0 mL), to yield the title compound (98.0 mg, 74%) as a colorless oil.

$^1$H-NMR (500 MHz, CDCl$_3$) δ ppm: 1.47-1.98 (6H, m), 2.13-2.28 (2H, m), 2.97-3.00 (1H, m), 3.76 (3H, s), 3.78 (3H, s), 3.85 (3H, s), 4.58-4.59 (1H, m), 5.21 (1H, d, J=16.6 Hz), 5.25 (1H, d, J=16.6 Hz), 6.17 (1H, d, J=2.0 Hz), 6.39-6.41 (3H, m), 7.19 (1H, d, J=8.8 Hz), 7.24 (1H, d, J=6.4 Hz), 7.28 (1H, d, J=8.8 Hz), 8.00 (1H, d, J=7.3 Hz), 8.47 (1H, d, J=5.9 Hz), 8.80 (1H, s).

(167d) 5-Chloro-2-fluoro-4-{[(1S,2S)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1S,2S)-2-(1-methyl-1H-pyrazol-5-yl)cyclohexyl]oxy}-N-(pyrimidin-4-yl)benzenesulfonamide (98.0 mg, 0.159 mmol) prepared in Example 167c, triethylsilane (0.10 mL), trifluoroacetic acid (1.0 mL) and dichloromethane (1.0 mL), to yield the title compound (67.0 mg, 90%) as a colorless solid.

$^1$H-NMR (500 MHz, DMSO-d$_6$) δ ppm: 1.48-1.84 (6H, m), 1.99-2.10 (2H, m), 3.18-3.21 (1H, m), 3.80 (3H, s), 4.91-4.92 (1H, m), 5.99 (1H, d, J=2.0 Hz), 6.96 (1H, brs), 7.10-7.12 (2H, m), 7.83 (1H, d, J=7.3 Hz), 8.26 (1H, brs), 8.58 (1H, s).

MS (ESI) m/z: 466 [M+H]+;
[α]$_D^{25}$=120.8 (c 1.04, DMSO).

Example 168

5-Chloro-2-fluoro-4-{[(1R,2R)-2-(1-methyl-1H-pyrazol-5-yl)cyclohexyl]oxy}-N-(pyrimidin-4-yl)benzenesulfonamide

[Formula 186]

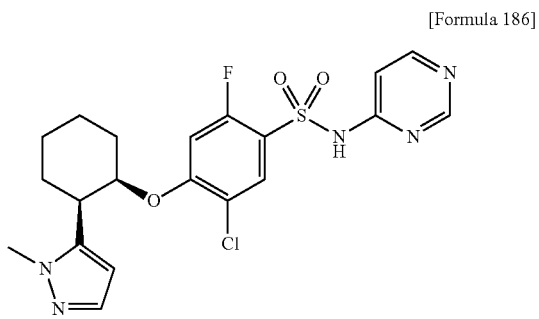 [SMILES: Cn1nccc1[C@H]1CCCC[C@H]1Oc1cc(F)c(S(=O)(=O)Nc2ccncn2)cc1Cl]

(168a) (1R,2R)-1-(1-Methyl-1H-pyrazol-5-yl)cyclohexane-1,2-diol

The reaction and aftertreatment were conducted in the same manner as in Example 102a by using the 5-(cyclohex-1-en-1-yl)-1-methyl-1H-pyrazole (1.00 g, 6.16 mmol) prepared in Example 123b, methanesulfonamide (586 mg, 6.16 mmol), t-butanol (10 mL), water (10 mL) and AD-mixβ (Sigma-Aldrich Corp.; 8.67 g), to yield the title compound (1.21 g, 99%) as a colorless oil.

(168b) (3aR,7aR)-3a-(1-Methyl-1H-pyrazol-5-yl)hexahydro-1,3-benzodioxol-2-one

The reaction and aftertreatment were conducted in the same manner as in Example 167a by using the (1R,2R)-1-(1-methyl-1H-pyrazol-5-yl)cyclohexane-1,2-diol (1.21 g, 6.17 mmol) prepared in Example 168a, dimethylaminopyridine (75.3 mg, 0.62 mmol), carbonyldiimidazole (3.50 g, 21.6 mmol) and toluene (20 mL), to yield the title compound (1.26 g, 92%) as a colorless oil.

(168c) (1R,2R)-2-(1-Methyl-1H-pyrazol-5-yl)cyclohexanol

The reaction and aftertreatment were conducted in the same manner as in Example 167b by using the (3aR,7aR)-3a-(1-methyl-1H-pyrazol-5-yl)hexahydro-1,3-benzodioxol-2-one (760 mg, 3.42 mmol) prepared in Example 168b, palladium carbon (10%; 760 mg) and THF (10 mL), to yield the title compound (133 mg, 22%) as a colorless oil.

(168d) 5-Chloro-N-(2,4-dimethoxybenzyl)-2-fluoro-4-{[(1R,2R)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (80.0 mg, 0.175 mmol) prepared in Example 20a, the (1R,2R)-2-(1-methyl-1H-pyrazol-5-yl)cyclohexanol (31.6 mg, 0.175 mmol) prepared in Example 168c, sodium hydride (63%; 8.0 mg, 0.210 mmol) and DMF (1.0 mL), to yield the title compound (55.0 mg, 51%) as a colorless oil.

(168e) 5-Chloro-2-fluoro-4-{[(1R,2R)-2-(1-methyl-1H-pyrazol-5-yl)cyclohexyl]oxy}-N-(pyrimidin-4-yl)benzenesulfonamide The reaction and aftertreatment were conducted in the same manner as in Example 1b by using the 5-chloro-N-(2,4-dimethoxybenzyl)-2-fluoro-4-{[(1R,2R)-2-(1-methyl-1H-pyrazol-5-yl)cyclohexyl]oxy}-N-(pyrimidin-4-yl)benzenesulfonamide (55.0 mg, 0.0893 mmol) prepared in Example 168d, triethylsilane (0.10 mL), trifluoroacetic acid (1.0 mL) and dichloromethane (1.0 mL), to yield the title compound (41.6 mg, 99%) as a colorless solid.

MS (ESI) m/z: 466 [M+H]+;
[α]$_D^{25}$=−116.1 (c 1.01, DMSO).

Example 169

2,6-Difluoro-4-{[(1R,2S)-2-(1H-pyrazol-4-yl)cyclohexyl]oxy}-N-(pyrimidin-4-yl)benzenesulfonamide

[Formula 187]

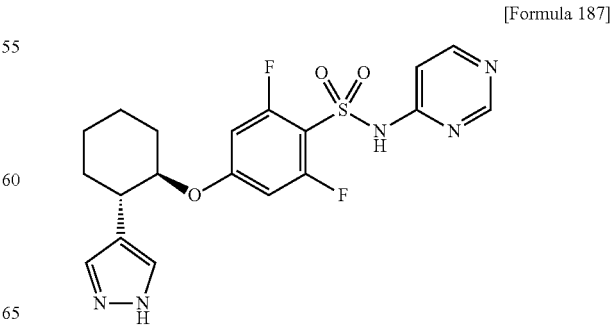

(169a) (1R*,2S*)-2-(1H-Pyrazol-4-yl)cyclohexanol

The reaction and aftertreatment were conducted in the same manner as in Example 155b by using 4-iodo-1H-pyrazole (5.82 g, 30.0 mmol), butyl lithium (2.69 M solution in hexane; 22.3 mL, 60.0 mmol), a boron trifluoride-diethyl ether complex (7.54 mL, 60.0 mmol), cyclohexene oxide (3.24 g, 33.0 mmol) and THF (120 mL), to yield the title compound (0.48 g, 10%) as a colorless solid.
$^1$H-NMR (500 MHz, CDCl$_3$) δ ppm: 1.26-1.51 (4H, m), 1.73-2.11 (4H, m), 2.43-2.48 (1H, m), 3.41-3.46 (1H, m), 7.51 (2H, s).

(169b) (1R,2S)-2-(1H-Pyrazol-4-yl)cyclohexanol

The (1R*,2S*)-2-(1H-pyrazol-4-yl)cyclohexanol prepared in Example 169a was optically resolved with CHIRALPAK AD-H (Daicel Corp.; hexane/ethanol=8:2) to yield the title compound as a colorless solid.

(169c) (1R,2S)-2-[1-(Methoxymethyl)-1H-pyrazol-4-yl]cyclohexanol

To a solution of the (1R,2S)-2-(1H-pyrazol-4-yl)cyclohexanol (170 mg, 1.02 mmol) prepared in Example 169b in DMF (5.0 mL), chloromethyl methyl ether (0.078 mL, 1.02 mmol) was added, and the reaction solution was stirred at room temperature for 2 hours. The reaction solution was vacuum concentrated, and the residue was then purified with silica gel chromatography (hexane/ethyl acetate=7:3) to yield the title compound (132 mg, 61%) as a colorless solid.
$^1$H-NMR (500 MHz, CDCl$_3$) δ ppm: 1.26-1.48 (4H, m), 1.74-2.09 (4H, m), 2.39-2.44 (1H, m), 3.34 (3H, s), 3.40-3.44 (1H, m), 5.35 (2H, s), 7.46 (1H, s), 7.49 (1H, s).

(169d) N-(2,4-Dimethoxybenzyl)-2,6-difluoro-4-({(1R,2S)-2-[1-(methoxymethyl)-1H-pyrazol-4-yl]cyclohexyl}oxy)-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (178 mg, 0.405 mmol) prepared in Example 27a, the (1R,2S)-2-[1-(methoxymethyl)-1H-pyrazol-4-yl]cyclohexanol (71.0 mg, 0.338 mmol) prepared in Example 169c, sodium hydride (63%; 19.3 mg, 0.507 mmol) and DMF (2.0 mL), to yield the title compound (62.2 mg, 29%) as a colorless oil.
$^1$H-NMR (400 MHz, CDCl$_3$) δ ppm: 1.37-1.65 (4H, m), 1.81-2.19 (4H, m), 2.78-2.84 (1H, m), 3.22 (3H, s), 3.77 (3H, s), 3.82 (3H, s), 3.98-4.04 (1H, m), 5.26 (2H, s), 5.28 (2H, s), 6.35-6.44 (4H, m), 7.18 (1H, dd, J=1.2, 5.9 Hz), 7.21 (1H, d, J=8.2 Hz), 7.34 (1H, s), 7.41 (1H, s), 8.44 (1H, d, J=6.3 Hz), 8.78 (1H, d, J=0.8 Hz).

(169e) 2,6-Difluoro-4-{[(1R,2S)-2-(1H-pyrazol-4-yl)cyclohexyl]oxy}-N-(pyrimidin-4-yl)benzenesulfonamide The reaction and aftertreatment were conducted in the same manner as in Example 147e by using the N-(2,4-dimethoxybenzyl)-2,6-difluoro-4-({(1R,2S)-2-[1-(methoxymethyl)-1H-pyrazol-4-yl]cyclohexyl}oxy)-N-(pyrimidin-4-yl)benzenesulfonamide (62.2 mg, 0.0988 mmol) prepared in Example 169d, triethylsilane (0.080 mL), dichloromethane (1.0 mL), trifluoroacetic acid (1.0 mL), methanol (6.0 mL) and 6 M hydrochloric acid (2.0 mL), to yield the title compound (37.0 mg, 85%) as a colorless solid.
$[α]_D^{25}$=−23.0 (c 1.04, DMSO).

Example 170

2-Fluoro-5-methyl-4-{[(1R,2S)-2-(1H-pyrazol-4-yl)cyclohexyl]oxy}-N-(pyrimidin-4-yl)benzenesulfonamide

[Formula 188]

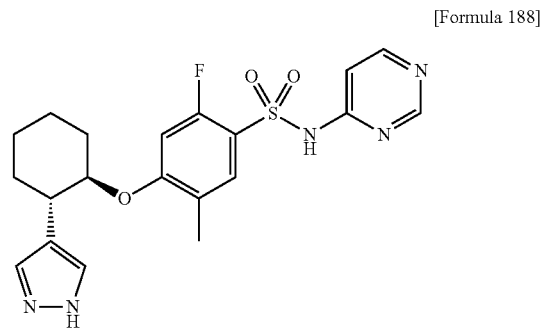 [SMILES: Cc1cc(S(=O)(=O)Nc2ccncn2)c(F)cc1O[C@@H]1CCCC[C@H]1c1cn[nH]c1]

(170a) N-(2,4-Dimethoxybenzyl)-2-fluoro-4-({(1R,2S)-2-[1-(methoxymethyl)-1H-pyrazol-4-yl]cyclohexyl}oxy)-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (154 mg, 0.354 mmol) prepared in Example 43a, the (1R,2S)-2-[1-(methoxymethyl)-1H-pyrazol-4-yl]cyclohexanol (61.8 mg, 0.294 mmol) prepared in Example 169c, sodium hydride (63%; 16.8 mg, 0.441 mmol) and DMF (2.0 mL), to yield the title compound (144 mg, 78%) as a colorless oil.
$^1$H-NMR (500 MHz, CDCl$_3$) δ ppm: 1.41-1.65 (4H, m), 1.80-2.20 (4H, m), 2.14 (3H, s), 2.85-2.90 (1H, m), 3.20 (3H, s), 3.76 (3H, s), 3.79 (3H, s), 4.00-4.04 (1H, m), 5.25 (2H, s), 5.27 (2H, s), 6.38-6.41 (3H, m), 7.19 (1H, d, J=8.3 Hz), 7.30 (1H, dd, J=1.5, 5.9 Hz), 7.34 (1H, s), 7.41 (1H, s), 7.68 (1H, d, J=7.8 Hz), 8.42 (1H, d, J=5.9 Hz), 8.76 (1H, d, J=1.0 Hz).

(170b) 2-Fluoro-5-methyl-4-{[(1R,2S)-2-(1H-pyrazol-4-yl)cyclohexyl]oxy}-N-(pyrimidin-4-yl)benzenesulfonamide The reaction and aftertreatment were conducted in the same manner as in Example 147e by using the N-(2,4-dimethoxybenzyl)-2-fluoro-4-({(1R,2S)-2-[1-(methoxymethyl)-1H-pyrazol-4-yl]cyclohexyl}oxy)-5-methyl-N-(pyrimidin-4-yl)benzenesulfonamide (144 mg, 0.230 mmol) prepared in Example 170a, triethylsilane (0.184 mL), dichloromethane (1.0 mL), trifluoroacetic acid (1.0 mL), methanol (15 mL) and 6 M hydrochloric acid (5.0 mL), to yield the title compound (51.7 mg, 52%) as a colorless solid.
$[α]_D^{25}$=−20.3 (c 0.979, DMSO).

Example 171

2,6-Difluoro-4-{[(1S,2R)-2-(1H-pyrazol-4-yl)cyclohexyl]oxy}-N-(pyrimidin-4-yl)benzenesulfonamide

[Formula 189]

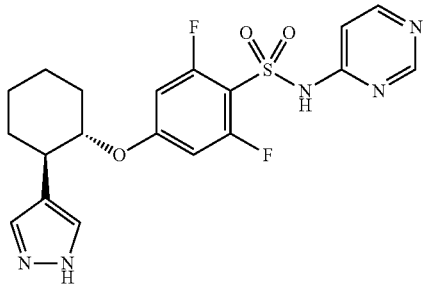

(171a) (1S,2R)-2-(1H-Pyrazol-4-yl)cyclohexanol

The (1R*,2S*)-2-(1H-pyrazol-4-yl)cyclohexanol prepared in Example 169a was optically resolved with CHIRALPAK AD-H (Daicel Corp.; hexane/ethanol=8:2) to yield the title compound as a colorless solid.

(171b) (1S,2R)-2-[1-(Methoxymethyl)-1H-pyrazol-4-yl]cyclohexanol

The reaction and aftertreatment were conducted in the same manner as in Example 169c by using the (1S,2R)-2-(1H-pyrazol-4-yl)cyclohexanol (144 mg, 0.866 mmol) prepared in Example 171a, chloromethyl methyl ether (0.069 mL, 0.908 mmol) and DMF (4.0 mL), to yield the title compound (132.2 mg, 73%) as a colorless oil.

(171c) N-(2,4-Dimethoxybenzyl)-2,6-difluoro-4-({(1S,2R)-2-[1-(methoxymethyl)-1H-pyrazol-4-yl]cyclohexyl}oxy)-N-(pyrimidin-4-yl)benzenesulfonamide The reaction and aftertreatment were conducted in the same manner as in Example 1a by using the N-(2,4-dimethoxybenzyl)-2,4,6-trifluoro-N-(pyrimidin-4-yl)benzenesulfonamide (156 mg, 0.355 mmol) prepared in Example 27a, the (1S,2R)-2-[1-(methoxymethyl)-1H-pyrazol-4-yl]cyclohexanol (62.2 mg, 0.296 mmol) prepared in Example 171b, sodium hydride (63%; 16.9 mg, 0.444 mmol) and DMF (2.0 mL), to yield the title compound (40.5 mg, 22%) as a colorless oil.

(171d) 2,6-Difluoro-4-{[(1S,2R)-2-(1H-pyrazol-4-yl)cyclohexyl]oxy}-N-(pyrimidin-4-yl)benzenesulfonamide The reaction and aftertreatment were conducted in the same manner as in Example 147e by using the N-(2,4-dimethoxybenzyl)-2,6-difluoro-4-({(1S,2R)-2-[1-(methoxymethyl)-1H-pyrazol-4-yl]cyclohexyl}oxy)-N-(pyrimidin-4-yl)benzenesulfonamide (40.5 mg, 0.0643 mmol) prepared in Example 171c, triethylsilane (0.055 mL), dichloromethane (1.0 mL), trifluoroacetic acid (1.0 mL), methanol (6.0 mL) and 6 M hydrochloric acid (2.0 mL), to yield the title compound (28.0 mg, 99%) as a colorless solid.

Example 172

2-Fluoro-5-methyl-4-{[(1S,2R)-2-(1H-pyrazol-4-yl)cyclohexyl]oxy}-N-(pyrimidin-4-yl)benzenesulfonamide

[Formula 190]

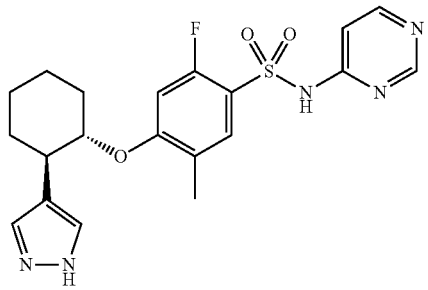

(172a) N-(2,4-Dimethoxybenzyl)-2-fluoro-4-({(1S,2R)-2-[1-(methoxymethyl)-1H-pyrazol-4-yl]cyclohexyl}oxy)-5-methyl-N-(pyrimidin-4-yl)benzenesulfonamide The reaction and aftertreatment were conducted in the same manner as in Example 1a by using the N-(2,4-dimethoxybenzyl)-2,4-difluoro-5-methyl-N-(pyrimidin-4-yl)benzenesulfonamide (174 mg, 0.400 mmol) prepared in Example 43a, the (1S,2R)-2-[1-(methoxymethyl)-1H-pyrazol-4-yl]cyclohexanol (70.0 mg, 0.333 mmol) prepared in Example 171a, sodium hydride (63%; 19.0 mg, 0.499 mol) and DMF (2.0 mL), to yield the title compound (61.5 mg, 30%) as a colorless oil.

(172b) 2-Fluoro-5-methyl-4-{[(1S,2R)-2-(1H-pyrazol-4-yl)cyclohexyl]oxy}-N-(pyrimidin-4-yl)benzenesulfonamide The reaction and aftertreatment were conducted in the same manner as in Example 147e by using the N-(2,4-dimethoxybenzyl)-2-fluoro-4-({(1S,2R)-2-[1-(methoxymethyl)-1H-pyrazol-4-yl]cyclohexyl}oxy)-5-methyl-N-(pyrimidin-4-yl)benzenesulfonamide (61.5 mg, 0.0983 mmol) prepared in Example 172a, triethylsilane (0.079 mL), dichloromethane (1.0 mL), trifluoroacetic acid (1.0 mL), methanol (15 mL) and 6 M hydrochloric acid (5.0 mL), to yield the title compound (42.0 mg, 99%) as a colorless solid. $[\alpha]_D^{25}=16.1$ (c 0.943, DMSO).

Preparation Example 1

Tablets can be obtained by mixing 5 g of the compound of Example 119, 90 g of lactose, 34 g of corn starch, 20 g of crystalline cellulose and 1 g of magnesium stearate with a blender and subjecting the thus obtained mixture to tablet compression by using a tableting machine.

Preparation Example 2

Tablets can be obtained by mixing 5 g of the compound of Example 122, 90 g of lactose, 34 g of corn starch, 20 g of crystalline cellulose and 1 g of magnesium stearate with a blender and subjecting the thus obtained mixture to tablet compression by using a tableting machine.

Preparation Example 3

Tablets can be obtained by mixing 5 g of the compound of Example 124, 90 g of lactose, 34 g of corn starch, 20 g of crystalline cellulose and 1 g of magnesium stearate with a blender and subjecting the thus obtained mixture to tablet compression by using a tableting machine.

Preparation Example 4

Tablets can be obtained by mixing 5 g of the compound of Example 143, 90 g of lactose, 34 g of corn starch, 20 g of crystalline cellulose and 1 g of magnesium stearate with a blender and subjecting the thus obtained mixture to tablet compression by using a tableting machine.

Preparation Example 5

Tablets can be obtained by mixing 5 g of the compound of Example 171, 90 g of lactose, 34 g of corn starch, 20 g of crystalline cellulose and 1 g of magnesium stearate with a blender and subjecting the thus obtained mixture to tablet compression by using a tableting machine.

Test Example 1

Construction and Cultivation of Cell Lines

HNav 1.7 and hNav β1 and β2 subunits cloned from human brain were stably expressed by using Lipofectamine (Invitrogen Corp.) in HEK293A cells, and stably expressing cell lines of hNav 1.7/β1/β2 were selected by taking an amount of expression as an indicator. As the culture medium, DMEM (Invitrogen Corp.) containing 20% fetal bovine serum (Hyclone Laboratories, Inc.), 100 U/ml penicillin (Invitrogen Corp.), 100 μg/ml streptomycin (Invitrogen Corp.), 200 μg/ml hygromycin B (Invitrogen Corp.), 200 μg/ml Zeocin (Invitrogen Corp.) and 1 μg/ml puromycin (Clontech Laboratories, Inc.) was used.

Test Example 2

Electrophysiological Evaluation (J. Biomol. Screen., 2006 August; 11(5): 488-96)

Current record was obtained by an automated patch clamp system "IonWorks Quattro (Molecular Devices Corporation)" in Population Patch Clamp mode. The operation was conducted in accordance with the operating procedure of the system. A Dulbecco's phosphate buffer containing calcium and magnesium (Sigma) was used as an extracellular fluid, and a low Cl-buffer (100 mM K-gluconate, 40 mM KCl, 3.2 mM $MgCl_2$, 5 mM EGTA, 5 mM Hepes, pH 7.3) was used as an intracellular fluid. A test compound was dissolved in dimethylsulfoxide (DMSO) to prepare a 30 mM stock solution, so as to produce 4-fold serial dilutions with the extracellular fluid for attaining a DMSO concentration of 0.3% in measurement.

The hNav 1.7/β1/β2 cells cultured to a 70-80% confluent state in a T150 flask (Sumilon) were washed with PBS and subsequently with versene (Invitrogen Corp.), and collected by allowing to react with 0.05% trypsin (Invitrogen Corp.) at 37° C. for 3 minutes. After washing with a culture medium, the resultant cells were suspended in an extracellular fluid at a concentration of $2 \times 10^{-6}$ cells/ml so as to be used for the measurement. The cell membrane was perforated by using an intracellular fluid including 100 μg/ml amphotericin B (Sigma).

Current response was obtained at a sampling frequency of 10 kHz. Leakage current correction was performed by applying a step pulse of −110 mV before a test pulse. The membrane potential was fixed at −100 mV for 5 seconds immediately before applying the test pulse.

In order to check the state-dependency of the inhibiting activity of a test compound, the test pulse was applied as follows: After applying a depolarization pulse of −10 mV for 5 msec., the potential was fixed at −100 mV for 200 msec., a potential (V1/2) at which approximately 50% of channels are inactivated was held for 2 seconds, and a depolarization pulse of −10 mV was applied for 50 msec. Such a test pulse was applied before adding the test compound and after cultivation of 5 minutes and 30 seconds with a solution of the test compound gradually added by 3.5 μl at each time. Since IonWorks Quattro has a measuring electrode head (E-head) and an agent supplying head (F-head) separated from each other, the membrane potential was not clamped during the addition and the cultivation of the test compound.

The inhibiting activity of the test compound was analyzed with respect to the responses to the two depolarization pulses. Data to be analyzed was selected under conditions that a ratio of a resistance value attained before adding the test compound to a resistance value attained after the addition fell in a range of 0.5 to 1.6, that a seal resistance value was 30 MS or more, and that the current response obtained before adding the test compound was ⅓ or more of an average of all wells. An inhibiting activity value was determined on the basis of currents generated in response to the depolarization pulses applied before and after adding the test compound, and a 50% inhibition concentration ($IC_{50}$) was calculated by regression analyzing a 6-point concentration response curve in accordance with the following sigmoidal dose-response function:

$y = Bottom + (Top - Bottom)(1 + 10^{[(Log\ EC50-x) \times Hill\ slope]})$

The values of $IC_{50}$ of the inhibiting activity of test compounds corresponding to the response caused by the second depolarization pulse (with a pre-pulse potential set to V1/2) are shown in Tables 7-1 and 7-2.

TABLE 7-1

| Compound (Example No.) | hNav1.7 $IC_{50}$ (μM) |
|---|---|
| 1 | 0.12 |
| 2 | 0.020 |
| 3 | 0.27 |
| 4 | 0.012 |
| 5 | 0.29 |
| 6 | 0.61 |
| 7 | 0.45 |
| 8 | 0.017 |
| 9 | 0.014 |
| 10 | 0.030 |
| 11 | 0.010 |
| 12 | 0.12 |
| 13 | 0.082 |
| 14 | 0.15 |
| 15 | 0.028 |
| 16 | 0.23 |
| 17 | 0.51 |
| 18 | 0.17 |
| 19 | 0.51 |

TABLE 7-1-continued

| Compound (Example No.) | hNav1.7 IC$_{50}$ (μM) |
|---|---|
| 20 | 0.045 |
| 21 | 0.25 |
| 22 | 0.52 |
| 23 | 0.13 |
| 24 | 0.023 |
| 25 | 0.095 |
| 26 | 0.20 |
| 27 | 0.043 |
| 28 | 0.046 |
| 29 | 1.8 |
| 30 | 0.50 |
| 31 | 0.058 |
| 32 | 1.0 |
| 33 | 0.30 |
| 34 | 0.25 |
| 35 | 0.099 |
| 36 | 0.50 |
| 37 | 0.21 |
| 38 | 0.24 |
| 39 | 1.0 |
| 40 | 0.33 |
| 41 | 0.16 |
| 42 | 0.091 |
| 43 | 0.024 |
| 44 | 0.33 |
| 45 | 0.19 |
| 46 | 0.030 |
| 47 | 0.12 |
| 48 | 0.016 |
| 49 | 0.66 |
| 50 | 0.047 |
| 51 | 0.75 |
| 52 | 0.083 |
| 53 | 0.33 |
| 54 | 0.039 |
| 55 | 0.039 |
| 56 | 0.25 |
| 57 | 0.075 |
| 58 | 0.66 |
| 59 | 0.031 |
| 60 | 0.037 |
| 61 | 0.0026 |
| 62 | 0.12 |
| 63 | 0.028 |
| 64 | 0.031 |
| 65 | 0.13 |
| 66 | 0.017 |
| 67 | 0.043 |
| 68 | 0.086 |
| 69 | 0.087 |
| 70 | 0.33 |
| 71 | 0.15 |
| 72 | 0.036 |
| 73 | 0.10 |
| 74 | — |
| 75 | >10 |
| 76 | — |
| 77 | — |
| 78 | 43 |
| 79 | 0.070 |
| 80 | 0.086 |
| 81 | 0.15 |
| 82 | 0.056 |
| 83 | 0.65 |
| 84 | 0.036 |
| 85 | 0.17 |
| 86 | 0.036 |

TABLE 7-2

| Compound (Example No.) | hNav1.7 IC$_{50}$ (μM) |
|---|---|
| 87 | 0.28 |
| 88 | 0.32 |
| 89 | 0.13 |
| 90 | 0.089 |
| 91 | 0.17 |
| 92 | 1.0 |
| 93 | 0.065 |
| 94 | 0.12 |
| 95 | 0.17 |
| 96 | 0.25 |
| 97 | 0.034 |
| 98 | 0.046 |
| 99 | 0.41 |
| 100 | 0.38 |
| 101 | 0.18 |
| 102 | 0.036 |
| 103 | 0.32 |
| 104 | 0.071 |
| 105 | 0.22 |
| 106 | 0.27 |
| 107 | 0.042 |
| 108 | 1.7 |
| 109 | 0.050 |
| 110 | 0.30 |
| 111 | 0.030 |
| 112 | 0.31 |
| 113 | 1.0 |
| 114 | 0.078 |
| 115 | 0.58 |
| 116 | 0.17 |
| 117 | 0.75 |
| 118 | 21 |
| 119 | 0.10 |
| 120 | 0.27 |
| 121 | 0.93 |
| 122 | 0.020 |
| 123 | — |
| 124 | 2.4 |
| 125 | 0.20 |
| 126 | 0.014 |
| 127 | 0.12 |
| 128 | 92 |
| 129 | 0.10 |
| 130 | 0.88 |
| 131 | 0.059 |
| 132 | 0.20 |
| 133 | 0.057 |
| 134 | 0.034 |
| 135 | 0.051 |
| 136 | 0.29 |
| 137 | 0.030 |
| 138 | 0.024 |
| 139 | 0.035 |
| 140 | 0.034 |
| 141 | 0.058 |
| 142 | 47 |
| 143 | 0.021 |
| 144 | 3.4 |
| 145 | — |
| 146 | 0.024 |
| 147 | 0.60 |
| 148 | 0.018 |
| 149 | 32 |
| 150 | 0.021 |
| 151 | 33 |
| 152 | 0.017 |
| 153 | >100 |
| 154 | 0.017 |
| 155 | 0.028 |
| 156 | 0.041 |
| 157 | 0.050 |
| 158 | 0.028 |
| 159 | 9.8 |
| 160 | 0.56 |
| 161 | 0.13 |
| 162 | 0.82 |
| 163 | 0.19 |

TABLE 7-2-continued

| Compound (Example No.) | hNav1.7 IC$_{50}$ (μM) |
|---|---|
| 164 | >10 |
| 165 | 0.040 |
| 166 | 0.059 |
| 167 | 4.6 |
| 168 | >10 |
| 169 | >10 |
| 170 | >10 |
| 171 | 0.043 |
| 172 | 0.034 |

Test Example 3

Thermal Hyperalgesia Assay

In the present invention, mice and rats affected by thermal hyperalgesia were used for evaluation.

A test compound was orally administered to an animal, and the thermal hyperalgesia was evaluated at each measurement time determined by a study director. Specifically, thermal stimulation was applied to the sole of hind paw of the animal, and latency until it showed escape behaviors such as licking and shaking was measured.

The test compound was evaluated by calculating a improvement rate of pain score (%) at a constant dose against the vehicle treatment group. Improvement rates of pain score (%) at a constant dose are shown in Tables 8-1 and 8-2 as "C" when the rate was 0 to 30%, as "B" when the rate was 31 to 60%, and as "A" when the rate was 61 to 100%.

TABLE 8-1

| Compound (Example No.) | Ratio of improving pain score (%) |
|---|---|
| 1 | — |
| 2 | — |
| 3 | — |
| 4 | — |
| 5 | — |
| 6 | — |
| 7 | — |
| 8 | — |
| 9 | — |
| 10 | — |
| 11 | — |
| 12 | — |
| 13 | — |
| 14 | — |
| 15 | A |
| 16 | — |
| 17 | — |
| 18 | — |
| 19 | — |
| 20 | — |
| 21 | — |
| 22 | — |
| 23 | A |
| 24 | — |
| 25 | A |
| 26 | — |
| 27 | — |
| 28 | C |
| 29 | A |
| 30 | B |
| 31 | A |
| 32 | — |
| 33 | A |
| 34 | — |
| 35 | B |

TABLE 8-1-continued

| Compound (Example No.) | Ratio of improving pain score (%) |
|---|---|
| 36 | — |
| 37 | C |
| 38 | A |
| 39 | — |
| 40 | A |
| 41 | B |
| 42 | C |
| 43 | B |
| 44 | C |
| 45 | C |
| 46 | C |
| 47 | A |
| 48 | A |
| 49 | — |
| 50 | B |
| 51 | B |
| 52 | B |
| 53 | — |
| 54 | C |
| 55 | C |
| 56 | B |
| 57 | B |
| 58 | B |
| 59 | C |
| 60 | C |
| 61 | — |
| 62 | B |
| 63 | C |
| 64 | C |
| 65 | B |
| 66 | A |
| 67 | C |
| 68 | B |
| 69 | B |
| 70 | — |
| 71 | A |
| 72 | C |
| 73 | A |
| 74 | — |
| 75 | — |
| 76 | — |
| 77 | — |
| 78 | C |
| 79 | C |
| 80 | C |
| 81 | C |
| 82 | B |
| 83 | B |
| 84 | B |
| 85 | B |
| 86 | A |

TABLE 8-2

| Compound (Example No.) | Ratio of improving pain score (%) |
|---|---|
| 87 | B |
| 88 | C |
| 89 | — |
| 90 | B |
| 91 | A |
| 92 | — |
| 93 | B |
| 94 | A |
| 95 | C |
| 96 | A |
| 97 | C |
| 98 | C |
| 99 | — |
| 100 | — |
| 101 | B |
| 102 | — |
| 103 | B |

TABLE 8-2-continued

| Compound (Example No.) | Ratio of improving pain score (%) |
|---|---|
| 104 | B |
| 105 | A |
| 106 | — |
| 107 | B |
| 108 | A |
| 109 | B |
| 110 | B |
| 111 | A |
| 112 | — |
| 113 | — |
| 114 | B |
| 115 | A |
| 116 | B |
| 117 | — |
| 118 | A |
| 119 | A |
| 120 | C |
| 121 | — |
| 122 | A |
| 123 | — |
| 124 | — |
| 125 | C |
| 126 | C |
| 127 | A |
| 128 | B |
| 129 | C |
| 130 | — |
| 131 | C |
| 132 | A |
| 133 | A |
| 134 | B |
| 135 | B |
| 136 | B |
| 137 | A |
| 138 | B |
| 139 | C |
| 140 | B |
| 141 | A |
| 142 | C |
| 143 | B |
| 144 | — |
| 145 | — |
| 146 | C |
| 147 | C |
| 148 | B |
| 149 | — |
| 150 | C |
| 151 | — |
| 152 | B |
| 153 | — |
| 154 | — |
| 155 | — |
| 156 | — |
| 157 | — |
| 158 | C |
| 159 | — |
| 160 | — |
| 161 | — |
| 162 | — |
| 163 | — |
| 164 | — |
| 165 | B |
| 166 | — |
| 167 | — |
| 168 | — |
| 169 | — |
| 170 | — |
| 171 | B |
| 172 | — |

INDUSTRIAL APPLICABILITY

The present compound or a pharmacologically acceptable salt thereof is useful because it can be used as an active ingredient of a pharmaceutical composition for treating and/or preventing pain, and sodium channel associated diseases or disorders such as central nervous system disorders.

What is claimed is:

1. A method of producing a compound represented by formula (I):

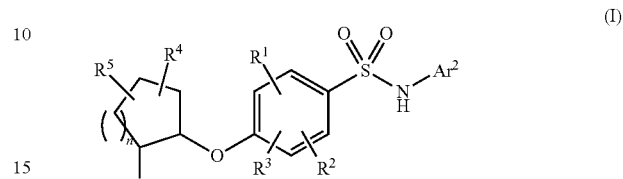

or a pharmacologically acceptable salt thereof,
wherein
$Ar^1$ and $Ar^2$ are each independently a heteroaryl group;
$R^1$, $R^2$ and $R^3$ are each independently a hydrogen atom, a halogen atom, a C1-C6 alkyl group, a halogenated C1-C6 alkyl group, a hydroxy C1-C6 alkyl group, a C1-C6 alkoxy C1-C6 alkyl group, a C3-C7 cycloalkyl group or a cyano group;
$R^4$ and $R^5$ are each independently a hydrogen atom, a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group or a C1-C6 alkoxy group; and
n is an integer of 1 to 3;
wherein the heteroaryl group is optionally substituted with one or two groups independently selected from a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group, a carboxy group, a cyano group, an amino group, a C1-C3 alkylamino group and a di-C1-C3 alkylamino group; and when the heteroaryl group is substituted with two such groups, the two groups are the same as or different from each other,
comprising a step of removing a protecting group, P, from the compound of formula (VI)

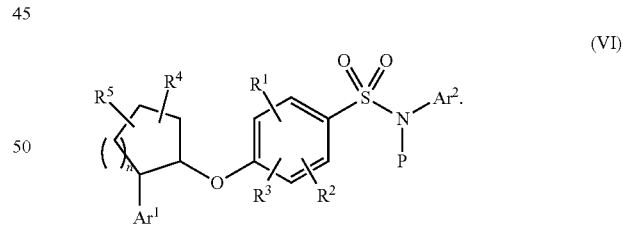

2. The method of claim 1, wherein the removal of the protecting group is conducted by reacting an acid and the compound represented by formula (VI) in a solvent.

3. The method of claim 2, wherein the solvent is selected from the group consisting of an ethers, a halogenated hydrocarbon, tetrahydrofuran, 1,4-dioxane and dichloromethane.

4. The method of claim 2, further comprising a scavenger.

5. The method of claim 4, wherein the scavenger is selected from the group consisting of trialkylsilane, aryl ether, triethylsilane and anisole.

6. The method of claim 2, wherein the acid is selected from the group consisting of an organic acid, an inorganic acid, trichloroacetic acid, trifluoroacetic acid, acetic acid, sulfuric acid and hydrochloric acid.

7. The method of claim 1, wherein the deprotection is conducted at a reaction temperature is 0° C. to 200° C.

8. The method of claim 1, wherein the reaction time is from 1 hour to 48 hours.

9. The method of claim 1, wherein the deprotecting of the compound of formula (VI) is in a solvent and in the presence of a palladium catalyst under hydrogen atmosphere.

10. The method of claim 9, wherein the solvent is selected from the group consisting of ethers, alcohols, tetrahydrofuran, methanol and ethanol.

11. The method of claim 9, wherein the catalyst is selected from the group consisting of a zero-valent palladium catalyst, a palladium-activated carbon and a palladium hydroxide-activated carbon.

12. The method of claim 9, wherein the reaction temperature is from −20° C. to 120° C.

13. The method of claim 9, wherein the reaction time is from 1 hour to 48 hours.

14. The method of claim 1, wherein P is selected from the group consisting of a formyl group, a phenylcarbonyl group, a methoxycarbonyl group, an ethoxycarbonyl group, a t-butoxycarbonyl group, a phenyloxycarbonyl group, a 9-fluorenylmethyloxycarbonyl group, an adamantyloxycarbonyl group, a benzyloxycarbonyl group, a benzylcarbonyl group, a benzyl group, a 2,4-dimethoxybenzyl group, a benzhydryl group, a trityl group and a phthaloyl group.

15. The method of claim 1, further comprising a step of:
reacting a compound of formula (IV) and a compound of formula (V) to produce a compound of formula (VI), (IV)

(V)

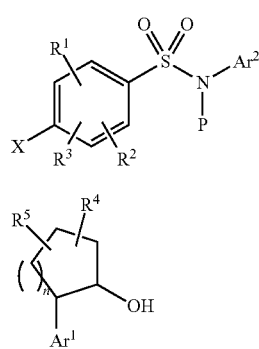

wherein X represents a halogen atom.

16. The method of claim 15, wherein the reaction of the compound of formula (IV) and the compound of formula (V) is performed in a solvent in the presence of a base.

17. The method of claim 16, wherein the solvent is selected from the group consisting of ethers, amides, tetrahydrofuran and N,N-dimethylformamide.

18. The method of claim 16, wherein the base is selected from the group consisting of alkali metal alkoxides, alkali metal hydrides, alkali metal hydroxides, sodium t-butoxide, potassium t-butoxide, sodium methoxide, potassium methoxide, sodium hydride, potassium hydride, sodium hydroxide and potassium hydroxide.

19. The method of claim 15, wherein the reaction temperature is 0° C. to 200° C.

20. The method of claim 15, wherein the reaction time is from 0.5 hours to 48 hours.

21. A method of producing a compound represented by formula (I):

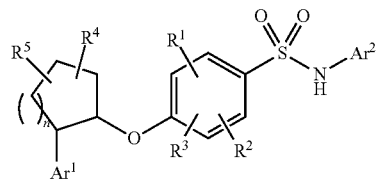

(I)

or a pharmacologically acceptable salt thereof,
wherein
Ar$^1$ and Ar$^2$ are each independently a heteroaryl group;
R$^1$, R$^2$ and R$^3$ are each independently a hydrogen atom, a halogen atom, a C1-C6 alkyl group, a halogenated C1-C6 alkyl group, a hydroxy C1-C6 alkyl group, a C1-C6 alkoxy C1-C6 alkyl group, a C3-C7 cycloalkyl group or a cyano group;
R$^4$ and R$^5$ are each independently a hydrogen atom, a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group or a C1-C6 alkoxy group; and
n is an integer of 1 to 3;
wherein the heteroaryl group is optionally substituted with one or two groups independently selected from a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group, a carboxy group, a cyano group, an amino group, a C1-C3 alkylamino group and a di-C1-C3 alkylamino group; and when the heteroaryl group is substituted with two such groups, the two groups are the same as or different from each other,
comprising a step of:
reacting a compound of formula (X) and a compound of formula (XI),

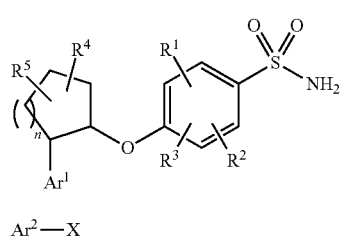

(X)

(XI)

wherein X represents a halogen atom.

22. The method of claim 21, wherein the reaction of the compound of formula (X) and the compound of formula (XI) is performed in a solvent in the presence of a base.

23. The method of claim 22, wherein the reaction is conducted in the presence of a copper catalyst and a ligand thereof.

24. The method of claim 22, wherein the solvent is selected from the group consisting of ethers, amides, halogenated hydrocarbons, tetrahydrofuran, N,N-dimethylformamide and dichloromethane.

25. The method of claim 22, wherein the base is selected from the group consisting of organic bases, alkali metal carbonates, triethylamine, cesium carbonate and potassium carbonate.

26. The method of claim 23, wherein the copper catalyst is selected from the group consisting of copper (I) chloride, copper (I) bromide, copper (I) iodide and copper (I) trifluoromethanesulfonate.

27. The method of claim 23, wherein the ligand is selected from the group consisting of N,N'-dimethylethylenediamine, trans-N,N'-dimethylcyclohexane-1,2-diamine and N,N'-dimethyl-1,2-cyclohexanediamine.

28. The method of claim 21, wherein the reaction temperature is 0° C. to 200° C.

29. The method of claim 21, wherein the reaction time is from 1 hour to 48 hours.

* * * * *